US010800747B2

(12) United States Patent
Davis et al.

(10) Patent No.: US 10,800,747 B2
(45) Date of Patent: Oct. 13, 2020

(54) MACROCYCLIC COMPOUNDS

(71) Applicant: Ziylo Limited, Bristol (GB)

(72) Inventors: Anthony Davis, Bristol (GB); Robert Tromans, Bristol (GB); Miriam Ruth Wilson, Bristol (GB); Michael Glen Orchard, Marlborough (GB); Andrew Michael Chapman, Bristol (GB); Michael Roger Tomsett, Bristol (GB); Johnathan Vincent Matlock, Bristol (GB)

(73) Assignee: ZIYLO LTD, Bristol (GB)

( * ) Notice: Subject to any disclaimer, the term of this patent is extended or adjusted under 35 U.S.C. 154(b) by 0 days.

(21) Appl. No.: 16/491,379

(22) PCT Filed: Mar. 15, 2018

(86) PCT No.: PCT/GB2018/050679
§ 371 (c)(1),
(2) Date: Sep. 5, 2019

(87) PCT Pub. No.: WO2018/167503
PCT Pub. Date: Sep. 20, 2018

(65) Prior Publication Data

US 2020/0017454 A1 Jan. 16, 2020

(30) Foreign Application Priority Data

Mar. 15, 2017 (GB) .................................. 1704125.2
Sep. 20, 2017 (GB) .................................. 1715210.9

(51) Int. Cl.
*C07D 259/00* (2006.01)
*C07D 493/10* (2006.01)
*G01N 33/58* (2006.01)
*G01N 33/66* (2006.01)

(52) U.S. Cl.
CPC ......... *C07D 259/00* (2013.01); *C07D 493/10* (2013.01); *G01N 33/582* (2013.01); *G01N 33/66* (2013.01); *G01N 2400/00* (2013.01); *G01N 2800/042* (2013.01)

(58) Field of Classification Search
CPC .................................................... C07D 259/00
See application file for complete search history.

(56) References Cited

FOREIGN PATENT DOCUMENTS

| | | | |
|---|---|---|---|
| WO | 9951570 | A1 | 10/1999 |
| WO | 2013160701 | A1 | 10/2013 |

OTHER PUBLICATIONS

Maverick. Helvetica Chimica Acta, 2003, 86, 1309-19 (Year: 2003).*
Davis et al., Carbohydrate Recognition Through Noncovalent Interactions: A Challenge for Biomimetic and Supramolecular Chemistry, Angew. Chem. Int. Ed., 1999, vol. 38, pp. 2978-2996.

* cited by examiner

*Primary Examiner* — Noble E Jarrell
(74) *Attorney, Agent, or Firm* — Jianjie Hu

(57) ABSTRACT

The present invention relates to macrocyclic compounds which are capable of selective binding to a target saccharide (e.g. glucose), making them particularly well suited for use in saccharide sensing applications. The present invention also relates to processes for the preparation of said compounds, to compositions and devices comprising them, and to their use in the detection of a target saccharide.

11 Claims, 77 Drawing Sheets
(76 of 77 Drawing Sheet(s) Filed in Color)

a)

b)

a)

b)

a)

b)

a)

b)

a)

b)

a)

b)

Binds to receptor 1

12

13

14

15

16

17

18

19

20

21

22

Binding minimal or undetectable

D-Mannitol

D-Gluconic acid

Methyl α-D-glucoside

N-Acetyl-D-glucosamine

D-Maltose

L-Fucose

Ascorbic acid

Uracil

Uric acid

Cytosine

Adenosine

L-Phenylalanine

L-Tryptophan

Paracetamol

A

B

MACROCYCLIC COMPOUNDS

CROSS-REFERENCE TO RELATED APPLICATIONS

This application is a 35 U.S.C. § 371 National Stage application of International Application PCT/GB2018/050679 (WO 2018/167503), filed Mar. 15, 2018, which claims priority to Great Britain Patent Applications 1704125.2, filed Mar. 15, 2017, and 1715210.9, filed Sep. 20, 2017; the contents of which are incorporated herein by reference.

INTRODUCTION

The present invention relates to macrocyclic compounds which are capable of selectively binding to a target saccharide (e.g. glucose), making them particularly well suited for use in saccharide sensing applications. The present invention also relates to processes for the preparation of said compounds, to compositions and devices comprising them, and to their use in the detection of a target saccharide.

BACKGROUND OF THE INVENTION

The detection and subsequent monitoring of saccharides, in particular glucose, has many practical applications in both medical and non-medical applications. For instance, the reliable detection of glucose in an individual's bloodstream underpins the vast majority of treatments currently available for the treatment of diabetes, a condition which the World Health Organisation (WHO) state affected around 422 million in 2014, and which it projects to be the 7th leading cause of death by 2030.

Diabetes, however, is not the only practical application for saccharide detection, the accurate determination of sugar levels in fermentation media, for example, in brewing processes and/or cell culturing, is also highly desired. Here, the ability to closely monitor the precise levels of sugars present during fermentation can be hugely advantageous in fine-tuning both the yield and properties of the end product.

Detection and subsequent monitoring of saccharides, however, is heavily reliant on the provision of saccharide receptor molecules which are capable of binding to, and thus detecting, saccharides in the aqueous media in which they are typically found, so called 'synthetic lectins'. However, historically, the binding of saccharides in aqueous media has proven to be a very challenging task for synthetic chemists, and even natural carbohydrate-binding proteins, known as lectins, struggle to display binding affinities in the order of magnitude commonly found in nature for such protein-substrate binding interactions.

Saccharides are hydrophilic species, often bearing hydromimetic hydroxyl groups, which makes them well hydrated and of significant resemblance to water molecules. In this regard, successful binding requires a receptor molecule to be able to distinguish between the hydroxyl groups of the saccharide and an array of water molecules, which are usually present in a much higher abundance than the target saccharide. Furthermore, for binding to occur, water must be displaced from both the receptor molecule and the saccharide, for which the energetic consequences are often difficult to predict, thereby making the modelling and design of such receptor molecules difficult.

Moreover, the ability to selectively target one saccharide molecule over other saccharide molecules also presents a significant challenge. For instance, for specific saccharide binding to occur, the receptor molecule must be able to distinguish between numerous saccharide molecules often bearing only very subtle structural differences (i.e. the configuration of a single asymmetric centre).

Despite the above challenges, a few successful synthetic saccharide receptor molecules, which are capable of selective saccharide recognition in aqueous media, have been reported (see, for example, WO2013160701). However, to further advance the use of such synthetic saccharide receptors in saccharide detection applications, such as those outlined above, there remains a need for new and improved receptor molecules which are capable of displaying higher affinities and/or selectivities towards specific target saccharides (e.g. glucose).

The present invention was devised with the foregoing in mind.

SUMMARY OF THE INVENTION

According to one aspect of the present invention, there is provided a compound, or a salt, hydrate or solvate thereof, as defined herein.

According to a second aspect of the present invention, there is provided a complex comprising a compound, or a salt, hydrate or solvate thereof, as defined herein, in association with a target saccharide.

According to a third aspect of the present invention, there is provided a complex comprising a compound, or a salt, hydrate or solvate thereof, as defined herein, in association with a displaceable reporter molecule.

According to a fourth aspect of the present invention, there is provided a composition comprising a compound, or a salt, hydrate or solvate thereof, as defined herein, and a displaceable reporter molecule.

According to a fifth aspect of the present invention there is provided a saccharide detection device comprising a complex, as defined herein, a composition, as defined herein, or a compound as defined herein.

According to another aspect of the present invention, there is provided a use of a complex, as defined herein, a composition, as defined herein, a saccharide detection device, as defined herein, or a compound, as defined herein, for detecting a target saccharide in an aqueous environment.

According to a further aspect of the present invention, there is provided a kit comprising a compound, as defined herein, and a displaceable reporter molecule.

According to a further aspect of the present invention, there is provided a process for preparing a compound, or a salt, hydrate or solvate thereof, as defined herein.

According to yet a further aspect of the present invention, there are provided novel intermediates as defined herein which are suitable for use in any one of the synthetic methods set out herein.

Features, including optional, suitable, and preferred features in relation to one aspect of the invention may also be features, including optional, suitable and preferred features in relation to any other aspect of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In FIG. 1*c*, ten intermolecular NH . . . O hydrogen bonds (with a distance of between 1.9 and 2.2 Å) can be seen, and FIG. 1*d* further depicts the close CH-π contacts made between the saccharide and compound of the present invention.

The calculated values for the Δδ are overlaid with the observed values giving $K_a$=51±3 $M^{-1}$ (5.46%).

Figure 35:
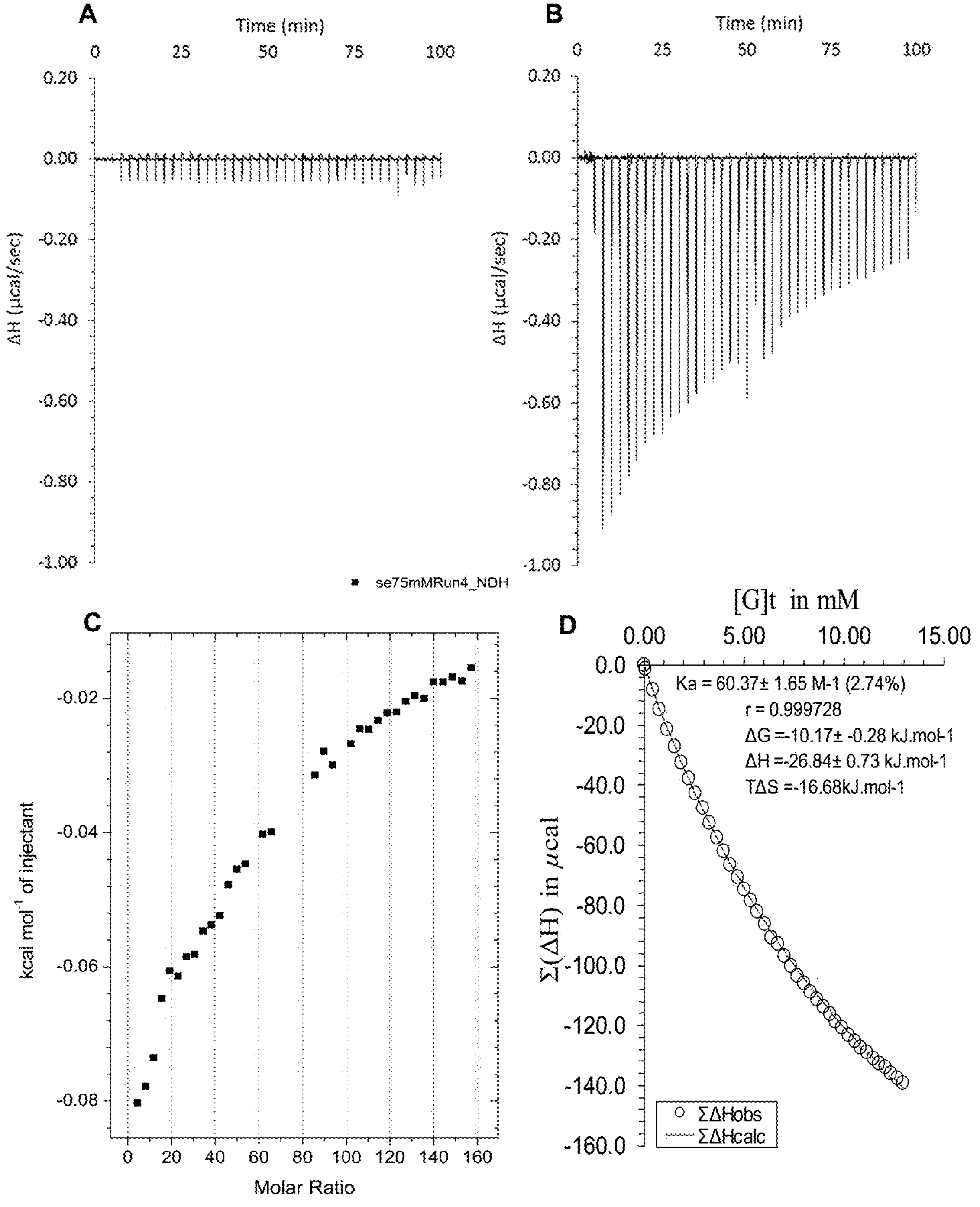

FIG. 35 shows the ITC binding results for receptor 1 (0.1 mM) titrated with D-fructose (75 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet ($K_a$=60.3±1.6 $M^{-1}$).

Figure 36:
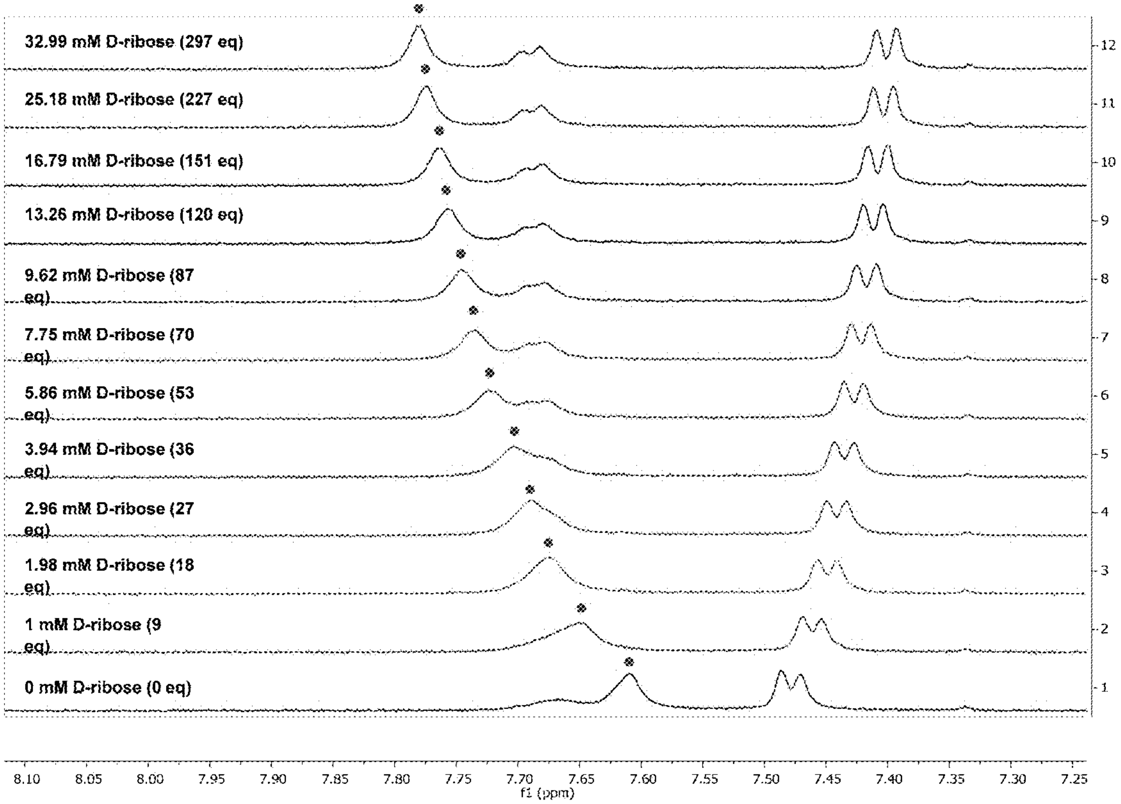
Figure 36:
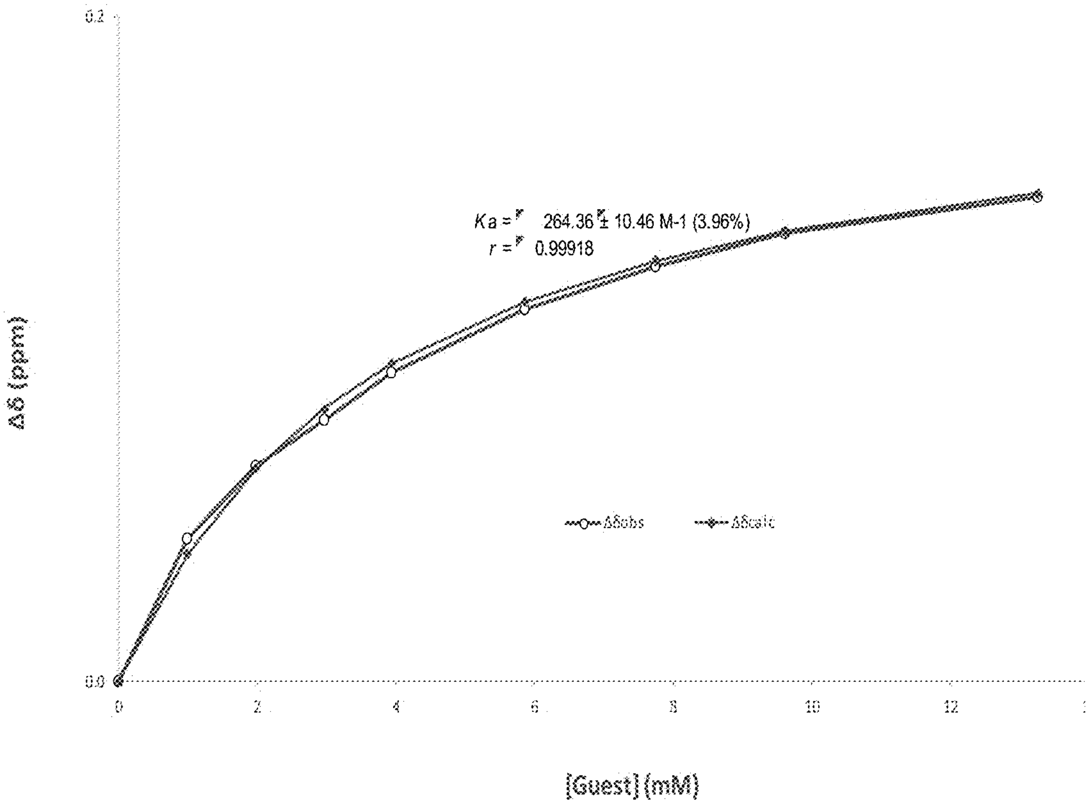

FIG. 36 shows: a) the partial $^1$H NMR spectra; and b) the binding analysis curve for receptor 1 (0.11 mM) titrated with a combined solution of D-ribose (250 mM) and receptor 1 (0.11 mM), in $D_2O$ buffered with 10 mM phosphate buffer solution (pH 7.4) at 298 K. Spectra imply binding with fast exchange on NMR timescale. Changes in chemical shift (Δδ ppm) of peak at 7.83 ppm (denoted with •) were plotted against increasing guest concentration (mM). The calculated values for the Δδ are overlaid with the observed values giving $K_a$=264±10 $M^{-1}$ (3.96%).

Figure 37:
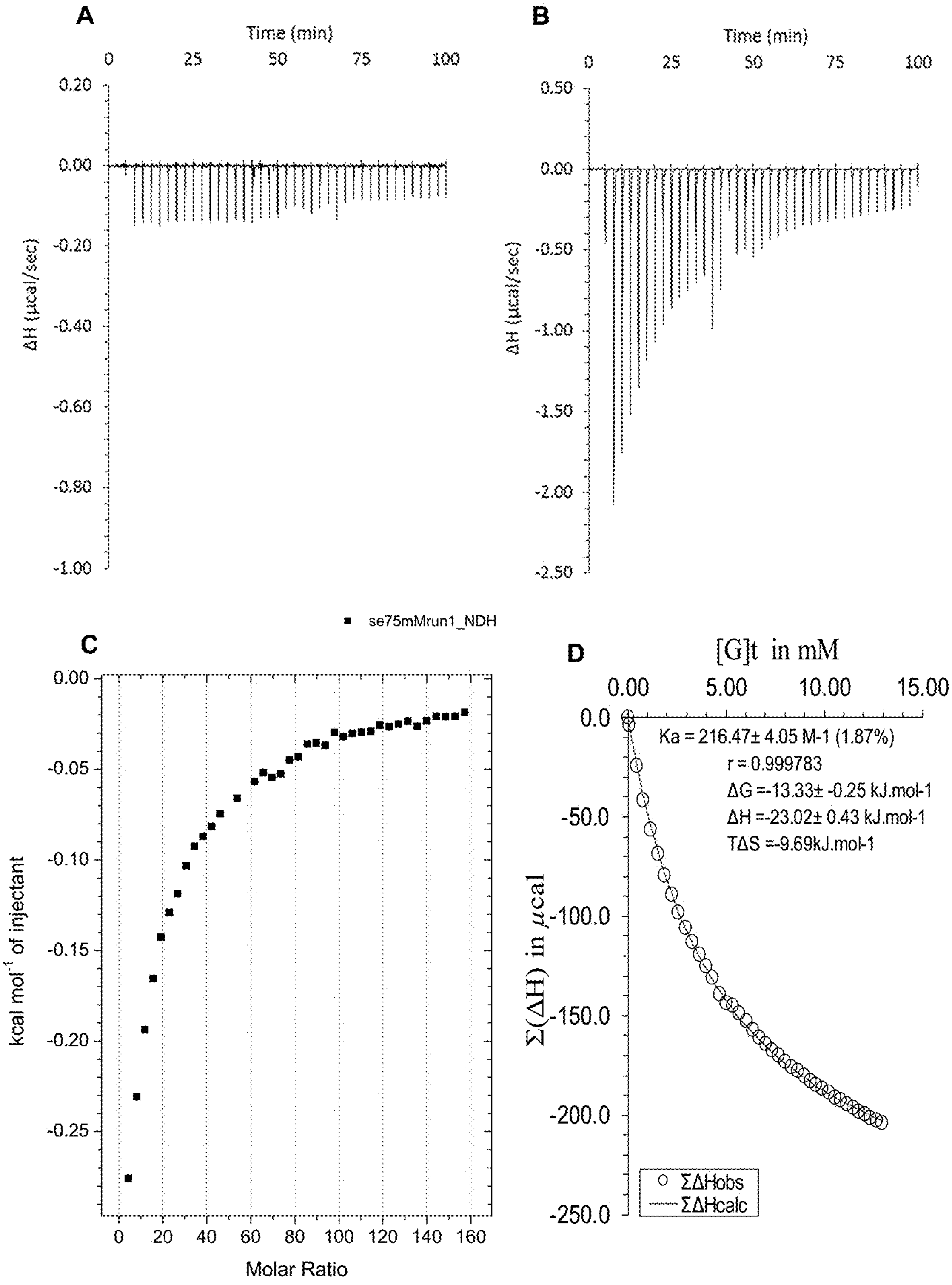

FIG. 37 shows the ITC binding results for receptor 1 (0.1 mM) titrated with D-ribose (75 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet ($K_a$=216.5±4.1 $M^{-1}$).

Figure 38:
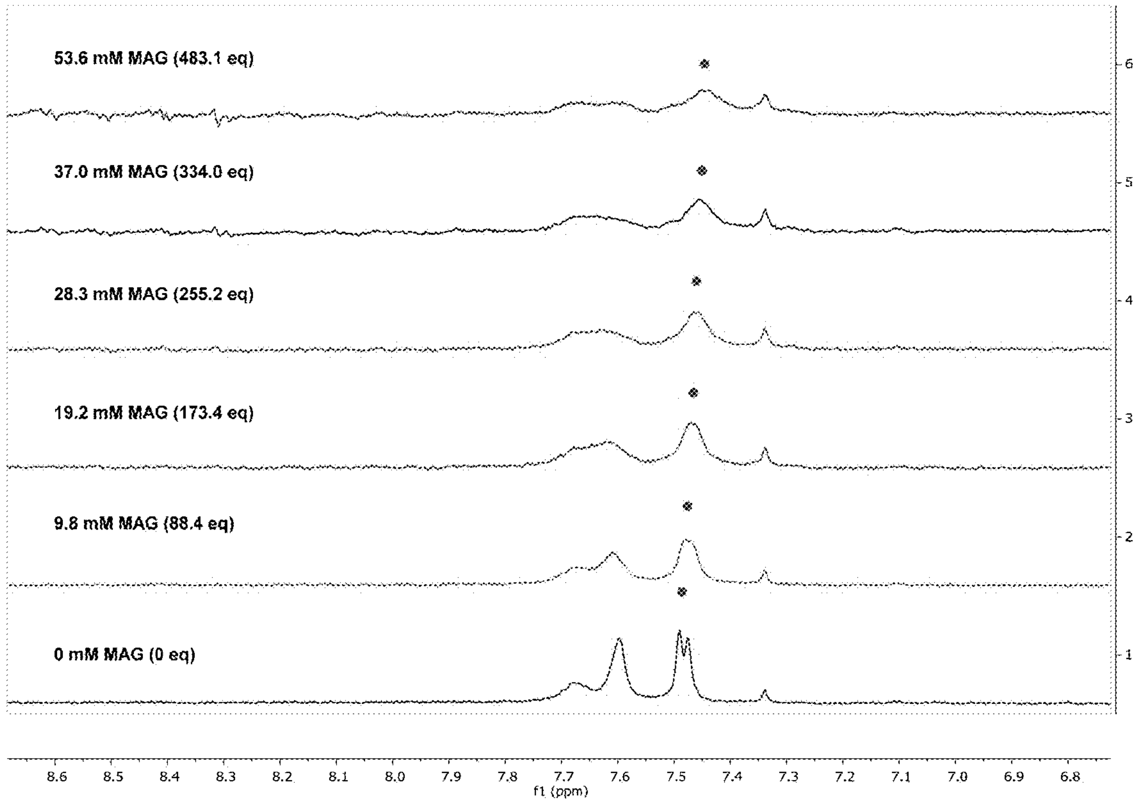
Figure 38:
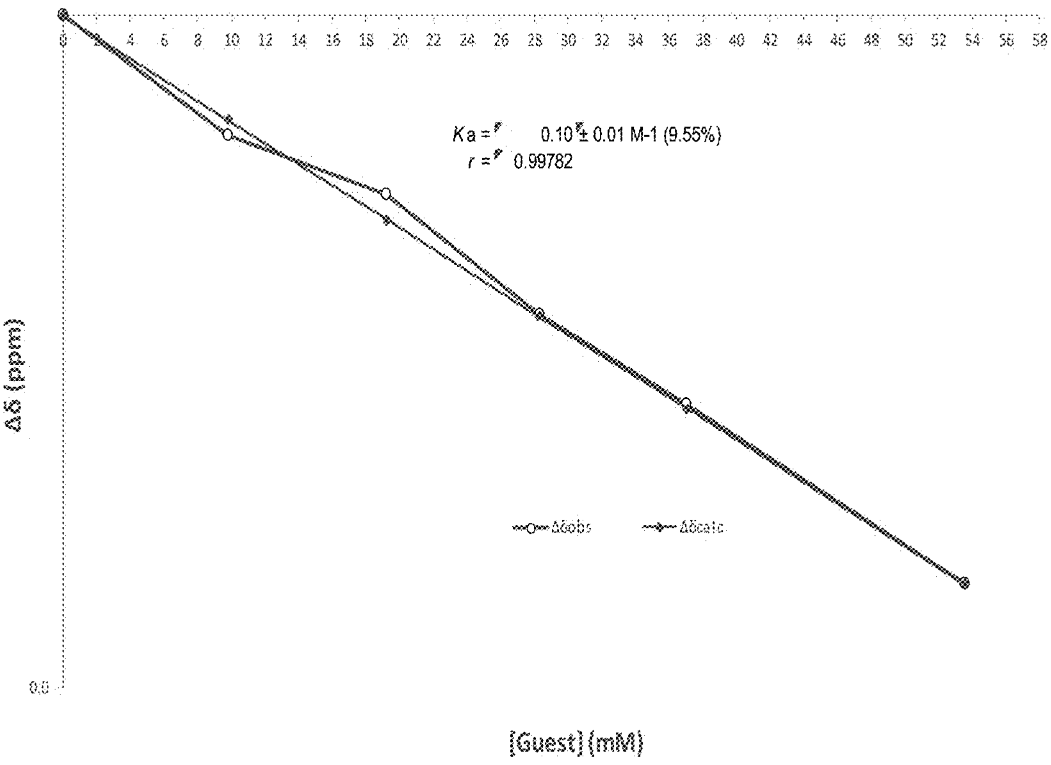

FIG. 38 shows: a) the partial $^1$H NMR spectra; and b) the binding analysis curve for receptor 1 (0.1 mM) titrated with a combined solution of methyl α-D-glucoside (500 mM) and receptor 1 (0.1 mM), in $D_2O$ buffered with 10 mM phosphate buffer solution (pH 7.4) at 298 K. Changes in chemical shift (Δδ ppm) of peak at 7.63 ppm (denoted with •) were plotted against increasing guest concentration (mM). The calculated values for the Δδ are overlaid with the observed values, which are effectively indicative of no binding taking place.

Figure 39:
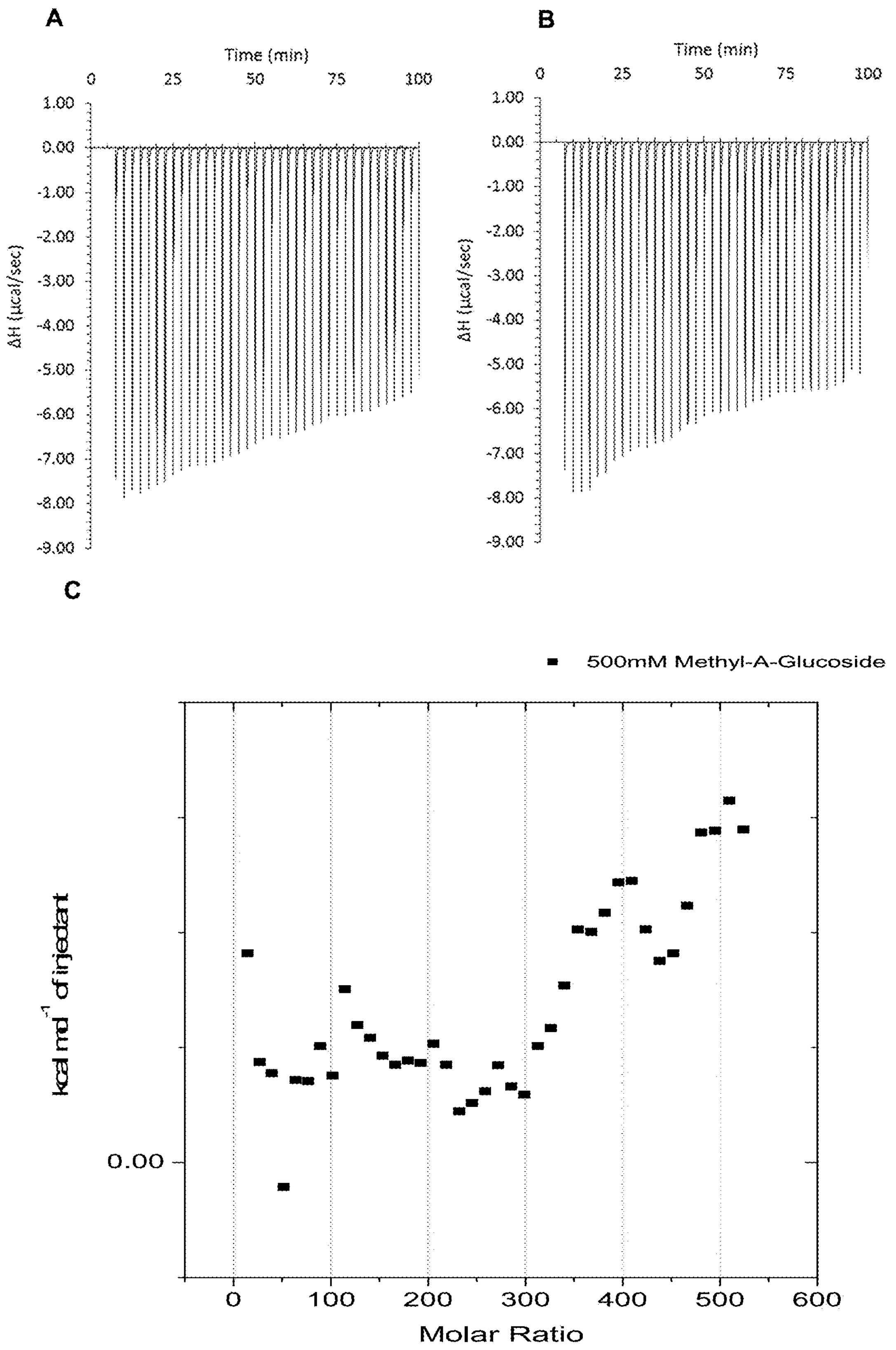

FIG. 39 shows for receptor 1 (0.06 mM) titrated with methyl-α-D-glucoside (500 mM) in $H_2O$, in which: A) shows the blank ITC run (addition of sugar into water); B) shows the actual run (sugar into receptor 1); and C) shows the plotted change in enthalpy vs molar ratio.

Figure 40:
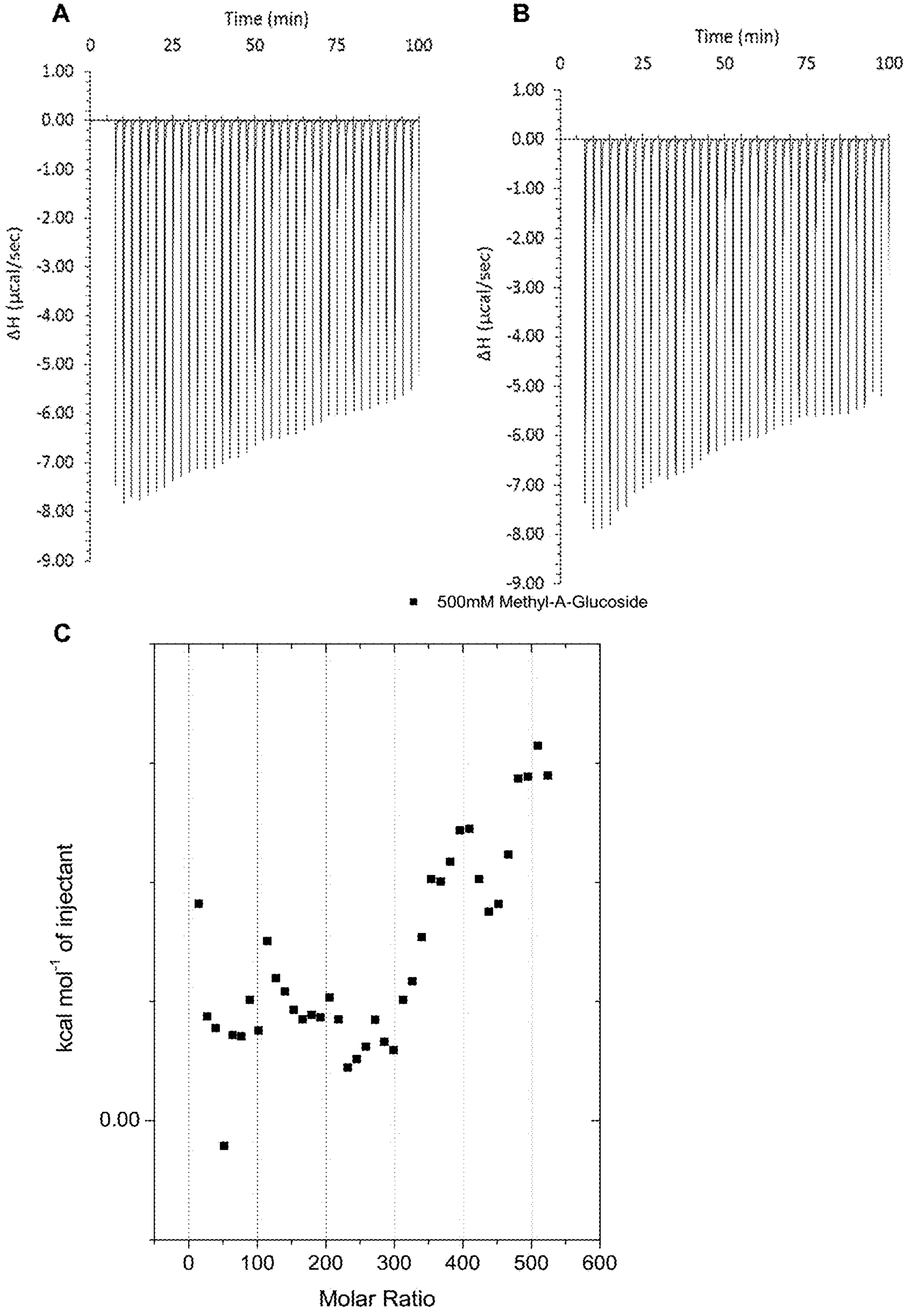

FIG. 40 shows the ITC binding results for receptor 1 (0.06 mM) titrated with methyl-α-D-glucoside (500 mM) in 10 mM phosphate buffer solution (pH 7.4), in which: A) shows the blank ITC run (addition of sugar into water); B) shows the actual run (sugar into receptor 1) and C) shows the plotted change in enthalpy vs molar ratio.

Figure 41:
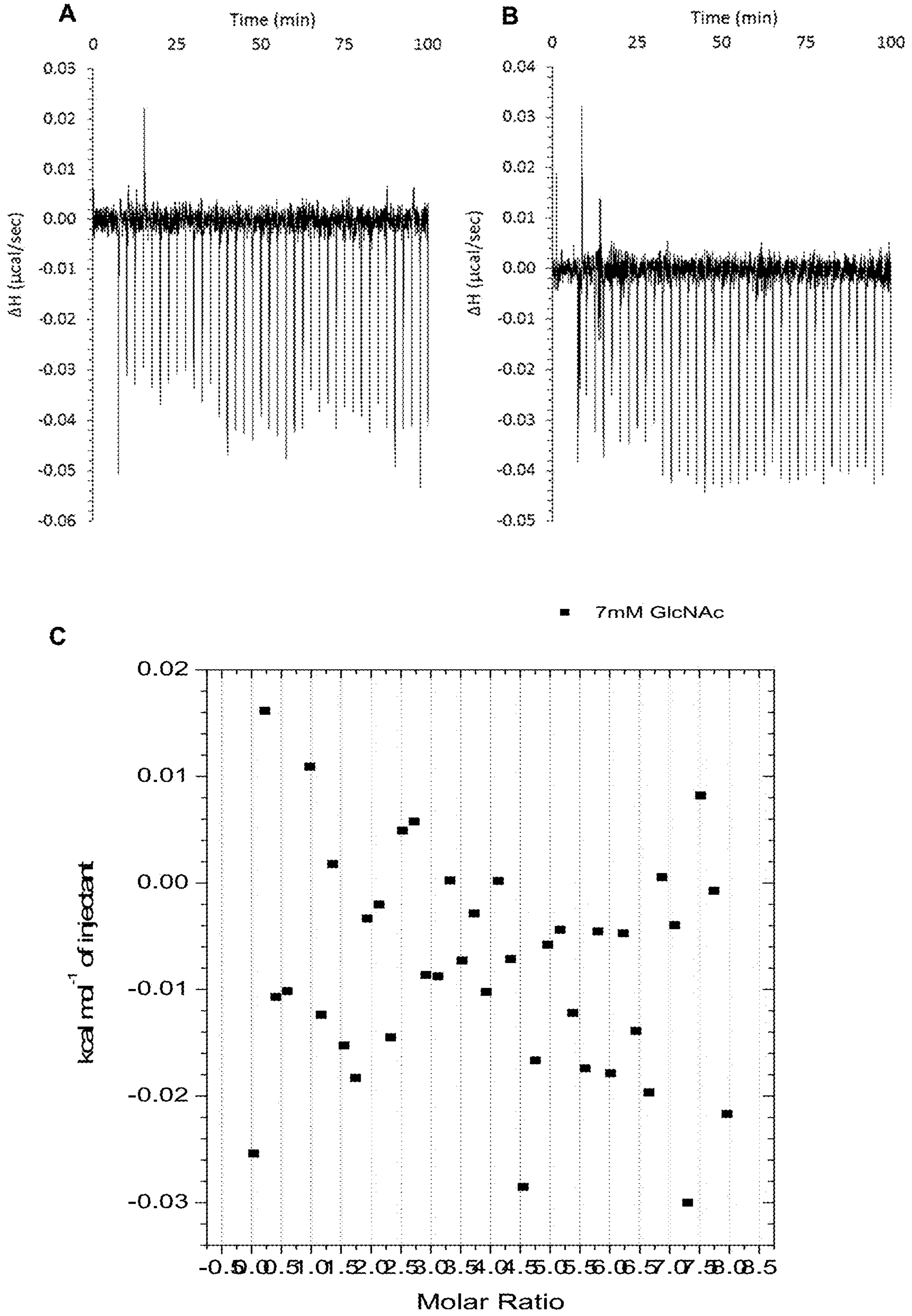

FIG. 41 shows the ITC results for receptor 1 (0.06 mM) titrated with N-acetyl-D-glucosamine (498 mM) in $H_2O$, in which: A) shows the blank ITC run (addition of sugar into water); B) shows the actual run (sugar into receptor 1); and C) shows the plotted change in enthalpy vs molar ratio.

Figure 42:
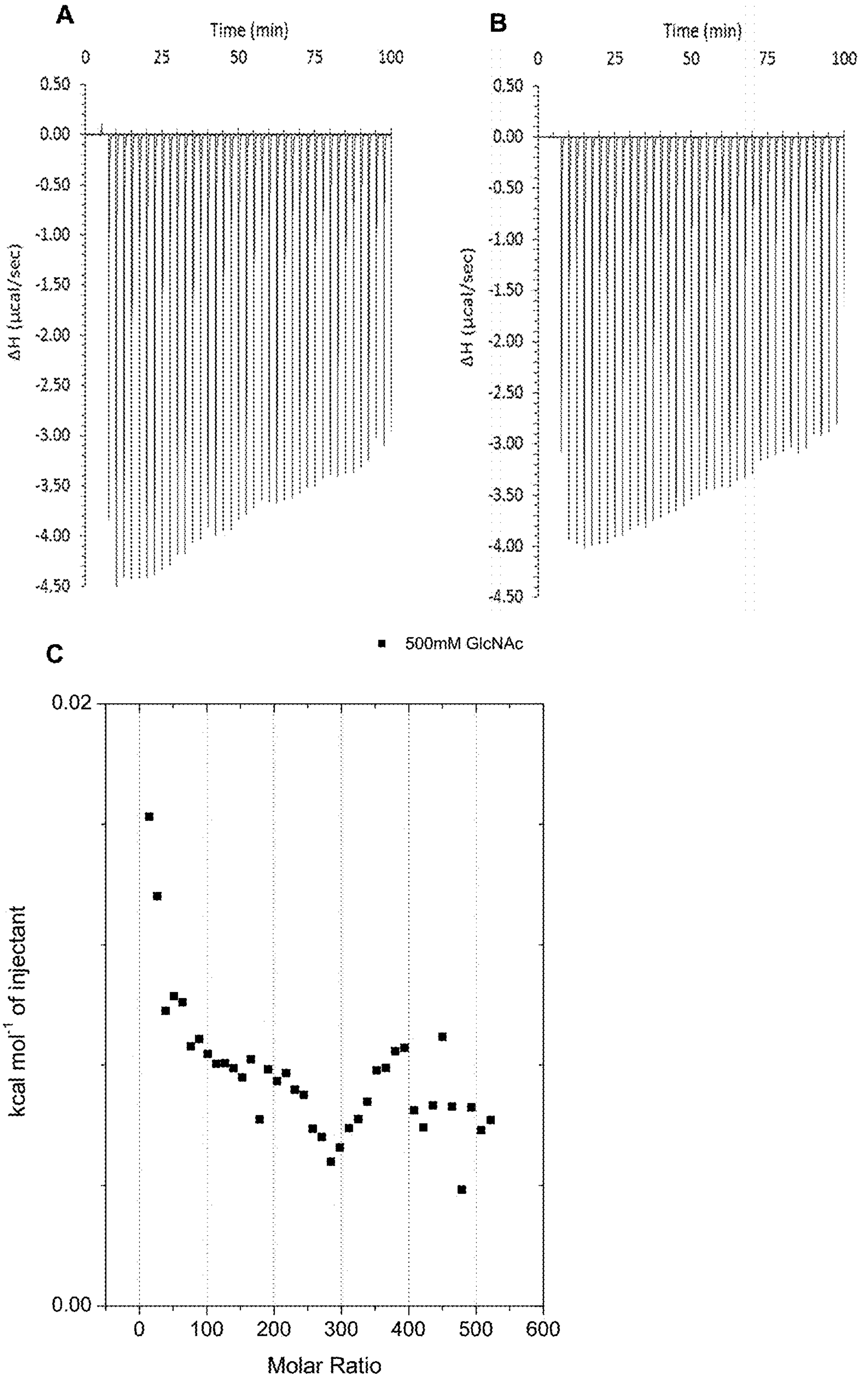

FIG. 42 shows the ITC binding results for receptor 1 (0.06 mM) titrated with N-acetyl-D-glucosamine (498 mM) in 10 mM phosphate buffer solution (pH 7.4), in which: A) shows the blank ITC run (addition of sugar into water); B) shows the actual run (sugar into receptor 1) and C) shows the plotted change in enthalpy vs molar ratio.

Figure 43:
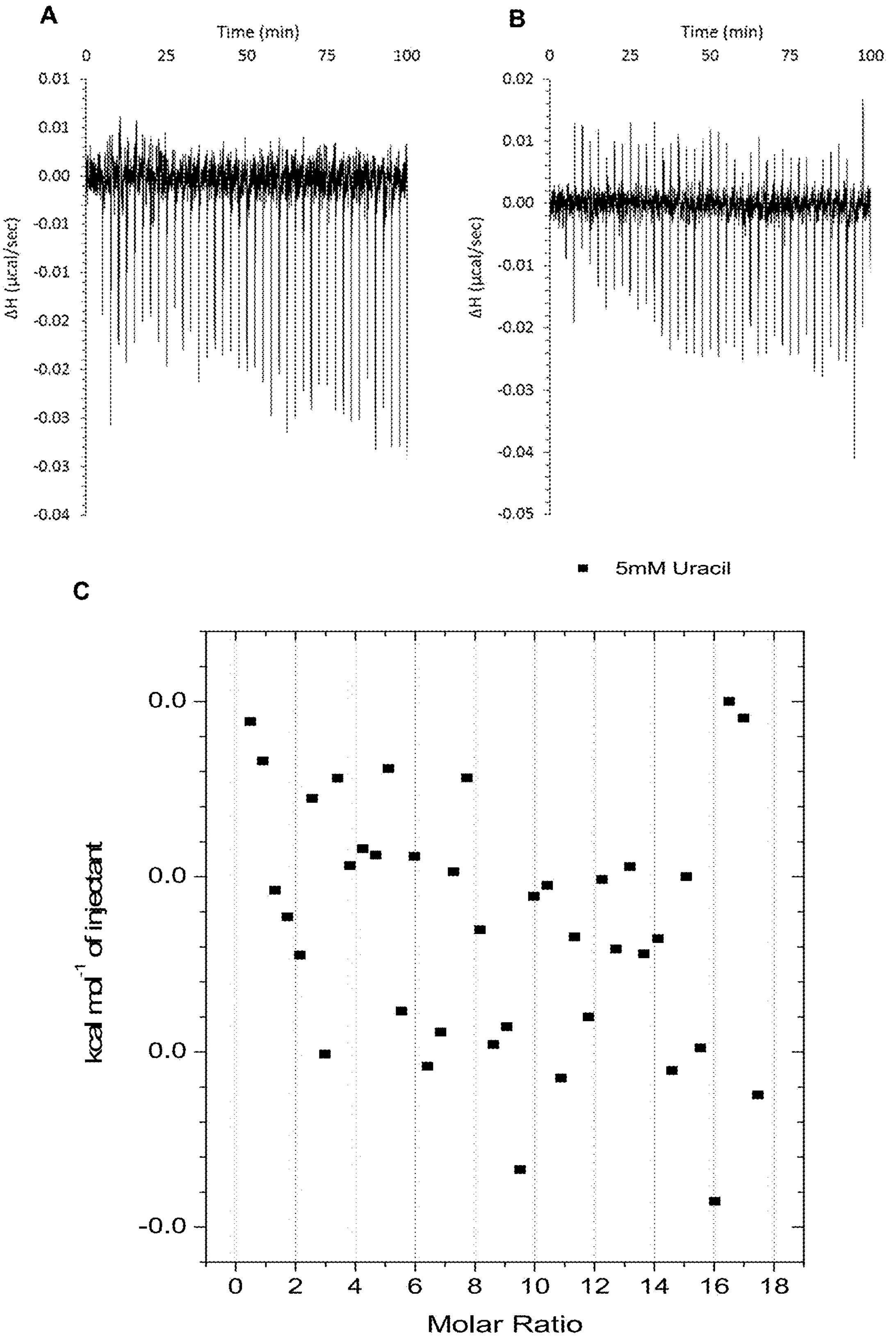

FIG. 43 shows for receptor 1 (0.06 mM) titrated with D-uracil (5 mM) in 10 mM PBS buffer (pH 7.4), in which: A) shows the blank ITC run (addition of sugar into water); B) shows the actual run (sugar into receptor 1); and C) shows the plotted change in enthalpy vs molar ratio.

Figure 44:
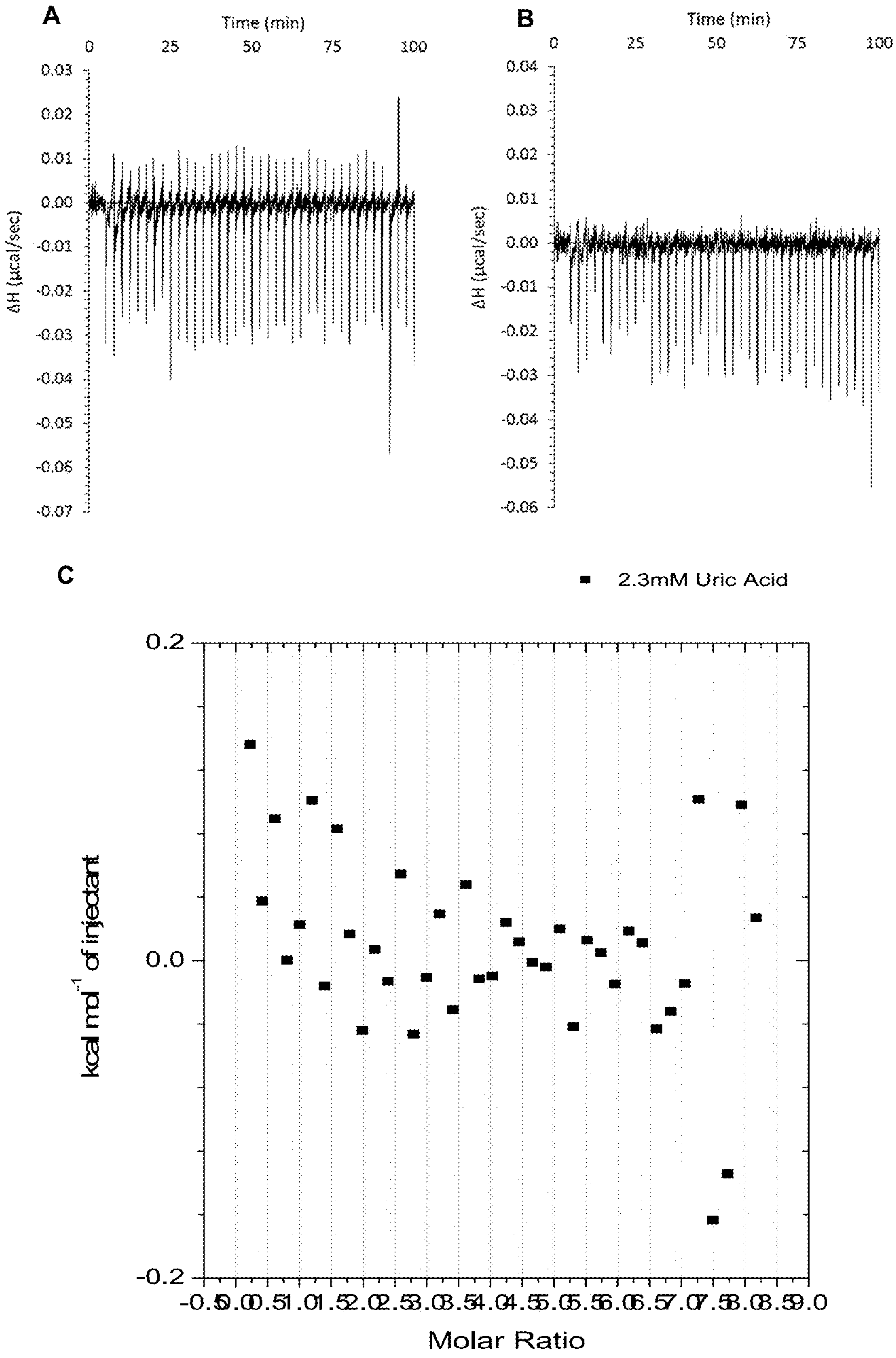

FIG. 44 shows for receptor 1 (0.06 mM) titrated with uric acid (2.34 mM) in 10 mM PBS buffer (pH 7.4), in which: A) shows the blank ITC run (addition of sugar into water); B) shows the actual run (sugar into receptor 1); and C) shows the plotted change in enthalpy vs molar ratio.

Figure 45:
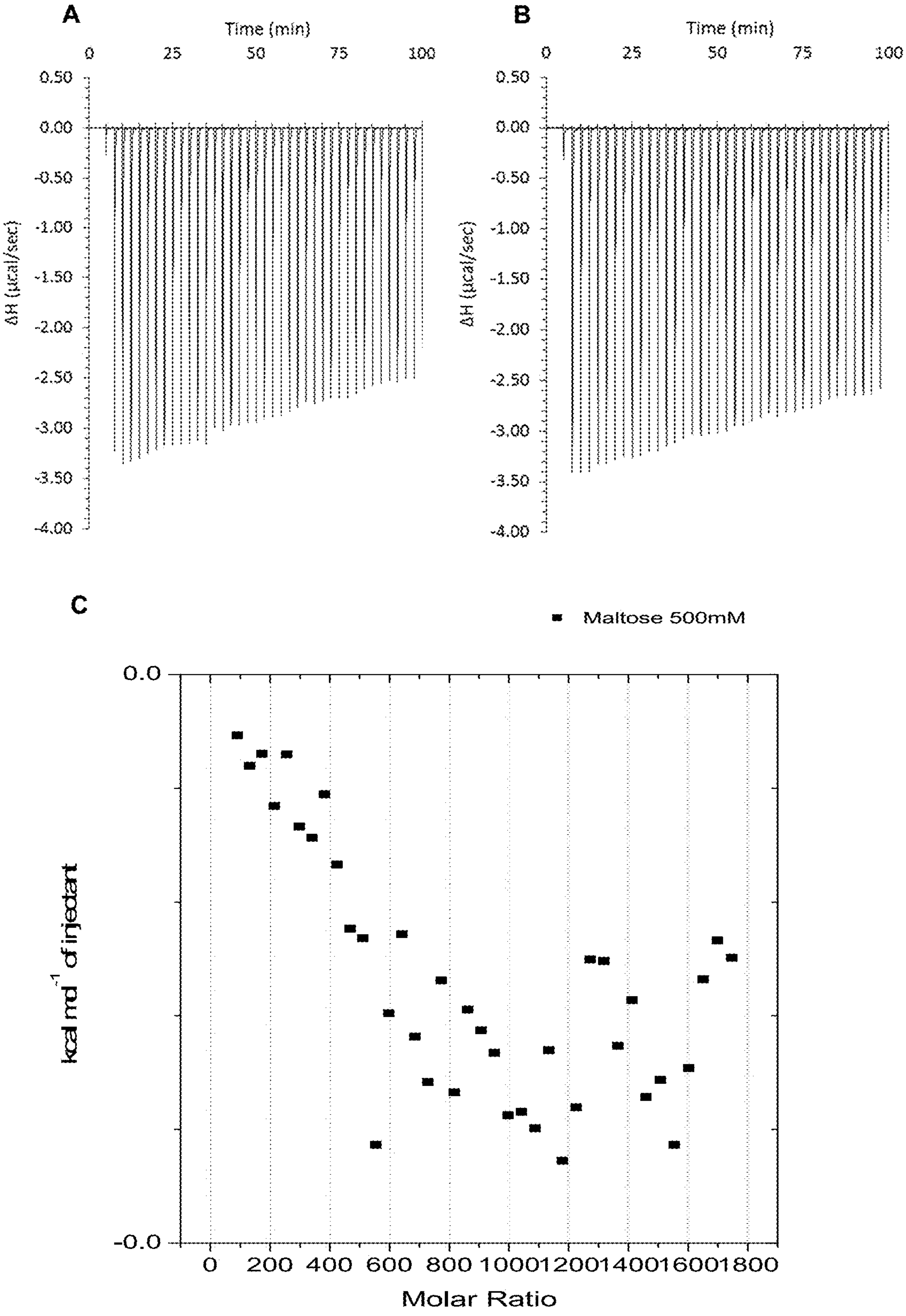

FIG. 45 shows the ITC results for receptor 1 (0.06 mM) titrated with maltose (500 mM) in $H_2O$, in which: A) shows the blank ITC run (addition of sugar into water); B) shows the actual run (sugar into receptor 1); and C) shows the plotted change in enthalpy vs molar ratio.

Figure 46:
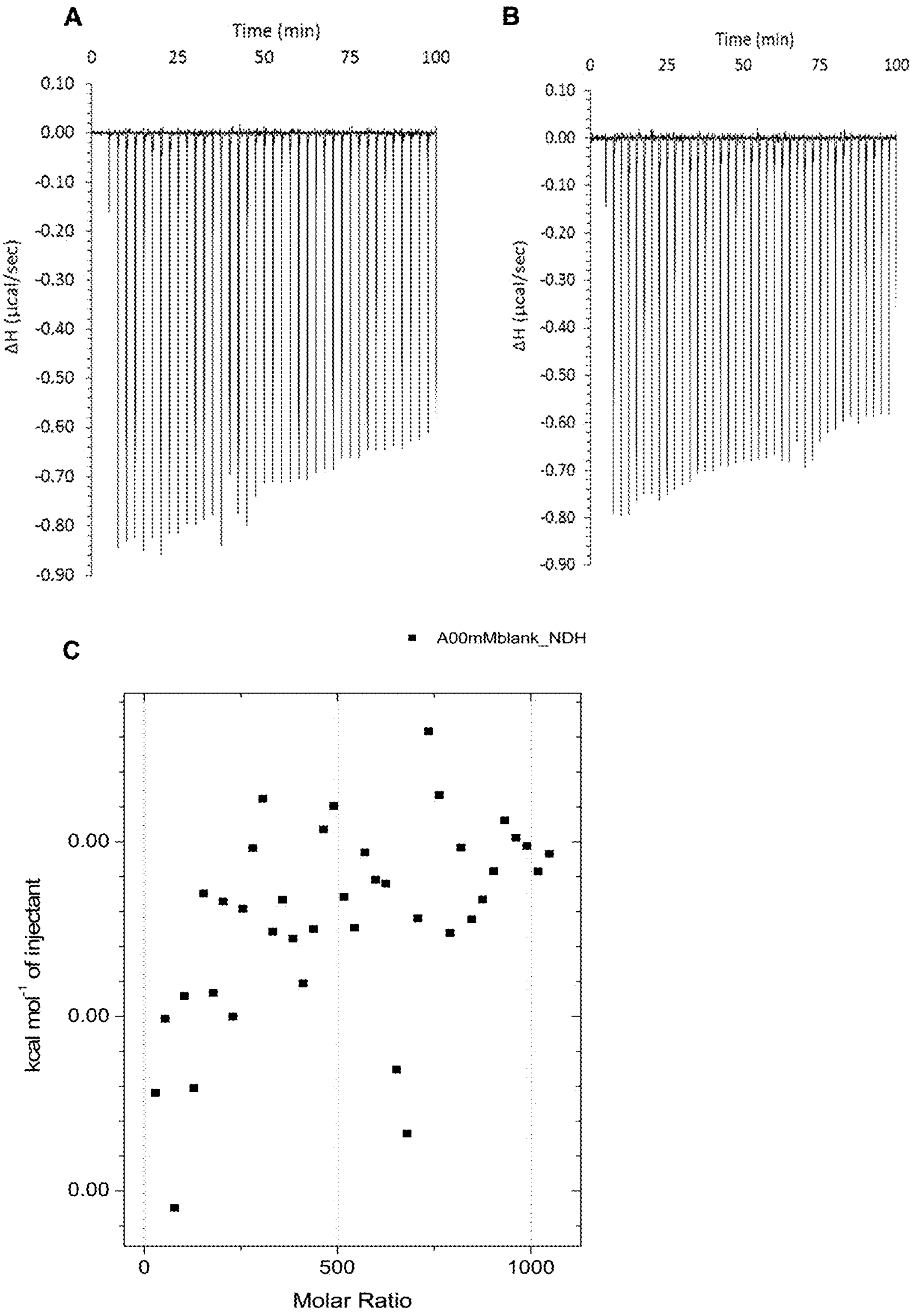

FIG. 46 shows the ITC binding results for receptor 1 (0.1 mM) titrated with D-Mannitol (500 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio.

Figure 47:
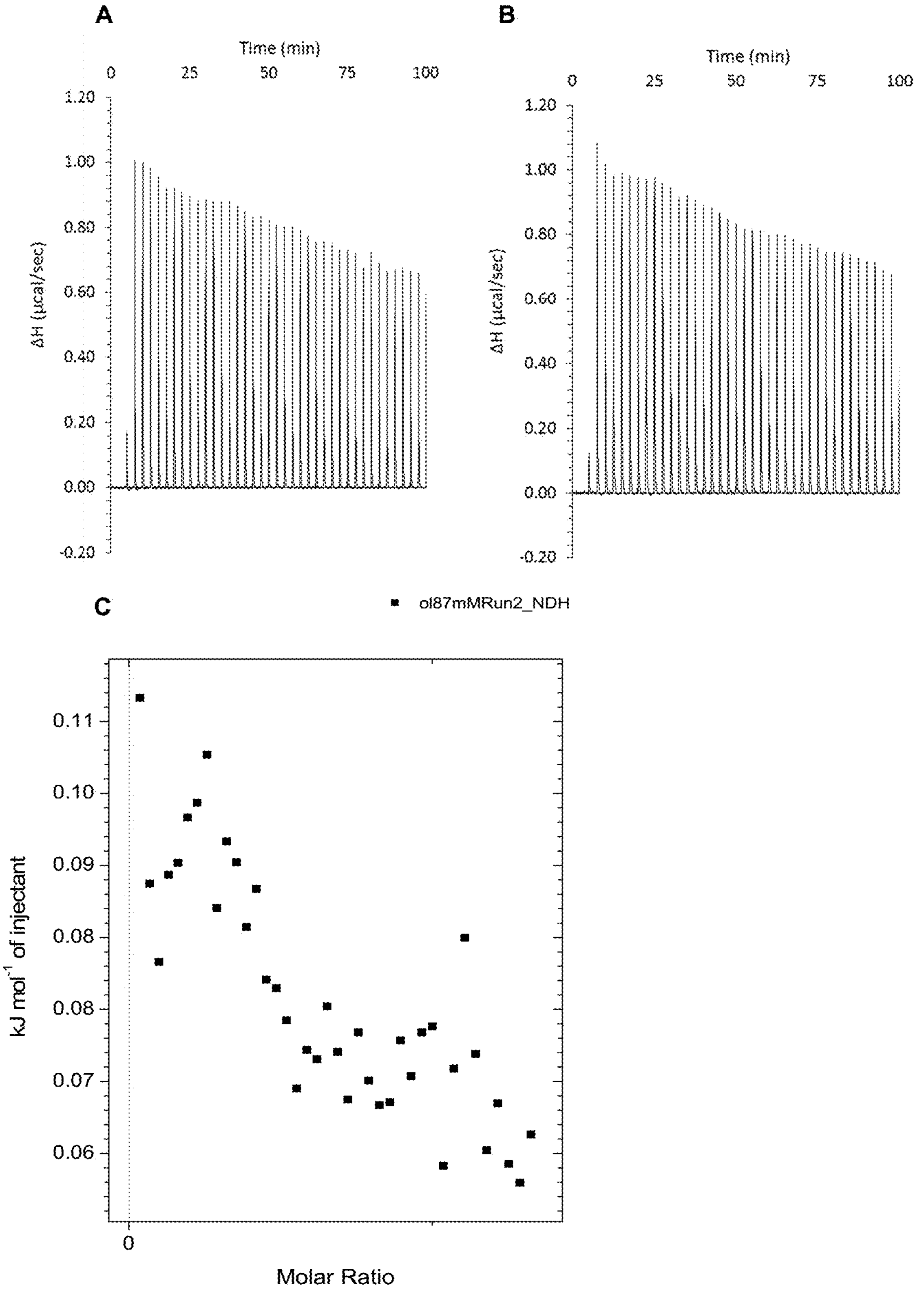

FIG. 47 shows the ITC binding results for receptor 1 (0.06 mM) titrated with paracetamol (87 mM) in 10 mM phosphate buffer solution (pH 7.4), in which: A) shows the blank ITC run (addition of substrate into water); B) shows the actual run (substrate into receptor 1); C) shows the plotted change in enthalpy vs molar ratio.

Figure 48:
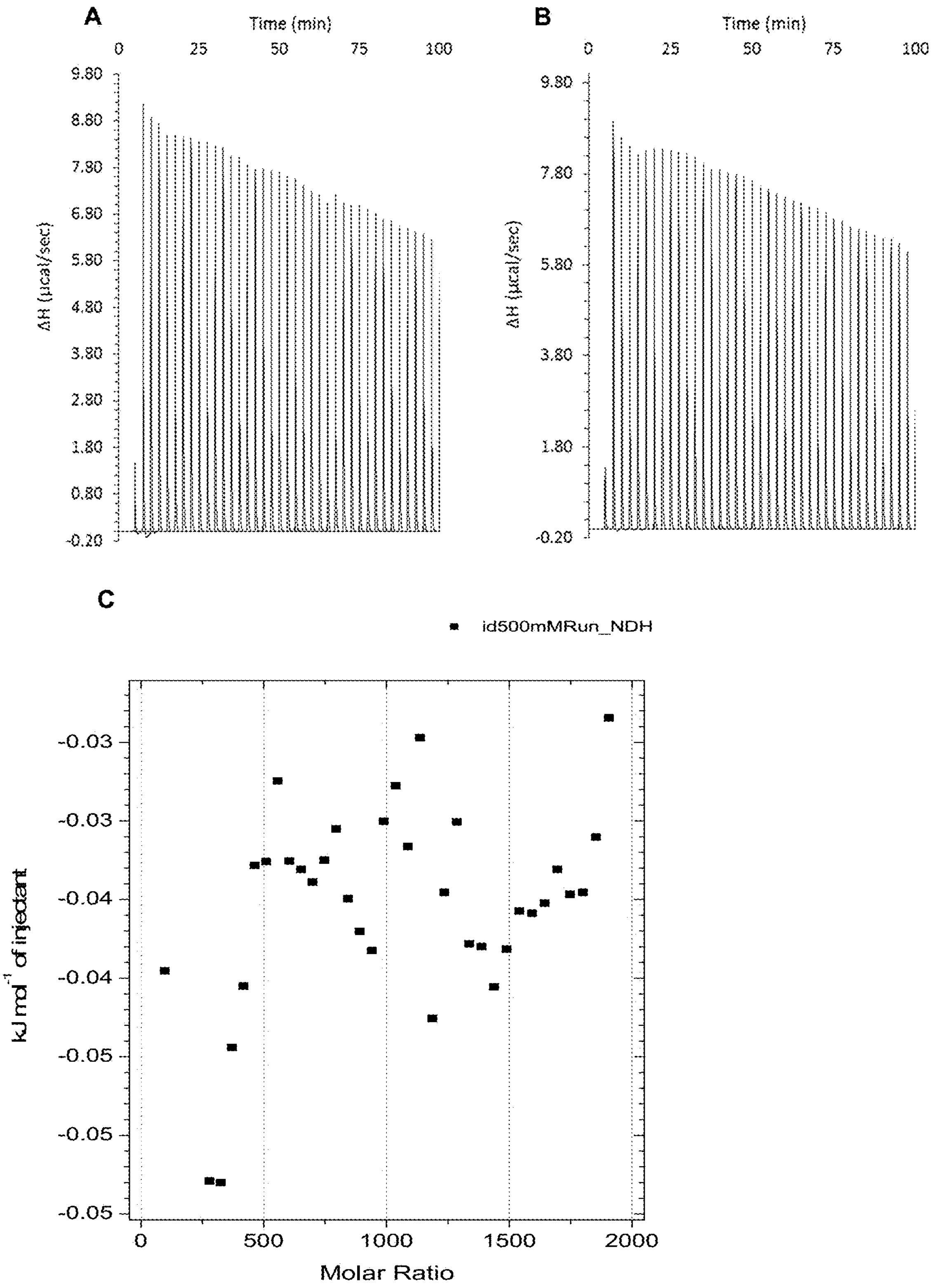

FIG. 48 shows the ITC binding results for receptor 1 (0.06 mM) titrated with ascorbic acid (500 mM) in 10 mM phosphate buffer solution (pH 7.4), in which: A) shows the blank ITC run (addition of substrate into water); B) shows the actual run (substrate into receptor 1); C) shows the plotted change in enthalpy vs molar ratio.

Figure 49:
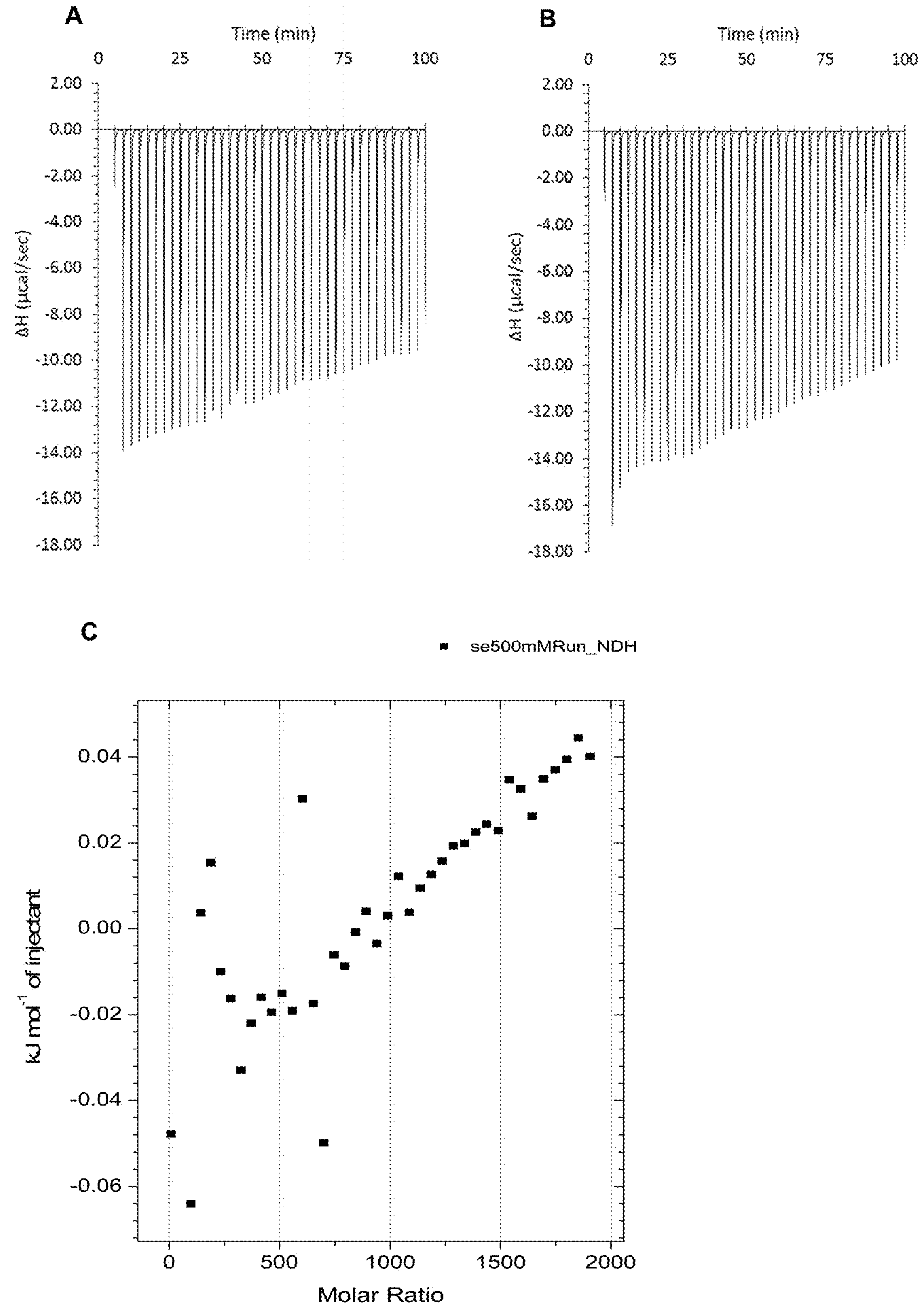

FIG. 49 shows the ITC binding results for receptor 1 (0.06 mM) titrated with L-fucose (500 mM) in 10 mM phosphate buffer solution (pH 7.4), in which: A) shows the blank ITC run (addition of substrate into water); B) shows the actual run (substrate into receptor 1); C) shows the plotted change in enthalpy vs molar ratio.

Figure 50:
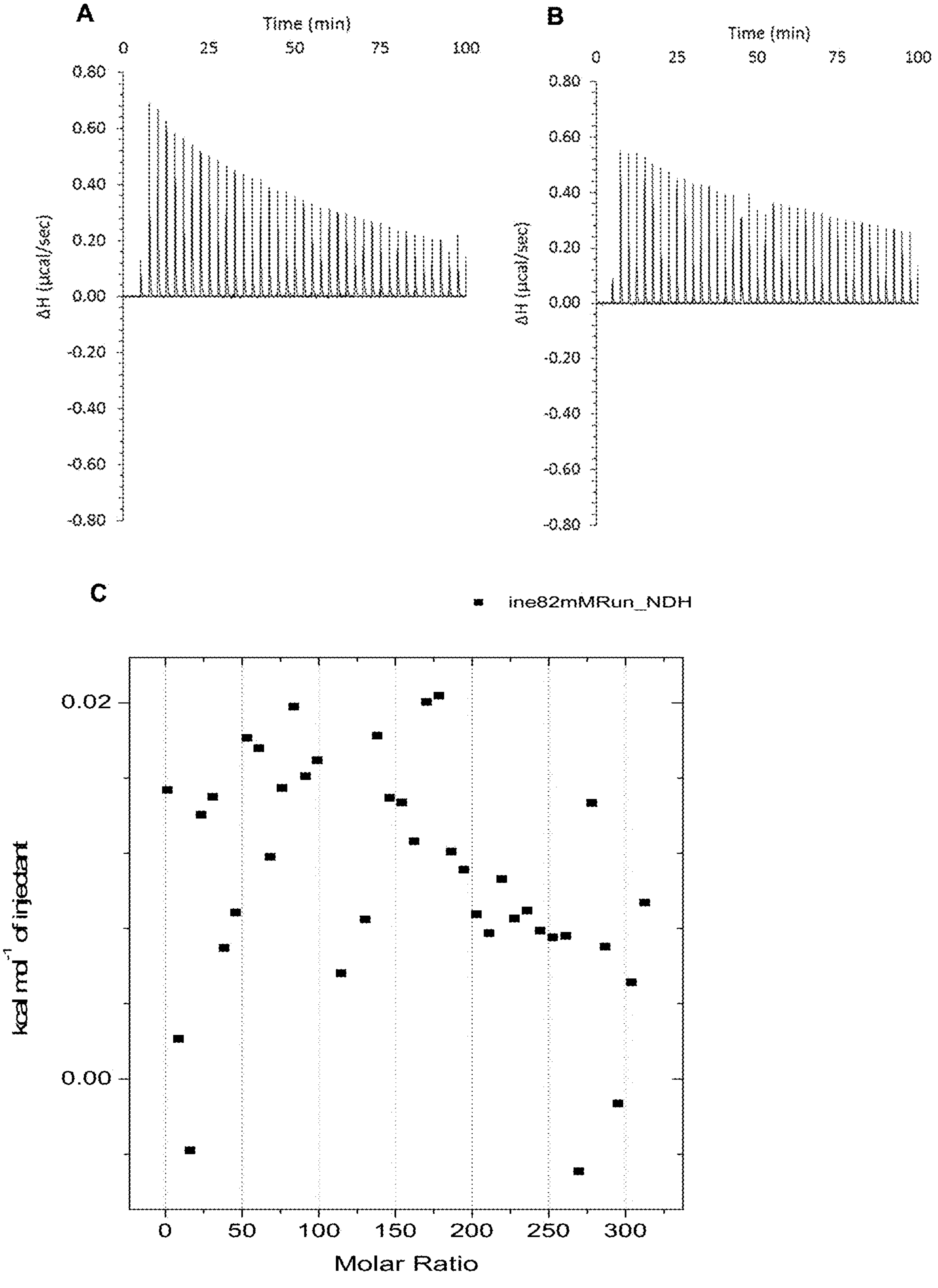

FIG. 50 shows the ITC binding results for receptor 1 (0.06 mM) titrated with L-phenylalanine (82 mM) in 10 mM phosphate buffer solution (pH 7.4), in which: A) shows the blank ITC run (addition of substrate into medium); B) shows the actual run (substrate into receptor 1); C) shows the plotted change in enthalpy vs molar ratio.

Figure 51:
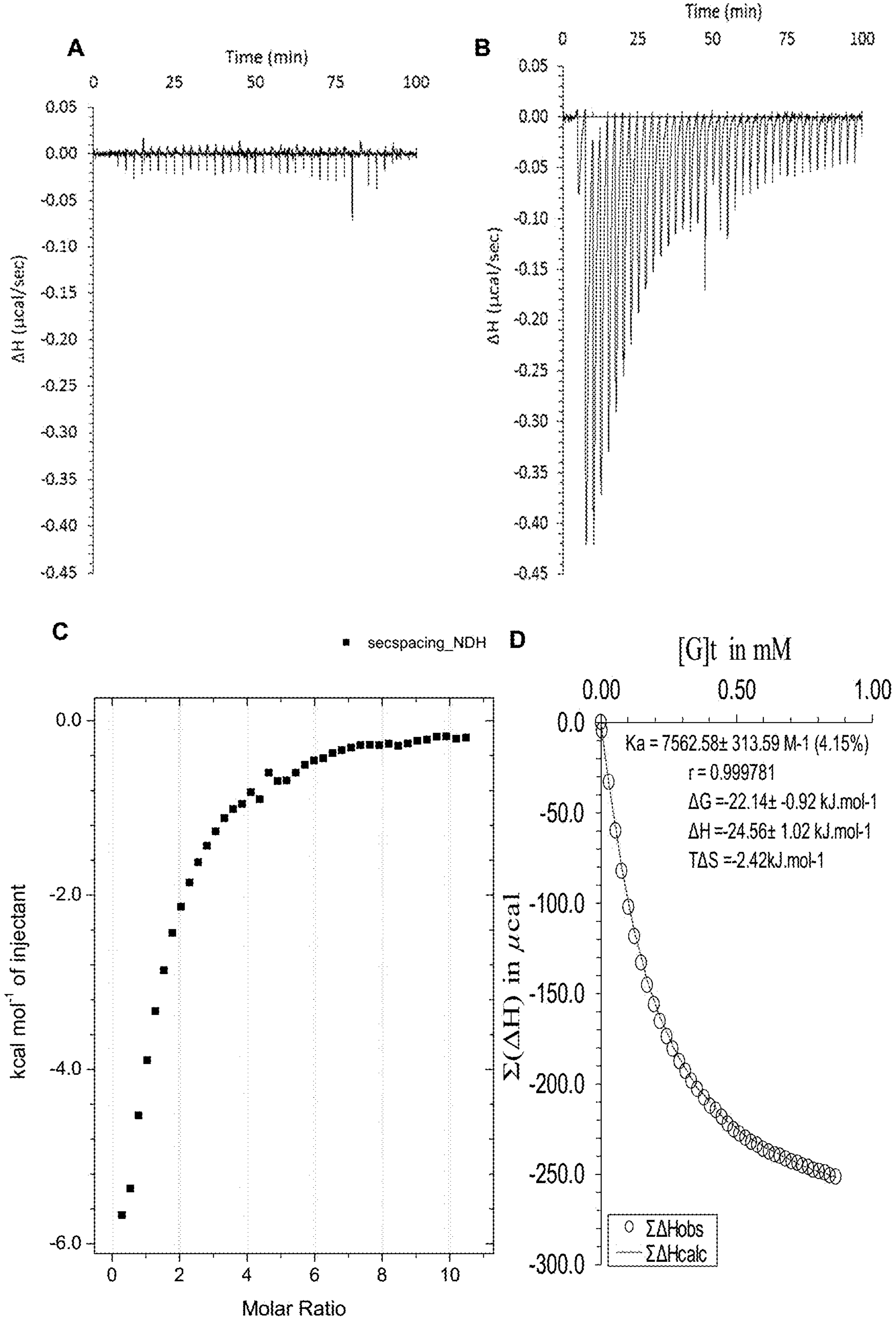

FIG. 51 shows the ITC binding results for receptor 1 (0.1 mM) titrated with myo inositol (5 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet ($K_a$=7563±313 $M^{-1}$).

Figure 52:
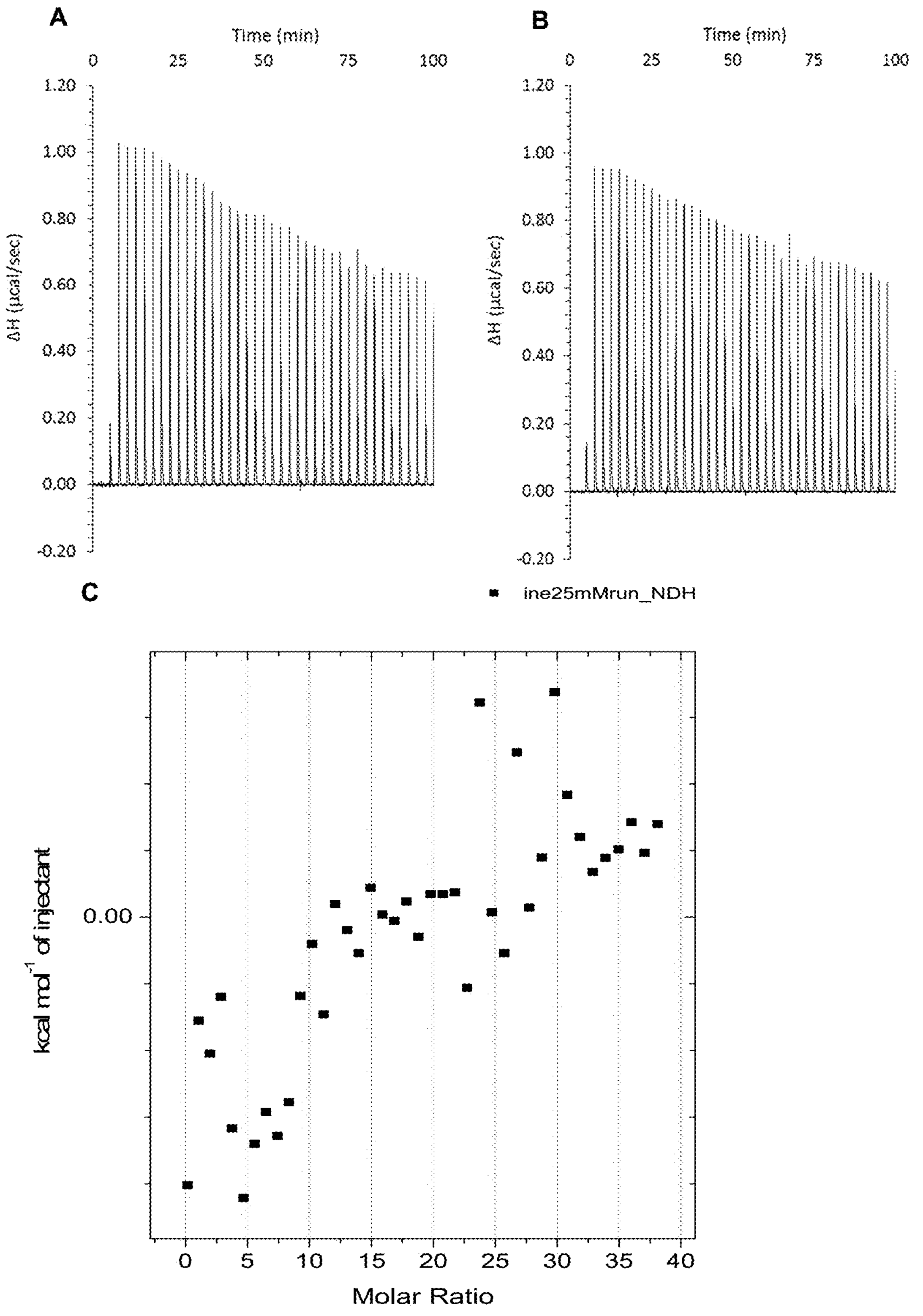

FIG. 52 shows the ITC binding results for receptor 1 (0.1 mM) titrated with Adenosine (500 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio.

Figure 53:
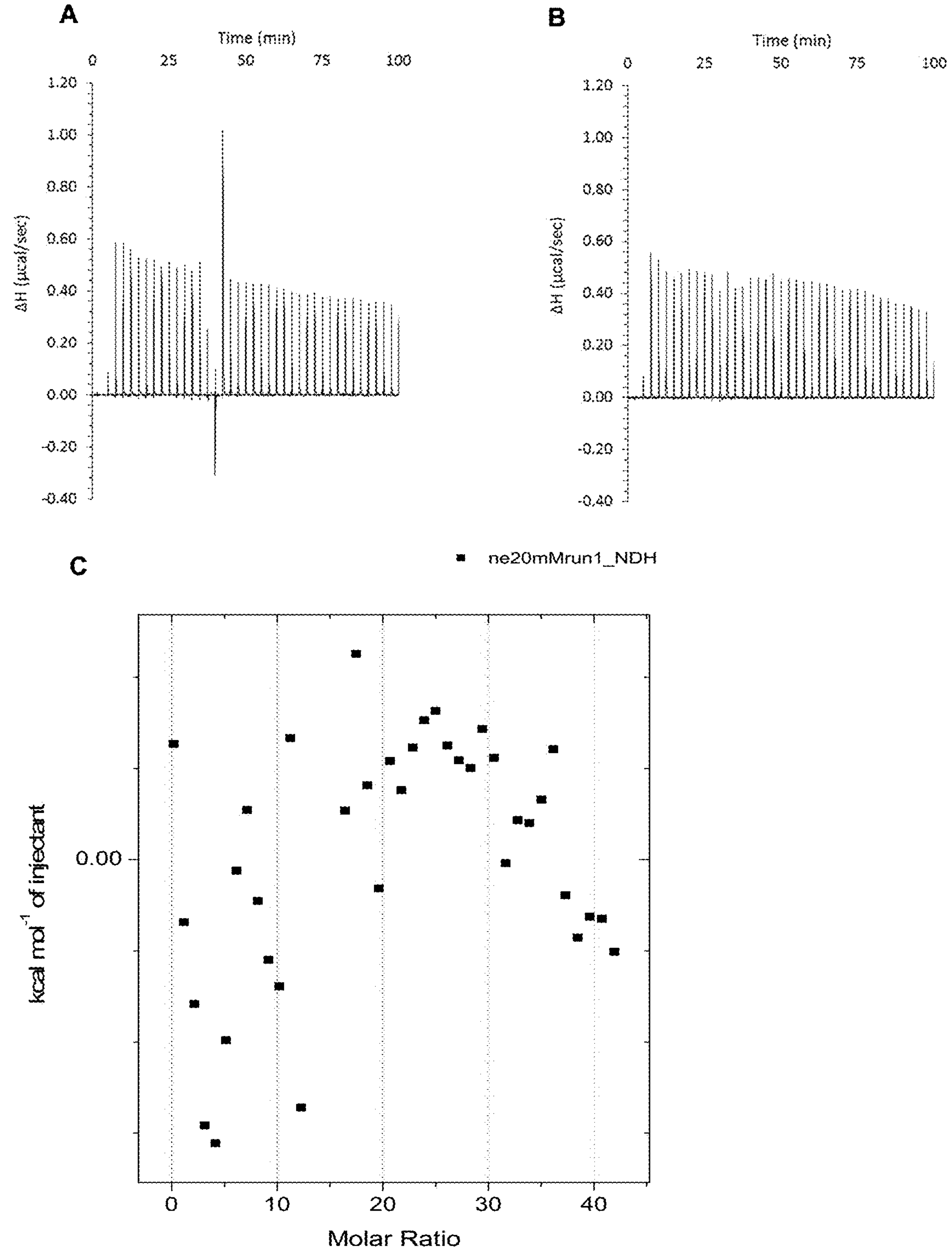

FIG. 53 shows the ITC binding results for receptor 1 (0.1 mM) titrated with cytosine (20 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio.

Figure 54:
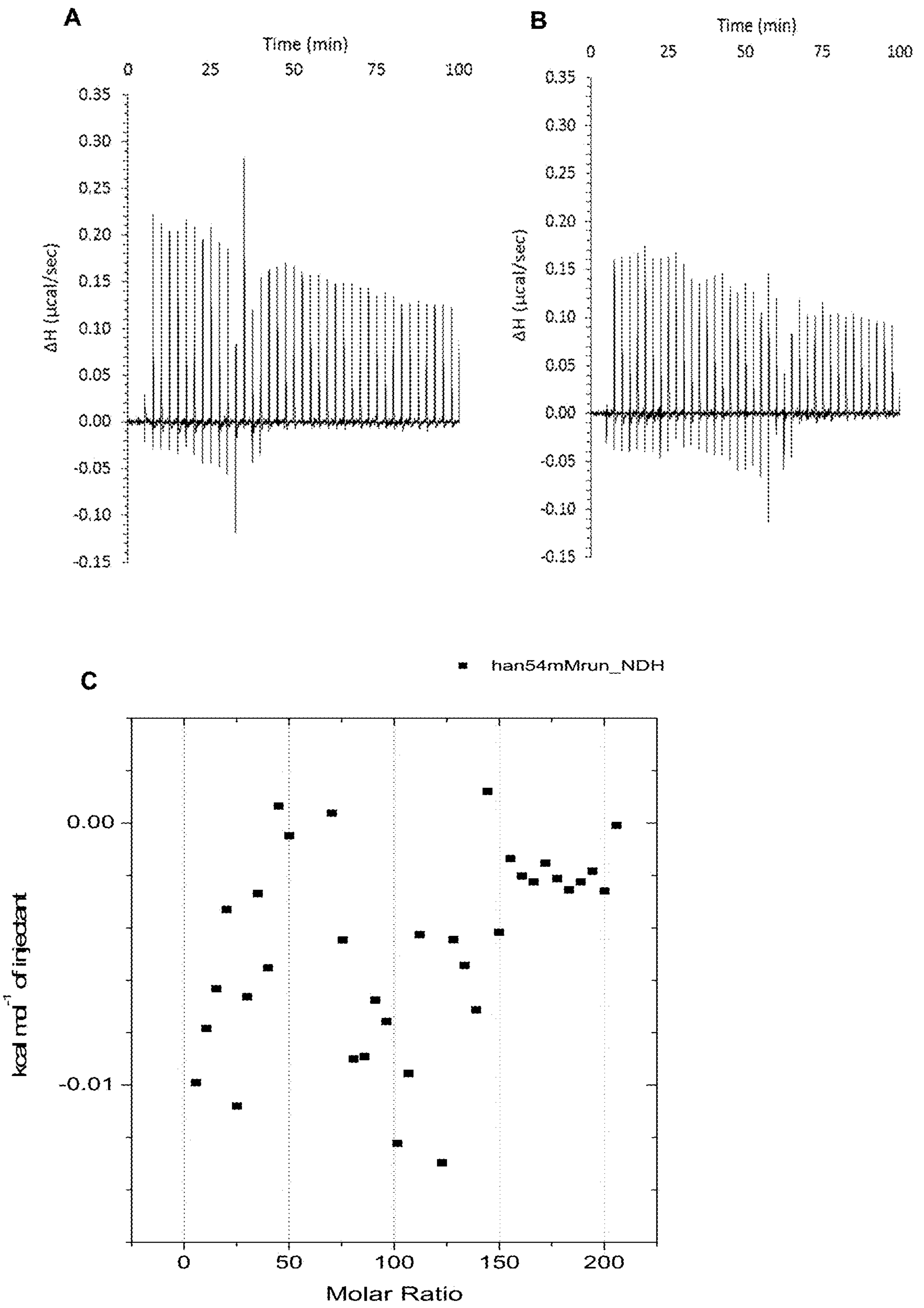

FIG. 54 shows the ITC binding results for receptor 1 (0.06 mM) titrated with L-tryptophan (54 mM) in 10 mM phosphate buffer solution (pH 7.4), in which: A) shows the blank ITC run (addition of substrate into medium); B) shows the actual run (substrate into receptor 1); C) shows the plotted change in enthalpy vs molar ratio.

Figure 55:
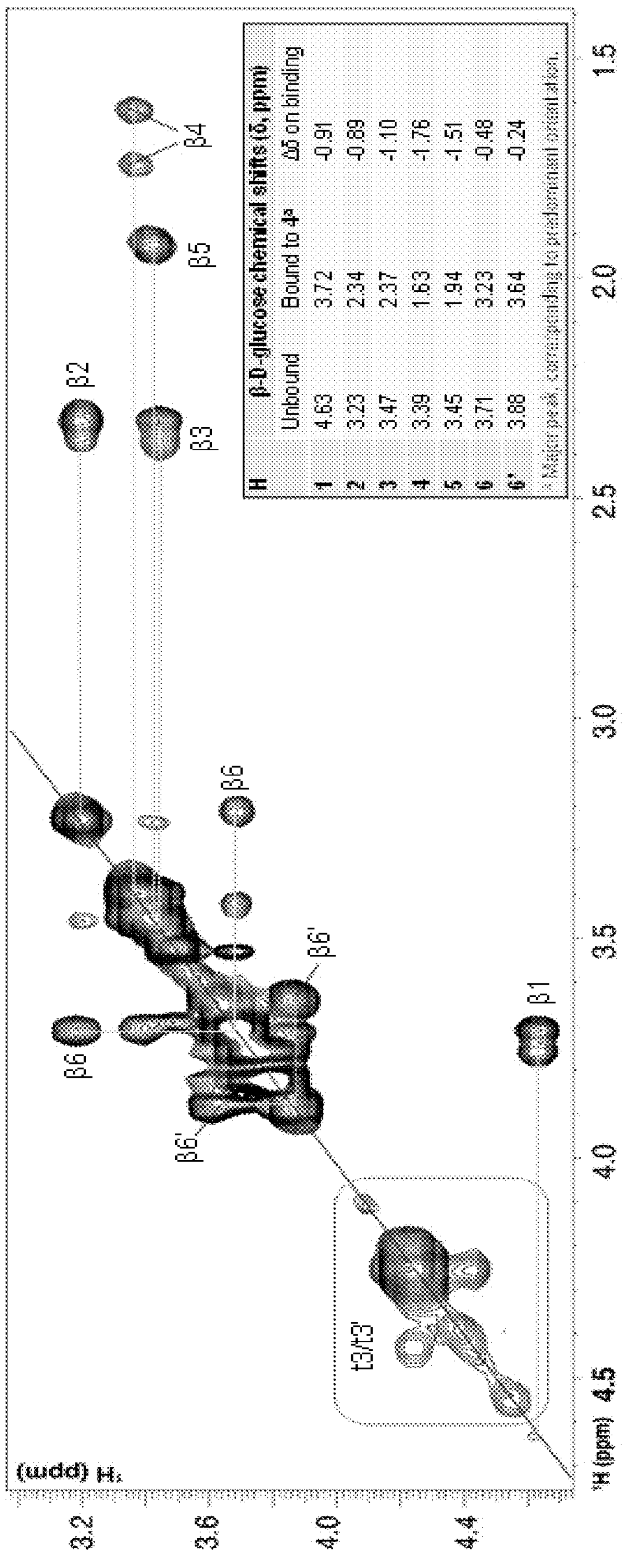

FIG. 55 shows the partial $^1$H NMR ROESY spectrum of receptor 1 (2 mM) with D-glucose (5 mM, 2.5 equivalents) in $D_2O$. Chemical exchange peaks (black, annotated) link CH protons on β-D-glucose in free and bound states. Chemical shifts for the glucose protons, with signal movements due to binding, are listed in the table. Signals for bound α-D-glucose were not observed under these conditions.

Figure 56:
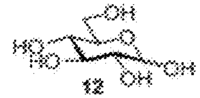
Figure 56:
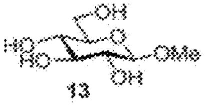
Figure 56:
Figure 56:
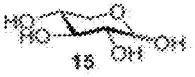
Figure 56:
Figure 56:
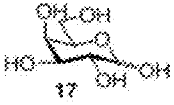
Figure 56:
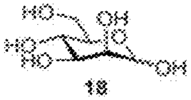
Figure 56:
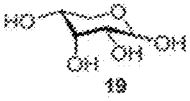
Figure 56:
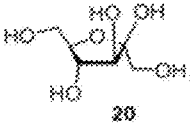
Figure 56:
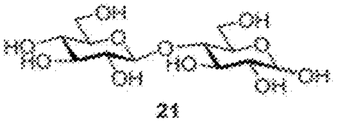
Figure 56:
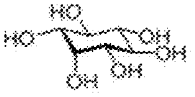
Figure 56:
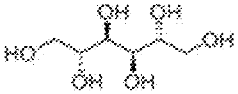
Figure 56:
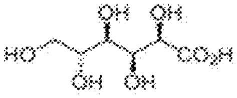
Figure 56:
Figure 56:
Figure 56:
Figure 56:
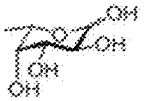
Figure 56:
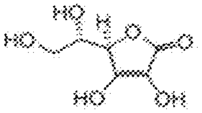
Figure 56:
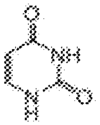
Figure 56:
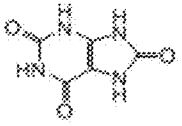
Figure 56:
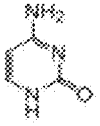
Figure 56:
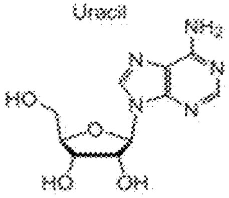
Figure 56:
Figure 56:
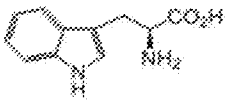
Figure 56:
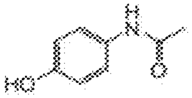

FIG. 56 shows the structures of the substrates tested for affinity with receptor 1.

Figure 57:
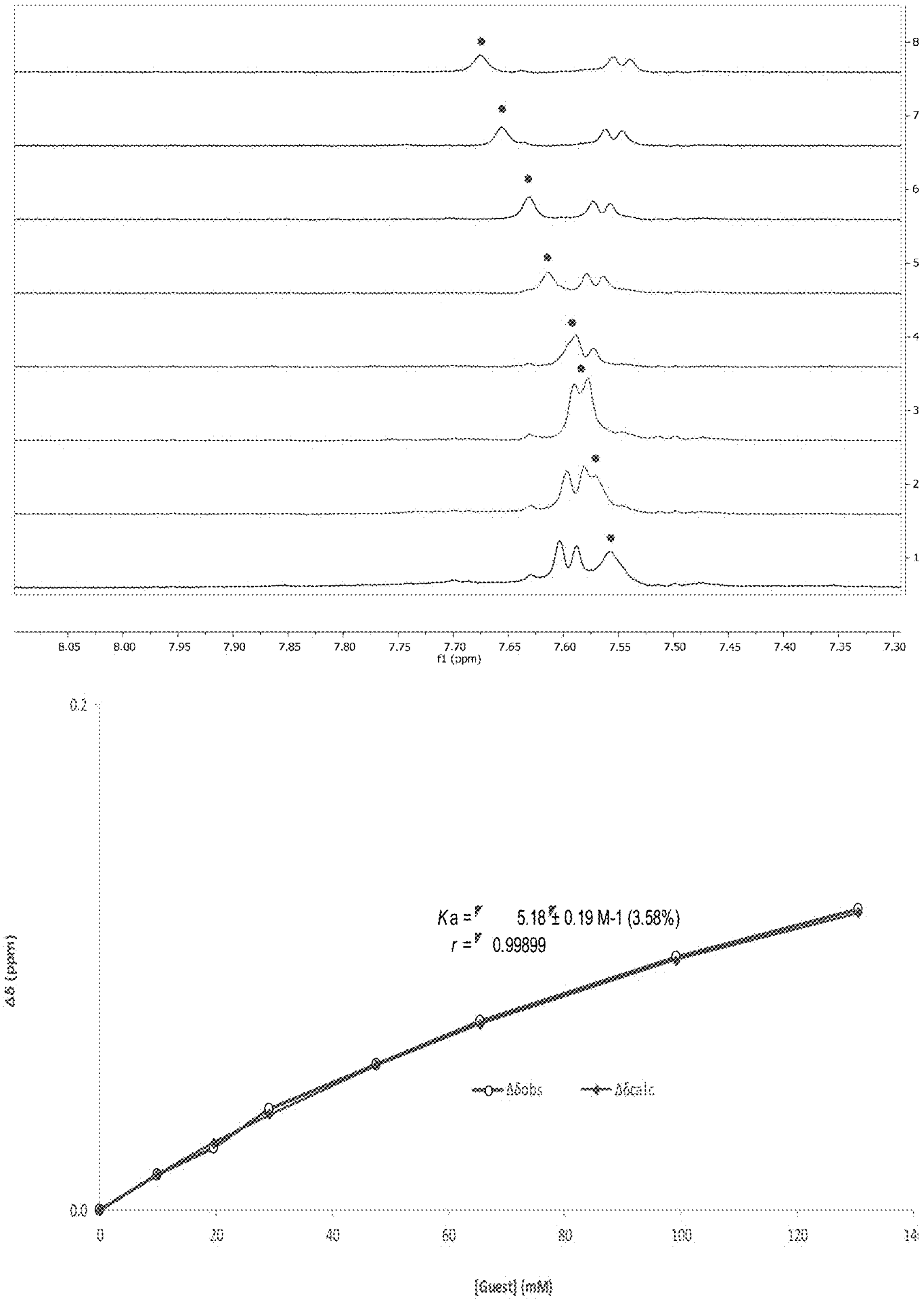

FIG. 57 shows the partial $^1$H NMR spectra (top) and binding analysis curve (bottom) for 90 (1 mM) titrated with a combined solution of D-glucose (1 M) and 90 (1 mM), in $D_2O$ with at pH 7.4 and 298 K. Change in chemical shifts (Δδ, ppm) denoted with • were plotted against D-glucose concentration (mM). The calculated values for M are overlaid with the observed values, giving $K_a$=5.1±0.2 M-1 (3.6%).

Figure 58:
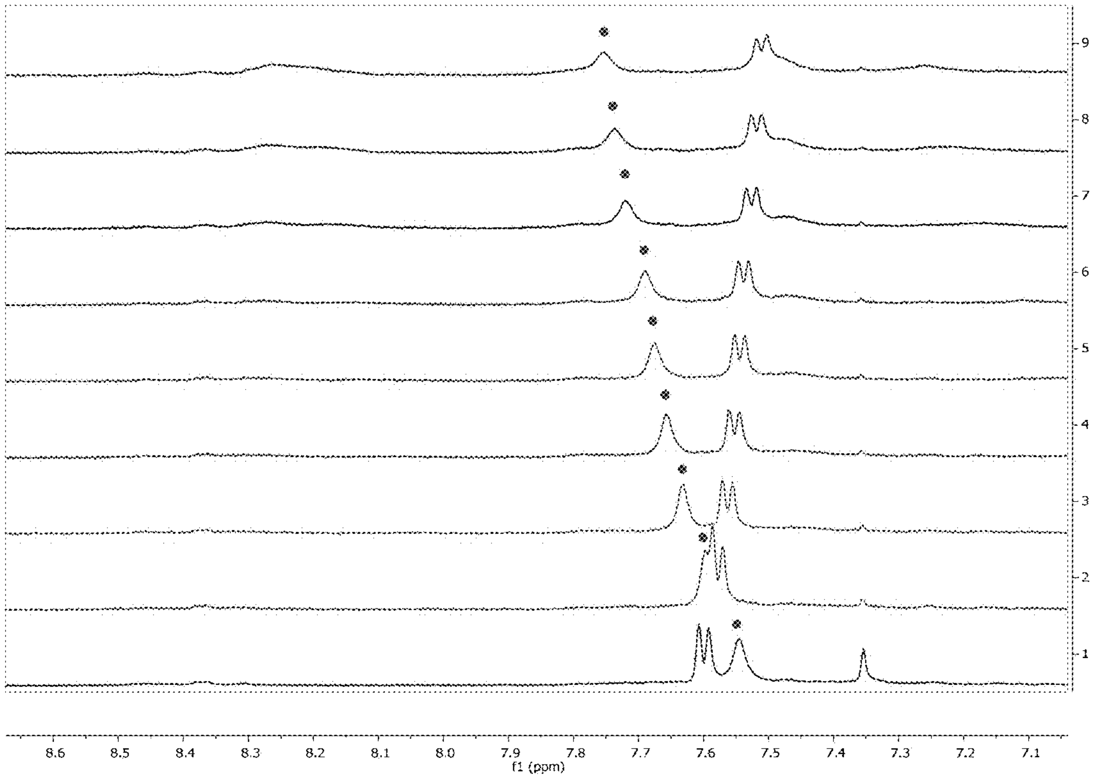
Figure 58:
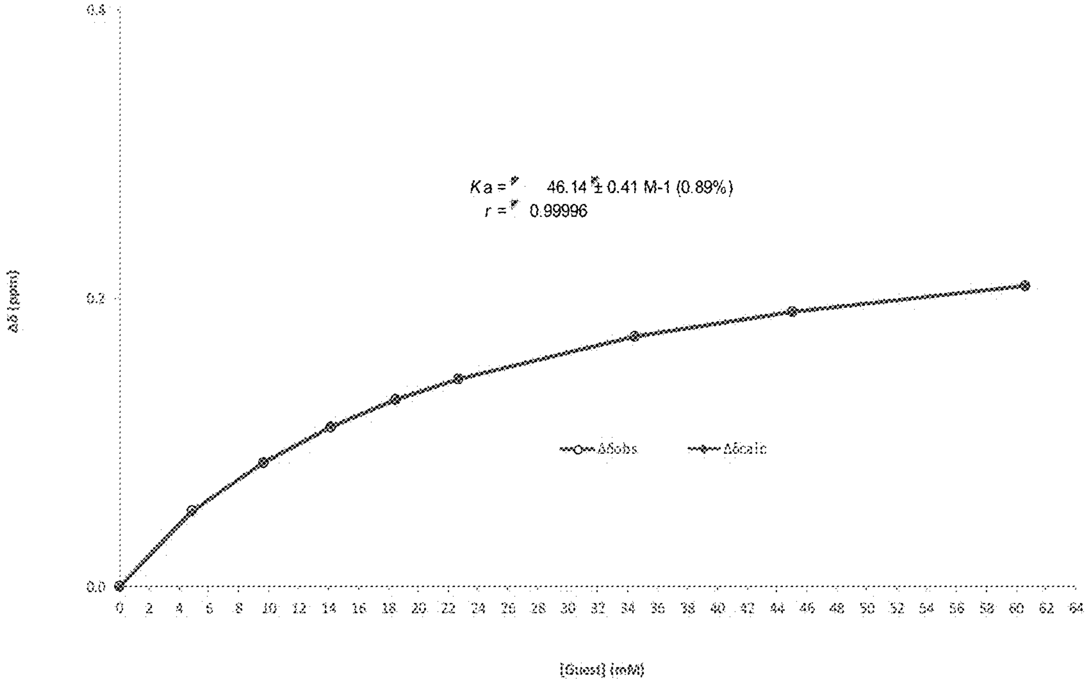

FIG. 58 shows the Partial $^1$H NMR spectra (top) and binding analysis curve (bottom) for 90 (0.25 mM) titrated with a combined solution of D-cellobiose (250 mM) and 90 (0.25 mM), in $D_2O$ with at pH 7.4 and 298 K. Change in chemical shifts (Δδ, ppm) denoted with • were plotted against D-cellobiose concentration (mM). The calculated values for M are overlaid with the observed values, giving $K_a$=46±0.4 M-1 (0.89%).

Figure 59:
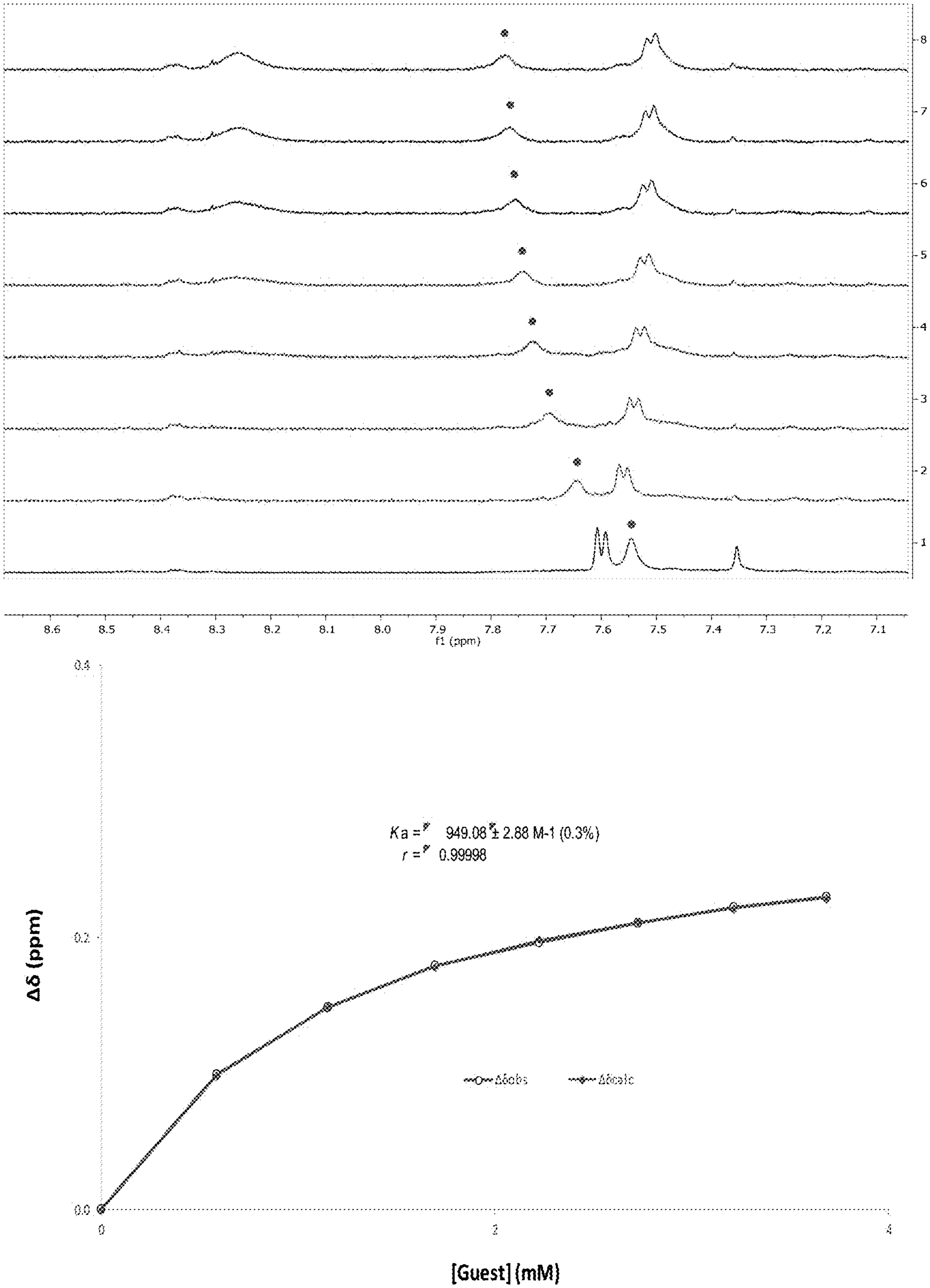

FIG. 59 shows the partial $^1$H NMR spectra (top) and binding analysis curve (bottom) for 90 (0.2 mM) titrated with a combined solution of D-cellotriose (15 mM) and 90 (0.2 mM), in $D_2O$ with at pH 7.4 and 298 K. Change in chemical shifts (Δδ, ppm) denoted with • were plotted against D-cellotriose concentration (mM). The calculated values for M are overlaid with the observed values, giving Ka=949±2.9 M-1 (0.3%).

Figure 60:
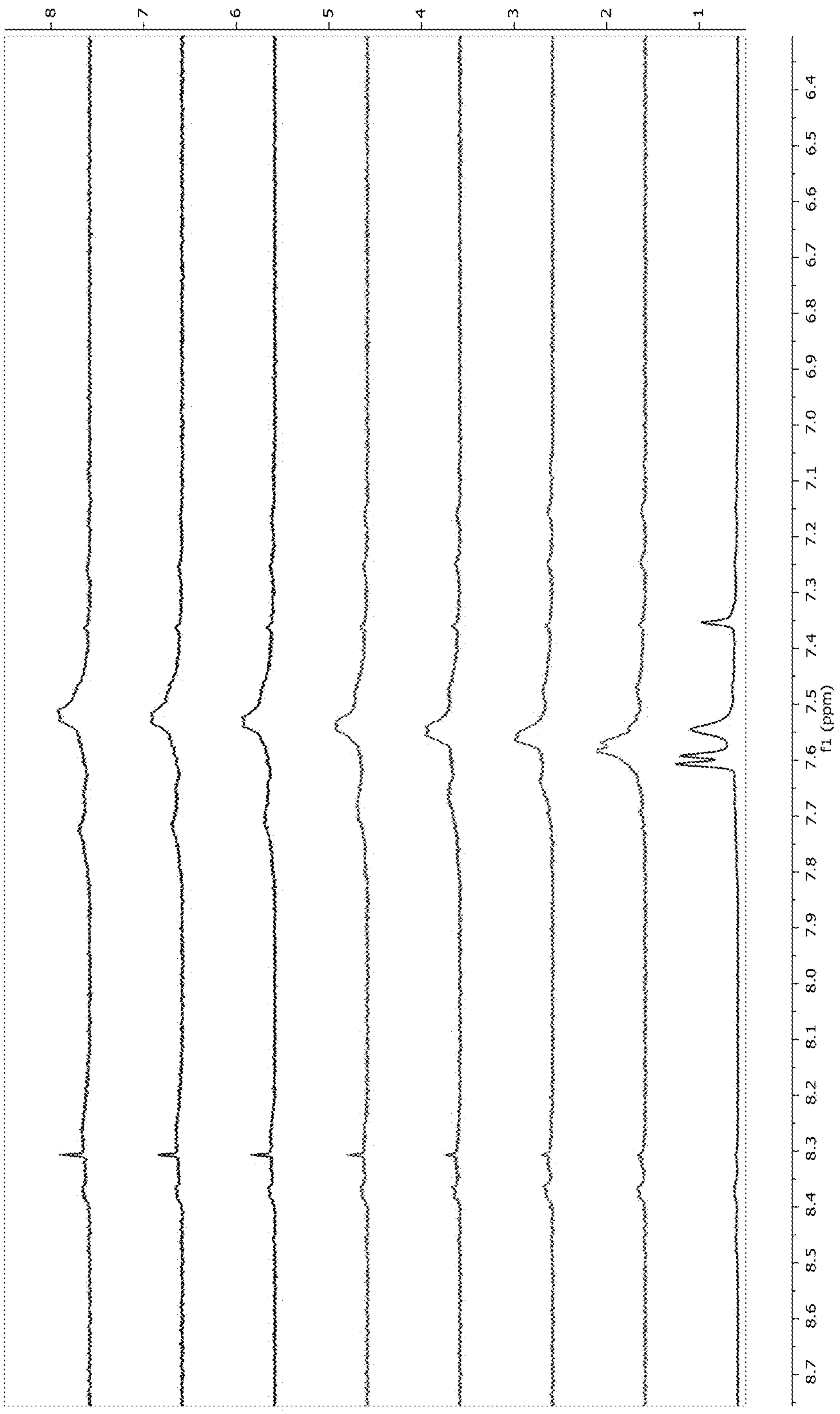

FIG. 60 shows the partial $^1$H NMR spectra for 90 (0.2 mM) titrated with a combined solution of D-cellotetraose (15 mM) and 90 (0.2 mM), in $D_2O$ with at pH 7.4 and 298 K. Spectra imply binding with intermediate rate of exchange, thus no $K_a$ was determinable.

Figure 61:
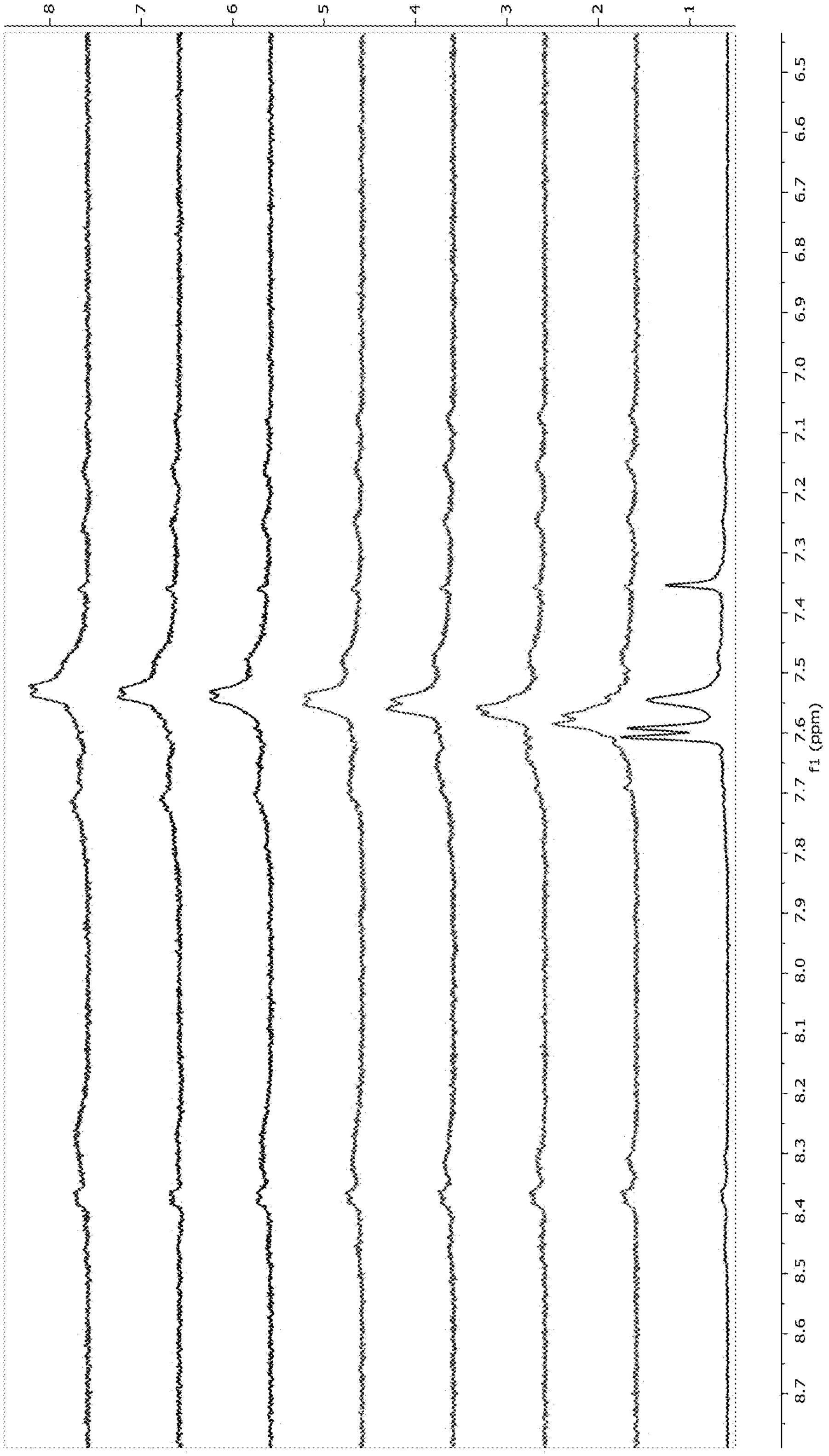

FIG. 61 shows the partial $^1$H NMR spectra for 90 (0.2 mM) titrated with a combined solution of D-cellopentaose (15 mM) and 90 (0.2 mM), in $D_2O$ with at pH 7.4 and 298 K. Spectra imply binding with intermediate rate of exchange, thus no $K_a$ was determinable.

Figure 62:
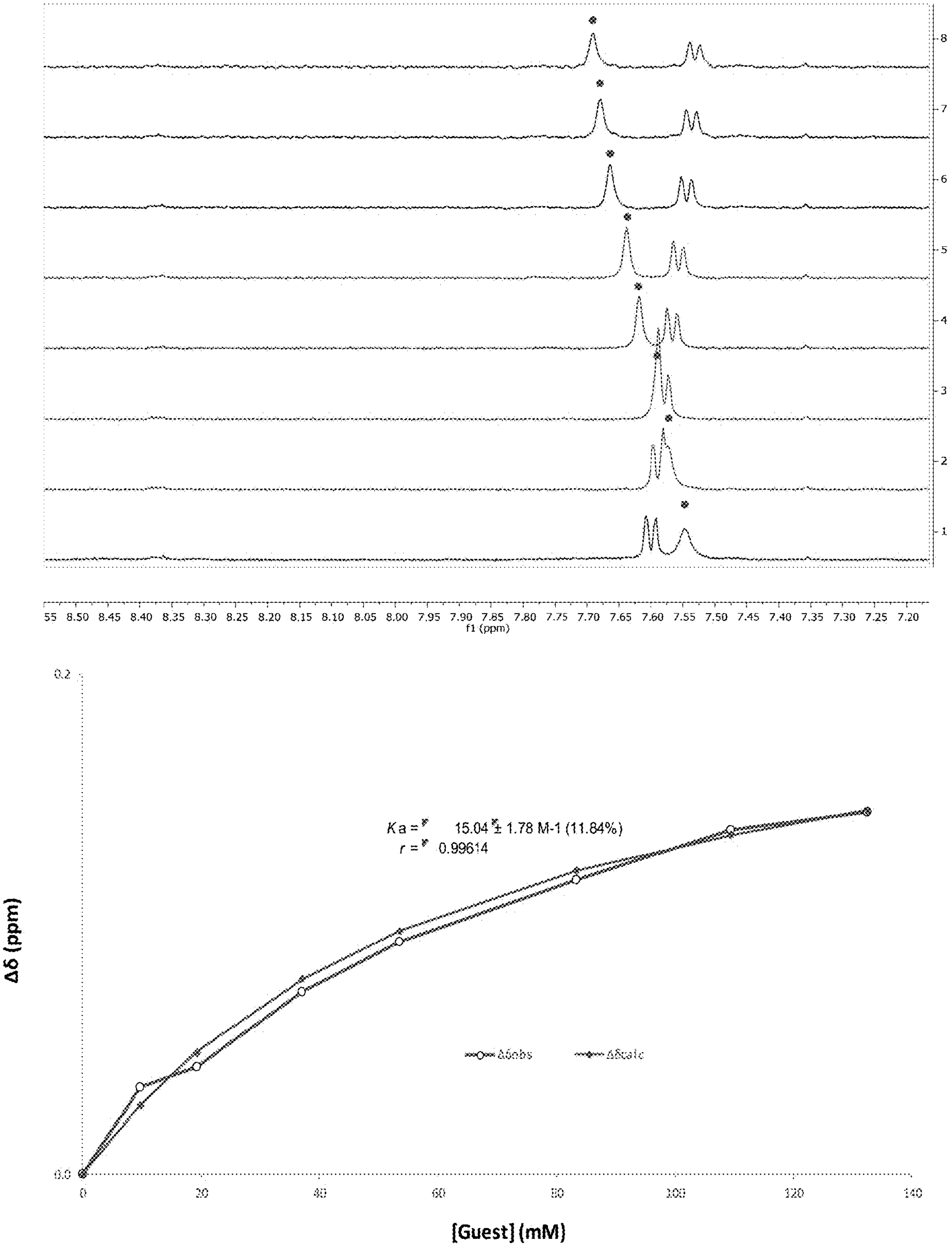

FIG. 62 shows the partial $^1$H NMR spectra (top) and binding analysis curve (bottom) for 90 (0.2 mM) titrated with a combined solution of D-maltose (500 mM) and 90 (0.2 mM), in $D_2O$ with at pH 7.4 and 298 K. Change in chemical shifts (Δδ, ppm) denoted with • were plotted against D-maltose concentration (mM). The calculated values for M are overlaid with the observed values, giving $K_a$=15±1.8 M-1 (11.8%).

Figure 63:
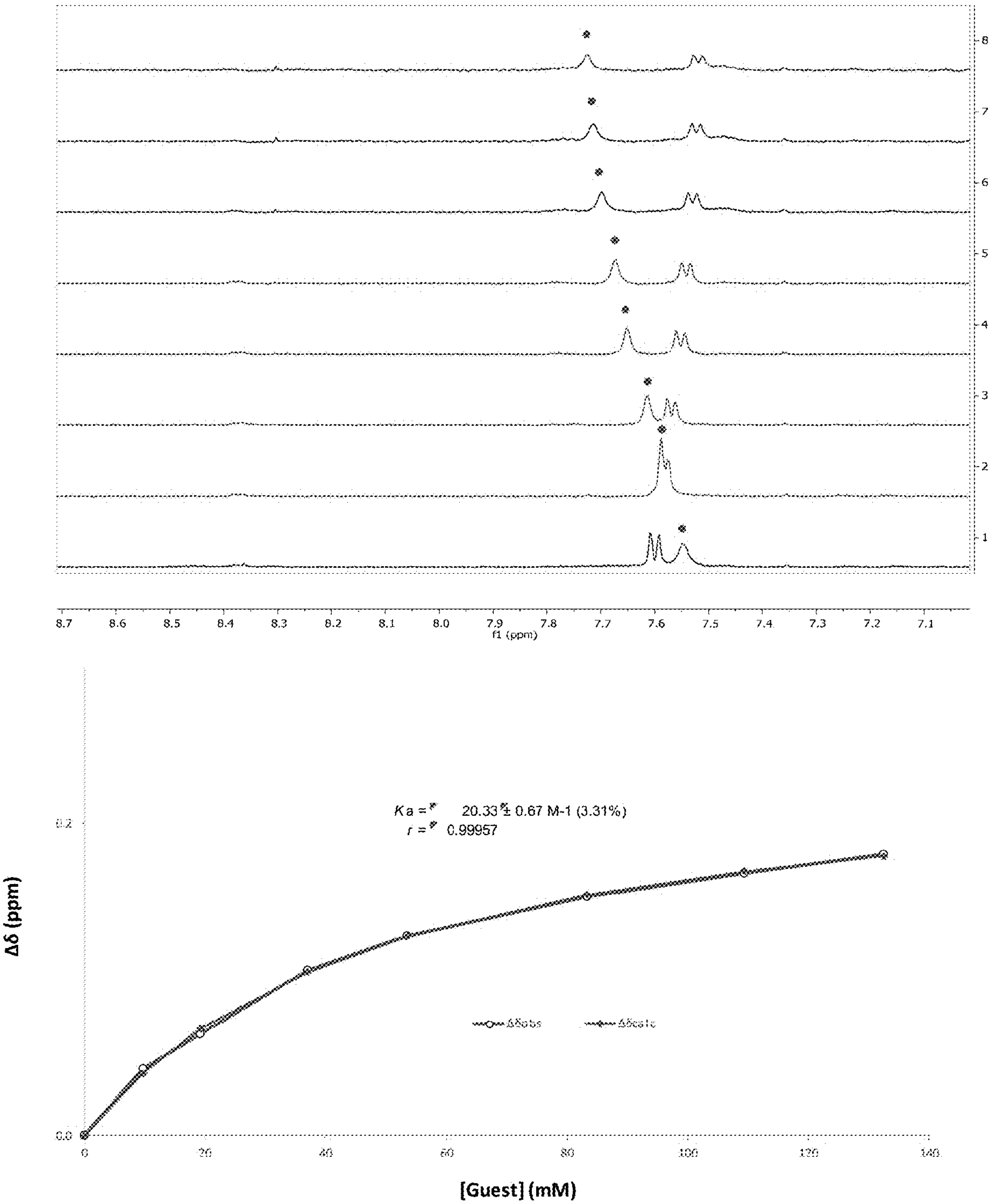

FIG. 63 shows the partial $^1$H NMR spectra (top) and binding analysis curve (bottom) for 90 (0.2 mM) titrated with a combined solution of D-maltotriose (500 mM) and 90 (0.2 mM), in $D_2O$ with at pH 7.4 and 298 K. Change in chemical shifts (Δδ, ppm) denoted with • were plotted against D-maltotriose concentration (mM). The calculated values for M are overlaid with the observed values, giving Ka=20±0.7 M-1 (3.3%).

Figure 64:
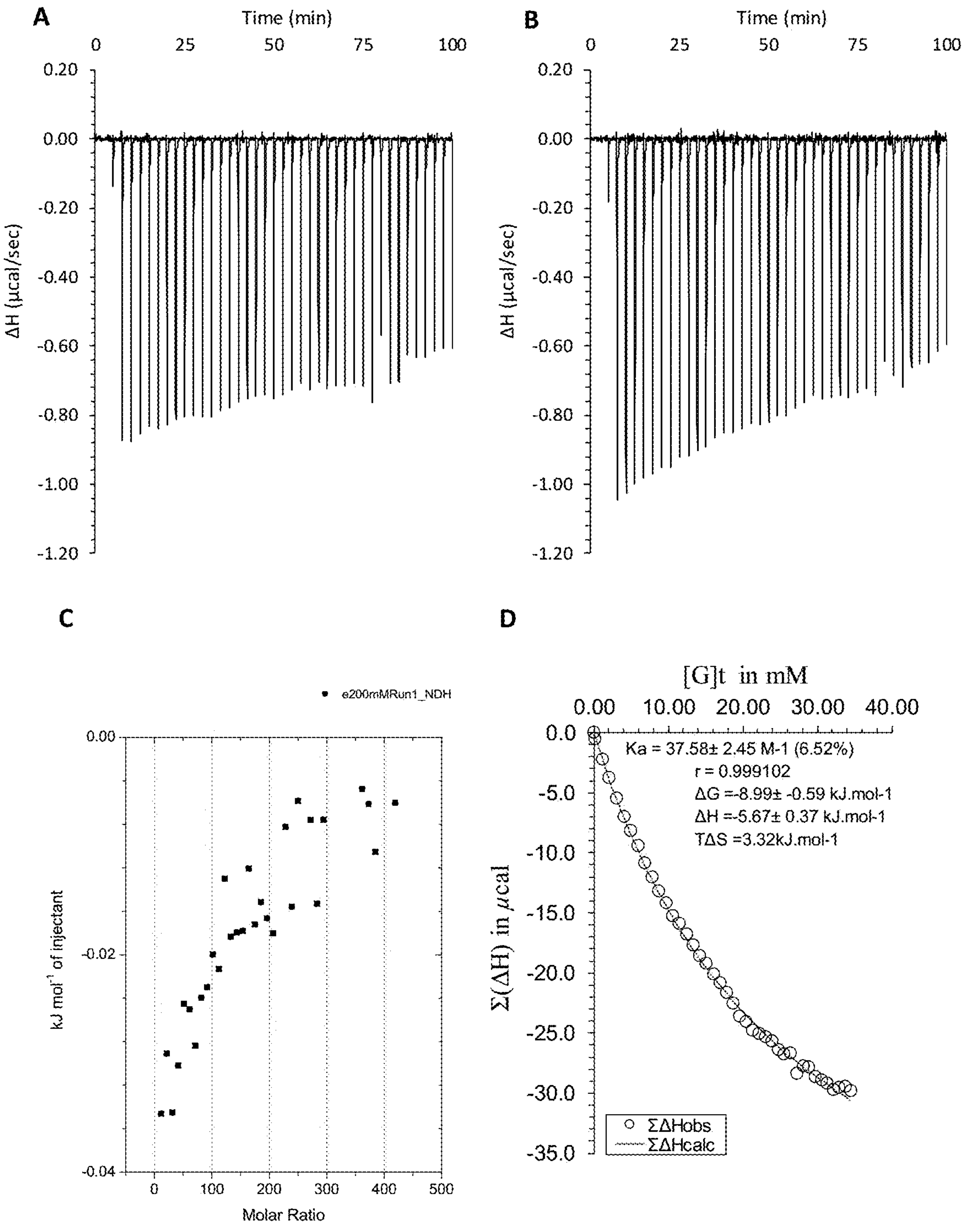

FIG. 64 shows the ITC binding results for 90 (0.2 mM) titrated with D-cellobiose (200 mM) in water at 298K, in which: A) shows the blank run (addition of substrate into water); B) shows the titration (substrate into receptor); C) shows the plotted change in enthalpy vs molar ratio; and D) shows the fit calculated using an Excel spreadsheet ($K_a$=37.6±2.5 $M^{-1}$).

Figure 65:
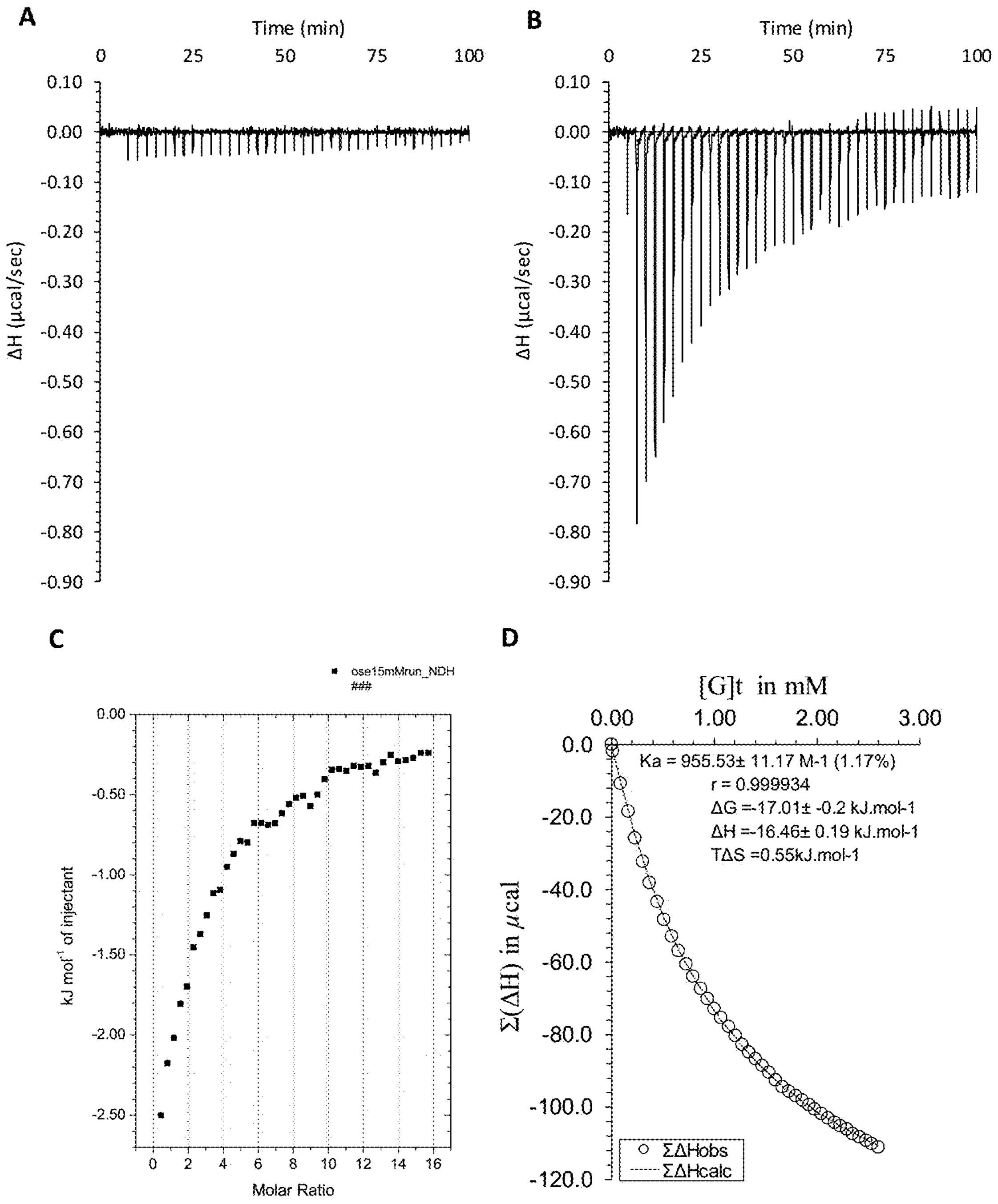

FIG. 65 shows the ITC binding results for 90 (0.2 mM) titrated with D-cellotriose (15 mM) in water at 298K, in which: A) shows the blank run (addition of substrate into water); B) shows the titration (substrate into receptor); C) shows the plotted change in enthalpy vs molar ratio; and D) shows the fit calculated using an Excel spreadsheet ($K_a$=955±11 $M^d$).

Figure 66:
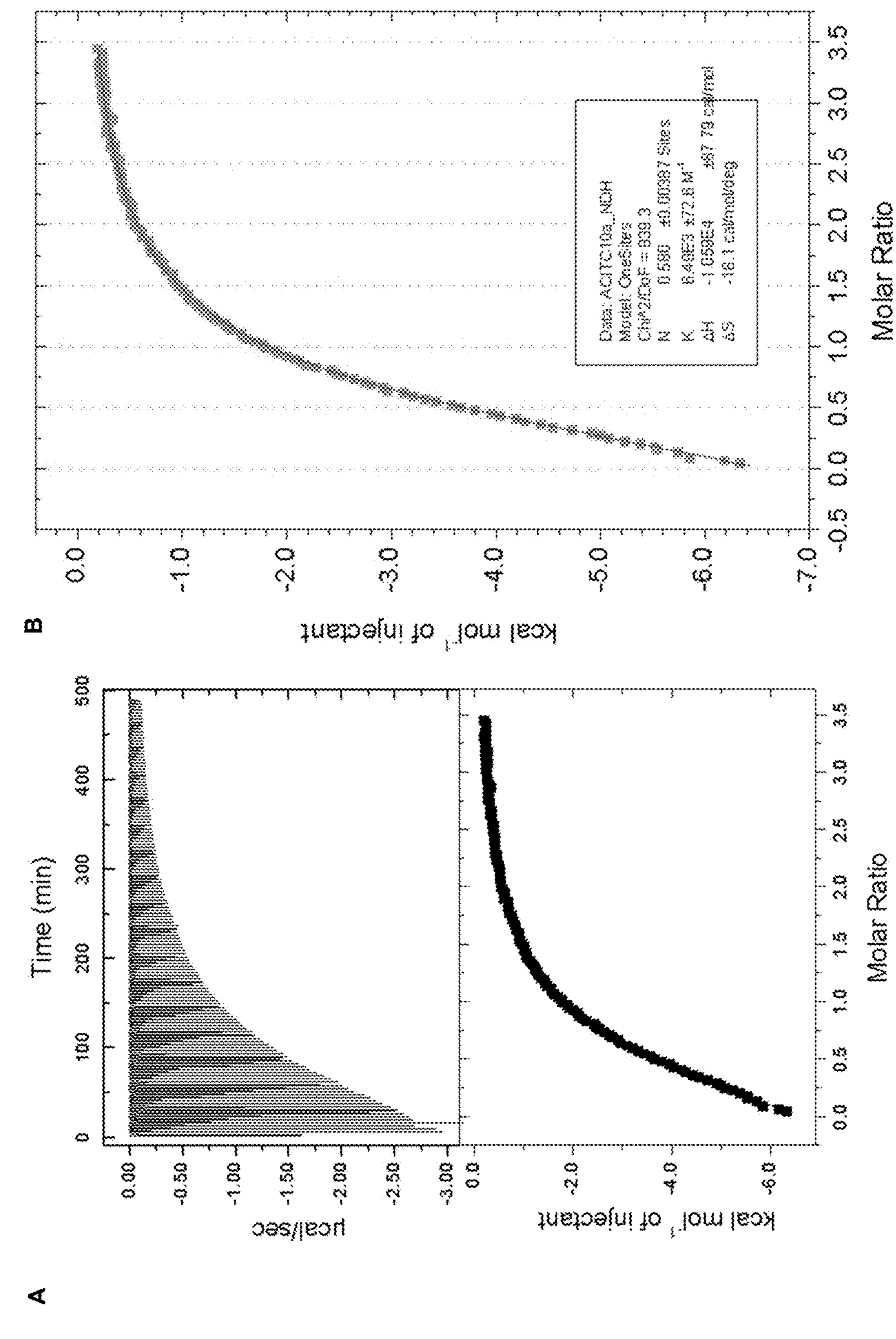

FIG. 66 shows: a) the ITC titration of d-glucose (7.1 mM) in 10 mM phosphate buffer into Receptor 4 (0.40 mM) in 10 mM. at 298 K; and b) an enlarged image of the kcal $mol^{-1}$ of injectant vs molar ratio trace. $K_a$ calculated at 6490 M-1+/−72.6 $M^{-1}$.

Figure 67:
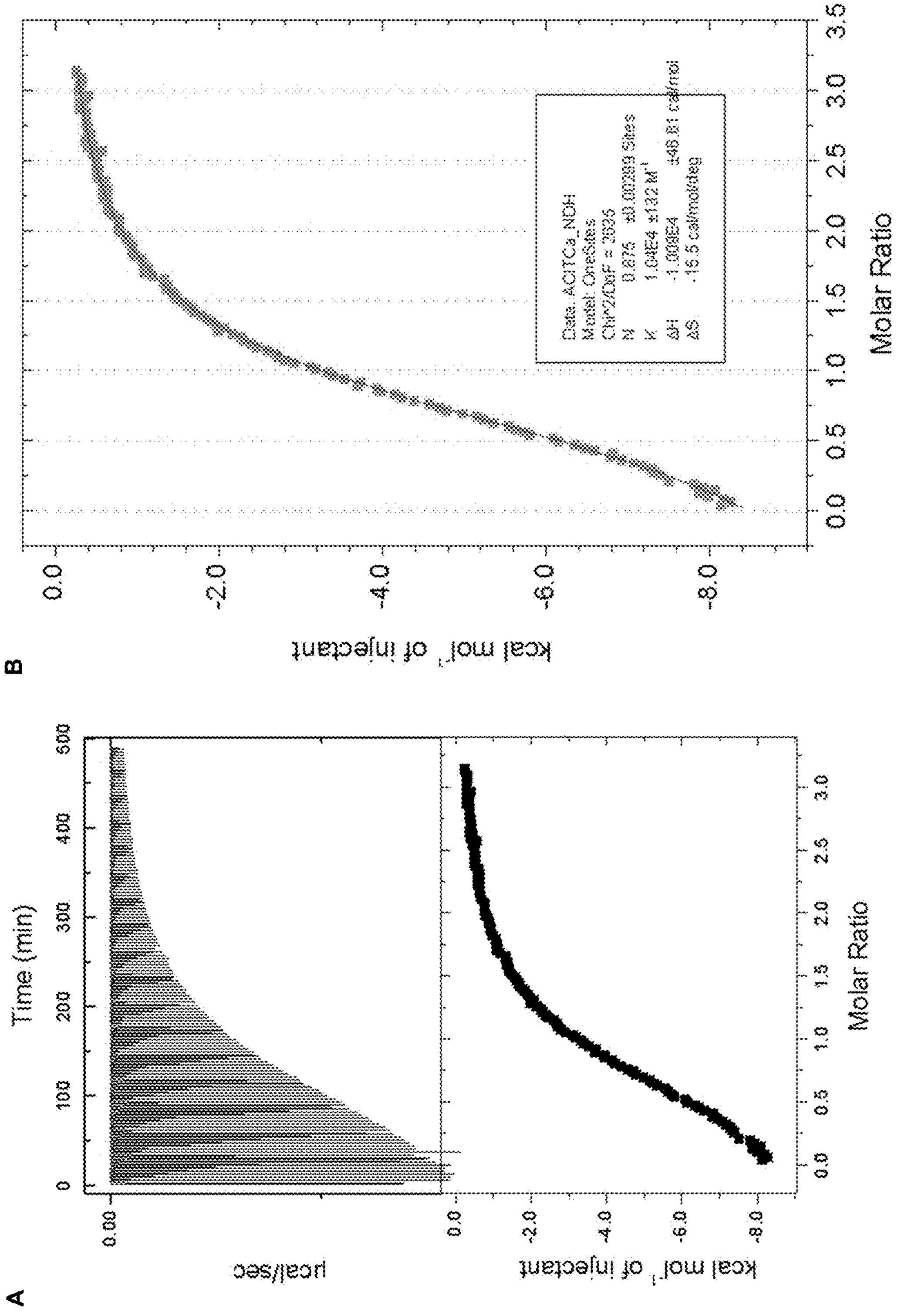

FIG. 67 shows: a) the ITC titration of d-glucose (7.1 mM) in 10 mM phosphate buffer into Receptor 5 (0.46 mM) in 10 mM. at 298 K; and b) an enlarged image of the kcal $mol^{-1}$ of injectant vs molar ratio trace. $K_a$ calculated at 10400 M-1+/−132 $M^{-1}$.

Figure 68:
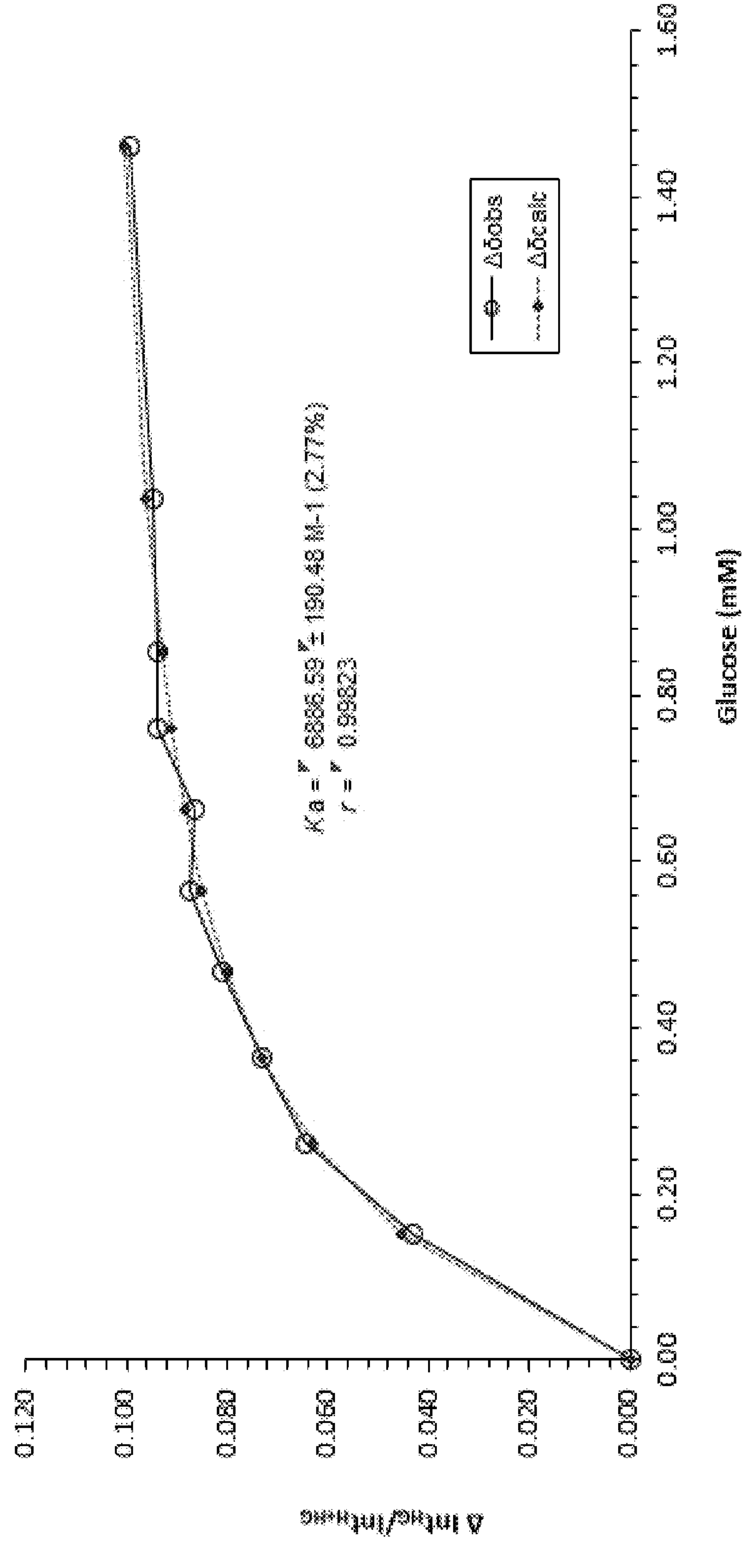

FIG. 68 shows the $^1$H NMR binding analysis curve generated following the titration of a combined solution of β-D-glucose (10 mM) and Receptor 7 (127 μM), in 10 mM PB, 140 mM NaCl, $D_2O$, into a solution of Receptor 7 (127 μM) in 10 mM PB, 140 mM NaCl, $D_2O$. $K_a$ calculated at 6886 $M^{-1}$+/−190 $M^{-1}$.

Figure 69:
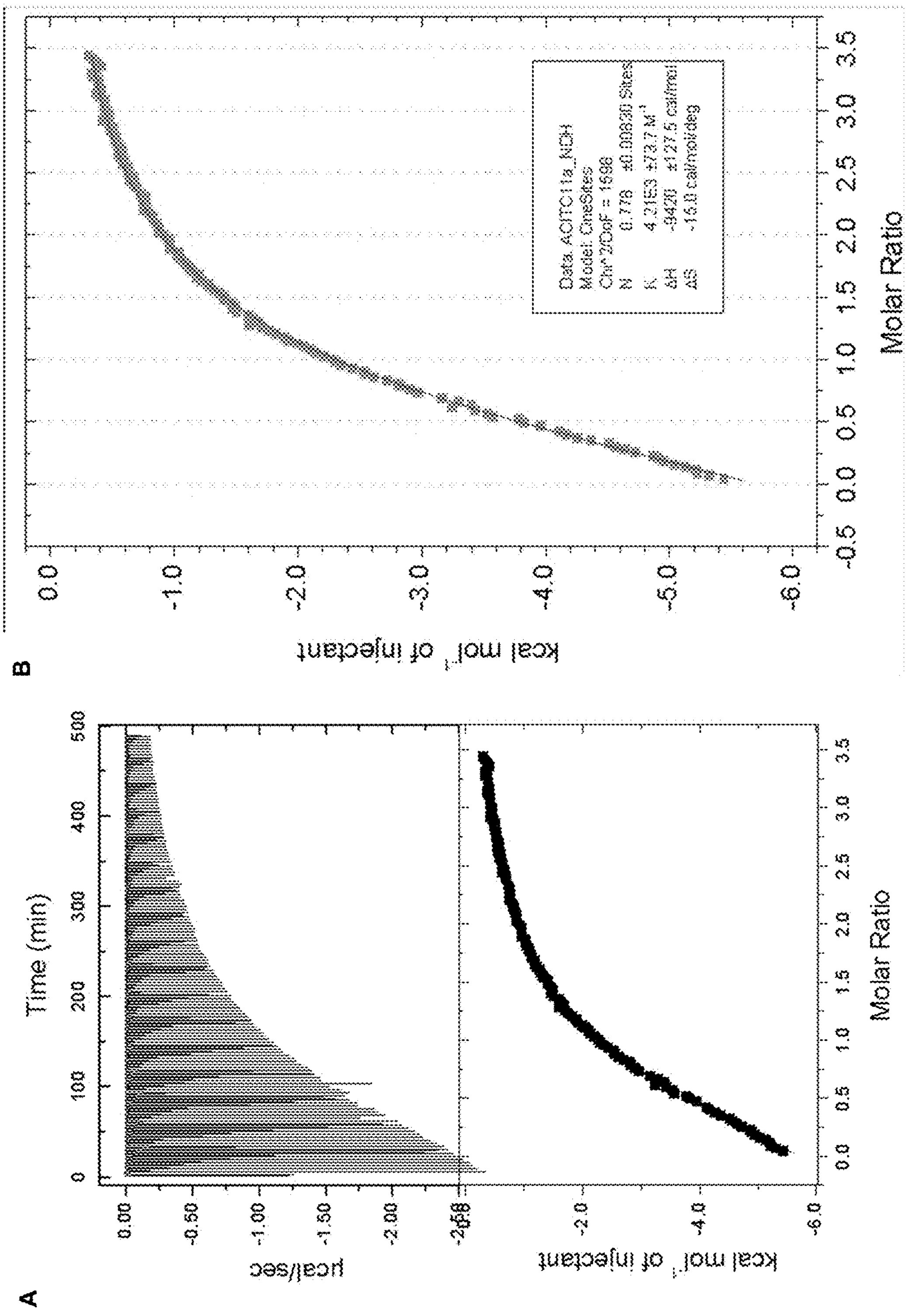

FIG. 69 shows: a) the ITC titration of d-glucose (7.1 mM) in 10 mM phosphate buffer into Receptor 8 (0.42 mM) in 10 mM. at 298 K; and b) an enlarged image of the kcal $mol^{-1}$ of injectant vs molar ratio trace. $K_a$ calculated at 4210 $M^{-1}$+/−73 $M^{-1}$.

Figure 70:
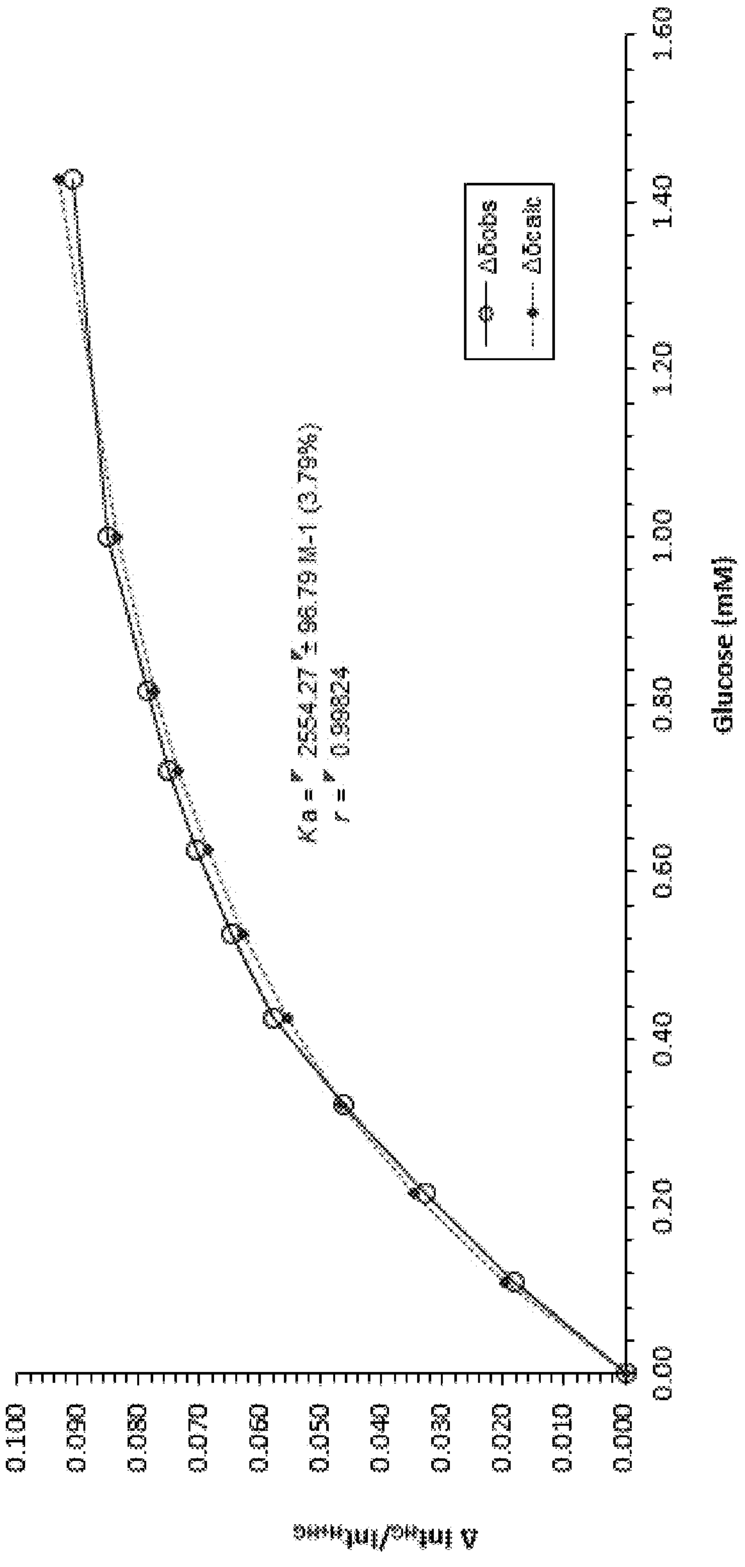

FIG. 70 shows the $^1$H NMR binding analysis curve generated following the titration of a combined solution of β-D-glucose (10 mM) and Recepor 9 (210 μM), in 10 mM PB, 140 mM NaCl, $D_2O$, into a solution of Receptor 9 (210 μM) in 10 mM PB, 140 mM NaCl, $D_2O$.

Figure 71:
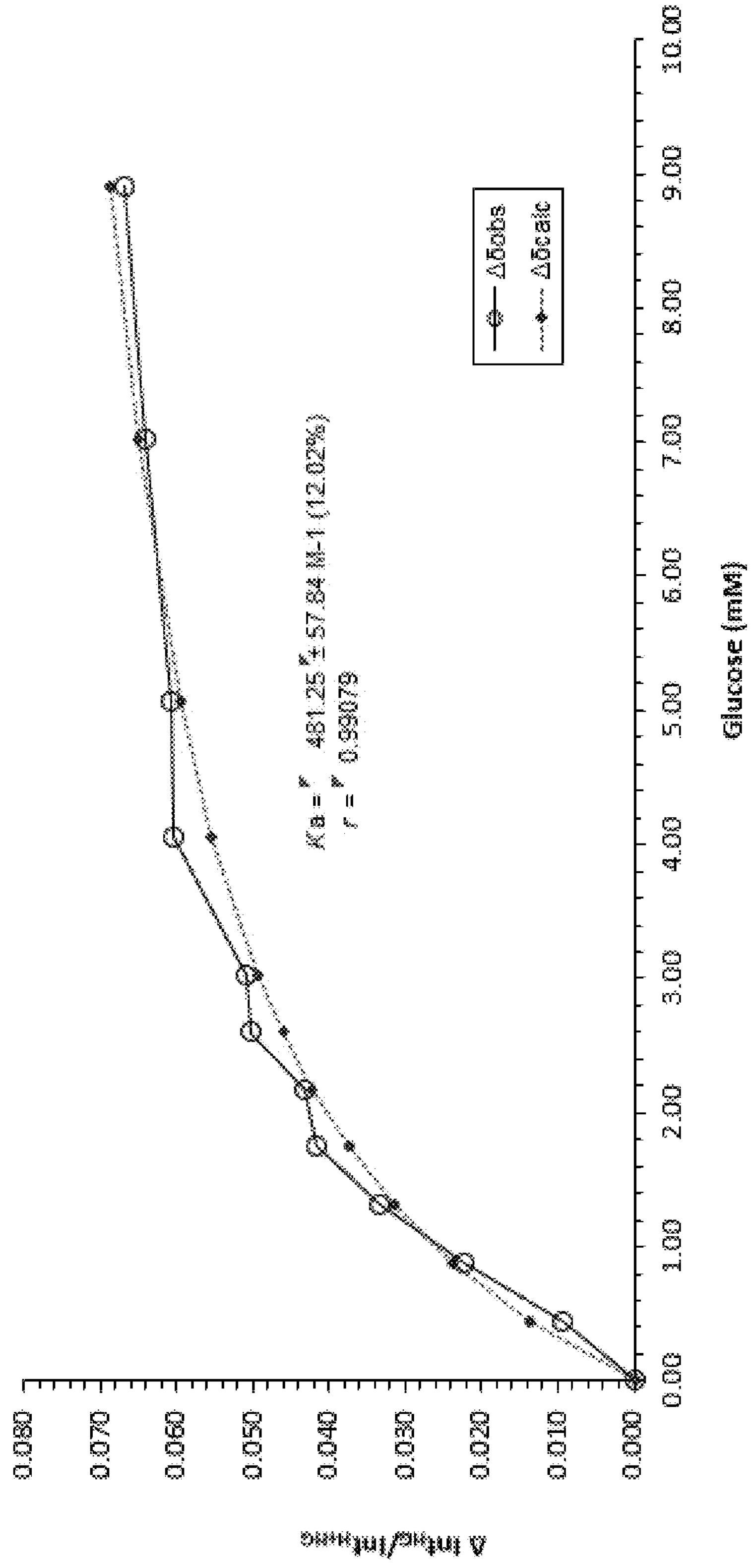

FIG. 71 shows the $^1$H NMR binding analysis curve generated following the titration of a combined solution of β-D-glucose (100 mM) and Recepor 10 (250 μM), in 10 mM PB, 140 mM NaCl, $D_2O$, into a solution of Receptor 10 (250 μM) in 10 mM PB, 140 mM NaCl, $D_2O$.

Figure 72:
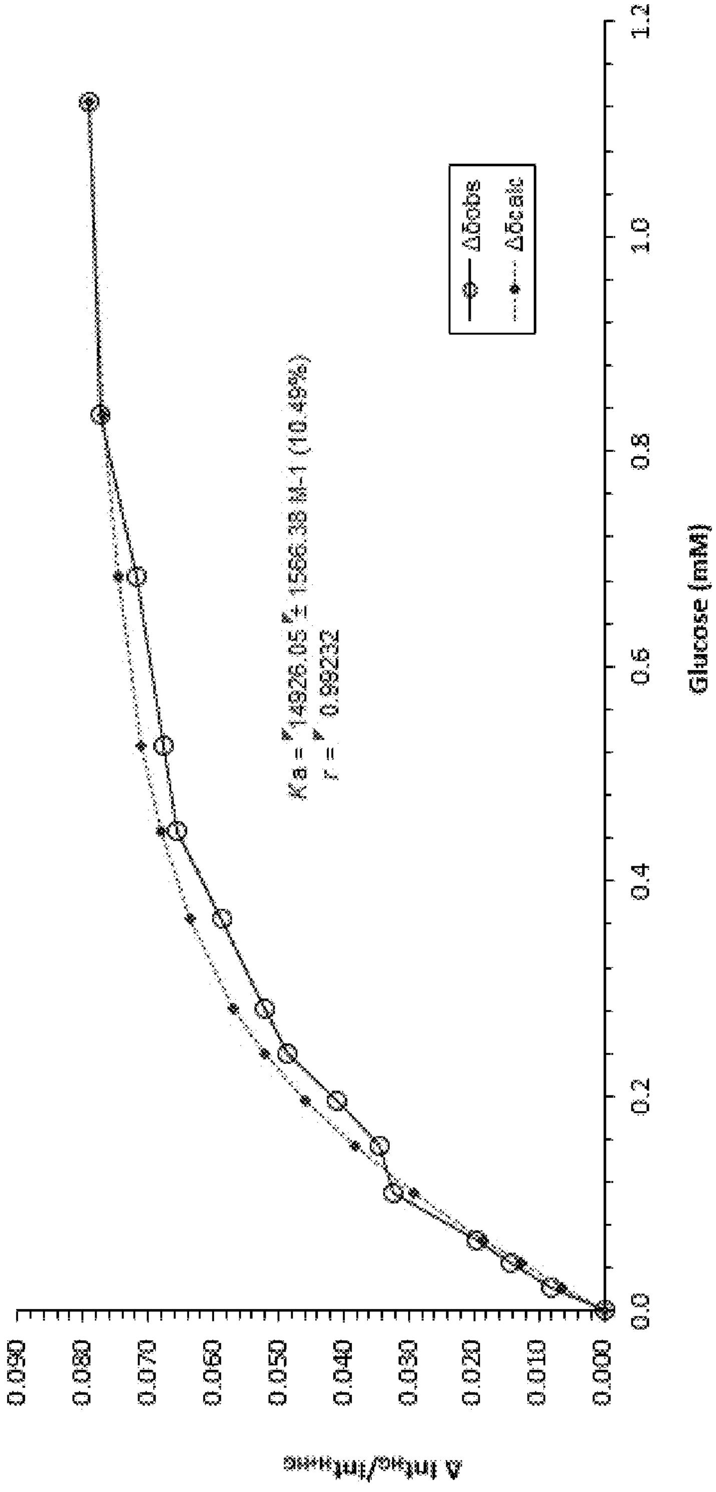

FIG. 72 shows the $^1$H NMR binding analysis curve generated following the titration of a combined solution of β-D-glucose (10 mM) and Recepor 13 (265 μM), in 10 mM PB, 140 mM NaCl, $D_2O$, into a solution of Receptor 13 (265 μM) in 10 mM PB, 140 mM NaCl, $D_2O$.

Figure 73:
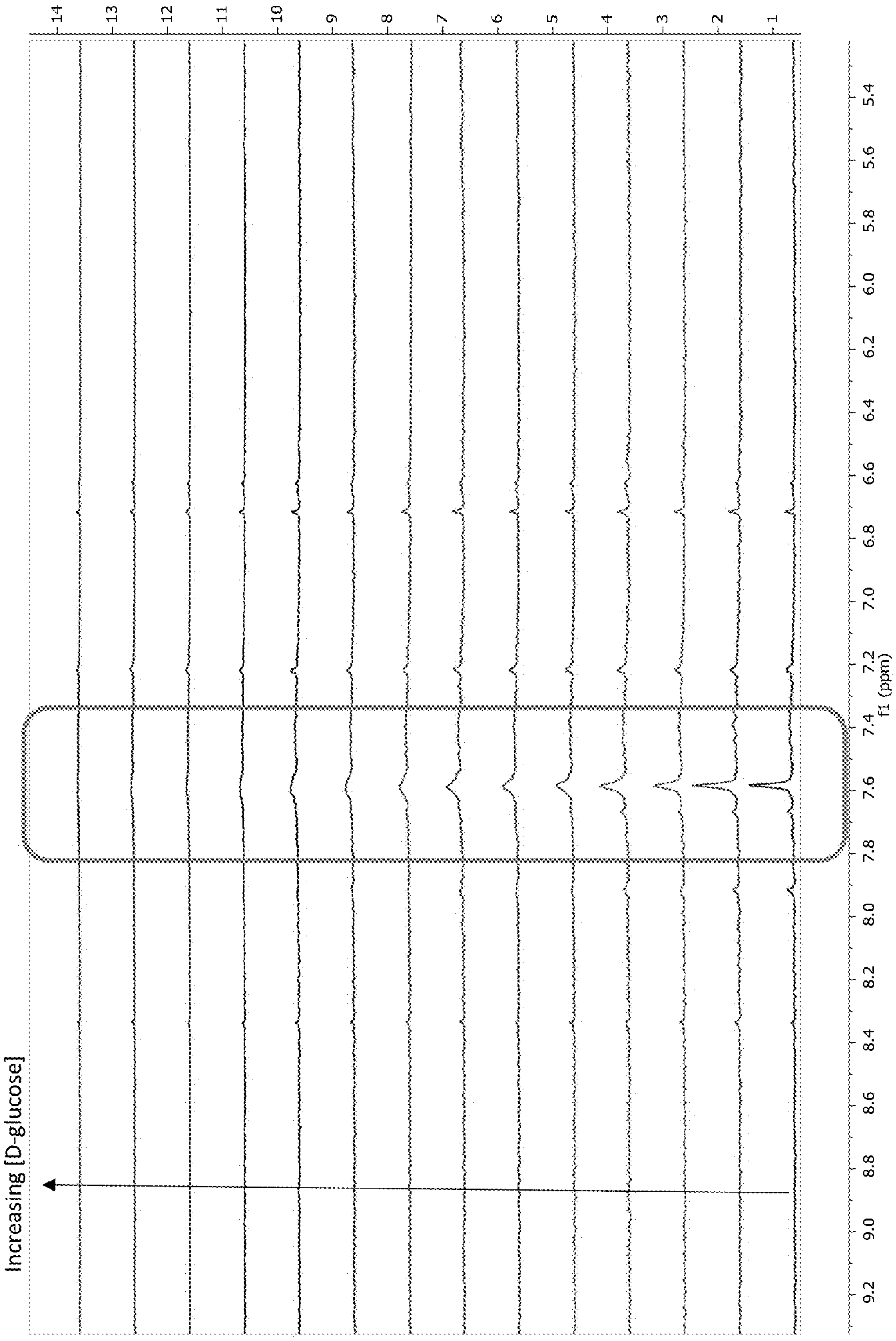

FIG. 73 shows the partial $^1$H NMR spectra for Receptor 11 (50 μM) in $D_2O$ (pH 7.4, 10 mM PBsoln) titrated with D-glucose (10 mM) with added Receptor 11 (50 μM) and 10 mM PBsoln. In making the assumption of receptor saturation at ~1 mM, half saturation would be at 0.5 mM. Therefore 1/0.5 mM=$K_a$~2000 $M^{-1}$.

Figure 74:
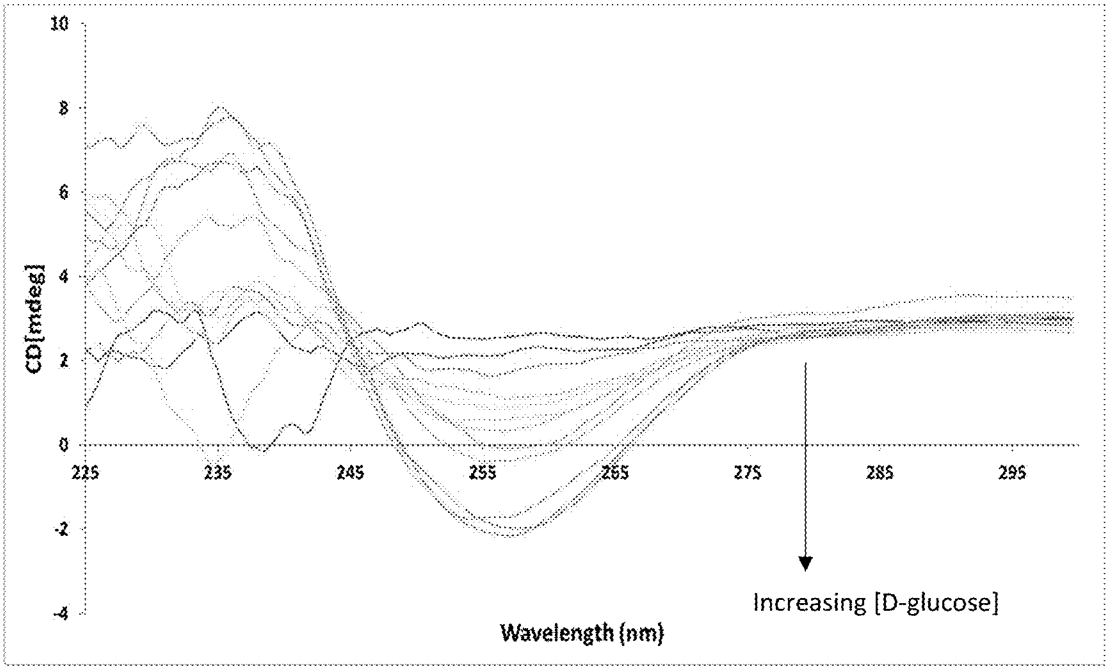
Figure 74:
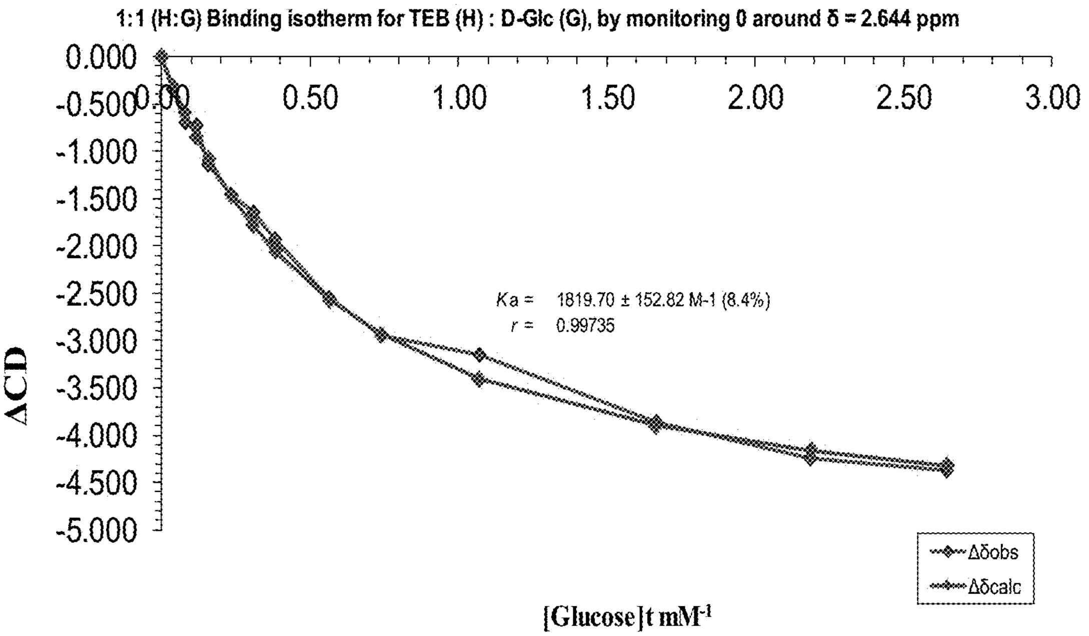

FIG. 74 shows: A) the circular dichroism (CD) spectra; and B) the binding analysis curve generated following the titration of D-glucose (10 mM) with added Receptor 11 (70 μM) and 10 mM PBsoln to a solution of Receptor 11 (70 μM) in water (pH 7.4 with 10 mM PBsoln).

Figure 75:
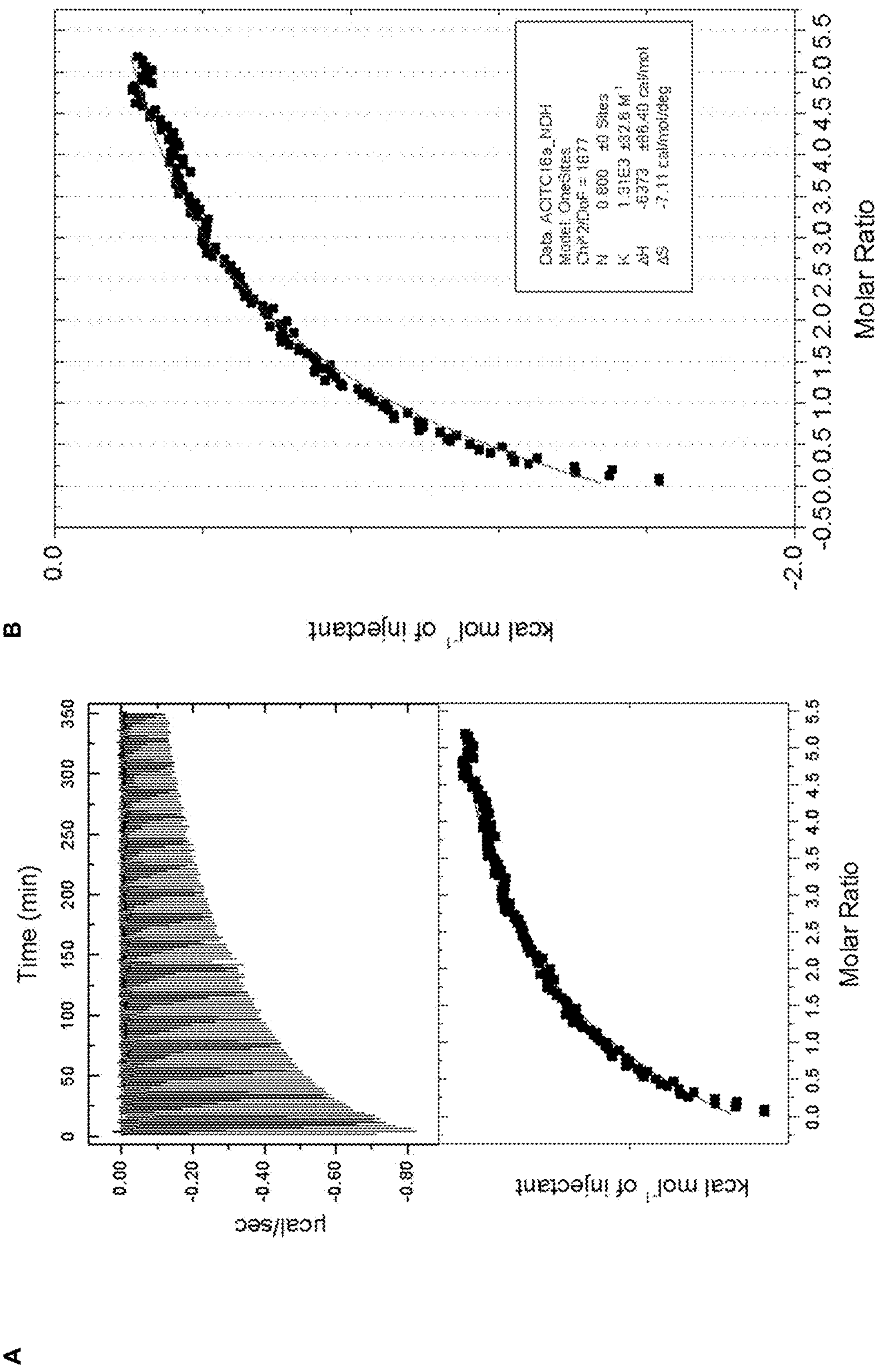

FIG. 75 shows: a) the ITC titration of d-glucose (7.73 mM) in 10 mM phosphate buffer into Receptor 13 (0.13 mM) in 10 mM at 298 K; and b) an enlarged image of the kcal $mol^{-1}$ of injectant vs molar ratio trace. $K_a$ calculated at 1310 $M^{-1}$+/−33 $M^{-1}$.

Figure 76:
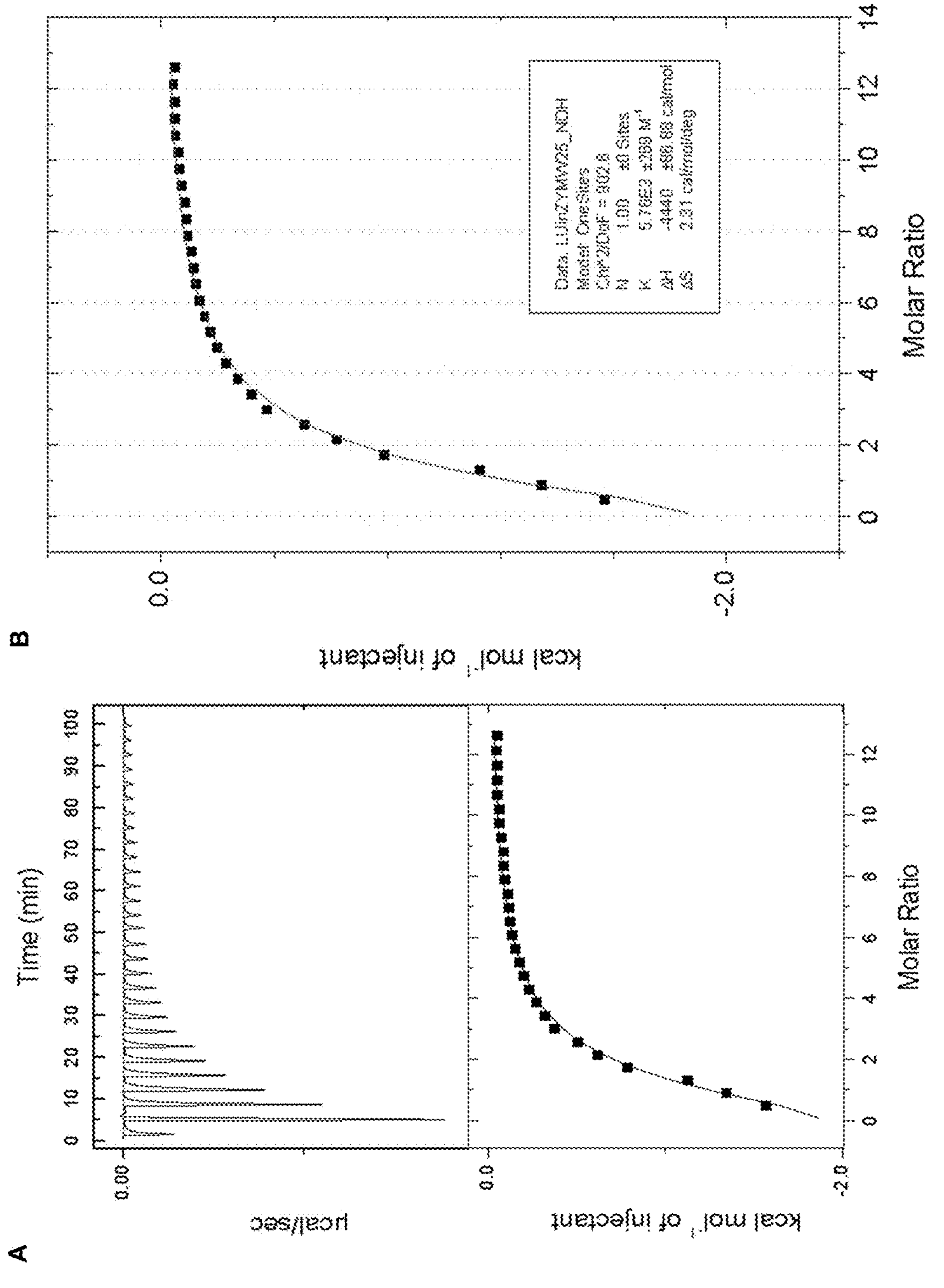

FIG. 76 shows: a) the ITC titration of d-glucose (7.10 mM) in 10 mM phosphate buffer into Receptor 3 (0.29 mM) in 10 mM. at 298 K; and b) an enlarged image of the kcal $mol^{-1}$ of injectant vs molar ratio trace. $K_a$ calculated at 5760 $M^{-1}$+/−269 $M^{-1}$.

Figure 77:
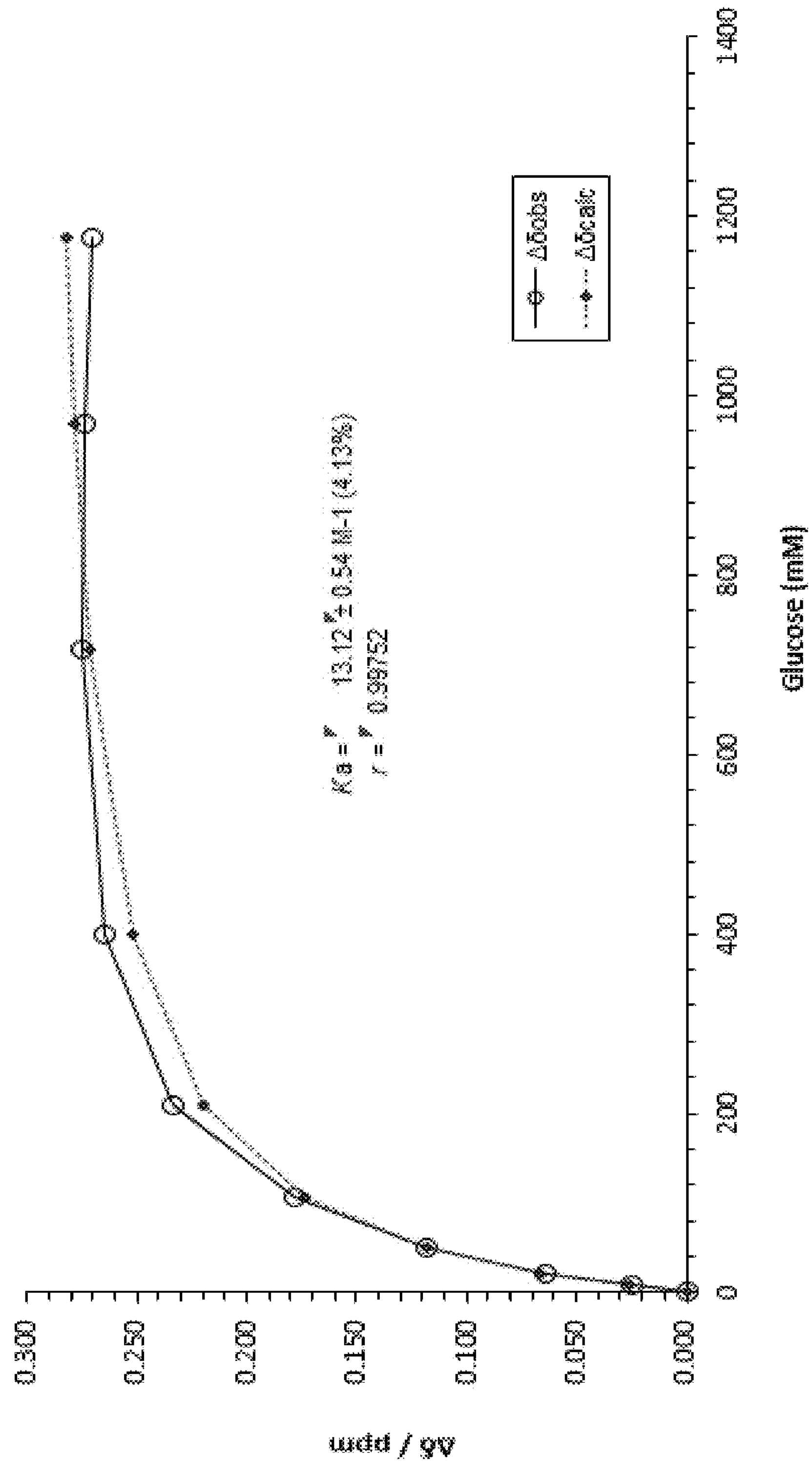

FIG. 77 shows the $^1$H NMR binding analysis curve generated following the titration of a combined solution of β-D-glucose (3.24 M) and Recepor 2 (265 μM) in $D_2O$, into a solution of Receptor 12 (223 μM) in $D_2O$ at 298 K.

DETAILED DESCRIPTION OF THE INVENTION

Definitions

Unless otherwise stated, the following terms used in the specification and claims have the following meanings set out below.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or examples of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "alkenyl" will be understood to include both straight and branched hydrocarbon groups comprising one or more carbon-carbon double bonds. Reference to, for example, "(2-6C)alkenyl" will be understood to refer to alkene groups containing from 3 to 6 carbon atoms and may includes, for example, hexenyl, pentenyl, butenyl, propenyl and ethylenyl.

The term "alkynyl" will be understood to include both straight and branched hydrocarbon groups comprising one or more carbon-carbon triple bonds. Again, reference to "(2-6C)alkynyl" groups will be understood to refer to alkyne groups containing from 3 to 6 carbon atoms and may includes, for example hexynyl, pentynyl, butynyl, propynyl and acetylenyl.

The term "(m-nC)" or "(m-nC) group" used alone or as a prefix, refers to any group having m to n carbon atoms.

An "alkylene," "alkenylene," or "alkynylene" group is an alkyl, alkenyl, or alkynyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene, ethylene, propylene, 2-methylpropylene, pentylene, and the like.

"(3-8C)cycloalkyl" means a hydrocarbon ring containing from 3 to 8 carbon atoms, for example, cyclopropyl, cyclobutyl, cyclopentyl, cyclohexyl, cycloheptyl or bicyclo [2.2.1]heptyl.

"(3-8C)cycloalkenyl" means a hydrocarbon ring containing from 3 to 8 carbon atoms and at least one double bond, for example, cyclobutenyl, cyclopentenyl, cyclohexenyl or cycloheptenyl, such as 3-cyclohexen-1-yl, or cyclooctenyl.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, $4^{th}$ Edition, Wiley Interscience, pages 131-133, 1992. Examples of bridged heterocyclyl ring systems include, aza-bicyclo [2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4]

octane, 2-oxa-6-azaspiro[3.4]octane, 2-azaspiro[3.3]heptanes, 2-oxa-6-azaspiro[3.3]heptanes, 7-oxa-2-azaspiro[3.5]nonane, 6-oxa-2-azaspiro[3.4]octane, 2-oxa-7-azaspiro[3.5]nonane and 2-oxa-6-azaspiro[3.5]nonane.

"Heterocyclyl(1-6C)alkyl" means a heterocyclyl group covalently attached to a (1-6C)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically, the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:

a benzene ring fused to a 5- or 6-membered ring containing 1, 2 or 3 ring heteroatoms;

a pyridine ring fused to a 5- or 6-membered ring containing 1, 2 or 3 ring heteroatoms;

a pyrimidine ring fused to a 5- or 6-membered ring containing 1 or 2 ring heteroatoms;

a pyrrole ring fused to a 5- or 6-membered ring containing 1, 2 or 3 ring heteroatoms;

a pyrazole ring fused to a 5- or 6-membered ring containing 1 or 2 ring heteroatoms;

a pyrazine ring fused to a 5- or 6-membered ring containing 1 or 2 ring heteroatoms;

an imidazole ring fused to a 5- or 6-membered ring containing 1 or 2 ring heteroatoms;

an oxazole ring fused to a 5- or 6-membered ring containing 1 or 2 ring heteroatoms;

an isoxazole ring fused to a 5- or 6-membered ring containing 1 or 2 ring heteroatoms;

a thiazole ring fused to a 5- or 6-membered ring containing 1 or 2 ring heteroatoms;

an isothiazole ring fused to a 5- or 6-membered ring containing 1 or 2 ring heteroatoms;

a thiophene ring fused to a 5- or 6-membered ring containing 1, 2 or 3 ring heteroatoms;

a furan ring fused to a 5- or 6-membered ring containing 1, 2 or 3 ring heteroatoms;

a cyclohexyl ring fused to a 5- or 6-membered heteroaromatic ring containing 1, 2 or 3 ring heteroatoms; and a cyclopentyl ring fused to a 5- or 6-membered heteroaromatic ring containing 1, 2 or 3 ring heteroatoms.

Particular examples of bicyclic heteroaryl groups containing a six-membered ring fused to a five-membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl, anthraceneyl and the like. In particular embodiment, an aryl is phenyl.

The term "halo" refers to any suitable halogen and may be selected from fluoro, chloro, bromo and iodo groups. Suitably, the term halo refers to fluoro, chloro or bromo groups, and most suitably, chloro groups.

The term "optionally substituted" refers to either groups, structures, or molecules that are substituted and those that are not substituted. The term "wherein a/any CH, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

The term "hydrophilic substituent group" will be understood to refer to a substituent group which has an affinity for water and tends to solvation. Accordingly, the term "hydrophilic substituent group" may be understood to encompass any substituent group which facilitates water solubility to the compounds of the present invention.

The term "hydrophilic polymer" will be understood to refer to any oligomer, polymer and/or copolymer comprising at least 3 repeat units (suitably at least 10 repeat units), wherein one or more of said repeat units (monomers) comprise a polar functional group with an affinity for water. The term "hydrophilic polymer" will be understood to encompass linear, branched and hyperbranched polymers. Suitably, the hydrophilic polymer is selected from a polycarboxylic acid, polycarboxylate, polyhydroxy, polyester, polyether, polyamine, polyamide, polyphosphate or polyoxyalkylene. More suitably, a polycarboxylic acid, polycarboxylate, polyhydroxy or polyether. Yet more suitably, the hydrophilic polymer is polyethylene glycol, polyvinylalcohol, polyacrylate, polyacrylamide or polyvinyl pyrrolidine. Most suitably, the hydrophilic polymer is polyethylene glycol or polyacrylamide.

The term "hydrophilic dendritric group" will be understood to refer to any dendrimer, dendron or branched molecule comprising one or more polar functional group with an affinity for water. That is, the term "hydrophilic dendritric group" will be understood to encompass any dendrimer, dendron or branched molecule which facilitates the water solubility of the compounds of the present invention. Moreover, the term "dendrimer" is a term of the art and will readily be understood to refer to a tree-like molecular architecture with a core or focal point, interior layers (otherwise known as "generations") which consist of repeating units of one or more building units attached to the core or focal point, and an exterior (outermost) layer of building units comprising terminal functional groups on the terminus of the dendrimer structure.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

According to one aspect of the present invention, there is provided a compound of Formula (I), or a salt, hydrate or solvate thereof, as shown below:

Formula (I)

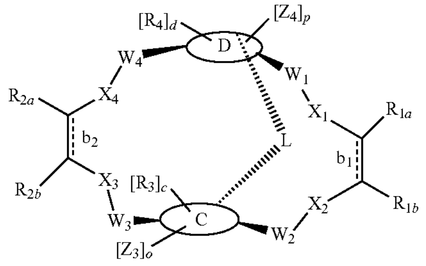

wherein:

bonds $b_1$ and $b_2$ are independently selected from a single bond or double bond;

$R_{1a}$, $R_{1b}$, $R_{2a}$ and $R_{2b}$ are independently selected from hydrogen, carbonyl, (1-8C)alkyl, (3-10C)cycloalkyl, aryl, heteroaryl and heterocyclyl, each of which, other than hydrogen and carbonyl, is optionally substituted by one or more substituent groups selected from (1-4C)alkyl, halo, (1-4C)haloalkyl, (1-4C)haloalkoxy, (1-4C)alkoxy, (1-4C)alkylamino, amino, cyano, hydroxyl, carboxy, carbamoyl, sulfamoyl, mercapto and a hydrophilic substituent group; or $R_{1a}$ and $R_{1b}$ are linked so as to form a group of the formula:

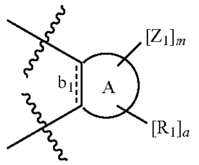

and/or $R_{2a}$ and $R_{2b}$ are linked so as to form a group of the formula:

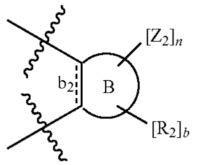

wherein:

∿ denotes the point of attachment;

bonds $b_1$ and $b_2$ are as described above;

Rings A and B are independently selected from aryl, heteroaryl, heterocyclyl, cycloalkyl and cycloalkenyl;

$R_1$ and $R_2$ are independently selected from (1-6C)alkyl, halo, (1-4C)haloalkyl, (1-4C)haloalkoxy, (1-6C) alkoxy, (1-4C)alkylamino, amino, cyano, hydroxyl, carboxy, carbamoyl, sulfamoyl and mercapto;

a and b are integers independently selected from 0 to 2;

m and n are integers independently selected from 0 to 2;

$Z_1$ and $Z_2$ are independently selected from a hydrophilic substituent group;

C and D are independently selected from aryl, heteroaryl, heterocyclyl, cycloalkyl, cycloalkenyl and a group of the formula:

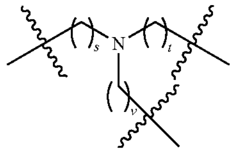

wherein:

s, t and v are integers independently selected from 1 or 2;

∿ denotes the point of attachment;

$R_3$ and $R_4$ are independently selected from halo, (1-4C) alkyl, (1-4C)alkoxy, amino, nitro, (1-4C)alkylamino, (1-4C)dialkylamino, (1-4C)haloalkyl, (1-4C)haloalkoxy, cyano, (2-4C)alkenyl, (2-4C)alkynyl and a group of the formula:

$-L^1-Y^1-Q^1$ wherein:

$L^1$ is absent or a (1-5C)alkylene optionally substituted by one or more substituents selected from (1-2C) alkyl and oxo;

$Y^1$ is absent or selected from a one of the following groups; O, S, SO, $SO_2$, $N(R_a)$, C(O), C(O)O, OC(O), $C(O)N(R_a)$, $N(R_a)C(O)$, $N(Rb)C(O)N(R_a)$, $N(R_a)C(O)O$, $OC(O)N(R_a)$, $S(O)_2N(R_a)$, and $N(R_a)SO_2$, wherein $R_a$ and $R_b$ are each independently selected from hydrogen and (1-4C)alkyl; and $Q^1$ is hydrogen, (1-8C)alkyl, (2-6C)alkenyl, (2-6C) alkynyl, aryl, (3-10C)cycloalkyl, (3-10C)cycloalkenyl, heteroaryl and heterocyclyl; wherein $Q^1$ is optionally further substituted by one or more substituent groups independently selected from (1-4C) alkyl, halo, (1-4C)haloalkyl, (1-4C)haloalkoxy, amino, (1-4C)aminoalkyl, cyano, hydroxy, carboxy, carbamoyl, sulfamoyl, mercapto, ureido, oxy, $NR_cR_d$, $OR_c$, $C(O)R_d$, $C(O)OR_c$, $OC(O)R_c$, $C(O)N(R_d)R_c$, $N(R_d)C(O)R_c$, $S(O)_yR_c$ (where y is 0, 1 or 2), $SO_2N(R_d)R_c$, $N(R_d)SO_2R_c$, $Si(R_c)(R_d)R_c$ and $(CH_2)_zNR_dR_c$ (where z is 1, 2 or 3); wherein $R_c$, $R_d$ and $R_e$ are each independently selected from hydrogen, (1-6C)alkyl and (3-6C)cycloalkyl; and $R_c$ and $R_d$ can be linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxyl; or two $R_3$ and/or two $R_4$ groups taken together may form a group of the formula:

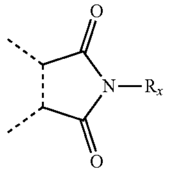

wherein:

$R_x$ is selected from hydrogen and (1-6C)alkyl optionally substituted by one or more substituent groups selected from halo, (1-4C)haloalkyl, (1-4C)haloalkoxy, cyano, hydroxy, sulfamoyl, mercapto, ureido, $NR_fR_g$, $OR_f$, $C(O)R_f$, $C(O)OR_f$, $OC(O)R_f$, $C(O)N(R_g)R_f$ and $N(R_g)C(O)R_f$, wherein $R_f$ and $R_g$ are selected from hydrogen and (1-4C)alkyl; and dashed lines represent the points of attachment to C and/or D;

$W_1$, $W_2$, $W_3$ and $W_4$ are independently selected from $CR_hR_i$, wherein $R_h$ and $R_i$ are selected from hydrogen and (1-2C)alkyl;

$X_1$, $X_2$, $X_3$ and $X_4$ are independently selected from a group of the formula:

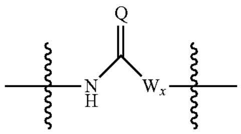

wherein:

denotes the point of attachment;

$W_x$ is selected from O or NH; and

Q is selected from O, S and $NR_j$, wherein $R_j$ is selected from hydrogen, (1-4C)alkyl, aryl, heteroaryl and sulfonyl;

$Z_3$ and $Z_4$ are independently selected from a hydrophilic substituent group;

L is absent or a linker, which optionally bears a hydrophilic substituent group $Z_5$;

c and d are integers independently selected from 0 to 4;

o and p are integers independently selected from 0 to 2;

and wherein:

i) the compound of Formula I is optionally attached to a displaceable reporter molecule via one or more of the substituent groups associated with $R_1$, $R_2$, $R_3$, $R_4$, $Z_1$, $Z_2$, $Z_3$, $Z_4$ and/or $Z_5$; and/or ii) the compound of Formula I is optionally attached to a substituent group of Formula A1 shown below at a position associated with one or more of the substituent groups $R_{1a}$, $R_{1b}$, $R_{2a}$, $R_{2b}$, $R_1$, $R_2$, $R_3$, $R_4$, $Z_1$, $Z_2$, $Z_3$, $Z_4$ and/or $Z_5$:

$$X_{2a}\text{-}L_{2a}\text{-}Z_{2a} \qquad \text{(Formula A1)}$$

wherein:

$X_{2a}$ is absent or selected from O, S, SO, $SO_2$, $N(R^{x2})$, C(O), C(O)O, OC(O), $C(O)N(R^{x2})$, $N(R^{x2})C(O)$, $N(R^{x2})C(O)N(R^{x2})$, $N(R^{x2})C(O)O$, $OC(O)N(R^{x2})$, $S(O)_2N(R^{x2})$ and $N(R^{x2})SO_2$, wherein $R^{x2}$ and $R^{x3}$ are each independently selected from hydrogen and (1-4C)alkyl;

$L_{2a}$ is absent or selected from (1-20C)alkylene, (1-20C)alkylene oxide, (1-20C)alkenyl and (1-20C)alkynyl, each of which being optionally substituted by one or more substituents selected from (1-2C)alkyl, aryl and oxo; and $Z_{2a}$ is selected from carboxy, carbamoyl, sulphamoyl, mercapto, amino, azido, (1-4C)alkenyl, (1-4C)alkynyl, $NR^{xc}R^{xd}$, $OR^{xc}$, $ONR^{xc}R^{xd}$, $C(O)X_a$, $C(Q^Z)OR^{xf}$, N═C═O, $NR^{xc}C(O)CH_2X_b$, $C(O)N(R^{xe})NR^{Xc}$—$R^{Xd}$, $S(O)_yX_a$ (where y is 0, 1 or 2), $SO_2N(R^{xe})NR^{xc}R^{xd}$, $Si(R^{xg})(R^{xh})R^{xi}$, S—S—$X_c$ an amino acid and

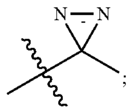;

wherein:

$X_a$ is a leaving group (e.g. halo or $CF_3$);

$X_b$ is a halo (e.g. iodo);

$X_c$ is an aryl or heteroaryl, optionally substituted with one or more substituents selected from halo, cyano and nitro;

$R^{xc}$, $R^{xd}$ and $R^{xe}$ are each independently selected from hydrogen and (1-6C)alkyl;

$R^{xf}$ is selected from hydrogen or (1-6C)alkyl, or $R^{xf}$ is a substituent group that renders $C(O)OR^{xf}$, when taken as a whole, to be an activated ester (e.g a hydroxysuccinimide ester, a hydroxy-3-sulfo-succinimide ester or a pentafluorophenyl ester);

$Q^z$ is selected from O or $^+NR^{Q1}R^{Q2}$, where $R^{Q1}$ and $R^{Q2}$ are independently selected from hydrogen and methyl; and $R^{xg}$, $R^{xh}$ and $R^{xi}$ are each independently selected from (1-4C)alkyl, hydroxy, halo and (1-4C) alkoxy;

with the proviso that the compound of Formula I comprises at least one hydrophilic substituent group (e.g. $Z_1$, $Z_2$, $Z_3$, $Z_4$ or $Z_5$).

To their surprise, the inventors have advantageously discovered that the compounds of the present invention display an exceptionally high affinity towards certain target saccharides (e.g. glucose) in aqueous media. Furthermore, it has also been discovered that the compounds of the present invention display unprecedented levels of selectivity towards certain target saccharides (e.g. glucose) over other structurally similar saccharides (e.g. mannose).

In addition to the remarkable affinities and selectivities displayed by the compounds of the present invention, the non-covalent interactions between the compounds of the present invention and the target saccharide, as opposed to covalent interactions, allow the compounds of the present invention to reversibly associate with certain target saccharides. Noting the aforementioned difficulties in the art associated with the development of efficient and selective saccharide receptor molecules, particularly in biologically relevant aqueous media, the compounds of the present invention clearly represent a unique and highly useful class of compounds for use in saccharide sensing applications.

Figure 1:
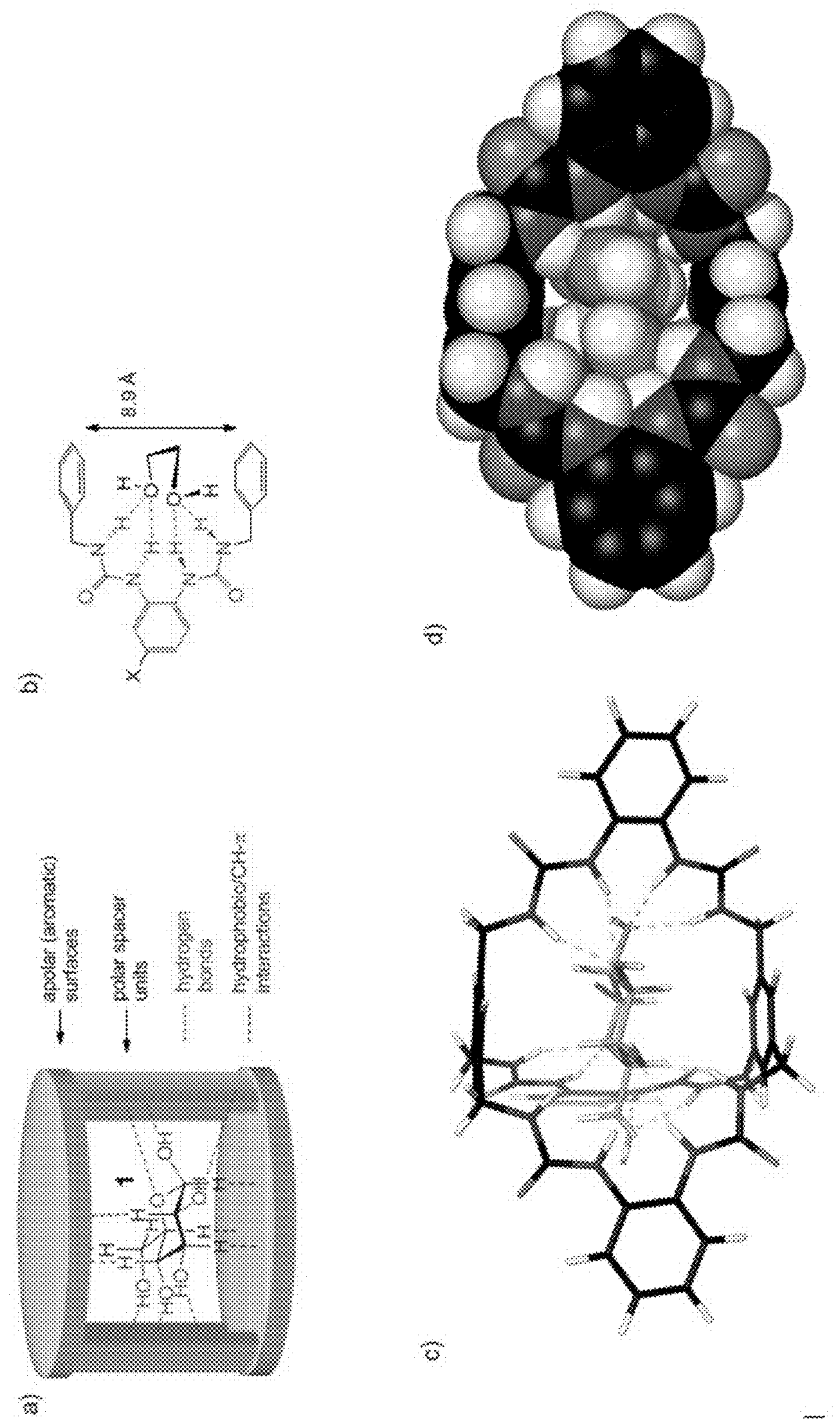
FIG. 1 shows schematic illustrations of the key interactions made between the target saccharide and the compounds of the present invention (FIGS. 1*a* and 1*b*), as well as molecular models of a ground state conformation of one particular compound of the present invention with glucose (FIGS. 1*c* and 1*d*).

Without wishing to be bound by theory, it is believed that one guiding principle in the design of the compounds of the present invention is complementarity. Suitably, both polar and apolar groups of the compounds of the present invention are positioned to make favourable contacts with the target saccharide. For instance, the substituent groups C and D are capable of making hydrophobic/CH-π contacts with axial CH groups of the saccharide, while the spacer groups (e.g. the bis-urea based motifs) are capable of forming hydrogen bond interactions to –0- and —OH units of the saccharide. Furthermore, the bis-urea based spacer groups of the compounds of the present invention also help to maintain a well-defined 'cavity', holding substituent groups C and D the correct distance apart for successful saccharide binding interactions to occur (i.e. between 8 and 10 Å, suitably, approximately 9 Å). For illustration purposes only, FIG. 1 shows both schematic illustrations of the key interactions made between the target saccharide and the compounds of the present invention (FIGS. 1*a* and 1*b*), as well as molecular models of a ground state conformation of one particular compound of the present invention with glucose (FIGS. 1*c* and 1*d*). In FIG. 1*c*, ten intermolecular NH . . . O hydrogen bonds (with a distance of between 1.9 and 2.2 Å) can be seen, and FIG. 1*d* further depicts the close CH-π contacts made between the saccharide and compound of the present invention.

The compounds of the present invention also benefit from high levels of water solubility, thereby allowing them to readily dissolve in, and thus be compatible for use in, the various aqueous media in which target saccharides commonly exist (i.e. in the bloodstream or in fermentation media). Thus, in an embodiment, the compounds of the present invention are water soluble. Suitably, the compounds of the present invention have water solubility of at least about 1 μM. More suitably, the compounds of the present invention have water solubility of at least about 100 μM. Yet more suitably, the compounds of the present invention have water solubility of at least about 500 μM. Even more suitably, the compounds of the present invention have water solubility of at least about 1 mM. Most suitably, the compounds of the present invention have water solubility of at least about 2 mM.

In another embodiment, the compounds of the present invention have water solubility of between 1 μM and 50 mM. Suitably, the compounds of the present invention have water solubility of between 1 μM and 20 mM. More suitably, the compounds of the present invention have water solubility of between 100 μM and 20 mM. Most suitably, the compounds of the present invention have water solubility of between 100 μM and 10 mM.

In a further embodiment, there is provided a compound of Formula (I), or a salt, hydrate or solvate thereof, as shown below:

Formula (I)

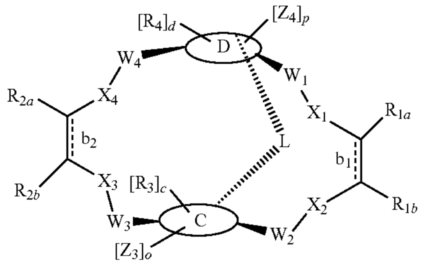

wherein:

bonds $b_1$ and $b_2$ are independently selected from a single bond or double bond;

$R_{1a}$, $R_{1b}$, $R_{2a}$ and $R_{2b}$ are independently selected from hydrogen, carbonyl, (1-8C)alkyl, (3-10C)cycloalkyl, aryl, heteroaryl and heterocyclyl, each of which, other than hydrogen and carbonyl, is optionally substituted by one or more substituent groups selected from (1-4C) alkyl, halo, (1-4C)haloalkyl, (1-4C)haloalkoxy, (1-4C) alkoxy, (1-4C)alkylamino, amino, cyano, hydroxyl, carboxy, carbamoyl, sulfamoyl, mercapto and a hydrophilic substituent group; or $R_{1a}$ and $R_{1b}$ are linked so as to form a group of the formula:

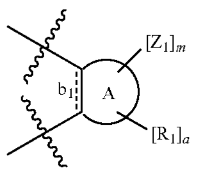

and/or $R_{2a}$ and $R_{2b}$ are linked so as to form a group of the formula:

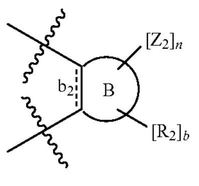

wherein:

denotes the point of attachment;

bonds $b_1$ and $b_2$ are as described above;

Rings A and B are independently selected from aryl, heteroaryl, heterocyclyl, cycloalkyl and cycloalkenyl;

$R_1$ and $R_2$ are independently selected from (1-6C)alkyl, halo, (1-4C)haloalkyl, (1-4C)haloalkoxy, (1-6C) alkoxy, (1-4C)alkylamino, amino, cyano, hydroxyl, carboxy, carbamoyl, sulfamoyl and mercapto;

a and b are integers independently selected from 0 to 2;

m and n are integers independently selected from 0 to 2;

$Z_1$ and $Z_2$ are independently selected from a hydrophilic substituent group;

C and D are independently selected from aryl, heteroaryl, heterocyclyl, cycloalkyl, cycloalkenyl and a group of the formula:

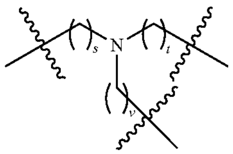

wherein:

s, t and v are integers independently selected from 1 or 2;

denotes the point of attachment;

$R_3$ and $R_4$ are independently selected from halo, (1-4C) alkyl, (1-4C)alkoxy, amino, nitro, (1-4C)alkylamino, (1-4C)dialkylamino, (1-4C)haloalkyl, (1-4C)haloalkoxy, cyano, (2-4C)alkenyl, (2-4C)alkynyl and a group of the formula:

$-L^1-Y^1-Q^1$ wherein:

$L^1$ is absent or a (1-5C)alkylene optionally substituted by one or more substituents selected from (1-2C) alkyl and oxo;

$Y^1$ is absent or selected from a one of the following groups; O, S, SO, $SO_2$, $N(R_a)$, C(O), C(O)O, OC(O), $C(O)N(R_a)$, $N(R_a)C(O)$, $N(R_b)C(O)N(R_a)$, $N(R_a)C(O)O$, $OC(O)N(R_a)$, $S(O)_2N(R_a)$, and $N(R_a)SO_2$, wherein $R_a$ and $R_b$ are each independently selected from hydrogen and (1-4C)alkyl; and $Q^1$ is hydrogen, (1-8C)alkyl, (2-6C)alkenyl, (2-6C) alkynyl, aryl, (3-10C)cycloalkyl, (3-10C)cycloalkenyl, heteroaryl and heterocyclyl; wherein $Q^1$ is optionally further substituted by one or more substituent groups independently selected from (1-4C) alkyl, halo, (1-4C)haloalkyl, (1-4C)haloalkoxy, amino, (1-4C)aminoalkyl, cyano, hydroxy, carboxy, carbamoyl, sulfamoyl, mercapto, ureido, oxy, $NR_cR_d$, $OR^c$, $C(O)R_d$, $C(O)OR_c$, $OC(O)R_c$, $C(O)N(R_d)R_c$, $N(R_d)C(O)R_c$, $S(O)_yR_c$ (where y is 0, 1 or 2), $SO_2N(R_d)R_c$, $N(R_d)SO_2R_c$, $Si(Re)(R_d)R_c$ and $(CH_2)_z NR_dR_c$ (where z is 1, 2 or 3); wherein $R_c$, $R_d$ and $R_e$ are each independently selected from hydrogen, (1-6C)alkyl and (3-6C)cycloalkyl; and $R_c$ and $R_d$ can be linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxyl; or two $R_3$ and/or two $R_4$ groups taken together form a group of the formula:

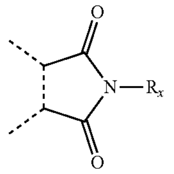

wherein:

$R_x$ is selected from hydrogen and (1-6C)alkyl optionally substituted by one or more substituent groups selected from halo, (1-4C)haloalkyl, (1-4C)haloalkoxy, cyano, hydroxy, sulfamoyl, mercapto, ureido, $NR_fR_g$, $OR_f$, $C(O)R_f$, $C(O)OR_f$, $OC(O)R_f$, $C(O)N(R_g)R_f$ and $N(R_g)C(O)R_f$, wherein $R_f$ and $R_g$ are selected from hydrogen and (1-4C)alkyl; and dashed lines represent the points of attachment to C and/or D;

$W_1$, $W_2$, $W_3$ and $W_4$ are independently selected from $CR_hR_i$, wherein $R_h$ and $R_i$ are selected from hydrogen and (1-2C)alkyl;

$X_1$, $X_2$, $X_3$ and $X_4$ are independently selected from a group of the formula:

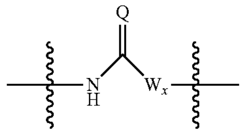

wherein:

denotes the point of attachment;

$W_x$ is selected from O or NH; and

Q is selected from O, S and $NR_j$, wherein $R_j$ is selected from hydrogen, (1-4C)alkyl, aryl, heteroaryl and sulfonyl;

$Z_3$ and $Z_4$ are independently selected from a hydrophilic substituent group;

L is absent or a linker, which optionally bears a hydrophilic substituent group $Z_5$;

c and d are integers independently selected from 0 to 4; and o and p are integers independently selected from 0 to 2;

and wherein the compound of Formula I is optionally attached to a displaceable reporter molecule via one or more of the substituent groups associated with $R_1$, $R_2$, $R_3$, $R_4$, $Z_1$, $Z_2$, $Z_3$, $Z_4$ and/or $Z_5$;

with the proviso that the compound of Formula I comprises at least one hydrophilic substituent group (e.g. $Z_1$, $Z_2$, $Z_3$, $Z_4$ or $Z_5$).

Particular compounds of the invention include, for example, compounds of the Formula I, or salts, hydrates and/or solvates thereof, wherein, unless otherwise stated, each of bonds $b_1$ and $b_2$, Rings A and B, C, D, $R_1$, $R_2$, $R_3$, $R_4$, $W_1$, $W_2$, $W_3$, $W_4$, $X_1$, $X_2$, $X_3$, $X_4$, $Z_1$, $Z_2$, $Z_3$, $Z_4$, $Z_5$, L, a, b, c, d, m, n, o, p and any associated substituent groups has any of the meanings defined hereinbefore or in any of paragraphs (1) to (60) hereinafter:—

(1) bonds $b_1$ and $b_2$ are single bonds;

(2) bonds $b_1$ and $b_2$ are double bonds;

(3) $R_{1a}$, $R_{1b}$, $R_{2a}$ and $R_{2b}$ are independently selected from (1-8C)alkyl, (3-10C)cycloalkyl, aryl, heteroaryl and heterocyclyl, each of which is optionally substituted by one or more substituent groups selected from (1-4C) alkyl, halo, (1-4C)haloalkyl, (1-4C)haloalkoxy, (1-4C) alkoxy, amino, cyano, hydroxyl and a hydrophilic substituent group; or $R_{1a}$ and $R_{1b}$ are linked so as to form a group of the formula:

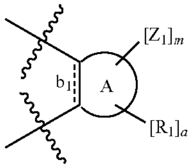

and/or $R_{2a}$ and $R_{2b}$ are linked so as to form a group of the formula:

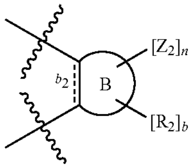

wherein:

∿∿ the point of attachment;

bonds $b_1$ and $b_2$ are as described above;

Rings A and B are independently selected from aryl, heteroaryl, heterocyclyl, cycloalkyl and cycloalkenyl;

$R_1$ and $R_2$ are independently selected from (1-4C) alkyl, halo, (1-4C)haloalkyl, (1-4C)haloalkoxy, (1-4C)alkoxy, (1-4C)alkylamino, amino, cyano, hydroxyl, carboxy, carbamoyl, sulfamoyl and mercapto;

a and b are integers independently selected from 0 to 2;

m and n are integers independently selected from 0 to 2;

$Z_1$ and $Z_2$ are independently selected from hydrophilic substituent groups;

(4) $R_{1a}$, $R_{1b}$, $R_{2a}$ and $R_{2b}$ are independently selected from aryl and heteroaryl, each of which is optionally substituted by one or more substituent groups selected from (1-4C)alkyl, halo, (1-4C)alkoxy, amino or hydroxyl; or $R_{1a}$ and $R_{1b}$ are linked so as to form a group of the formula:

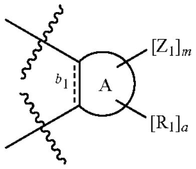

and/or $R_{2a}$ and $R_{2b}$ are linked so as to form a group of the formula:

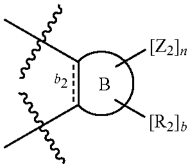

wherein:

∿∿ denotes the point of attachment;

bonds $b_1$ and $b_2$ are as described above;

Rings A and B are independently selected from aryl, heteroaryl, heterocyclyl, cycloalkyl and cycloalkenyl;

$R_1$ and $R_2$ are independently selected from (1-4C) alkyl, halo, (1-4C)haloalkyl, (1-4C)haloalkoxy, (1-4C)alkoxy, (1-4C)alkylamino, amino, cyano, hydroxyl, carboxy, carbamoyl, sulfamoyl and mercapto;

a and b are integers independently selected from 0 to 2;

m and n are integers independently selected from 0 to 2;

$Z_1$ and $Z_2$ are independently selected from hydrophilic substituent groups;

(5) $R_{1a}$ and $R_{1b}$ are linked so as to form a group of the formula:

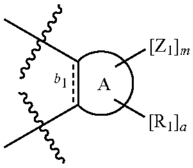

and $R_{2a}$ and $R_{2b}$ are linked so as to form a group of the formula:

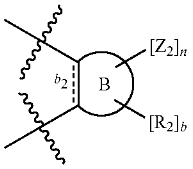

wherein:

∿∿ denotes the point of attachment;

bonds $b_1$ and $b_2$ are as described above;

Rings A and B are independently selected from aryl, heteroaryl, heterocyclyl, cycloalkyl or cycloalkenyl;

$R_1$ and $R_2$ are independently selected from (1-4C) alkyl, halo, (1-4C)haloalkyl, (1-4C)haloalkoxy, (1-4C)alkoxy, (1-4C)alkylamino, amino, cyano, hydroxyl, carboxy, carbamoyl, sulfamoyl and mercapto;

a and b are integers independently selected from 0 to 2;

m and n are integers independently selected from 0 to 2;

$Z_1$ and $Z_2$ are independently selected from hydrophilic substituent groups;

(6) Rings A and B are independently selected from aryl, heteroaryl and heterocyclyl (e.g. pyrrolidinyl);

(7) Rings A and B are independently selected from aryl and heteroaryl;

(8) Rings A and B are aryl;

(9) Rings A and B are independently selected from phenyl, pyridyl, naphthyl, and pyrrolidinyl;

(10) Rings A and B are phenyl or pyrrolidinyl, preferably phenyl;

(11) $R_i$ and $R_2$ are independently selected from (1-4C)alkyl, halo, (1-4C)haloalkyl, (1-4C)haloalkoxy, (1-4C)alkoxy, (1-4C)alkylamino, amino, cyano and hydroxyl;

(12) $R_i$ and $R_2$ are independently selected from (1-4C)alkyl, halo, amino, cyano and hydroxyl;

(13) C and D are independently selected from aryl, heteroaryl, heterocyclyl, cycloalkyl, cycloalkenyl and a group of the formula:

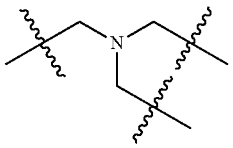 [SMILES: *CN(C*)C*]

wherein  denotes the point of attachment;

(14) C and D are independently selected from aryl, heteroaryl, heterocyclyl, cycloalkyl, cycloalkenyl;

(15) C and D are independently selected from aryl and heteroaryl;

(16) C and D are independently selected from phenyl, naphthenyl and anthracenyl;

(17) C and D are phenyl;

(18) C and D are anthracenyl;

(19) $R_3$ and $R_4$ are independently selected from halo, (1-4C)alkyl, (1-4C)alkoxy, amino, nitro, (1-4C)alkylamino, (1-4C)dialkylamino, (1-4C)haloalkyl, (1-4C)haloalkoxy, cyano, (2-4C)alkenyl, (2-4C)alkynyl and a group of the formula:

$-L^1-Y^1-Q^1$ wherein:

$L^1$ is absent or (1-5C)alkylene;

$Y^1$ is absent or selected from a one of the following groups; O, S, SO, $SO_2$, $N(R_a)$, C(O), C(O)O, OC(O), $C(O)N(R_a)$, $N(R_a)C(O)$, $N(R_b)C(O)N(R_a)$, $N(R_a)C(O)O$, $OC(O)N(R_a)$, $S(O)_2N(R_a)$, and $N(R_a)SO_2$, wherein $R_a$ and $R_b$ are each independently selected from hydrogen and (1-4C)alkyl; and $Q^1$ is hydrogen, (1-8C)alkyl, (2-6C)alkenyl, (2-6C)alkynyl, aryl, (3-10C)cycloalkyl, (3-10C)cycloalkenyl, heteroaryl and heterocyclyl; wherein $Q^1$ is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulfamoyl, mercapto, ureido, oxy, $NR_cR_d$, $OR^c$, $C(O)R_d$, $C(O)OR_c$, $OC(O)R_c$, $C(O)N(R_d)R_c$, $N(R_d)C(O)R_c$, $S(O)_yR_c$ (where y is 0, 1 or 2), $SO_2N(R_d)R_c$, $N(R_d)SO_2R_c$, $Si(Re)(R_d)R_c$ and $(CH_2)_zNR_dR_c$ (where z is 1, 2 or 3); wherein $R_c$, $R_d$ and $R_e$ are each independently selected from hydrogen, (1-6C)alkyl or (3-6C)cycloalkyl; and two $R_3$ and/or two $R_4$ groups taken together may form a group of the formula:

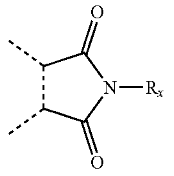

wherein:

$R_x$ is selected from hydrogen and (1-6C)alkyl optionally substituted by one or more substituent groups selected from halo, (1-4C)haloalkyl, (1-4C)haloalkoxy, cyano, hydroxy, sulfamoyl, mercapto, ureido, $NR_fR_g$, $OR_f$, $C(O)R_f$, $C(O)OR_f$, $OC(O)R_f$, $C(O)N(R_g)R_f$ and $N(R_g)C(O)R_f$, wherein $R_f$ and $R_g$ are selected from hydrogen and (1-4C)alkyl; and dashed lines represent the points of attachment to C and/or D;

(20) $R_3$ and $R_4$ are independently selected from halo, (1-4C)alkyl, (1-4C)alkoxy, amino, nitro, (1-4C)alkylamino, (1-4C)dialkylamino, (1-4C)haloalkyl, (1-4C)haloalkoxy, cyano, (2-4C)alkenyl, (2-4C)alkynyl and a group of the formula:

$-L^1-Y^1-Q^1$ wherein:

$L^1$ is absent or a (1-5C)alkylene;

$Y^1$ is absent or selected from a one of the following groups; O, S, SO, $SO_2$, $N(R_a)$, C(O), C(O)O, OC(O), $C(O)N(R_a)$ and $N(R_a)C(O)$, wherein $R_a$ is selected from hydrogen and (1-4C)alkyl; and $Q^1$ is hydrogen, (1-8C)alkyl, (2-6C)alkenyl, (2-6C)alkynyl, aryl, (3-10C)cycloalkyl, (3-10C)cycloalkenyl, heteroaryl and heterocyclyl; wherein $Q^1$ is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, $NR_cR_d$, $OR_c$, $C(O)R_d$, $C(O)OR_c$, $OC(O)R_c$, $C(O)N(R_d)R_c$ and $N(R_d)C(O)R_c$; wherein $R_c$ and $R_d$ are each independently selected from hydrogen and (1-6C)alkyl; and two $R_3$ and/or two $R_4$ groups taken together may form a group of the formula:

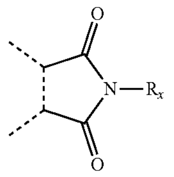

wherein:

$R_x$ is selected from hydrogen and (1-6C)alkyl optionally substituted by one or more substituent groups selected from halo, (1-4C)haloalkyl, (1-4C)haloalkoxy, cyano, hydroxy, sulfamoyl, mercapto, ureido, $NR_fR_g$, $OR_f$, $C(O)R_f$, C(O)

$OR_f$, $OC(O)R_f$, $C(O)N(R_g)R_f$ and $N(R_g)C(O)R_f$, wherein $R_f$ and $R_g$ are selected from hydrogen and (1-4C)alkyl; and dashed lines represent the points of attachment to C and/or D;

(21) $R_3$ and $R_4$ are independently selected from halo, (1-4C)alkyl, (1-4C)alkoxy, amino, nitro, (1-4C)alkylamino, (1-4C)dialkylamino, (1-4C)haloalkyl, (1-4C) haloalkoxy, cyano, (2-4C)alkenyl, (2-4C)alkynyl and a group of the formula:

$-L^1-Y^1-Q^1$ wherein:

$L^1$ is absent or (1-5C)alkylene;

$Y^1$ is absent or selected from a one of the following groups; O, $N(R_a)$, C(O), C(O)O, OC(O), $C(O)N(R_a)$ and $N(R_a)C(O)$, wherein $R_a$ is selected from hydrogen and (1-4C)alkyl; and $Q^1$ is hydrogen, (1-8C)alkyl, aryl, (3-10C)cycloalkyl, (3-10C)cycloalkenyl, heteroaryl and heterocyclyl; wherein $Q^1$ is optionally further substituted by one or more substituent groups independently selected from (1-4C)alkyl, halo, (1-4C)haloalkyl, (1-4C)haloalkoxy, amino, (1-4C) aminoalkyl, cyano, hydroxy, $NR_cR_d$, $OR_c$, $C(O)R_d$, $C(O)OR_c$, $OC(O)R_c$, $C(O)N(R_d)R_c$ and $N(R_d)C(O)R_c$; wherein $R_c$ and $R_d$ are each independently selected from hydrogen and (1-6C) alkyl; and two $R_3$ and/or two $R_4$ groups taken together may form a group of the formula:

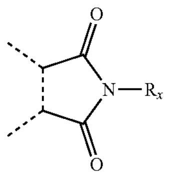

wherein:

$R_x$ is selected from hydrogen and (1-6C)alkyl optionally substituted by one or more substituent groups selected from halo, (1-4C)haloalkyl, $NR_fR_g$, $OR_f$, $C(O)R_f$, $C(O)OR_f$ and $C(O)N(R_g)R_f$, wherein $R_f$ and $R_g$ are selected from hydrogen and (1-4C)alkyl; and dashed lines represent the points of attachment to C and/or D;

(22) $R_3$ and $R_4$ are independently selected from halo, (1-4C)alkyl, (1-4C)alkoxy, amino, nitro, (1-4C)alkylamino, (1-4C)dialkylamino, (1-4C)haloalkyl, (1-4C) haloalkoxy, cyano, (2-4C)alkenyl, (2-4C)alkynyl and a group of the formula:

$-L^1-Y^1-Q^1$ wherein:

$L^1$ is absent or a (1-5C)alkylene optionally substituted by one or more substituents selected from (1-2C)alkyl and oxo;

$Y^1$ is absent or selected from a one of the following groups; O, S, SO, $SO_2$, $N(R_a)$, C(O), C(O)O, OC(O), $C(O)N(R_a)$, $N(R_a)C(O)$, $N(R_b)C(O)N(R_a)$, $N(R_a)C(O)O$, $OC(O)N(R_a)$, $S(O)_2N(R_a)$, and $N(R_a)SO_2$, wherein $R_a$ and $R_b$ are each independently selected from hydrogen and (1-4C) alkyl; and $Q^1$ is hydrogen, (1-8C)alkyl, (2-6C)alkenyl, (2-6C) alkynyl, aryl, (3-10C)cycloalkyl, (3-10C)cycloalkenyl, heteroaryl and heterocyclyl; wherein $Q^1$ is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulfamoyl, mercapto, ureido, oxy, $NR_cR_d$, $OR_c$, $C(O)R_d$, $C(O)OR_c$, $OC(O)R_c$, $C(O)N(R_d)R_c$, $N(R_d)C(O)R_c$, $S(O)_yR_c$ (where y is 0, 1 or 2), $SO_2N(R_d)R_c$, $N(R_d)SO_2R_c$, $Si(Re)(R_d)R_c$ and $(CH_2)_zNR_dR_c$ (where z is 1, 2 or 3); wherein $R_c$, $R_d$ and $R_e$ are each independently selected from hydrogen, (1-6C)alkyl and (3-6C)cycloalkyl; and $R_c$ and $R_d$ can be linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C) haloalkoxy, (1-4C)alkoxy, (1-4C)alkylamino, amino, cyano and hydroxyl;

(23) $R_3$ and $R_4$ are independently selected from halo, (1-4C)alkyl, (1-4C)alkoxy, amino, nitro, (1-4C)alkylamino, (1-4C)dialkylamino, (1-4C)haloalkyl, (1-4C) haloalkoxy, cyano, (2-4C)alkenyl, (2-4C)alkynyl and a group of the formula:

$-L^1-Y^1-Q^1$ wherein:

$L^1$ is absent or (1-5C)alkylene;

$Y^1$ is absent or selected from a one of the following groups; O, S, SO, $SO_2$, $N(R_a)$, C(O), C(O)O, OC(O), $C(O)N(R_a)$ and $N(R_a)C(O)$, wherein $R_a$ is selected from hydrogen and (1-4C)alkyl; and $Q^1$ is hydrogen, (1-8C)alkyl, (2-6C)alkenyl, (2-6C) alkynyl, aryl, (3-10C)cycloalkyl, (3-10C)cycloalkenyl, heteroaryl and heterocyclyl; wherein $Q^1$ is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulfamoyl, mercapto, ureido, oxy, $NR_cR_d$, $OR_E$, $C(O)R_d$, $C(O)OR_c$, $OC(O)R_c$, $C(O)N(R_d)R_c$, $N(R_d)C(O)R_c$, $S(O)_yR_c$ (where y is 0, 1 or 2), $SO_2N(R_d)R_c$, $N(R_d)SO_2R_c$, $Si(Re)(R_d)R_c$ and $(CH_2)_zNR_dR_c$ (where z is 1, 2 or 3); wherein $R_c$, $R_d$ and $R_e$ are each independently selected from hydrogen, (1-6C)alkyl and (3-6C)cycloalkyl;

(24) $R_3$ and $R_4$ are independently selected from halo, (1-4C)alkyl, (1-4C)alkoxy, amino, nitro, (1-4C)haloalkyl, (1-4C)haloalkoxy, cyano and a group of the formula:

$-L^1-Y^1-Q^1$ wherein:

$L^1$ is absent or (1-2C)alkylene;

$Y^1$ is absent or selected from a one of the following groups; O, $N(R_a)$, C(O), C(O)O, OC(O), $C(O)N(R_a)$ and $N(R_a)C(O)$, wherein $R_a$ is selected from hydrogen and (1-4C)alkyl; and $Q^1$ is hydrogen, (1-8C)alkyl, aryl, (3-10C)cycloalkyl, heteroaryl and heterocyclyl; wherein $Q^1$ is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, $NR_cR_d$, $OR_c$, $C(O)R_d$, $C(O)OR_c$, $OC(O)R_c$, $C(O)N(R_d)R_c$ and $N(R_d)C(O)R_c$; wherein $R_c$ and $R_d$ are each independently selected from hydrogen and (1-6C)alkyl;

(25) $R_3$ and $R_4$ are independently selected from halo, (1-4C)alkyl, (1-4C)alkoxy, amino, nitro, (1-4C)haloalkyl, (1-4C)haloalkoxy, cyano and a group of the formula:

$-L^1-Y^1-Q^1$ wherein:

$L^1$ is absent or (1-2C)alkylene;

$Y^1$ is absent or selected from a one of the following groups; O, $N(R_a)$, C(O)O and $C(O)N(R_a)$, wherein $R_a$ is selected from hydrogen and (1-4C)alkyl; and $Q^1$ is hydrogen, (1-8C)alkyl, aryl and heteroaryl; wherein $Q^1$ is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, $NR_cR_d$, $OR_c$, $C(O)R_d$, $C(O)OR_c$, $OC(O)R_c$, $C(O)N(R_d)R_c$ and $N(R_d)C(O)R_c$; wherein $R_c$ and $R_d$ are each independently selected from hydrogen and (1-6C)alkyl;

(26) $R_3$ and $R_4$ are independently selected from halo, (1-4C)alkyl, (1-4C)alkoxy, amino, nitro, (1-4C)haloalkyl, (1-4C)haloalkoxy, cyano and a group of the formula:

$-L^1-Y^1-Q^1$ wherein:

$L^1$ is absent or (1-2C)alkylene;

$Y^1$ is absent or selected from a one of the following groups; O, $N(R_a)$, C(O)O and $C(O)N(R_a)$, wherein $R_a$ is selected from hydrogen and (1-4C)alkyl; and $Q^1$ is hydrogen or (1-8C)alkyl; wherein said (1-8C)alkyl is optionally further substituted by one or more substituent groups independently selected from halo, amino, (1-4C)aminoalkyl, hydroxy, $NR_cR_d$, $OR_c$, $C(O)R_d$, $C(O)OR_c$ and $C(O)N(R_d)R_c$; wherein $R_c$ and $R_d$ are each independently selected from hydrogen and (1-2C)alkyl;

(27) $R_3$ and $R_4$ are independently selected from halo, (1-4C)alkyl, (1-4C)alkoxy, amino, nitro, (1-4C)haloalkyl, (1-4C)haloalkoxy and cyano;

(28) $R_3$ and $R_4$ are independently selected from (1-4C)alkyl and (1-4C)alkoxy;

(29) $W_1$, $W_2$, $W_3$ and $W_4$ are independently selected from $CR_hR_i$, wherein $R_h$ and $R_i$ are selected from hydrogen and methyl;

(30) $W_1$, $W_2$, $W_3$ and $W_4$ are each $CH_2$;

(31) $X_1$, $X_2$, $X_3$ and $X_4$ are independently selected from a group of the formula:

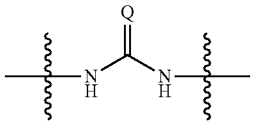

wherein:

∿∿∿ denotes the point of attachment; and

Q is selected from O, S and $NR_j$, wherein $R_j$ is selected from hydrogen, (1-4C)alkyl and aryl;

(32) $X_1$, $X_2$, $X_3$ and $X_4$ are independently selected from a group of the formula:

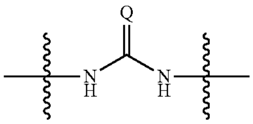

wherein:

∿∿∿ denotes the point of attachment; and

Q is selected from O and S;

(33) $X_1$, $X_2$, $X_3$ and $X_4$ are each a group of the formula:

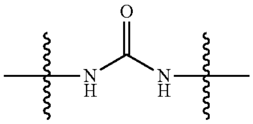 [SMILES: *NC(=O)N*]

wherein:

∿∿∿ denotes the point of attachment;

(34) $Z_1$, $Z_2$, $Z_3$, $Z_4$ and $Z_5$ are independently selected from a hydrophilic substituent group, wherein said hydrophilic substituent comprises one or more hydrophilic functional groups selected from carboxylic acids, carboxylate ions, carboxylate esters, hydroxyl, amines, amides, ethers, ketone and aldehyde groups, ureas, nitro groups, sulphates, sulphonates, phosphates, phosphonates, and combinations thereof;

(35) $Z_1$, $Z_2$, $Z_3$, $Z_4$ and $Z_5$ are independently selected from a hydrophilic substituent group, wherein said hydrophilic substituent comprises one or more hydrophilic functional groups selected from carboxylic acids, carboxylate ions, carboxylate esters, hydroxyl, amines, amides, ethers, ketone groups, aldehyde groups and combinations thereof;

(36) $Z_1$, $Z_2$, $Z_3$, $Z_4$ and $Z_5$ are independently selected from a hydrophilic substituent group, wherein said hydrophilic substituent comprises one or more hydrophilic functional groups selected from carboxylic acids, carboxylate ions, hydroxyls, amines and combinations thereof;

(37) $Z_1$, $Z_2$, $Z_3$, $Z_4$ and $Z_5$ are independently selected from a hydrophilic polymer (e.g. polyethylene glycol), a hydrophilic dendritic group or $C(O)OM_1$, wherein $M_1$ is hydrogen or a cation (e.g. Na, Li, $NH_4$);

(38) $Z_1$, $Z_2$, $Z_3$, $Z_4$ and $Z_5$ are independently selected from a hydrophilic polymer (e.g. polyethylene glycol) or a hydrophilic dendritic group;

(39) $Z_1$, $Z_2$, $Z_3$, $Z_4$ and $Z_5$ are independently selected from a hydrophilic polymer (e.g. polyethylene glycol) or dendritic group comprising between 1 and 5 generations of building units and a terminal functional group $T_1$, wherein each building unit is independently selected from a group of Formula A:

$-L^2-L^{2a}-V-$ (Formula A)

wherein:

$L^2$ is selected from O, C(O), C(O)O, OC(O), $C(O)N(R_r)$, $N(R_r)C(O)$, $N(R_s)C(O)N(R_r)$, $N(R_r)C(O)O$, $OC(O)N(R_r)$, $S(O)_2N(R_r)$, and $N(R_r)SO_2$, wherein $R_{r'}$ and $R_s$ are each independently selected from hydrogen and (1-4C)alkyl;

$L^{2a}$ is a bond or a (1-4C)alkylene;

V is absent or a group of the formula:

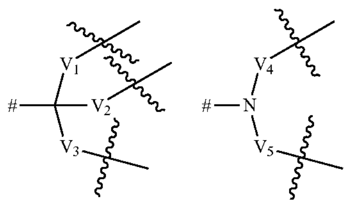

wherein:

$V_1$, $V_2$, $V_3$, $V_4$ and $V_5$ are independently selected from a (1-6C)alkylene optionally interrupted by one or more groups selected from O, S and $NR_t$, wherein $R_t$ is selected from hydrogen and (1-2C) alkyl;

# denotes the point of attachment to one of Rings A, B, C, D or E;

∿∿∿ denotes the point of attachment to either another group of Formula A or a terminal functional group $T_1$; and the terminal functional group $T_1$ is selected from $NH_2$, OH, $C(O)OM_x$, $C(O)OR_u$ and $C(O)NHR_u$, wherein $R_u$ is selected from hydrogen, (1-4C)alkyl, (1-4C) alkoxy, hydroxy(1-4C)alkyl, (2-4C)alkenyl, (2-4C) alkynyl, ethylene glycol and polyethylene glycol, and wherein $M_x$ is a cation (e.g. Na, Li, $NH_4$);

(40) $Z_1$, $Z_2$, $Z_3$, $Z_4$ and $Z_5$ are independently selected from a hydrophilic polymer (e.g. polyethylene glycol) or a dendritic group comprising between 1 and 5 generations of building units and a terminal functional group $T_1$, wherein each building unit is independently selected from a group of Formula A:

$-L^2-L^{2a}-V-$ (Formula A)

wherein:

$L^2$ is selected from O, C(O), C(O)O, OC(O), C(O)N($R_{r'}$) and N($R_{r'}$)C(O), wherein $R_{r'}$ is selected from hydrogen and (1-4C)alkyl;

$L^{2a}$ is a bond or a (1-4C)alkylene;

V is absent or a group of the formula:

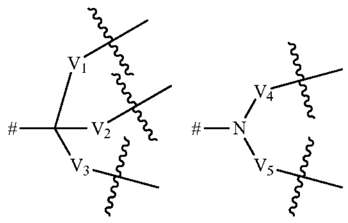

wherein:

$V_1$, $V_2$, $V_3$, $V_4$ and $V_5$ are independently selected from a (1-6C)alkylene optionally interrupted by one or more groups selected from O, S and $NR_t$, wherein $R_t$ is selected from hydrogen and (1-2C) alkyl;

# denotes the point of attachment to one of Rings A, B, C, D or E;

∿∿∿ denotes the point of attachment to either another group of Formula A or a terminal functional group $T_1$; and the terminal functional group $T_1$ is selected from OH, $C(O)OM_x$, $C(O)OR_u$ and $C(O)NHR_u$, wherein $R_u$ is selected from hydrogen, (1-4C)alkyl, (1-4C)alkoxy, hydroxy(1-4C)alkyl, (2-4C)alkenyl, (2-4C)alkynyl, ethylene glycol and polyethylene glycol, and wherein $M_x$ is a cation (e.g. Na, Li, $NH_4$);

(41) $Z_1$, $Z_2$, $Z_3$, $Z_4$ and $Z_5$ are independently selected from a dendritic group comprising between 1 and 4 generations of building units and a terminal functional group $T_1$, wherein each building unit is independently selected from a group of Formula A:

$-L^2-L^{2a}-V-$ (Formula A)

wherein:

$L^2$ is selected from O, C(O), C(O)O, OC(O), C(O)N($R_{r'}$) and N($R_{r'}$)C(O), wherein $R_{r'}$ is selected from hydrogen and (1-4C)alkyl;

$L^{2a}$ is a bond or a (1-4C)alkylene;

V is absent or a group of the formula:

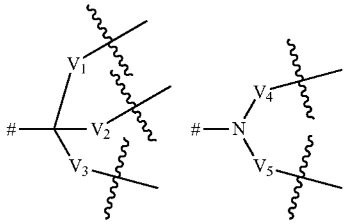

wherein:

$V_1$, $V_2$, $V_3$, $V_4$ and $V_5$ are independently selected from a (1-6C)alkylene optionally interrupted by one or more groups selected from O and $NR_t$, wherein $R_t$ is selected from hydrogen and (1-2C) alkyl;

# denotes the point of attachment to one of Rings A, B, C, D or E;

∿∿∿ denotes the point of attachment to either another group of Formula A or a terminal functional group $T_1$; and the terminal functional group $T_1$ is selected from OH, $C(O)OM_x$, $C(O)OR_u$ and $C(O)NHR_u$, wherein $R_u$ is selected from hydrogen, (1-4C)alkyl, (1-4C)alkoxy and hydroxy(1-4C)alkyl, wherein $M_x$ is a cation (e.g. Na, Li, $NH_4$);

(42) $Z_1$, $Z_2$, $Z_3$, $Z_4$ and $Z_5$ are independently selected from a hydrophilic polymer or a dendritic group comprising between 1 and 4 generations of building units and a terminal functional group $T_1$, wherein each building unit is independently selected from a group of Formula A:

$-L^2-L^{2a}-V-$ (Formula A)

wherein:

$L^2$ is selected from O, C(O), C(O)O and C(O)N($R_{r'}$), wherein $R_{r'}$ is selected from hydrogen and (1-4C) alkyl;

$L^{2a}$ is a bond or a (1-4C)alkylene;

V is absent or a group of the formula:

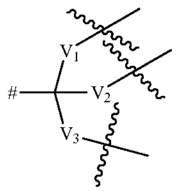

wherein:

$V_1$, $V_2$, and $V_3$ are independently selected from a (1-6C)alkylene optionally interrupted by one or more groups selected from oxygen atoms;

# denotes the point of attachment to one of Rings A, B, C, D or E;

∿∿∿ denotes the point of attachment to either another group of Formula A or a terminal functional group $T_1$; and the terminal functional group $T_1$ is selected from OH, C(O)O$M_x$, C(O)O$R_u$ and C(O)NH$R_u$, wherein $R_u$ is selected from hydrogen, (1-4C)alkoxy and hydroxy(1-4C)alkyl, wherein $M_x$ is a cation (e.g. Na, Li, $NH_4$);

(43) $Z_1$, $Z_2$, $Z_3$, $Z_4$ and $Z_5$ are independently selected from a dendritic group comprising between 1 and 4 generations of building units and a terminal functional group $T_1$, wherein each building unit is independently selected from a group of Formula A:

$-L^2-L^{2a}-V-$ (Formula A)

wherein:

$L^2$ is selected from O, C(O)O and C(O)N($R_r$), wherein $R_r$ is selected from hydrogen and (1-4C)alkyl;

$L^{2a}$ is a bond or a (1-4C)alkylene;

V is a group of the formula:

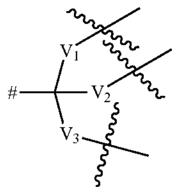

wherein:

$V_1$, $V_2$, and $V_3$ are independently selected from a (1-6C)alkylene optionally interrupted by one or more groups selected from oxygen atoms;

# denotes the point of attachment to one of Rings A, B, C, D or E;

∿∿∿ denotes the point of attachment to either another group of Formula A or a terminal functional group $T_1$; and the terminal functional group $T_1$ is selected from OH and C(O)O$M_x$, wherein $M_x$ is a cation (e.g. Na, Li, $NH_4$);

(44) $Z_1$, $Z_2$, $Z_3$, $Z_4$ and $Z_5$ are independently selected from a dendritic group comprising between 1 and 3 generations of building units and a terminal functional group $T_1$, wherein each building unit is independently selected from a group of Formula A:

$-L^2-L^{2a}-V-$ (Formula A)

wherein:

$L^2$ is C(O)N($R_r$), wherein $R_r$ is selected from hydrogen and (1-4C)alkyl;

$L^{2a}$ is a bond or a (1-2C)alkylene;

V is a group of the formula:

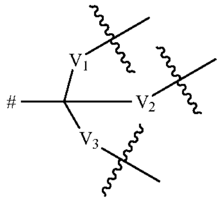

wherein:

$V_1$, $V_2$, and $V_3$ are independently selected from a (1-4C)alkylene optionally interrupted by one or more groups selected from oxygen atoms;

# denotes the point of attachment to one of Rings A, B, C, D or E;

∿∿∿ denotes the point of attachment to either another group of Formula A or a terminal functional group $T_1$; and the terminal functional group $T_1$ is selected is C(O)O$M_x$, wherein $M_x$ is a cation (e.g. Na, Li, $NH_4$);

(45) L is absent or a linker of between 8 and 12 atoms in length (e.g. 10 atoms in length), which optionally bears a hydrophilic substituent group $Z_5$;

(46) L is absent;

(47) L is a linker of between 8 and 12 atoms in length (e.g. 10 atoms in length), which optionally bears a hydrophilic substituent group $Z_5$;

(48) L is absent or selected from a group of the formula:

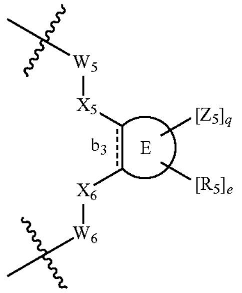

wherein:

∿∿∿ denotes the point of attachment;

$W_5$ and $W_6$ are independently selected from $CR_kR_l$, wherein $R_k$ and $R_l$ are selected from hydrogen and (1-2C)alkyl;

$X_5$ and $X_6$ are independently selected from a group of the formula:

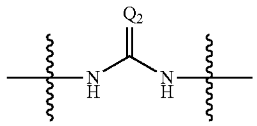

wherein:

denotes the point of attachment; and $Q_2$ is selected from O, S and $NR_m$, wherein $R_m$, is selected from hydrogen, (1-4C)alkyl, aryl, heteroaryl and sulfonyl;

bond $b_3$ is a single or double bond;

Ring E is selected from aryl, heteroaryl, heterocyclyl, cycloalkyl and cycloalkenyl;

$R_5$ is selected from (1-4C)alkyl, halo, (1-4C)haloalkyl, (1-4C)haloalkoxy, (1-4C)alkoxy, (1-4C) alkylamino, amino, cyano, hydroxyl, carboxy, carbamoyl, sulfamoyl and mercapto;

$Z_5$ is a hydrophilic substituent group as defined herein;

q is an integer from 0 to 2; and e is an integer from 0 to 2;

(49) L is absent or selected from a group of the formula:

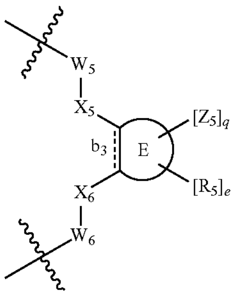

wherein:

denotes the point of attachment;

$W_5$ and $W_6$ are $CH_2$;

$X_5$ and $X_6$ are independently selected from a group of the formula:

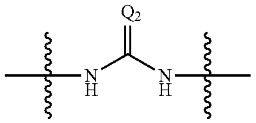

wherein:

denotes the point of attachment; and $Q_2$ is selected from O or S;

bond $b_3$ is a single or double bond;

Ring E is selected from aryl and heteroaryl; and $R_5$ is selected from (1-4C)alkyl, halo, (1-4C)haloalkyl, (1-4C)haloalkoxy, (1-4C)alkoxy, (1-4C) alkylamino, amino, cyano, hydroxyl, carboxy, carbamoyl, sulfamoyl and mercapto;

$Z_5$ is a hydrophilic substituent group as defined herein;

q is an integer from 0 to 1; and e is an integer from 0 to 1;

(50) L is absent or selected from a group of the formula:

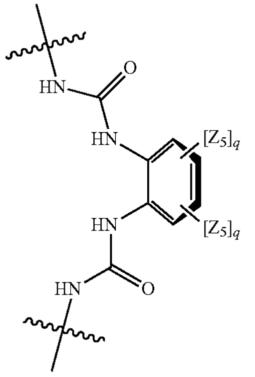

wherein:

$R_5$ is selected from (1-4C)alkyl, halo, (1-4C)haloalkyl, (1-4C)haloalkoxy, (1-4C)alkoxy, (1-4C) alkylamino, amino, cyano, hydroxyl, carboxy, carbamoyl, sulfamoyl and mercapto;

$Z_5$ is a hydrophilic substituent group as defined herein;

q is an integer from 0 to 1; and e is an integer from 0 to 1;

(51) L is absent or selected from a group of the formula:

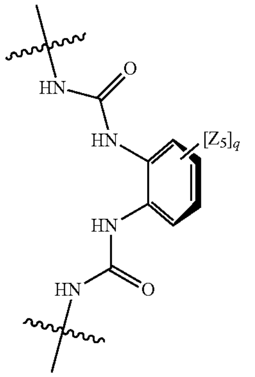

wherein:

$R_5$ is selected from (1-4C)alkyl, halo, (1-4C)haloalkyl, (1-4C)haloalkoxy, (1-4C)alkoxy, (1-4C) alkylamino, amino, cyano, hydroxyl, carboxy, carbamoyl, sulfamoyl and mercapto;

$Z_5$ is a hydrophilic substituent group as defined herein; and q is 1;

(52) c and d are integers independently selected from 0 to 4 (e.g. 0 to 3);

(53) c and d are integers independently selected from 1 to 3;

(54) one of c and d is 3 and the other is an integer selected from 0 to 3;

(55) one of c and d is 3 and the other is an integer selected from 1 to 3;

(56) c and d are both 3;

(57) a and b are integers independently selected from 0 to 1;

(58) a and b are 0;

(59) m, n, o and p are integers independently selected from 0 to 1;

(60) m and n are 1 and o and p are 0.

In paragraphs (39) to (44) above, the term "generation" will be readily understood to refer to the number of layers of building units (e.g. groups of Formula A) that make up the dendritic group. The term "generation" is a term of the art commonly used in the field of dendrimer chemistry and will be readily understood by the skilled person. For example, a one generation dendritic group will be understood to have one layer (generation) of building units, e.g. –[[building unit]]. A two generation dendritic group has two layers of building units, for example, when the building units have trifunctional branching points, the dendritic group may be: –[[building unit][building unit]$_3$], a three generation dendritic group has three layers of building units, for example –[[building unit][building unit]$_3$[building unit]$_9$]. In this regard, the person skilled in the art will readily appreciate that when the dendritic group comprises 1 generation of building units of Formula A, ∿∿∿ denotes the attachment point to the terminal functional group $T_1$. Moreover, when the dendritic group comprises 2 generations of building units of Formula A, the person skilled in the art will appreciate that for the first generation of building units of Formula A, ∿∿∿ denotes the attachment point to a second generation of building units of Formula A, and for the second generation of building units of Formula A, ∿∿∿ denotes the attachment point to the terminal functional group $T_1$.

For illustration purposes only, below there is provided a schematic representations of both a dendritic group comprising one generation of building units of Formula A and a dendritic group comprising two generations of building units of Formula A. In the schematic, A corresponds to a building unit of Formula A with a trifunctional branching point, as described hereinabove, and $T_1$ corresponds to the terminal functional group $T_1$, as described hereinabove.

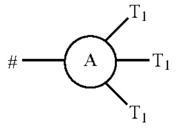

Dendritric group comprising one generation of building units

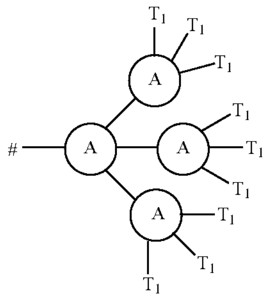

Dendritic group comprising two generations of building units

In an embodiment, at least one of integers m, n, o or p is 1 or more. In this regard, it will be understood that at least one of $Z_1$, $Z_2$, $Z_3$, $Z_4$ or $Z_5$ is present.

In another embodiment, a (displaceable) reporter molecule is attached to the compound of Formula I via one or more of the substituent groups $R_1$, $R_2$, $R_3$, $R_4$, $Z_1$, $Z_2$, $Z_3$, $Z_4$ or $Z_5$. Suitably, the (displaceable) reporter molecule is attached to the compound of Formula I via one or more of the hydrophilic substituent groups $Z_1$, $Z_2$, $Z_3$, $Z_4$ or $Z_5$. It will be understood that the (displaceable) reporter molecule may be attached to one or more of the substituent groups $R_1$, $R_2$, $R_3$, $R_4$, $Z_1$, $Z_2$, $Z_3$, $Z_4$ or $Z_5$ directly or via a suitable linker (e.g. a polyethylene glycol linker).

Suitably, the (displaceable) reporter molecule is attached to one or more of the substituent groups $Z_1$, $Z_2$, $Z_3$, $Z_4$ or $Z_5$.

Suitably, the (displaceable) reporter molecule is an aromatic molecule and/or dye molecule. More suitably, the (displaceable) reporter molecule is an aromatic molecule, most suitably, a fluorescent aromatic molecule (e.g. fluoresceinamine or tetramethylrhodamine isothiocyanate).

As defined hereinabove, the compound of Formula I may be optionally attached to a substituent group of Formula A1 at a position associated with one or more of the substituent groups $R_{1a}$, $R_{1b}$, $R_{2a}$, $R_{2b}$, $R_1$, $R_2$, $R_3$, $R_4$, $Z_1$, $Z_2$, $Z_3$, $Z_4$ and/or $Z_5$ (e.g. one or more of the substitutent groups $R_1$ or $R_2$ or one or more of the substituent groups $R_3$ or $R_4$). It will therefore be appreciated that the substituent group of Formula A1 may either take the place of the one or more substituent groups $R_{1a}$, $R_{1b}$, $R_{2a}$, $R_{2b}$, $R_1$, $R_2$, $R_3$, $R_4$, $Z_1$, $Z_2$, $Z_3$, $Z_4$ and/or $Z_5$, or the substituent group of Formula A1 may be attached to the one or more substituent groups $R_{1a}$, $R_{1b}$, $R_{2a}$, $R_{2b}$, $R_1$, $R_2$, $R_3$, $R_4$, $Z_1$, $Z_2$, $Z_3$, $Z_4$ and/or $Z_5$. Suitably, when present, the substituent group of Formula A1 takes the place of the one or more substituent groups $R_{1a}$, $R_{1b}$, $R_{2a}$, $R_{2b}$, $R_1$, $R_2$, $R_3$, $R_4$, $Z_1$, $Z_2$, $Z_3$, $Z_4$ and/or $Z_5$.

In an embodiment, the compound of Formula I may be optionally attached to a substituent group of Formula A1 at a position associated with one or more of the substituent groups $R_{1a}$, $R_{1b}$, $R_{2a}$, $R_{2b}$, $R_1$, $R_2$, $R_3$ and/or $R_4$ (e.g. one or more of the substitutent groups $R_1$ or $R_2$ and/or one or more of the substituent groups $R_3$ or $R_4$), wherein the substituent group of Formula A1 is of the formula show below:

$X_{2a}$-$L_{2a}$-$Z_{2a}$ (Formula A1)

wherein $X_{2a}$ is absent or selected from O, S, SO, $SO_2$, $N(R^{x2})$, C(O), C(O)O, OC(O), $C(O)N(R^{x2})$ and $N(R^{x2})C(O)$, wherein $R^{x2}$ is selected from hydrogen and (1-4C)alkyl;

$L_{2a}$ is absent or selected from (1-20C)alkylene, (1-20C) alkylene oxide, (1-20C)alkenyl and (1-20C)alkynyl, each of which being optionally substituted by one or more substituents selected from (1-2C)alkyl, aryl and oxo; and $Z_{2a}$ is selected from carboxy, carbamoyl, sulphamoyl, mercapto, amino, azido, (1-4C)alkenyl, (1-4C)alkynyl, $NR^{xc}R^{xd}$, $OR^{xc}$, $ONR^{xc}R^{xd}$, $C(O)X_a$, $C(O)OR^{xf}$, N═C═O, $NR^{xc}C(o)CH_2X_b$, $C(O)N(R^e)NR_{xc}R^{xd}$, $S(O)_yX_a$ (where y is 0, 1 or 2), $SO_2N(R^{xe})NR^{xc}R^{xd}$, $Si(R^{xg})(R^{Xh})R^{xi}$ and an amino acid;

wherein:

$X_a$ is hydrogen or a leaving group (e.g. halo or $CF_3$);

$X_b$ is a halo (e.g. iodo);

$R^{xc}$, $R^{xd}$ and $R^{xe}$ are each independently selected from hydrogen and (1-6C)alkyl;

$R^{xf}$ is selected from hydrogen and (1-6C)alkyl, or $R^{xf}$ is a substituent group that renders $C(O)OR^{xf}$, when taken as a whole, to be an activated ester (e.g a hydroxysuccinimide ester, a hydroxy-3-sulfo-succinimide ester or a pentafluorophenyl ester);

$R^{xg}$, $R^{xh}$ and $R^{xi}$ are each independently selected from (1-4C)alkyl, hydroxy, halo and (1-4C)alkoxy.

In another embodiment, the compound of Formula I may be optionally attached to a substituent group of Formula A1 at a position associated with one or more of the substituent groups $R_{1a}$, $R_{1b}$, $R_{2a}$, $R_{2b}$, $R_1$, $R_2$, $R_3$ and/or $R_4$, wherein the substituent group of Formula A1 is of the formula show below:

$X_{2a}$-$L_{2a}$-$Z_{2a}$ (Formula A1)

wherein $X_{2a}$ is absent or selected from O, S, SO, $SO_2$, $N(R^{x2})$, C(O), C(O)O, OC(O), $C(O)N(R^{x2})$ and $N(R^{x2})C(O)$, wherein $R^{x2}$ is selected from hydrogen and (1-4C)alkyl;

$L_{2a}$ is absent or selected from (1-20C)alkylene, (1-20C) alkylene oxide, (1-20C)alkenyl and (1-20C)alkynyl, each of which being optionally substituted by one or more substituents selected from (1-2C)alkyl, aryl and oxo; and $Z_{2a}$ is selected from carboxy, carbamoyl, sulphamoyl, mercapto, amino, azido, (1-4C)alkenyl, (1-4C)alkynyl, $NR^{xc}R^{xd}$, $OR^{xc}$, $C(O)X_a$, $C(O)OR^{xf}$, N═C═O, $NR^{xc}C(O)CH_2X_b$ and C(O) N $(R^{xe})NR^{Xc}R^{Xd}$;

wherein:

$X_a$ is hydrogen or a leaving group (e.g. halo or $CF_3$);

$X_b$ is a halo (e.g. iodo);

$R^{xc}$, $R^{xd}$ and $R^{xe}$ are each independently selected from hydrogen and (1-6C)alkyl;

$R^{xf}$ is selected from hydrogen and (1-6C)alkyl, or $R^{xf}$ is a substituent group that renders $C(O)OR^{xf}$, when taken as a whole, to be an activated ester (e.g a hydroxysuccinimide ester, a hydroxy-3-sulfo-succinimide ester or a pentafluorophenyl ester);

$R^{xg}$, $R^{xh}$ and $R^{xi}$ are each independently selected from (1-4C)alkyl, hydroxy, halo and (1-4C)alkoxy.

In a further embodiment, the compound of Formula I may be optionally attached to a substituent group of Formula A1 at a position associated with one or more of the substituent groups $R_{1a}$, $R_{1b}$, $R_{2a}$, $R_{2b}$, $R_1$, $R_2$, $R_3$ and/or $R_4$, wherein the substituent group of Formula A1 is of the formula show below:

$$X_{2a}\text{-}L_{2a}\text{-}Z_{2a} \quad \text{(Formula A1)}$$

wherein $X_{2a}$ is absent or selected from O, $N(R^2)$, C(O)O, OC(O), $C(O)N(R^2)$ and $N(R^{x2})C(O)$, wherein $R^{x2}$ is selected from hydrogen and (1-4C)alkyl;

$L_{2a}$ is absent or selected from (1-20C)alkylene, (1-20C) alkylene oxide, (1-20C)alkenyl and (1-20C)alkynyl, each of which being optionally substituted by one or more substituents selected from (1-2C)alkyl and oxo; and $Z_{2a}$ is selected from carboxy, carbamoyl, sulphamoyl, mercapto, amino, azido, (1-4C)alkenyl, (1-4C)alkynyl, $NR^{xc}R^{xd}$, $OR^{xc}$, $C(O)OR^{xf}$ and N═C═O;

wherein:

$R^{xc}$ and $R^{xd}$ are each independently selected from hydrogen and (1-6C)alkyl; and $R^{xf}$ is selected from hydrogen and (1-6C)alkyl, or $R^{xf}$ is a substituent group that renders $C(O)OR^{xf}$, when taken as a whole, to be an activated ester (e.g a hydroxysuccinimide ester, a hydroxy-3-sulfo-succinimide ester or a pentafluorophenyl ester).

In yet a further embodiment, the compound of Formula I may be optionally attached to a substituent group of Formula A1 at a position associated with one or more of the substituent groups $R_{1a}$, $R_{1b}$, $R_{2a}$, $R_{2b}$, $R_1$, $R_2$, $R_3$ and/or $R_4$, wherein the substituent group of Formula A1 is of the formula show below:

$$X_{2a}\text{-}L_{2a}\text{-}Z_{2a} \quad \text{(Formula A1)}$$

wherein $X_{2a}$ is absent or selected from O, $N(R^2)$, C(O)O and $C(O)N(R^2)$, wherein $R^2$ is selected from hydrogen and (1-4C)alkyl;

$L_{2a}$ is absent or selected from (1-10C)alkylene, (1-10C) alkylene oxide, (1-10C)alkenyl and (1-10C)alkynyl, each of which being optionally substituted by one or more substituents selected from (1-2C)alkyl and oxo; and $Z_{2a}$ is selected from carboxy, carbamoyl, sulphamoyl, mercapto, amino, azido, (1-4C)alkenyl, (1-4C)alkynyl, $NR^{xc}R^{xd}$, $OR^{xc}$, $C(O)OR^{xf}$ and N═C═O;

wherein:

$R^{xc}$ and $R^{xd}$ are each independently selected from hydrogen and (1-6C)alkyl; and $R^{xf}$ is selected from hydrogen, (1-6C)alkyl, succinimide, 3-sulfo-succinimide and pentafluorophenyl.

Suitably, a heteroaryl or heterocyclyl group as defined herein is a monocyclic heteroaryl or heterocyclyl group comprising one, two or three heteroatoms selected from N, O or S.

Suitably, a heteroaryl is a 5- or 6-membered heteroaryl ring comprising one, two or three heteroatoms selected from N, O or S.

Suitably, a heterocyclyl group is a 4-, 5- or 6-membered heterocyclyl ring comprising one, two or three heteroatoms selected from N, O or S. Most suitably, a heterocyclyl group is a 5-, 6- or 7-membered ring comprising one, two or three heteroatoms selected from N, O or S [e.g. morpholinyl (e.g. 4-morpholinyl), pyridinyl, piperazinyl, homopiperazinyl or pyrrolidinonyl].

Suitably an aryl group is phenyl or anthracenyl, most suitably phenyl.

Suitably, bonds $b_1$ and $b_2$ are as defined in any one of paragraphs (1) or (2) above.

Suitably, $R_{1a}$, $R_{1b}$, $R_{2a}$ and $R_{2b}$ are as defined in any one of paragraphs (3) to (5) above.

Most suitably, $R_{1a}$, $R_{1b}$, $R_{2a}$ and $R_{2b}$ are as defined in paragraph (5) above.

Suitably, Rings A and B are as defined in any one of paragraphs (6) to (10) above. Most suitably, Rings A and B are phenyl.

Suitably, $R_1$ and $R_2$ are as defined in any one of paragraphs (11) to (12) above.

Suitably, C and D are as defined in any one of paragraphs (13) to (18) above. Most suitably, C and D are as defined in any one of paragraphs (17) or (18) above.

Suitably, $R_3$ and $R_4$ are as defined in any one of paragraphs (19) to (28) above. Most suitably, $R_3$ and $R_4$ are as defined in paragraph (28) above.

Suitably, $W_1$, $W_2$, $W_3$ and $W_4$ are as defined in any one of paragraphs (29) or (30) above.

Suitably, $X_1$, $X_2$, $X_3$ and $X_4$ are as defined in any one of paragraphs (31) to (33) above.

Most suitably, $X_1$, $X_2$, $X_3$ and $X_4$ are as defined in paragraph (33) above.

Suitably, $Z_1$, $Z_2$, $Z_3$, $Z_4$ and $Z_5$ are as defined in any one of paragraphs (34) to (44) above.

Most suitably, $Z_1$, $Z_2$, $Z_3$, $Z_4$ and $Z_5$ are as defined in paragraph (44) above.

Suitably, L is as defined in any one of paragraphs (45) to (51) above.

Suitably, integers c and d are as defined in any one of paragraphs (52) to (56).

Suitably, integers a and b are as defined in any one of paragraphs (57) to (58) above.

Suitably, integers m, n, o and p are as defined in any one of paragraphs (59) to (60) above.

In a particular group of compounds of the invention, $R_{1a}$ and $R_{1b}$ together with $R_{2a}$ and $R_{2b}$ are linked to form Rings A and B respectively, i.e. the compounds have the structural formula Ia (a sub-definition of Formula (I)) shown below, or a salt, hydrate and/or solvate thereof:

Formula Ia

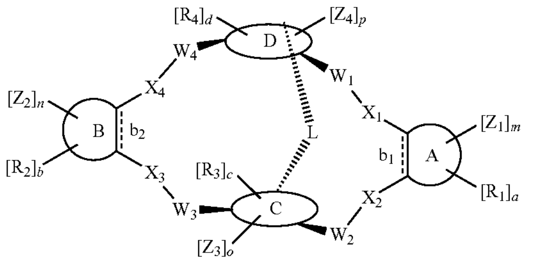

wherein, each of bonds $b_1$ and $b_2$, $R_1$, $R_2$, $R_3$, $R_4$, $Z_1$, $Z_2$, $Z_3$, $Z_4$, a, b, c, d, m, n, o, p, L, C, D and Rings A and B, are as defined hereinabove.

In an embodiment of the compounds of Formula Ia:

bonds $b_1$ and $b_2$ are as defined in any one of paragraphs (1) or (2) above;

Rings A and B are as defined in any one of paragraphs (6) to (10) above;

$R_1$ and $R_2$ are as defined in any one of paragraphs (11) to (12) above;

C and D are as defined in any one of paragraphs (13) to (18) above;

$R_3$ and $R_4$ are as defined in any one of paragraphs (19) to (28) above;

$W_1$, $W_2$, $W_3$ and $W_4$ are as defined in any one of paragraphs (29) to (30) above;

$X_1$, $X_2$, $X_3$ and $X_4$ are as defined in any one of paragraphs (31) to (33) above;

$Z_1$, $Z_2$, $Z_3$, $Z_4$ and $Z_5$ are as defined in any one of paragraphs (34) to (44) above;

L is as defined in any one of paragraphs (45) to (51) above;

integers c and d are as defined in any one of paragraphs (52) to (56) above integers a and b are as defined in any one of paragraphs (57) to (58) above; and integers m, n, o and p are as defined in any one of paragraphs (59) to (60) above.

In another embodiment of the compounds of Formula Ia:

bonds $b_1$ and $b_2$ are as defined in paragraph (2) above;

Rings A and B are as defined in paragraph (10) above;

$R_1$ and $R_2$ are as defined in paragraphs (12) above;

C and D are as defined in any one of paragraphs (17) or (18) above;

$R_3$ and $R_4$ are as defined in paragraph (28) above;

$W_1$, $W_2$, $W_3$ and $W_4$ are as defined in paragraph (30) above;

$X_1$, $X_2$, $X_3$ and $X_4$ are as defined in paragraph (33) above;

$Z_1$, $Z_2$, $Z_3$, $Z_4$ and $Z_5$ are as defined in any one of paragraphs (42) to (44) above;

L is as defined in paragraphs (51) above;

integers c and d are as defined in any one of paragraphs (52) to (56) above;

integers a and b are as defined in any one of paragraphs (57) to (58) above; and integers m, n, o and p are as defined in any one of paragraphs (59) to (60) above.

In a particular group of compounds of the invention, $R_{1a}$ and $R_{1b}$ together with $R_{2a}$ and $R_{2b}$ are linked to form Rings A and B respectively, Q is O and $W_1$, $W_2$, $W_3$ and $W_4$ are $CH_2$, i.e. the compounds have the structural formula Ib (a sub-definition of Formula (I)) shown below, or a salt, hydrate and/or solvate thereof:

Formula Ib

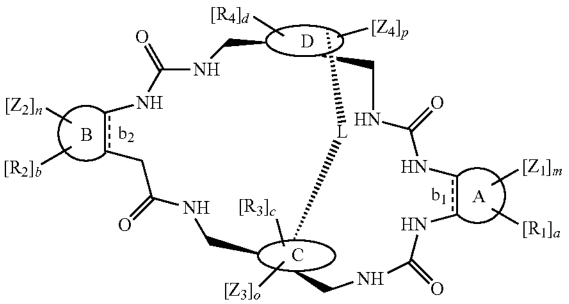

wherein, each of bonds $b_1$ and $b_2$, $R_1$, $R_2$, $R_3$, $R_4$, $Z_1$, $Z_2$, $Z_3$, $Z_4$, a, b, c, d, m, n, o, p, L, C, D and Rings A and B, are as defined hereinabove.

In an embodiment of the compounds of Formula Ib:

bonds $b_1$ and $b_2$ are as defined in any one of paragraphs (1) or (2) above;

Rings A and B are as defined in any one of paragraphs (6) to (10) above;

$R_1$ and $R_2$ are as defined in any one of paragraphs (11) to (12) above;

C and D are as defined in any one of paragraphs (13) to (18) above;

$R_3$ and $R_4$ are as defined in any one of paragraphs (19) to (28) above;

$Z_1$, $Z_2$, $Z_3$, $Z_4$ and $Z_5$ are as defined in any one of paragraphs (34) to (44) above;

L is as defined in any one of paragraphs (45) to (51) above;

integers c and d are as defined in any one of paragraphs (52) to (56) above;

integers a and b are as defined in any one of paragraphs (57) to (58) above; and integers m, n, o and p are as defined in any one of paragraphs (59) to (60) above.

In another embodiment of the compounds of Formula Ib:

bonds $b_1$ and $b_2$ are as defined in paragraph (2) above;

Rings A and B are as defined in paragraph (10) above;

$R_1$ and $R_2$ are as defined in paragraphs (12) above;

C and D are as defined in any one of paragraphs (17) or (18) above;

$R_3$ and $R_4$ are as defined in paragraph (28) above;

$Z_1$, $Z_2$, $Z_3$, $Z_4$ and $Z_5$ are as defined in any one of paragraphs (40) to (44) above;

L is as defined in paragraphs (51) above;

integers c and d are as defined in any one of paragraphs (52) to (56) above;

integers a and b are as defined in any one of paragraphs (57) to (58) above; and integers m, n, o and p are as defined in any one of paragraphs (59) to (60) above.

In another particular group of compounds of the invention, $R_{1a}$ and $R_{1b}$ together with $R_{2a}$ and $R_{2b}$ are linked to form Rings A and B respectively, Q is O, $W_1$, $W_2$, $W_3$ and $W_4$ are $CH_2$, and L is as shown below, i.e. the compounds have the structural formula Ic (a sub-definition of Formula (I)) shown below, or a salt, hydrate and/or solvate thereof:

Formula Ic

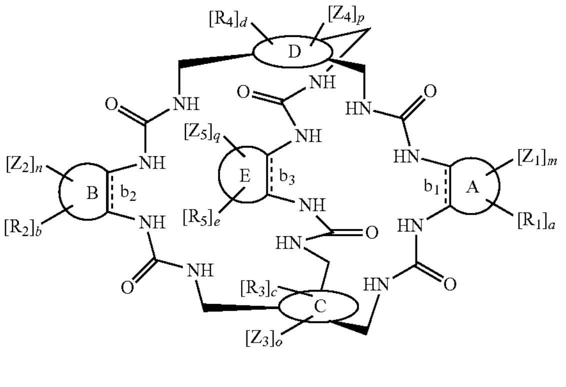

wherein, each of bonds $b_1$, $b_2$ and $b_3$, $R_1$, $R_2$, $R_3$, $R_4$, $R_5$, $Z_1$, $Z_2$, $Z_3$, $Z_4$, $Z_5$, a, b, c, d, e, m, n, o, p, q, C, D and Rings A, B and E are as defined hereinabove.

In an embodiment of the compounds of Formula Ic:

bonds $b_1$ and $b_2$ are as defined in any one of paragraphs (1) or (2) above;

Rings A and B are as defined in any one of paragraphs (6) to (10) above;

$R_1$ and $R_2$ are as defined in any one of paragraphs (11) to (12) above;

C and D are as defined in any one of paragraphs (13) to (18) above;

$R_3$ and $R_4$ are as defined in any one of paragraphs (19) to (28) above;

$Z_1$, $Z_2$, $Z_3$, $Z_4$ and $Z_5$ are as defined in any one of paragraphs (34) to (44) above;

bond $b_3$, Ring E, $R_5$ and integers e and q are as defined in any one of paragraphs (48) to (49) above;

integers c and d are as defined in any one of paragraphs (52) to (56) above;

integers a and b are as defined in any one of paragraphs (57) to (58) above; and integers m, n, o and p are as defined in any one of paragraphs (59) to (60) above.

In another embodiment of the compounds of Formula Ic:

bonds $b_1$ and $b_2$ are as defined in paragraph (2) above;

Rings A and B are as defined in paragraph (10) above;

$R_1$ and $R_2$ are as defined in paragraph (12) above;

C and D are as defined in any one of paragraphs (17) to (18) above;

$R_3$ and $R_4$ are as defined in paragraph (28) above;

$Z_1$, $Z_2$, $Z_3$, $Z_4$ and $Z_5$ are as defined in any one of paragraphs (40) to (44) above;

bond $b_3$, Ring E, $R_5$ and integers e and q are as defined in paragraph (49) above;

integers c and d are as defined in any one of paragraphs (52) to (56) above;

integers a and b are as defined in any one of paragraphs (57) to (58) above; and integers m, n, o and p are as defined in any one of paragraphs (59) to (60) above.

In yet another particular group of compounds of the invention, Q is O, $W_1$, $W_2$, $W_3$ and $W_4$ are $CH_2$, and L is as shown below, Rings A, B and E are phenyl, integers m and n are 1 and integers a, b and e are 0, i.e. the compounds have the structural formula Id (a sub-definition of Formula (I)) shown below, or a salt, hydrate and/or solvate thereof:

Formula Id

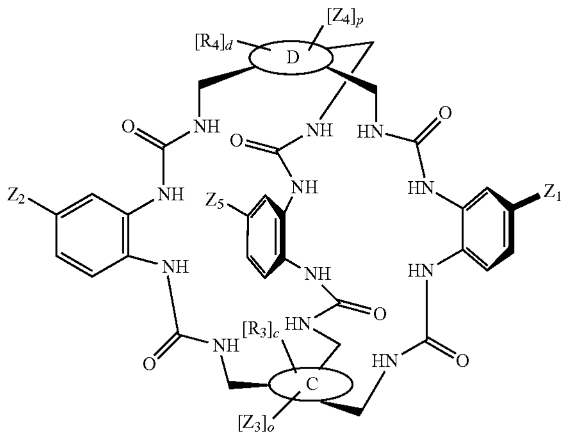

wherein, each of $R_3$, $R_4$, $Z_1$, $Z_2$, $Z_3$, $Z_4$, $Z_5$, c, d, o, p and Rings C and D are as defined hereinabove.

In an embodiment of the compounds of Formula Id:

Rings C and D are as defined in any one of paragraphs (13) to (18) above;

$R_3$ and $R_4$ are as defined in any one of paragraphs (19) to (28) above;

$Z_1$, $Z_2$, $Z_3$, $Z_4$ and $Z_5$ are as defined in any one of paragraphs (34) to (44) above;

integers c and d are as defined in any one of paragraphs (42) to (56) above; and integers o and p are as defined in any one of paragraphs (59) to (60) above.

In another particular group of compounds of the invention, Q is O, $W_1$, $W_2$, $W_3$ and $W_4$ are $CH_2$, and L is as shown below, Rings A, B and E are phenyl, integers m and n are 1 and integers a, b and e are 0, i.e. the compounds have the structural formula Ie (a sub-definition of Formula (I)) shown below, or a salt, hydrate and/or solvate thereof:

Formula Ie

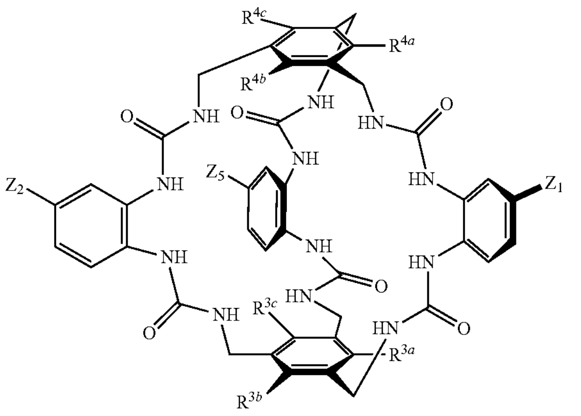

wherein, each of $Z_1$, $Z_2$, $Z_3$, $Z_4$ and $Z_5$ are as defined hereinabove and $R^{3a}$, $R^{3b}$, $R^{3c}$, $R^{4a}$, $R^{4b}$ and $R^{4c}$ are independently selected from hydrogen, halo, (1-4C)alkyl, (1-4C) alkoxy, amino, nitro, (1-4C)alkylamino, (1-4C)dialkylamino, (1-4C)haloalkyl, (1-4C)haloalkoxy, cyano, (2-4C) alkenyl, (2-4C)alkynyl and a group of the formula:

$-L^{1a}-Y^{1a}-Q^{1a}$ wherein:

$L^{1a}$ is absent or (1-2C)alkylene optionally substituted by one or more substituents selected from (1-2C) alkyl and oxo;

$Y^{1a}$ is absent or O, S, SO, $SO_2$, $N(R_n)$, C(O), C(O)O, OC(O), $C(O)N(R_n)$ and $N(R_n)C(O)$, wherein $R_n$ is selected from hydrogen and (1-4C)alkyl; and $Q^1$a is hydrogen, (1-8C)alkyl, (2-6C)alkenyl, (2-6C) alkynyl, aryl, (3-10C)cycloalkyl, (3-10C)cycloalkenyl, heteroaryl and heterocyclyl; wherein $Q^{1a}$ is optionally further substituted by one or more substituent groups independently selected from (1-4C) alkyl, halo, (1-4C)haloalkyl, (1-4C)haloalkoxy, amino, (1-4C)aminoalkyl, cyano, hydroxy, carboxy, carbamoyl, sulfamoyl, mercapto, ureido, oxy, $NR_oR_p$, $OR_o$, $C(O)R_o$, $C(O)OR_o$, $OC(O)R_o$, $C(O)N(R_p)R_o$, $N(R_p)C(O)R_o$, $S(O)_{y1}R_o$ (where y1 is 0, 1 or 2), $SO_2N(R_o)R_o$, $N(R_p)SO_2R_o$, $Si(R_q)(R_p)R_o$ and $(CH_2)_{z1}NR_oR_p$ (where $z_1$ is 1, 2 or 3); wherein $R_o$, $R_p$ and $R_q$ are each independently selected from hydrogen and (1-6C)alkyl.

In an embodiment of the compounds of Formula Ie:

$Z_1$, $Z_2$, $Z_3$, $Z_4$ and $Z_5$ are as defined in any one of paragraphs (34) to (42) above; and $R^{3a}$, $R^{3b}$, $R^{3c}$, $R^{4a}$, $R^{4b}$ and $R^{4c}$ are independently selected from hydrogen, halo, (1-4C)alkyl, (1-4C)alkoxy, amino, nitro, (1-4C) alkylamino, (1-4C)dialkylamino, (1-4C)haloalkyl, (1-4C)haloalkoxy, cyano, (2-4C)alkenyl, (2-4C)alkynyl and a group of the formula:

$$-L^{1a}-Y^{1a}-Q^{1a}$$

wherein:

$L^{1a}$ is absent or (1-2C)alkylene;

$Y^{1a}$ is absent or O, S, SO, $SO_2$, $N(R_l)$, C(O), C(O)O, OC(O), $C(O)N(R_n)$ and $N(R_n)C(O)$, wherein $R_n$ is selected from hydrogen and (1-4C)alkyl; and $Q^{1a}$ is hydrogen, (1-8C)alkyl, (2-6C)alkenyl, (2-6C) alkynyl, aryl, (3-10C)cycloalkyl, (3-10C)cycloalkenyl, heteroaryl or heterocyclyl; wherein $Q^{1a}$ is optionally further substituted by one or more substituent groups independently selected from (1-4C)alkyl, halo, (1-4C)haloalkyl, (1-4C) haloalkoxy, amino, (1-4C)aminoalkyl, cyano, hydroxy, carboxy, carbamoyl, sulfamoyl and mercapto In another embodiment of the compounds of Formula Ie:

$Z_1$, $Z_2$, $Z_3$, $Z_4$ and $Z_5$ are as defined in paragraph (42) above; and $R^{3a}$, $R^{3b}$, $R^{3c}$, $R^{4a}$, $R^{4b}$ and $R^{4c}$ are independently selected from hydrogen, halo, (1-4C)alkyl, (1-4C)alkoxy, amino, nitro, (1-4C)alkylamino, (1-4C) dialkylamino, (1-4C)haloalkyl, (1-4C)haloalkoxy, cyano, (2-4C)alkenyl and (2-4C)alkynyl.

In another embodiment of the compounds of Formula Ie:

$Z_1$, $Z_2$, $Z_3$, $Z_4$ and $Z_5$ are as defined in paragraph (42) above; and $R^{3a}$, $R^{3b}$, $R^{3c}$, $R^{4a}$, $R^{4b}$ and $R^{4c}$ are independently selected from hydrogen, halo, (1-4C)alkyl, (1-4C)alkoxy, amino, nitro, (1-4C)alkylamino, (1-4C)dialkylamino, (1-4C)haloalkyl, (1-4C)haloalkoxy, cyano, (2-4C)alkenyl and (2-4C)alkynyl, with the proviso that $R^{3a}$, $R^{3b}$ and $R^{3C}$ cannot all be hydrogen.

In another embodiment of the compounds of Formula Ie:

$Z_1$, $Z_2$, $Z_3$, $Z_4$ and $Z_5$ are as defined in paragraph (42) above; and $R^{3a}$, $R^{3b}$, $R^{3c}$, $R^{4a}$, $R^{4b}$ and $R^{4c}$ are independently selected from halo, (1-4C)alkyl, (1-4C)alkoxy, amino, nitro, (1-4C)alkylamino, (1-4C)dialkylamino, (1-4C)haloalkyl, (1-4C)haloalkoxy, cyano, (2-4C)alkenyl and (2-4C)alkynyl.

In another embodiment of the compounds of Formula Ie:

$Z_1$, $Z_2$, $Z_3$, $Z_4$ and $Z_5$ are as defined in paragraph (44) above; and $R^{3a}$, $R^{3b}$, $R^{3c}$, $R^{4a}$, $R^{4b}$ and $R^{4c}$ are independently selected from hydrogen and (1-4C)alkyl.

In another embodiment of the compounds of Formula Ie:

$Z_1$, $Z_2$, $Z_3$, $Z_4$ and $Z_5$ are as defined in paragraph (44) above; and $R^3$, $R^{3b}$, $R^{3c}$, $R^{4a}$, $R^{4b}$ and $R^{4c}$ are independently selected from hydrogen, (1-4C)alkoxy and (1-4C)alkyl.

In another embodiment of the compounds of Formula Ie:

$Z_1$, $Z_2$, $Z_3$, $Z_4$ and $Z_5$ are as defined in paragraph (44) above; and $R^{3a}$, $R^{3b}$, $R^{3c}$, $R^{4a}$, $R^{4b}$ and $R^{4c}$ are independently selected from (1-4C)alkoxy and (1-4C)alkyl.

In another embodiment of the compounds of Formula Ie:

$Z_1$, $Z_2$, $Z_3$, $Z_4$ and $Z_5$ are as defined in paragraph (44) above; and $R^{3a}$, $R^{3b}$, $R^{3c}$, $R^{4a}$, $R^{4b}$ and $R^{4c}$ are independently a (1-4C)alkyl (e.g. ethyl).

In yet a further group of compounds of the invention, $R_{1a}$ and $R_{1b}$ together with $R_{2a}$ and $R_{2b}$ are linked to form Rings A and B respectively, Q is O, L is absent and $W_1$, $W_2$, $W_3$ and $W_4$ are $CH_2$, i.e. the compounds have the structural formula If (a sub-definition of Formula (I)) shown below, or a salt, hydrate and/or solvate thereof:

Formula If

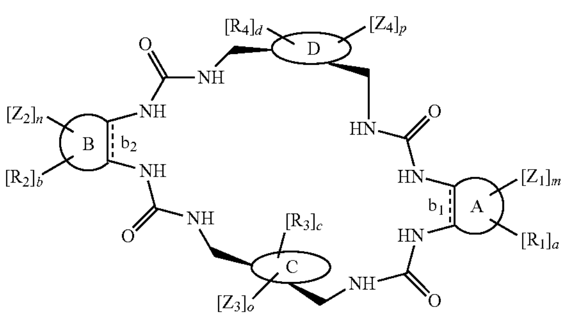

wherein, each of bonds $b_1$ and $b_2$, $R_1$, $R_2$, $R_3$, $R_4$, $Z_1$, $Z_2$, $Z_3$, $Z_4$, a, b, c, d, m, n, o, p, C, D and Rings A and B are as defined hereinabove.

In an embodiment of the compounds of Formula If:

bonds $b_1$ and $b_2$ are as defined in any one of paragraphs (1) or (2) above;

Rings A and B are as defined in any one of paragraphs (6) to (10) above;

$R_1$ and $R_2$ are as defined in any one of paragraphs (11) to (12) above;

C and D are as defined in any one of paragraphs (13) to (18) above;

$R_3$ and $R_4$ are as defined in any one of paragraphs (19) to (28) above;

$Z_1$, $Z_2$, $Z_3$ and $Z_4$ are as defined in any one of paragraphs (34) to (44) above;

integers c and d are as defined in any one of paragraphs (52) to (56) above;

integers a and b are as defined in any one of paragraphs (57) to (58) above; and integers m, n, o and p are as defined in any one of paragraphs (59) to (60) above.

In another embodiment of the compounds of Formula If:

bonds $b_1$ and $b_2$ are as defined in paragraph (2) above;

Rings A and B are as defined in paragraph (10) above;

$R_1$ and $R_2$ are as defined in paragraph (12) above;

C and D are as defined in any one of paragraphs (17) to (18) above;

$R_3$ and $R_4$ are as defined in paragraph (28) above;

$Z_1$, $Z_2$, $Z_3$ and $Z_4$ are as defined in any one of paragraphs (38) to (44) above;

integers c and d are as defined in any one of paragraphs (52) to (56) above;

integers a and b are as defined in any one of paragraphs (57) to (58) above; and integers m, n, o and p are as defined in any one of paragraphs (52) to (53) above.

In another particular group of compounds of the invention, Q is O, L is absent, $W_1$, $W_2$, $W_3$ and $W_4$ are $CH_2$, Rings A and B are phenyl and Rings C and D are anthracenyl, i.e. the compounds have the structural formula Ig (a sub-definition of Formula (I)) shown below, or a salt, hydrate and/or solvate thereof:

Formula Ig

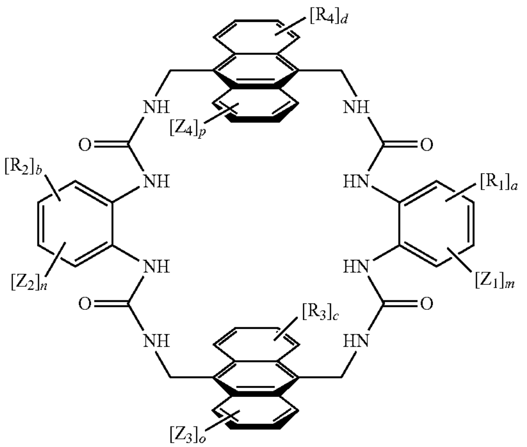

wherein each of $R_1$, $R_2$, $R_3$, $R_4$, $Z_1$, $Z_2$, $Z_3$, $Z_4$, a, b, c, d, m, n, o and p are as defined hereinabove.

In an embodiment of the compounds of Formula Ig:

$R_1$ and $R_2$ are as defined in any one of paragraphs (11) to (12) above;

$R_3$ and $R_4$ are as defined in any one of paragraphs (19) to (28) above;

$Z_1$, $Z_2$, $Z_3$ and $Z_4$ are as defined in any one of paragraphs (34) to (44) above;

integers c and d are as defined in paragraphs (52) above;

integers a and b are as defined in any one of paragraphs (57) to (58) above; and integers m, n, o and p are as defined in any one of paragraphs (59) to (60) above.

Particular compounds of the present invention include any of the compounds exemplified in the present application, or a salt, solvate or hydrate thereof, and, in particular, any of the following:

i)

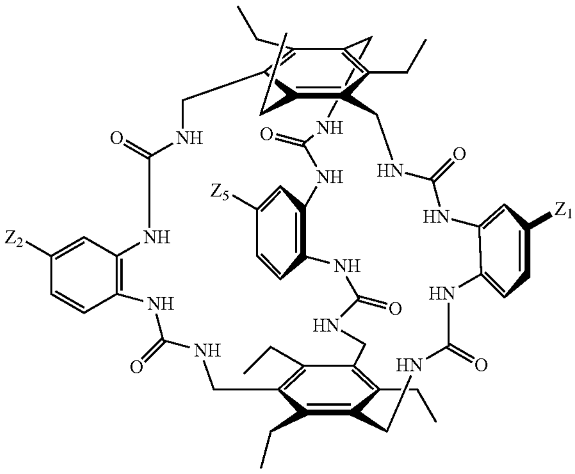

ii)

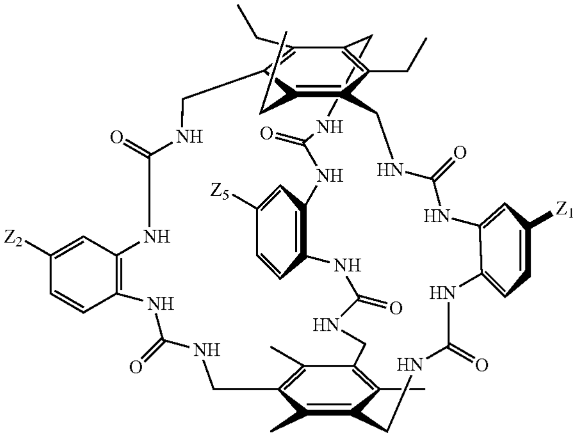

iii)

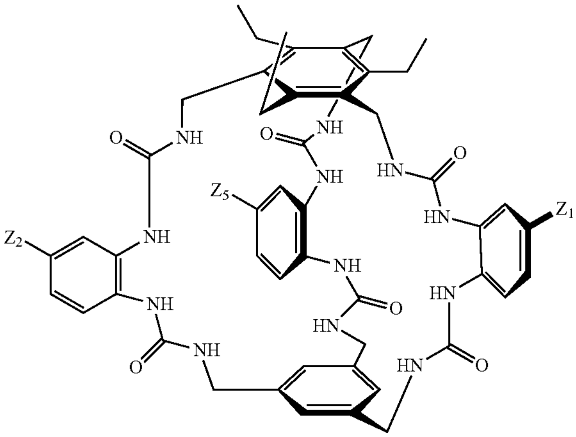

-continued
iv)
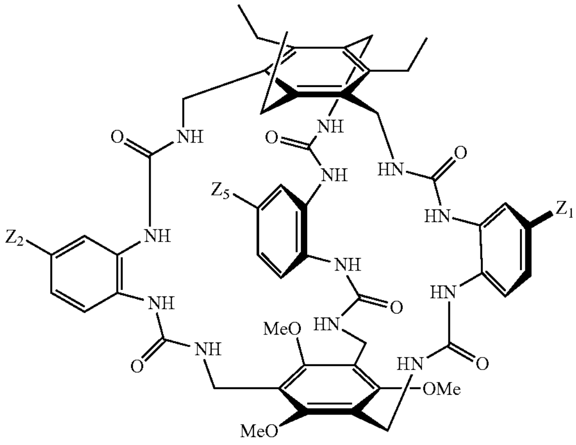
v)
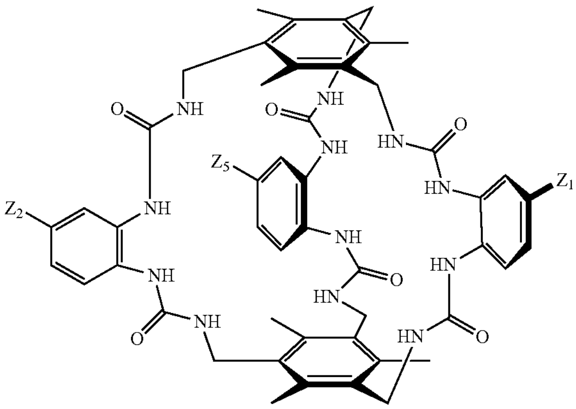
vi)
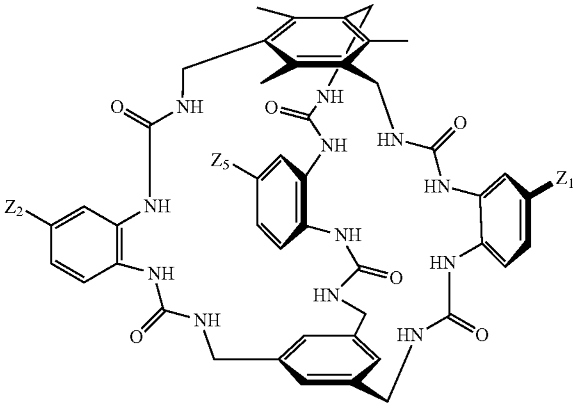
-continued
vii)
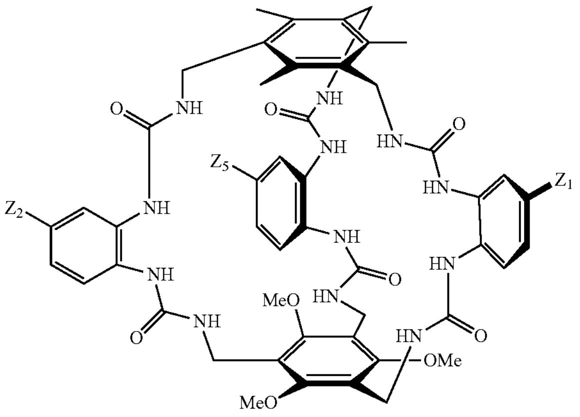
viii)
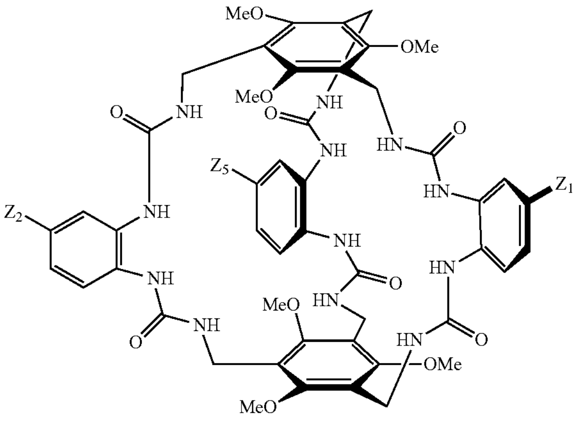
ix)
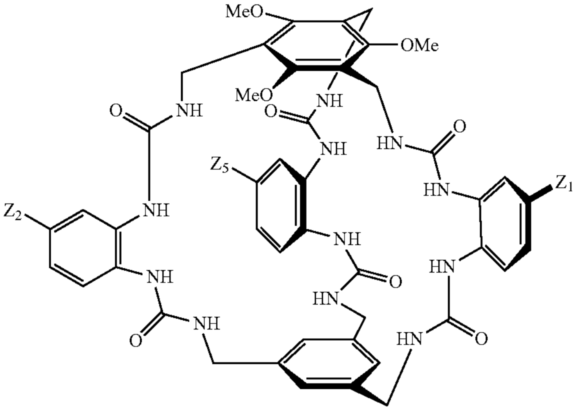

-continued
x)
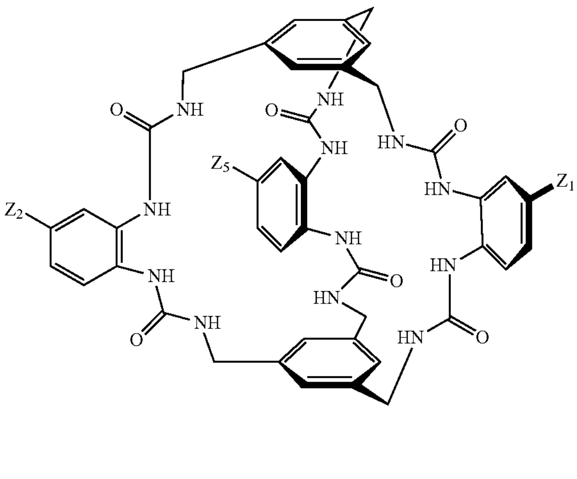
xi)
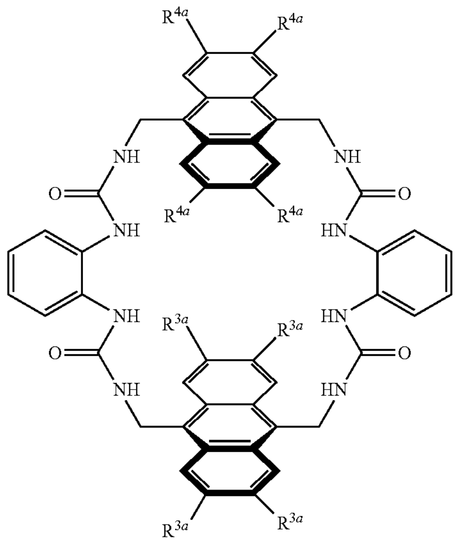
xii)
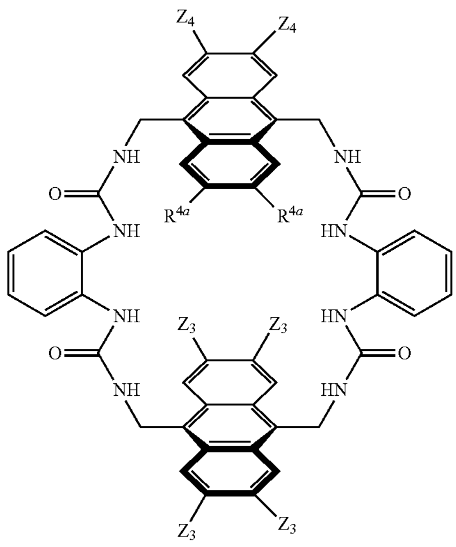
-continued
xiii)
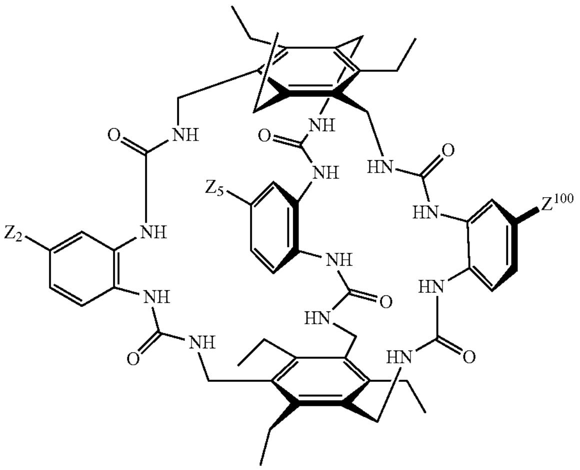
xiv)
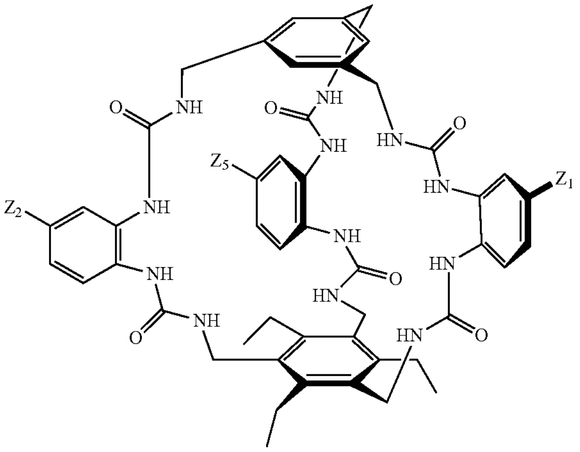
xv)
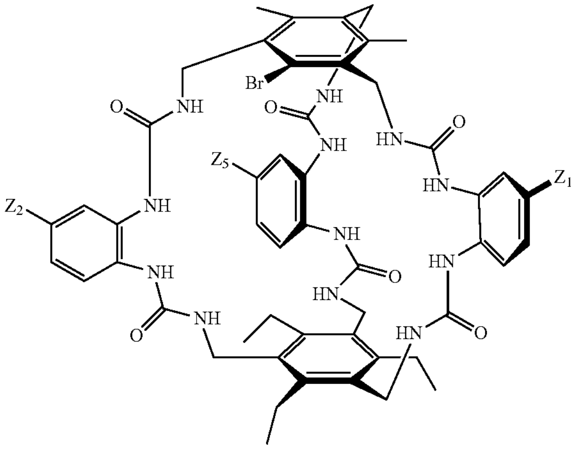

-continued
xvi)
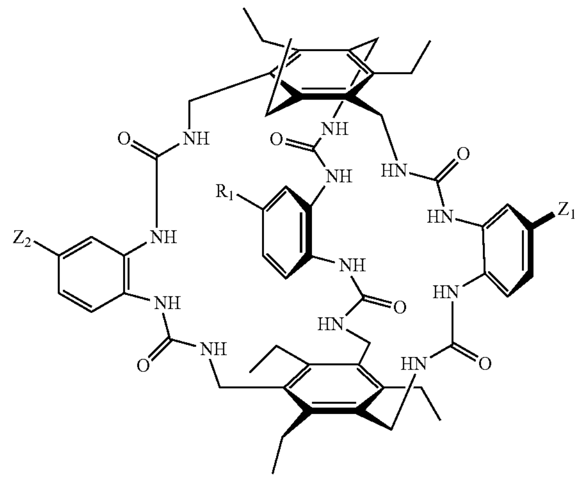
xvii)
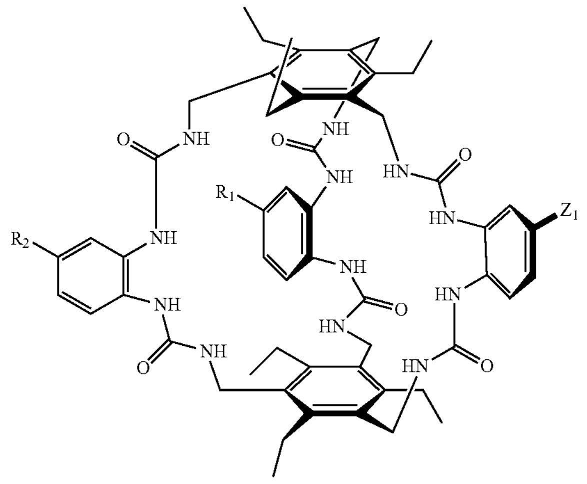
xviii)
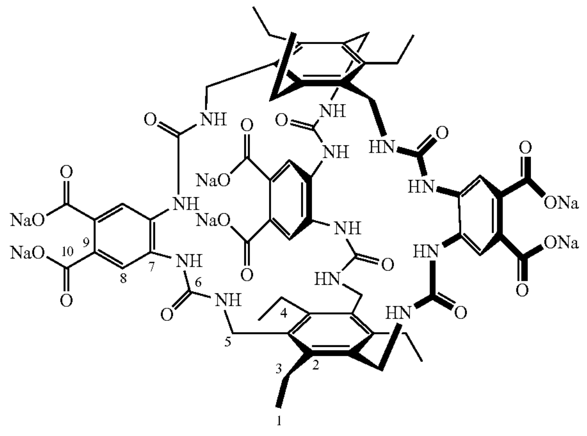
-continued
xix)
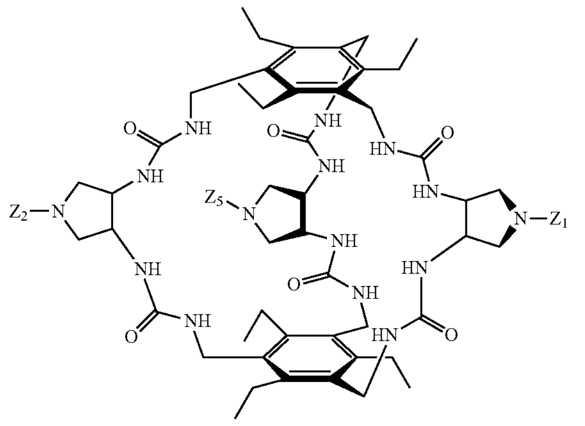
wherein:
each of $Z_1$, $Z_2$ and $Z_5$ are independently selected from one of the following groups:
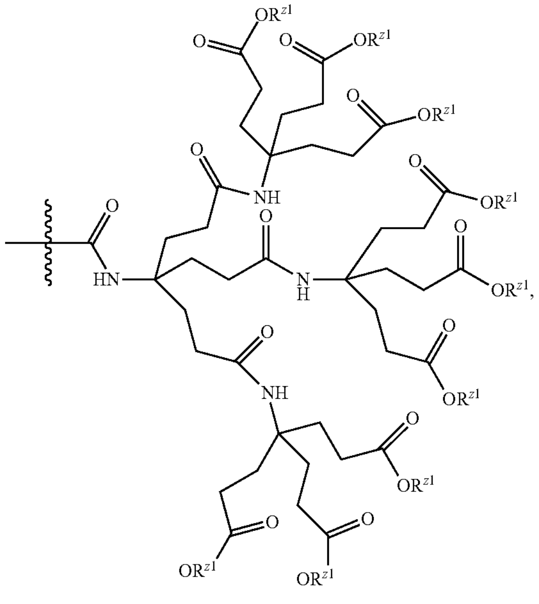
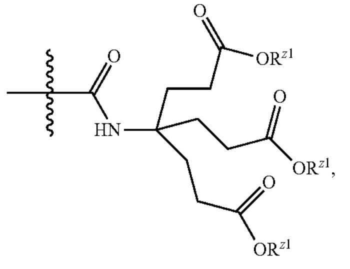

-continued

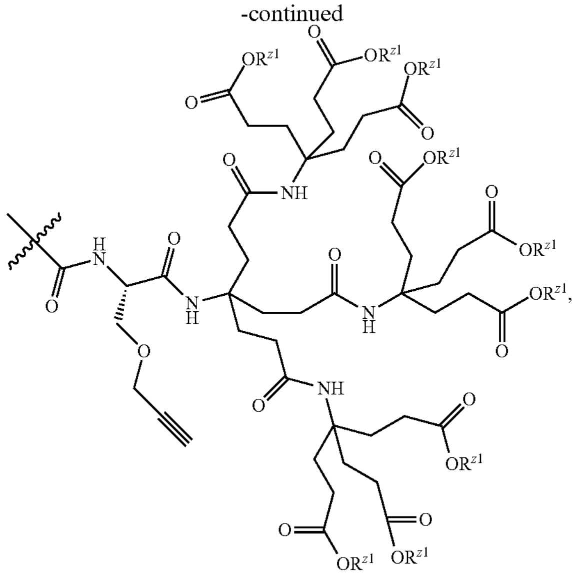

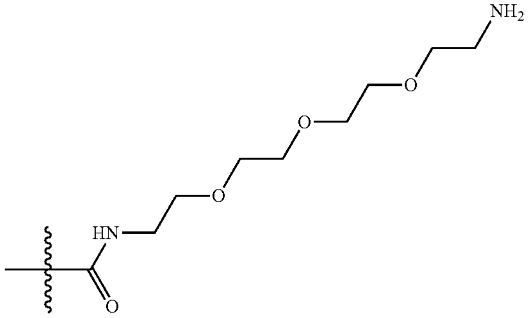

wherein each $R^{z1}$ is independently selected from hydrogen or Na (i.e. the carboxy group is either a carboxylic acid or a sodium salt thereof);

each of $Z_3$ and $Z_4$ is a group of the formula:

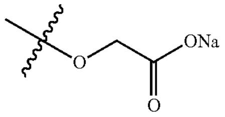

$Z^{100}$ is a group of the formula:

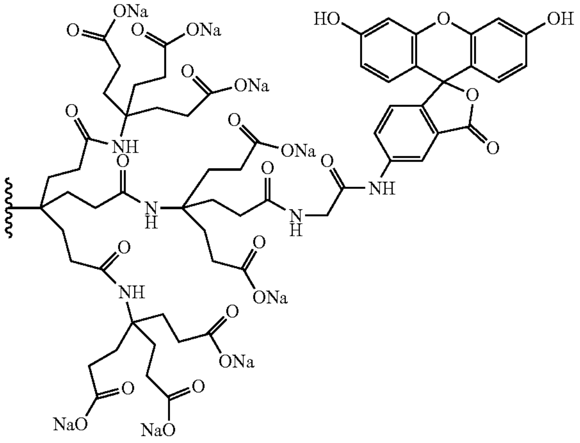

$R_1$ and $R_2$ are groups of the formula:

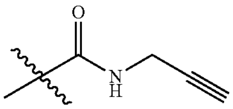 [SMILES: *C(=O)NCC#C]

$R^{3a}$ and $R^{4a}$ are independently selected from hydrogen or methoxy;

and wherein ∿∿∿ denotes the point of attachment.

Particular compounds of the present invention include any of the compounds exemplified in the present application, or a salt, solvate or hydrate thereof, and, in particular, any of the following:

i)

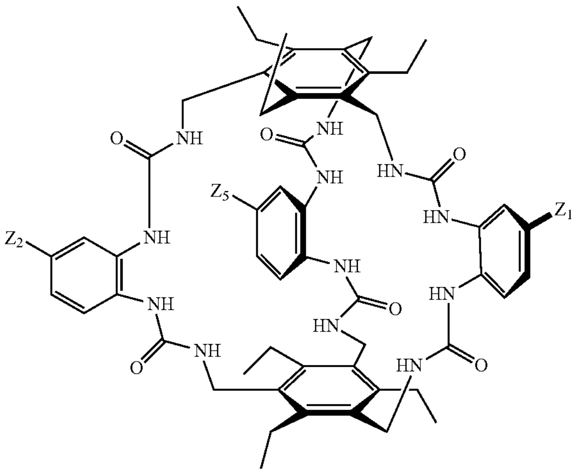

ii)

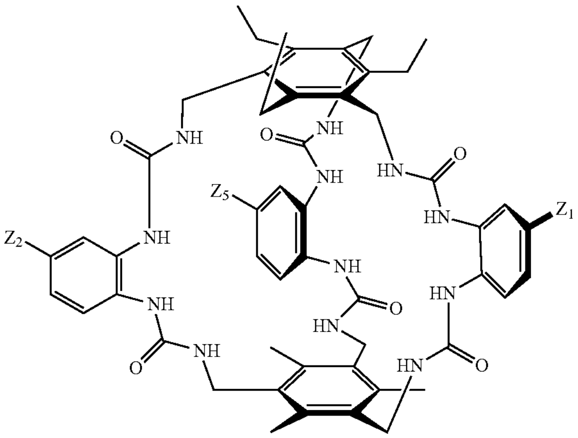

-continued
iii)
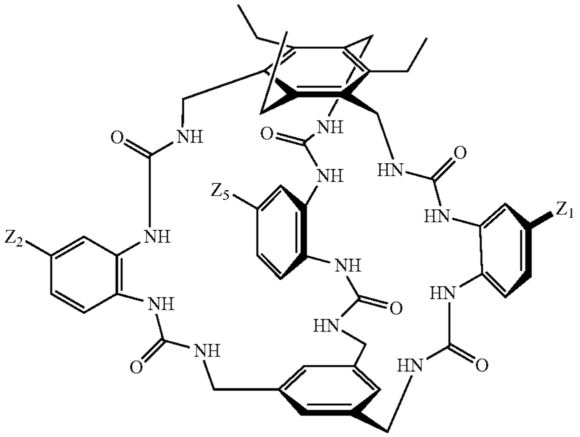
iv)
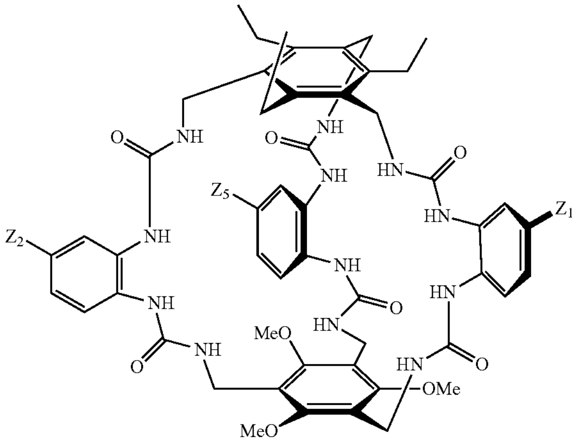
v)
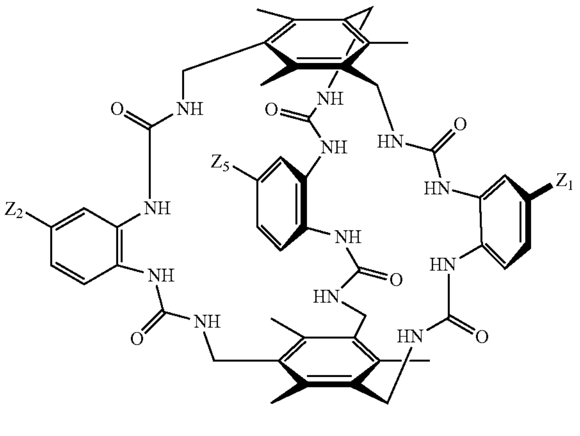
-continued
vi)
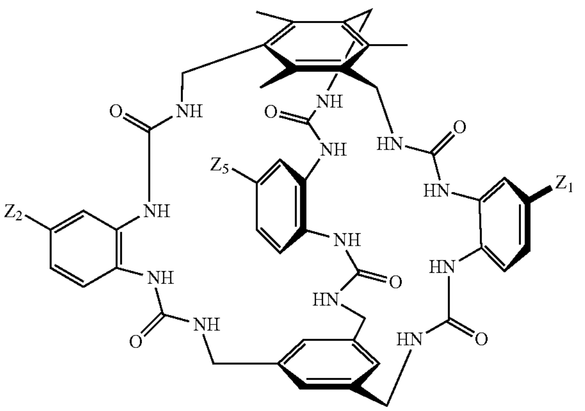
vii)
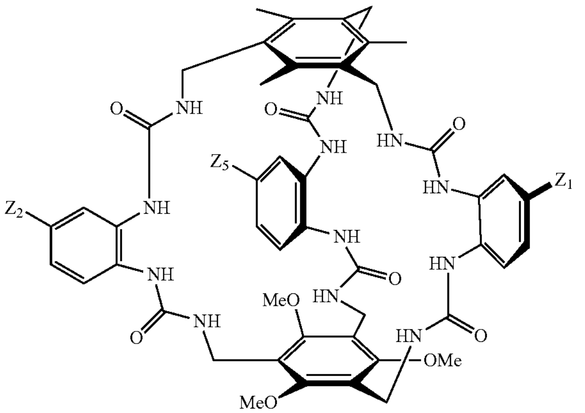
viii)
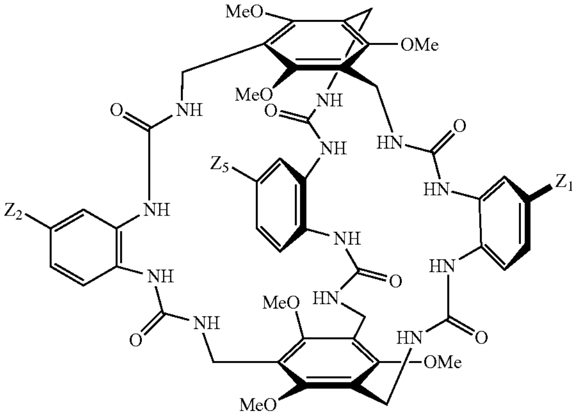

-continued
ix)
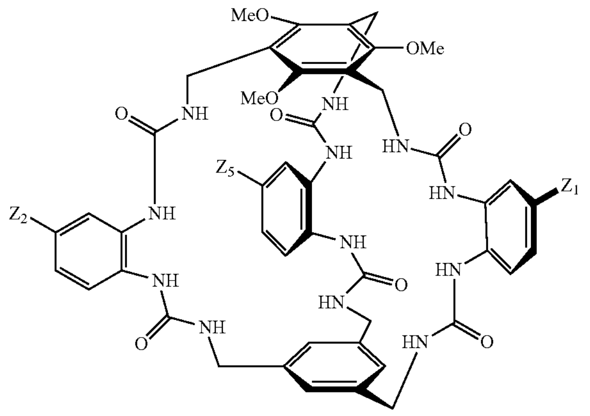
x)
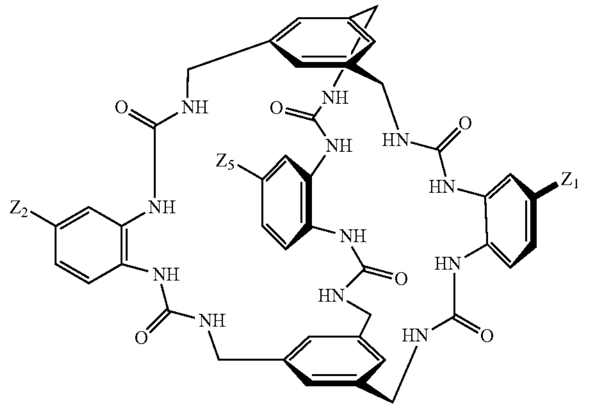
xi)
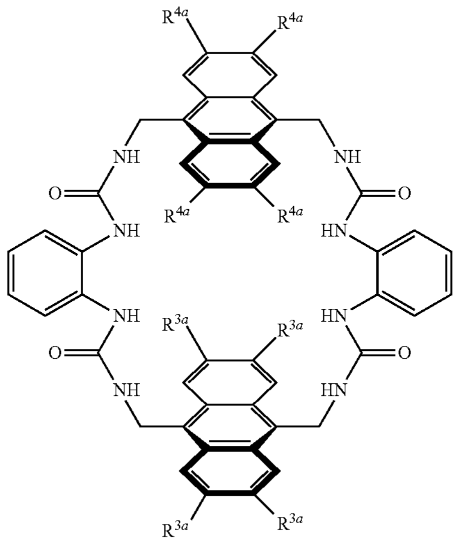
-continued
xii)
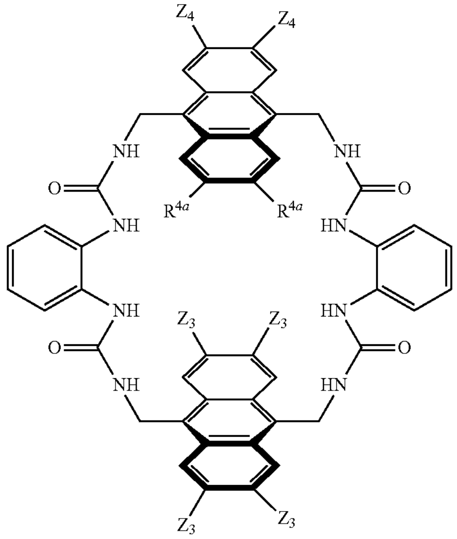
xiii)
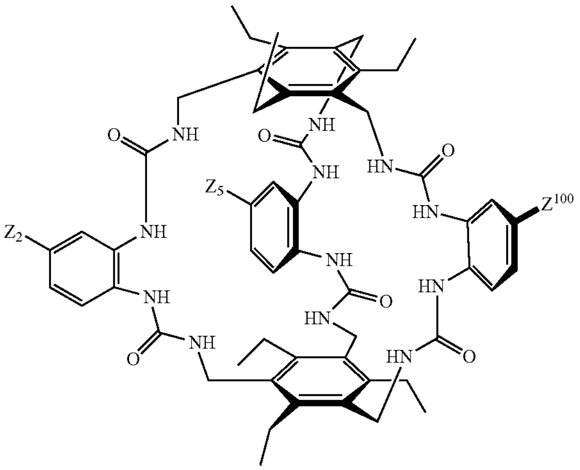
wherein:
each of $Z_1$, $Z_2$ and $Z_5$ are independently selected one of the following groups:

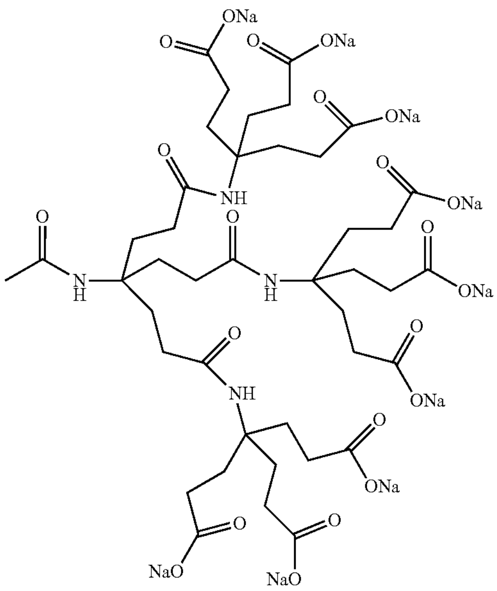

or

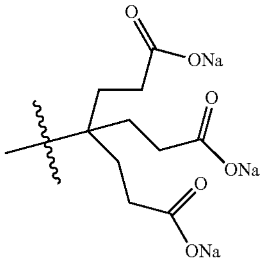

each of $Z_3$ and $Z_4$ is a group of the formula:

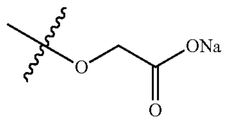

$Z^{100}$ is a group of the formula:

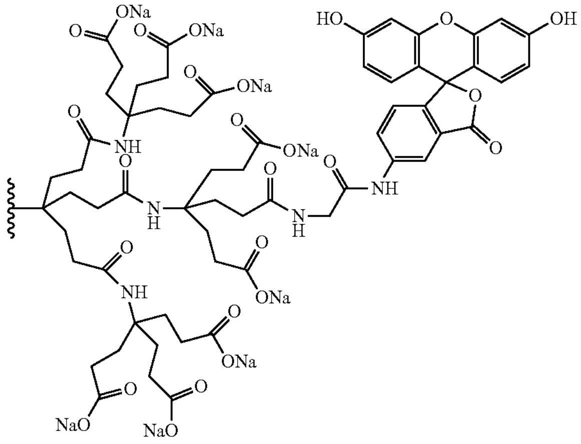

$R^{3a}$ and $R^{4a}$ are independently selected from hydrogen or methoxy;

and wherein ∿∿∿ denotes the point of attachment.

Further particular compounds of the present invention include any of the compounds exemplified in the present application, or a salt, solvate or hydrate thereof, and, in particular, any of the following:

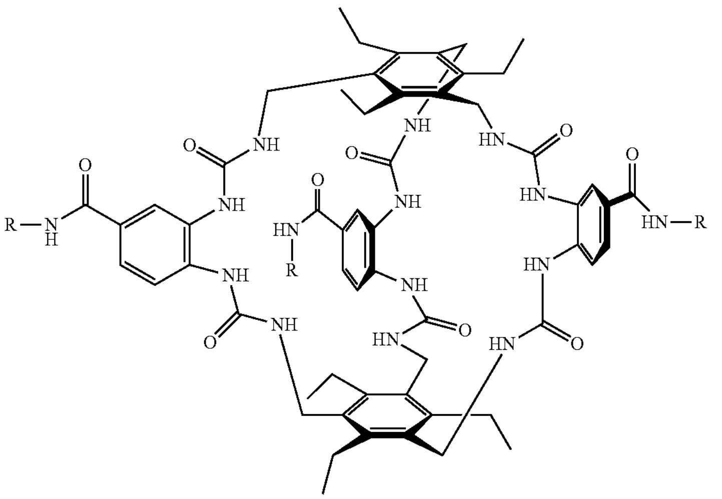

R =

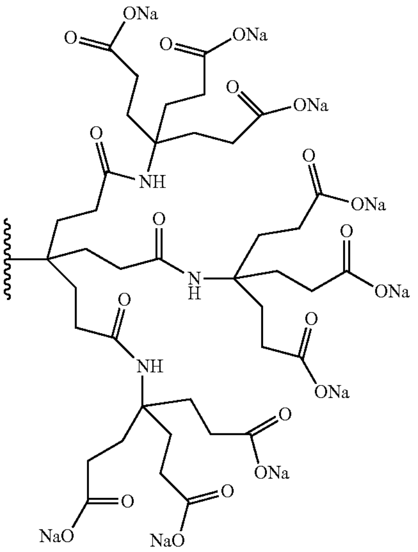

-continued
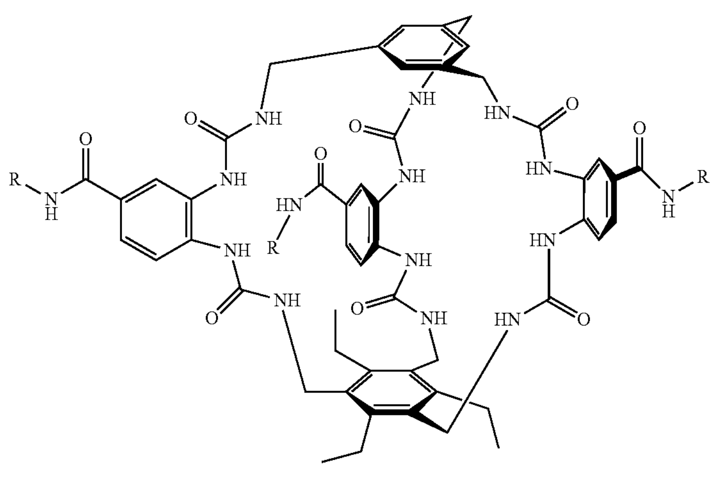
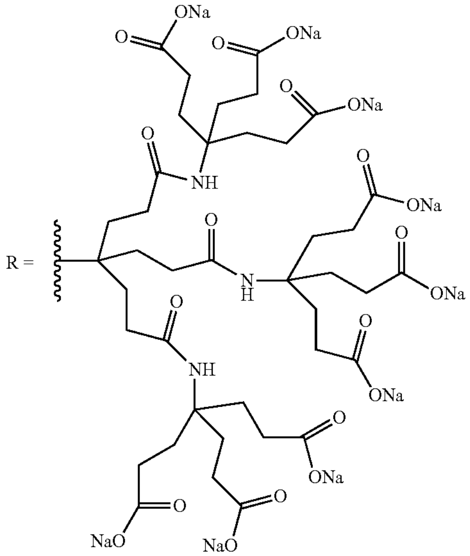
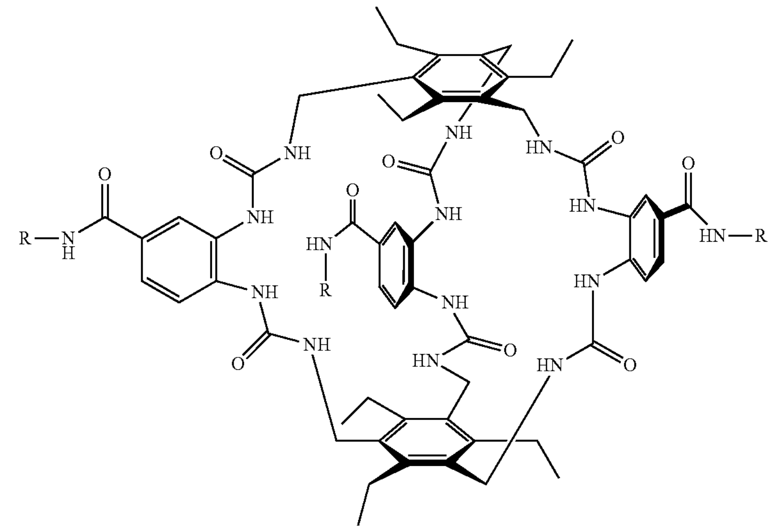
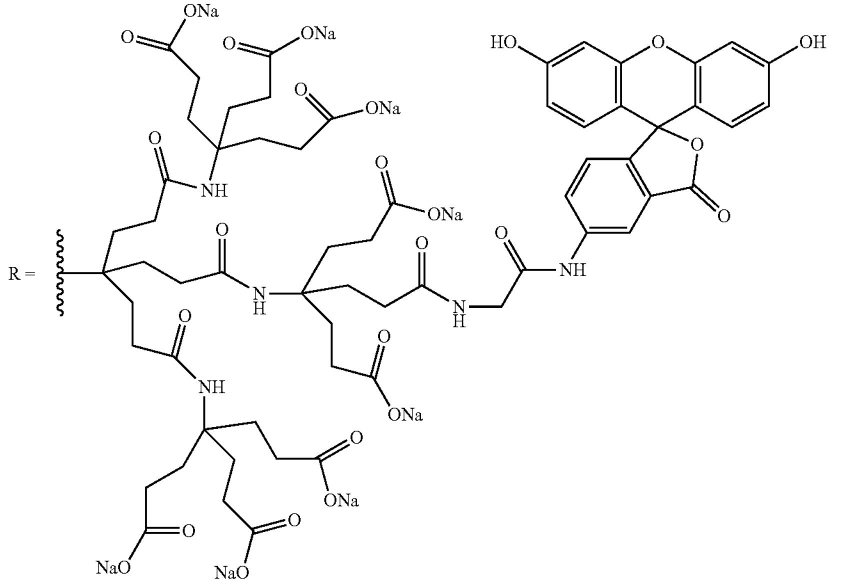

-continued
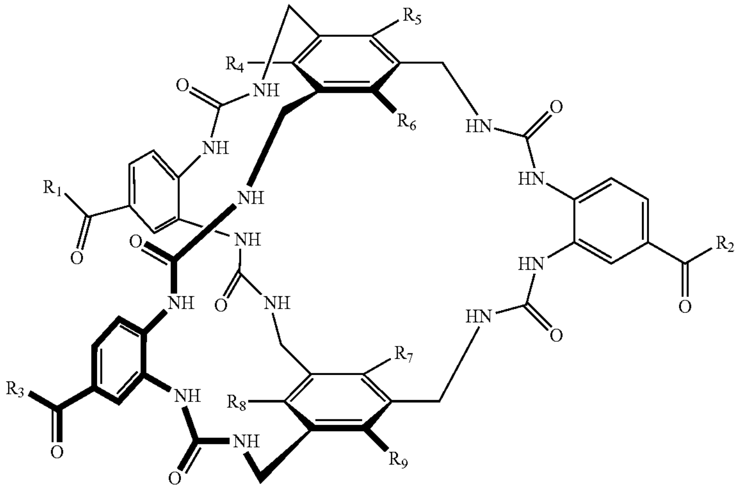
$R_4 = R_5 = Me$
$R_6 = Br$
$R_7, R_8 = R_9 = Et$
$R_1 = R_2 = R_3 =$
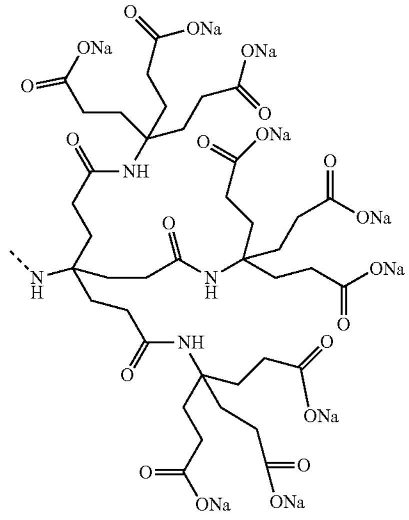
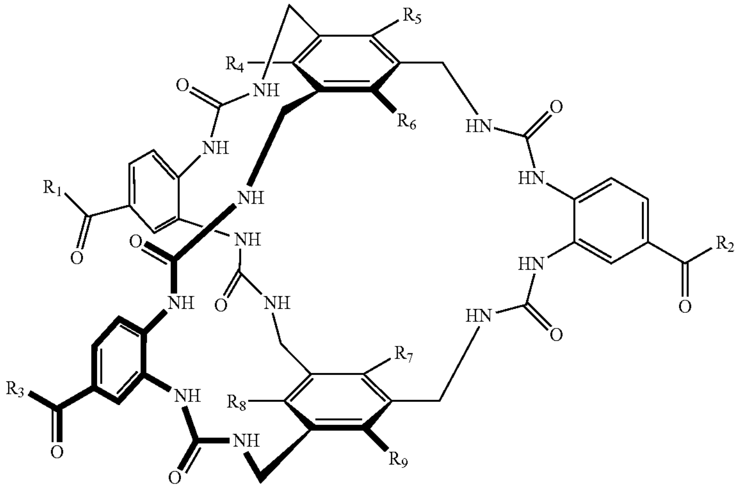
$R_4 = R_5 = R_6 = R_7 = R_8 = R_9 = Et$ -continued
$R_1 = R_2 =$ 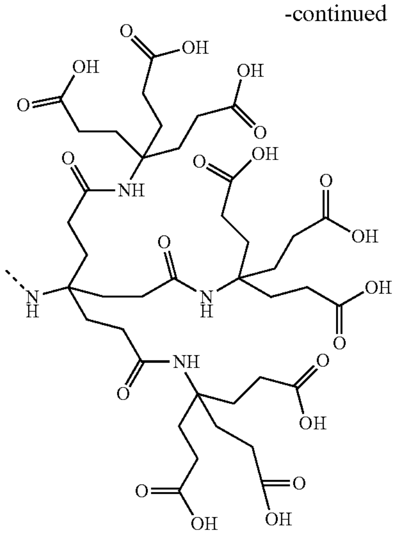
$R_2 =$ 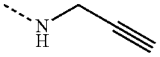
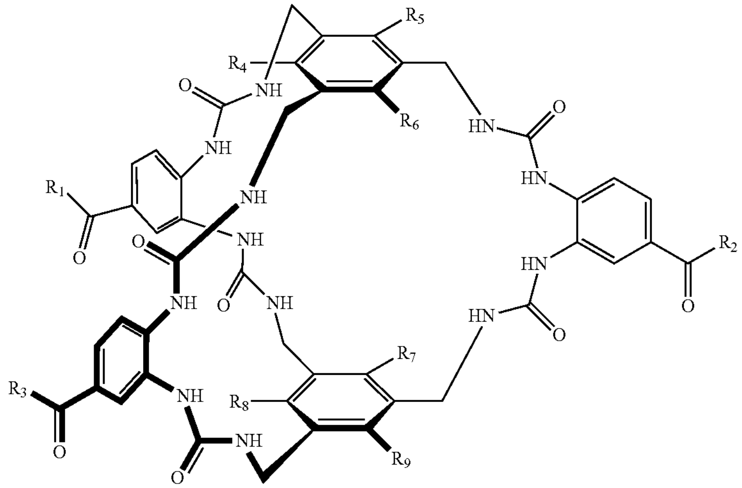
$R_4 = R_5 = R_6 = R_7 = R_8 = R_9 = Et$
$R_1 =$ 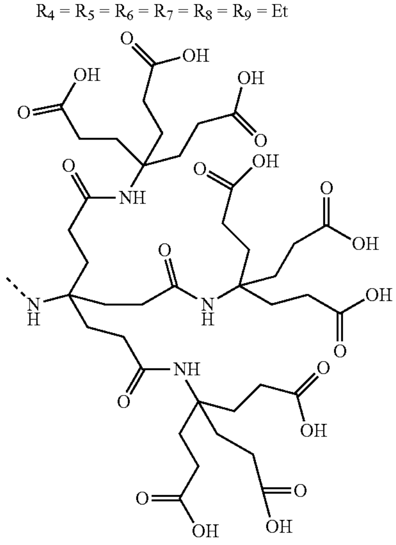
$R_2 = R_3 =$ 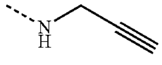

-continued
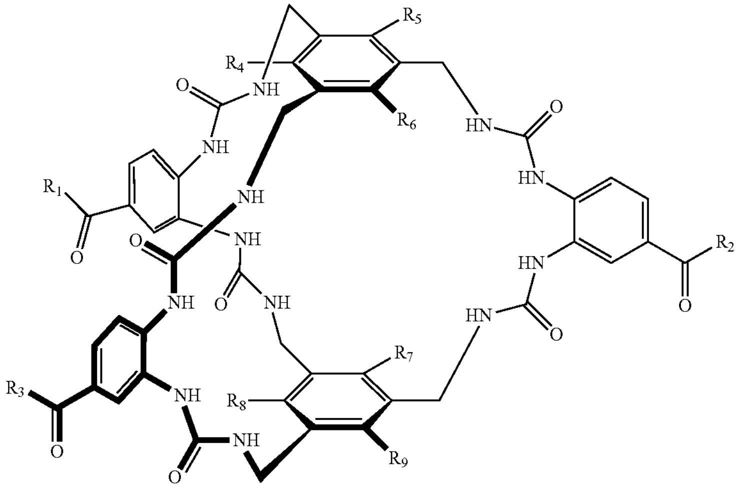
$R_4 = R_5 = R_6 = R_7 = R_8 = R_9 = Et$
$R_1$ = 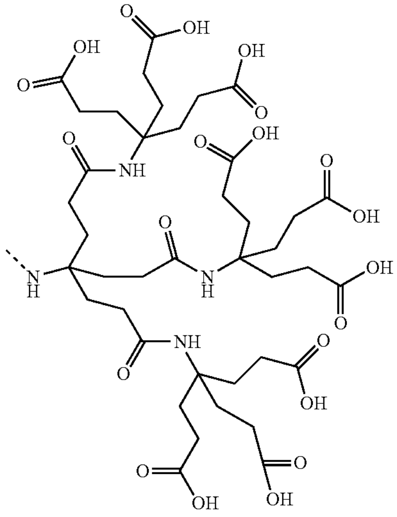
$R_2 = R_3$ = 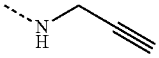
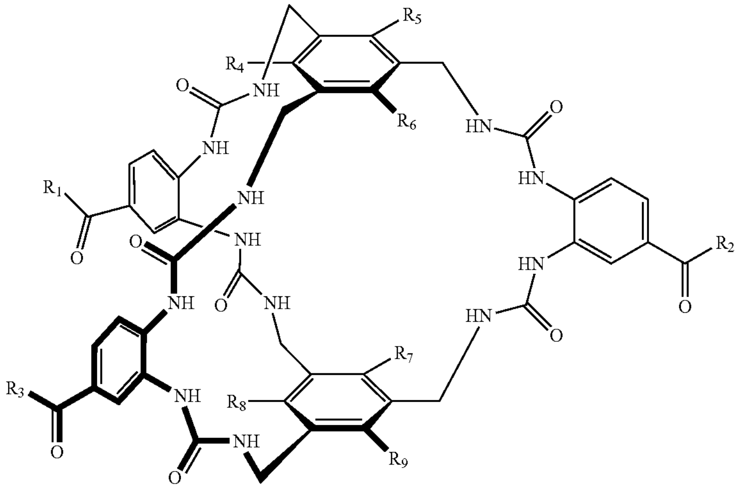
$R_4 = R_5 = R_6 = R_7 = R_8 = R_9 = Me$ -continued
$R_1 = R_2 = R_3 =$
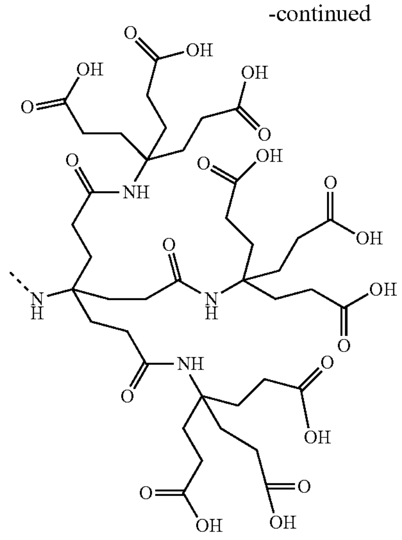
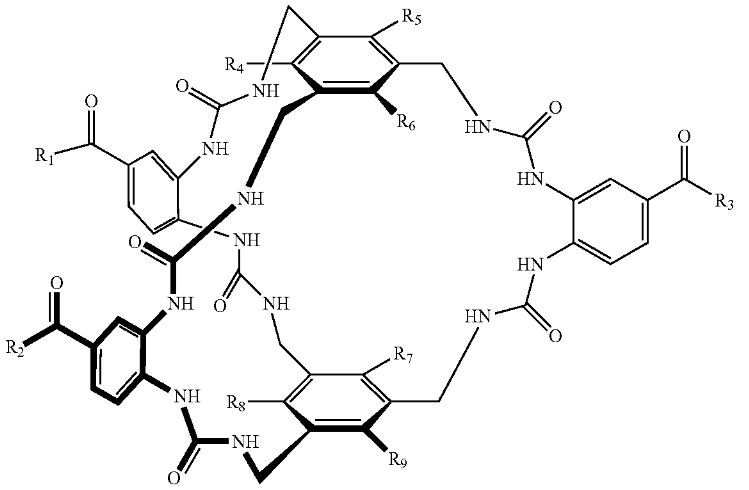
$R_1 = R_2 = R_3 =$
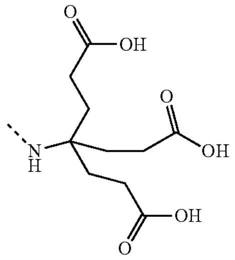
$R_4 = R_5 = R_6 = R_7 = R_8 = R_9 = Et$
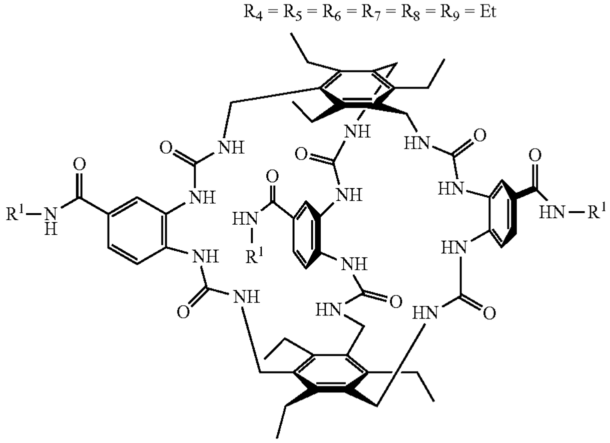
$R^1 =$
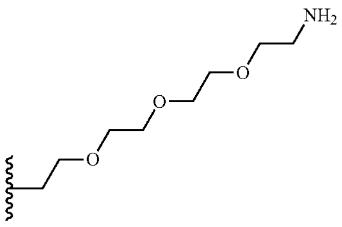

-continued
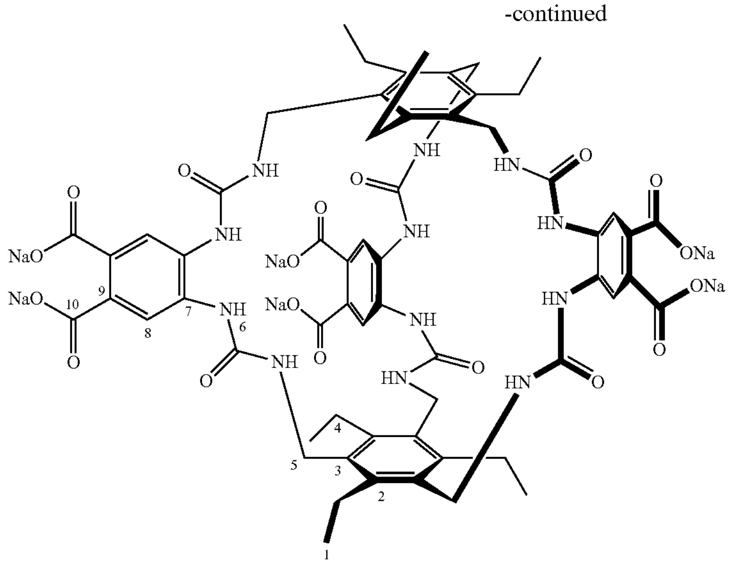
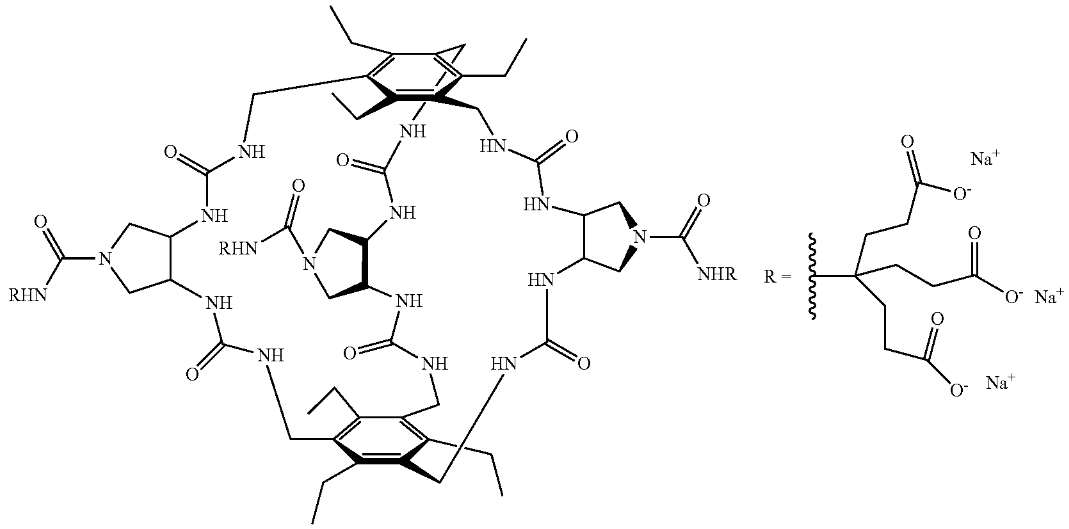
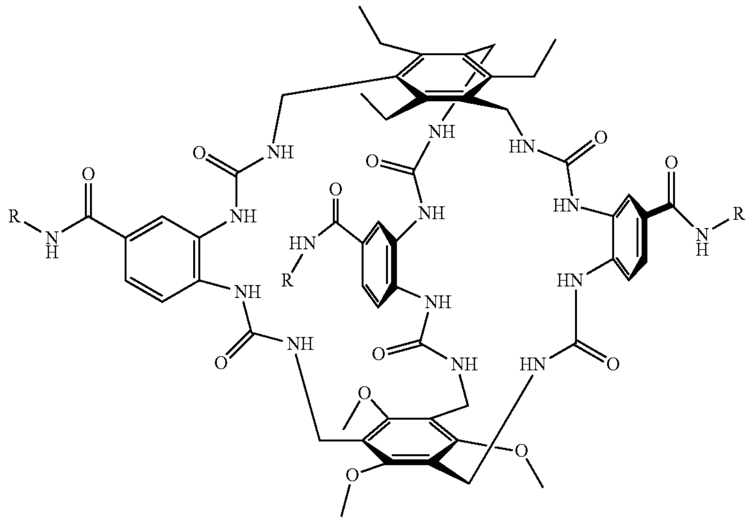

-continued
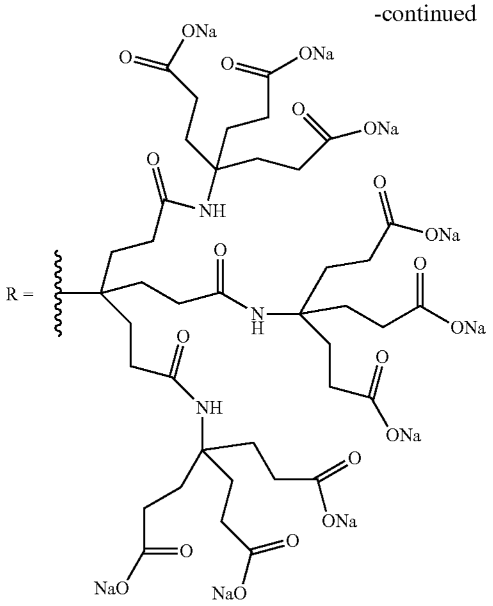
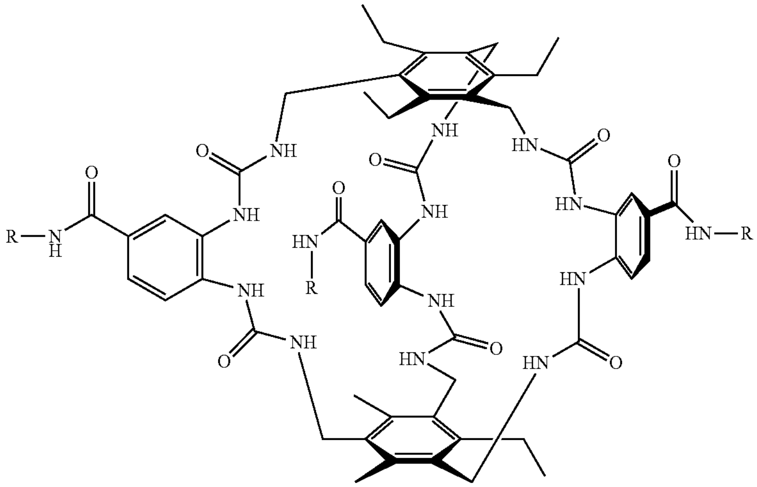
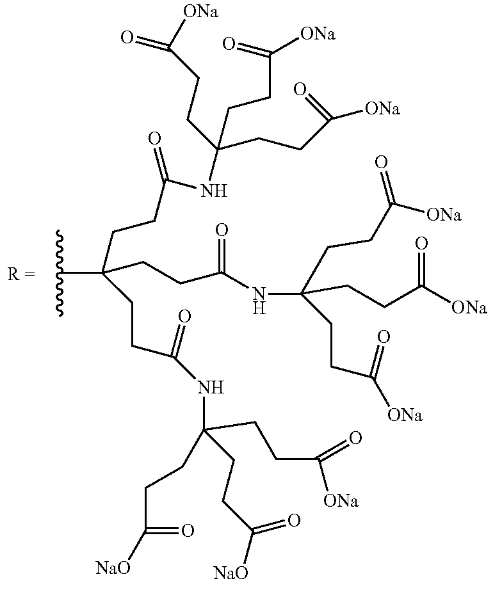

Further particular compounds of the present invention include any of the compounds exemplified in the present application, or a salt, solvate or hydrate thereof, and, in particular, any of the following:
i)
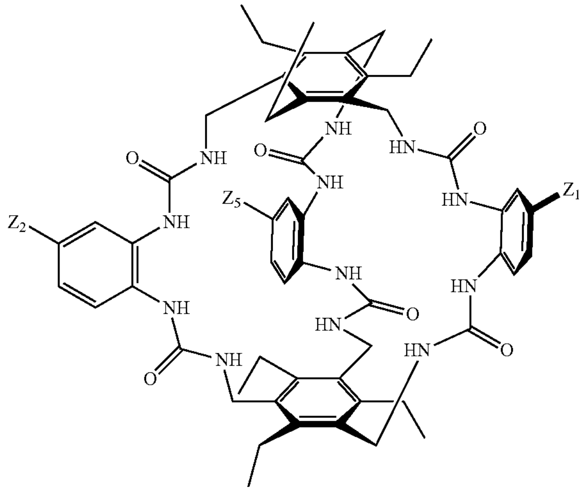
wherein each of $Z_1$, $Z_2$ and $Z_5$ is a group of the formula:
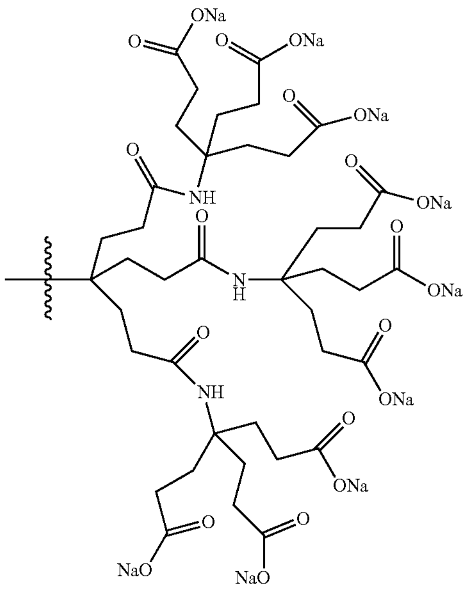
wherein ∿ denotes the point of attachment;
ii)
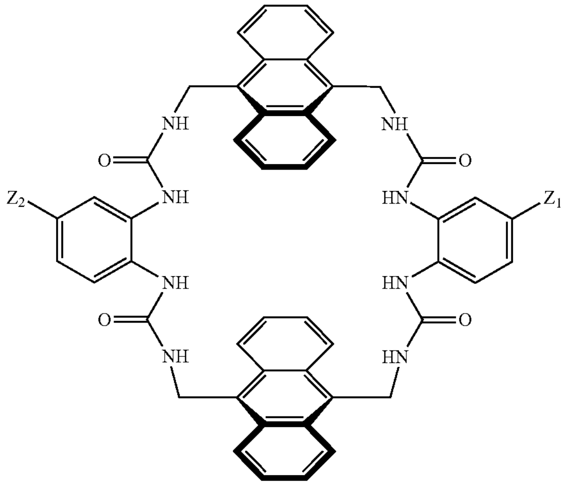
wherein each of $Z_1$, and $Z_2$ is a group of the formula:
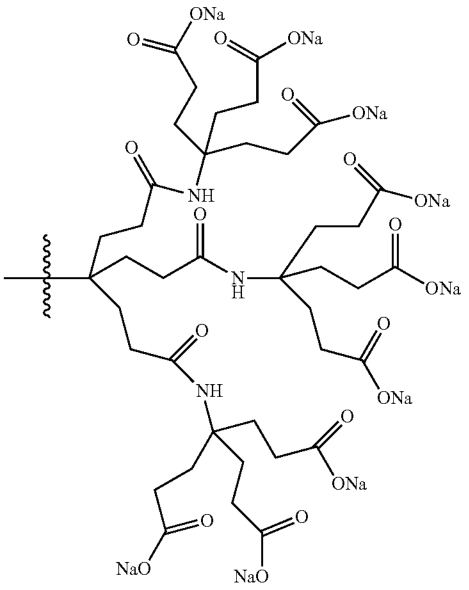

wherein ∿∿∿ denotes the point of attachment;
iii)
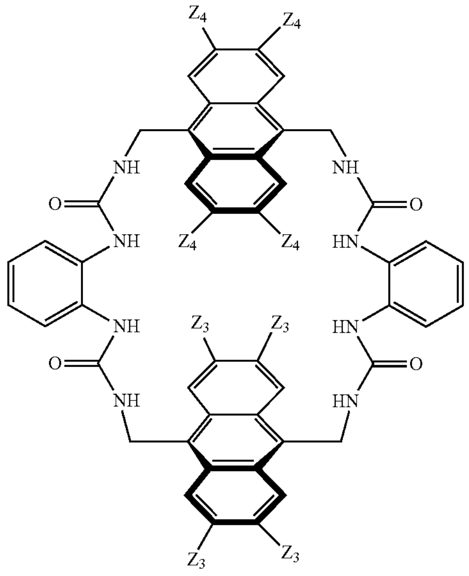
wherein each of $Z_3$, and $Z_4$ is a group of the formula:
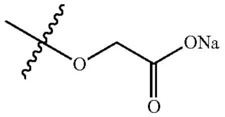
wherein ∿∿∿ denotes the point of attachment;
iv)
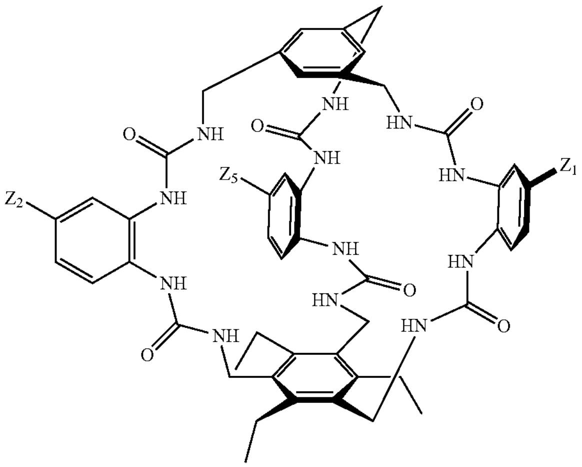
wherein each of $Z_1$, $Z_2$ and $Z_5$ is a group of the formula:
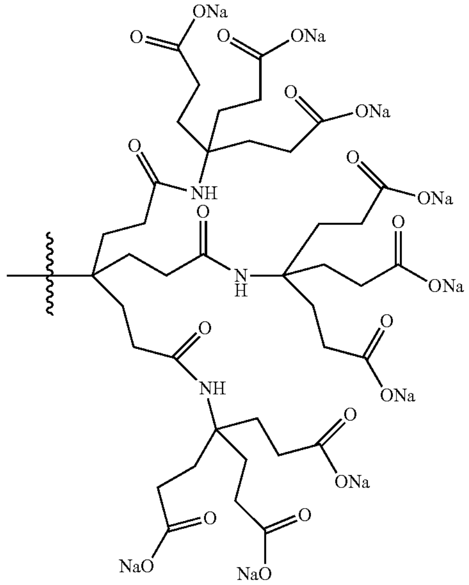
wherein ∿∿∿ denotes the point of attachment; or
v)
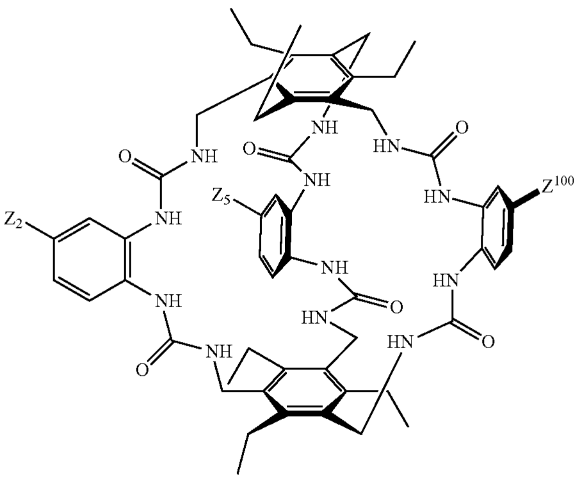

wherein each of $Z_2$ and $Z_5$ is a group of the formula:

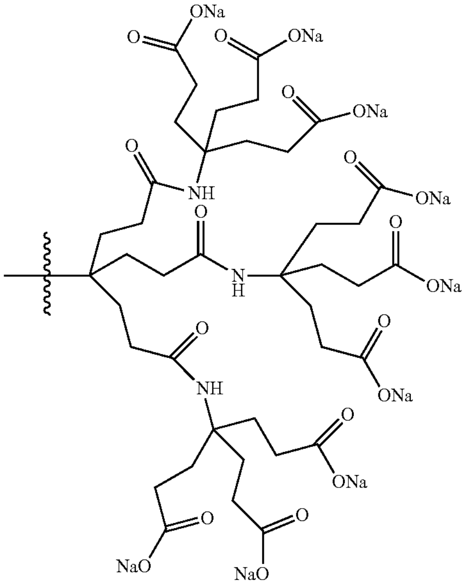

$Z^{100}$ is a group of the formula:

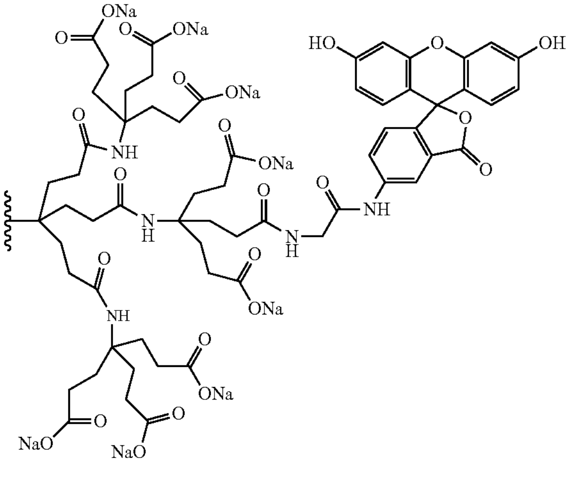

and wherein ∿∿∿ denotes the point of attachment.

Yet further particular compounds of the present invention include any of the compounds exemplified in the present application, or a salt, solvate or hydrate thereof, and, in particular, any of the following:

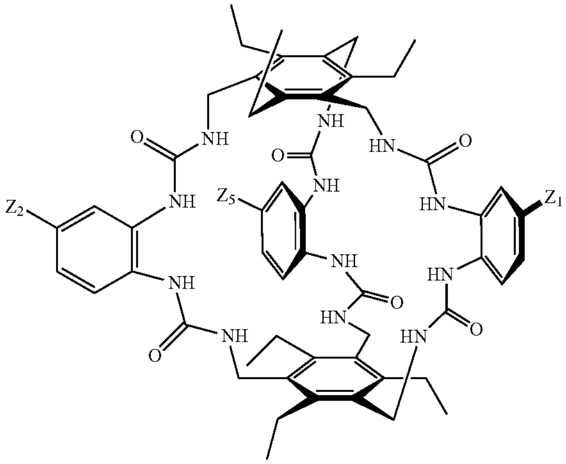

wherein each of $Z_1$, $Z_2$ and $Z_5$ is a group of the formula:

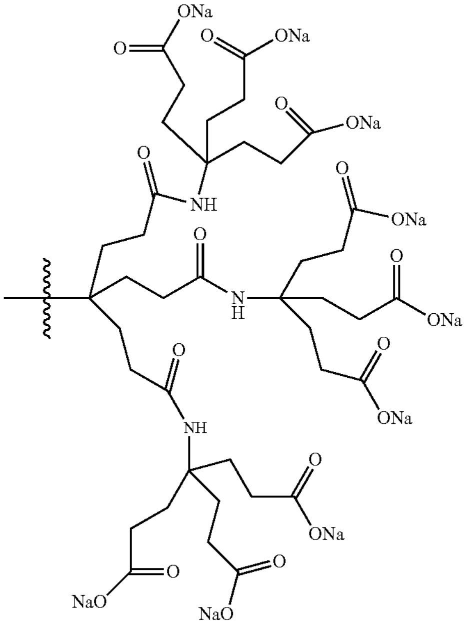

wherein ∿∿ denotes the point of attachment;
ii)
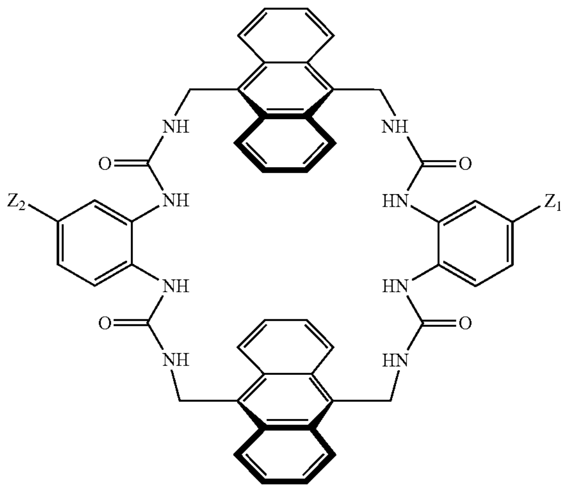
wherein each of $Z_1$, and $Z_2$ is a group of the formula:
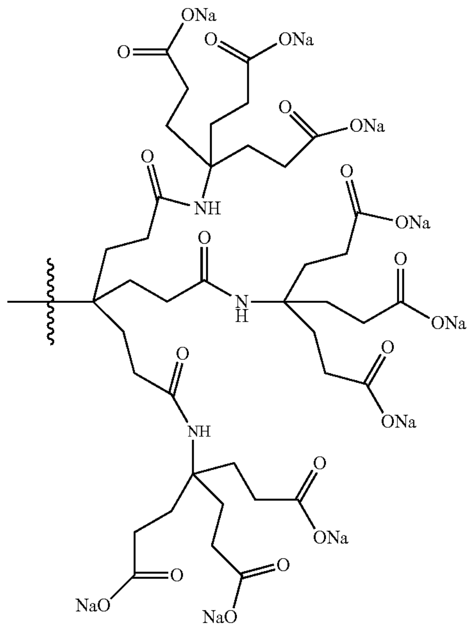
wherein ∿∿ denotes the point of attachment;
iii)
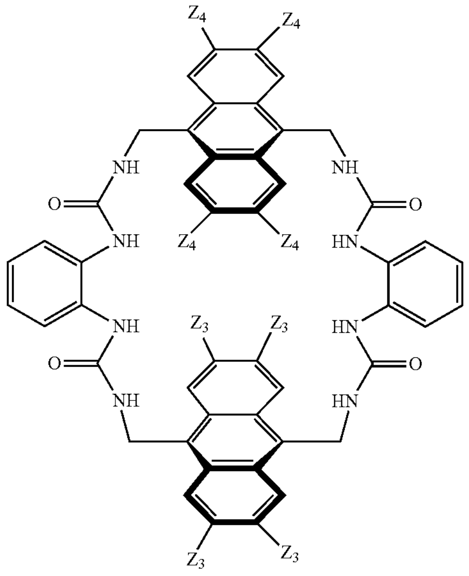
wherein each of $Z_3$, and $Z_4$ is a group of the formula:
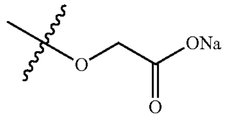
wherein ∿∿ denotes the point of attachment.
Suitably, the compound of the present invention is as follows:
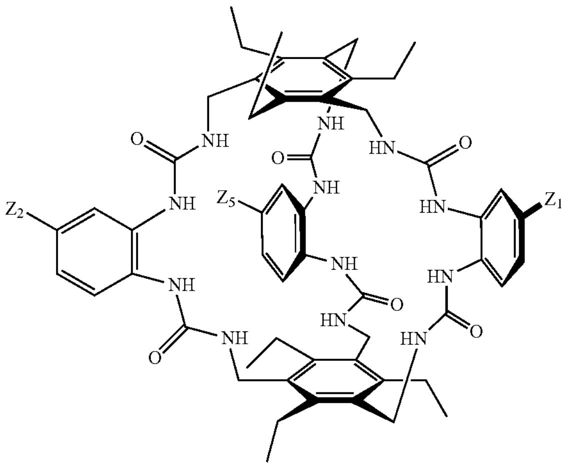

wherein each of $Z_1$, $Z_2$ and $Z_5$ is a group of the formula:

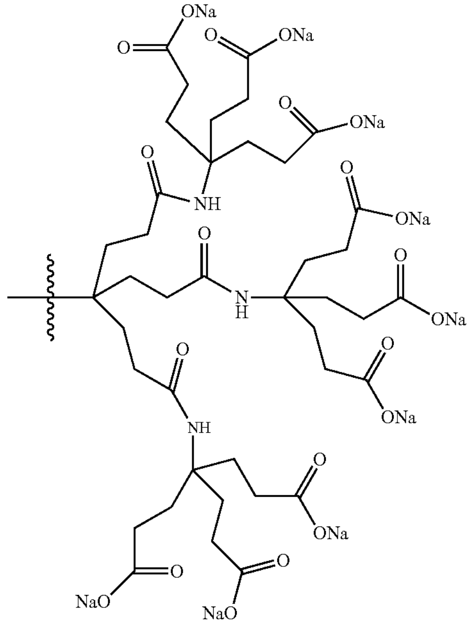

wherein ~~~ denotes the point of attachment.

In certain embodiments of the present invention, the compound is not the following compound:

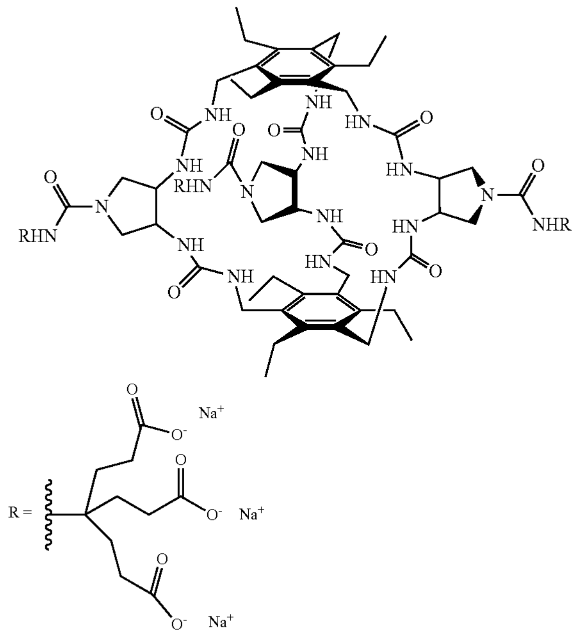

The solid and dashed lines used in Formulae I, Ia, Ib, Ic, Id, Ie, If and Ig hereinabove will be readily understood to have been used for illustration purposes only (i.e. to display the relative orientation of the compounds of the present invention). They do not refer to the absolute configuration (i.e. stereochemistry) of the compounds shown.

A suitable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable salt of a compound of the invention which is sufficiently acidic is an alkali metal salt, for example a sodium or potassium salt, an alkaline earth metal salt, for example a calcium or magnesium salt, an ammonium salt or a salt with an organic base which affords an acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that are capable of saccharide recognition.

The present invention also encompasses compounds of the invention as defined herein which comprise one or more isotopic substitutions. For example, H may be in any isotopic form, including 1H, 2H(D), and 3H (T); C may be in any isotopic form, including 12C, 13C, and 14C; and O may be in any isotopic form, including 16O and 18O; and the like.

It is also to be understood that certain compounds of the Formula (I), and sub-formulae Ia to If, may exist in solvated as well as unsolvated forms such as, for example, hydrated forms. It is to be understood that the invention encompasses all such solvated forms that are capable of saccharide recognition.

It is also to be understood that certain compounds of the Formula (I), and sub-formulae Ia to If, may exhibit polymorphism, and that the invention encompasses all such forms that are capable of saccharide recognition.

Compounds of the Formula (I), and sub-formulae Ia to Ig, may exist in a number of different tautomeric forms and references to compounds of the Formula (I), and sub-formulae Ia to If, include all such forms. For the avoidance of doubt, where a compound can exist in one of several tautomeric forms, and only one is specifically described or shown, all others are nevertheless embraced by Formula I. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

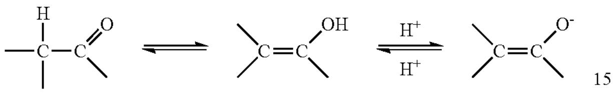

keto enol enolate

Compounds of the Formula (I), and sub-formulae Ia to Ig, containing an amine function may also form N-oxides. A reference herein to a compound of the Formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the saccharide binding capabilites defined herein.

Immobilisation

In an embodiment, the compound of the present invention is immobilised on or in a solid or semi-solid support. The person skilled in the art of organic, synthetic chemistry will understand the term "solid or semi-solid support" to refer to any suitable support in which the compound of the invention may be immobilised on or incorporated within. Suitably, the solid and/or semi-solid support is selected from a polymeric matrix (e.g. a polystyrene bead) and/or a gel (e.g. a hydrogel or sol-gel). More suitably, the solid support is a polymeric matrix (e.g. a polystyrene bead) and the semi-solid support is a gel (e.g. a hydrogel or solgel).

In an embodiment, the polymeric matrix and/or gel comprises one or more homopolymer, copolymer and/or cross-linked polymer. Suitably, the polymeric matrix and/or gel comprises one or more polymer selected from polyethylene glycol, poloxamer, polyacrylamide, polyacrylate, polyalkylacrylate, polyvinylpyrrolidine, polyvinylalcohol, polystyrene, polycarboxylate ethers, polyurethanes, polyallyamine, polyethylenimine, polysaccharides and mixtures and/or derivatives thereof.

In an embodiment, the polymeric matrix and/or gel comprises one or more water soluble polymer. Suitably, the polymeric matrix and/or gel comprises one or more water soluble polymer selected from polyethylene glycol, polyacrylamide, polyvinylalcohol and polycarboxylate. More suitably, the polymeric matrix and/or gel comprises one or more water soluble polymer selected from polyethylene glycol or polyacrylamide.

It will be understood that the compound of the present invention may be attached (immobilised) to the solid or semi-solid support by any suitable means known in the art. The attachment of the compound of the present invention to the solid or semi-solid support may therefore take the form of one or more covalent and/or non-covalent interactions.

In an embodiment, the compound of the present invention is chemically linked (covalently attached) to the polymeric matrix and/or gel. The compound of the present invention may be chemically linked to the polymeric matrix and/or gel at any suitable position of the compound and the attachment may take the form of any suitable bond. Suitably, the compound of the present invention is chemically linked to the polymeric matrix and/or gel via one or more of the substitutent groups associated with at least one of the substituent groups $R^1$, $R^2$, $R^3$, $R^4$, $R^1$, $Z^1$, $Z^2$, $Z^3$, $Z^4$ or $Z^5$. More suitably, the the compound of the present invention is chemically linked to the polymeric matrix and/or gel via one or more of the substitutent groups associated with at least one of the substituent groups $Z_1$, $Z_2$, $Z_3$, $Z_4$ or $Z_5$.

In an embodiment, the compound of the present invention is chemically linked (covalently attached) to the polymeric matrix and/or gel via a linker, $L_2$. It will be understood that the linker, $L_2$, may be any group capable of forming a covalent attachment between the compound of the present invention and the polymeric matrix and/or gel. The linker, $L_2$, may take the form of a bond (e.g. an amide bond) or may be in the form of a suitable cross-linker molecule, used to couple together the compound of the present invention and the polymeric matrix and/or gel. The person skilled in the art will be able to select suitable cross-linker molecules for use in covalently coupling the compounds of the present invention to the polymeric matrix and/or gel.

In another embodiment, the compound of the present invention is associated with and/or physically incorporated within the polymeric matrix and/or gel via non-covalent interactions. It will be understood that any suitable non-covalent interaction may be utilised for association between the compound of the present invention and the polymeric matrix and/or gel. Non-limiting examples of suitable non-covalent interactions include: hydrogen-bonding interactions, ionic interactions, hydrophobic interactions, van der Waal interactions and combinations thereof.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively, an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively, an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of Formula (I) will vary depending on the nature of Rings A and B, C, D, $R_1$, $R_2$, $R_3$, $R_4$, $W_1$, $W_2$, $W_3$, $W_4$, $X_1$, $X_2$, $X_3$, $X_4$, $Z_1$, $Z_2$, $Z_3$, $Z_4$, $Z_5$, L, a, b, c, d, m, n, o, p and any substituent groups associated therewith. Suitable processes for their preparation are described further in the accompanying Examples.

In certain embodiments, the compounds of the present invention (i.e. the compounds of Formula (I)) are prepared according to Method A or Method B, shown below:

Method A reacting a compound of Formula III, as shown below:

Formula III

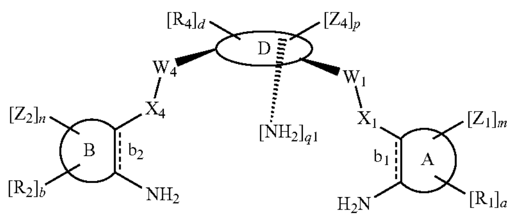

wherein, bonds $b_1$ and $b_2$, Rings A and B, D, $W_1$, $W_4$, $X_1$, $X_4$, $Z_1$, $Z_2$, $Z_4$, $R_1$, $R_2$, $R_4$ and integers a, b, d, m, n and p are as defined hereinabove, and $q^1$ is an integer selected from 0 or 1;

with a compound of Formula IV:

Formula IV

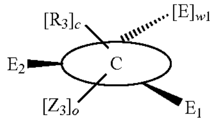

wherein, C, $R_3$, $Z_3$, c and o are as defined hereinabove, $w^1$ is and integer from 0 to 1 and $E_1$, $E_2$ and $E_3$ are each selected from a group of Formula X1, shown below:

Formula X1

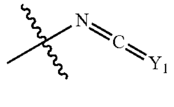

denotes the point of attachment; and $Y_1$ is selected from O, S or $NR_j$, wherein $R_j$ is as defined herein;

and, optionally, thereafter, and if necessary:

i) removing any protecting groups present;

ii) converting the compound of Formula (I) into another compound of Formula (I); and/or iii) forming a salt, hydrate or solvate thereof;

Method B reacting a compound of Formula V, as shown below:

Formula V

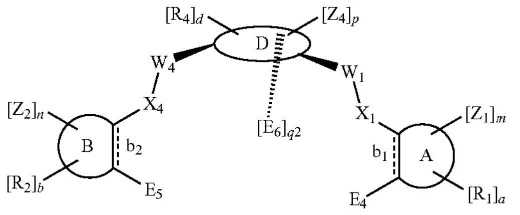

wherein, bonds $b_1$ and $b_2$, Rings A and B, D, $W_1$, $W_4$, $X_1$, $X_4$, $Z_1$, $Z_2$, $Z_4$, $R_1$, $R_2$, $R_4$ and integers a, b, d, m, n and p are as defined in hereinabove, $q^2$ is an integer selected from 0 or 1 and $E_4$, $E_5$ and $E_6$ are each selected from a group of Formula X2, shown below:

Formula X2

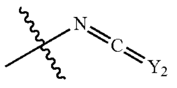

wherein denotes the point of attachment; and $Y_2$ is selected from O, S or $NR_j$, wherein $R_j$ is as defined herein;

with a compound of Formula VI:

Formula VI

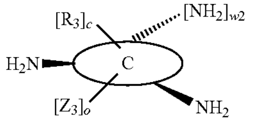

wherein, C, $R_3$, $Z_3$ and integers c and o are as defined in hereinabove, and $w^2$ is and integer from 0 to 1;

and, optionally, thereafter, and if necessary:

i) removing any protecting groups present;

ii) converting the compound of Formula (I) into another compound of Formula (I); and/or iii) forming a salt, hydrate or solvate thereof.

Suitably, Method A and/or B described hereinabove is carried out in the presence of one or more of the following:

a base;

a template a catalyst; and/or an activating agent.

In an embodiment, Method A and/or B is conducted in the presence of a base. Non-limiting examples of suitable bases include NaOH, KOH, potassium tert-butoxide, trimethylamine, diisopropylethylamine, diisopropylmethylamine, N-methylmorpholine, piperidine, 2,2,6,6-tetramethylpiperidine, pyridine, 2,6-dimethylpyrridine, methylimidazole, 4-(Dimethylamino)pyridine (DMAP) and 1,8-diazabicyclo (5.4.0)undec-7-ene (DBU). Suitably, the base is pyridine, 4-(Dimethylamino)pyridine (DMAP) or methylimidazole. Most suitably, the base is pyridine.

In another embodiment, Method A and/or Method B is conducted in the presence of a template. The term "template" will be understood to be a term of the art and refers to a molecule which is capable of reversibly associating with one or more of the starting materials and/or intermediates and/or final products of a reaction, and in doing so helps to promote the generation of one or more of the final products of the reaction. Non-limiting examples of suitable templates include octyl-β-glucoside, methyl-β-glucoside, octyl-β-galactoside, methyl-β-galactoside, octyl-β-mannoside and methyl-β-mannoside. Suitably, the template is octyl-β-glucoside.

It will be understood that the template may be used in any suitable amount. Suitably, the mole ratio of template to the compound of Formula III or the compound of Formula V is from between 0.1:1 to 10:1. More suitably, the the mole ratio of template to the compound of Formula III or the compound of Formula V is from between 0.5:1 to 5:1. Most suitably, the mole ratio of template to the compound of Formula III or the compound of Formula V is from between 0.5:1 to 2:1.

In a particular embodiment, Method A and/or Method B is conducted in the presence of a base (e.g. 4-dimethylaminopyridine) and a template (e.g. octyl-β-glucoside).

In certain embodiments, Method A and B may be conducted in the presence of one or both of a catalyst and/or an activating agent. The term "catalysts" will be understood to be any suitable reagent that helps to promote the rate of the reaction between the compounds of Formulae III and IV and V and VI without undergoing any permanent chemical change. Whereas, the term "activating agent" will be understood to be any suitable agent that reacts with one or more of the starting materials of the reaction to help promote the reactivity of said starting material in the reaction.

It will be appreciated that any suitable reaction conditions may be used in Methods A and B defined hereinabove. Furthermore, it will be understood that the reaction conditions used in Methods A and B will vary according to the specific functional groups present. A person skilled in the art will be able to select suitable reaction conditions (e.g. temperature, pressures, reaction times, concentration etc.) to use in either Method A or Method B.

In an embodiment, Method A and/or B is conducted at a temperature of between −100° C. and 200° C. Suitably, the process of the present invention is conducted at a temperature of between 0° C. and 150° C. More suitably, the process of the present invention is conducted at a temperature of between 0° C. and 100° C. Most suitably, the process of the present invention is conducted at a temperature of between 0° C. and 75° C.

In another embodiment, Method A and/or B is carried out in an organic solvent. The organic solvent may be used to solubilise the compounds of Formulae III, IV, V and VI thereby facilitate reaction therebetween. Accordingly, it will be understood that the organic solvent selected will depend on the specific compound selected. Suitable organic solvents may include, but are not limited to, chloroform, dichloromethane, DMF, DMSO, acetonitrile, tetrahydrofuran (THF), N-Methyl-2-pyrrolidone (NMP), 2-methyltetrahydrofuran (2M-THF) and mixtures thereof.

In certain embodiments, Method A and/or Method B is carried out in pyridine.

In another embodiment, Method A and/or B is carried out under anhydrous conditions.

In further embodiment, Methods A and B are conducted under an inert atmosphere (i.e. under nitrogen or argon).

The resultant compounds of the present invention (i.e. compounds of Formula (I)) may be isolated and purified using techniques well known in the art. A non-limiting example of a suitable technique is chromatography, particularly high performance liquid chromatography (HPLC).

Intermediates

In another aspect, the present invention provides novel intermediates, as defined herein, which are suitable for use in the synthetic methods as set out herein.

Thus, in a particular aspect of the present invention, there is provided a compound of Formula III or Formula V, or a salt, solvate, ester or hydrate thereof, as shown below:

Formula III

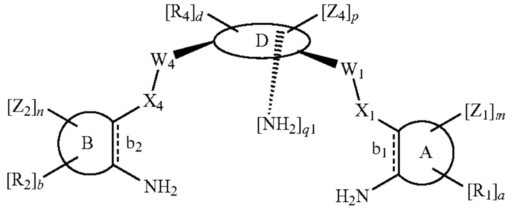

Formula V

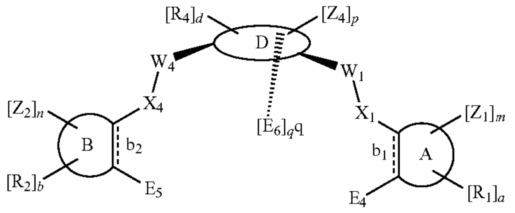

wherein, each of bonds, $b_1$ and $b_2$, Rings A and B, D, $W_1$, $W_4$, $X_1$, $X_4$, $Z_1$, $Z_2$, $Z_4$, $R_1$, $R_2$, $R_4$, a, b, d, m, n, p, $E_4$, $E_5$, $E_6$, $q^1$ and $q^2$ are as defined hereinabove.

Preferred and suitable substituent groups for each of Rings A and B, D, $W_1$, $W_4$, $X_1$, $X_4$, $Z_1$, $Z_2$, $Z_4$, $R_1$, $R_2$, $R_4$, a, b, d, m, n and p in respect of the compounds of Formula III will be understood to be analogous to the preferred and suitable substituent groups for each of Rings A and B, D, $W_1$, $W_4$, $X_1$, $X_4$, $Z_1$, $Z_2$, $Z_4$, $R_i$, $R_2$, $R_4$, a, b, d, m, n and p for the compounds of Formula (I) described hereinabove.

In certain embodiments, the compounds of Formula III and/or Formula V may be optionally attached to a substituent group of Formula A1 as defined hereinabove, at a position associated with one or more of the substituent groups $R_{1a}$, $R_{1b}$, $R_{2a}$, $R_{2b}$, $R_1$, $R_2$, $R_3$, $R_4$, $Z_1$, $Z_2$, $Z_3$, $Z_4$ and/or $Z_5$.

In a particular embodiment, the present invention provides the following compounds, or salts, solvates, ester or hydrates thereof:

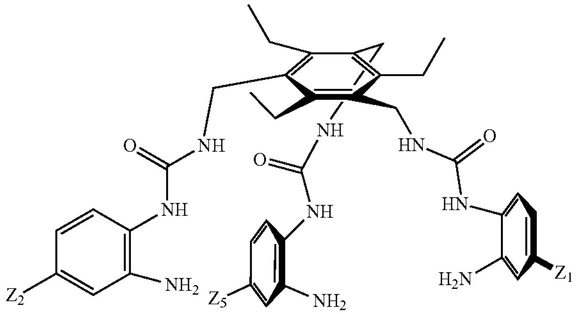

-continued

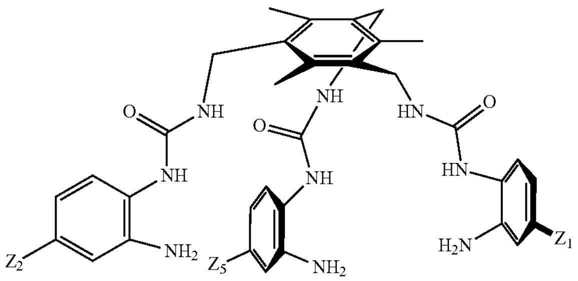

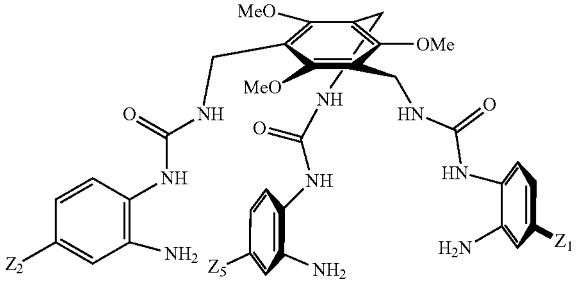

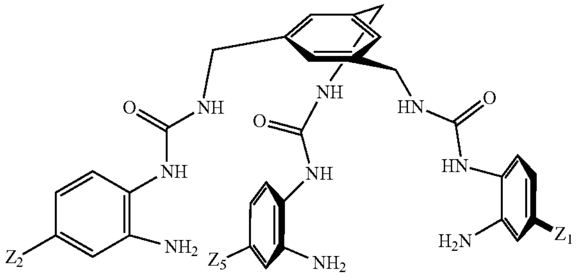

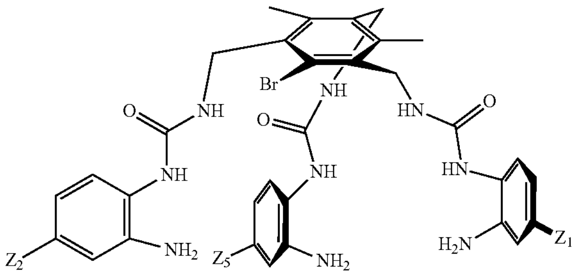

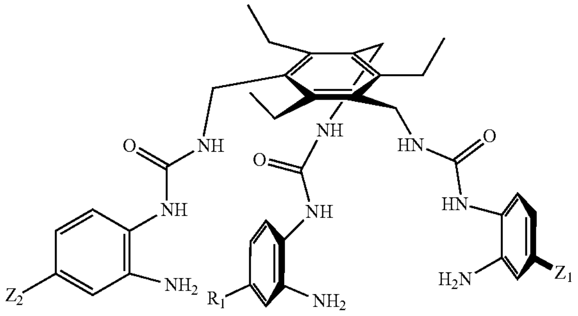

-continued
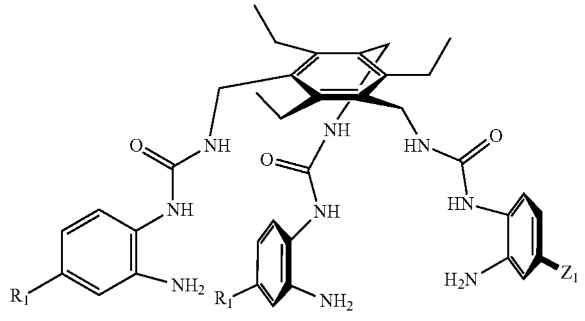
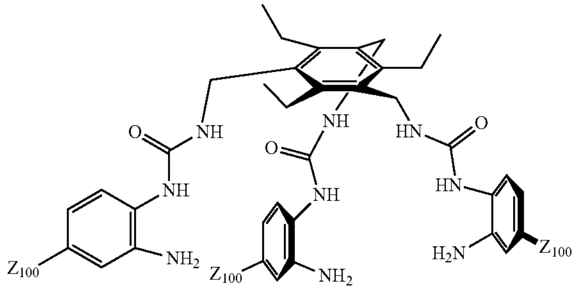
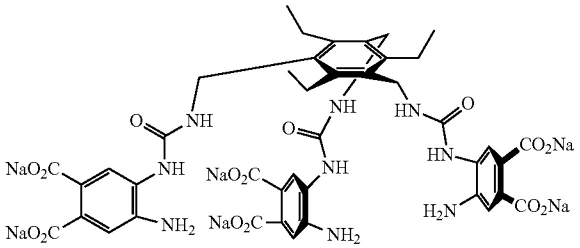
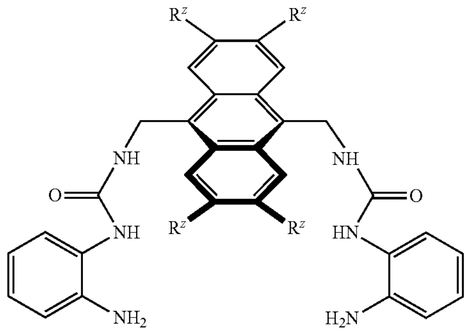
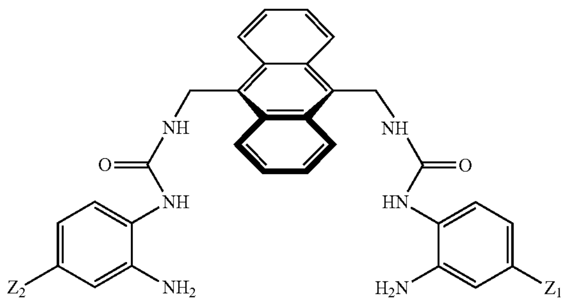
-continued
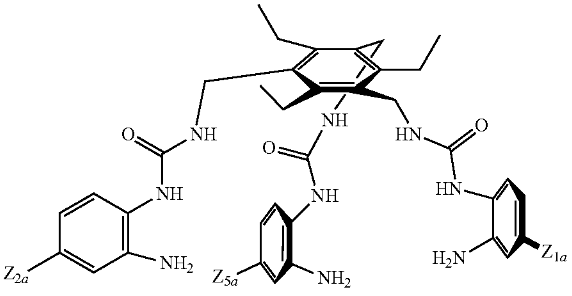
wherein:
$R^z$ is selected from $—OCH_2C(O)ONa$, $—OCH_2C(O)OC(CH_3)_3$ or $—OCH_2C(O)OCH_3$;
$R_1$ is a group of the formula:
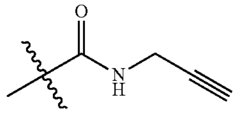 [SMILES: *C(=O)NCC#C]
each of $Z_1$, $Z_2$ and $Z_5$ is a group of the formula:
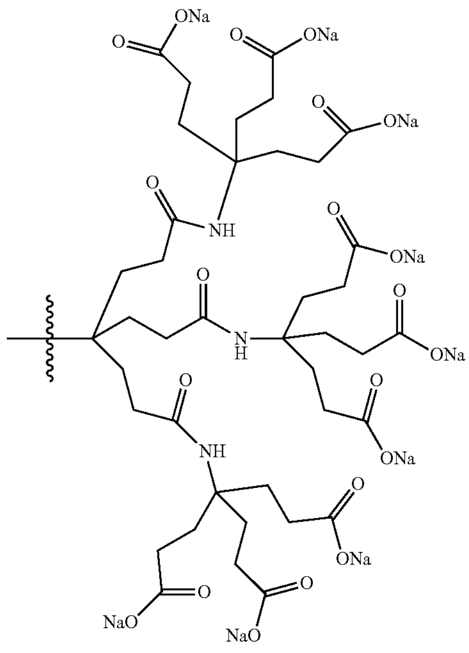

each $Z_{100}$ is a group of the formula:
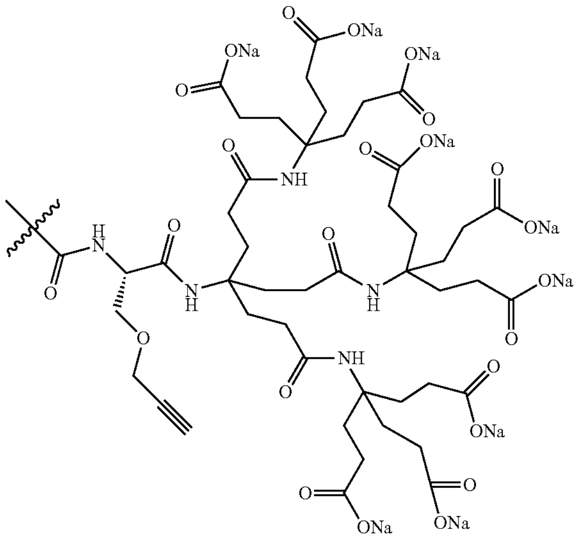
and $Z_{1a}$, $Z_{2a}$ and $Z_{5a}$ are selected from:
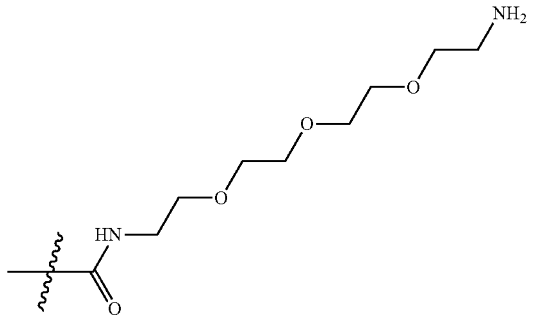 [SMILES: *C(=O)NCCOCCOCCOCCN]
wherein ∿∿ denotes the point of attachment; or
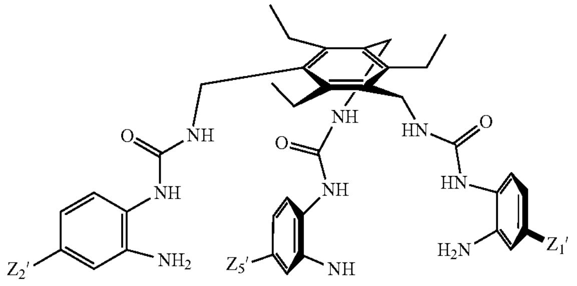
wherein $Z_{1'}$, $Z_{2'}$ and $Z_{5'}$ is a group of the formula:
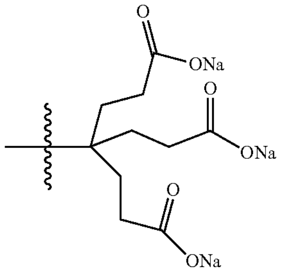
In a particular embodiment, the present invention provides the following compounds, or salts, solvates, ester or hydrates thereof:
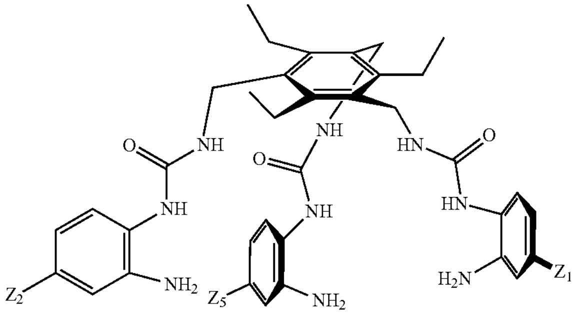
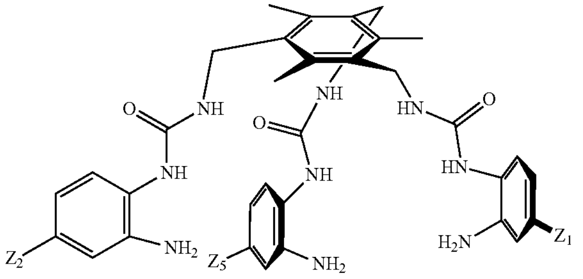
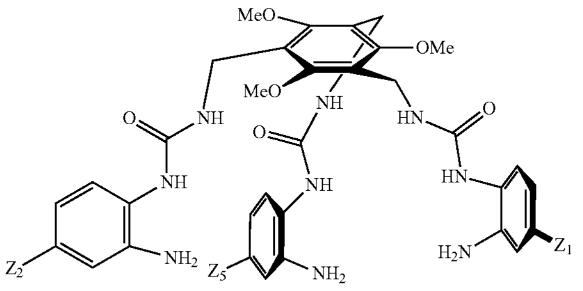
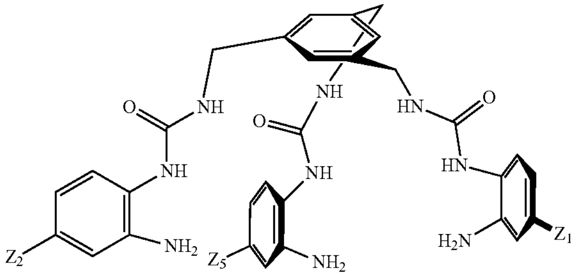

-continued

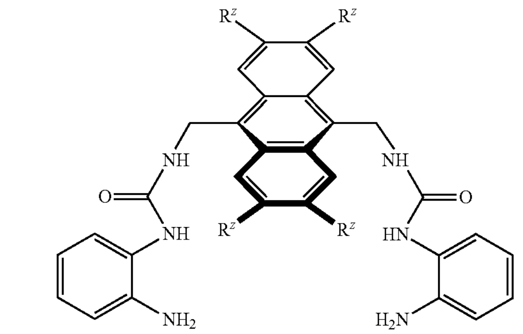

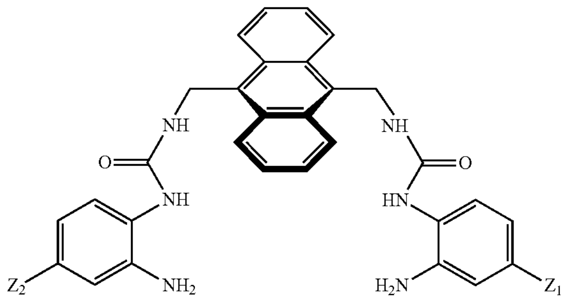

wherein:

$R^z$ is selected from $—OCH_2C(O)ONa$, $—OCH_2C(O)OC(CH_3)_3$ or $—OCH_2C(O)OCH_3$; and each of $Z_1$, $Z_2$ and $Z_5$ is a group of the formula:

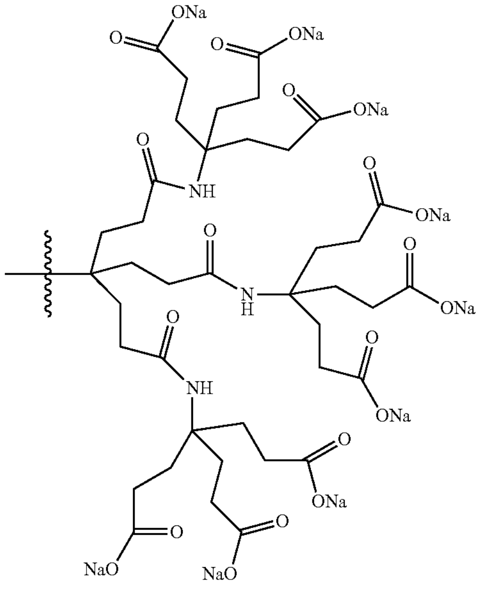

wherein ∿ denotes the point of attachment; or

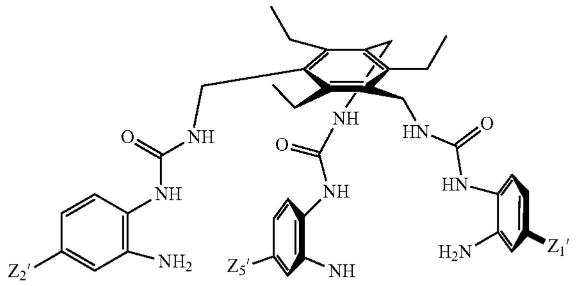

wherein $Z_{1'}$, $Z_{2'}$, and $Z_{5'}$ is a group of the formula:

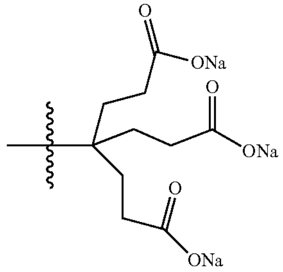

In another particular embodiment, the present invention provides the following compounds, or salts, solvates, ester or hydrates thereof:

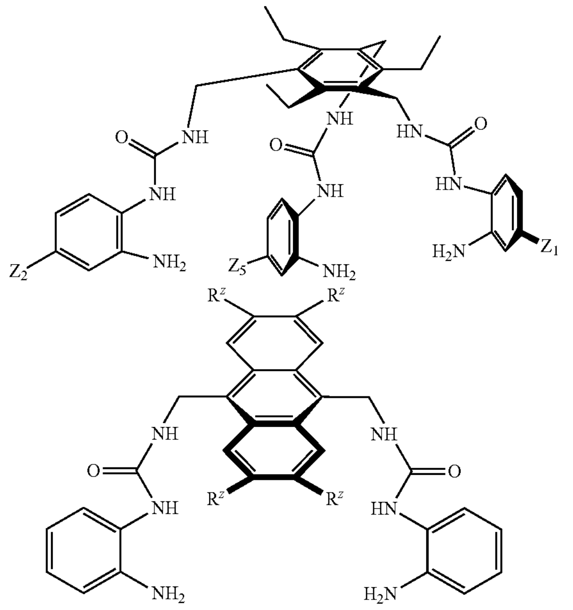

-continued

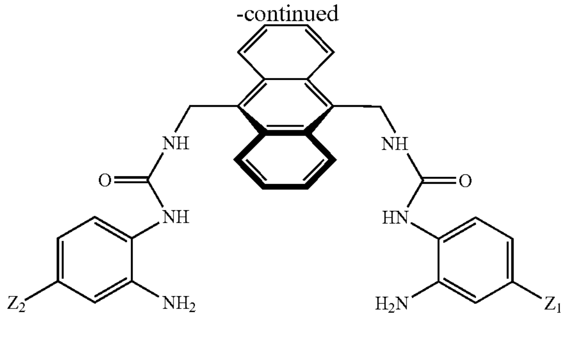

wherein:

$R^z$ is selected from $-OCH_2C(O)ONa$, $-OCH_2C(O)OC(CH_3)_3$ or $-OCH_2C(O)OCH_3$; and each of $Z_1$, $Z_2$ and $Z_5$ is a group of the formula:

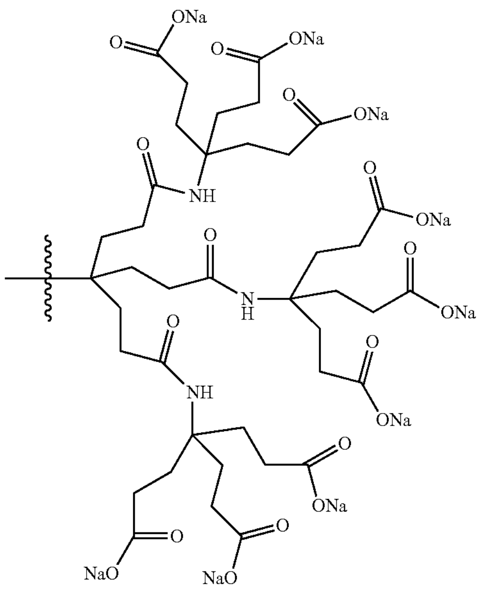

wherein ∿∿ denotes the point of attachment.

Saccharide Recognition

The compounds of the present invention are advantageously capable of association with one or more target saccharides in an aqueous medium. It will be understood that the association between the compounds of the present invention and the one or more target saccharides may involve one or more covalent and/or non-covalent interactions therebetween. Suitably, the compounds of the present invention are capable of association with the one or more target saccharides through non-covalent interations (e.g. CH-π interactions, van der Waal interactions and polar interactions) only, which advantageously makes the compounds of the present invention suitable for use in reversible saccharide association and subsequent continuous saccharide detection.

The isothermal titration calorimetry (ITC) studies described in the Examples section hereinbelow may be used to measure the saccharide binding affinity of the compounds of the present invention. It will be appreciated that other suitable techniques known in the art may also similarly be used to determine saccharide binding affinity. Non-limiting examples of other suitable techniques include fluorescence titrations, UV-vis titrations and/or $^1H$ NMR titrations.

Although the saccharide binding affinities of the compounds of Formula I vary with structural change, as expected, the compounds of the invention were found to demonstrate saccharide (e.g. glucose) binding affinity in ITC studies described in the Examples section hereinbelow.

In general, the compounds of the invention demonstrate a binding affinity ($K_a$) towards the target saccharide (e.g. glucose) in water of equal to or greater than 10 $M^{-1}$ in the ITC study described in the Examples section hereinbelow. Suitably, the the compounds of the invention demonstrate a binding affinity ($K_a$) towards the target saccharide (e.g. glucose) in water of equal to or greater than 50 $M^{-1}$. More suitably the compounds of the invention demonstrate a binding affinity ($K_a$) towards the target saccharide (e.g. glucose) in water of equal to or greater than 100 $M^{-1}$. Yet more suitably, the compounds of the invention demonstrate a binding affinity ($K_a$) towards the target saccharide (e.g. glucose) in water of equal to or greater than 500 $M^{-1}$. Even more suitably, the compounds of the invention demonstrate a binding affinity ($K_a$) towards the target saccharide (e.g. glucose) in water of equal to or greater than 1000 $M^{-1}$. Most suitably, the compounds of the invention demonstrate a binding affinity ($K_a$) towards the target saccharide (e.g. glucose) in water of equal to or greater than 2000 $M^{-1}$.

In a particular embodiment, the compounds of the invention demonstrate a binding affinity ($K_a$) towards the target saccharide (e.g. glucose) in water of equal to or greater than 5000 $M^{-1}$, most suitably, equal to or greater than 10000 $M^{-1}$.

The compounds of the present invention also advantageously demonstrate a selectivity towards saccharides comprising all-equatorial substituents over those comprising at least one axial substituent (e.g. mannose). In certain embodiment, the compounds of the present invention also demonstrate a selectivity towards monosaccharides over di-, tri and oligosaccharides.

Suitably, the compounds of the present invention display a binding affinity ($K_a$) towards saccharides comprising all-equatorial substituents (e.g. glucose) which is at least 2 times higher than the binding affinity ($K_a$) displayed towards saccharides comprising at least one axial substituent (e.g. mannose). More suitably, the compounds of the present invention display a binding affinity ($K_a$) towards saccharides comprising all-equatorial substituents (e.g. glucose) which is at least 5 times higher than the binding affinity ($K_a$) displayed towards saccharides comprising at least one axial substituent (e.g. mannose). Yet more suitably, the compounds of the present invention display a binding affinity ($K_a$) towards saccharides comprising all-equatorial substituents (e.g. glucose) which is at least 50 times higher than the binding affinity ($K_a$) displayed towards saccharides comprising at least one axial substituent (e.g. mannose). Even more suitably, the compounds of the present invention display a binding affinity ($K_a$) towards saccharides comprising all-equatorial substituents (e.g. glucose) which is at least 100 times higher than the binding affinity ($K_a$) displayed towards saccharides comprising at least one axial substituent (e.g. mannose). Most suitably, the compounds of the present invention display a binding affinity ($K_a$) towards saccharides comprising all-equatorial substituents (e.g. glucose) which is at least 500 times higher than the binding affinity ($K_a$) displayed towards saccharides comprising at least one axial substituent (e.g. mannose).

Furthermore, the compounds of the present invention also advantageously demonstrate a selectivity towards saccharides comprising all-equatorial substituents (e.g. glucose) over other commonly occurring small molecules. Non-limiting examples of such commonly occurring small molecules include, purines and pyrimidines (e.g. cytidine, adenosine, guanosine, uridine, adenine, cytosine, thymine, uracil, uric acid, hypoxantine and xanthine), organic acids (e.g. glutaric acid and glutamic acid) and amino acids (e.g. histidine, phenylanaline, tryptophan etc.). One problem commonly associated with saccharide receptors known in the art is that they often display some affinity towards such small molecules, which effectively 'poisons' the receptors affinity towards the target saccharide when such small molecules are present. Advantageously, compounds of the present invention show little to no affinity towards such small molecules and thus do not suffer from such 'poisoning' effects.

Complexes and Compositions

According to a further aspect of the invention, there is provided a complex comprising a compound of the present invention, as defined herein, in association with a target saccharide.

It will be appreciated that preferred and suitable compounds of the present invention in relation to the complex will be analogous to the preferred and suitable compounds described hereinabove in respect of the compounds of the present invention per se.

In an embodiment, the target sacharride is a saccharide comprising all equatorial substituents. More suitably, the target saccharide is a monosaccharide comprising all equatorial substituents. Most suitably, the target saccharide is glucose (e.g. β-glucose).

In another aspect of the present invention, there is provided a complex comprising a compound of the present invention, as defined herein, in association with a displaceable reporter molecule.

In an embodiment, the complex comprises a compound of Formula Ib, Ic or Id, as defined herein, in association with a displaceable receptor molecule.

The displaceable reporter molecule will be understood to be any compound which is capable of association (binding) with the compound of the present invention in the absence of a target saccharide (e.g. glucose), and which is capable of dissociation from the compound of the present invention, and detectable, of upon exposure of the composition to a target saccharide.

In an embodiment, the displaceable reporter molecule is an aromatic molecule and/or dye molecule. Suitably, the displaceable reporter molecule is an aromatic molecule. More suitably, the displaceable reporter molecule is a fluorescent aromatic molecule (e.g. fluoresceinamine or tetramethylrhodamine isothiocyanate).

Suitably, the displaceable reporter molecule has an emission wavelength of between 300 nm and 1000 nm. More suitably, the displaceable reporter molecule has an emission wavelength of between 300 nm and 800 nm. Yet more suitably, the displaceable reporter molecule has an emission wavelength of between 500 nm and 700 nm.

In certain embodiments, the displaceable reporter molecule is attached to a saccharide (e.g. a glucoside). Suitably, the displaceable reporter molecule is attached to a saccharide (e.g. a glucoside) via a linker (e.g. an alkyl linker).

According to a further aspect of the invention there is provided a composition comprising a compound of the invention as defined hereinbefore, or a salt, hydrate or solvate thereof, and a displaceable reporter molecule which is capable of association with said compound.

In an embodiment, there is provided a composition comprising a compound of Formula Ib, Ic or Id, as defined hereinabove, or a salt, hydrate or solvate thereof, and a displaceable reporter molecule which is capable of association with said compound.

Suitably, the displaceable receptor molecule is an aromatic molecule and/or dye molecule, more suitably an aromatic molecule, and most suitably a fluorescent aromatic molecule (e.g. fluoresceinamine or tetramethylrhodamine isothiocyanate).

In another embodiment, the composition of the invention comprises a diluent and/or carrier. Suitably, the diluent and/or carrier is a pharmaceutically acceptable diluent and/or carrier, suitable for use in, for example, veterinary and/or medicinal applications (i.e. administration to an animal and/or human body).

According to a further aspect of the invention there is provided a composition comprising a compound of the invention as defined hereinbefore, or a salt, hydrate or solvate thereof, and a pharmaceutically acceptable diluent and/or carrier.

It will be appreciated that the compositions of the present invention may also comprise one or more additional excipients. Additional excipients may be included to improve various properties of the formulation, such as, for example, formulation stability, biocompatibility and administrability. A person skilled in the art will be able to select suitable excipients to include based on conventional knowledge in the formulation field.

A non-limiting list of possible additional excipients that may be added to the compositions of the present invention include: pH modifiers, surfactants, viscosity modifiers, tonicity agents, sterilising agents, preservatives, lubricants and solubility enhancers.

In another embodiment, the composition of the present invention comprises one or more additional saccharide detection agents. Suitable saccharide detection agents for incorporation in the composition of the present invention include known saccharide binding compounds (e.g. boronic acid based compounds) and/or saccharide specific enzymes (e.g. glucose oxidase (GOx)).

The composition of the invention may be obtained by any conventional procedure, using conventional formulation excipients, well known in the art.

Applications, Devices and Kits

The present invention provides compounds that display saccharide (e.g. glucose) binding affinity in water. Furthermore, in certain embodiments, the compounds of the present invention display a selectivity towards all-equitorial saccharides over saccharides comprising one or more axial substituents.

The present invention therefore provides a use of a compound, as defined herein (e.g. a compound of Formula If or Ig), a complex, as defined herein, a composition, as defined herein, or a saccharide detection device, as defined herein, for detecting a target saccharide in an aqueous environment. Suitably, the target saccharide is an all-equitorial saccharide, more suitably, an all-equitorial monosaccharide, and most suitably, glucose (e.g. β-glucose).

In an embodiment, the aqueous environment is blood or blood plasma.

In another embodiment, the aqueous environment is a fermentation and/or cell culturing medium.

In embodiments in which a displaceable reporter molecule is used, it will be appreciated that the displaceable reporter molecule is dissociated from the compound of the present invention, and subsequently detected, upon exposure of the composition, or saccharide detection device, to a target saccharide (e.g. glucose).

According to another aspect of the present invention, there is provided a use of a complex, as defined herein, a composition, as defined herein, a saccharide detection device, as defined herein, or a compound, as defined herein (e.g. a compound of Formula If or Ig), for the diagnosis of a condition which results in, or is otherwise associated with, an abnormal concentration of, and/or a change in the concentration of, a target saccharide. Suitably, the target saccharide is an all-equitorial saccharide, more suitably, an all-equitorial monosaccharide, and most suitably, glucose (e.g. β-glucose).

In an embodiment, the diagnosis of a condition which results in, or is otherwise associated with, an abnormal concentration of, and/or a change in the concentration of, a target saccharide is carried out in vivo.

In another embodiment, the diagnosis of a condition which results in, or is otherwise associated with, an abnormal concentration of, and/or a change in the concentration of, a target saccharide is carried out in vitro or on a sample (i.e. blood sample) removed from the human and/or animal body.

In a further embodiment, the condition is diabetes.

According to another aspect of the present invention there is provided a saccharide detection device comprising a composition, as defined herein, or a compound, as defined herein.

Suitably, the device is in a form compatible for introduction into a human and/or animal body. More suitably, the device is in a form compatible for introduction into direct contact with the bloodstream of a human and/or animal patient. Non-limiting examples of suitable devices for introduction into a human and/or animal body include a pellet, tablet, capsule, stent and/or chip.

In another embodiment, the device is in a form compatible for introduction into a fermentation medium and/or cell culturing medium. Non-limiting examples of suitable devices for introduction into a fermentation medium and/or cell culturing medium include a fibre optic cable and/or a stent.

The excellent binding affinities and selectivities displayed towards glucose by certain compounds of the present invention makes them particularly well suited for application in glucose responsive insulin based systems. Glucose responsive insulin based systems are well known by those skilled in the art, and are typically insulin based systems which are activated (e.g. switched on) by an increase in the concentration of glucose.

Thus, in another aspect of the present invention, there is provided a use of a compound, as defined herein (e.g. a compound of Formula I, Ia, Ib, Ic, Id, Ie, If or Ig), in a glucose responsive insulin based system.

According to another aspect of the present invention, there is provided a complex comprising a compound, as defined herein (e.g. a compound of Formula I, Ia, Ib, Ic, Id, Ie, If or Ig) covalently attached to insulin.

According to yet another aspect of the present invention, there is provided a kit comprising of a compound, as defined herein (e.g. a compound of Formula I, Ia, Ib, Ic, Id, Ie, If or Ig) and insulin.

In an embodiment, there is provided a kit comprising a compound of Formula Ib, Ic or Id, as defined herein, and insulin.

According to a further aspect of the present invention, there is provided a kit comprising a compound of the present invention and a (displaceable) reporter molecule.

In an embodiment, there is provided a kit comprising a compound of Formula Ib, Ic or Id, as defined herein, and a (displaceable) reporter molecule.

EXAMPLES

The patent or application file contains at least one drawing executed in color. Copies of this patent or patent application publication with color drawing(s) will be provided by the Office upon request and payment of the necessary fee.

Embodiments of the invention will be described, by way of example only, with reference to the accompanying drawings, in which:

FIG. 1 shows schematic illustrations of the key interactions made between the target saccharide and the compounds of the present invention (FIGS. 1*a* and 1*b*), as well as molecular models of a ground state conformation of one particular compound of the present invention with glucose (FIG. 1*c* and Id). In FIG. 1*c*, ten intermolecular NH . . . O hydrogen bonds (with a distance of between 1.9 and 2.2 Å) can be seen, and FIG. 1*d* further depicts the close CH-π contacts made between the saccharide and compound of the present invention.

Figure 2:
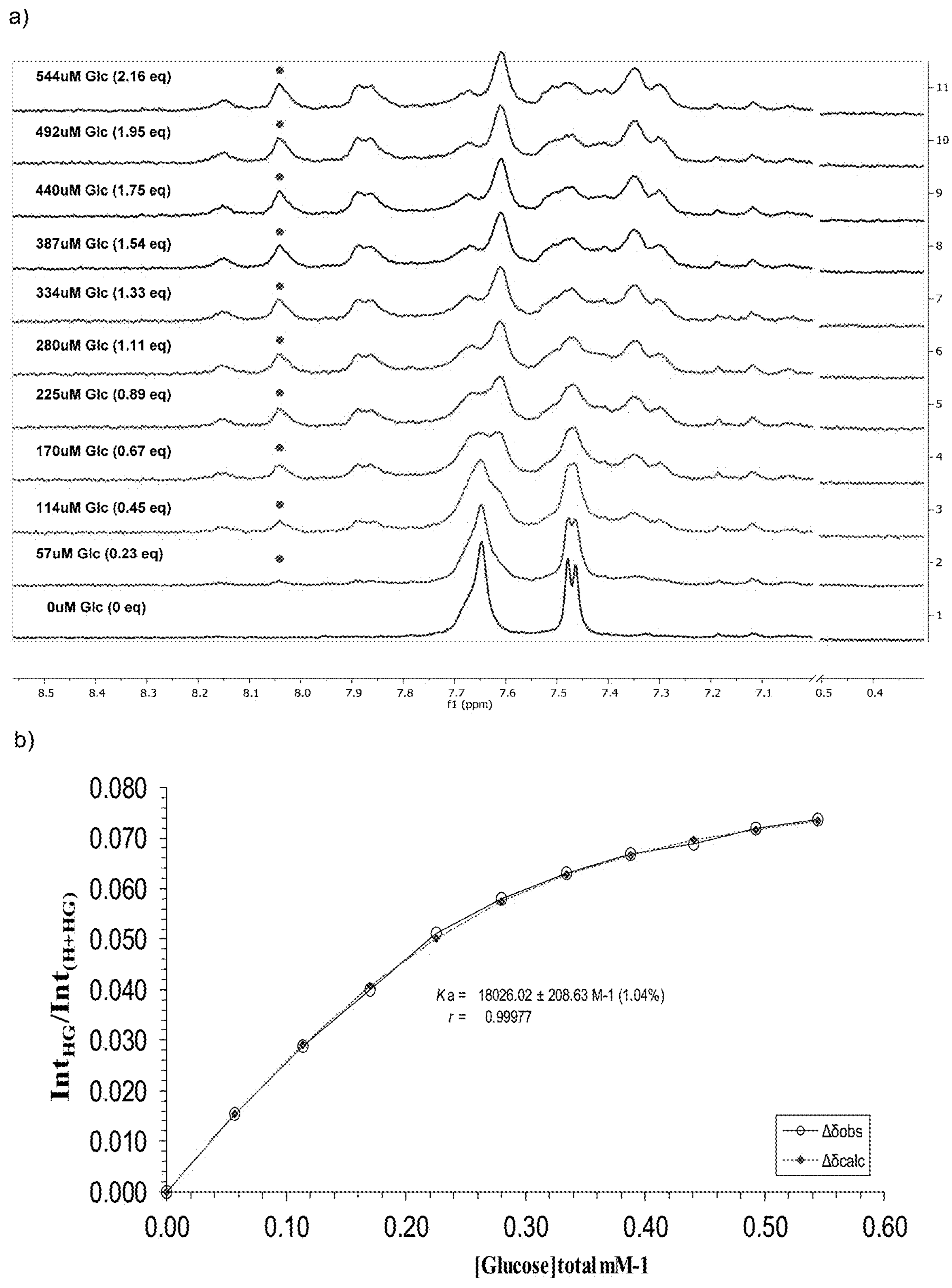
FIG. 2 shows: a) the partial $^1$H NMR spectra; and b) the binding analysis curve for receptor 1 (0.25 mM) titrated with a combined solution of D-glucose (9.6 mM) and receptor 1 (0.25 mM), in $D_2O$ buffered with 10 mM phosphate buffer solution (pH 7.4) at 298 K. Spectra imply binding with slow exchange on NMR timescale. Integrations of peak at 8.04 ppm (denoted with •) versus region 8.22-7.21 ppm were plotted against D-glucose concentration (mM). The calculated values for the integrals are overlaid with the observed values, giving $K_a$=18,026±208 $M^{-1}$ (1.04%).

FIG. 2 shows: a) the partial $^1$H NMR spectra; and b) the binding analysis curve for receptor 1 (0.25 mM) titrated with a combined solution of D-glucose (9.6 mM) and receptor 1 (0.25 mM), in $D_2O$ buffered with 10 mM phosphate buffer solution (pH 7.4) at 298 K. Spectra imply binding with slow exchange on NMR timescale. Integrations of peak at 8.04 ppm (denoted with *) versus region 8.22-7.21 ppm were plotted against D-glucose concentration (mM). The calculated values for the integrals are overlaid with the observed values, giving $K_a$=18,026±208 $M^{-1}$ (1.04%).

Figure 3:
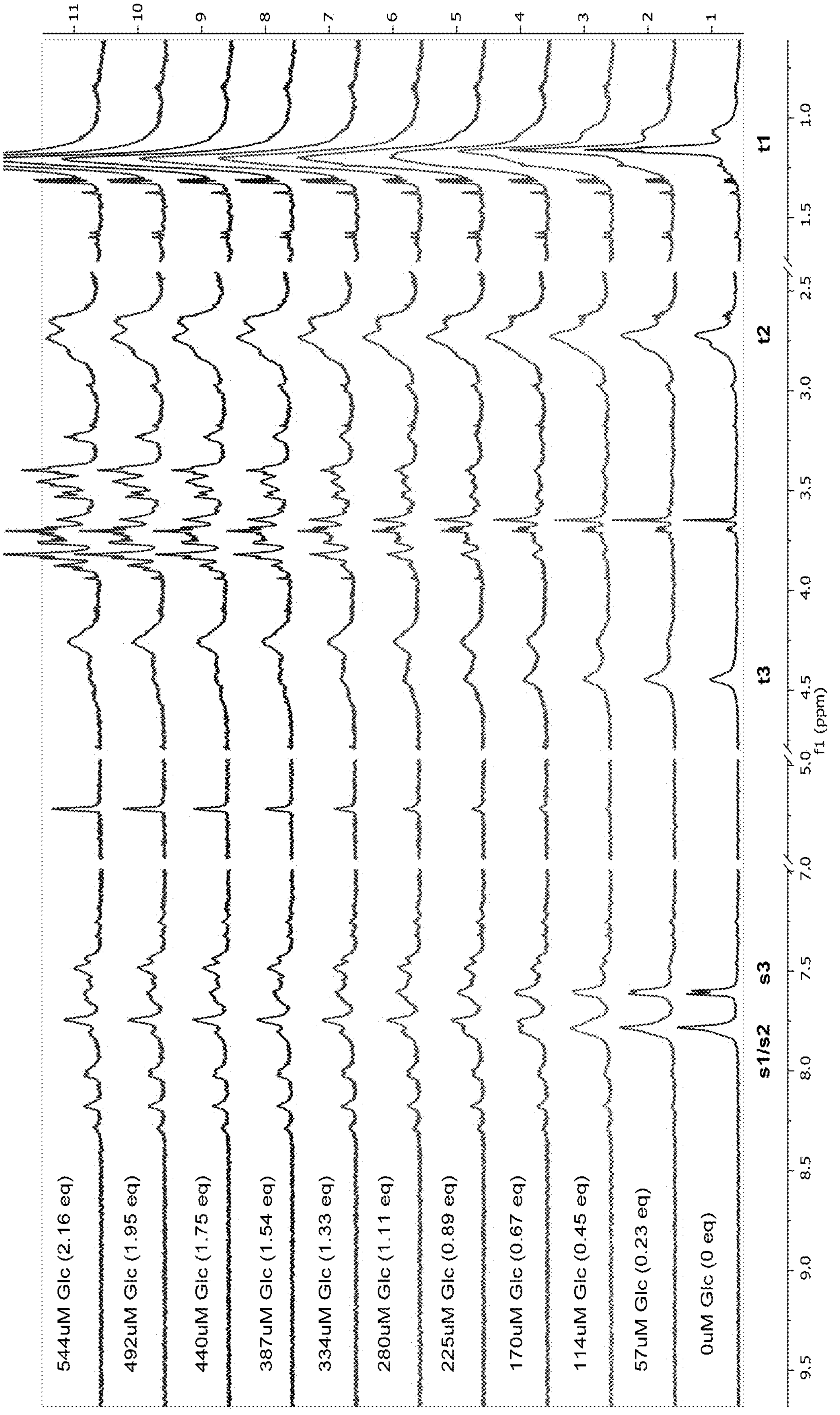
FIG. 3 shows the $^1$H NMR spectra for receptor 1 (0.25 mM) titrated with a combined solution of D-glucose (9.6 mM) and receptor 1 (0.25 mM), in $D_2O$ buffered with 10 mM phosphate buffer solution (pH 7.4) at 298 K.

FIG. 3 shows the $^1$H NMR spectra for receptor 1 (0.25 mM) titrated with a combined solution of D-glucose (9.6 mM) and receptor 1 (0.25 mM), in $D_2O$ buffered with 10 mM phosphate buffer solution (pH 7.4) at 298 K.

Figure 4:
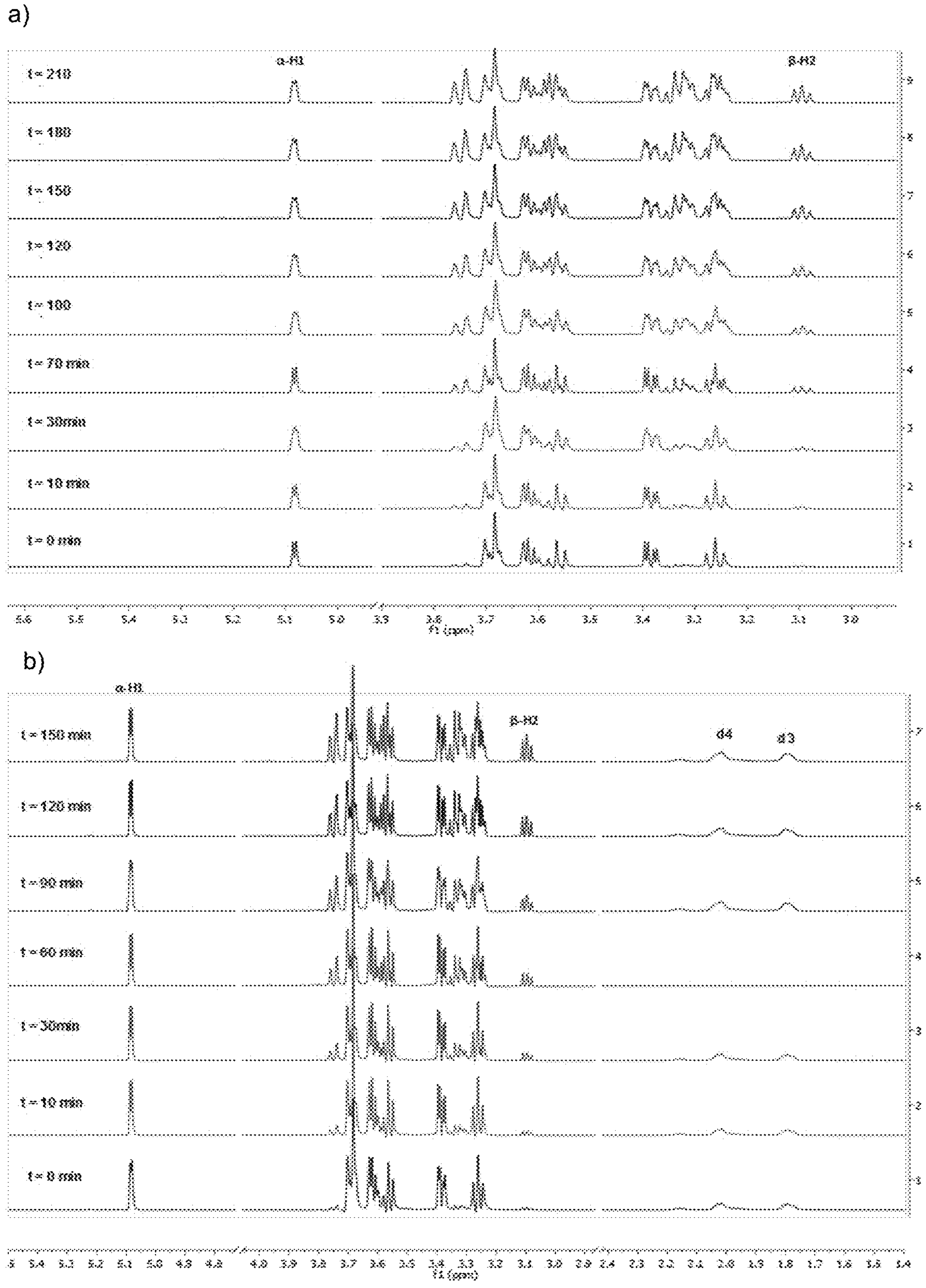
FIG. 4 shows the $^1$H NMR spectra at certain time intervals of: a) α-D-glucose (5 mM, and b) α-D-glucose (5 mM) with receptor 1 (0.2 mM). Relative integrals of α-H1 (5.22 ppm) and β-H2 (3.23 ppm) protons over time were calculated to determine if receptor 1 affected the rate of anomerisation between α and β-D-glucose. Rate of anomerisation was found to be independent of receptor 1 (see Table 2).

FIG. 4 shows the $^1$H NMR spectra at certain time intervals of: a) α-D-glucose (5 mM, and b) α-D-glucose (5 mM) with receptor 1 (0.2 mM). Relative integrals of α-$H_1$ (5.22 ppm) and β-$H_2$ (3.23 ppm) protons over time were calculated to determine if receptor 1 affected the rate of anomerisation between a and β-D-glucose. Rate of anomerisation was found to be independent of receptor 1 (see Table 2).

Figure 5:
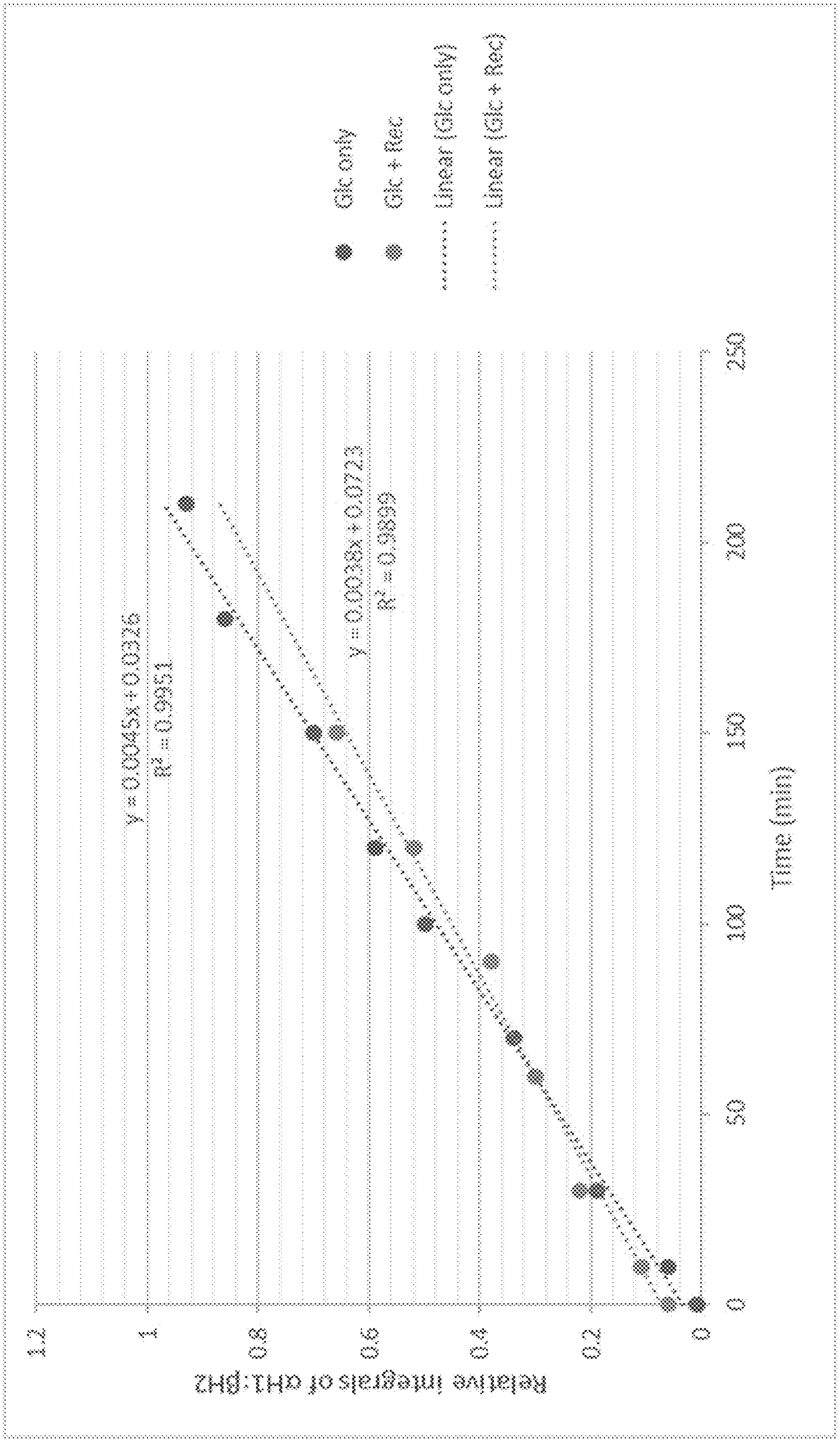
FIG. 5 shows a plot of relative integrals of αH1:βH2 versus time (min). Similar gradients suggest receptor does not affect the rate of anomerisation of D-glucose.

FIG. 5 shows a plot of relative integrals of αH1: β$H_2$ versus time (min). Similar gradients suggest receptor does not affect the rate of anomerisation of D-glucose.

Figure 6:
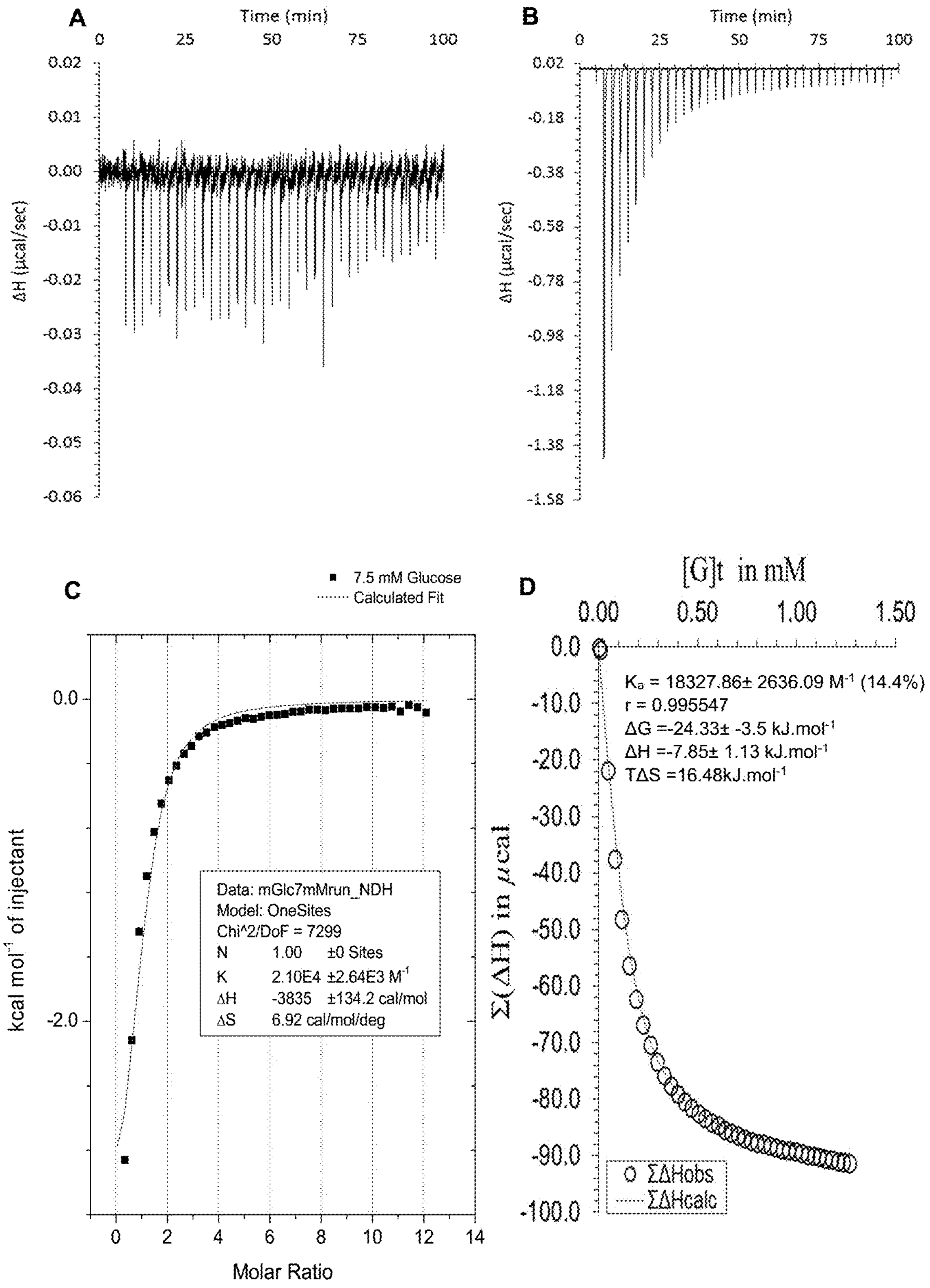
FIG. 6 shows the ITC binding results for receptor 1 (0.13 mM) titrated with glucose (7.5 mM) in $H_2O$, in which: A) shows the blank ITC run (addition of sugar into water); B) shows the actual run (sugar into receptor 1); C) shows the plotted change in enthalpy vs molar ratio and the fit calculated with the supplied ITC software ($K_a$=21,000±2640 $M^{-1}$); and D) shows the fit calculated using an Excel spreadsheet to corroborate the result.

FIG. 6 shows the ITC binding results for receptor 1 (0.13 mM) titrated with glucose (7.5 mM) in $H_2O$, in which: A) shows the blank ITC run (addition of sugar into water); B) shows the actual run (sugar into receptor 1); C) shows the plotted change in enthalpy vs molar ratio and the fit calculated with the supplied ITC software ($K_a$=21,000±2640 $M^{-1}$); and D) shows the fit calculated using an Excel spreadsheet to corroborate the result.

Figure 7:
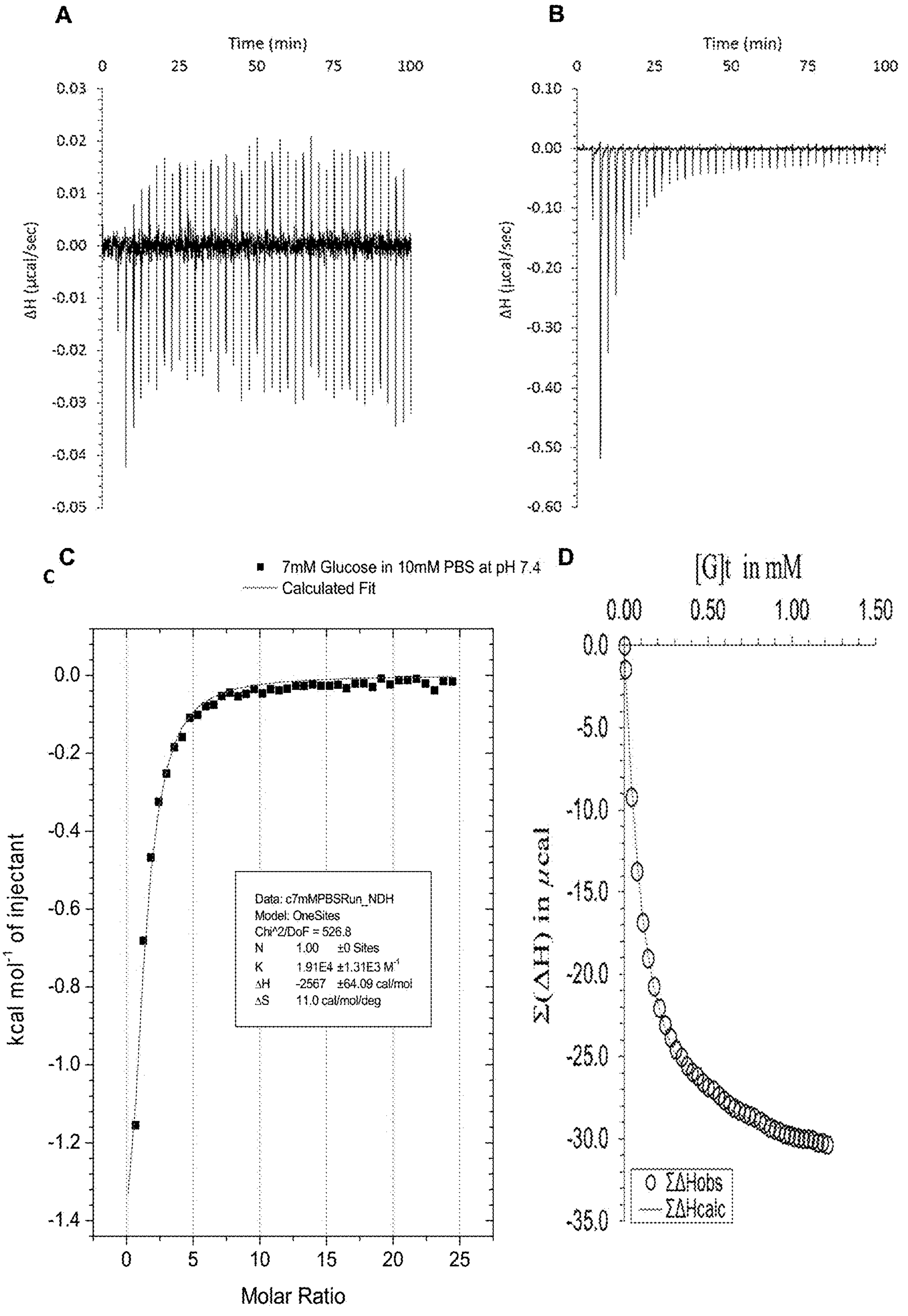
FIG. 7 shows the ITC binding results for receptor 1 (0.06 mM) titrated with D-glucose (7 mM) in 10 mM PBS buffer (pH 7.4), in which: A) shows the blank ITC run (addition of sugar into water); B) shows the actual run (sugar into receptor 1); C) shows the plotted change in enthalpy vs molar ratio and the fit calculated with the supplied ITC software ($K_a$=19,100±1310 $M^{-1}$); and D) shows the fit calculated using an Excel spreadsheet to corroborate the result.

FIG. 7 shows the ITC binding results for receptor 1 (0.06 mM) titrated with D-glucose (7 mM) in 10 mM PBS buffer (pH 7.4), in which: A) shows the blank ITC run (addition of sugar into water); B) shows the actual run (sugar into receptor 1); C) shows the plotted change in enthalpy vs molar ratio and the fit calculated with the supplied ITC software ($K_a$=19,100±1310 $M^{-1}$); and D) shows the fit calculated using an Excel spreadsheet to corroborate the result.

Figure 8:
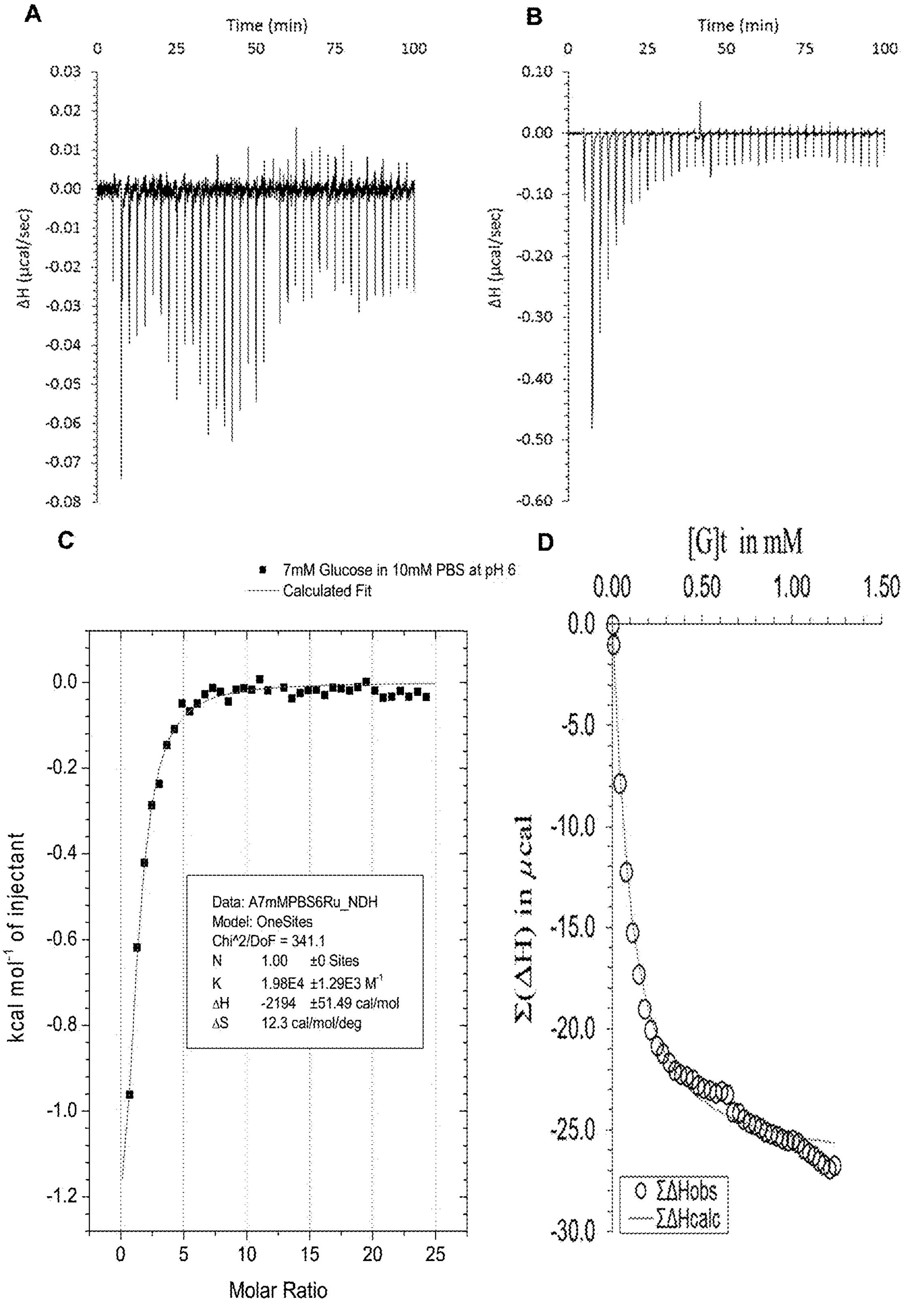
FIG. 8 shows the ITC binding results for receptor 1 (0.06 mM) titrated with D-glucose (7 mM) in 10 mM PBS buffer (pH 6), in which: A) shows the blank ITC run (addition of sugar into water); B) shows the actual run (sugar into receptor 1); C) shows the plotted change in enthalpy vs molar ratio and the fit calculated with the supplied ITC software ($K_a$=19,800±1290 $M^{-1}$); and D) shows the fit calculated using an Excel spreadsheet to corroborate the result.

FIG. 8 shows the ITC binding results for receptor 1 (0.06 mM) titrated with D-glucose (7 mM) in 10 mM PBS buffer (pH 6), in which: A) shows the blank ITC run (addition of sugar into water); B) shows the actual run (sugar into receptor 1); C) shows the plotted change in enthalpy vs molar ratio and the fit calculated with the supplied ITC software ($K_a$=19,800±1290 $M^{-1}$); and D) shows the fit calculated using an Excel spreadsheet to corroborate the result.

Figure 9:
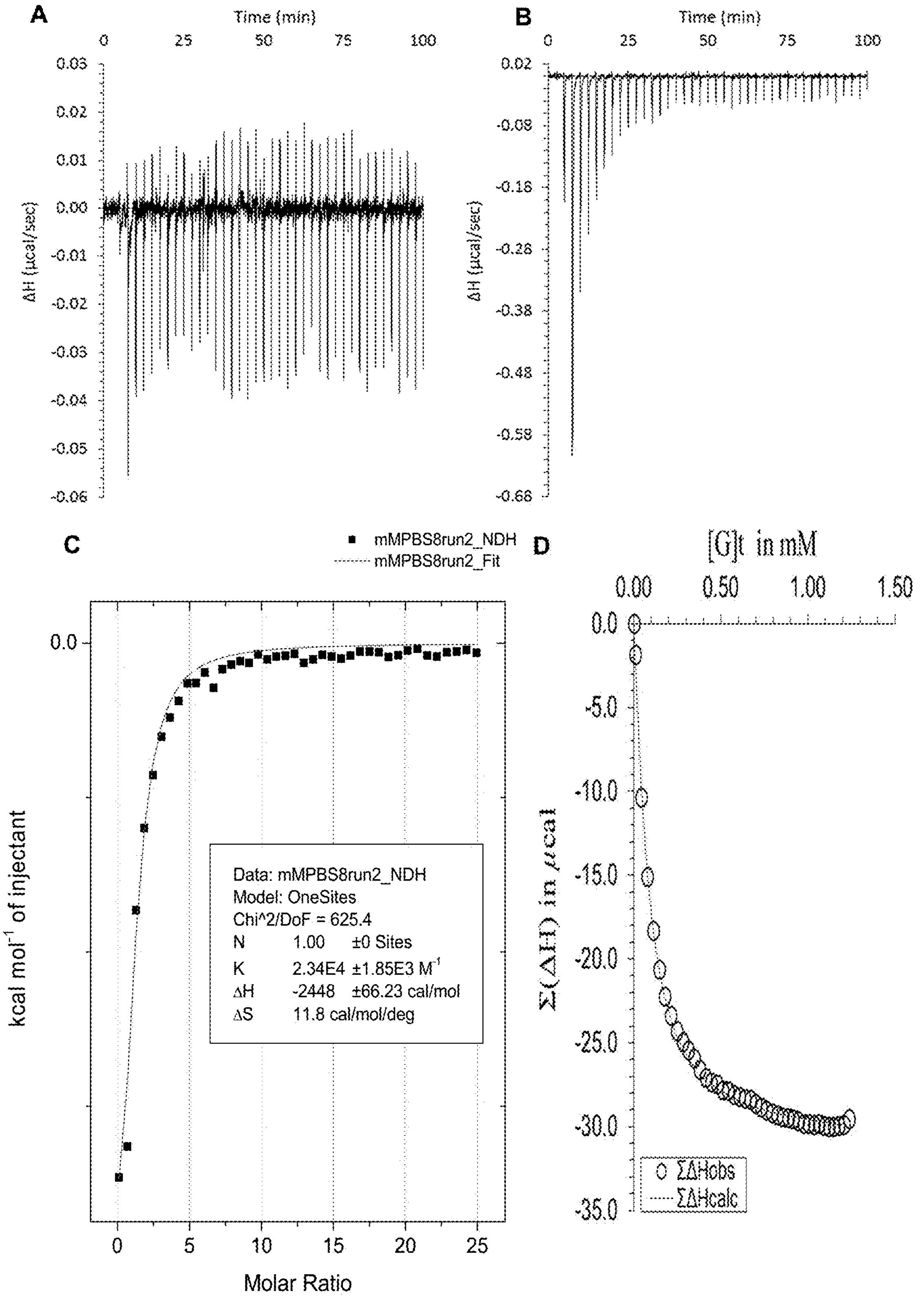
FIG. 9 shows the ITC binding results for receptor 1 (0.06 mM) titrated with D-glucose (7 mM) in 10 mM PBS buffer (pH 8), in which: A) shows the blank ITC run (addition of sugar into water); B) shows the actual run (sugar into receptor 1); C) shows the plotted change in enthalpy vs molar ratio and the fit calculated with the supplied ITC software ($K_a$=23,400±1850 $M^{-1}$); and D) shows the fit calculated using an Excel spreadsheet to corroborate the result.

FIG. 9 shows the ITC binding results for receptor 1 (0.06 mM) titrated with D-glucose (7 mM) in 10 mM PBS buffer (pH 8), in which: A) shows the blank ITC run (addition of sugar into water); B) shows the actual run (sugar into receptor 1); C) shows the plotted change in enthalpy vs molar ratio and the fit calculated with the supplied ITC software ($K_a$=23,400±1850 $M^{-1}$); and D) shows the fit calculated using an Excel spreadsheet to corroborate the result.

Figure 10:
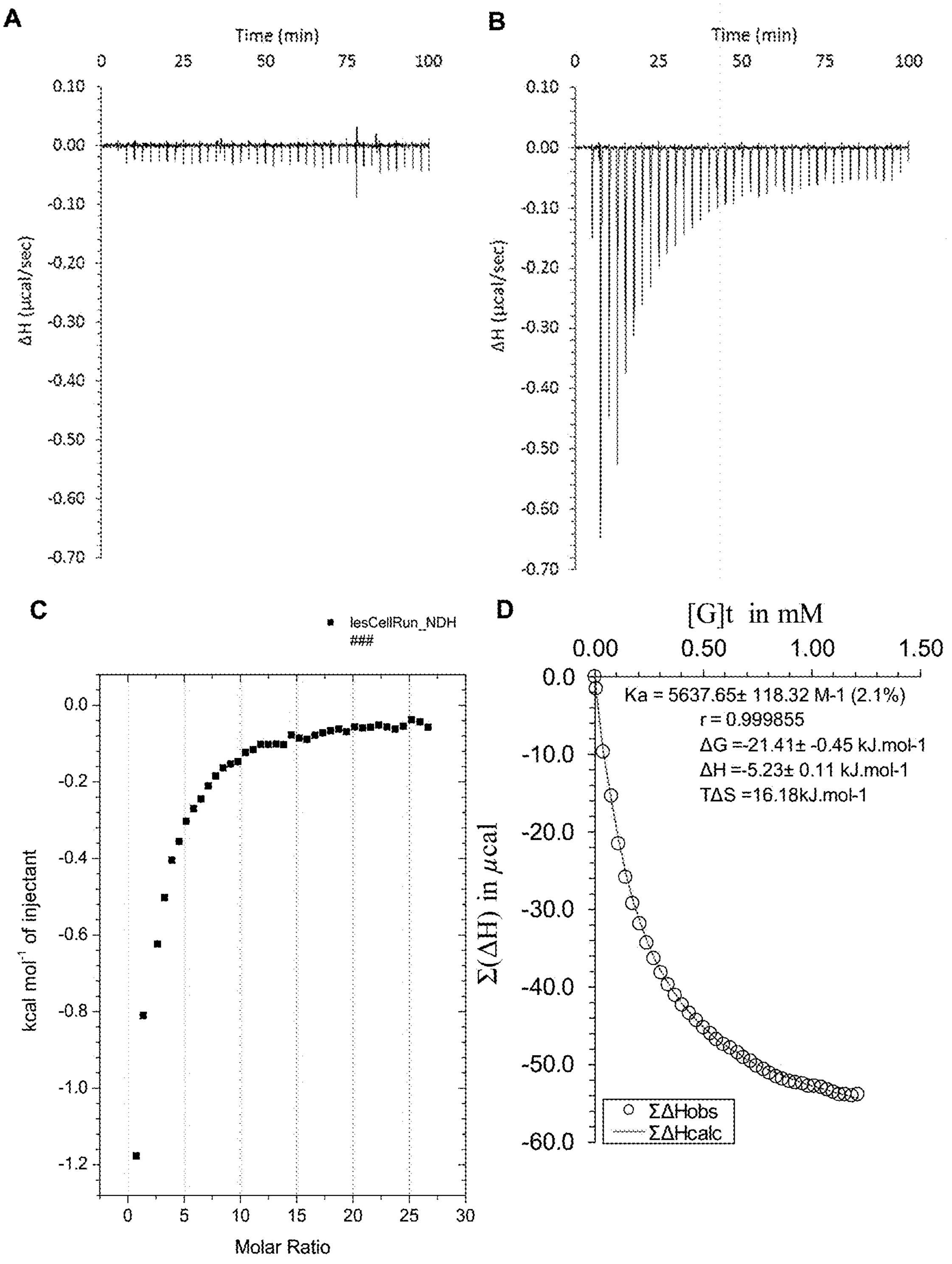
FIG. 10 shows the ITC binding results for receptor 1 (0.06 mM) titrated with D-glucose (7 mM) in DMEM Cell Culture Medium (no glucose, 10 k MWCO, 90% v/v) and 10 mM phosphate buffer solution (pH 7.4), in which: A) shows the blank ITC run (addition of sugar into medium); B) shows the actual run (sugar into receptor 1); C) shows the plotted change in enthalpy vs molar ratio; and D) shows the fit calculated using an Excel spreadsheet (Ka=5637±118 $M^{-1}$).

FIG. 10 shows the ITC binding results for receptor 1 (0.06 mM) titrated with D-glucose (7 mM) in DMEM Cell Culture Medium (no glucose, 10 k MWCO, 90% v/v) and 10 mM phosphate buffer solution (pH 7.4), in which: A) shows the blank ITC run (addition of sugar into medium); B) shows the actual run (sugar into receptor 1); C) shows the plotted change in enthalpy vs molar ratio; and D) shows the fit calculated using an Excel spreadsheet (Ka=5637±118 $M^{-1}$).

Figure 11:
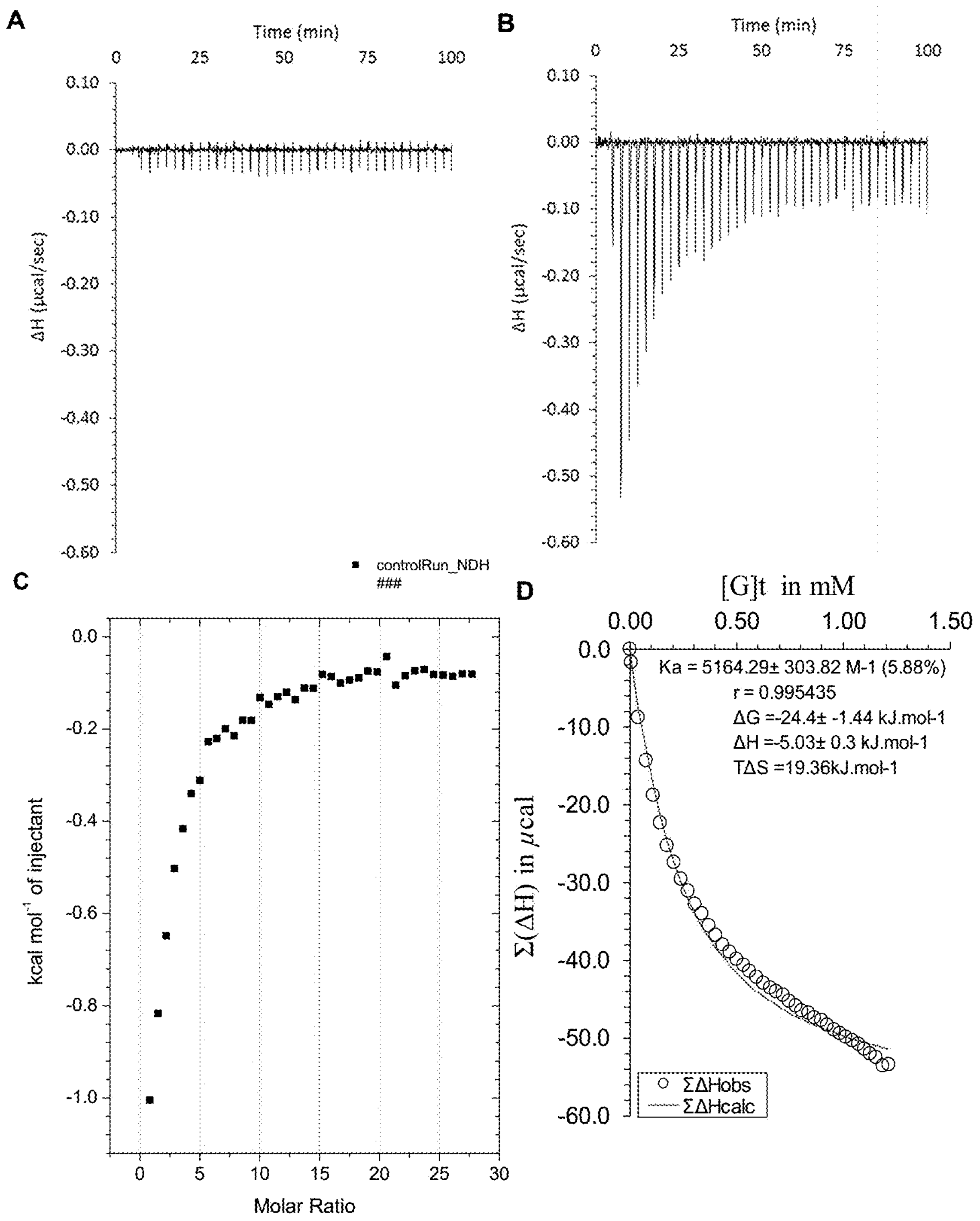
FIG. 11 shows the ITC binding results for receptor 1 (0.06 mM) titrated with D-glucose (7 mM) in 10 mM phosphate buffer solution (pH 7.4) with added salts: ferric nitrate (0.2 μM), calcium chloride (1.8 mM), magnesium sulfate (0.81 mM), potassium chloride (5.3 mM), sodium bicarbonate (44 mM), sodium chloride (110 mM) and sodium phosphate monobasic (0.9 mM), in which: A) shows the blank ITC run (addition of substrate into medium); B) shows the actual run (substrate into receptor 1); C) shows the plotted change in enthalpy vs molar ratio; and D) shows the fit calculated using an Excel spreadsheet (Ka=5164±303 $M^{-1}$).

FIG. 11 shows the ITC binding results for receptor 1 (0.06 mM) titrated with D-glucose (7 mM) in 10 mM phosphate buffer solution (pH 7.4) with added salts: ferric nitrate (0.2 μM), calcium chloride (1.8 mM), magnesium sulfate (0.81 mM), potassium chloride (5.3 mM), sodium bicarbonate (44 mM), sodium chloride (110 mM) and sodium phosphate monobasic (0.9 mM), in which: A) shows the blank ITC run (addition of substrate into medium); B) shows the actual run (substrate into receptor 1); C) shows the plotted change in enthalpy vs molar ratio; and D) shows the fit calculated using an Excel spreadsheet (Ka=5164±303 $M^{-1}$).

Figure 12:
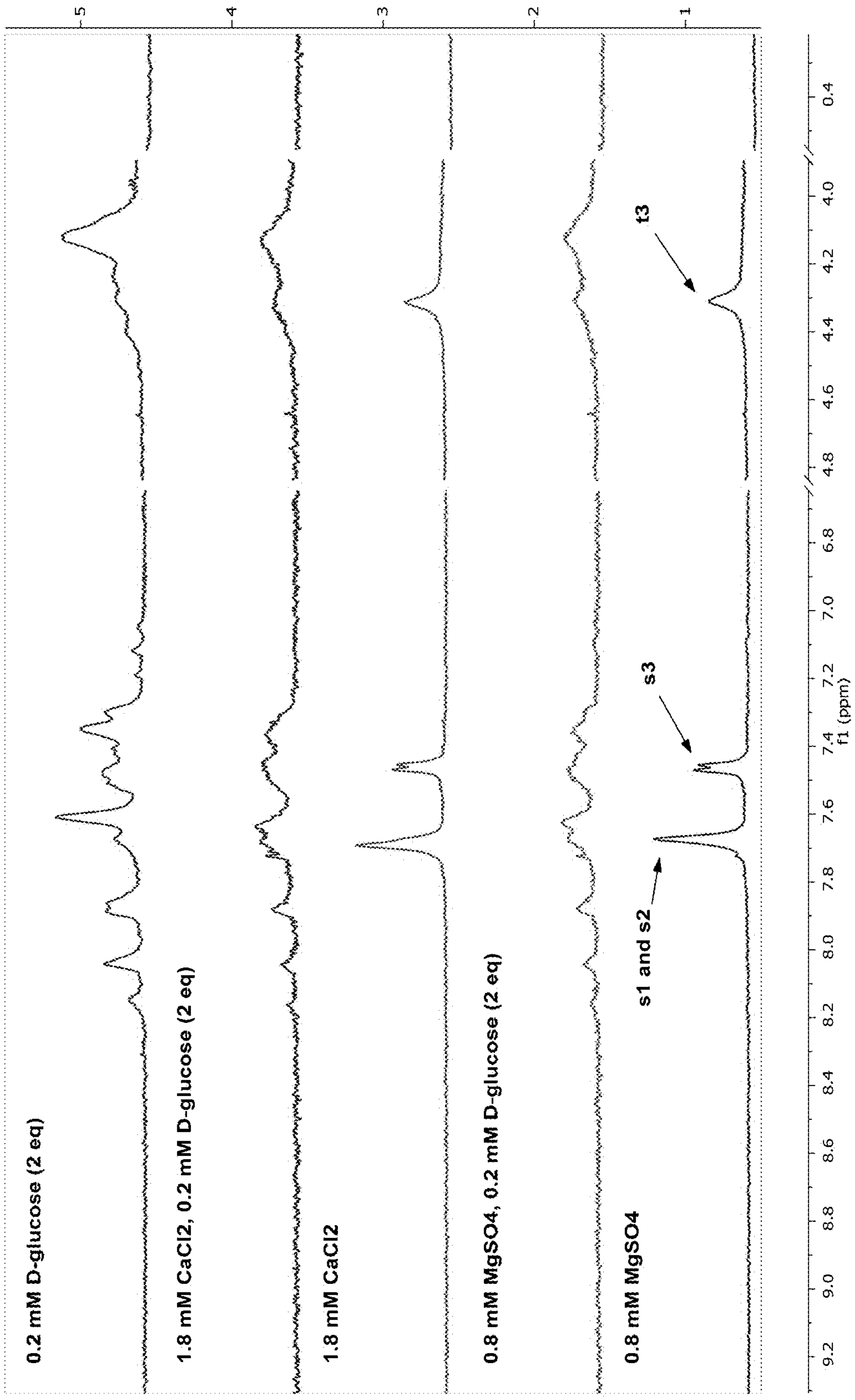
FIG. 12 shows $^1$H NMR spectra showing receptor 1 (0.1 mM) dissolved in $D_2O$ with 10 mM phosphate buffer (pH 7.4) at 298 K. Addition of $MgSO_4$ (0.8 mM) and $CaCl_2$ (1.8 mM), which are the concentrations present in DMEM cell culture media, to free receptor showed a small change in chemical shift (6 in ppm) for proton s2. Addition of 2 equivalents (0.2 mM) of D-glucose did not saturate the receptor. Addition of this same concentration of glucose to free receptor in $D_2O$ with no added salts (top spectrum) did saturate the receptor, suggesting that $Ca^{2+}$ and $Mg^{2+}$ inhibit binding.

FIG. 12 shows $^1$H NMR spectra showing receptor 1 (0.1 mM) dissolved in $D_2O$ with 10 mM phosphate buffer (pH 7.4) at 298 K. Addition of $MgSO_4$ (0.8 mM) and $CaCl_2$ (1.8 mM), which are the concentrations present in DMEM cell culture media, to free receptor showed a small change in chemical shift (b in ppm) for proton s2. Addition of 2 equivalents (0.2 mM) of D-glucose did not saturate the receptor. Addition of this same concentration of glucose to free receptor in $D_2O$ with no added salts (top spectrum) did saturate the receptor, suggesting that $Ca^{2+}$ and $Mg^{2+}$ inhibit binding.

Figure 13:
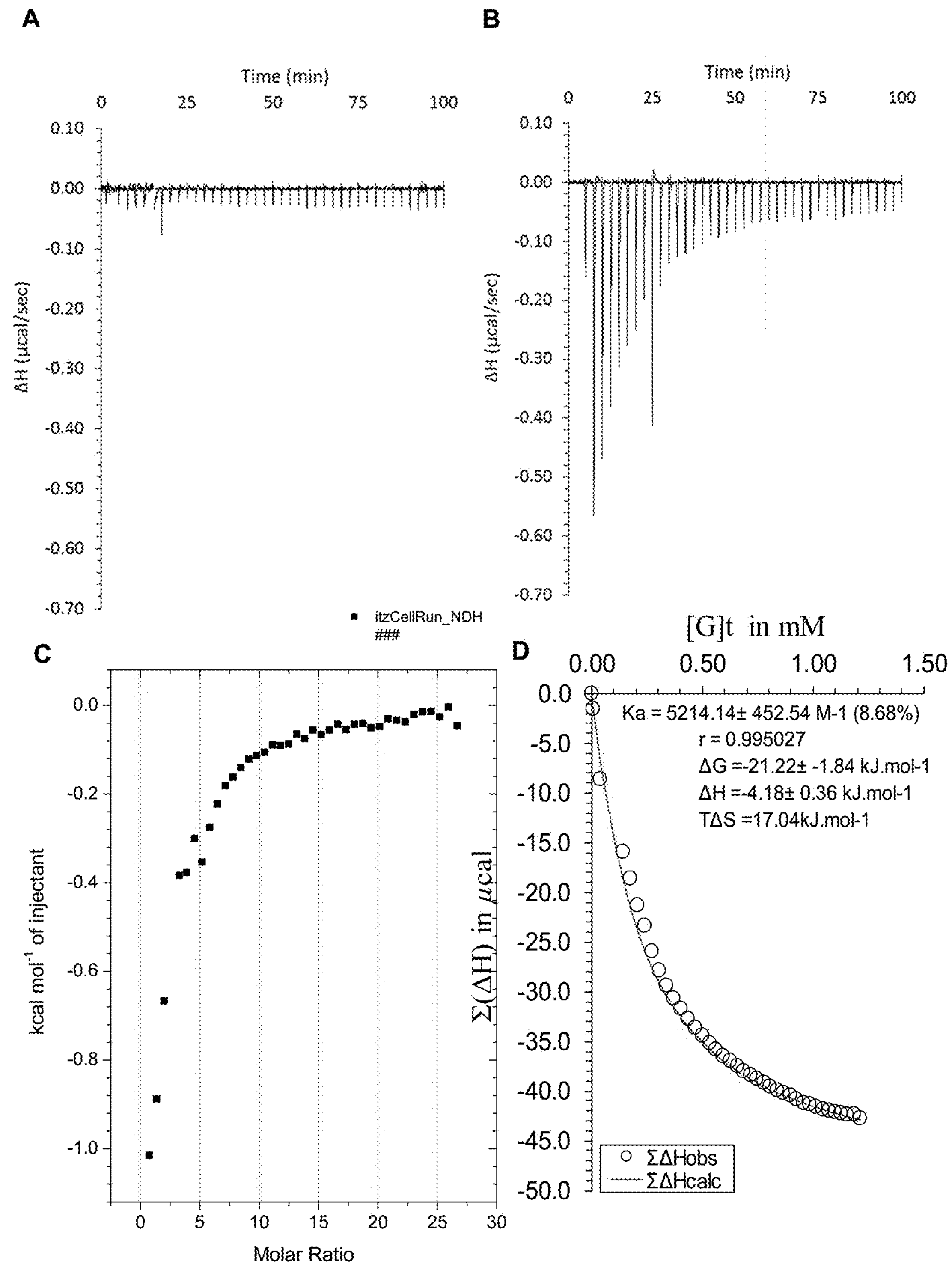
FIG. 13 shows the ITC binding results for receptor 1 (0.06 mM) titrated with D-glucose (7 mM) in Leibovitz's L-15 Cell Culture Medium (no glucose, 10 k MWCO, 90% v/v) and 10 mM phosphate buffer solution (pH 7.4), in which: A) shows the blank ITC run (addition of sugar into medium); B) shows the actual run (sugar into receptor 1); C) shows the plotted change in enthalpy vs molar ratio; and D) shows the fit calculated using an Excel spreadsheet (Ka=5214±452 $M^{-1}$).

FIG. 13 shows the ITC binding results for receptor 1 (0.06 mM) titrated with D-glucose (7 mM) in Leibovitz's L-15 Cell Culture Medium (no glucose, 10 k MWCO, 90% v/v) and 10 mM phosphate buffer solution (pH 7.4), in which: A) shows the blank ITC run (addition of sugar into medium); B) shows the actual run (sugar into receptor 1); C) shows the plotted change in enthalpy vs molar ratio; and D) shows the fit calculated using an Excel spreadsheet (Ka=5214±452 $M^{-1}$).

Figure 14:
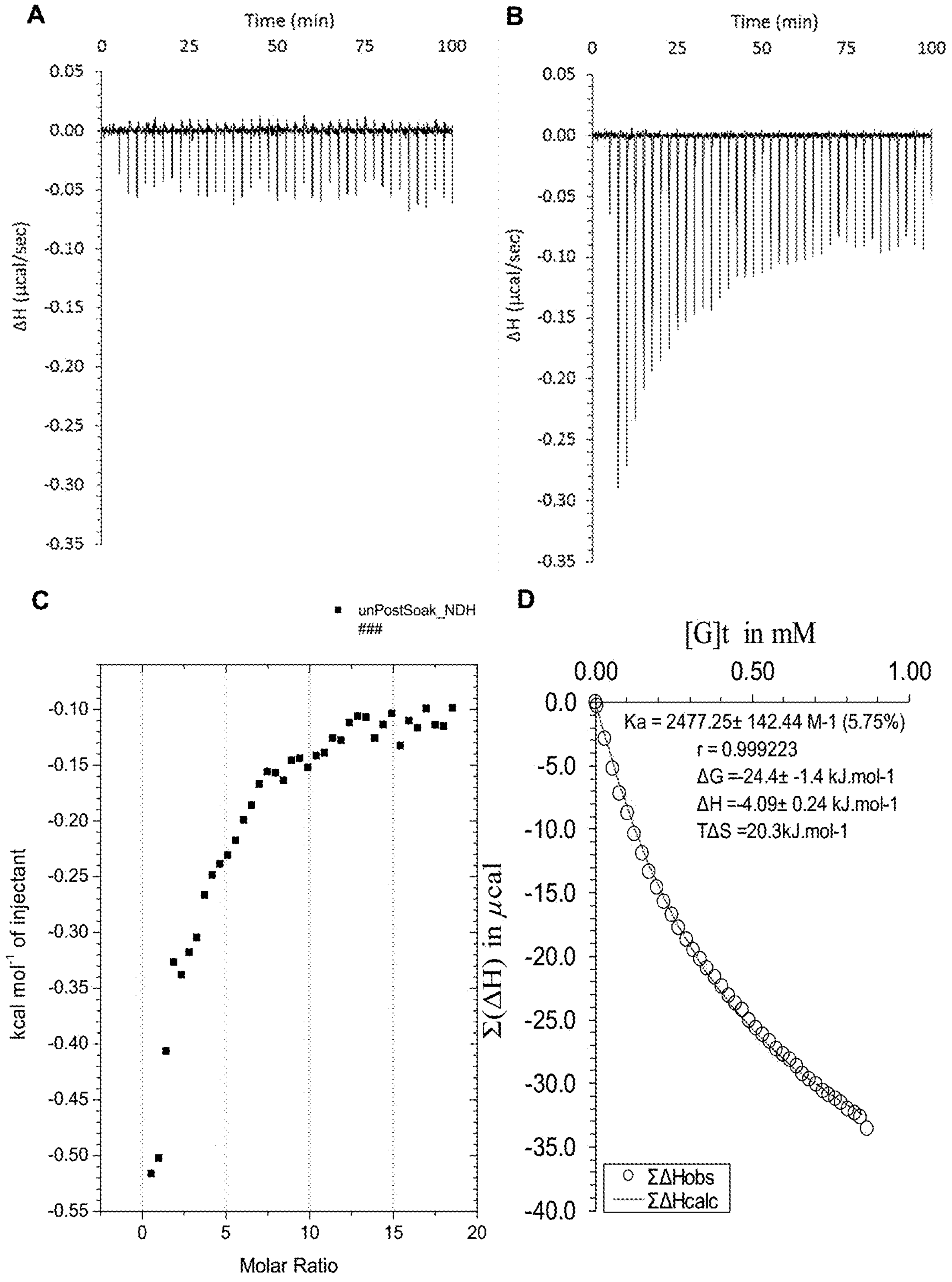
FIG. 14 shows the ITC binding results for receptor 1 (0.06 mM) titrated with D-glucose (5 mM) in Human Blood Serum (no glucose, 10 k MWCO, 90% v/v) and 10 mM phosphate buffer solution (pH 8.5), in which: A) shows the blank ITC run (addition of sugar into medium); B) shows the actual run (sugar into receptor 1); C) shows the plotted change in enthalpy vs molar ratio; and D) shows the fit calculated using an Excel spreadsheet (Ka=2477±142 $M^{-1}$).

FIG. 14 shows the ITC binding results for receptor 1 (0.06 mM) titrated with D-glucose (5 mM) in Human Blood Serum (no glucose, 10 k MWCO, 90% v/v) and 10 mM phosphate buffer solution (pH 8.5), in which: A) shows the blank ITC run (addition of sugar into medium); B) shows the actual run (sugar into receptor 1); C) shows the plotted change in enthalpy vs molar ratio; and D) shows the fit calculated using an Excel spreadsheet (Ka=2477±142 $M^{-1}$).

Figure 15:
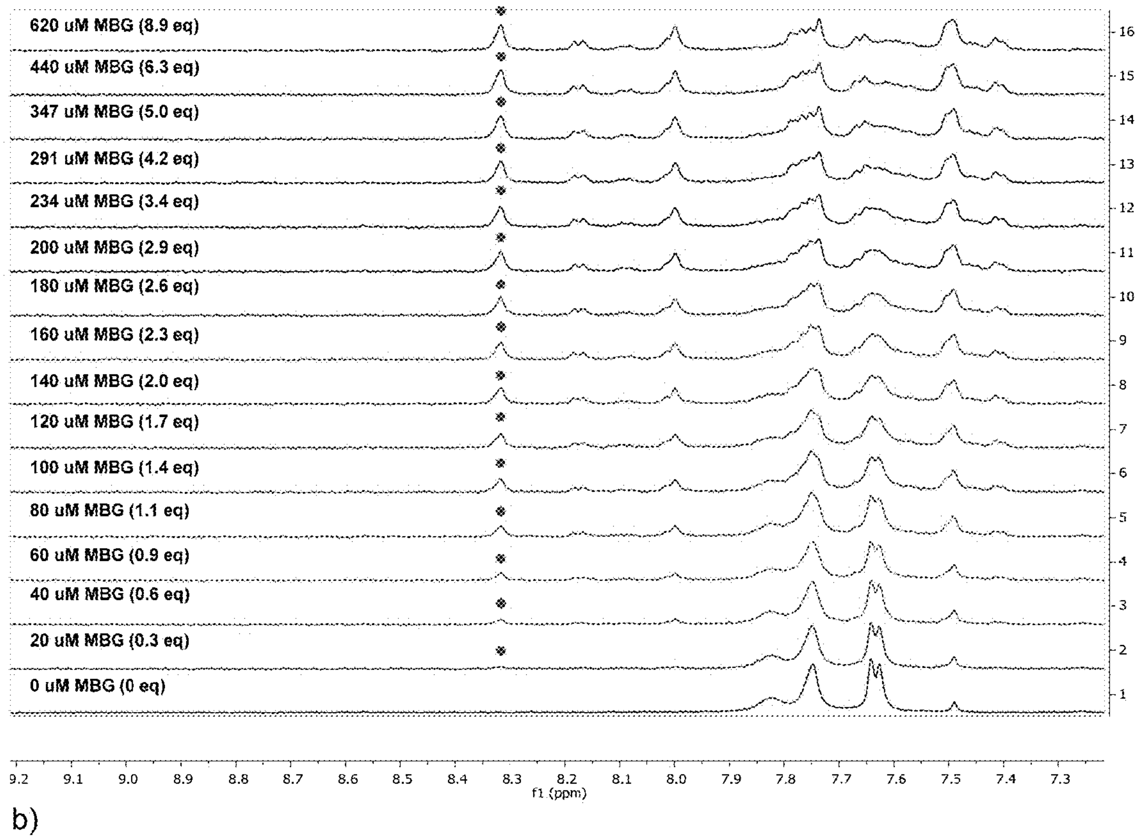
FIG. 15 shows: a) the $^1$H NMR spectra; and b) the binding analysis curve for receptor 1 (0.07 mM) titrated with a combined solution of D-methyl-β-glucoside (10 mM) and receptor 1 (0.07 mM), in $D_2O$ buffered with 10 mM phosphate buffer solution (pH 7.4) at 298 K. Spectra imply binding with slow exchange on NMR timescale. Integrations of peak at 8.31 ppm (denoted with •) versus region 8.36-7.36 ppm were plotted against guest concentration (mM). The calculated values for the integrals are overlaid with the observed values, giving $K_a$=7522±414 $M^{-1}$ (5.51%).
Figure 15:
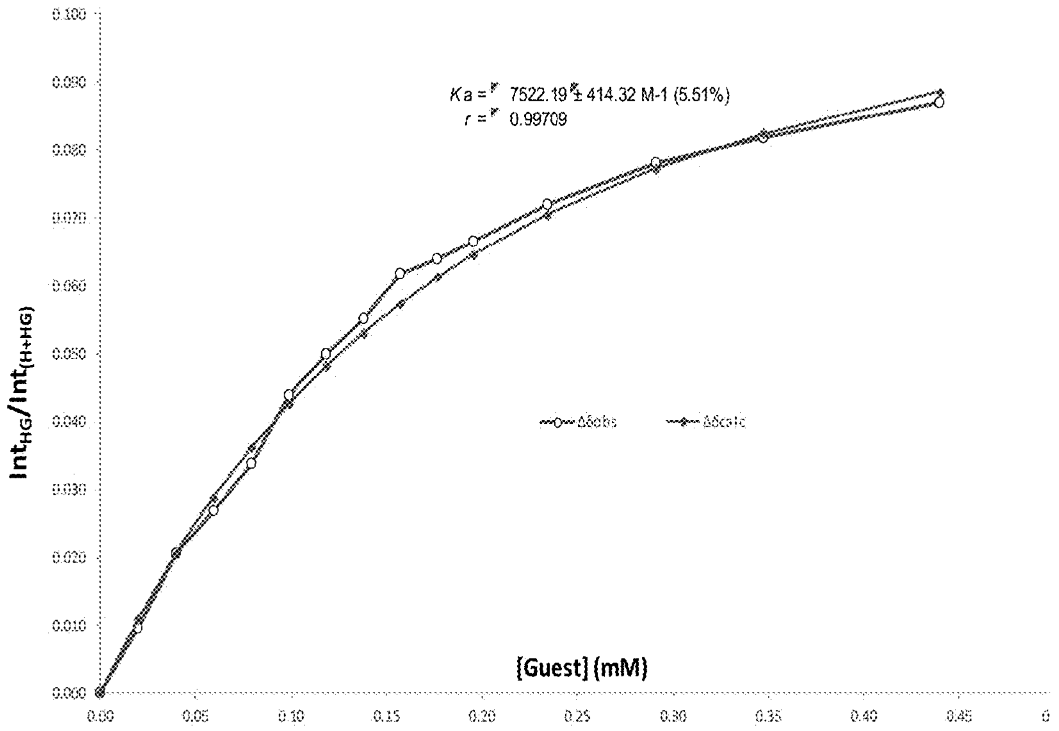

FIG. 15 shows: a) the $^1$H NMR spectra; and b) the binding analysis curve for receptor 1 (0.07 mM) titrated with a combined solution of D-methyl-β-glucoside (10 mM) and receptor 1 (0.07 mM), in $D_2O$ buffered with 10 mM phosphate buffer solution (pH 7.4) at 298 K. Spectra imply binding with slow exchange on NMR timescale. Integrations of peak at 8.31 ppm (denoted with*) versus region 8.36-7.36 ppm were plotted against guest concentration (mM). The calculated values for the integrals are overlaid with the observed values, giving $K_a$=7522±414 $M^{-1}$ (5.51%).

Figure 16:
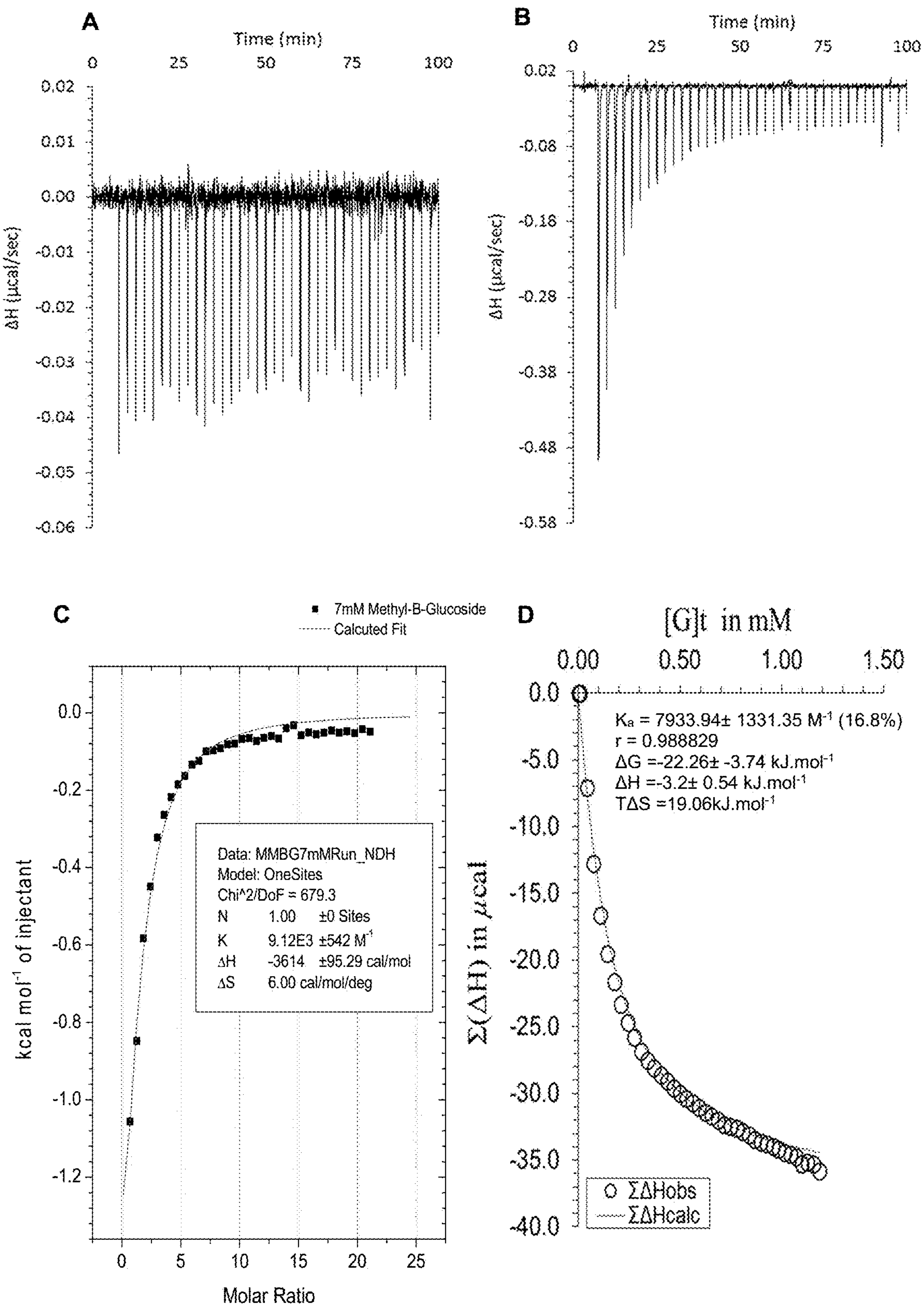
FIG. 16 shows the ITC binding results for receptor 1 (0.13 mM) titrated with methyl-β-D-glucoside (7 mM) in $H_2O$, in which: A) shows the blank ITC run (addition of sugar into water); B) shows the actual run (sugar into receptor 1); C) shows the plotted change in enthalpy vs molar ratio and the fit calculated with the supplied ITC software ($K_a$=9120±542 $M^{-1}$); and D) shows the fit calculated using an Excel spreadsheet to corroborate the result.

FIG. 16 shows the ITC binding results for receptor 1 (0.13 mM) titrated with methyl-β-D-glucoside (7 mM) in $H_2O$, in which: A) shows the blank ITC run (addition of sugar into water); B) shows the actual run (sugar into receptor 1); C) shows the plotted change in enthalpy vs molar ratio and the fit calculated with the supplied ITC software ($K_a$=9120±542 $M^{-1}$); and D) shows the fit calculated using an Excel spreadsheet to corroborate the result.

Figure 17:
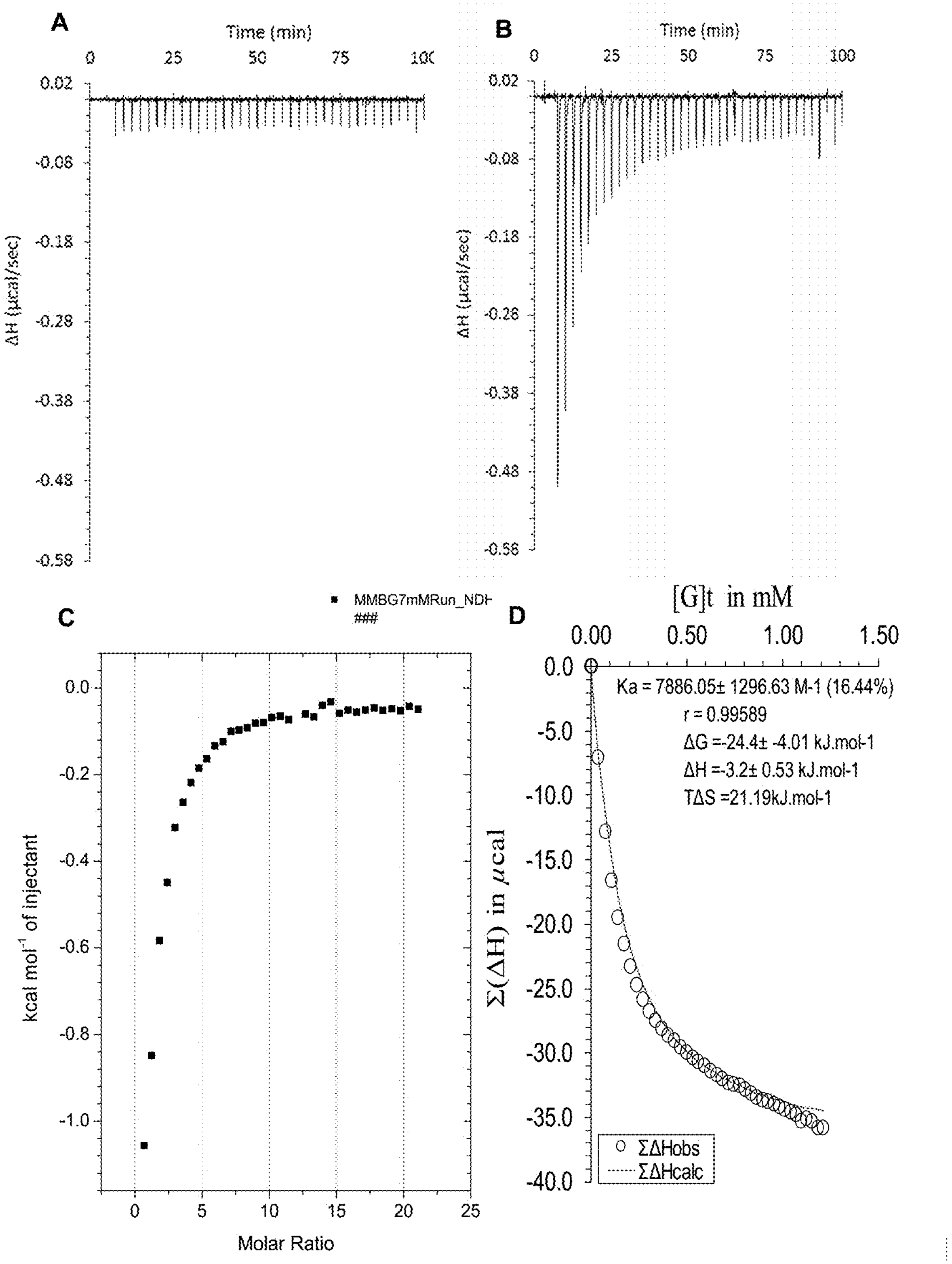
FIG. 17 shows the ITC binding results for receptor 1 (0.06 mM) titrated with methyl-β-D-glucoside (7 mM) in 10 mM phosphate buffer solution (pH 7.4), in which: A) shows the blank ITC run (addition of sugar into water); B) shows the actual run (sugar into receptor 1); C) shows the plotted change in enthalpy vs molar ratio; and D) shows the fit calculated using an Excel spreadsheet ($K_a$=7886±1296 $M^{-1}$).

FIG. 17 shows the ITC binding results for receptor 1 (0.06 mM) titrated with methyl-β-D-glucoside (7 mM) in 10 mM phosphate buffer solution (pH 7.4), in which: A) shows the blank ITC run (addition of sugar into water); B) shows the actual run (sugar into receptor 1); C) shows the plotted change in enthalpy vs molar ratio; and D) shows the fit calculated using an Excel spreadsheet ($K_a$=7886±1296 $M^{-1}$).

Figure 18:
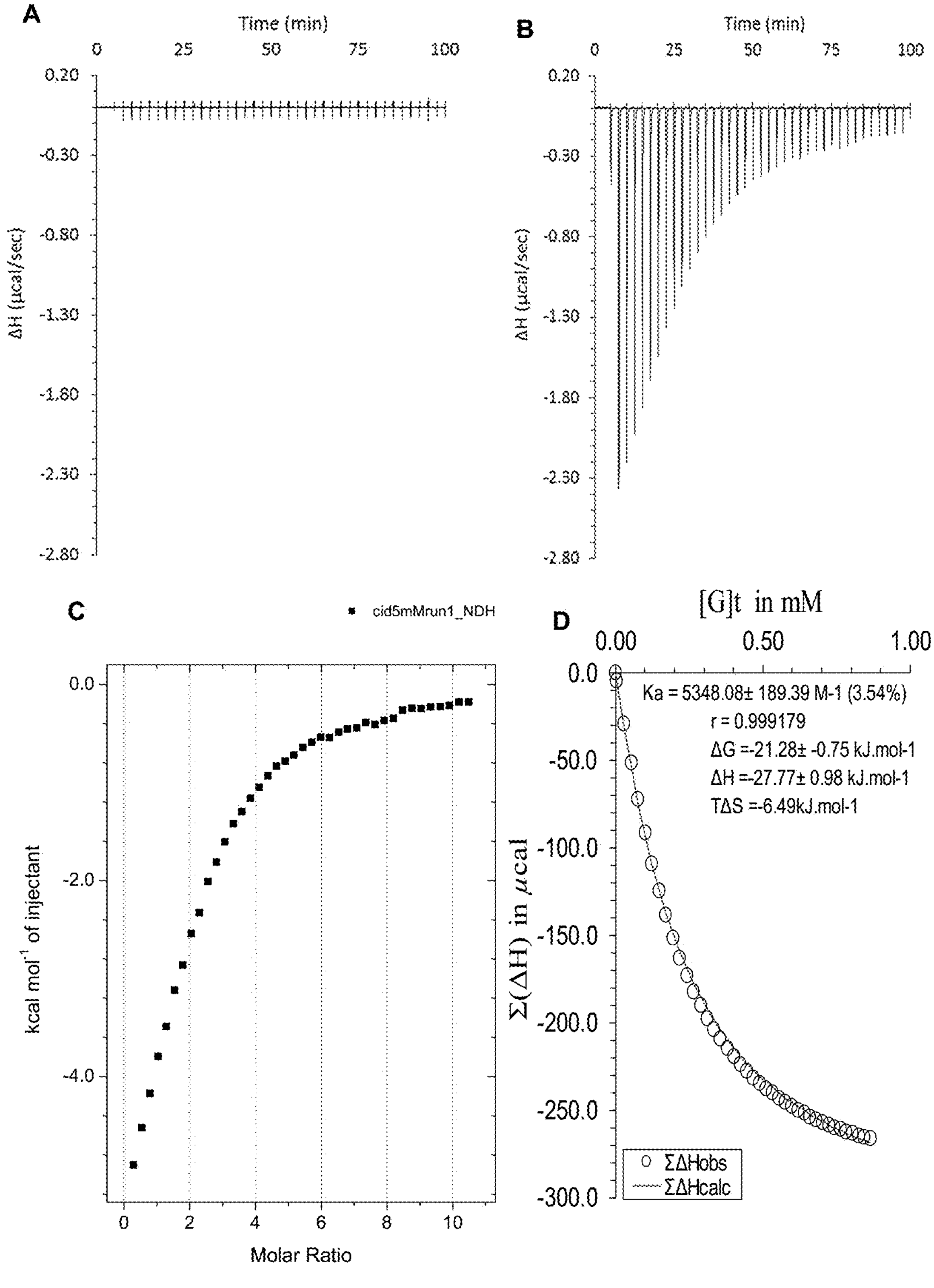
FIG. 18 shows the ITC binding results for receptor 1 (0.1 mM) titrated with D-glucuronic acid (5 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet (Ka=5348±189 $M^{-1}$).

FIG. 18 shows the ITC binding results for receptor 1 (0.1 mM) titrated with D-glucuronic acid (5 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet (Ka=5348±189 $M^{-1}$).

Figure 19:
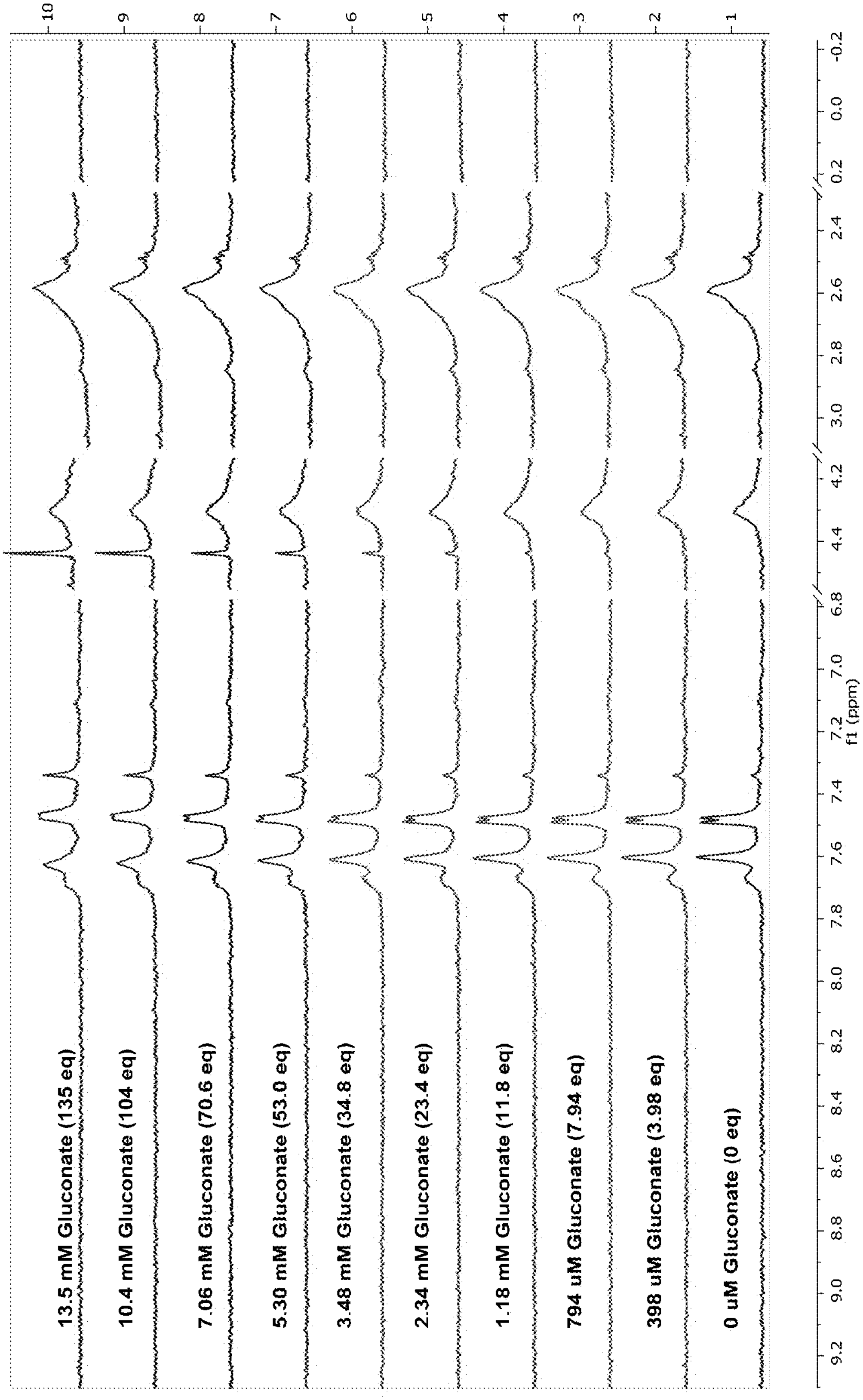
FIG. 19 shows the $^1$H NMR spectra for receptor 1 (0.1 mM) titrated with a combined solution of D-gluconate (10 mM) and receptor 1 (0.1 mM), in $D_2O$ buffered with 10 mM phosphate buffer solution (pH 7.4) at 298 K. Spectra imply no binding was observed, despite some broadening of peaks at high concentrations of guest.

FIG. 19 shows the $^1$H NMR spectra for receptor 1 (0.1 mM) titrated with a combined solution of D-gluconate (10 mM) and receptor 1 (0.1 mM), in $D_2O$ buffered with 10 mM phosphate buffer solution (pH 7.4) at 298 K. Spectra imply no binding was observed, despite some broadening of peaks at high concentrations of guest.

Figure 20:
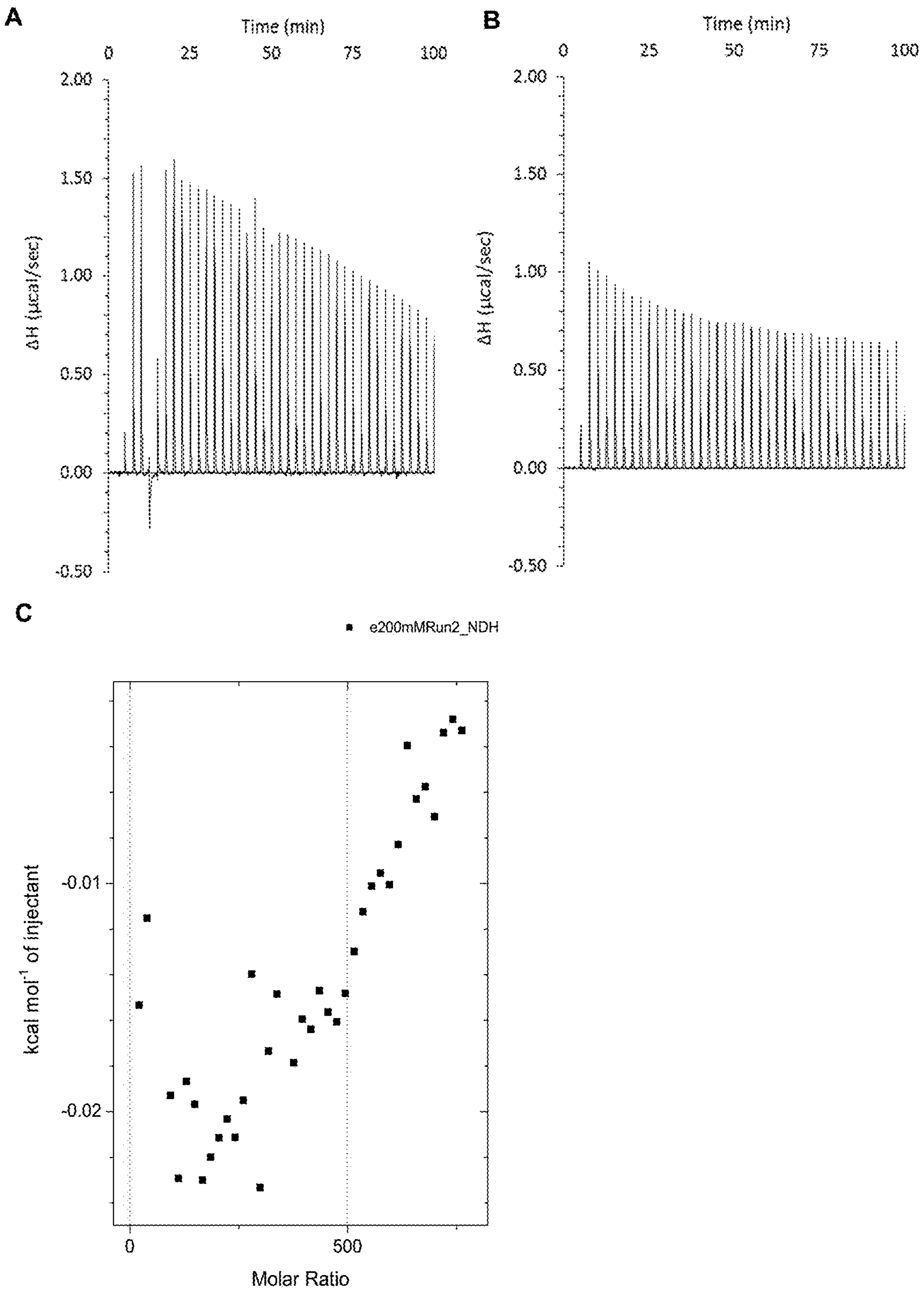
FIG. 20 shows the ITC binding results for receptor 1 (0.06 mM) titrated with Glucono-δ-lactone/gluconic acid (200 mM) in 10 mM phosphate buffer solution (pH 7.4), in which: A) shows the blank ITC run (addition of substrate into water); B) shows the actual run (substrate into receptor 1); C) shows the plotted change in enthalpy vs molar ratio.

FIG. 20 shows the ITC binding results for receptor 1 (0.06 mM) titrated with Glucono-b-lactone/gluconic acid (200 mM) in 10 mM phosphate buffer solution (pH 7.4), in which: A) shows the blank ITC run (addition of substrate into water); B) shows the actual run (substrate into receptor 1); C) shows the plotted change in enthalpy vs molar ratio.

Figure 21:
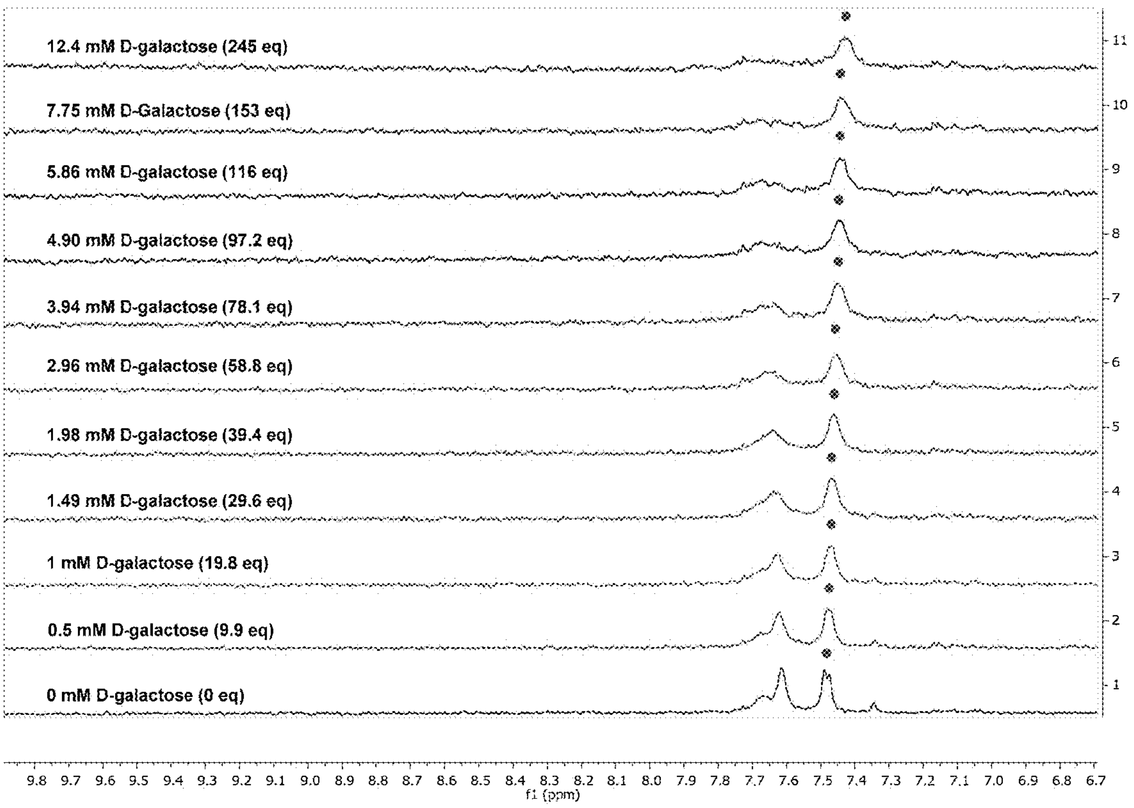
FIG. 21 shows: a) the partial $^1$H NMR spectra; and b) the binding analysis curve for receptor 1 (0.05 mM) titrated with a combined solution of D-galactose (250 mM) and receptor 1 (0.05 mM), in $D_2O$ buffered with 10 mM phosphate buffer solution (pH 7.4) at 298 K. Spectra imply binding with fast/intermediate exchange on NMR timescale. Changes in chemical shift (Δδ ppm) of peak at 7.63 ppm (denoted with •) were plotted against increasing guest concentration (mM). The calculated values for the Δδ are overlaid with the observed values giving $K_a$=132±13 $M^{-1}$ (10.2%).
Figure 21:
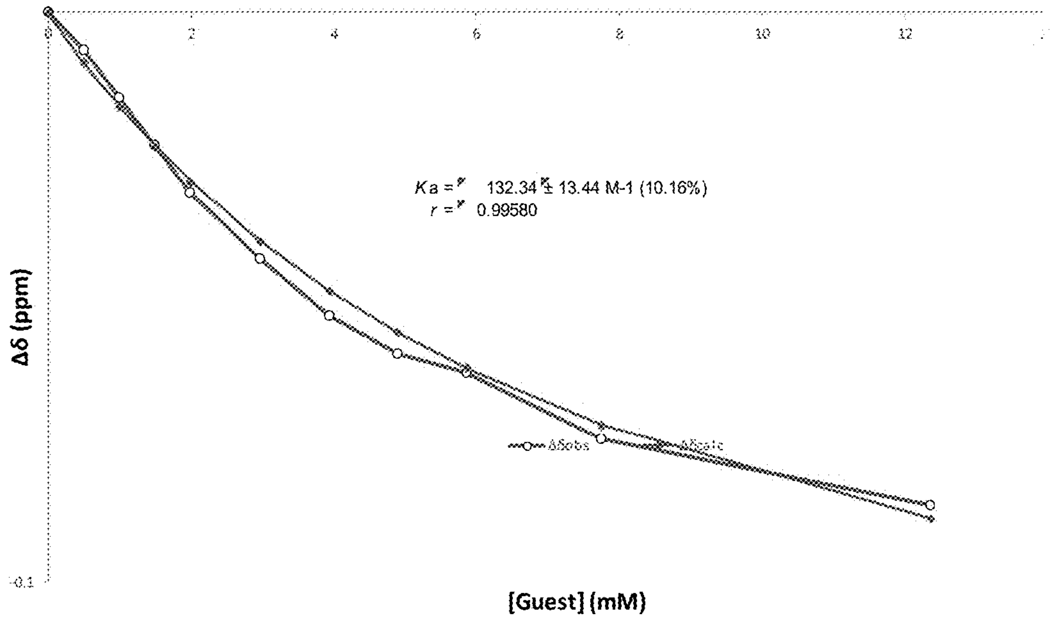

FIG. 21 shows: a) the partial $^1$H NMR spectra; and b) the binding analysis curve for receptor 1 (0.05 mM) titrated with a combined solution of D-galactose (250 mM) and receptor 1 (0.05 mM), in $D_2O$ buffered with 10 mM phosphate buffer solution (pH 7.4) at 298 K. Spectra imply binding with fast/intermediate exchange on NMR timescale. Changes in chemical shift (Δδ ppm) of peak at 7.63 ppm (denoted with *) were plotted against increasing guest concentration (mM). The calculated values for the Δδ are overlaid with the observed values giving $K_a$=132±13 $M^{-1}$ (10.2%).

Figure 22:
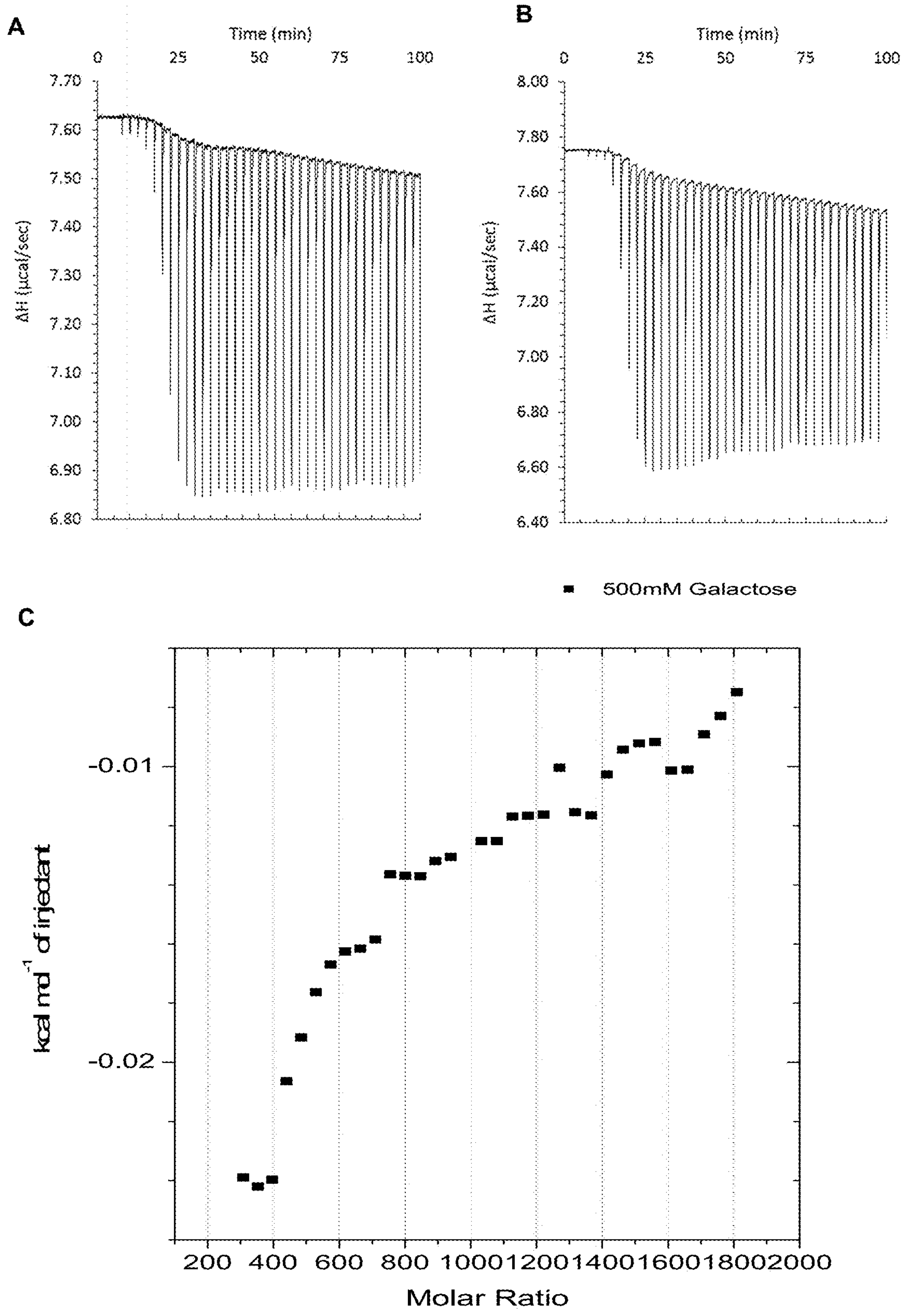
FIG. 22 shows for receptor 1 (0.06 mM) titrated with D-galactose (518 mM) in $H_2O$, in which: A) shows the blank ITC run (addition of sugar into water); B) shows the actual run (sugar into receptor 1); and C) shows the plotted change in enthalpy vs molar ratio.

FIG. 22 shows for receptor 1 (0.06 mM) titrated with D-galactose (518 mM) in $H_2O$, in which: A) shows the blank ITC run (addition of sugar into water); B) shows the actual run (sugar into receptor 1); and C) shows the plotted change in enthalpy vs molar ratio.

Figure 23:
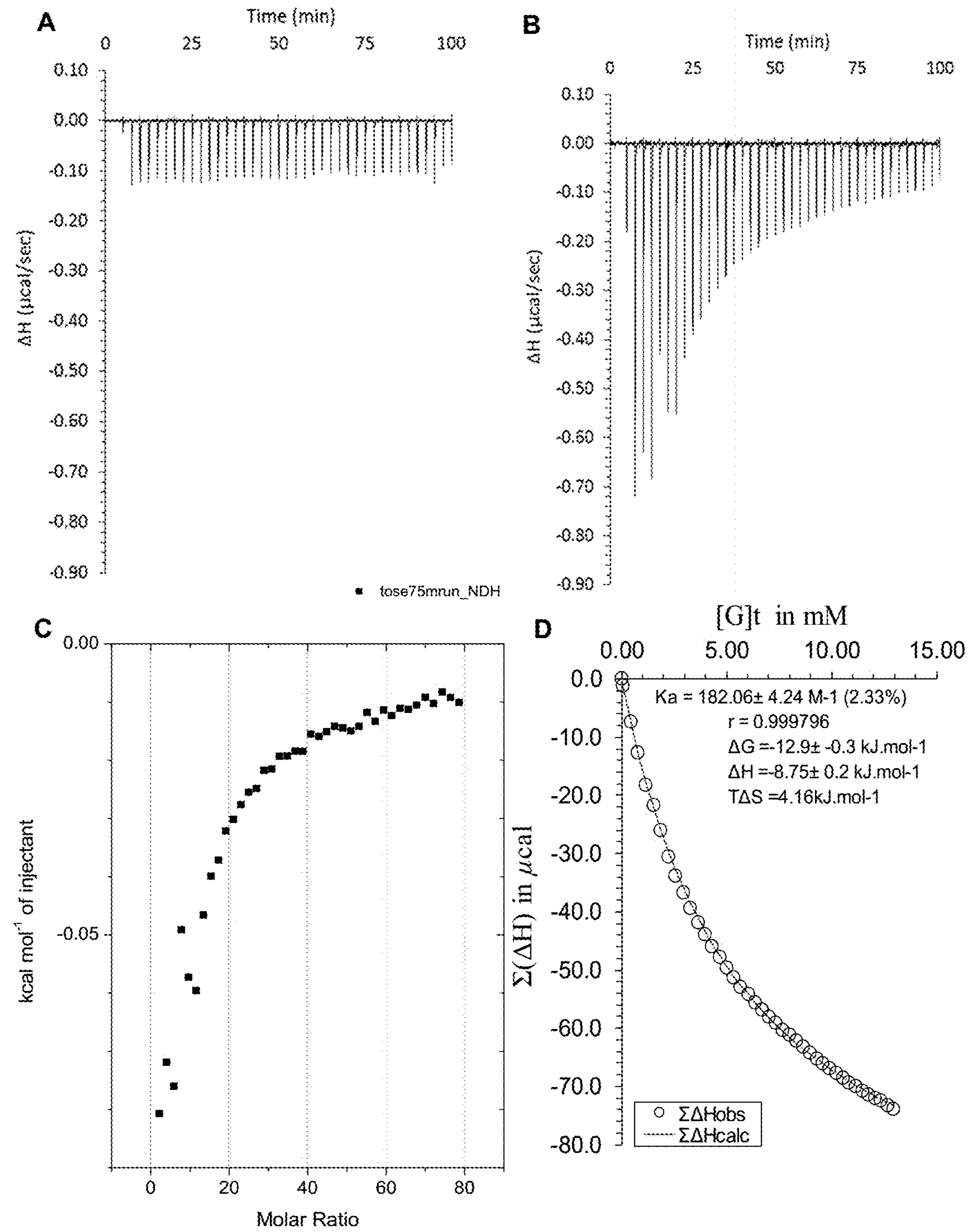
FIG. 23 shows the shows the ITC binding results for receptor 1 (0.1 mM) titrated with D-galactose (75 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet (Ka=182±4.2 $M^{-1}$).

FIG. 23 shows the shows the ITC binding results for receptor 1 (0.1 mM) titrated with D-galactose (75 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet (Ka=182±4.2 $M^{-1}$).

Figure 24:
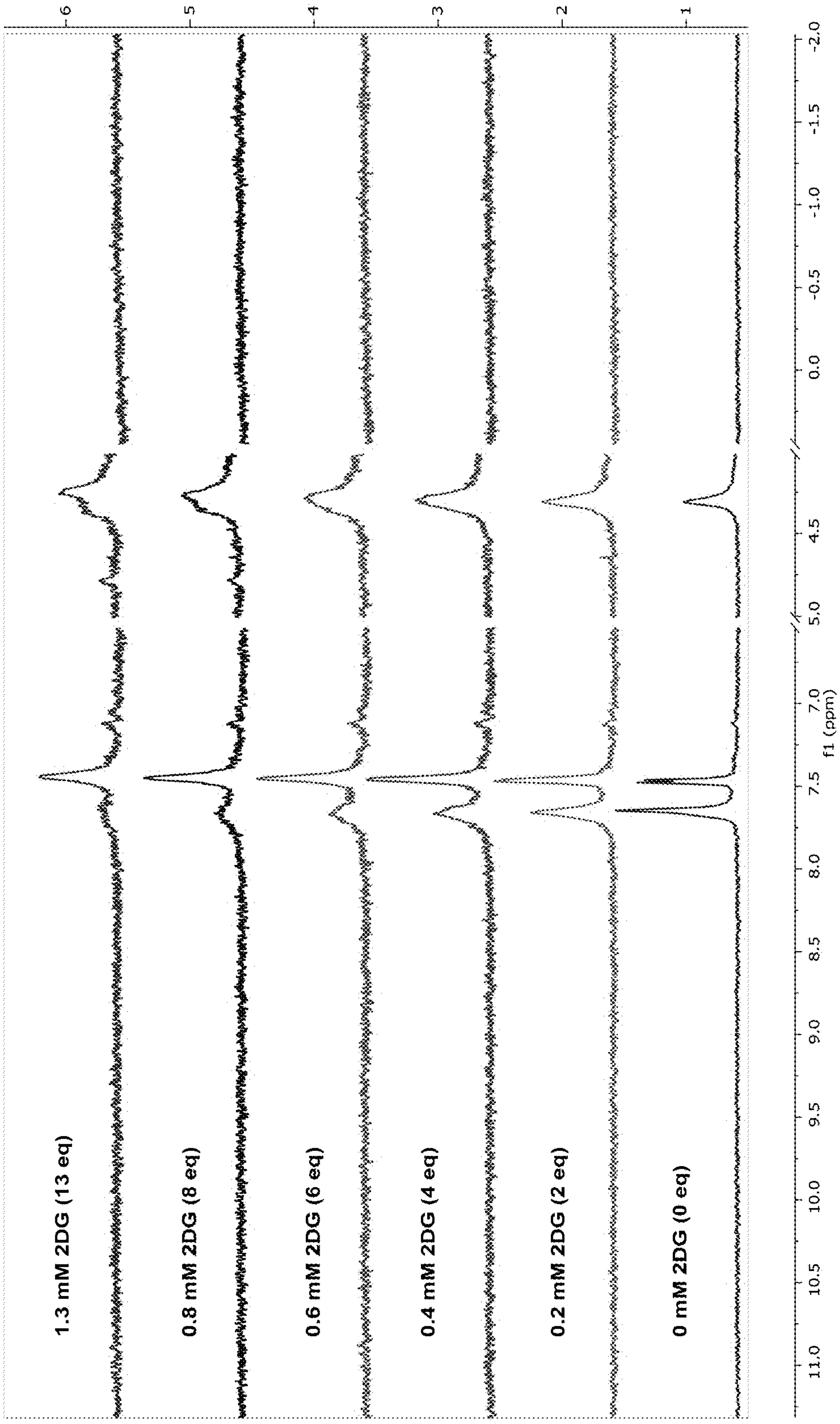
FIG. 24 shows the partial $^1$H NMR spectra for receptor 1 (0.1 mM) titrated with a combined solution of 2-deoxy-D-glucose (50 mM) and receptor 1 (0.1 mM), in $D_2O$ buffered with 10 mM phosphate buffer solution (pH 7.4) at 298 K. Spectra imply binding with intermediate rate of exchange (rate between fast and slow exchange rates between H and HG species) on NMR timescale. Due to severe broadening of peaks for receptor 1 upon addition of guest, no $K_a$ was determinable.

FIG. 24 shows the partial $^1$H NMR spectra for receptor 1 (0.1 mM) titrated with a combined solution of 2-deoxy-D-glucose (50 mM) and receptor 1 (0.1 mM), in $D_2O$ buffered with 10 mM phosphate buffer solution (pH 7.4) at 298 K.

Spectra imply binding with intermediate rate of exchange (rate between fast and slow exchange rates between H and HG species) on NMR timescale. Due to severe broadening of peaks for receptor 1 upon addition of guest, no $K_a$ was determinable.

Figure 25:
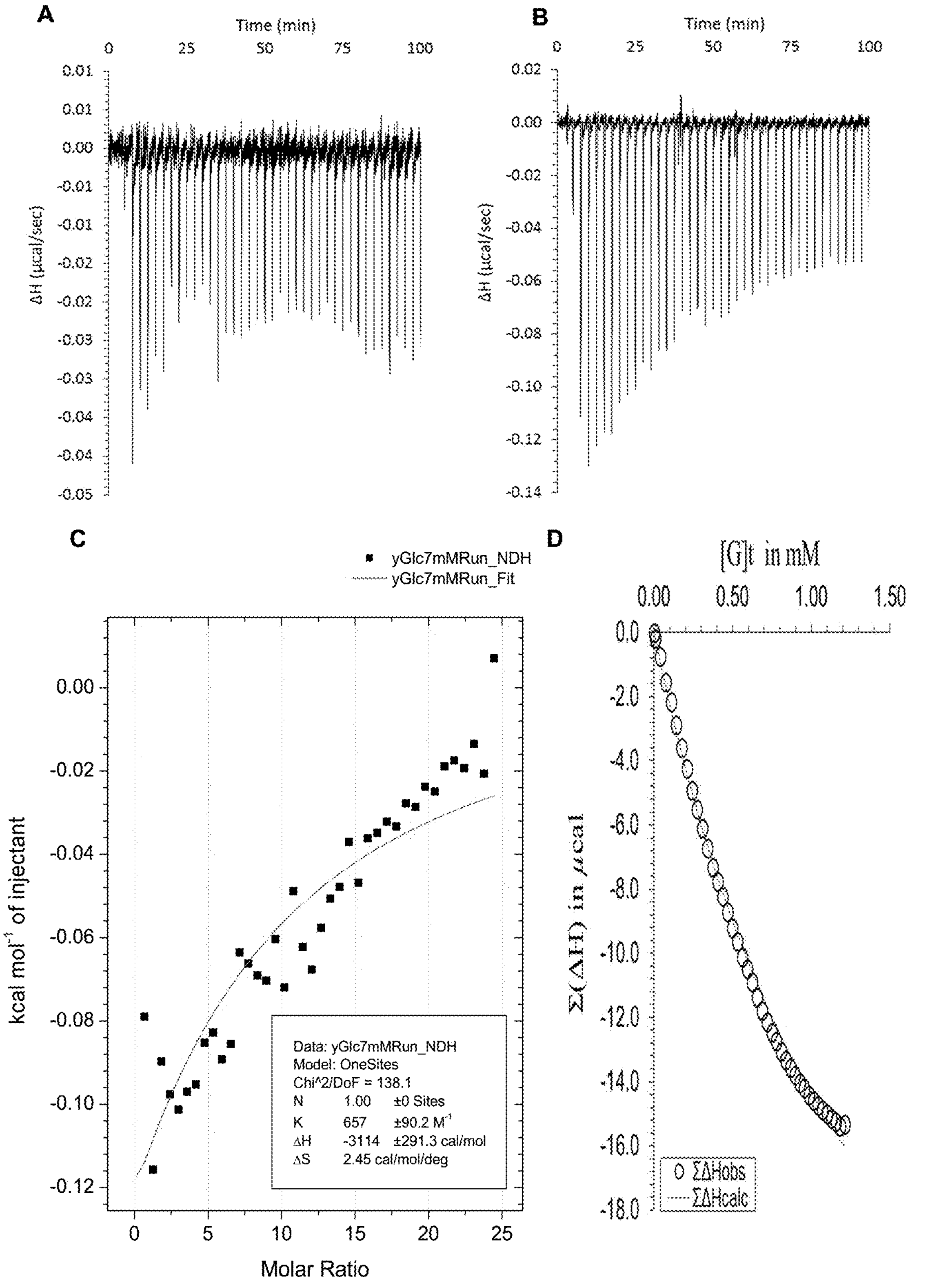
FIG. 25 shows the ITC binding results for receptor 1 (0.06 mM) titrated with 2-deoxy-D-glucose (7 mM) in $H_2O$, in which: A) shows the blank ITC run (addition of sugar into water); B) shows the actual run (sugar into receptor 1); C) shows the plotted change in enthalpy vs molar ratio and the fit calculated with the supplied ITC software ($K_a$=657±90 $M^{-1}$); and D) shows the fit calculated using an Excel spreadsheet to corroborate the result.

FIG. 25 shows the ITC binding results for receptor 1 (0.06 mM) titrated with 2-deoxy-D-glucose (7 mM) in $H_2O$, in which: A) shows the blank ITC run (addition of sugar into water); B) shows the actual run (sugar into receptor 1); C) shows the plotted change in enthalpy vs molar ratio and the fit calculated with the supplied ITC software ($K_a$=657±90 $M^{-1}$); and D) shows the fit calculated using an Excel spreadsheet to corroborate the result.

Figure 26:
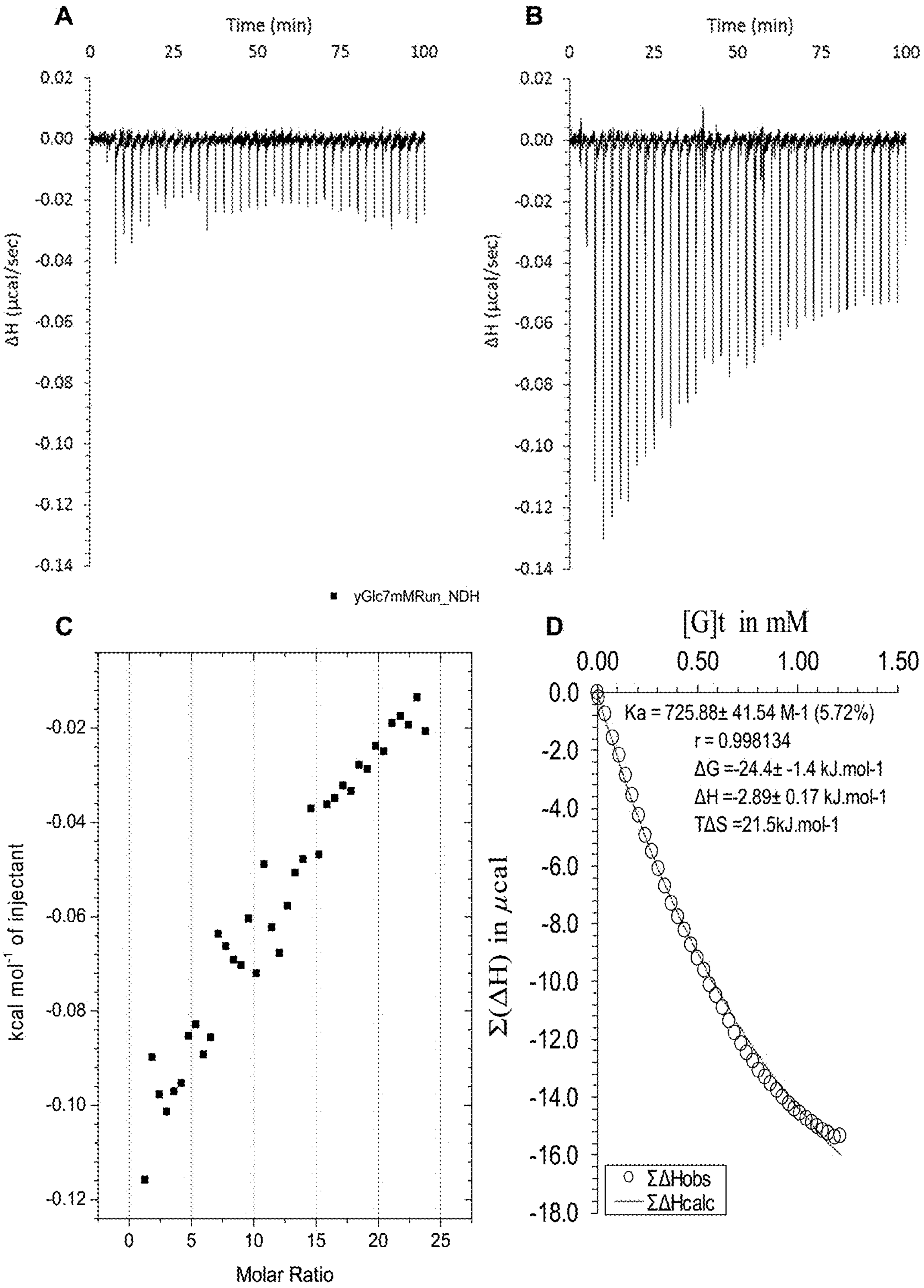
FIG. 26 shows the ITC binding results for receptor 1 (0.06 mM) titrated with 2-deoxy-D-glucose (7 mM) in 10 mM phosphate buffer solution (pH 7.4), in which: A) shows the blank ITC run (addition of sugar into water); B) shows the actual run (sugar into receptor 1); C) shows the plotted change in enthalpy vs molar ratio; and D) shows the fit calculated using an Excel spreadsheet (Ka=725±41 $M^{-1}$).

FIG. 26 shows the ITC binding results for receptor 1 (0.06 mM) titrated with 2-deoxy-D-glucose (7 mM) in 10 mM phosphate buffer solution (pH 7.4), in which: A) shows the blank ITC run (addition of sugar into water); B) shows the actual run (sugar into receptor 1); C) shows the plotted change in enthalpy vs molar ratio; and D) shows the fit calculated using an Excel spreadsheet (Ka=725±41 $M^{-1}$).

Figure 27:
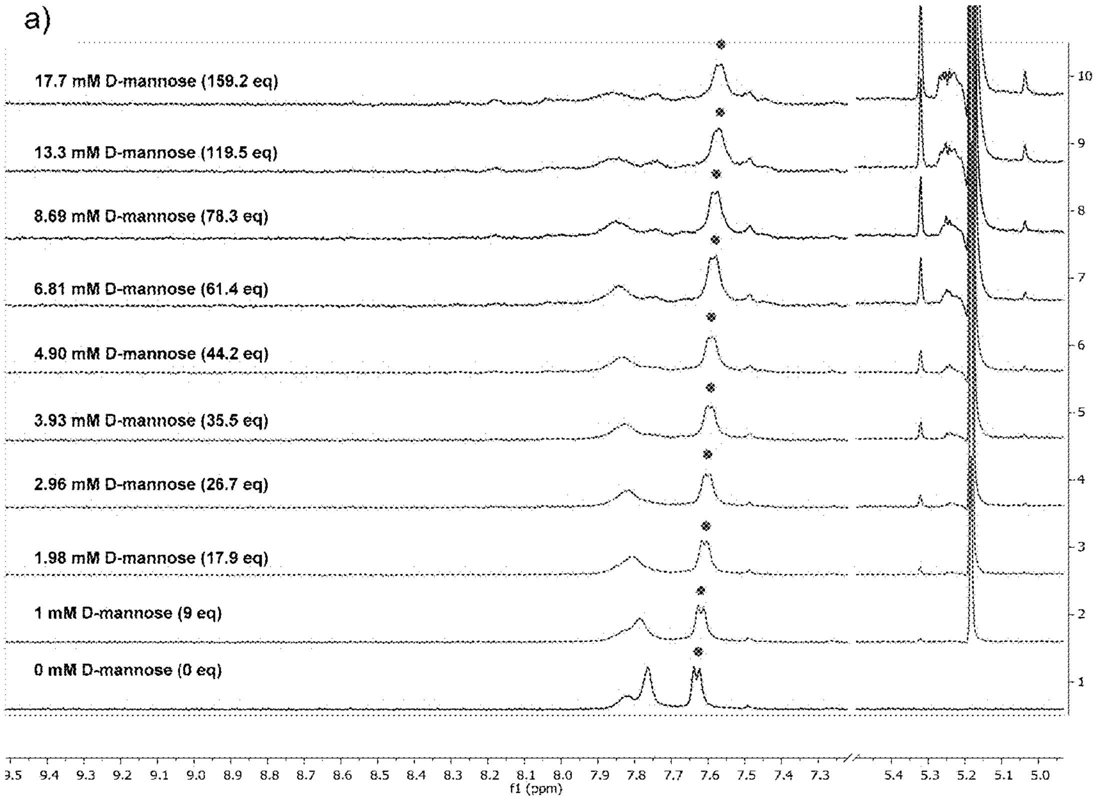
FIG. 27 shows: a) the partial $^1$H NMR spectra; and b) the binding analysis curve for receptor 1 (0.11 mM) titrated with a combined solution of D-mannose (250 mM) and receptor 1 (0.11 mM), in $D_2O$ buffered with 10 mM phosphate buffer solution (pH 7.4) at 298 K. Spectra imply binding with fast/intermediate exchange on NMR timescale. Changes in chemical shift (Δδ ppm) of peak at 7.63 ppm (denoted with •) were plotted against increasing guest concentration (mM). The calculated values for the Δδ are overlaid with the observed values giving $K_a$=140±2 $M^{-1}$ (1.31%).
Figure 27:
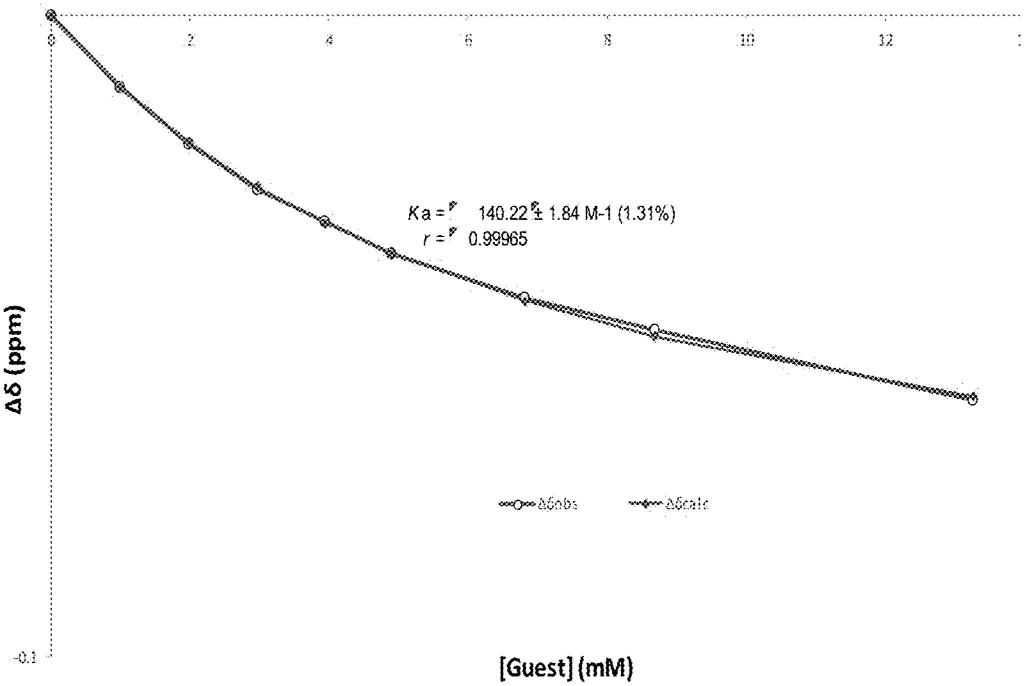

FIG. 27 shows: a) the partial $^1$H NMR spectra; and b) the binding analysis curve for receptor 1 (0.11 mM) titrated with a combined solution of D-mannose (250 mM) and receptor 1 (0.11 mM), in $D_2O$ buffered with 10 mM phosphate buffer solution (pH 7.4) at 298 K. Spectra imply binding with fast/intermediate exchange on NMR timescale. Changes in chemical shift (Δβ ppm) of peak at 7.63 ppm (denoted with *) were plotted against increasing guest concentration (mM). The calculated values for the Δδ are overlaid with the observed values giving $K_a$=140±2 $M^{-1}$ (1.31%).

Figure 28:
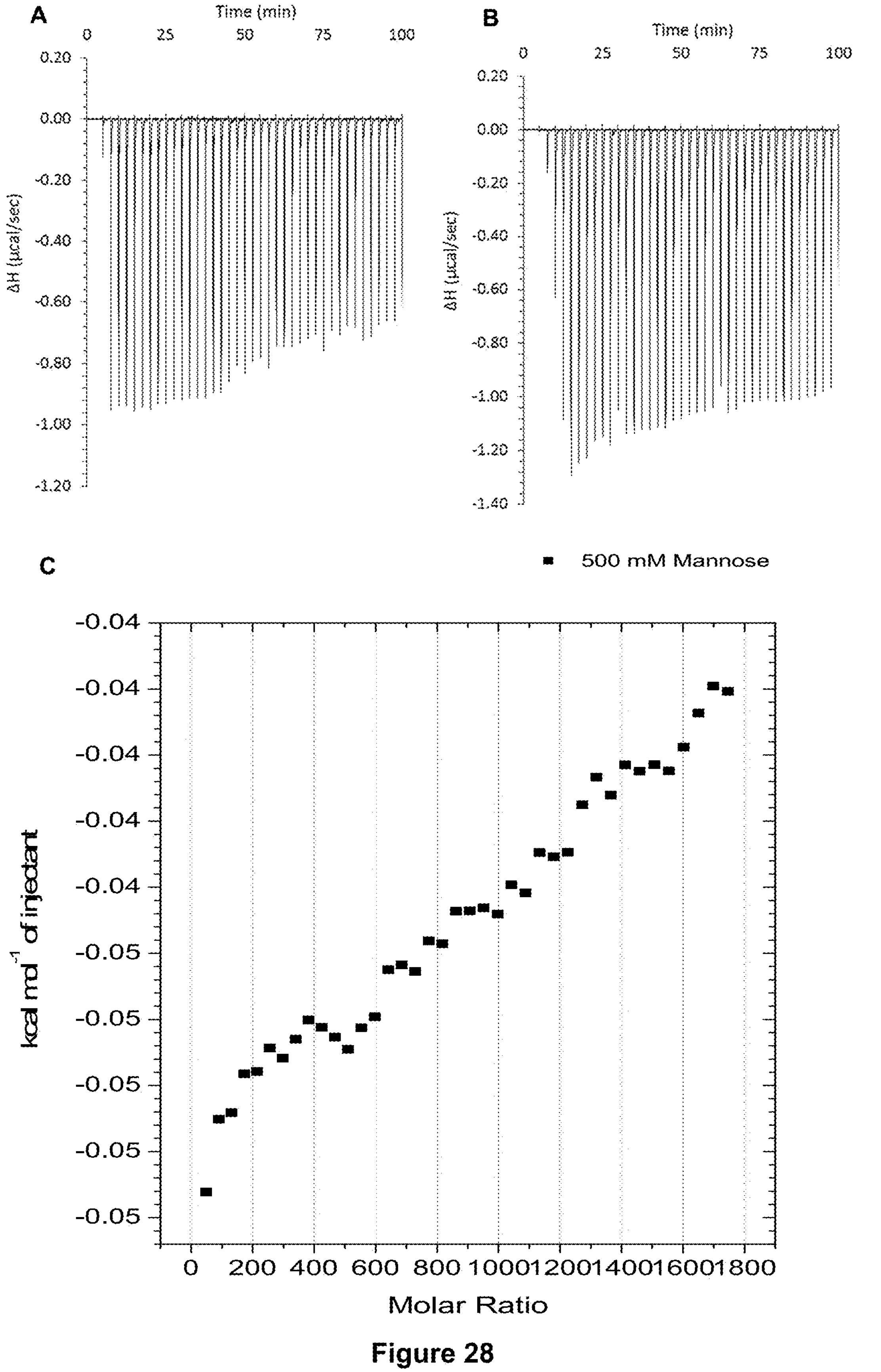
FIG. 28 shows for receptor 1 (0.06 mM) titrated with D-Mannose (504 mM) in $H_2O$, in which: A) shows the blank ITC run (addition of sugar into water); B) shows the actual run (sugar into receptor 1); and C) shows the plotted change in enthalpy vs molar ratio.

FIG. 28 shows for receptor 1 (0.06 mM) titrated with D-Mannose (504 mM) in $H_2O$, in which: A) shows the blank ITC run (addition of sugar into water); B) shows the actual run (sugar into receptor 1); and C) shows the plotted change in enthalpy vs molar ratio.

Figure 29:
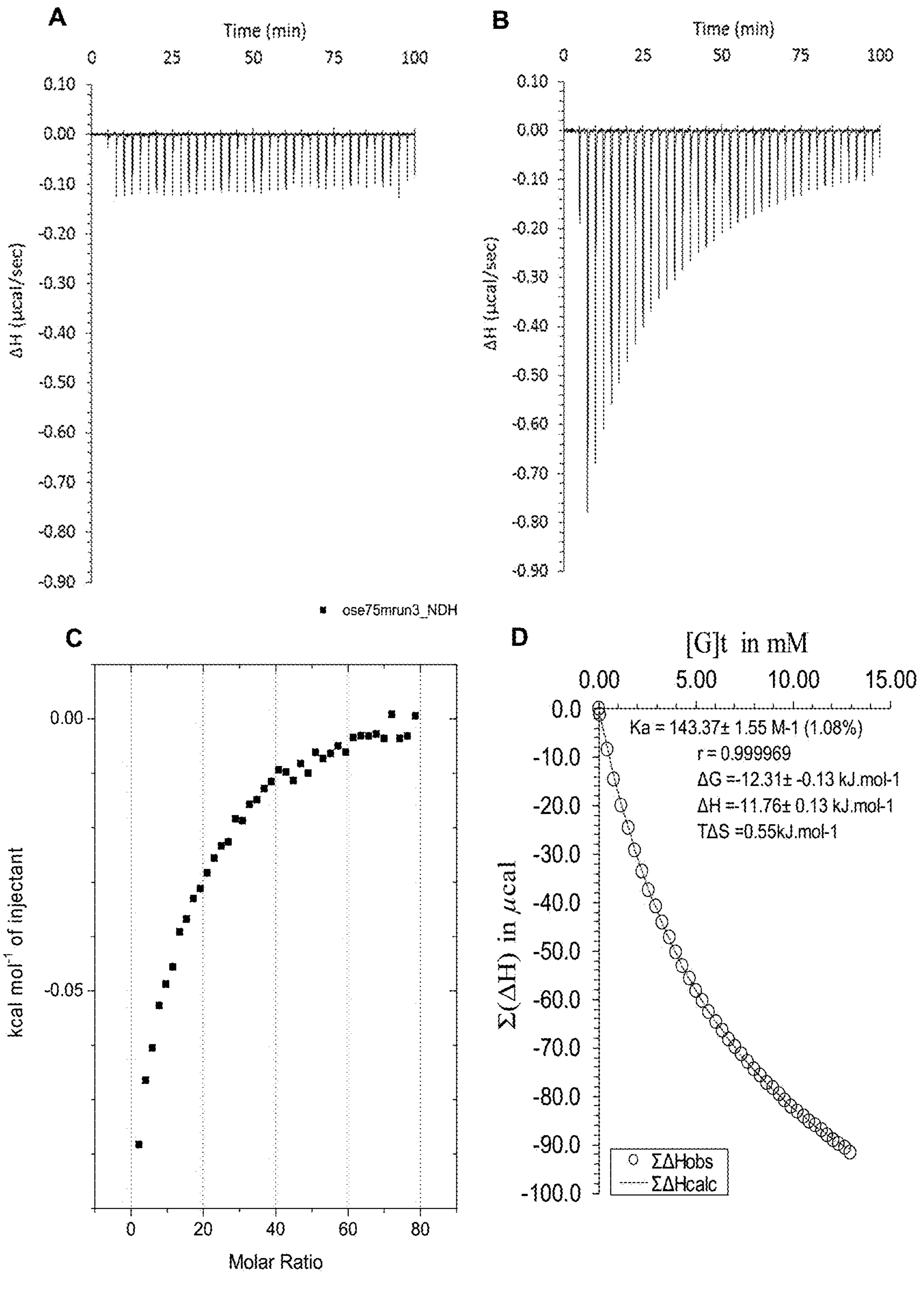
FIG. 29 shows the ITC binding results for receptor 1 (0.1 mM) titrated with D-mannose (75 mM) in 10 mM phosphate buffer solution (pH 7.4) in which: A) shows the blank ITC run (addition of substrate into medium); B) shows the actual run (substrate into receptor 1XX); C) shows the plotted change in enthalpy vs molar ratio; and D) shows the fit calculated using an Excel spreadsheet ($K_a$=143±1.5 $M^{-1}$).

FIG. 29 shows the ITC binding results for receptor 1 (0.1 mM) titrated with D-mannose (75 mM) in 10 mM phosphate buffer solution (pH 7.4) in which: A) shows the blank ITC run (addition of substrate into medium); B) shows the actual run (substrate into receptor 1XX); C) shows the plotted change in enthalpy vs molar ratio; and D) shows the fit calculated using an Excel spreadsheet ($K_a$=143±1.5 $M^{-1}$).

Figure 30:
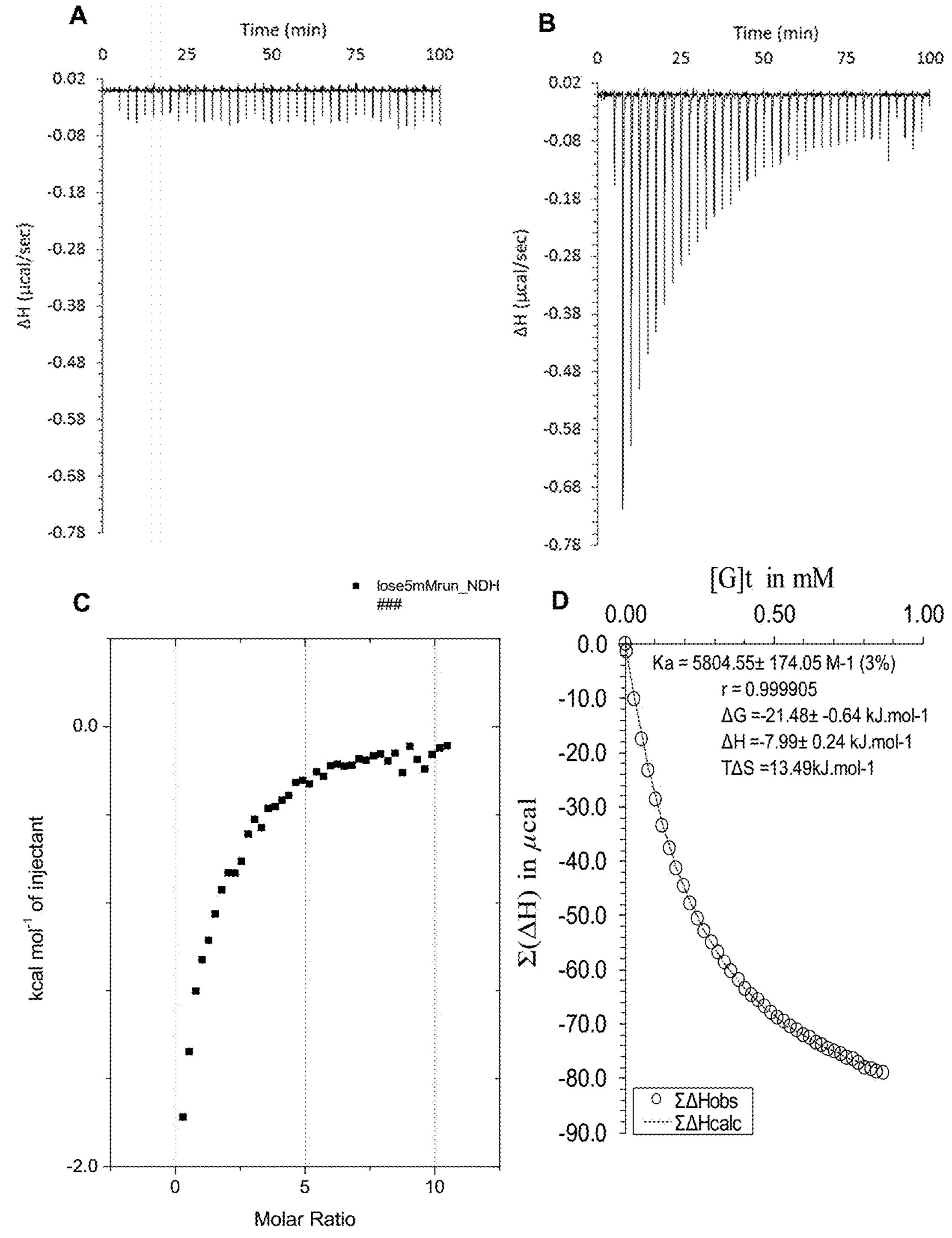
FIG. 30 shows the ITC binding results for receptor 1 (0.1 mM) titrated with D-xylose (5 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet ($K_a$=5804±174 $M^{-1}$).

FIG. 30 shows the ITC binding results for receptor 1 (0.1 mM) titrated with D-xylose (5 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet ($K_a$=5804±174 $M^{-1}$).

Figure 31:
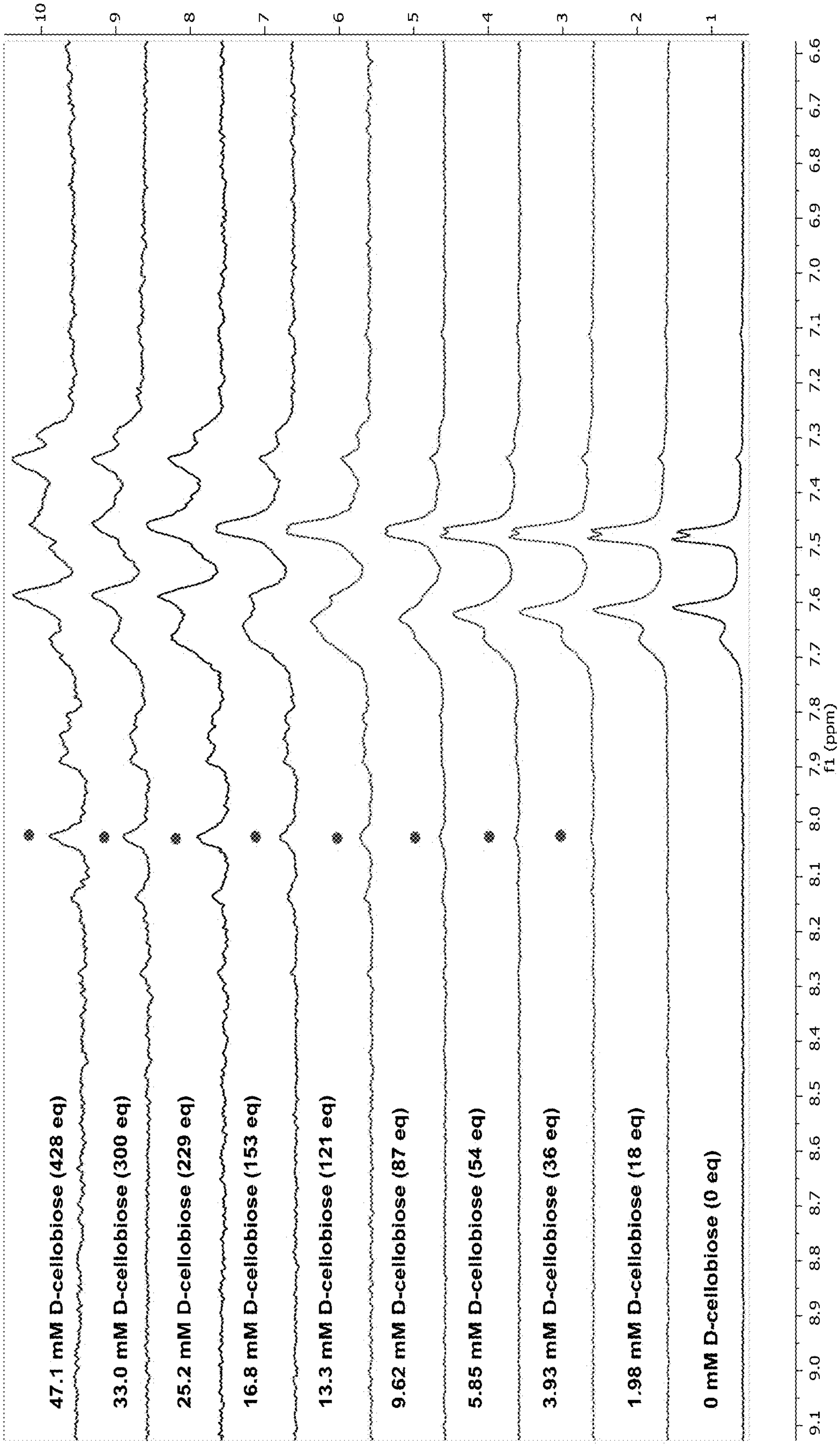
FIG. 31 shows the partial $^1$H NMR spectra for receptor 1 (0.11 mM) titrated with a combined solution of D-cellobiose (250 mM) and receptor 1 (0.11 mM), in $D_2O$ buffered with 10 mM phosphate buffer solution (pH 7.4) at 298 K. Spectra imply binding with slow exchange on NMR timescale. Integrations of peak at 8.02 ppm (denoted with •) versus region 8.36-7.36 ppm were used to calculate the $K_a$ ($M^{-1}$) at each point of addition (see Table 3), an average of these calculated values gives Ka=31±2.66 (9%).

FIG. 31 shows the partial $^1$H NMR spectra for receptor 1 (0.11 mM) titrated with a combined solution of D-cellobiose (250 mM) and receptor 1 (0.11 mM), in $D_2O$ buffered with 10 mM phosphate buffer solution (pH 7.4) at 298 K. Spectra imply binding with slow exchange on NMR timescale. Integrations of peak at 8.02 ppm (denoted with *) versus region 8.36-7.36 ppm were used to calculate the $K_a$ ($M^{-1}$) at each point of addition (see Table 3), an average of these calculated values gives $K_a$=31±2.66 (9%).

Figure 32:
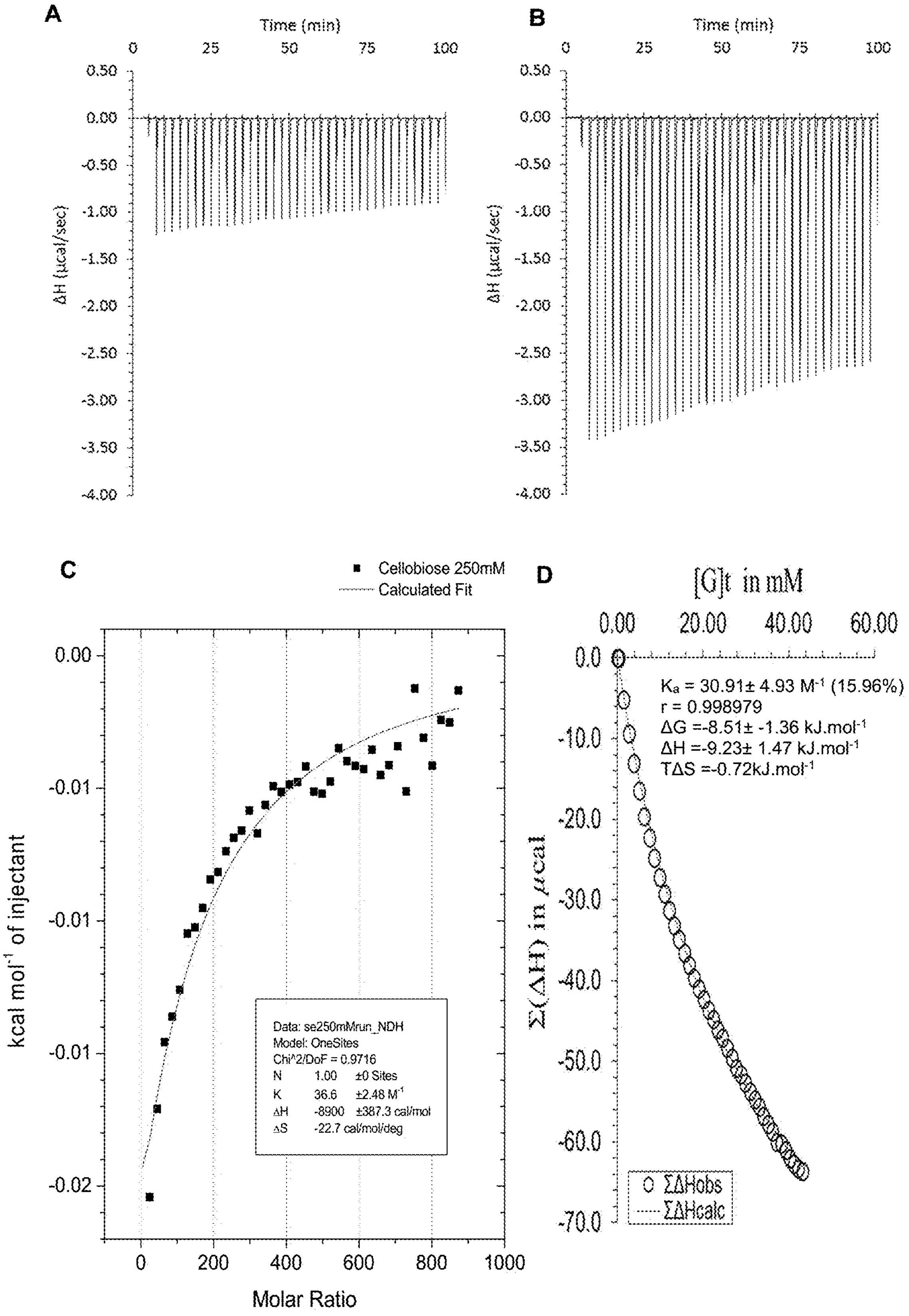
FIG. 32 shows the ITC binding results for receptor 1 (0.06 mM) titrated with cellobiose (250 mM) in $H_2O$, in which: A) shows the blank ITC run (addition of sugar into water); B) shows the actual run (sugar into receptor 1); C) shows the plotted change in enthalpy vs molar ratio and the fit calculated with the supplied ITC software ($K_a$=36.6±2.5 $M^{-1}$); and D) shows the fit calculated using an Excel spreadsheet to corroborate the result
Figure 33:
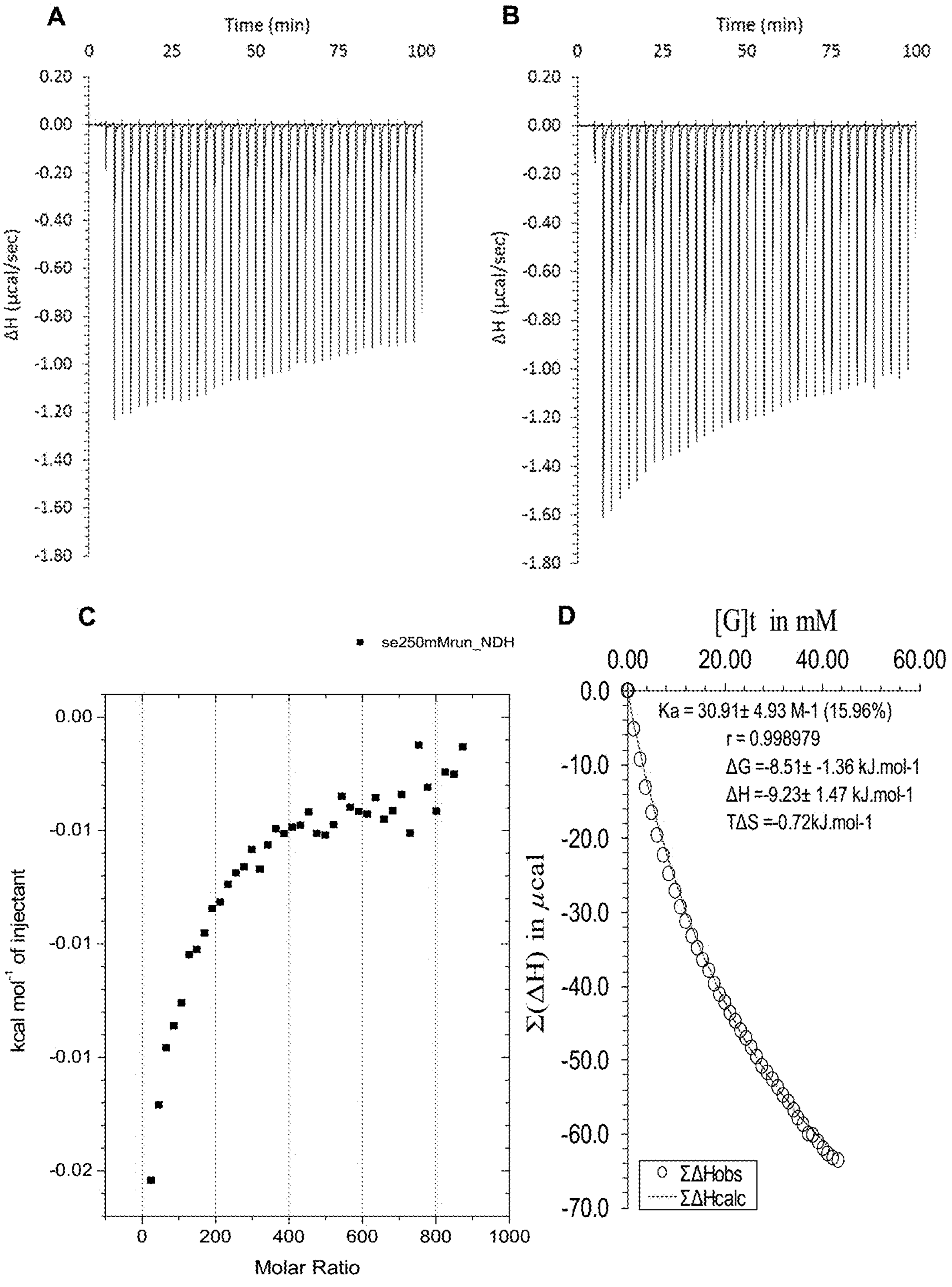
FIG. 33 shows the ITC binding results for receptor 1 (0.6 mM) titrated with D-cellobiose (250 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet ($K_a$=30.9±4.9 $M^{-1}$).

FIG. 32 shows the ITC binding results for receptor 1 (0.06 mM) titrated with cellobiose (250 mM) in $H_2O$, in which: A) shows the blank ITC run (addition of sugar into water); B) shows the actual run (sugar into receptor 1); C) shows the plotted change in enthalpy vs molar ratio and the fit calculated with the supplied ITC software ($K_a$=36.6±2.5 $M^{-1}$); and D) shows the fit calculated using an Excel spreadsheet to corroborate the result FIG. 33 shows the ITC binding results for receptor 1 (0.6 mM) titrated with D-cellobiose (250 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet ($K_a$=30.9±4.9 $M^{-1}$).

Figure 34:
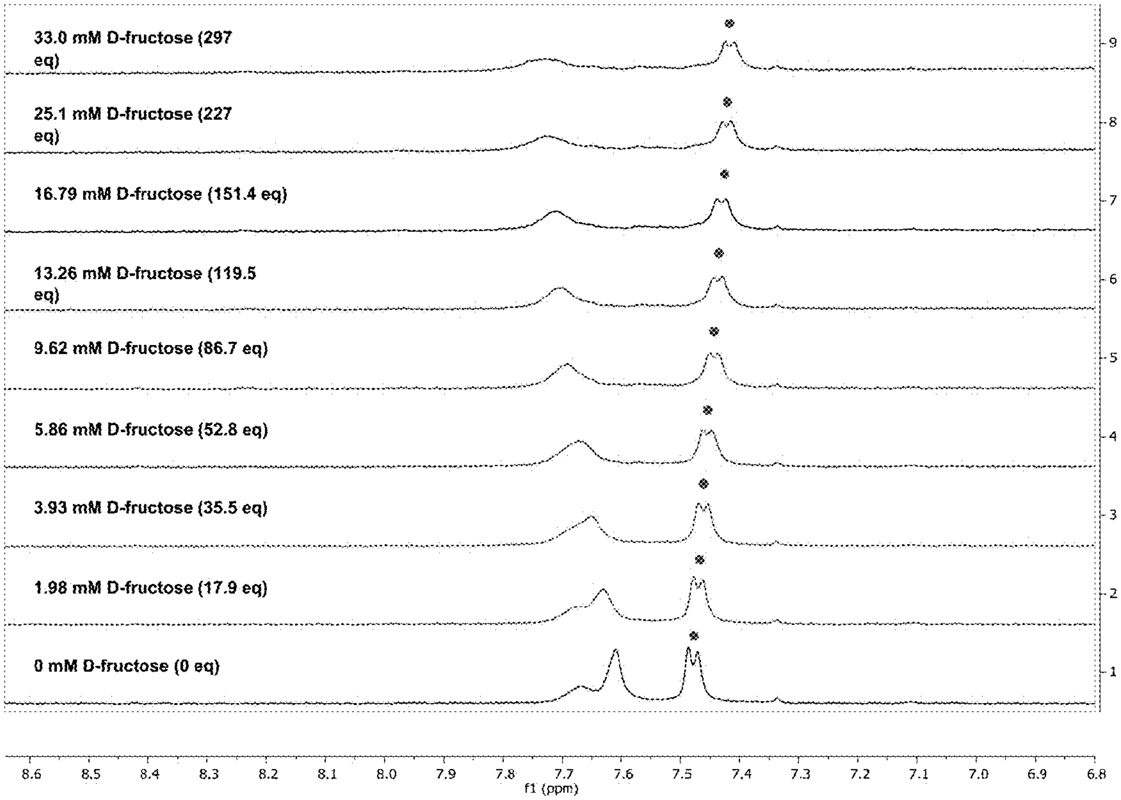
FIG. 34 shows: a) the partial $^1$H NMR spectra; and b) the binding analysis curve for receptor 1 (0.11 mM) titrated with a combined solution of D-fructose (250 mM) and receptor 1 (0.11 mM), in $D_2O$ buffered with 10 mM phosphate buffer solution (pH 7.4) at 298 K. Spectra imply binding with fast/intermediate exchange on NMR timescale. Changes in chemical shift (Δδ ppm) of peak at 7.63 ppm (denoted with •) were plotted against increasing guest concentration (mM).
Figure 34:
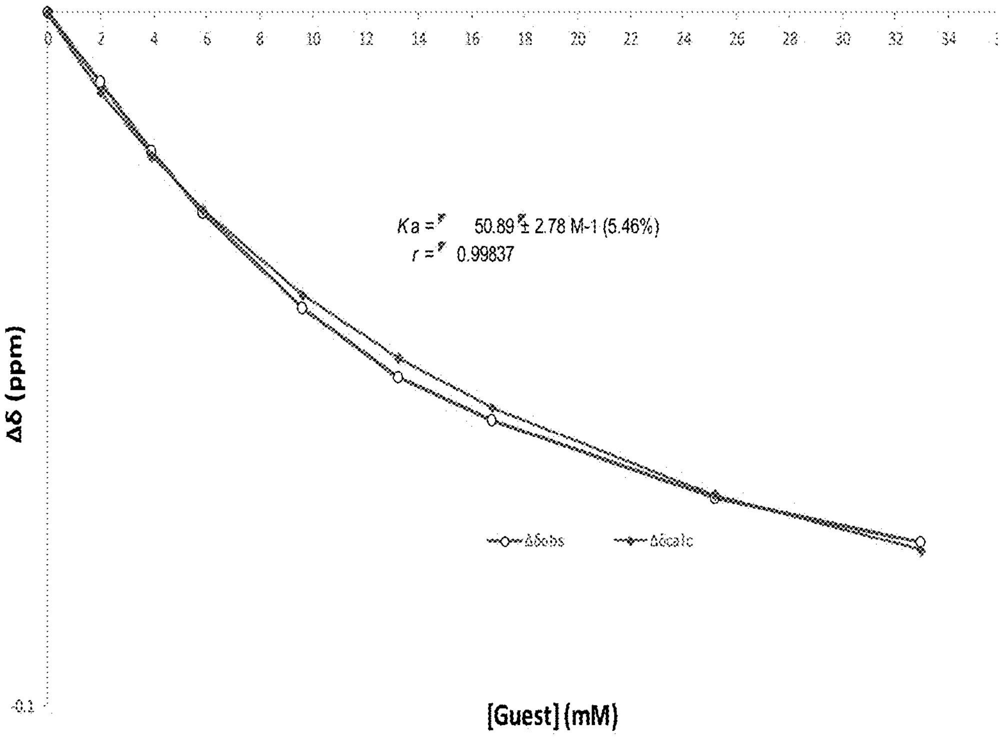

FIG. 34 shows: a) the partial $^1$H NMR spectra; and b) the binding analysis curve for receptor 1 (0.11 mM) titrated with a combined solution of D-fructose (250 mM) and receptor 1 (0.11 mM), in $D_2O$ buffered with 10 mM phosphate buffer solution (pH 7.4) at 298 K. Spectra imply binding with fast/intermediate exchange on NMR timescale. Changes in chemical shift (Δδ ppm) of peak at 7.63 ppm (denoted with *) were plotted against increasing guest concentration (mM). The calculated values for the Δδ are overlaid with the observed values giving $K_a$=51±3 $M^{-1}$ (5.46%).

FIG. 35 shows the ITC binding results for receptor 1 (0.1 mM) titrated with D-fructose (75 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet ($K_a$=60.3±1.6 $M^{-1}$).

FIG. 36 shows: a) the partial $^1$H NMR spectra; and b) the binding analysis curve for receptor 1 (0.11 mM) titrated with a combined solution of D-ribose (250 mM) and receptor 1 (0.11 mM), in $D_2O$ buffered with 10 mM phosphate buffer solution (pH 7.4) at 298 K. Spectra imply binding with fast exchange on NMR timescale. Changes in chemical shift (Δδ ppm) of peak at 7.83 ppm (denoted with *) were plotted against increasing guest concentration (mM). The calculated values for the Δδ are overlaid with the observed values giving $K_a$=264±10 $M^{-1}$ (3.96%).

FIG. 37 shows the ITC binding results for receptor 1 (0.1 mM) titrated with D-ribose (75 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet ($K_a$=216.5±4.1 $M^{-1}$).

FIG. 38 shows: a) the partial $^1$H NMR spectra; and b) the binding analysis curve for receptor 1 (0.1 mM) titrated with a combined solution of methyl α-D-glucoside (500 mM) and receptor 1 (0.1 mM), in $D_2O$ buffered with 10 mM phosphate buffer solution (pH 7.4) at 298 K. Changes in chemical shift (Δβ ppm) of peak at 7.63 ppm (denoted with *) were plotted against increasing guest concentration (mM). The calculated values for the &A are overlaid with the observed values, which are effectively indicative of no binding taking place.

FIG. 39 shows for receptor 1 (0.06 mM) titrated with methyl-α-D-glucoside (500 mM) in $H_2O$, in which: A) shows the blank ITC run (addition of sugar into water); B) shows the actual run (sugar into receptor 1); and C) shows the plotted change in enthalpy vs molar ratio.

FIG. 40 shows the ITC binding results for receptor 1 (0.06 mM) titrated with methyl-α-D-glucoside (500 mM) in 10 mM phosphate buffer solution (pH 7.4), in which: A) shows the blank ITC run (addition of sugar into water); B) shows the actual run (sugar into receptor 1) and C) shows the plotted change in enthalpy vs molar ratio.

FIG. 41 shows the ITC results for receptor 1 (0.06 mM) titrated with N-acetyl-D-glucosamine (498 mM) in $H_2O$, in which: A) shows the blank ITC run (addition of sugar into water); B) shows the actual run (sugar into receptor 1); and C) shows the plotted change in enthalpy vs molar ratio.

FIG. 42 shows the ITC binding results for receptor 1 (0.06 mM) titrated with N-acetyl-D-glucosamine (498 mM) in 10 mM phosphate buffer solution (pH 7.4), in which: A) shows the blank ITC run (addition of sugar into water); B) shows the actual run (sugar into receptor 1) and C) shows the plotted change in enthalpy vs molar ratio.

FIG. 43 shows for receptor 1 (0.06 mM) titrated with D-uracil (5 mM) in 10 mM PBS buffer (pH 7.4), in which: A) shows the blank ITC run (addition of sugar into water); B) shows the actual run (sugar into receptor 1); and C) shows the plotted change in enthalpy vs molar ratio.

FIG. 44 shows for receptor 1 (0.06 mM) titrated with uric acid (2.34 mM) in 10 mM PBS buffer (pH 7.4), in which: A) shows the blank ITC run (addition of sugar into water); B) shows the actual run (sugar into receptor 1); and C) shows the plotted change in enthalpy vs molar ratio.

FIG. 45 shows the ITC results for receptor 1 (0.06 mM) titrated with maltose (500 mM) in $H_2O$, in which: A) shows the blank ITC run (addition of sugar into water); B) shows the actual run (sugar into receptor 1); and C) shows the plotted change in enthalpy vs molar ratio.

FIG. 46 shows the ITC binding results for receptor 1 (0.1 mM) titrated with D-Mannitol (500 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio.

FIG. 47 shows the ITC binding results for receptor 1 (0.06 mM) titrated with paracetamol (87 mM) in 10 mM phosphate buffer solution (pH 7.4), in which: A) shows the blank ITC run (addition of substrate into water); B) shows the actual run (substrate into receptor 1); C) shows the plotted change in enthalpy vs molar ratio.

FIG. 48 shows the ITC binding results for receptor 1 (0.06 mM) titrated with ascorbic acid (500 mM) in 10 mM phosphate buffer solution (pH 7.4), in which: A) shows the blank ITC run (addition of substrate into water); B) shows the actual run (substrate into receptor 1); C) shows the plotted change in enthalpy vs molar ratio.

FIG. 49 shows the ITC binding results for receptor 1 (0.06 mM) titrated with L-fucose (500 mM) in 10 mM phosphate buffer solution (pH 7.4), in which: A) shows the blank ITC run (addition of substrate into water); B) shows the actual run (substrate into receptor 1); C) shows the plotted change in enthalpy vs molar ratio.

FIG. 50 shows the ITC binding results for receptor 1 (0.06 mM) titrated with L-phenylalanine (82 mM) in 10 mM phosphate buffer solution (pH 7.4), in which: A) shows the blank ITC run (addition of substrate into medium); B) shows the actual run (substrate into receptor 1); C) shows the plotted change in enthalpy vs molar ratio.

FIG. 51 shows the ITC binding results for receptor 1 (0.1 mM) titrated with myo inositol (5 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio; and D) shows the fit calculated using an Excel spreadsheet ($K_a$=7563±313 $M^{-1}$).

FIG. 52 shows the ITC binding results for receptor 1 (0.1 mM) titrated with Adenosine (500 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio.

FIG. 53 shows the ITC binding results for receptor 1 (0.1 mM) titrated with cytosine (20 mM) in 10 mM phosphate buffer solution (pH 7.4) in which: A) shows the blank ITC run (addition of substrate into medium); B) shows the actual run (substrate into receptor 1); C) shows the plotted change in enthalpy vs molar ratio.

FIG. 54 shows the ITC binding results for receptor 1 (0.06 mM) titrated with L-tryptophan (54 mM) in 10 mM phosphate buffer solution (pH 7.4), in which: A) shows the blank ITC run (addition of substrate into medium); B) shows the actual run (substrate into receptor 1); C) shows the plotted change in enthalpy vs molar ratio.

FIG. 55 shows the partial $^1$H NMR ROESY spectrum of receptor 1 (2 mM) with D-glucose (5 mM, 2.5 equivalents) in $D_2O$. Chemical exchange peaks (black, annotated) link CH protons on I-D-glucose in free and bound states. Chemical shifts for the glucose protons, with signal movements due to binding, are listed in the table. Signals for bound α-D-glucose were not observed under these conditions.

FIG. 56 shows the structures of the substrates tested for affinity with receptor 1.

FIG. 57 shows the partial $^1$H NMR spectra (top) and binding analysis curve (bottom) for 90 (1 mM) titrated with a combined solution of D-glucose (1 M) and 90 (1 mM), in $D_2O$ with at pH 7.4 and 298 K. Change in chemical shifts (Δδ, ppm) denoted with * were plotted against D-glucose concentration (mM). The calculated values for Δδ are overlaid with the observed values, giving $K_a$=5.1±0.2 $M^{-1}$ (3.6%).

FIG. 58 shows the Partial $^1$H NMR spectra (top) and binding analysis curve (bottom) for 90 (0.25 mM) titrated with a combined solution of D-cellobiose (250 mM) and 90 (0.25 mM), in $D_2O$ with at pH 7.4 and 298 K. Change in chemical shifts (Δδ, ppm) denoted with * were plotted against D-cellobiose concentration (mM). The calculated values for Δδ are overlaid with the observed values, giving $K_a$=46±0.4 $M^{-1}$ (0.89%).

FIG. 59 shows the partial $^1$H NMR spectra (top) and binding analysis curve (bottom) for 90 (0.2 mM) titrated with a combined solution of D-cellotriose (15 mM) and 90 (0.2 mM), in $D_2O$ with at pH 7.4 and 298 K. Change in chemical shifts (Δδ, ppm) denoted with * were plotted against D-cellotriose concentration (mM). The calculated values for Δδ are overlaid with the observed values, giving $K_a$=949±2.9 $M^{-1}$ (0.3%).

FIG. 60 shows the partial $^1$H NMR spectra for 90 (0.2 mM) titrated with a combined solution of D-cellotetraose (15 mM) and 90 (0.2 mM), in $D_2O$ with at pH 7.4 and 298 K. Spectra imply binding with intermediate rate of exchange, thus no $K_a$ was determinable.

FIG. 61 shows the partial $^1$H NMR spectra for 90 (0.2 mM) titrated with a combined solution of D-cellopentaose (15 mM) and 90 (0.2 mM), in $D_2O$ with at pH 7.4 and 298 K. Spectra imply binding with intermediate rate of exchange, thus no $K_a$ was determinable.

FIG. 62 shows the partial $^1$H NMR spectra (top) and binding analysis curve (bottom) for 90 (0.2 mM) titrated with a combined solution of D-maltose (500 mM) and 90 (0.2 mM), in $D_2O$ with at pH 7.4 and 298 K. Change in chemical shifts (Δδ, ppm) denoted with * were plotted against D-maltose concentration (mM). The calculated values for Δδ are overlaid with the observed values, giving $K_a$=15±1.8 $M^{-1}$ (11.8%).

FIG. 63 shows the partial $^1$H NMR spectra (top) and binding analysis curve (bottom) for 90 (0.2 mM) titrated with a combined solution of D-maltotriose (500 mM) and 90 (0.2 mM), in $D_2O$ with at pH 7.4 and 298 K. Change in chemical shifts (Δδ, ppm) denoted with * were plotted against D-maltotriose concentration (mM). The calculated values for $\Delta\delta$ are overlaid with the observed values, giving $K_a$=20±0.7 $M^{-1}$ (3.3%).

FIG. 64 shows the ITC binding results for 90 (0.2 mM) titrated with D-cellobiose (200 mM) in water at 298K, in which: A) shows the blank run (addition of substrate into water); B) shows the titration (substrate into receptor); C) shows the plotted change in enthalpy vs molar ratio; and D) shows the fit calculated using an Excel spreadsheet ($K_a$=37.6±2.5 $M^{-1}$).

FIG. 65 shows the ITC binding results for 90 (0.2 mM) titrated with D-cellotriose (15 mM) in water at 298K, in which: A) shows the blank run (addition of substrate into water); B) shows the titration (substrate into receptor); C) shows the plotted change in enthalpy vs molar ratio; and D) shows the fit calculated using an Excel spreadsheet ($K_a$=955±11 $M^{-1}$).

FIG. 66 shows: a) the ITC titration of d-glucose (7.1 mM) in 10 mM phosphate buffer into Receptor 4 (0.40 mM) in 10 mM. at 298 K; and b) an enlarged image of the kcal $mol^{-1}$ of injectant vs molar ratio trace. $K_a$ calculated at 6490 $M^{-1}$+/−72.6 $M^{-1}$.

FIG. 67 shows: a) the ITC titration of d-glucose (7.1 mM) in 10 mM phosphate buffer into Receptor 5 (0.46 mM) in 10 mM. at 298 K; and b) an enlarged image of the kcal $mol^{-1}$ of injectant vs molar ratio trace. $K_a$ calculated at 10400 $M^{-1}$+/−132 $M^{-1}$.

FIG. 68 shows the $^1$H NMR binding analysis curve generated following the titration of a combined solution of β-D-glucose (10 mM) and Receptor 7 (127 μM), in 10 mM PB, 140 mM NaCl, $D_2O$, into a solution of Receptor 7 (127 μM) in 10 mM PB, 140 mM NaCl, $D_2O$. $K_a$ calculated at 6886 $M^{-1}$+/−190 $M^{-1}$.

FIG. 69 shows: a) the ITC titration of d-glucose (7.1 mM) in 10 mM phosphate buffer into Receptor 8 (0.42 mM) in 10 mM. at 298 K; and b) an enlarged image of the kcal $mol^{-1}$ of injectant vs molar ratio trace. $K_a$ calculated at 4210 $M^{-1}$+/−73 $M^{-1}$.

FIG. 70 shows the $^1$H NMR binding analysis curve generated following the titration of a combined solution of β-D-glucose (10 mM) and Receptor 9 (210 μM), in 10 mM PB, 140 mM NaCl, $D_2O$, into a solution of Receptor 9 (210 μM) in 10 mM PB, 140 mM NaCl, $D_2O$.

FIG. 71 shows the $^1$H NMR binding analysis curve generated following the titration of a combined solution of β-D-glucose (100 mM) and Receptor 10 (250 μM), in 10 mM PB, 140 mM NaCl, $D_2O$, into a solution of Receptor 10 (250 μM) in 10 mM PB, 140 mM NaCl, $D_2O$.

FIG. 72 shows the $^1$H NMR binding analysis curve generated following the titration of a combined solution of β-D-glucose (10 mM) and Receptor 13 (265 μM), in 10 mM PB, 140 mM NaCl, $D_2O$, into a solution of Receptor 13 (265 μM) in 10 mM PB, 140 mM NaCl, $D_2O$.

FIG. 73 shows the the partial $^1$H NMR spectra for Receptor 11 (50 μM) in $D_2O$ (pH 7.4, 10 mM PBsoln) titrated with D-glucose (10 mM) with added Receptor 11 (50 μM) and 10 mM PBsoln. In making the assumption of receptor saturation at ~1 mM, half saturation would be at 0.5 mM. Therefore 1/1.5 mM=$K_a$~2000 $M^{-1}$.

FIG. 74 shows: A) the circular dichroism (CD) spectra; and B) the binding analysis curve generated following the titration of D-glucose (10 mM) with added Receptor 11 (70 μM) and 10 mM PBsoln to a solution of Receptor 11 (70 μM) in water (pH 7.4 with 10 mM PBsoln).

FIG. 75 shows: a) the ITC titration of d-glucose (7.73 mM) in 10 mM phosphate buffer into Receptor 13 (0.13 mM) in 10 mM at 298 K; and b) an enlarged image of the kcal $mol^{-1}$ of injectant vs molar ratio trace. $K_a$ calculated at 1310 $M^{-1}$+/−33 $M^{-1}$.

FIG. 76 shows: a) the ITC titration of d-glucose (7.10 mM) in 10 mM phosphate buffer into Receptor 3 (0.29 mM) in 10 mM. at 298 K; and b) an enlarged image of the kcal $mol^{-1}$ of injectant vs molar ratio trace. $K_a$ calculated at 5760 $M^{-1}$+/−269 $M^{-1}$.

FIG. 77 shows the $^1$H NMR binding analysis curve generated following the titration of a combined solution of β-D-glucose (3.24 M) and Receptor 2 (265 μM) in $D_2O$, into a solution of Receptor 12 (223 μM) in $D_2O$ at 298 K.

Materials and Methods

Commercial reagents were purchased from Sigma-Aldrich, Alfa-Aesar or Acros Organics and were used without further purification unless otherwise specified. All air and moisture sensitive manipulations were carried out using standard vacuum line and Schlenk techniques, or in a drybox containing a purified argon atmosphere. Solvents for air and moisture sensitive manipulations were obtained from an Anhydrous Engineering Solvent Purification System or distilled and dried over activated molecular sieves.

Column chromatography was performed using silica gel 60 (Sigma Aldrich) and a suitable eluent. TLC was performed using aluminium backed TLC plates (Merck-Keiselgel 60 F254) and visualised using UV fluorescence and/or developed using ninhydrin, potassium permanagante, EtOH/$H_2SO_4$, vanillin, $Pd(OAc)_2/H_2O$ or iodine.

HPLC chromatography was performed using a Waters 600 Controller with a Waters 2998 Photodiode Array Detector. For analytical runs a XSELECT CSH C18 5 μm (4.6×150 mm) column was used and for preparative runs a XSELECT CSH Prep C18 5 μm OBD (19×250 mm) column was used, normally with an acetone-water solvent mixture.

$^1$H and $^{13}$C NMR spectra were recorded on Varian VNMR 400 MHz, Jeol Eclipse 400 MHz, Varian VNMR 500 MHz, Bruker cryogenically cooled 500 MHz and Varian VNMR cryogenically cooled S600 MHz spectrometers. All spectra were obtained at ambient temperature unless stated otherwise. All $^1$H and $^{13}$C NMR chemical shifts are reported relative to tetramethylsilane as an internal standard and in $CDCl_3$ unless otherwise stated, with H (residual) and $^{13}$C chemical shifts of the solvent as a secondary standard.

IR spectra were recorded on Perkin-Elmer Spectrum One FT-IR spectrometer with an ATR accessory and frequencies reported in wavenumbers ($cm^{-1}$). ESI-LRMS (electrospray ionisation low resolution mass spectrometry) was performed on a VG Analytical Quattro, ESI-HRMS (electrospray ionisation high resolution mass spectrometry) was performed on a Bruker Daltonics Apex IV and MALDI-MS (matrix-assisted laser desorption/ionisation) was performed on an Applied Biosystems 4700. Elemental analysis was performed on a EuroVector EA3000 Elemental Analyser.

$^1$H-NMR titrations were performed on a Varian VNMR cryogenically cooled S600 spectrometer. Solutions of saccharides in $D_2O$ (99.9%), containing receptor at a known concentration to be used in the experiment, were prepared and allowed to equilibrate overnight before use if necessary. Aliquots were then added to an NMR tube containing a known concentration of receptor solution (typically 100 μM-400 μM). The receptor concentration was therefore held constant while the carbohydrate concentration was increased. The sample tube was shaken after each addition and $^1$H-NMR spectra were acquired at 298 K.

Isothermal Titration (Micro)Calorimetry (ITC) experiments were performed on a MicroCal iTC200 microcalorimeter and/or a MicroCali VP-ITC. ITC experiments were carried out at 298 K. Saccharide solutions were prepared in HPLC-grade water and allowed to equilibrate overnight if necessary. The sample cell was charged with a known concentration of receptor solution in HPLC-grade water (typically 50 μM-200 μM). Then, aliquots (typically 1.0 μL) of carbohydrate solution were added and the evolution of heat was followed as a function of time. Heats of dilution were measured by injecting the same carbohydrate solution into HPLC-grade water, using identical conditions. For every addition, the heat of dilution was subtracted from the heat of binding using a MicroCal software programme implemented in ORIGIN 7.0. This gave an XY matrix of heat vs. total guest concentration. This matrix was then imported into a specially written Excel programme to fit the data to a 1:1 binding model to give a Ka. ΔG can be derived from Ka, and ΔS can be derived from ΔH and ΔG using common thermodynamic equations. This method of analysis was used in conjunction with fits for $K_a$ calculated using the MicroCal software to corroborate the results obtained.

Synthetic Procedures

Bicyclic Receptor Synthesis

Scheme 1 - Synthetic procedure used to prepare 1,3,5-triethyl-2,4,6-tris(isocyanatomethyl)benzene (Compound 103)

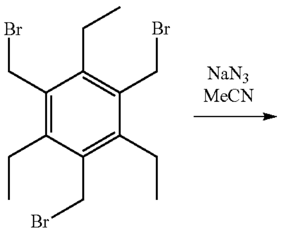

104

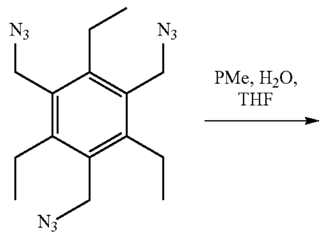

105
92%

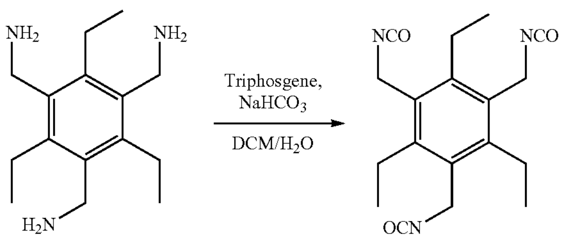

106
90%

103
78%

1,3,5-triethyl-2,4,6-tris(aminomethyl)benzene (Compound 106)

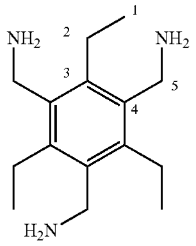 [SMILES: CCc1c(CN)c(CC)c(CN)c(CC)c1CN]

Under an inert $N_2$ atmosphere, 1,3,5-tris(bromomethyl)-2,4,6-triethylbenzene 104 (324 mg, 0.74 mmol) was dissolved in anhydrous DMF (4.5 mL) and $NaN_3$ (157 mg, 2.42 mmol) added. The reaction was heated to 60° C. for 16 hours. The reaction mixture as then diluted with ethyl acetate (20 mL) and washed with water (3×20 mL), dried ($MgSO_4$) and filtered. DMF (4 mL) was added to the filtrate and the solvent removed under vacuum to a volume of –4 mL. Conversion to tris-azide 105 was confirmed by $^1H$ NMR (220 mg, 0.68 mmol, 92%). The resultant DMF solution was transferred to a degassed anhydrous solution of THF (22 mL) and $PMe_3$ (1M in THF, 4.1 mL) under an inert $N_2$ atmosphere. The reaction mixture was stirred at room temperature for 1 hour and degassed $H_2O$ (5 mL) added, with the reaction mixture stirred for a further 16 hours. The solvent and excess $PMe_3$ was then evaporated by bubbling $N_2$ through the solution, and the crude residue suspended in $H_2O$ (~10 mL). The suspension was then freeze dried to afford 106 (148 mg, 0.61 mmol, 90%) as a white solid. $^1H$ NMR: (400 MHz, ($CDCl_3$): 1.24 (t, J=7.5 Hz, 9H, C(1)H), 2.83 (q, J=7.5 Hz, 6H, C(2)H), 3.88 (s, 6H, C(5)$H_2$); $^{13}C$ NMR: (100 MHz, ($CDCl_3$): δ 16.8 (C(1)$_2$), 22.6 (C(2)), 39.7 (C(5)H), 137.4 (C3), 140.4 (C4); LRMS: ($ESI^+$) Found $[M+Na]^+$: 272.2

1,3,5-triethyl-2,4,6-tris(isocyanatomethyl)benzene (Compound 103)

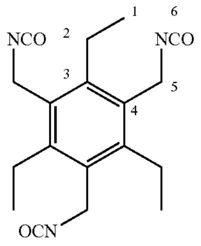

Method A

A flask was charged with 106 (30 mg, 0.12 mmol) and $NaHCO_3$ (20 mg, 0.24 mmol). $CH_2Cl_2$ (5 mL) and $H_2O$ (5 mL) were added, the mixture cooled to 0° C. and rapidly stirred. Triphosgene (40 mg, 0.13 mmol) was added and the reaction mixture vigorously stirred at room temperature for 1 hour. The reaction mixture was diluted with $CH_2Cl_2$ (20 mL) and brine (10 mL), and the organic layer separated, dried ($MgSO_4$) and the solvent removed under vacuum to afford 103 (50 mg, 0.166 mmol, 78%) as a colourless oil.

Method B

Under an inert $N_2$ atmosphere, a flask was charged with triphosgene (1.81 g, 6.1 mmol). Anhydrous toluene (70 mL) was added. A solution of 106 (500 mg, 2.0 mmol) in anhydrous toluene (40 mL) was added dropwise over a period of 7 minutes. The reaction mixture was heated to reflux and stirred for a further 75 min. The reaction mixture was allowed to cool down and the solvent removed under high vacuum. The residue was then redissolved in about 40 mL toluene and filtered on cotton wool. The solvent was removed under high vacuum to afford 103 (630 mg, 1.9 mmol, 95%) as an oil that slowly crystallised into a light yellow solid.

$^1$H NMR: (400 MHz, ($CDCl_3$): 1.26 (t, J=7.6 Hz, 9H, C(1)H), 2.84 (q, J=7.6 Hz, 6H, C(2)H), 4.49 (s, 6H, C(5)$H_2$); $^{13}$C NMR: (100 MHz, ($CDCl_3$): δ 16.1 (C(1)$H_2$), 22.8 (C(2)H), 40.4 (C(5)H), 123.1 (C6), 132.4 (C3), 143.1 (C4); $V_{max}$ 2973, 2933, 2875, 2243, 1495, 1453, 1335, 1042, 856, 577 $cm^{-1}$; LRMS: (ESI) Found $[M+Na]^+$: 350.1. HRMS: ($ESI^+$) calculated for $C_{18}H_{21}N_3O_3Na^+$: 350.1475, found $[M+Na]^+$: 350.1474.

Fmoc Protected Tert-Butyl G2 Linker (Compound 84)

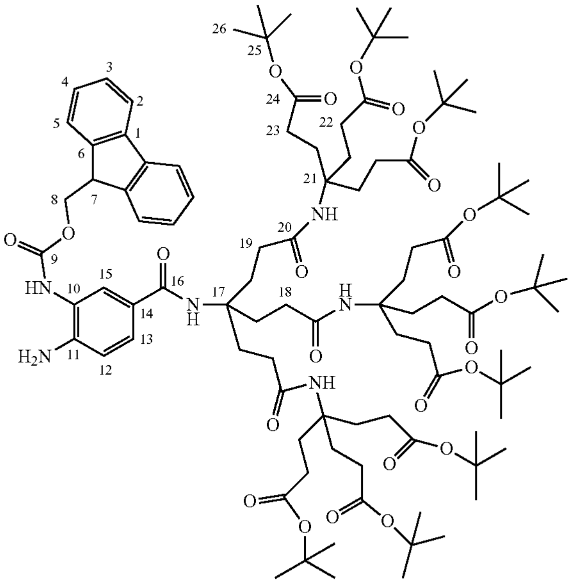 [SMILES: CC(C)(C)OC(=O)CCC(CCC(=O)OC(C)(C)C)(CCC(=O)OC(C)(C)C)NC(=O)CCC(CCC(=O)NC(CCC(=O)OC(C)(C)C)(CCC(=O)OC(C)(C)C)CCC(=O)OC(C)(C)C)(CCC(=O)NC(CCC(=O)OC(C)(C)C)(CCC(=O)OC(C)(C)C)CCC(=O)OC(C)(C)C)NC(=O)c1ccc(N)c(NC(=O)OCC2c3ccccc3-c3ccccc32)c1]

Method A

Under an inert $N_2$ atmosphere, Fmoc-amino benzoic acid 67 (983 mg, 2.63 mmol), HBTU (996 mg, 2.63 mmol) and HOBt (355 mg, 2.63 mmol) were suspended in anhydrous THF (30 mL). DIPEA (1.2 mL, 6.57 mmol) was added and the reaction stirred at room temperature for 10 minutes. Second generation dendritic amine 82 (3.1 g, 2.19 mmol) was then added and the reaction stirred for 24 hours. The solvent was then removed under vacuum and the crude residue purified by flash column chromatography (3% MeOH:$CH_2Cl_2$) to afford 84 (3.49 g, 2.01 mmol, 92%) as an off-white solid.

Method B

Under an inert $N_2$ atmosphere, 67 (5 g, 15.3 mmol), HBTU (5.03 g, 15.3 mmol) and HOBt.$H_2O$ (2.06 g mg, 15.3 mmol) were suspended in anhydrous THF (60 mL). DIPEA (7.2 mL, 38.3 mmol) was added and the reaction stirred at room temperature for 1 hour. The solvent was removed under vacuum and the crude residue dissolved in ethyl acetate (100 mL) and then poured into water (300 mL). The precipitate was then filtered and air dried to afford the crude HOBt ester/tetramethyl urea complex (1:1, 4.36 g, 7.19 mmol, Mw=607.67 g $mol^{-1}$) which was used without further purification. The crude HOBt ester complex was then suspended in anhydrous THF (60 mL) and 82 (9.4 g, 6.54 mmol) and DIPEA (2.1 mL, 12.3 mmol) added. The reaction mixture was stirred at room temperature for 24 hours and the solvent removed under vacuum. The crude residue was then purified by flash column chromatography (5% MeOH: $CH_2Cl_2$) to afford 84 (9.02 g, 5.19 mmol, 86%) as an off white solid.

$^1$H NMR: (400 MHz, ($CDCl_3$): δ 1.43 (s, 81H, C(26)$H_3$), 1.95 (m, 18H, C(23)$H_2$), 2.11 (t, J=7.2 Hz, 6H, C(18)$H_2$), 2.17 (m, 18H, C(22)$H_2$), 2.25 (t, J=7.2 Hz, 6H, C(19)$H_2$), 4.27 (m, 3H, C(7)H and $NH_2$), 4.47 (d, J=7.4 Hz, 2H, C(8) $H_2$), 6.08 (s, 3H, NH), 6.76 (d, J=8.4 Hz, 1H, C(13)H), 7.26-7.31 (m, 2H, C(4)H), 7.38 (t, J=7.4 Hz, 2H, C(3)H), 7.57-7.69 (m, 2H, C(5)H), 7.71 (d, J=8.7 Hz, 1H, C(2)H), 7.75 (d, J=7.6 Hz, 3H, C(2)H), 7.78 (d, J=2.1 Hz, 1H, C(15) H), 8.54 (s, 1H, NH); $^{13}$C NMR: (100 MHz, ($CDCl_3$): δ 28.0 (C26), 29.8 (C22), 29.9 (C23), 31.8 (C19), 32.2 (C18), 47.2 (C7), 53.4 (C17), 57.4 (C21), 67.3 (C8), 80.6 (C25) 116.6 (C12), 119.9 (C2), 122.6 (C10), 124.6 (C14), 125.3 (C4), 126.0 (C15), 126.8 (C13), 127.0 (C5), 127.6 (C3), 141.3 (C1), 143.8 (C6), 145.3 (C11), 154.9 (C9), 166.6 (C16), 172.7 (C24), 173.1 (C20); $V_{max}$ 2977, 2963, 1752, 1723, 1689, 1637, 1535, 1367, 1242, 1151, 1098, 844 $cm^{-1}$; HRMS: ($ESI^+$) Found $[M+2Na]^{2+}$: 921.0252.

Fmoc-amino benzoic acid (67) was prepared according to literature procedure as described in *Angew. Chem.*, 2008, 120, 6957.

Second generation dendritic amine (82) was prepared according to literature procedure as described in *Angew. Chem. Int. Ed.*, 2015, 54, 2057

Triamino G2MM Tert-Butyl Protected Triethylbenzene Half Receptor (Compound 108)

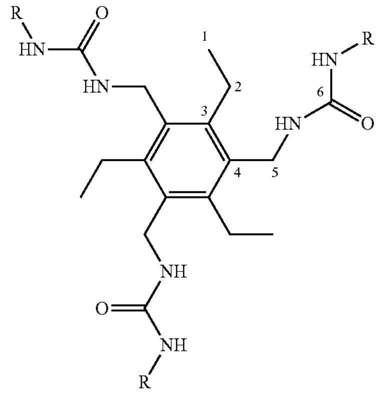

-continued

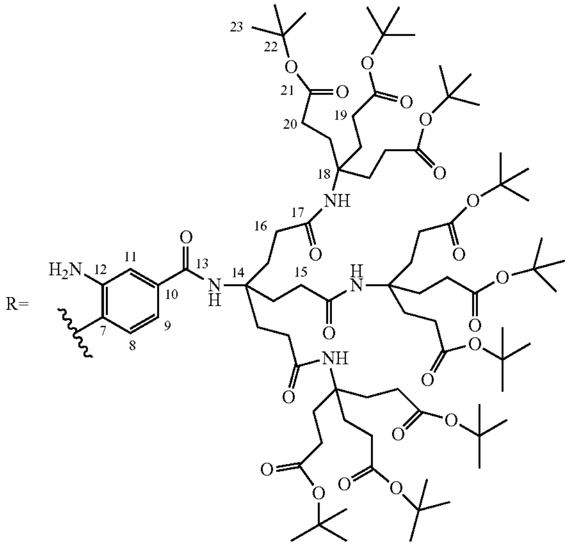

Under an inert $N_2$ atmosphere, 84 (600 mg, 0.35 mmol) was dissolved in a solution of 103 (28 mg, 0.086 mmol) in anhydrous dichloromethane (5 mL). Anhydrous pyridine (40 µL) was added and the reaction heated to reflux for 16 hours, after which it was cooled to room temperature and the solvent removed under vacuum. The crude residue was purified by flash column chromatography (1:1, EtOAc: $CH_2Cl_2$→4% MeOH:$CH_2Cl_2$) to afford 107 (400 mg, 0.072 mmol, 84%) as a white solid. Conversion to 107 was confirmed by limited NMR studies* and high resolution mass spectrometry ($ESI^+$): m/z calculated for $[M+3Na]^{3+}$ 2869.6877, found 1928.1169, calculated for $[M+4Na]^{4+}$: 1451.8339, found 1451.8320. Under an inert $N_2$ atmosphere, 107 (300 mg, 0.052 mmol) was dissolved in anhydrous dichloromethane (8 mL) and cooled to 0° C. DBU (50 µL, 0.30 mmol) was added dropwise and the reaction mixture warmed to room temperature and stirred for 1 hour. The solvent was removed under vacuum and the crude product purified by flash column chromatography (4% MeOH: $CH_2Cl_2$) to afford 108 (238 mg, 0.047 mmol, 91%) as a white solid. $^1$H NMR: (400 MHz, ($CD_3OD$): δ 1.24 (t, J=7.6 Hz, C(1)$\underline{H}_3$), 1.43 (s, 243H, C(23)$\underline{H}_3$), 1.94 (m, 54H, C(20)$\underline{H}_2$), 2.09 (m, 18H, C(15)$\underline{H}_2$), 2.18 (m, 54H, C(19)$\underline{H}_2$), 2.23 (m, 18H, C(16)$\underline{H}_2$), 2.86 (m, 6H, C(2)$\underline{H}_2$), 4.51 (s, 6H, C(5)$\underline{H}_2$), 7.21 (dd, J=2.1, 8.4 Hz, 3H, C(9)$\underline{H}$), 7.29 (d, J=2.1 Hz, 3H, C(11)$\underline{H}$), 7.4 (d, J=8.4 Hz, 3H, C(8)$\underline{H}$), 7.4 (s, 9H, NH), 7.91 (s, 3H, NH); $^{13}$C NMR: (100 MHz, ($CDCl_3$): δ 17.0 ($\underline{C}$1), 22.5 ($\underline{C}$2), 28.5 ($\underline{C}$23), 30.5 ($\underline{C}$19), 30.7 ($\underline{C}$20), 32.3 ($\underline{C}$15), 32.6 ($\underline{C}$16), 37.9 ($\underline{C}$5), 58.9 ($\underline{C}$18), 59.4 ($\underline{C}$14), 81.6 ($\underline{C}$22), 117.4 ($\underline{C}$11), 118.9 ($\underline{C}$9) 124.5 ($\underline{C}$8), 130.0 ($\underline{C}$10), 132.9 ($\underline{C}$3), 133.8 ($\underline{C}$7), 141.4 ($\underline{C}$12), 145.1 ($\underline{C}$4), 157.9 ($\underline{C}$6), 170.1 ($\underline{C}$13), 174.4 ($\underline{C}$21), 175.6 ($\underline{C}$17); HRMS: ($ESI^+$) Found $[M+3Na]^{3+}$: 1706.0490.

* Limited NMR studies were only possible due to slow conformational exchange of 107 resulting in very broad signals of low intensity.

Tert-Butyl Protected Triethylbenzene Receptor (Compound 1a)

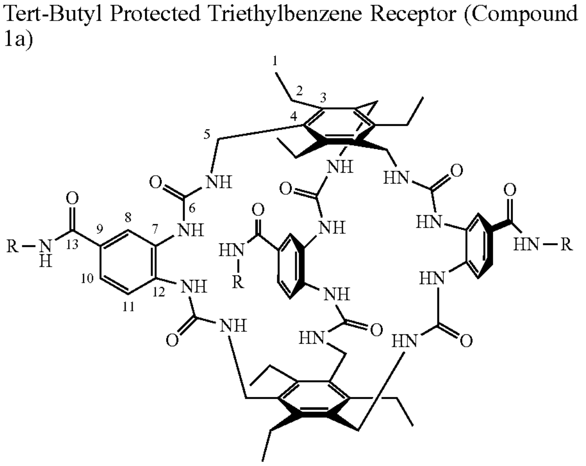

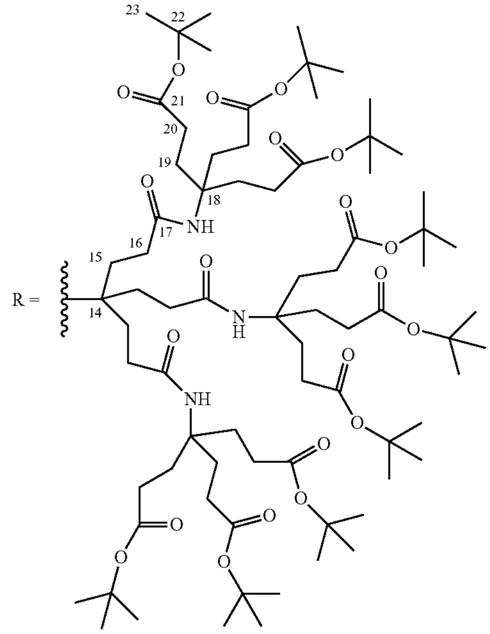

Method A

Under an inert $N_2$ atmosphere, 108 (124 mg, 0.024 mmol) was dissolved in anhydrous dichloromethane (50 ml) and heated to reflux. A solution of 103 (8 mg, 0.024 mmol) in anhydrous dichloromethane (3 mL) was added and the reaction stirred at reflux for 3 days. The reaction mixture was cooled to room temperature and the solvent removed under vacuum. The crude product was purified by reverse-phase HPLC and then freeze dried to Ia (20 mg, 0.004 mmol, 15%) as a white solid.

Method B

Under an inert $N_2$ atmosphere, 108 (200 mg, 0.04 mmol), Octyl-glucoside (23 mg, 0.08 mmol) and 4-dimethylaminopyridine (14 mg, 0.12 mmol) were dissolved in anhydrous dichloromethane (35 mL). A solution of 103 (13 mg, 0.04 mmol) in anhydrous dichloromethane (5 mL) was added and the reaction stirred at reflux for 2 days. The reaction mixture as cooled to room temperature and the solvent removed under vacuum. The crude product was purified by reverse phase HPLC and then freeze dried to Ia (85 mg, 0.016 mmol, 40%) as a white solid.

$^1$H NMR: (400 MHz, ($CD_3OD$): δ 1.24 (m, 18H C(1)$\underline{H}_3$), 1.43 (s, 243H, C(23)$\underline{H}_3$), 1.95 (m, 54H, C(20)$\underline{H}_2$), 2.13 (m, 18H, C(15)$\underline{H}_2$), 2.20 (m, 54H, C(19)$\underline{H}_2$), 2.25 (m, 18H, C(16)$\underline{H}_2$), 2.74, 2.84 (br m, 6H, C(2)$\underline{H}_2$), 4.40, 4.49 (br s, 6H, C(5)$\underline{H}_2$), 7.43 (s, 9H, NH), 7.63 (d, J=8.7 Hz, 3H, C(10)$\underline{H}$), 8.03 (d, J=8.7 Hz, 3H, C(11)$\underline{H}$), 8.07 (s, 3H, C(8)$\underline{H}$); $^{13}$C NMR: (100 MHz, ($CDCl_3$): δ 15.5, 15.6 ($\underline{C}$1), 22.3, 22.5 ($\underline{C}$2), 27.1 ($\underline{C}$23), 29.1 ($\underline{C}$19), 29.3 ($\underline{C}$20), 30.8 ($\underline{C}$15), 31.0 ($\underline{C}$16), 37.5 ($\underline{C}$5), 57.3 ($\underline{C}$18), 58.1 ($\underline{C}$14), 80.2 ($\underline{C}$22), 120.3 ($\underline{C}$11), 123.5 ($\underline{C}$8), 124.1 ($\underline{C}$10), 127.6 ($\underline{C}$7), 129.4 ($\underline{C}$9), 132.0, 132.6 ($\underline{C}$3), 135.0 ($\underline{C}$12), 143.0, 143.2 ($\underline{C}$4), 155.8, 156.6 ($\underline{C}$6), 168.2 ($\underline{C}$13), 173.0 ($\underline{C}$21), 174.1 ($\underline{C}$17); HRMS: ($ESI^+$) Found $[M+3Na]^{3+}$: 1816.1093.

Triethylbenzene Receptor (Receptor 1)

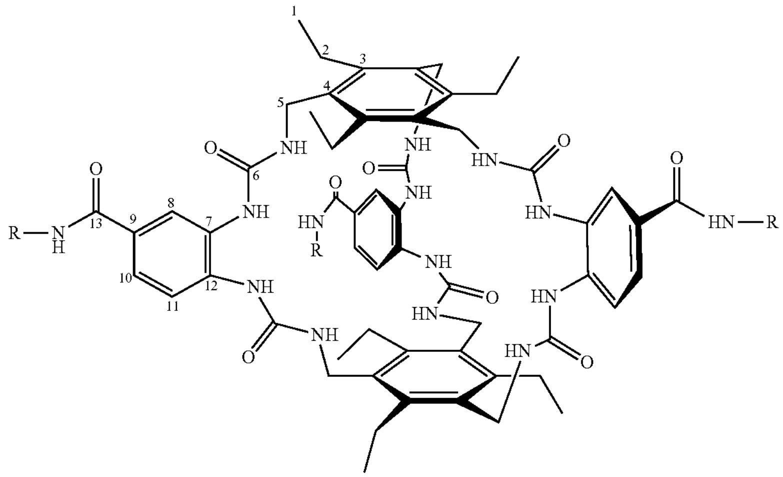

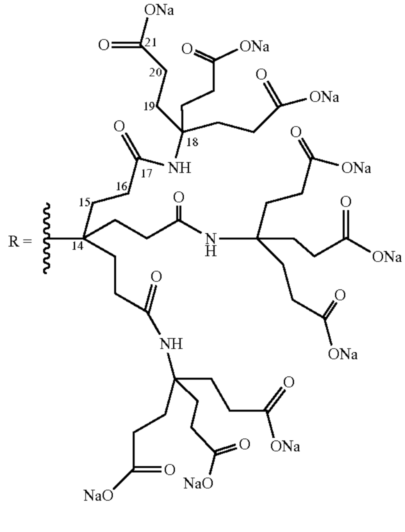

1a (3.5 mg, 0.65 μmol) was dissolved in HPLC grade dichloromethane (1.6 ml). Trifluoroacetic acid (0.4 mL) was added and the reaction stirred at room temperature for 16 hours. The solvent was then removed under a flow of nitrogen, the crude product suspended in water and freeze dried. The resultant solid was then suspended in water, neutralised to pH 7 with NaOH (aq) and then freeze dried to afford receptor 1 (3.3 mg, 0.62 μmol, 95%) as a white solid. $^1$H NMR: (400 MHz, ($D_2O$): δ 1.17 (m, 18H C(1)$\underline{H}_3$), 1.94 (m, 54H, C(20)$\underline{H}_2$), 2.12 (m, 18H, C(15)$\underline{H}_2$), 2.18 (m, 54H, C(19)$\underline{H}_2$), 2.31 (m, 18H, C(16)$\underline{H}_2$), 2.76 (br m, 6H, C(2)$\underline{H}_2$), 4.46 (br s, 6H, C(5)$\underline{H}_2$), 7.61 (d, J=9.6 Hz, 3H, C(10)$\underline{H}$), 7.82 (br m, 6H, C(11)H, C(8)$\underline{H}$); $^{13}$C NMR: (100 MHz, ($CDCl_3$): δ 18.0, 18.1 ($\underline{C}$1), 25.0, 25.2 ($\underline{C}$2), 32.6 ($\underline{C}$15), 32.7 ($\underline{C}$19), 32.9 ($\underline{C}$16), 33.3 ($\underline{C}$20), 40.1, 40.3 ($\underline{C}$5), 60.7 ($\underline{C}$18), 61.3 ($\underline{C}$14), 120.0 ($\underline{C}$11), 121.6 ($\underline{C}$10), 122.8 ($\underline{C}$8), 125.7 ($\underline{C}$7), 130.0 ($\underline{C}$9), 134.7, 135.0 ($\underline{C}$3), 135.6 ($\underline{C}$12), 146.7, 146.9 ($\underline{C}$4), 159.6, 159.9 ($\underline{C}$6), 170.3 ($\underline{C}$13), 177.8 ($\underline{C}$17), 184.1 ($\underline{C}$17).

Compound 8d

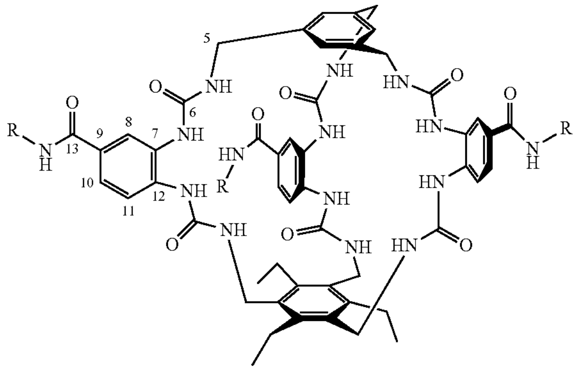

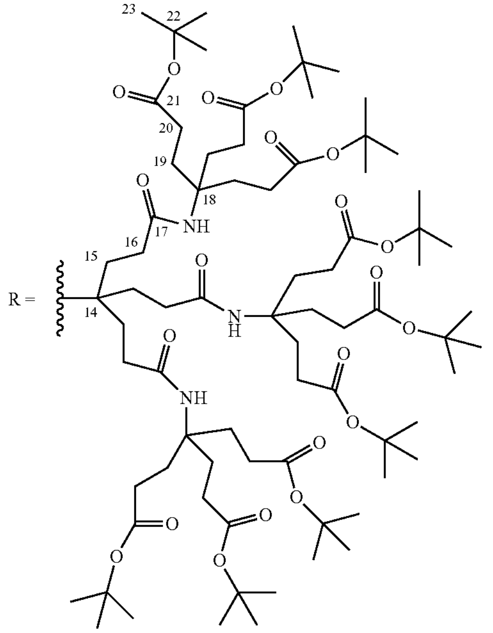

A schlenk flask equipped with a magnetic stirrer was charged with 108 (200.0 mg, 0.04 mmol), DMAP (14.5 mg, 0.12 mmol) and n-octyl glucoside (23.2 mg, 0.08 mmol) were added to the flask and placed under nitrogen. Anhydrous DCM (40 mL) was added and the reactive was warmed to 34° C. A solution of compound 5 (12.5 mg, 0.051 mmol) in toluene (ca. 85% purity) was added to the flask and the reaction was allowed to stir for 16 hours. The solvent was removed completely and the crude product was purified by reverse phase MPLC on a C18 SNAP Ultra 60 g cartridge eluting (10% acetone:water for 1 CV, a gradient of 10-95% acetone:water for 10 CV and 95% acetone:water for 2 CV). White solid (67 mg, 0.012 mmol, 32%).

Compound 8e-Receptor 2

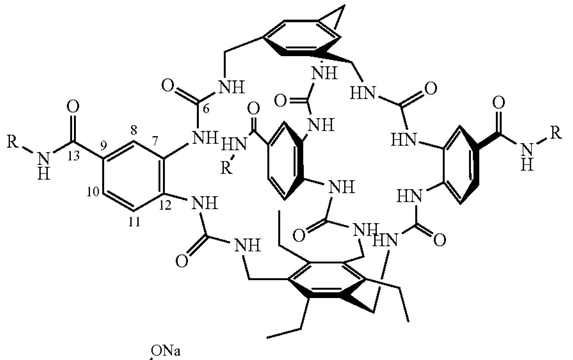

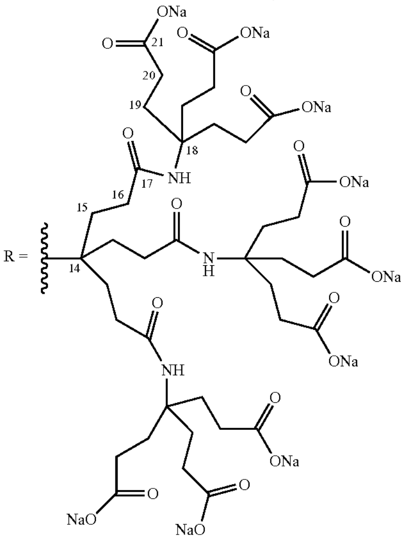

Method A:

Compound 8d was dissolved in anhydrous DCM (Vol: 6 mL) and TFA (1.74 mL, 22.67 mmol) at RT. The resulting off yellow solution was stirred for 2 h at room temperature. Volatiles were removed under vacuum to give a yellow solid. The solid which was purified by reverse phase MPLC on a C18 SNAP Ultra 60 g cartridge by loading the sample in 1:1 $MeOH/H_2O$+0.1% formic acid). The resulting white solid was neutralised using 100 mM NaOH solution to pH 7 and the resulting solution concentrated to dryness under vacuum. White crystalline solid (37 mg, 0.008 mmol, 74%).

Method B:

The solid obtained from Compound 44 was dissolved in anhydrous $CH_2Cl_2$ (5.9 mL) and TFA (1.7 mL, 23 mmol) was added at RT. The resulting off yellow solution was stirred for 2 h at RT or until complete by TLC (product on the baseline in 60% $EtOAc/CH_2Cl_2$). The solvent/TFA were removed under vacuum (rotary evaporator then high vacuum) to give a yellow solid. The solid was purified by reverse phase chromatography (loading sample in 1:1 $MeOH/H_2O$+0.1% formic acid). Fr 2-7 taken and concentrated under vacuum. The resulting white solid was neutralised using 100 mM NaOH solution to pH 7 and the resulting solution concentrated under vacuum (rotary evaporator/cold finger with liquid $N_2$) to give Compound 45 as a white crystalline solid (37 mg, 75%).

$^1H$ NMR: (500 MHz, $D_2O$, 298 K): δ 7.74 (br d, J=7.1 Hz, 3H, $H_9$), 7.59 (d, J=8.6 Hz, 3H, $H_8$), 7.48 (s, 3H, NH), 7.40 (s, 3H, $H_6$), 7.01 (s, 3H, $H_1$), 4.40 (br s, 6H, $H_{12}$), 3.93 (br s, 6H, $H_3$), 2.70 (br s, 6H, $H_{15}$), 2.20 (br s, 18H, $H_{20}$), 2.07 (m, 72H, $H_{19}$+$H_{24}$), 1.83 (m, 54H, $H_{23}$), 1.07 (br t, 9H, $H_{16}$). $^{13}C$ NMR (126 MHz, $D_2O$) δ 173.2, 166.0, 160.0, 149.4, 148.1, 135.5, 131.1, 128.9, 122.8, 121.6, 119.6, 118.0, 117.4, 114.5, 113.9, 49.5, 49.0, 48.9, 43.1, 33.8, 28.6, 22.0, 21.6, 21.2, 21.1, 13.5, 6.3.

Compound 9-Receptor 3

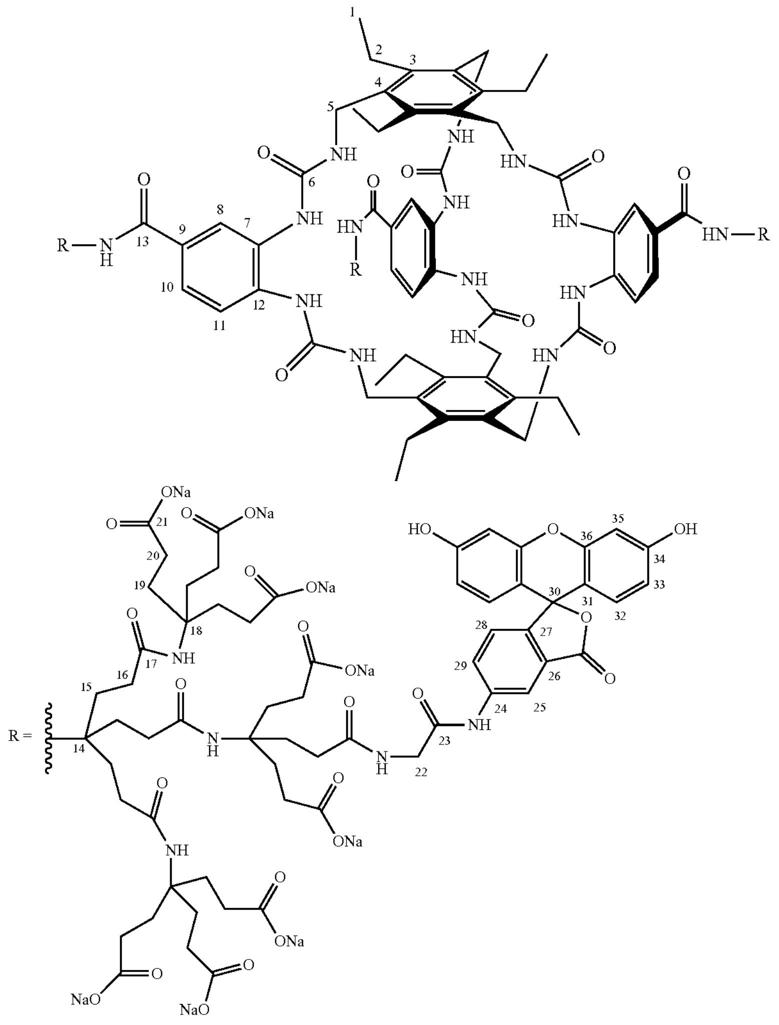

Triethylbenzene receptor 1 (15.0 mg, 0.003 mol), HBTU (W: 2.6 mg, 0.006 mmol) and 5-(aminoacetamido)fluorescein (21.8 mg, 0.048 mmol) were dissolved in DMF (1.25 mL) and $H_2O$ (1.25 mL). The reaction mixture was stirred in the dark, at room temperature for 16 hr then concentrated under reduced pressure. The crude reaction mixture was neutralised to ~pH 7 with aq. NaOH then concentrated under reduced pressure. Purified by reverse phase flash chromatography on a 12 g SNAP Ultra C18 cartridge elution with 1CV 20% MeOH/$H_2O$+0.1% formic acid to 65% MeOH/$H_2O$+0.1% formic acid over 8 CV to 100% $H_2O$+0.1% formic acid over 0.5CV then 100% $H_2O$+0.1% formic acid for 3 CV. Product containing fractions were combined, concentrated under reduced pressure, neutralised to pH 7 then lyophilised to give compound 9 as an orange powder. $^1H$ NMR: (400 MHz, $D_2O$, 298 K): δ 7.91-7.28 (m, 15H, Ar), 7.25-6.89 (m, 9H, Ar), 6.73-6.32 (m, 12H, Ar), 4.52-4.04 (m, 12H, $H_5$), 4.02-3.81 (m, 6H, $H_{22}$), 2.59-1.61 (m, 156H, $H_{1+15+16+19+20}$), 1.21-0.82 (m, 18H, $H_1$).

Key Intermediates

Compound A1

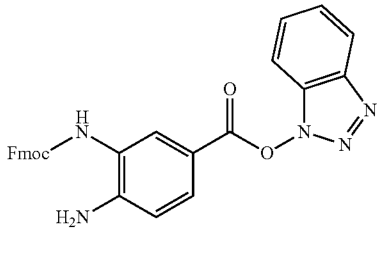

3,4-Diaminobenzoic acid (41.000 g, 0.269 mol) was mixed with Saturated $NaHCO_3$ (0.40 L) and acetonitrile (0.40 L) to give a brown slurry. Next, solid Fmoc-OSu (99.99 g, 0.296 mol) was added in portions over 5 minutes. The heterogenous suspension was allowed to stir at room temperature for 16 hours and then acidified with 1M $HCl_{(aq)}$. The solids were collected on a frit and washed with cold diethyl ether (3×100 mL), hexane (3×100 mL), then MeOH (3×50 mL) and then dried under vacuum. Brown solid (101 g, 0.269 mol, 100%). This intermediate (10.000 g, 0.027 mol), HOBt (8.181 g, 0.053 mol), and HBTU (20.259 g, 0.053 mol) were dissolved in THF (300) mL) and DIPEA (18.610 mL, 0.107 mol). The heterogenous slurry was stirred at room temperature for 90 minutes after which the solvent was removed in vacuo to afford a viscous oil. The oil was dissolved in EtOAc (80 ml) and was added to a rapidly stirring mixture of water (200 ml) and EtOAc (40 mL). After ca. 2 mins a precipitate formed and diethyl ether (100 mL) was added to the flask. After stirring for 10 minutes, the solids were collected by filtration and washed with water (3×10 mL) and diethyl ether (2×10 mL) before drying under vacuum for 16 hours. $^1H$ NMR: (500 MHz, DMSO-$d_6$) δ 8.94 (s, 1H), 8.14 (dd, J=17.7, 8.4 Hz, 2H), 8.01-7.93 (m, 1H), 7.90 (d, J=7.6 Hz, 2H), 7.87-7.68 (m, 6H), 7.68-7.61 (m, 1H), 7.54 (dt, J=11.5, 7.5 Hz, 1H), 7.42 (t, J=7.4 Hz, 2H), 7.34 (t, J=7.6 Hz, 2H), 6.89 (d, J=8.6 Hz, 1H), 6.46 (s, 2H), 4.44 (s, 2H), 4.31 (s, 1H), 3.40 (s, 7H), 3.03 (s, 7H), 2.50 (s, 4H).

Compound 2

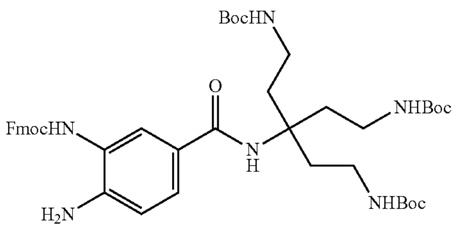

A 100 mL Schlenk flask was charged with compound A1 (2.750 g mg, 2.263 mmol), N,N-diisopropylethylamine (0.585 mL, 3.341 mmol) and anhydrous THF (10 mL). Solid 3-(2-aminoethyl)pentane-1,3,5-N-Boc-triamine* (0.800 g, Moles: 1.911 mmol) was added and the homogenous solution/suspension was left to stir. After 72 hours, TLC ($SiO_2$, 7:3 EtOAc:DCM) indicated complete consumption of starting materials and formation of the product. The solvent was removed in vacuo and the crude residue was extracted with DCM (2×10 mL). The filtrate was concentrated to dryness and the residue purified by MPLC (12%→100% DCM in EtOAc). Orange amorphous solid (1.154 g, 1.413 mmol, 74%). $^1H$ NMR: (400 Hz, $CDCl_3$) δ 7.00-7.82 (m, 11H, ArH), 6.71 (2H, d, J=8.13 Hz, N$\underline{H}_2$), 3.14 (6H, q, J=7 Hz, C$\underline{H}_2$NH), 2.04 (app. s, 6H, CC$\underline{H}_2$), 1.40 (27H, s, C(C$\underline{H}_3$)$_3$). MS: ($ESI^+$) calculated for $C_{44}H_{60}N_6O_9Na^+$: 839.4314, found $[M+Na]^+$: 839.4318.

*Carter, T. S.; Mooibroek, T. J.; Stewart, P. F. N.; Crump, M. P.; Galan, M. C. & Davis, A. P. *Angewandte Chemie International Edition,* 2016, 55, 9311-9315.

Compound 3b

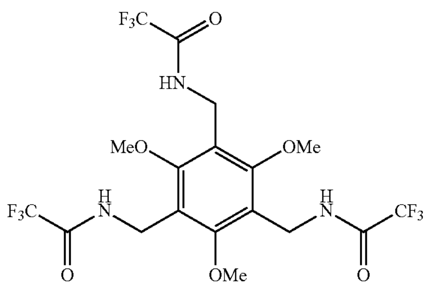

NaH (1.05 g, 26.3 mmol, 60% in mineral oil) was added to a Schlenk flask (100 mL) and placed under nitrogen. The mineral oil was removed by washing the solids with 3×25 mL petroleum ether 60-80 OC. The washed NaH was suspended in anhydrous DMF (10 mL) and vigorously stirred for ca. 10 mins whilst cooling in an ice bath. Solid trifluoroacetamide (4.46 g, 39.46 mmol) was added portion-wise under a nitrogen counter-flow. After five minutes of stirring the mixture was let warm to room temperature. Once the evolution of gas had completely stopped (within 1 hour), solid 1,3,5-tribromomethyl-2,4,6-trimethoxylbenzene* (2.00 g, 4.39 mmol) was added portion-wise under a nitrogen counter-flow and the resulting white suspension was stirred at room temperature. After ca. 18 hours, the suspension was poured into 0.5 M HCl (150 mL) and the light orange precipitate collected on a frit. The solids were washed with water (2×10 mL) and then dried under vacuum overnight (ca. $10^{-2}$ mbar). Off-white solid (2.44 g, 4.491 mol, 102%). The crude product was used without further purification and contained 2-3% DMF (quantified by $^1H$ NMR spectroscopy). $^1H$ NMR: (400 MHz, DMSO-$d_6$) δ d. 4.40 (6H, $^3J_{HH}$=4.6 Hz, ArC$\underline{H}_2$NHC(O)$CF_3$), s. 3.70 (9H, OC$\underline{H}_3$). $^{13}C$ NMR: (400 MHz, DMSO-$d_6$) δ q. 158.3 ($^2J_{CF}$=37.1 Hz, C(O)$CF_3$), 137.3, 132.1 (Ar), q. 116.1 ($^1J_{CF}$=287.9 Hz, $CF_3$), 62.5 (NH$\underline{C}H_2$Ar), 32.1 ($OCH_3$).

*Rosien, J.; Seichter, W.; Mazik, M., *Organic and Biomolecular Chemistry,* 2013. 11(38), 6569-8579.

Compound 3c

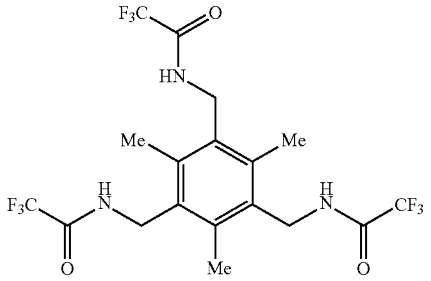

Prepared by an analogous route using 1,3,5-tribromomethyl-2,4,6-trimethylbenzene to Compound 3b. Off-white solid (4.86 g, 0.01 mol 82%). $^1H$ NMR: (500 MHz, $CDCl_3$/MeOH-$d_4$) δ s. 4.47 (6H, ArC$\underline{H}_2$NHC(O)$CF_3$), s. 2.26 (9H, OC$\underline{H}_3$). $^{13}C$ NMR: (125 MHz, $CDCl_3$/MeOH-$d_4$) δ q. 157.6 ($^2J_{CF}$=37.2 Hz, C(O)$CF_3$), 137.8, 131.1 (Ar), q. 115.9 ($^1J_{CF}$=287.3 Hz, $CF_3$), 39.4 Ar$\underline{C}H_2$NHC(O)$CF_3$), 16.0 (Ar $\underline{C}H_3$). MS:($APCI^-$) 493.9

Compound 3d

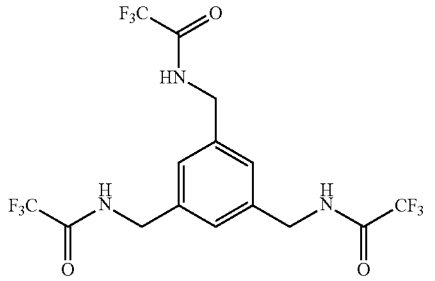

Prepared by an analogous route to Compound 3b using 1,3,5-tris(bromomethyl)benzene (5.07 g, 0.014 mol). The crude product was purified by reverse phase MPLC on a C18 SNAP Ultra 60 g cartridge eluting (10% acetone:water for 1 CV, a gradient of 10-95% acetone:water for 10 CV and 95% acetone:water for 2 CV). White solid (2.16 g, 0.005 mol, 34%). $^1$H NMR: (400 MHz, MeOH-$d_4$) δ 7.07, (s, 3H, ArH), 4.35 (6H, $^3J_{HH}$=4.6 Hz, $ArCH_2N(O)HCF_3$). $^{13}$C NMR: (125 MHz, MeOH-$d_4$) δ q. 158.1 ($^2J_{CF}$=36.9 Hz, $C(O)CF_3$), 138.1, 132.2 (Ar), q. 114.6 ($^1J_{CF}$=286.9 Hz, $CF_3$), 125.9 (Ar), 42.3, $ArCH_2NHC(O)CF_3$).

Compound 4a

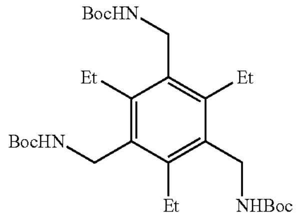

NaH (3.809 g, 0.095 mol, 60% in mineral oil) was added to a Schlenk flask (100 mL) and placed under nitrogen. The mineral oil was removed by washing the solids with 3×25 mL petroleum ether 60-80° C. The washed NaH was suspended in anhydrous DMF (40 mL) and vigorously stirred for ca. 10 mins whilst cooling in an ice bath. Solid trifluoroacetamide (16.147 g, 0.143 mol) was added portion-wise under a nitrogen counter-flow. After five minutes of stirring the mixture was let warm to room temperature. Once the evolution of gas had completely stopped (within 1 hour), solid 1,3,5-tribromomethyl-2,4,6-trimethoxylbenzene* (7.00 g, 0.016 mol) was added portion-wise under a nitrogen counter-flow and the resulting white suspension was stirred at room temperature. After ca. 18 hours, the suspension was poured into 0.5 M HCl (150 mL) and the light orange precipitate collected on a frit. The solids were washed with water (2×10 mL) and then dried under vacuum overnight (ca. $10^{-2}$ mbar). Off-white solid (7.910 g, 0.015 mol 93%). The intermediate acetamide (4.90 g, 0.009 mol) was dissolved in methanol (38.6 mL) and water (38.6 mL). NaOH (1.05 g, 3.150 mol) was added and the reaction mixture was left to stir for ca. 18 hours at 65° C. Solid $Boc_2O$ (7.287 g, 0.033 mol) and triethylamine (2.534 mL, 0.026 mol) were added and the reaction was left to stir for a further 4 hours at ambient temperature. The reaction mixture was diluted with DCM (200 mL) and washed with sat. aq. $NaHCO_3$ (200 mL), 1 M NaOH (200 mL) and brine (100 mL). The organic phase was concentrated to dryness and the resultant crude product purified by MPLC (0→50% MeOH in DCM). Colourless solid (4.820 g, 0.009 mol, 96%). $^1$H NMR: (400 MHz, $CDCl_3$) δ m.br 4.33 (9H, $ArCH_2NHCO_2C(CH_3)_3$), NH), q. 2.71 (6H, $^3J_{HH}$=7.5 Hz, $ArCH_2CH_3$), s. 1.44 (27H, $CO_2C(CH_3)_3$), t. 1.19 (9H, $^3J_{HH}$=7.5 Hz, $ArCH_2CH_3$). $^{13}$C NMR: (125 MHz, $CDCl_3$) δ 155.5 ($CO_2C(CH_3)_3$), 143.9, 132.6 (Ar), 79.7 ($CO_2C(CH_3)_3$), 38.9 Ar $CH_2NHCO_2C(CH_3)_3$), 28.6 ($CO_2C(CH_3)_3$), 23.0 (Ar $CH_2CH_3$), 16.7 ($ArCH_2CH_3$).

*Rosien, J.; Seichter, W.; Mazik, M., *Organic and Biomolecular Chemistry*, 2013, 11(38), 6569-6579.

Compound 4b

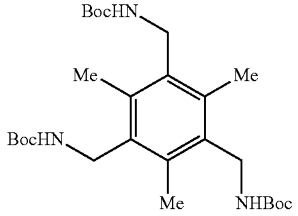

Compound 3c (9.123 g, 0.013 mol) was dissolved in MeOH (125 mL), and NaOH (1.689 g, 0.042 mol) at room temp overnight. 0.040 mol) was added followed by BOC anhydride (11.702 g, 0.054 mol) and left to stir overnight. The solvent was removed under vacuum and crude product partitioned between DCM and $H_2O$. The organic fractions were combined and washed with 0.5M HCl (50 ml), dried with $MgSO_4$ and concentrated under vacuum to give an off white solid. Purified by MPLC (0→20% EtOAc in petrol). Colourless crystalline solid (5.62 g, 0.011 mol, 83%). $^1$H NMR: (500 MHz, $CDCl_3$) δ d. 4.33 (9H, Ar$CH_2NHCO_2C(CH_3)_3$), NH), s. 2.37 (9H, $ArCH_3$), s. 1.44 (27H, $CO_2C(CH_3)_3$). $^{13}$C NMR: (125 MHz, $CDCl_3$) δ 155.7 ($CO_2C(CH_3)_3$), 136.9, 133.5 (Ar), 79.7 ($CO_2C(CH_3)_3$), 40.0 $ArCH_2NHCO_2C(CH_3)_3$), 28.5 ($CO_2C(CH_3)_3$), 16.0 (Ar $CH_3$).

Compound 4c

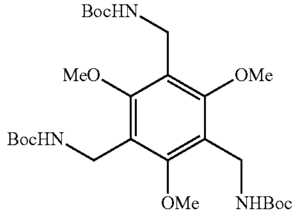

Prepared by an analogous route to Compound 4b using Compound 3b (0.919 g, 1.69 mmol) Purified by MPLC (0→40% EtOAc in petroleum ether). Colourless crystalline solid (0.655 g, 1.15 mmol 68%). $^1$H NMR: (4500 MHz, $CDCl_3$) δ d 4.38 (6H, $^3J_{HH}$=4.2 Hz $ArCH_2NHCO_2C(CH_3)_3$), s. 3.79 (9H, $OCH_3$) 1.43 (27H, $CO_2C(CH_3)_3$).

Compound 4d

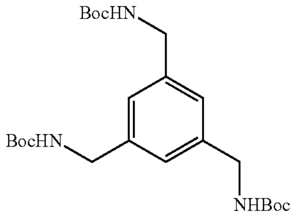

Prepared in an analogous fashion to Compound 4b using Compound 3d (2.155 g, 0.005 mol) was dissolved in MeOH (30 mL). Solid NaOH (0.599 g, 0.015 mol). Purified by MPLC (50% EtOAc in DCM) and then recrystalised from DCM/petrol. Colourless crystalline solid (0.88 g, 0.002 mmol 40%). $^1$H NMR: (400 MHz, $CDCl_3$) δ s. 7.08 (1H, Ar H) d. 4.24 (6H, $^3J_{HH}$=6.6 Hz, $ArCH_2N(O)OC(CH_3)_3$), s. 1.46 (9H, $C(CH_3)_3$). $^{13}$C NMR: (125 MHz, $CDCl_3$) δ 155.7 ($CO_2C(CH_3)_3$), 136.8 (Ar), 125.2 (Ar), 78.9 ($CO_2C(CH_3)_3$), 45.2 ($ArCH_2NHCO_2C(CH_3)_3$), 28.2 ($CO_2C(CH_3)_3$).

Compound 5a

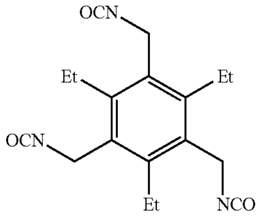

Method A:

A pre-dried 250 mL round-bottomed flask fitted with a nitrogen inlet and reflux condenser and mounted in a heating block was charged with triphosgene (1.78 g, 6 mmol). The flask was placed under vacuum (ca. $10^{-2}$ mbar) for 10 min the re-filled with nitrogen. Anhydrous toluene (150 mL) was added to give a colourless, homogenous solution. To this, a solution of 1,3,5-triaminomethyl-2,4,6-triethylbenzene (0.5 g, 2 mmol) that had been previously dried by one azeotropic distillation of toluene (80 mL), in anhydrous toluene (20 mL) was added via syringe over 10 mins. After the addition was complete the temperature was raised to 125° C. and the reaction allowed to reflux. After 75 min. the flask was allowed to cool to room temperature and the solvent removed in a rotary evaporator. The residue was extracted with toluene (3×10 mL) and concentrated to dryness to give a pale-yellow oil that crystallised on standing. Pale yellow crystalline solid (350 mg, 1.07 mmol, 54%).

Method B:

A pre-dried 200 mL Schlenk flask was charged with a magnetic stirrer and Compound 4a (1.266 g, 2.25 mmol) and then placed under a nitrogen atmosphere. 2-chloropyridine (1.7 mL, 20.21 mmol) and anhydrous DCM (70 mL) were added via syringe to give a colourless, homogenous solution. Triflic anhydride (1.5 mL, 10.11 mmol) was added dropwise at ambient temperature over 2 mins with stirring (400 rpm). The reaction was stirred for 30 mins before a small aliquot of the reaction mixture (ca. 50 mL) was withdrawn and analysed by TLC ($SiO_2$, 50% $Et_2O$ in petrol), which revealed complete consumption of the starting material ($R_f$=0.24) and conversion to 5a ($R_f$=0.5). The solvent was removed on a rotary evaporator to give an off-white solid. The solids were extracted with $Et_2O$ (×2 15 mL) and passed through an alumina plug (20 mm×20 mm), eluting with a further 20 mL of $Et_2O$. The colourless filtrate was evaporated to dryness and the residue recrystalised from hexane. Colourless crystalline solid (0.435 g, 1.33 mmol, 59%). $^1$H NMR: (400 MHz, Toluene-$d_6$) δ s. 3.93 (6H, $ArCH_2NCO$), m. 2.51-2.37 (6H, $ArCH_2CH_3$), m. 0.96-0.86 (9H, $ArCH_2CH_3$). $^{13}$C NMR: (100 MHz, Toluene-$d_6$) 143.2, 132.6 (Ar), 124.0 (NCO), 40.4 ($ArCH_2NCO$), 22.8 ($ArCH_2CH_3$), 16.0 ($ArCH_2CH_3$).

Compound 5b

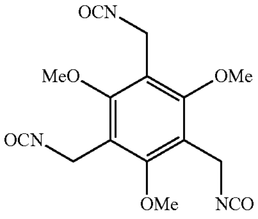

Prepared by an analogous route to Compound 5a (Method B) using Compound 4c (0.351 g, 0.616 mmol) Colourless crystalline solid (0.144 g, 0.432 mmol 70%). $^1$H NMR: (400 MHz, Toluene-$d_8$) δ d. 3.90 (6H, $ArCH_2NCO$), s. 3.40 (9H, $OCH_3$). $^{13}$C NMR: (125 MHz, Toluene-$d_8$) δ 159.7 (Ar), 121.4 (NCO), 62.9 ($ArOCH_3$), 36.2 ($ArCH_2NCO$).

Compound 5c

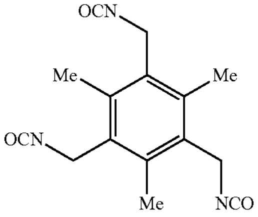

Prepared by an analogous route to Compound 5a (Method B) using Compound 4b (0.300 g, 0.985 mmol) Colourless crystalline solid (0.198 g, 0.694 mmol, 71%). $^1$H NMR: (500 MHz, Toluene-$d_8$) δ s. 3.73 (6H, $ArCH_2NCO$), s. 1.91 (9H, $CH_3$). $^{13}$C NMR: (125 MHz, Toluene-$d_8$) δ 135.9, 133.4 (Ar), 124.4 ($ArCH_2NCO$), 41.2 ($ArCH_2NCO$), 15.1 (Ar $CH_3$).

Compound 5d

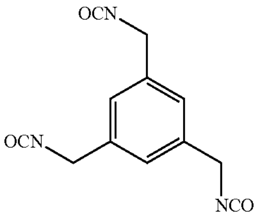

Prepared by an analogous route to Compound 5a (Method B) using Compound 4d (0.250 g, 0.537 mmol). Colourless oil (0.062 g, 0.255 mmol, 48%). $^1$H NMR: (500 MHz, Toluene-$d_8$) δ s. 6.56 (3H, ArH), s. 3.64 (6H, $ArCH_2NCO$). $^{13}$C NMR: (125 MHz, Toluene-$d_8$) δ 138.4 (Ar), 124.2 (Ar, $ArCH_2NCO$), 45.7 ($ArCH_2NCO$).

Compound 5e

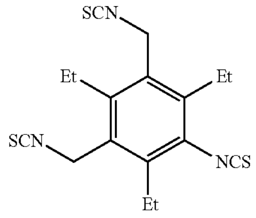

A pre-dried round bottom flask was charged with 1,3,5-triaminomethyl-2,4,6-triethylbenzene tristrifluoroacetate (0.535 g, 0.905 mmol). THF (9 mL) was added, followed by $CS_2$ (1.100 mL, 18.100 mmol) and DCC (0.585 mg, 2.806 mmol). The reaction was stirred for 16 h and then concentrated under vacuum. The resultant residue was triturated with DCM and the filtrate purified by MPLC (5% EtOAc/DCM→40%) to give a white solid (0.168 g, 0.447 mmol, 49%). $^1$H NMR: (400 MHz, $CDCl_3$) δ s. 4.74 (6H, ArC$\underline{H}_2$NCS), q. 2.84 (6H, J=7.6 Hz, ArC$\underline{H}_2$$CH_3$), t. 1.26 (9H, J=7.6 Hz, ArC$H_2$C$\underline{H}_3$). $^{13}$C NMR: (100 MHz, $CDCl_3$) 144.2, 132.4 (Ar), 130.1 (NCS), 42.9 (Ar$\underline{C}$$H_2$NCS), 23.2 (Ar$\underline{C}$$H_2$$CH_3$), 15.8 (ArC$H_2$$\underline{C}$$H_3$).

Compound 5f

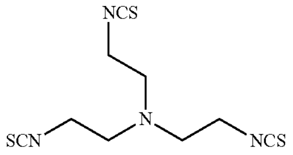

A pre-dried round bottom flask was charged with tris(2-aminotheyl)amine (5.000 g, 0.033 mol). THF (500 mL) was added, followed by $CS_2$ (40.0 mL, 0.660 mol) and DCC (21.258 g, 0.102 mol). The reaction was stirred for 16 h and then filtered. The filtrate was then concentrated under vacuum. The resultant residue was triturated with DCM and the filtrate purified by MPLC (12% EtOAc/DCM→30%) to give a yellow solid (3.340 g, 0.023 mmol, 71%). $^1$H NMR: (500 MHz, $CDCl_3$) δ t. 4.74 (6H, J=6.2 Hz, NC$H_2$C$\underline{H}_2$NCS), t. 2.96 (6H, J=6.2 Hz, NC$\underline{H}_2$C$H_2$NCS). $^{13}$C NMR: (125 MHz, $CDCl_3$) 132.8 (N$\underline{C}$S), 54.5 (N$\underline{C}$$H_2$C$H_2$NCS), 44.4 (NC$H_2$$\underline{C}$$H_2$NCS).

Compound 6b

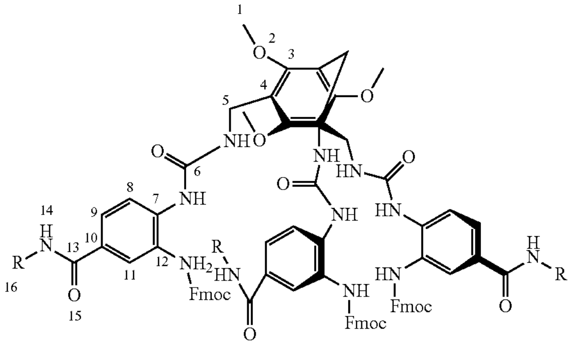

-continued

R =

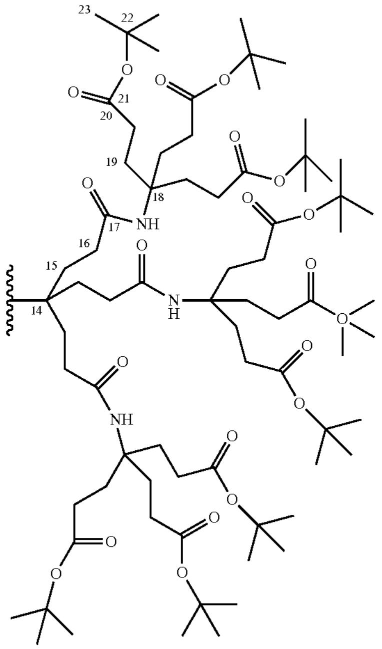

A pre-dried Schlenk tube was charged with compound 5b (18 mg, 0.053 mmol) and compound 84 (333 mg, 0.186 mmol) under a flow of nitrogen. Dry THF (3 mL) and anhydrous pyridine (0.024 mL, 0.053 mmol) was added. A flake of $MoO_2Cl_2$ was added under a flow of nitrogen. The reaction was stirred for 16 h. The reaction mixture was concentrated to dryness and the crude residue purified by MPLC (2:3 EtOAc:DCM) to give a brown solid (174 mg, 0.030 mmol, 57%). $^1$H NMR: (500 MHz, $CDCl_3$) δ m. 7.77-7.07 (33H, Ar$\underline{H}$), m. 4.56-4.06 (15H, ArC$\underline{H}_{2j}$, $CO_2$C$\underline{H}_2$C$\underline{H}$), s. 3.66 (9H, ArOC$\underline{H}_3$), m. 2.31-1.80z (144H, NHC$\underline{H}_2$C$\underline{H}_2$C(O)), s. 1.34 (162H, $CO_2$C(C$\underline{H}_3$)$_3$), s. 1.33 (81H, $CO_2$C(C$\underline{H}_3$)$_3$). $^{13}$C NMR: (125 MHz, $CDCl_3$) δ 173.1, 173.0 ($\underline{C}$ONH), 172.7, 172.7 ($CO_2$C(C$H_3$)$_3$), 172.6 (Ar$\underline{C}$ONHR), 166.6 (NH$\underline{C}$(O)NH), 158.4 ($\underline{C}$OC$H_3$), 153.9 ($\underline{C}O_2$C$H_2$CH), 143.8 ($\underline{C}$NHFmoc), 143.6 (Fmoc 4°), 141.3 ($\underline{C}$NHFmoc), 141.2 (Fmoc 4°), 127.7 (Fmoc Ar), 127.7, 127.7 ($\underline{C}$C$O_2$NHR), 127.1 (Fmoc Ar), 127.0 ($\underline{C}$NHC(O)NH), 125.3, 125.3 ($\underline{C}$H$\underline{C}$HCNH), 124.5 (Fmoc Ar), 120.0 (Fmoc Ar), 119.9 ($\underline{C}$H$\underline{C}$NHFmoc), 119.9 ($\underline{C}$C$H_2$NHC(O)NH), 80.5, 80.4 ($CO_2$$\underline{C}$(C$H_3$)$_3$), 67.3 ($CO_2$$\underline{C}$$H_2$CH), 60.4 (ArO$\underline{C}$$H_3$), 57.4, 57.4 ($\underline{C}$(C$H_2$C$H_2$C$O_2$)$_3$), 57.4 ($\underline{C}$(C$H_2$C$H_2$CONH)$_3$), 47.2 ($CO_2$C$H_2$$\underline{C}$H), 39.2 (Ar$\underline{C}$$H_2$NHC(O)NH), 32.2 (C$H_2$$\underline{C}$$H_2$C$O_2$C(C$H_3$)$_3$), 31.7 (C$H_2$$\underline{C}$$H_2$CONH), 29.8 ($\underline{C}$$H_2$C$H_2$CONH), 29.7 ($\underline{C}$$H_2$C$H_2$C$O_2$C(C$H_3$)$_3$), 28.0 ($CO_2$C($\underline{C}$$H_3$)$_3$).

Compound 6c

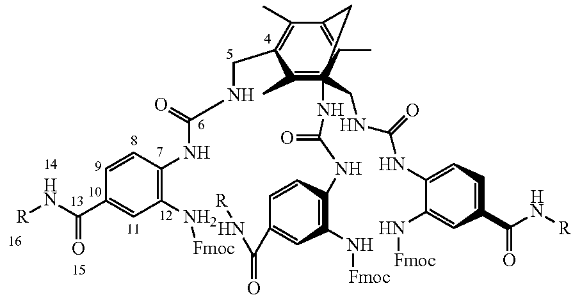

-continued

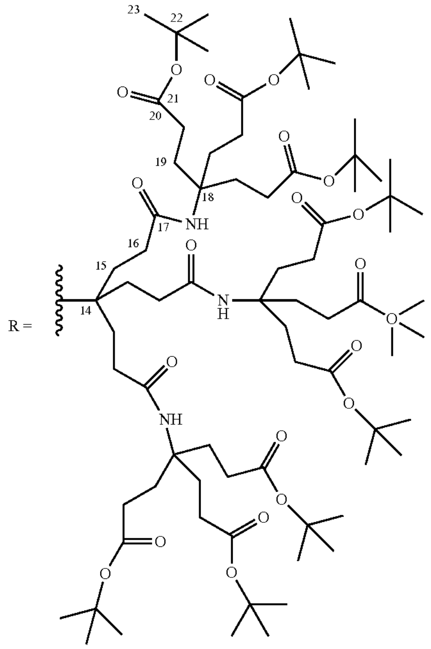

A pre-dried Schlenk tube was charged with compound 84 (441 mg, 0.245 mmol) under a flow of nitrogen and a solution of compound 5c (20 mg, 0.070 mmol) in THF (0.5 mL) added. Dry THF (3.5 mL) and anhydrous pyridine (0.006 mL, 0.070 mmol) was added. The reaction was stirred for 16 h at 50° C. The reaction mixture was concentrated to dryness and the crude residue purified by reverse phase MPLC on a 120 g SNAP Ultra C18 cartridge elution (70-95% acetone/$H_2O$) to give a white solid (197 mg, 0.035 mmol, 50%). $^1$H NMR: (400 MHz, methanol-$d_4$) δ m. 7.86-7.03 (33H, ArH), m. 4.48-4.04 (15H, $ArC\underline{H}_2$, $CO_2C\underline{H}_2C\underline{H}$), s. 2.37 (9H, $ArC\underline{H}_3$), m. 2.31-1.86z (144H, $NHC\underline{H}_2C\underline{H}_2C(O)$), s. 1.40 (243H, $CO_2C(C\underline{H}_3)_3$). $^{13}$C NMR: (125 MHz, methanol-$d_4$) δ 175.6, 175.5 (CONH), 174.4 ($\underline{C}O_2C(CH_3)_3$), 174.4 ($Ar\underline{C}ONHR$), 157.1 ($NH\underline{C}(O)NH$), 153.0 ($\underline{C}O_2CH_2CH$), 145.0 ($\underline{C}NHFmoc$), 142.6 (Fmoc 4°), 134.4 ($\underline{C}CH_3$), 131.2 (Fmoc Ar), 128.9 ($\underline{C}CO_2NHR$), 128.2 ($\underline{C}NHC(O)NH$), 126.3 ($\underline{C}H\underline{C}HCNH$), 121.4 (Fmoc Ar), 121.1 ($\underline{C}HCNHFmoc$), 121.1 ($\underline{C}CH_2NHC(O)NH$), 81.6 ($CO_2\underline{C}(CH_3)_3$), 59.4, 58.8 ($\underline{C}(CH_2CH_2CO_2)_3$), 58.7 ($\underline{C}(CH_2CH_2CONH)_3$), 40.1 ($Ar\underline{C}H_2NHC(O)NH$), 30.7 ($CH_2\underline{C}H_2CO_2C(CH_3)_3$), 30.5 ($CH_2\underline{C}H_2$—CONH), 28.5 ($\underline{C}H_2CH_2CONH$, $\underline{C}H_2CH_2CO_2C(\underline{C}H_3)_3$), 28.4 ($CO_2C(\underline{C}H_3)_3$), 16.2 ($Ar\underline{C}H_3$).

Compound 6d

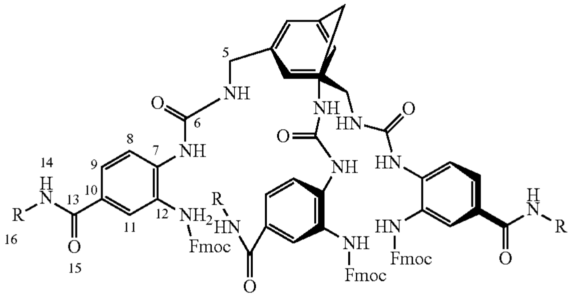

-continued

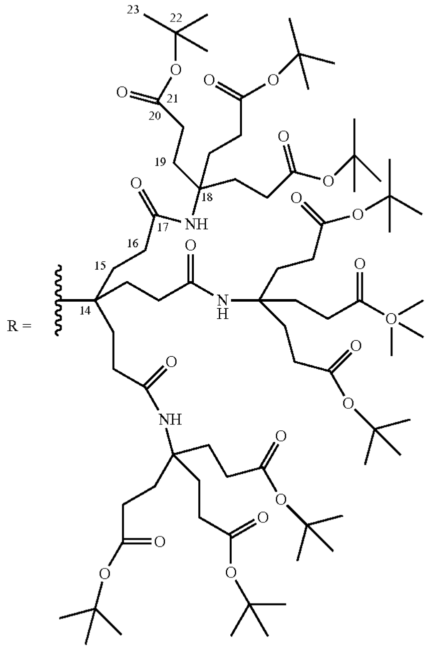

A pre-dried Schlenk tube was charged with compound 84 (441 mg, 0.245 mmol) under a flow of nitrogen and a solution of compound 5d (212 mg, 0.049 mmol) in THF (0.5 mL) was added. Dry THF (2.5 mL) and anhydrous pyridine (0.004 mL, 0.049 mmol) was added. The reaction was stirred for 32 h. The reaction mixture was concentrated to dryness and the crude residue purified by reverse phase MPLC on a 120 g SNAP Ultra C18 cartridge elution (70-95% acetone/$H_2O$) to give a white solid (110 mg, 0.020 mmol, 40%). $^1$H NMR: (500 MHz, methanol-$d_4$) (m. 8.03-7.06 (33H, ArH), m. 4.55-4.17 (15H, $ArC\underline{H}_2$, $CO_2C\underline{H}_2C\underline{H}$), m. 2.27-1.85 (144H, $NHC\underline{H}_2C\underline{H}_2C(O)$), s. 1.41 (243H, $CO_2C(C\underline{H}_3)_3$). $^{13}$C NMR: (125 MHz, methanol-$d_4$) δ 175.5 ($\underline{C}ONH$), 174.4 ($\underline{C}O_2C(CH_3)_3$), 174.4 ($Ar\underline{C}ONHR$), 157.3 ($NH\underline{C}(O)NH$), 153.9 ($\underline{C}O_2CH_2CH$), 143.8 ($\underline{C}NHFMoc$), 143.6 (Fmoc 4°), 141.1 (Fmoc 4°), 129.0 ($\underline{C}CO_2NHR$), 127.7 (Fmoc Ar), 126.3 ($\underline{C}H\underline{C}HCNH$), 124.4 (Fmoc Ar), 122.0 ($\underline{C}HCCH_2NH\underline{C}(O)NH$), 120.9 ($\underline{C}HCNHFmoc$), 120.0 (Fmoc Ar), 81.6 ($CO_2\underline{C}(CH_3)_3$), 58.7 ($\underline{C}(CH_2CH_2CO_2)_3$, $\underline{C}(CH_2CH_2CONH)_3$), 40.7 ($CO_2CH_2\underline{C}H$), 40.1 ($Ar\underline{C}H_2NHC(O)NH$), 30.7 ($CH_2\underline{C}H_2CO_2C(CH_3)_3$), 30.5 ($CH_2\underline{C}H_2CONH$), 28.5 ($\underline{C}H_2CH_2CONH$, $\underline{C}H_2CH_2CO_2C(CH_3)_3$), 28.5 ($CO_2C(\underline{C}H_3)_3$).

Compound 6h-1 and 6h-2

Compound 6h-1

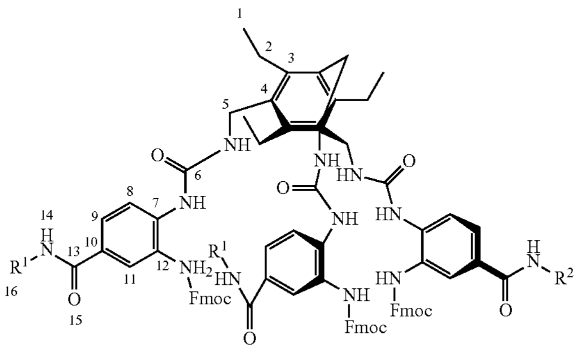

-continued

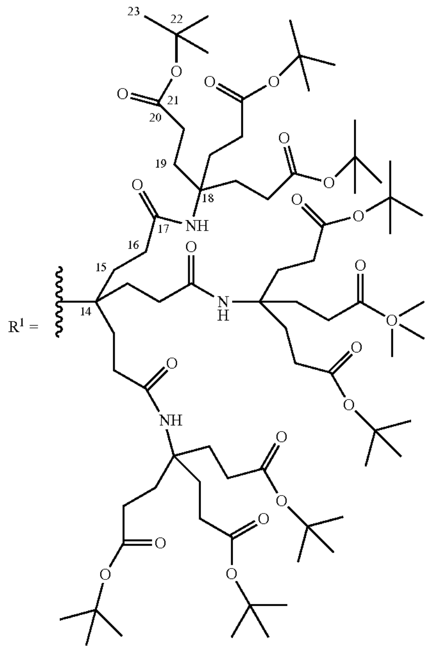

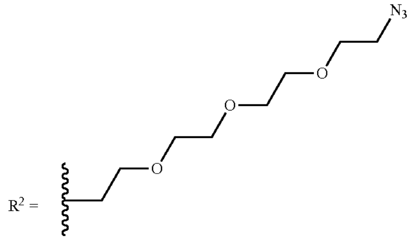

Compound 6h-2

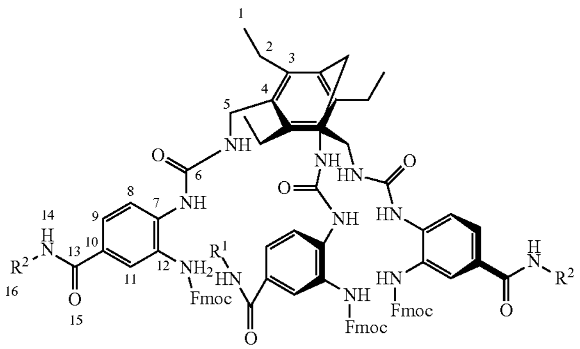

-continued

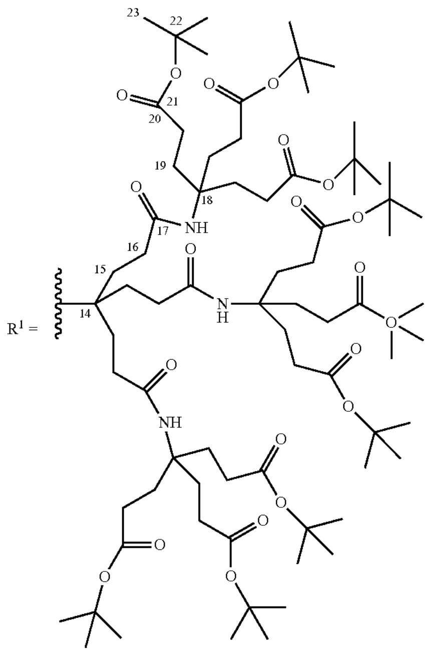

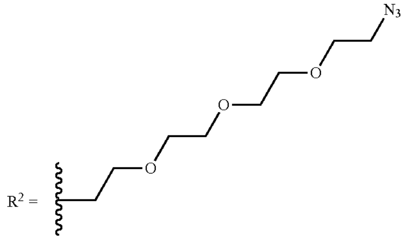

A Schlenk flasked was charged with a stirrer bar, compound 84 (0.933 g, 0.519 mmol) and compound 5a (0.100 g, 0.305 mmol) were dissolved in anhydrous THF (6 mL), pyridine (0.147 mL, 1.833 mmol) was added and the mixture was then heated to 50° C. for 5 hours. Compound 11 (0.228 g, 0.397 mmol) in anhydrous THF (1 mL) was added in one portion and the reaction stirred for a further 12 hours. The reaction mixture was transferred to a RBF washing the Schlenk with $CH_2Cl_2$ before concentrating under vacuum. The crude residue obtained was then purified by reverse phase flash chromatography on a 120 g SNAP Ultra C18 cartridge elution (1CV 85% acetone/$H_2O$, 10 CV 85-95% acetone/$H_2O$, 2CV 95% acetone) gave resolved peaks (fr17-29) 6h-1 (511 mg, 37%) and (fr8-15) 6h-2 (458 mg, 46%).

Compound 6h-1

$^1H$ NMR: (400 MHz, ($CD_3OD$): δ 8.02-7.46 (19H, br. m, ArH), 7.46-7.11 (14H, br. m, ArH), 4.60-4.30 (12H, br. m, $NHCH_2Ph$ and FmocH), 4.19 (3H, br. s, $NHCH_2Ph$ and FmocH), 3.71-3.55 (14H, m, PEG $CH_2$), 3.33 (2H, m, PEG $CH_2$), 2.85 (6H, br. s, $CH_2$), 2.35-1.86 (96H, m, dendrimer $CH_2$), 1.42 (162H, s, $CH_3$), 1.23 (9H, br. s, $CH_3$); HRMS: ($ESI^+$) calculated for $C_{244}H_{352}N_{21}O_{57}Na_3^{2+}$: 1520.8407, found $[M+3Na]^{3+}$: 1520.8395.

Compound 6h-2

$^1H$ NMR: (400 MHz, ($CD_3OD$): δ 8.01-7.51 (19H, br. m, ArH), 7.43-7.17 (14H, br. m, ArH), 4.54-4.25 (12H, br. m, $NHCH_2Ph$ and FmocH), 4.15 (3H, br. s, $NHCH_2Ph$ and FmocH), 3.69-3.47 (28H, m, PEG $CH_2$), 3.26 (4H, m, PEG $CH_2$), 2.82 (6H, br. s, $CH_2$), 2.33-1.80 (48H, m, dendrimer $CH_2$), 1.42 (81H, s, $CH_3$), 1.17 (9H, br. s, $CH_3$);

Compound 6i

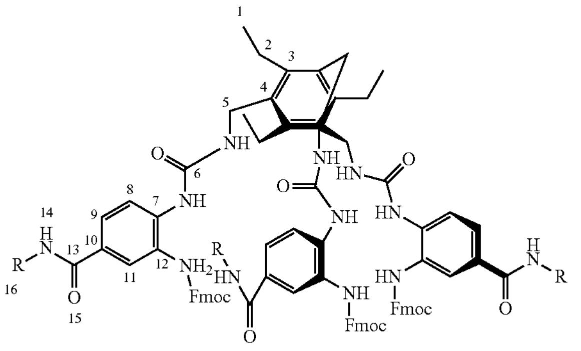

R =

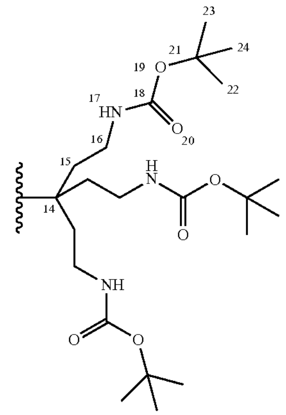

Into a dry Schlenk equipped with a stirrer bar, compound 5a (55.0 mg, 0.168 mmol) and compound 2 (480 mg, 0.588 mmol) were weighed. Anhydrous THF (3.3 mL) was added. The reaction mixture was stirred at 50 degrees for 20 hours, then transferred to a round bottom flask and concentrated to dryness. The crude product was purified by MPLC, on a 60 g C18 SNAP ULTRA cartridge, elution (3CV 70% acetone/water, 10CV 70-95% acetone/water, 3CV 95% acetone) produced a resolved peak (fr18-22). White solid 273 mg, 59%. $^1$H NMR: (400 MHz, $CD_3OD$) δ 7.05-7.85 (33H, m, ArH), 4.35 (3H, s, Flu-CH), 4.26 (6H, s, Flu-$CH\underline{H_2}O$), 3.01 (18H, m, $H_{16}$), 2.71 (6H, m, $Ar\underline{CH_2}CH_3$), 1.93 (18H, m, $H_{15}$), 1.30 (81H, s, $^t$Bu), 1.06 (9H, t, J=7.00 Hz, $ArCH_2C\underline{H_3}$). $^{13}$C NMR: (101 MHz, $CD_3OD$) δ 15.59 (9C, $Ar\underline{C}H_2C\underline{H_3}$), 22.23 (3C, $Ar\underline{C}H_2C\underline{H_3}$), 27.31 (27C, $^t$Bu), 34.89 (9C, $C\underline{C}H_2CH_2NH$), 35.21 (9C, $CCH_2\underline{C}H_2NH$), peak not observed (1C, Flu-$CH\underline{C}H_2$), 51.32 (1C, $\underline{C}(CH_2CH_2NHBoc)_3$), peak not observed (9C, $^t$Bu), peak not observed (1C, Flu-CH), 119.60-127.47 (60C, Ar), 141.28 (9C, Boc $\underline{C}$=O), 143.64 (1C, Fmoc $\underline{C}$=O), 156.89 (1C, Ar—$\underline{C}$=O).

Compound 7b

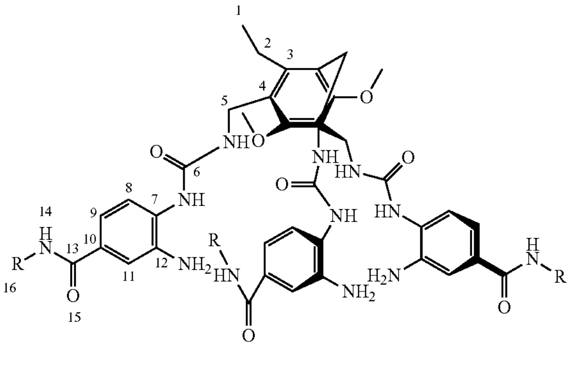

R =

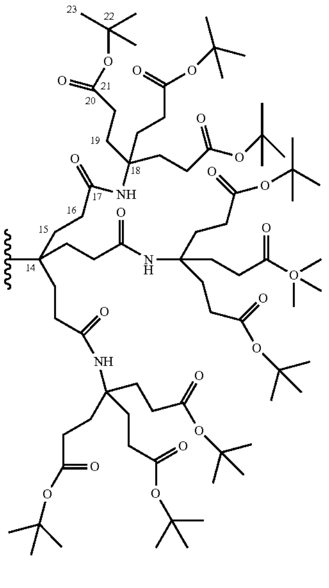

To a stirred solution of 6b (0.170 g, 0.030 mmol) was in DCM (5 mL) at 0° C., was added distilled DBU (0.006 mL, 0.040 mmol). The reaction was stirred at 0° C. for 2 h before concentrating under vacuum. The crude residue obtained was then purified by reverse phase flash chromatography on a 120 g SNAP Ultra C18 cartridge elution (1CV 80% acetone/$H_2O$, 10 CV 80-95% acetone/$H_2O$, 2CV 95% acetone) to give an off-white solid (0.133 g, 0.026 mmol, 89%). $^1$H NMR: (500 MHz, methanol-$d_4$) δ m. 7.30-7.27 (3H, CHCNH (Ar)), m. 7.22-7.15 (6H, $C\underline{H}CHCNH$, $C\underline{H}CNH_2$ (Ar)), s. 4.54 (6H, $Ar\underline{CH_2}NH$), s. 3.89 (9H, $ArOC\underline{H_3}$), m. 2.25-1.91 (144H, $NH\underline{CH_2}\underline{CH_2}C(O)$), s. 1.43 (243H, $CO_2C(C\underline{H_3})_3$). $^{13}$C NMR: (125 MHz, methanol-$d_4$) δ 175.5, 175.4 ($\underline{C}$ONH), 174.4, 174.3 ($\underline{C}O_2C(CH_3)_3$), 170.6, 170.0 (Ar$\underline{C}$ONHR), 160.2 ($NH\underline{C}(O)NH$), 157.9 ($\underline{C}OCH_3$), 141.4, 140.7 ($\underline{C}NH_2$), 134.7, 132.7 ($\underline{C}CO_2NHR$), 129.9, 125.6 ($\underline{C}NHC(O)NH$), 124.4, 123.6, 120.7, 118.8 ($\underline{C}H\underline{C}HCNH$), 117.2, 116.6 ($\underline{C}HCNH_2$), 115.5 ($\underline{C}CH_2NHC(O)NH$), 81.6 ($CO_2\underline{C}(CH_3)_3$), 59.3 ($ArO\underline{C}H_3$), 58.7, 58.6 ($\underline{C}(CH_2CH_2CO_2)_3$), 54.8 ($\underline{C}(CH_2CH_2CONH)_3$), 35.0, 35.0 ($Ar\underline{C}H_2NHC(O)NH$), 32.7, 32.5 ($CH_2\underline{C}H_2CO_2C(CH_3)_3$), 32.2, 32.2 ($CH_2\underline{C}H_2CONH$), 30.7 ($\underline{C}H_2CH_2CONH$), 30.4, ($\underline{C}H_2CH_2CO_2C(CH_3)_3$), 28.5, 28.4 ($CO_2C(\underline{C}H_3)_3$).

Compound 7c

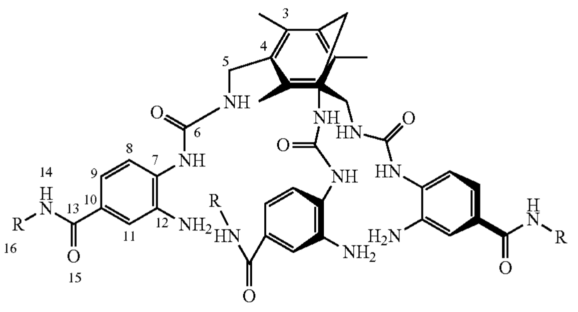

R =

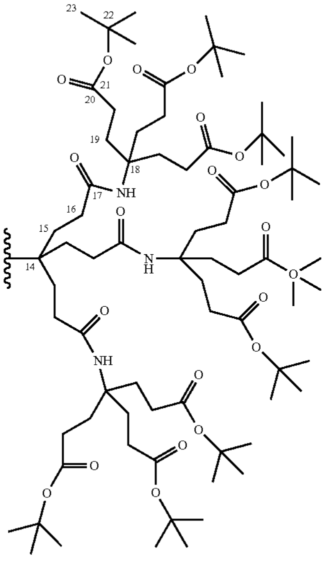

Prepared in a manner analogous to 7b from compound 6c (0.097 g, 0.017 mmol). Purified by reverse phase flash chromatography on a 120 g SNAP Ultra C18 cartridge elution (1CV 80% acetone/$H_2O$, 10 CV 80-95% acetone/$H_2O$, 2CV 95% acetone) to give a white solid (0.072 g, 0.014 mmol, 85%). $^1H$ NMR: (500 MHz, methanol-$d_4$) δ m. 7.42-7.30 (3H, CHCNH (Ar)) m. 7.31-7.29 $CHCNH_2$(Ar)), m. 7.23-7.19 (3H, CHCHCNH (Ar)), m. 4.54-4.48 (6H, $ArCH_2NH$), s. 2.49 (6H, $ArCH_3$), s. (3H, $ArCH_3$), m. 2.28-1.90 (144H, $NHCH_2CH_2C(O)$), s. 1.44 (243H, $CO_2C(CH_3)_3$). $^{13}C$ NMR: (125 MHz, methanol-$d_4$) δ 175.5 (CONH), 174.4, 174.3 ($CO_2C(CH_3)_3$), 170.1 (ArCONHR), 158.1 (NH C(O)NH), 141.3 ($CNH_2$), 135.4 ($CCO_2NHR$), 134.7 (CNHC(O)NH), 130.0 ($CCH_3$), 124.4, 118.9 (CHCHCNH), 117.4 ($CHCNH_2$), 111.4 ($CCH_2NHC(O)NH$), ($C(CH_2CH_2CONH)_3$), 81.6 ($CO_2C(CH_3)_3$), 58.7 (C ($CH_2CH_2CO_2)_3$, $C(CH_2CH_2CONH)_3$), 40.3 (Ar $CH_2NHC(O)NH$), 32.5 ($CH_2CH_2CO_2C(CH_3)_3$), 32.2 ($CH_2$ $CH_2CONH$), 30.7 ($CH_2CH_2CONH$), 30.5, ($CH_2CH_2CO_2C(CH_3)_3$), 28.4 ($CO_2C(CH_3)_3$), 16.3 ($ArCH_3$).

Compound 7d

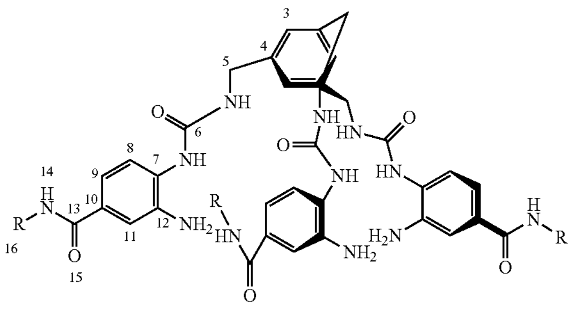

R =

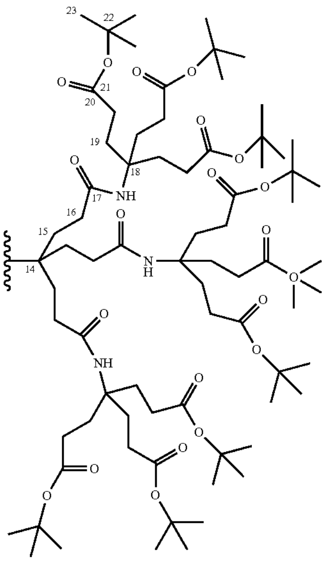

Prepared in a manner analogous to 7b from compound 6d (0.110 g, 0.020 mmol). Purified by reverse phase flash chromatography on a 120 g SNAP Ultra C18 cartridge elution (1CV 80% acetone/$H_2O$, 10 CV 80-95% acetone/$H_2O$, 2CV 95% acetone) to give a white solid (0.022 g, 0.004 mmol, 21%). $^1H$ NMR: (500 MHz, methanol-$d_4$) δ m. 7.43-7.13 (12H, Ar), m. 4.50-4.29 (6H, $ArCH_2NH$), m. 2.34-1.86 (144H, $NHCH_2CH_2C(O)$), s. 1.43 (243H, $CO_2C(CH_3)_3$). $^{13}C$ NMR: (HSQC) (125 MHz, methanol-$d_4$) δ 175.5 (CONH), 174.4 ($CO_2C(CH_3)_3$), 174.4 (ArCONHR), 157.3 (NHC(O)NH), 141.2 ($CNH_2$), 135.4 ($CCO_2NHR$), 134.7 (CNHC(O)NH), 126.3 (CHCHCNH), 124.4, (CHCHCNH), 122.0 ($CHCCH_2NHC(O)NH$), 118.9 (CH CHCNH), 115.6 ($CHCNH_2$), 81.6 ($CO_2C(CH_3)_3$), 58.7 ($C(CH_2CH_2CO_2)_3$, $C(CH_2CH_2CONH)_3$), 44.4 (Ar $CH_2NHC(O)NH$), 35.1 ($CH_2CH_2CO_2C(CH_3)_3$), 34.6 ($CH_2$ $CH_2CONH$), 30.4 ($CH_2CH_2CONH$), 30.2, ($CH_2CH_2CO_2C(CH_3)_3$), 28.0 ($CO_2C(CH_3)_3$).

Compound 7e

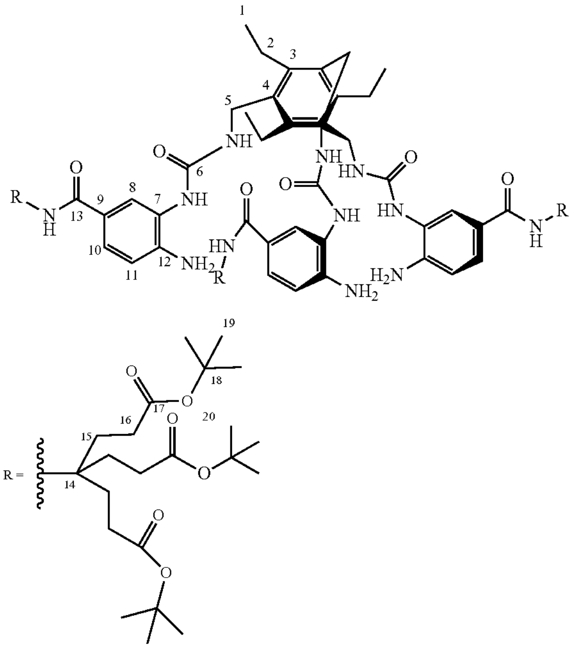

Compound 13 (231 mg, 0.30 mmol) was dried by azeotrope with toluene, then under an inert $N_2$ atmosphere was dissolved in anhydrous dichloromethane (1.5 mL). Pyridine (41 uL, 0.51 mmol) was added, followed by a solution of compound 5a (8 mg, 0.086 mmol) in anhydrous dichloromethane (0.5 mL) and the reaction mixture was stirred at 34° C. until complete by TLC. The solvent was removed under vacuum and the crude product purified by flash column chromatography ($SiO_2$, EtOAC:$CH_2Cl_2$ 1:4 to 1:2 then MeOH:$CH_2Cl_2$ 5:95) to afford the FMOC-protected intermediate. HRMS: ($ESI^+$) calculated for $C_{150}H_{192}N_{12}Na_3O_{30}^{3+}$ 983.7859, found $[M+3Na]^{3+}$: 983.7844. Under an inert $N_2$ atmosphere, the FMOC-protected intermediate (140 mg, 0.053 mmol) was dissolved in anhydrous dichloromethane (9 mL) and cooled to 0° C. DBU (50 μL, 0.34 mmol) was added dropwise and the reaction mixture warmed to room temperature and stirred for 1 hour. The solvent was removed under vacuum and the crude product purified by flash column chromatography ($SiO_2$, $CH_2Cl_2$ then 7.5% MeOH:$CH_2Cl_2$) to afford compound 7e (95 mg, 0.048 mmol, 91%). $^1$H NMR: (400 MHz, $CD_3OD$, 298 K): δ 7.40 (s, 3H, NH), 7.35 (d, J=8.2 Hz, 3H, $H_{11}$), 7.21 (d, J=2.0 Hz, 3H, $H_8$), 7.10 (dd, J=8.2, 2.0 Hz, 3H, $H_{10}$), 4.52 (s, 6H, $H_5$), 2.94-2.87 (m, 6H, $H_2$), 2.30-2.25 (m, 18H, $H_{16}$), 2.12-2.06 (m, 18H, His), 1.45 (s, 81H, $H_{19}$), 1.26 (t, J=7.4 Hz, 9H, $H_1$); HRMS: ($ESI^+$) calculated for $C_{105}H_{164}N_{12}O_{24}^{2+}$ 989.1002, found $[M+2H]^{2+}$: 989.1004.

Compound 11

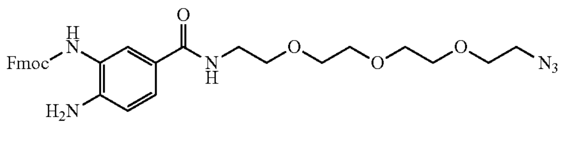

Prepared in an analogous fashion to compound 2 by treating compound A1 (3.308 g, 5.443 mmol), (3.308 g, Moles: 5.443 mmol) was added and dissolved in S1 (Vol: 22.680 mL). R3 (Vol: 1.270 mL, Moles: 7.258 mmol) was added dropwise followed by R2 (Vol: 1.000 mL, Moles: 4.536 mmol) and the reaction was left to stir until complete by TLC. TLC 70% EtOAc/$CH_2Cl_2$ showed the reaction to be complete at 24 h (visualised by UV/weak ninhydrin stain). The reaction mixture was transferred to a RBF—washing with $CH_2Cl_2$ and concentrated under vacuum to yield a brown residue. The crude product was purified by flash column chromatography eluting with 50% to 100% EtOAc/$CH_2Cl_2$. Colourless amorphous solid (2.50 g, 4.35 mmol, 80%). $^1$H NMR: (400 MHz, $CDCl_3$) δ 7.74 (d, J=7.5 Hz, 2H, ArH), 7.60 (d, J=2.0 Hz, 2H, ArH), 7.45 (s, 1H, ArH), 7.38 (t, J=7.5 Hz, 2H, ArH), 7.26 (d, J=9.6 Hz, 2H, ArH), 7.05 (s, 1H, ArH), 6.84 (s, 1H ArH), 6.65 (d, J=8.4 Hz, 1H C(O)N$HCH_2$), 4.49 (s, 1H, Flu-$CH_2$), 4.18 (s, 2H, Flu-$OCH_2$), 3.68-3.45 (m, 14H, $OCH_2$), 3.27 (t, J=5.0 Hz, 2H C(O)NHC$H_2$), 1.34 (d, J=6.7 Hz, 2H, $N_3CH_2$).

Compound 12

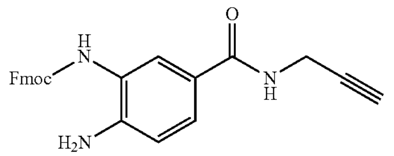

Prepared in an analogous fashion to compound 2 by treating compound A1 (2.000 g, 3.291 mmol) in 16.5 mL DCM and DIPEA (0.917 mL, 5.266 mmol) with propargyl amine (0.422 mL, Moles: 6.583 mmol) for 72 hours. Purified by column chromatography using ethyl acetate as the eluent. White solid (1.36 g, 3.290 mmol, 99%). $^1$H NMR: (400 MHz, Methanol-$d_4$) δ 7.95 (d, J=7.5 Hz, 2H, ArH), 7.89-7.80 (m, 3H, ArH), 7.61 (d, J=8.4 Hz, 1H, ArH), 7.52 (t, J=7.4 Hz, 2H, ArH), 7.44 (s, 2H), 6.87 (d, J=8.4 Hz, 1H, ArH), 4.45 (s, 2H), 4.40 (s, 1H, Flu-$CH_2$), 4.17 (d, J=2.5 Hz, 2H, Flu-$OCH_2$), 2.87 (t, J=2.4 Hz, 1H, $CH_2CCH$), 2.67 (p, J=1.9 Hz, 2H, $CH_2CCH$).

Compound 13

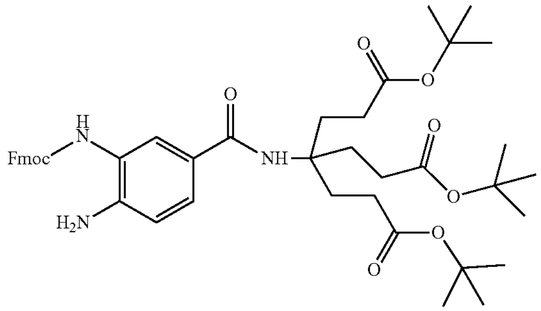

A 50 mL RBF was charged with compound A1 (500 mg, 1.017 mmol), di-tert-butyl-4-amino-4-(3-(tert-butoxy)-3-oxopropyl)heptanedioate* (560 mg, 1.35 mmol) (560 mg, 1.35 mmol) and anhydrous toluene (10 mL). The slurry was evaporated to dryness and the residue re-dissolved in anhydrous pyridine (5 mL) and DCM (3 mL). The mixture was stirred at 50° C. for 16 hours. The solvent was removed to give a viscous brown oil, which was partitioned between EtOAc and 1M aq HCl. The organic phase was washed with water then brine. The combined organic fractions were concentrated and then absorbed onto silica gel and purified by flash chromatography (EtOAc:DCM (20-50%). Pink powder (467 mg, 0.612 mmol, 60%). $^1$H NMR: (400 MHz, $CDCl_3$) δ 7.79 (d, J=7.6 Hz, 2H, ArH), 7.64 (d, J=2.1 Hz, 1H, ArH), 7.43 (t, J=7.5 Hz, 2H, ArH), 7.34 (s, 3H, ArH), 6.78 (d, J=9.0 Hz, 1H, NH), 6.60 (s, 1H, ArH), 6.30 (s, 1H, ArH), 4.56 (s, 2H, Flu-$CH_2$O), 4.28 (s, 1H, Flu-$CH_2$), 4.08 (s, 2H), 2.30 (dd, J=8.8, 6.7 Hz, 6H, $CH_2$C(O)), 2.16-2.04 (m, 6H, $CCH_2$), 1.44 (s, 24H, $C(CH_3)_3$).

*Newkome, George R.; Weis, Claus D. *Organic Preparations and Procedures International,* 1996, vol. 28, #4 p. 495-498

Compound 14

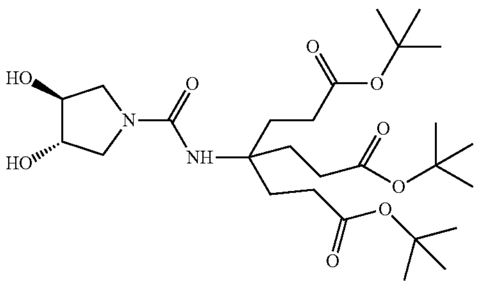

A Schlenk flash was charged with (3S,4S)-pyrrolidine-3, 4-idol (100.0 mg, 0.970 mmol), di-tert-butyl 4-(3-(tert-butoxy)-3-oxopropyl)-4-isocyanatoheptanedioate (385.4 mg, 0.873 mmol) and anhydrous DMF under $N_2$ to give orange solution. The solution was left to stir for 16 hours the poured into water (10 mL) and extracted with EtOAc (10 mL). The organic layer was separated, dried and concentrated to dryness. Off white solid. (430 mg, 0.79 mmol, 81%). $^1$H NMR: (400 MHz, $CDCl_3$) δ 4.65 (s, 1H, C(O)NH), 4.15-4.06 (m, 2H, CHOH), 3.95 (s, 2H, OH), 3.52 (dd, J=10.9, 4.2 Hz, 2H, $NCH_2$), 3.21 (d, J=10.8 Hz, 2H, $NCH_2$), 2.17 (dd, J=9.0, 6.7 Hz, 6H, $CH_2$C(O)), 2.02-1.82 (m, 6H, $CCH_2$), 1.37 (s, 27H, $C(CH_3)_3$). $^{13}$C NMR: (125 MHz, $CDCl_3$) δ 176.8 (s, NC(O)N), 168.1 (s, $CCO_2C$), 79.7 (s, $CO_2C(CH_3)_3$), 75.7 (s, COH), 51.5 (s, $CH_2N$), 30.8 (s, $CH_2$C(O)), 29.8 (s, $CCH_2$), 28.1 (s, $CO_2C(CH_3)_3$).

Compound 15

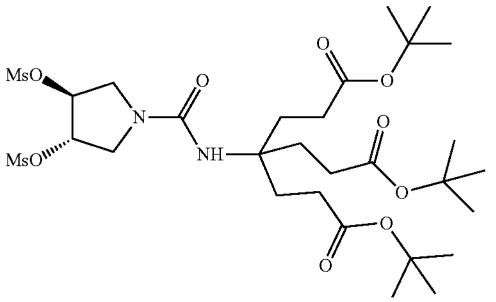

A Schlenk flash was charged with Compound 14 (400.0 mg, 0.734 mmol) anhydrous DCM and TEA (0.409 mL, 2.93 mmol) and neat methylsulfonyl chloride (0.125 mL, 1.62 mmol) was added dropwise. The orange solution was allowed to stir overnight to give turbid orange solution. TLC ($SiO_2$, 100% EtOAc) indicated complete consumption of the starting material to a new product (Rf=0.4). Water was added (10 mL) and the organic layer separated, dried with $MgSO_4$ and concentrated to dryness. Orange crystalline solid (428 mg, 0.611 mmol, 83%). $^1$H NMR: (400 MHz, $CDCl_3$) δ 5.42 (s, 1H, C(O)NH), 5.2 (d, J=4.5, 2H, C $HOS(O_2)O$), 3.77 (dd, J=12.2, 4.5 Hz, 2H, $NCH_2$), 3.65 (d, J=12.2 Hz, 2H, $NCH_2$), 3.11, (s, 1H, $CH_3S(O)_2O$), 2.24 (t, J=8.0 Hz, 6H, $CH_2$C(O)), 1.97 (m, 6H, $CCH_2$), 1.42 (s, 27H, $C(CH_3)_3$). $^{13}$C NMR: (125 MHz, $CDCl_3$) δ 176.9 (s, N C(O)N), 168.3 (s, $CCO_2C$), 79.8 (s, $CO_2C(CH_3)_3$), 79.0 (s, $CH_3S(O)_2OC$), 49.0 ($CH_2N$), 38.6 (s, $CH_3S(O)_2O$), 30.5 (s, $CH_2$C(O)), 30.2 (s, $CCH_2$), 28.4 (s, $CO_2C(CH_3)_3$).

Compound 15a

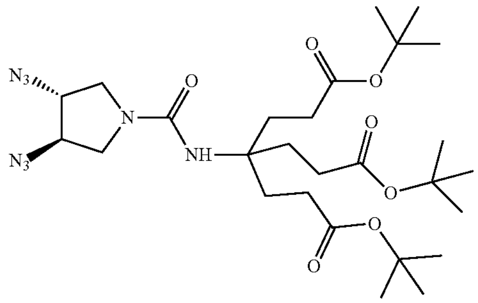

Compound 15 (428.0 mg, 0.611 mmol), dissolved in dry DMF and solid $NaN_3$ (119.2 mg, 1.833 mmol, 3.000 eq) added in one portion. The orange suspension was heated to 100° C. for 16 h to give a dark brown solution. Partitioned between EtOAc and water, washed with ×2 10 mL 5% LiCl(aq), brine (1×10 mL), dried over $MgSO_4$ then concentrated to dryness with ca. 1 g silica gel. This silica absorbed crude product was loaded onto a frit on top of 1 cm×2 cm plug of fresh silica and eluted with 50% EtOAc in petrol (ca. 20 mL). The colourless filtrate was evaporated to dryness. Colouress crystalline solid (256 mg, 0.43 mmol, 74%). $^1$H NMR: (400 MHz, $CDCl_3$) δ 5.21 (s, 1H, C(O)NH), 3.92 (m, 2H, $CHN_3$), 3.60 (dd, J=10.9, 5.7 Hz, 2H, $NCH_2$), 3.30 (ds, J=10.9, 3.3 Hz, 2H, $NCH_2$), 2.19 (t, J=7.5 Hz, 6H, C $H_2$C(O)), 1.92 (m, 6H, $CCH_2$), 1.37 (s, 27H, $C(CH_3)_3$). $^{13}$C NMR: (125 MHz, $CDCl_3$) δ 176.8 (s, NC(O)N), 169.3 (s, C $CO_2C$), 79.8 (s, $CO_2C(CH_3)_3$), 64.0 (s, $CN_3$), 48.5 (s, $CH_2N$), 30.3 (s, $CH_2$C(O)), 29.9 (s, $CCH_2$), 28.3 (s, $CO_2$ $C(CH_3)_3$).

Compound 16

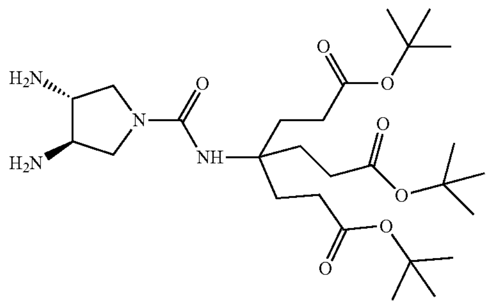

Compound 15a (200.0 mg, 0.336 mmol) was dissolved in EtOH (1.000 mL) and mixed with 10% Pd/C (25.0 mg, 0.235 mmol). The reaction flask was purged nitrogen and then a hydrogen. The resulting mixture was stirred for 20 hours under a hydrogen atmosphere (supplied from a balloon). The crude reaction mixture was filtered through Celite™ washing and concentrated under reduced pressure. The crude product was purified by flash column chromatography ($SiO_2$, $MeCN:CH_2Cl_2$ 1:4 then $MeOH:CH_2Cl_2$ 1:9) to afford compound 16 (93 mg, 0.171 mmol, 51%). $^1H$ NMR: (400 MHz, $CDCl_3$, 298 K): δ 4.59 (s, 1H, NH), 3.63 (dd, J=10.1, 5.3 Hz, 2H, $H_8$), 3.08 (q, J=5.7, 5.0 Hz, 2H, $H_9$), 2.94 (dd, J=10.3, 5.7 Hz, 2H, $H_8$), 2.17 (t, J=7.8 Hz, 6H, $H_4$), 1.95-1.85 (m, 6H, $H_5$), 1.38 (s, 27H, $H_1$). $^{13}C$ NMR: (100 MHz, $CDCl_3$, 298 K): δ 173.18 ($C_3$), 155.63 ($C_7$), 80.57 ($C_2$), 58.37 ($C_9$), 56.74 ($C_6$), 52.03 ($C_8$), 30.53 ($C_5$), 29.91 ($C_4$), 28.13 ($C_1$); HRMS: ($ESI^+$) calculated for $C_{27}H_{50}N_4NaO_7^+$ 565.3572, found $[M+Na]^+$: 565.3547.

Compound 200—1,3,5-tris(bromomethyl)-2-bromo-4,6-dimethylbenzene

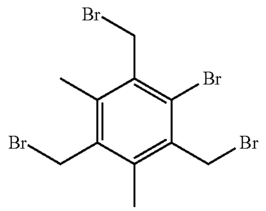

2-bromo-4,6-dimethylbenzene (5.000 g, 0.027 mol, 1.000 eq), paraformaldehyde (12.736 g, 0.424 mol, 15.700 eq) and AcOH/HBr 33% (70 mL) were added to a dry 200 mL round bottom flask. The mixture was stirred while $ZnBr_2$ (15.211 g, 0.068 mol, 2.500 eq) was slowly added and the mixture was heated to 90° C. After 24 hours, an additional portion paraformaldehyde (12.736 g, 0.424 mol, 15.700 eq) and 2.7 g $ZnBr_2$ (12.736 g, 0.424 mol, 15.700 eq) was added. The yellow solution was heated an additional. 140 hours. The reaction mixture was then cooled to room temperature and the colourless crystals isolated by filtration, washing with AcOH (3×10 mL) and then water until the pH of the filtrate was neutral. Dried under vacuum for 2 day to afford colourless crystals (7.50 g, 0.016 mol, 60%).

$^1H$ NMR (400 MHz, $CDCl_3$) δ 4.78 (s, 4H, $CH_2$), 4.54 (s, 2H, $CH_2$), 2.54 (s, 6H, $CH_3$).

Compound 201—1,3,5-tris(azidomethyl)-2-bromo-4,6-dimethylbenzene

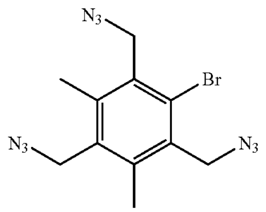 [SMILES: Cc1c(CN=[N+]=[N-])c(C)c(CN=[N+]=[N-])c(Br)c1CN=[N+]=[N-]]

1,3,5-tris(bromomethyl)-2-bromo-4,6-dimethylbenzene (1.326 g, 2.859 mmol) was dissolved in dry DMF (30.000 mL) under nitrogen and stirred while $NaN_3$ (1.115 g, 17.154 mmol). The reaction mixture was heated to 40° C. and stirred overnight. The reaction was cooled and poured into water (100 mL) and ppt extracted with EtOAc (3×50 mL). The combined organic fractions were washed with 5% LiCl (2×20 mL) and then brine, dried ($MgSO_4$) and concentrated to dryness behind a blast shield to afford a colourless oil the crystallised on standing. (1.00 g, 2.856 mmol, 99%).

$^1H$ NMR (400 MHz, $CDCl_3$) δ 4.72 (s, 4H, $CH_2$), 4.55 (s, 2H, $CH_2$), 2.50 (s, 6H, $CH_3$).

Compound 202—1,3,5-tris(aminomethyl)-2-bromo-4,6-dimethylbenzene trihydrochloride

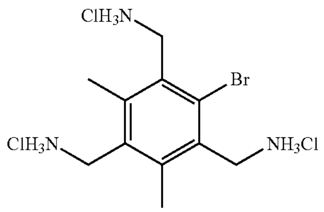

1,3,5-tris(azidomethyl)-2-bromo-4,6-dimethylbenzene (0.600 g, 1.713 mmol, 1.000 eq) and triphenylphopshine (3.011 g, 11.48 mmol, 6.7) were dissolved in THF (12 mL) and water (0.375 mL, 20.78 mmol, 12.13 eq) added. Stirred at 40° C. overnight. Solvent removed completely and treated with 0.5 M HCl. (10 mL). Extracted with EtOAc (2×10 mL) and the water layered reserved and concentrated to near dryness the added to rapidly stirred acetone (20 mL). The white precipitate was collected on a frit and washed with acetone (10 mL) and the dried under vacuum. Colourless solid (0.65 g, 1.71 mmol, 99%).

$^1H$ NMR (400 MHz, $D_2O$) δ 4.54 (s, 4H, $CH_2$), 4.38 (s, 2H, $CH_2$), 2.53 (s, 6H, $CH_3$).

Compound 203—di-tert-butyl ((2-bromo-5-(((tert-butoxycarbonyl)amino)methyl)-4,6-dimethyl-1,3-phenylene)bis(methylene))dicarbamate

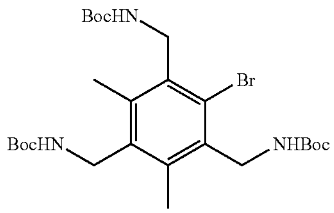 [SMILES: Cc1c(CNC(=O)OC(C)(C)C)c(C)c(CNC(=O)OC(C)(C)C)c(Br)c1CNC(=O)OC(C)(C)C]

1,3,5-tris(aminomethyl)-2-bromo-4,6-dimethylbenzene trihydrochloride (0.68 g, 1.78 mmol), $BOC_2O$ (2.33 g, 10.7 mmol) and triethylamine (1.5 mL, 10.7 mmol) was dissolved in MeOH (70 mL) and stirred at room temperature overnight. The solvent was removed and the residue portioned between EtOAc (50 mL) and 0.5 M citric acid. The aqueous layer was extracted with EtOAc (2×20 mL) and the combined organic fractions combined, dried ($MgSO_4$) and concentrated to dryness to yield a colourless oil which crystallised upon standing (0.80 g, 1.4 mmol, 78%)

$^1H$ NMR (400 MHz, $CDCl_3$) δ 4.77 (br. s, 2H, NH), 4.55 (d, J=5.7 Hz, 4H, $CH_2$), 4.36 (br. s, 3H, NH and $CH_2$), 2.48 (s, 6H, $CH_3$), 1.44 (s, 9H, $CH_3$);

Compound 204—1-bromo-2,4,6-tris(isocyanatomethyl)-3,5-dimethylbenzene

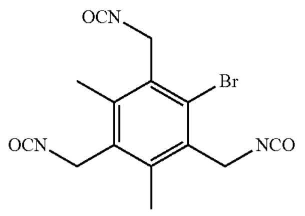

Prepared by an analogous route to Compound 103 using Compound 202 (0.20 g, 0.35 mmol) to give Compound 204 as a light pink crystalline solid (94 mg, 0.27 mmol, 77%).

$^{1}$H NMR (400 MHz, $CDCl_3$) δ 4.70 (s, 4H, $CH_2$), 4.49 (s, 2H, $CH_2$), 2.52 (s, 6H, $CH_3$);

$^{13}$C NMR (101 MHz, $CDCl_3$) δ 138.4 (C), 135.1 (C), 134.4 (C), 129.1 (C), 124.4 (C), 45.6 ($CH_2$), 41.3 ($CH_2$), 16.7 ($CH_3$);

HRMS ($ESI^+$) calculated for $C_{14}H_{13}BrN_3O_3^+$: requires 350.0135, found $[M+H]^+$: 350.0139.

Compound 205

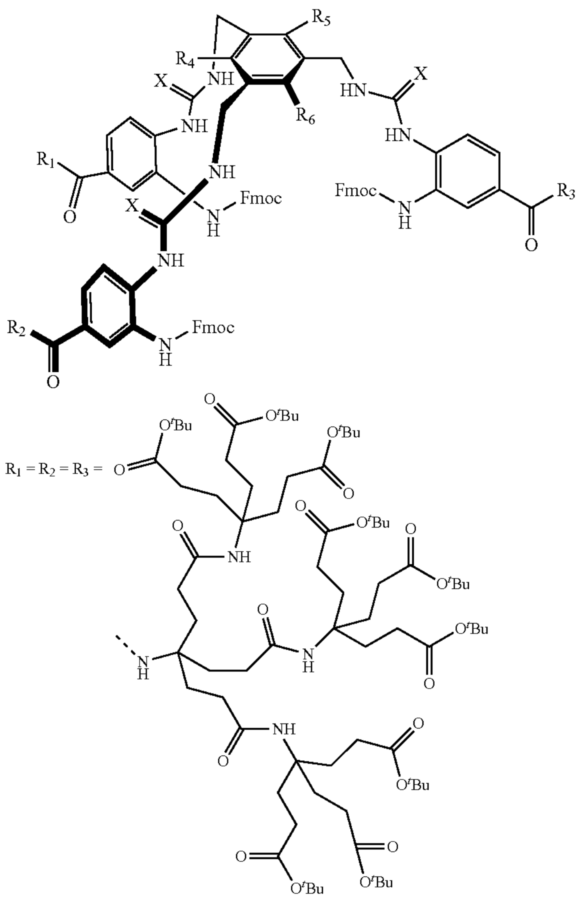

$R_4 = R_5 = Me$
$R_6 = Br$
$X = O$

A Schlenk was dried under vacuum by heat-gun and allowed to cool to RT. Compound 84 (628.4 mg, 0.350 mmol, 3.5 eq) was added to the flask and dissolved in anhydrous toluene (5 mL). The solvent was removed on the line to azeotropically dry the reagent and the resulting residue left to dry for 30 mins prior to use. The solid was re-dissolved in anhydrous toluene (4 mL) and a solution of 1-bromo-2,4,6-tris(isocyanatomethyl)-3,5-dimethylbenzene (Compound 204, 35.0 mg, 0.100 mmol, 1.0 eq) in anhydrous toluene (1 mL) was added to the flask. Pyridine (0.048 mL, 0.600 mmol, 6.0 eq) was added and the reaction heated to 34° C. for 24 h. (N.B. the reaction became a vibrant orange colour overtime). TLC (5% $MeOH/CH_2Cl_2$, UV and Seebach visualisation) indicated that the reaction was complete. The reaction was concentrated under vacuum and purified by reverse phase flash chromatography (on a SNAP Ultra C18 120 g cartridge, 70:30 Acetone:Water to 100:0 over 12 CV). Fraction 6-11 contained excess 3-G2MM Linker which was recovered and fraction 15-18 contained Compound 205 as an off-white foam (348 mg, 61%).

$^{1}$H NMR (400 MHz, $CD_3OD$) δ 8.09-7.49 (br. m, 19H, ArH), 7.51-7.10 (br. m, 14H, ArH), 4.74-4.54 (br. m, 4H, benzylic $CH_2$ and FmocH), 4.51-4.05 (br. s, 11H, benzylic $CH_2$ and FmocH), 2.50 (br. s, 6H, methyl $CH_3$), 2.31-1.81 (m, 144H, dendrimer $CH_2$), 1.41 (s, 243H, dendrimer $CH_3$);

HRMS (Nanospray $ESI^+$) calculated for $C_{308}H_{466}BrN_{21}O_{75}^{4+}$: requires 1435.8134, found $[M+4H]^{4+}$: 1435.8147.

Compound 206

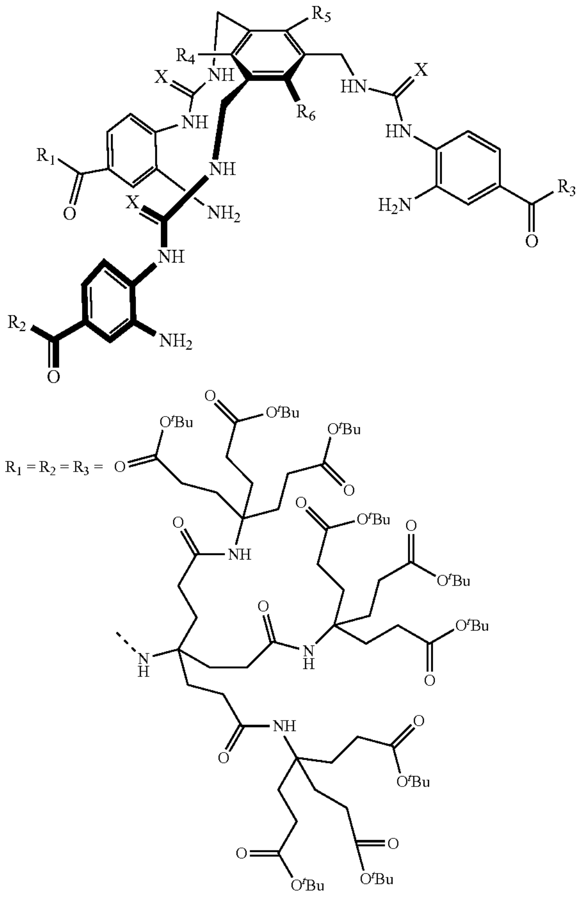

$R_4 = R_5 = Me$
$R_6 = Br$
$X = O$

Compound 205 (327.0 mg, 0.057 mmol, 1.000 eq) was dissolved in anhydrous $CH_2Cl_2$ (2.9 mL) and cooled to 0° C. DBU (0.051 mL, 0.342 mmol, 6.0 eq) was added dropwise and the reaction stirred for 2 h. The reaction mixture was then concentrated under vacuum and purified by reverse phase flash chromatography (on a SNAP Ultra C18 60 g cartridge, 70:30 Acetone:Water to 100:0 over 12 CV) to give the Compound 206 as a light pink solid (0.278 g, 97%).

$^1H$ NMR (400 MHz, $CD_3OD$) δ 7.40 (dd, J=8.3, 3.5 Hz, 3H, ArH), 7.30 (d, J=2.1 Hz, 3H, ArH), 7.21 (dd, J=8.3, 2.1 Hz, 3H, ArH), 4.73 (br. s, 4H, benzylic $CH_2$), 4.52 (br. s, 2H, benzylic $CH_2$), 2.60 (br. s, 6H, $CH_3$), 2.31-2.14 (m, 72H, dendrimer $CH_2$), 2.13-2.04 (m, 18H, dendrimer $CH_2$), 2.00-1.88 (m, 54H, dendrimer $CH_2$), 1.44 (s, 243H, dendrimer $CH_3$);

$^{13}C$ NMR (126 MHz, $CD_3OD$) δ 175.5 (C), 174.4 (C), 170.1 (C), 158.1 (C), 158.0 (C), 141.4 (C), 140.2 (C), 137.1 (C), 136.1 (C), 132.8 (C), 130.7 (C), 130.0 (C), 129.9 (C), 124.4 (CH), 118.9 (CH), 117.3 (CH), 81.7 (C), 59.4 (C), 58.7 (C), 32.5 ($CH_2$), 32.2 ($CH_2$), 30.7 ($CH_2$), 30.5 ($CH_2$), 28.5 ($CH_3$), 17.1 ($CH_3$);

HRMS (Nanospray $ESI^+$) calculated for $C_{263}H_{435}BrN_{21}O_{69}^{3+}$: requires 1691.0137, found $[M+3H]^{3+}$: 1691.0132.

Compound 207

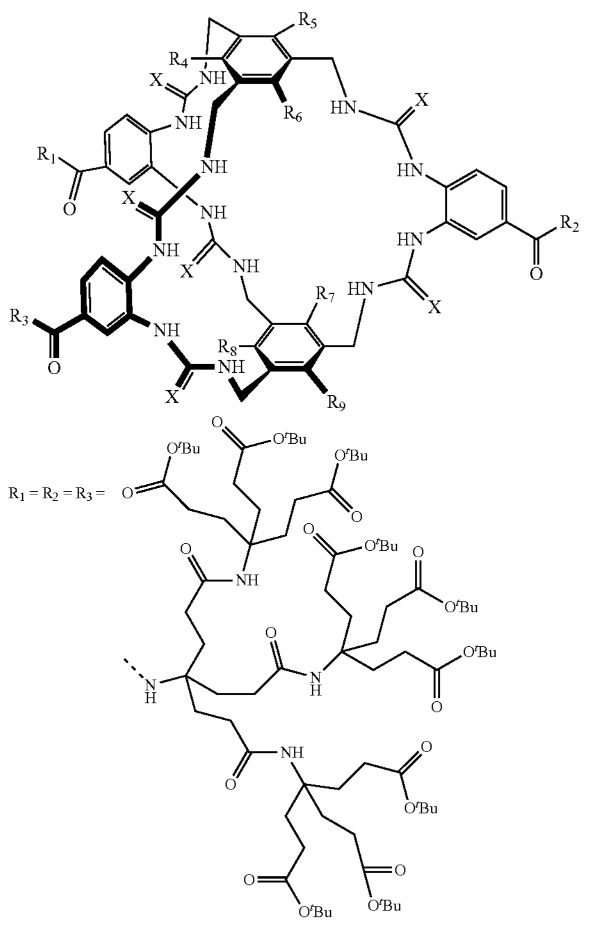

$R_4 = R_5 = Me$
$R_6 = Br$
$R_7 = R_8 = R_9 = Et$
X = O

Dissolved Compound 206 (270.0 mg, 0.053 mmol, 1.0 eq) in anhydrous pyridine (22.3 mL and heated the reaction mixture to 40° C. in a dry syn, external temperature of heat probe set to 40° C. in a separate pear-shaped flask TEB NCO (Compound 103, 20.9 mg, 0.064 mmol, 1.2 eq) was dissolved in anhydrous $CH_{22}$ (2.3 mL). The TEB NCO solution was added by syringe pump at 0.85 mL/h. Once the addition was complete the reaction was left overnight at 40° C. The reaction mixture was concentrated under vacuum on a liquid nitrogen cold finger rotary evaporator to dryness. The resulting foam was co-evaporated with toluene twice and the resulting foam purified by reverse phase chromatography (loading in MeCN and eluting on a SNAP Ultra C18 60 g cartridge starting at Acetone:Water 70:30 to 100:0 over 12 CV). Fraction 3-6 contained Compound 207 as a colourless foam (196 mg, 68%).

$^1H$ NMR (500 MHz, $CD_3OD$) δ 8.20-7.83 (m, 4H, ArH), 7.73-7.56 (m, 5H, ArH), 7.44 (s, 5H, NH), 4.55-4.31 (m, 12H, benzylic $CH_2$), 2.96-2.74 (m, 6H, ethyl $CH_2$), 2.55 (s, 6H, methyl $CH_3$a), 2.36-1.80 (m, 144H, dendrimer $CH_2$), 1.44 (s, 243H, dendrimer $CH_3$), 1.25-1.16 (m, 9H, ethyl $CH_3$);

$^{13}C$ NMR (126 MHz, $CD_3OD$) δ 175.5, 175.4, 174.3, 169.5, 169.3, 158.3, 158.0, 157.9, 157.5, 144.4, 144.4, 139.7, 136.9, 136.2, 135.2, 134.3, 134.1, 132.7, 132.0, 131.4, 130.7, 129.8, 125.9, 125.8, 125.1, 124.5, 122.6, 81.6, 59.5, 59.4, 58.8, 58.7, 43.5, 40.1, 38.9, 32.4, 32.2, 32.2, 30.7, 30.7, 30.4, 28.5, 23.6, 17.1, 16.9, 16.7;

HRMS (Nanospray $ESI^+$) calculated for $C_{281}H_{455}BrN_{24}O_{72}Na^{3+}$: requires 1808.0615, found $[M+2H+Na]^{3+}$: 1808.0601.

Compound 208-Receptor 4

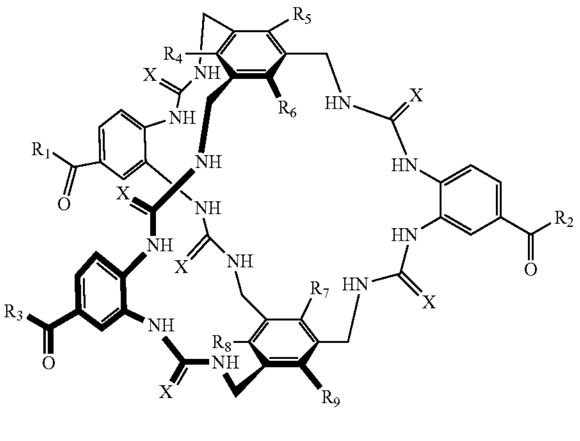

-continued $R_1 = R_2 = R_3 =$

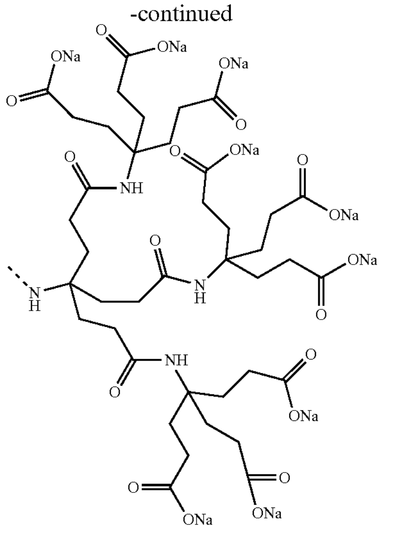

$R_4 = R_5 = Me$
$R_6 = Br$
$R_7 = R_8 = R_9 = Et$
X = O

Dissolved Compound 207 (196 mg, 0.036 mmol, 1.0 eq) in $CH_2Cl_2$ (9.0 mL) and TFA (2.4 mL) was added. The reaction was left overnight at RT and added dropwise to 300 mL of $H_2O$ to precipitate the acid. This suspension was centrifuged in 50 mL batches and then washed and sonicated with $H_2O$. The isolated solid was then dried under high vacuum to give Compound 208 as a colourless solid (108 mg, 77%).

$^1$H NMR (500 MHz, DMSO-$d_6$) δ 12.04 (s, 27H, COOH), 8.23-7.66 (m, 6H, ArH), 7.59-7.41 (m, 3H, ArH), 7.41-7.16 (m, 6H, NH), 6.67-6.34 (m, 6H, NH), 4.45-4.20 (m, 12H, benzylic $CH_2$), 2.81 (s, 6H, ethyl $CH_2$), 2.47 (s, 6H, methyl $CH_3$), 2.28-1.75 (m, 144H, dendrimer $CH_2$), 1.20-1.08 (m, 9H, ethyl $CH_3$);

$^{13}$C NMR (126 MHz, DMSO-$d_6$) δ 174.4, 172.4, 165.7, 158.5, 158.3, 156.0, 155.6, 154.8, 150.6, 142.9, 138.0, 135.4, 135.1, 134.7, 133.9, 133.5, 133.1, 130.2, 129.7, 129.1, 122.9, 78.7, 57.4, 56.4, 30.8, 30.4, 29.0, 28.1 22.4, 16.7, 16.2.

Compound 209

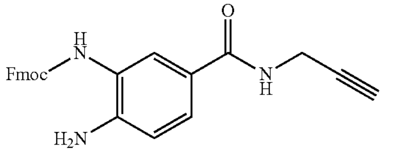

Prepared in an analogous fashion to Compound 2 by treating HBTU activated linker (Compound A1, 14.3 g, 11.8 mmol, 1.0 eq) in $CH_2Cl_2$ (16.5 mL) and DIPEA (2.7 mL, 21 mmol, 1.8 eq) with propargyl amine (1.6 mL, 25 mmol, 2.1 eq) for 72 hours. Purified by column chromatography using ethyl acetate as the eluent to give Compound 209 as colourless solid (2.24 g, 5.4 mmol, 46%).

$^1$H NMR (400 MHz, $CD_3OD$) δ 7.87-7.60 (m, 5H, ArH), 7.57-7.45 (m, 1H, ArH), 7.45-7.23 (m, 4H, ArH), 6.79 (d, J=8.4 Hz, 1H, ArH), 4.45 (br. s, 2H, Fmoc $CH_2$), 4.27 (br. s, 1H, Fmoc CH), 4.11 (d, J=2.5 Hz, 2H, alkyne $CH_2$), 2.56 (p, J=2.5 Hz, 1H, alkyne CH).

HRMS (ESI$^+$) calculated for $C_{25}H_{21}N_3O_3Na^+$: requires 434.1475, found $[M+Na]^+$: 434.1479.

Compounds 210a and 210b

Compound 210a

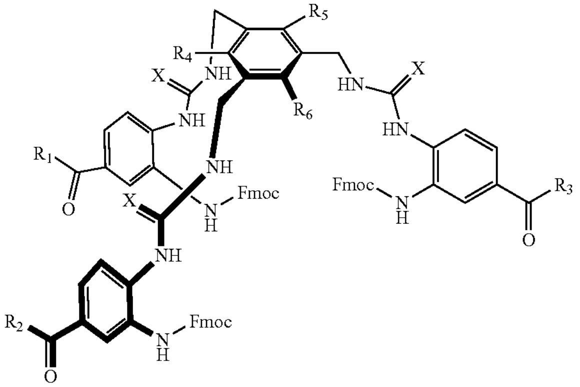

$R_1 = R_2 =$

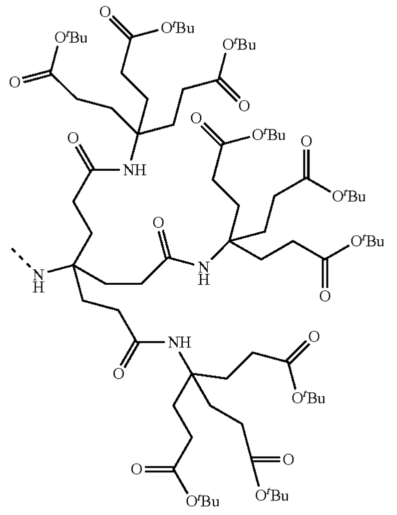

$R_3 =$

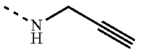

$R_4 = R_5 = R_6 = Et$
X = O

Compound 210b

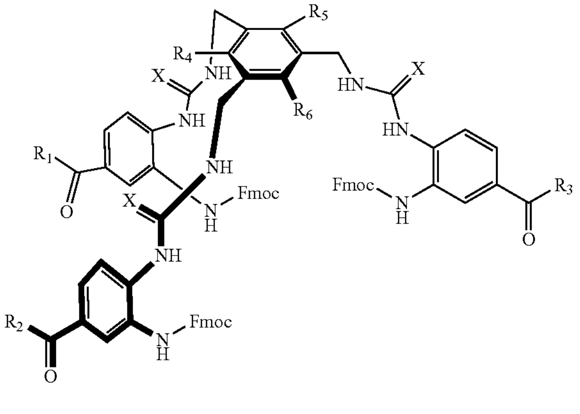

-continued

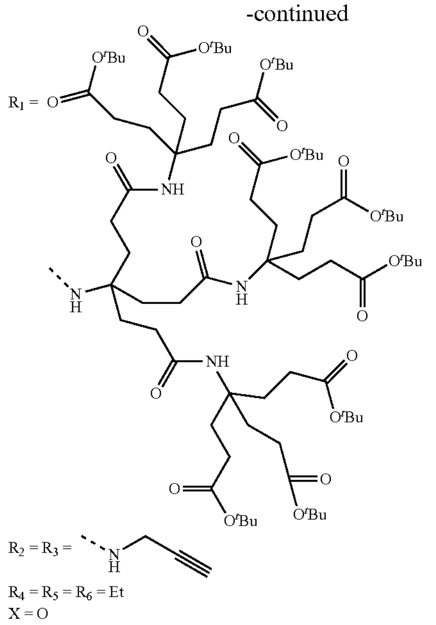

A Schlenk flasked was charged with a stirrer bar, Compound 84 (0.933 g, 0.519 mmol, 1.7 eq) and Compound 5a (0.100 g, 0.305 mmol, 1.0 eq) and dissolved in anhydrous THF (6 mL) and pyridine (0.145 mL, 1.833 mmol, 6.0 eq) then heated to 50° C. for 5 h. Compound 209 (0.189 g, 0.458 mmol, 1.5 eq) was added in one portion and the reaction stirred for a further 12 h. The reaction mixture was transferred to an RBF washing the Schlenk with $CH_2Cl_2$ before concentrating under vacuum. The crude residue obtained was then purified by reverse phase flash chromatography (loaded with MeCN) on a 120 g SNAP Ultra C18 cartridge elution (1CV 85% acetone/$H_2O$, 10 CV 85-95% acetone/$H_2O$, 2CV 95% acetone) to give (fr18-24) identified as Compound 210b a colourless solid (312 mg, 35%), (fr37-47) identified as Compound 210a a colourless solid (524 mg, 40%) and (fr57-60) identified as Compound 108 as colourless solid (354 mg, 20%).

$^1$H NMR Compound 210a (400 MHz, $CDCl_3$) δ 8.06-7.54 (m, 19H, ArH), 7.48-7.11 (14H, m, ArH), 4.60-4.28 (m, 13H, benzylic $CH_2$ and FmocH), 4.23-4.09 (m, 4H, benzylic $CH_2$, FmocH and alkyne $CH_2$), 2.84 (br. s, 6H, ethyl $CH_2$), 2.61 (t, J=2.5 Hz, 1H, alkyne CH), 2.31-1.87 (m, 96H, dendrimer $CH_2$), 1.43 (s, 162H, dendrimer $CH_3$), 1.20 (br. s, 9H, ethyl $CH_3$);

HRMS Compound 210a (Nanospray $ESI^+$) calculated for $C_{239}H_{342}N_{18}O_{54}Na_2^{2+}$: requires 2188.2210, found $[M+2Na]^{2+}$: 2188.2224.

$^1$H NMR Compound 210b (400 MHz, $CDCl_3$) δ 8.01-7.51 (m, 19H, ArH), 7.47-7.07 (m, 14H, ArH), 4.61-4.27 (m, 13H, benzylic $CH_2$ and FmocH), 4.21-4.08 (m, 4H, benzylic $CH_2$, FmocH and alkyne $CH_2$), 2.84 (br. s, 6H, ethyl $CH_2$), 2.61 (t, J=2.5 Hz, 2H, alkyne CH), 2.34-1.82 (m, 48H, dendrimer $CH_2$), 1.44 (s, 81H, dendrimer $CH_3$), 1.19 (br. s, 9H, ethyl $CH_3$);

HRMS Compound 210b (Nanospray $ESI^+$) calculated for $C_{166}H_{213}N_{15}O_{33}Na_2^{2+}$: requires 1495.7634, found $[M+2Na]^{2+}$: 1495.7628.

Compound 211

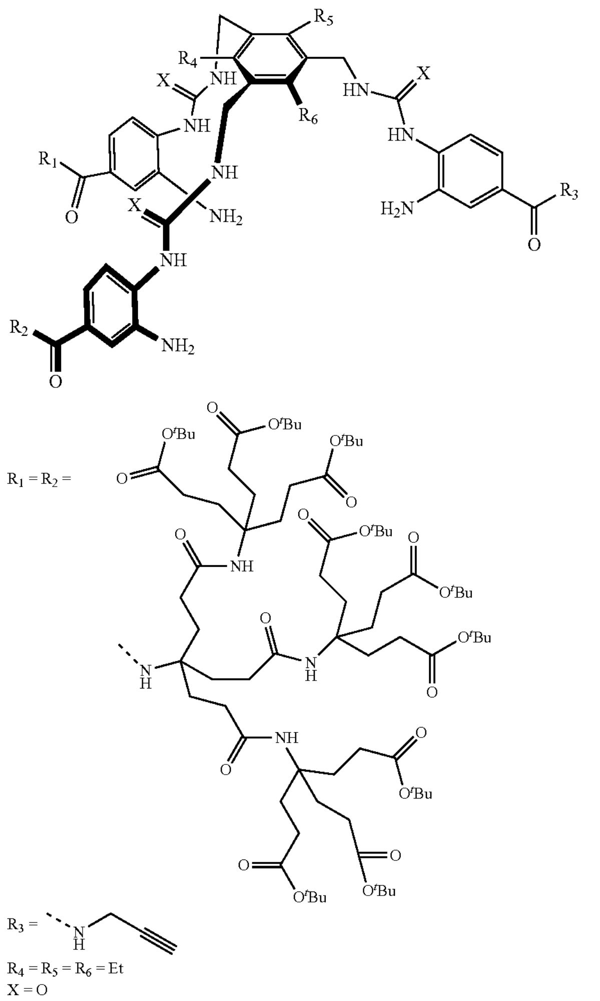

A RBF charged with Compound 210a (0.524 g, 0.121 mmol, 1.0 eq) dissolved in anhydrous $CH_2Cl_2$ (6 mL) under nitrogen was cooled to 0° C. DBU (0.108 mL, 0.726 mmol, 6.0 eq) was added dropwise and the reaction mixture was left for 2 h at 0° C. The reaction mixture was then concentrated under vacuum and purified by normal phase flash chromatography on a SNAP KP-Sil 50 g cartridge (eluting with $CH_2Cl_2$:MeOH 100:0 to 90:10 over 12 CV). This material was then purified by reverse phase chromatography (loaded with MeCN) on a SNAP Ultra C18 60 g cartridge (eluting with Acetone:Water 75:25 to 100:0 over 12 CV) to give Compound 211 as a colourless solid (0.200 g, 0.055 mmol, 45%).

$^1$H NMR (500 MHz, $CD_3OD$) δ 7.69-7.54 (m, 1H, ArH) 7.46-7.32 (m, 3H, ArH), 7.33-7.26 (m, 2H, ArH), 7.23-7.19 (m, 2H, ArH), 7.17-7.12 (m, 1H, ArH), 4.54-4.43 (m, 6H, benzylic $CH_2$) 4.11 (d, J=2.5, 2H, alkyne $CH_2$), 2.88 (m, 6H, ethyl $CH_2$), 2.58 (t, J=2.5, 1H, alkyne CH), 2.32-2.03 (m, 60H, dendrimer $CH_2$), 2.01-1.84 (m, 36H, dendrimer $CH_2$), 1.43 (s, 162H, dendrimer $CH_3$), 1.25 (m, 9H, ethyl $CH_3$);

HRMS (Nanospray $ESI^+$) calculated for $C_{194}H_{315}N_{18}O_{48}^{3+}$: requires 1222.4271, found $[M+3H]^{3+}$: 1222.4281.

Compound 212

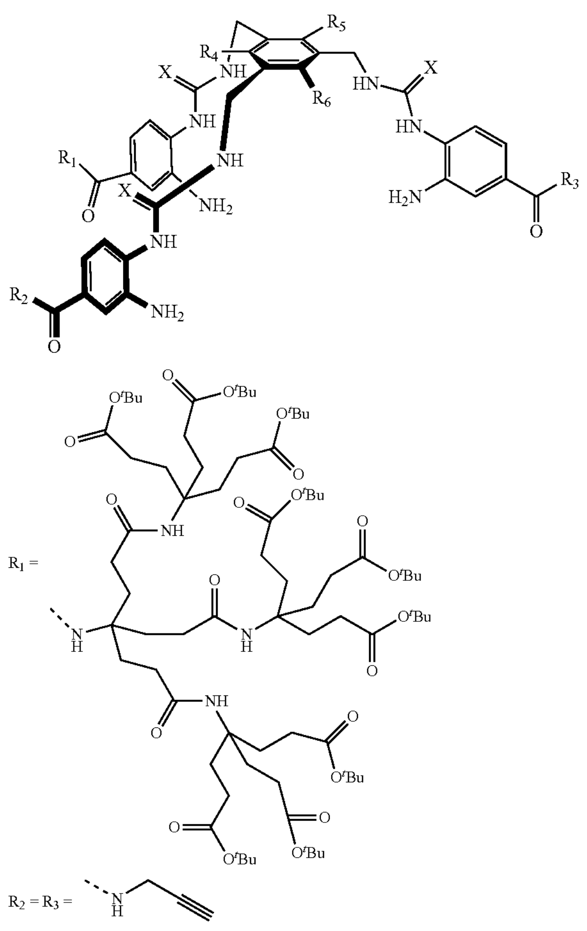

$R_4 = R_5 = R_6 = Et$
$X = O$

Compound 213

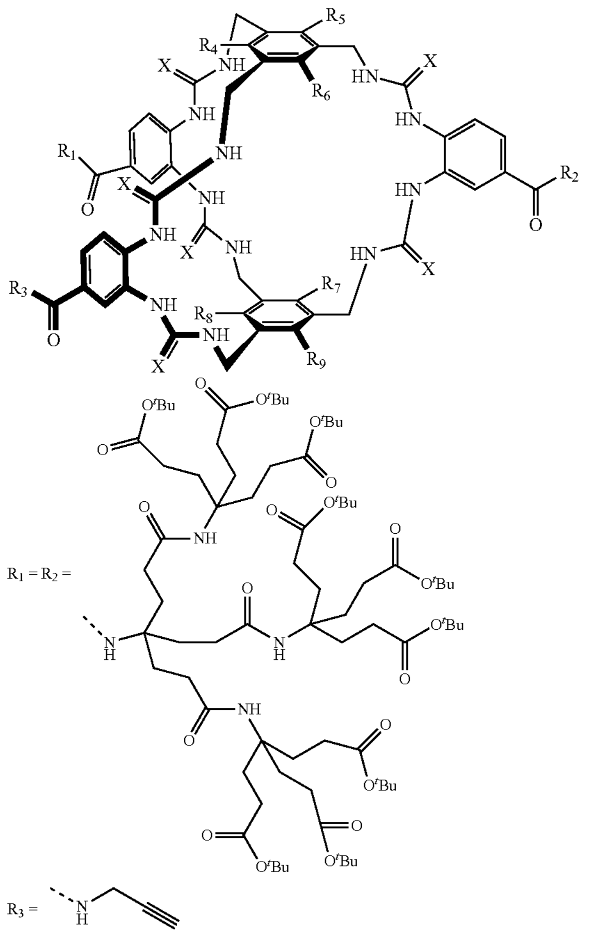

$R_4 = R_5 = R_6 = R_7 = R_8 = R_9 = Et$
$X = O$

A RBF charged with Compound 210b (0.312 g, 0.106 mmol, 1.0 eq) dissolved in anhydrous $CH_2Cl_2$ (5.3 mL) under nitrogen was cooled to 0° C. DBU (0.095 mL, 0.635 mmol, 6.0 eq) was added dropwise and the reaction mixture was left for 2 h at 0° C., The reaction mixture was then concentrated under vacuum and purified by normal phase flash chromatography on a SNAP KP-Sil 50 g cartridge eluting ($CH_2Cl_2$:MeOH 100:0 to 90:10 over 12 CV). This material was then purified by reverse phase chromatography (loaded with MeCN) on a SNAP Ultra 018 60 g cartridge (eluting with Acetone:Water 75:25 to 100:0 over 12 CV) to give Compound 212 as a colourless solid (0.130 g, 0.057 mmol, 54%).

$^1$H NMR (500 MHz, $CD_3OD$) δ 7.71-7.50 (m, 1H, ArH) 7.46-7.32 (m, 3H, ArH), 7.31-7.22 (m, 2H, ArH), 7.22-7.16 (m, 1H, ArH), 7.16-7.06 (m, 2H, ArH), 4.61-4.34 (m, 6H, benzylic $CH_2$) 4.11 (br. s, 4H, alkyne $CH_2$), 2.88 (q, J=7.5, 6H, ethyl $CH_2$), 2.58 (t, J=2.5, 2H, alkyne CH), 2.33-2.04 (m, 30H, dendrimer $CH_2$), 2.02-1.86 (m, 18H, dendrimer $CH_2$), 1.44 (s, 81H, dendrimer $CH_3$), 1.24 (t, J=7.5, 9H, ethyl $CH_3$);

HRMS (Nanospray $ESI^+$) calculated for $C_{121}H_{185}N_{15}O_{27}{}^{2+}$: requires 1140.6798, found $[M+2H]^{2+}$: 1140.6805.

Dissolved Compound 211 (200.0 mg, 0.055 mmol, 1.0 eq) in anhydrous pyridine (22.9 mL) and heated the reaction to 40° C. in a dry syn, external temperature of heat probe set to 40° C. In a separate pear-shaped flask Compound 5a (21.6 mg, 0.066 mmol, 1.2 eq) was dissolved in anhydrous $CH_2Cl_2$ (2.3 mL). The Compound 5a solution was added by syringe pump at 0.85 mL/h. Once the addition was complete the reaction was left overnight at 40° C. The reaction mixture was concentrated under vacuum on a liquid nitrogen cold finger rotary evaporator to dryness. The resulting foam was co-evaporated with toluene twice and the resulting foam purified by reverse phase chromatography (loading in MeCN and eluting on a SNAP Ultra C18 60 g cartridge starting at Acetone:Water 70:30 to 100:0 over 12 CV). Fraction 5-9 contained Compound 213 as a colourless foam (115 mg, 53%).

$^1$H NMR (500 MHz, $CD_3OD$) δ 8.07-7.94 (m, 6H, ArH), 7.68 (d, J=8.4 Hz, 2H, ArH), 7.63 (d, J=8.4 Hz, 1H, ArH), 7.46 (s, 1H, NH), 4.59-4.34 (m, 12H, benzylic $CH_2$), 4.17 (d, J=2.5 Hz, 2H, alkyne $CH_2$), 3.00-2.85 (m, 6H, ethyl $CH_2$), 2.85-2.74 (m, 6H, ethyl $CH_2$), 2.63 (t, J=2.5 Hz, 1H, alkyne CH), 2.36-2.09 (m, 60H, dendrimer $CH_2$), 1.97 (t, J=8.2 Hz, 36H, dendrimer $CH_2$), 1.45 (s, 162H, dendrimer $CH_3$), 1.26-1.18 (m, 18H, dendrimer $CH_3$);

$^{13}$C NMR (126 MHz, $CD_3OD$) δ 175.5, 175.5, 174.4, 169.3, 169.0, 158.4, 158.3, 157.2, 157.2, 144.5, 144.5, 144.4, 137.1, 136.9, 134.3, 134.2, 134.0, 133.8, 131.2, 130.1, 130.1, 129.4, 126.1, 125.9, 125.5, 125.3, 122.7, 122.3, 81.6, 80.8, 72.2, 59.4, 58.8, 58.7, 38.9, 38.8, 38.8, 38.7, 32.4, 32.2, 30.7, 30.4, 28.4, 23.6, 16.8, 16.7, 16.6;

HRMS (Nanospray $ESI^+$) calculated for $C_{212}H_{336}N_{21}O_{51}{}^{3+}$: requires 1331.4802, found $[M+3H]^3$: 1331.4784.

Compound 214-Receptor 5

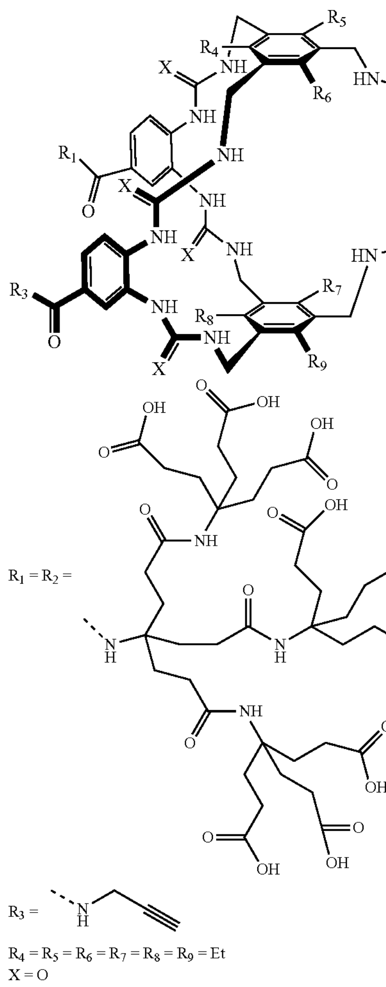

Dissolved Compound 213 (111 mg, 0.028 mmol, 1.0 eq) in $CH_2Cl_2$ (7.0 mL) and TFA (1.9 mL) was added. The reaction was left overnight at RT and added dropwise to 300 mL of $H_2O$ to precipitate the acid. This suspension was centrifuged in 50 mL batches and then washed and sonicated with $H_2O$. The isolated solid was then dried under high vacuum to give Compound 214 as a colourless solid (36 mg, 43%).

$^1$H NMR (500 MHz, DMSO-$d_6$) δ 12.02 (s, 27H, COOH), 8.73 (s, 1H, NH), 8.19-7.67 (m, 6H, ArH), 7.64-7.12 (m, 9H, ArH and NH), 6.48 (s, 3H, NH), 6.39 (s, 3H, NH), 4.52-4.15 (m, 12H, benzylic $CH_2$), 4.11-3.93 (m, 2H, alkyne $CH_2$), 3.34 (s, 6H, NH), 3.09 (s, 1H, alkyne CH), 2.82 (s, 6H, ethyl $CH_2$), 2.66 (s, 6H, ethyl $CH_2$), 2.28-1.62 (m, 144H, dendrimer $CH_2$), 1.26-1.01 (m, 18H, ethyl $CH_3$);

$^{13}$C NMR (126 MHz, DMSO-$d_6$) 174.9, 172.9, 166.0, 165.9, 156.4, 156.1, 155.0, 142.8, 142.7, 135.5, 135.4, 133.9, 133.8, 133.4, 133.3, 129.2, 128.7, 128.4, 127.5, 124.6, 123.9, 123.6, 123.1, 119.9, 119.3, 82.1, 73.1, 57.9, 56.8, 37.6, 37.2, 31.2, 30.8, 29.5, 28.9, 28.6, 22.8, 22.5, 16.8, 16.7.

Compound 215

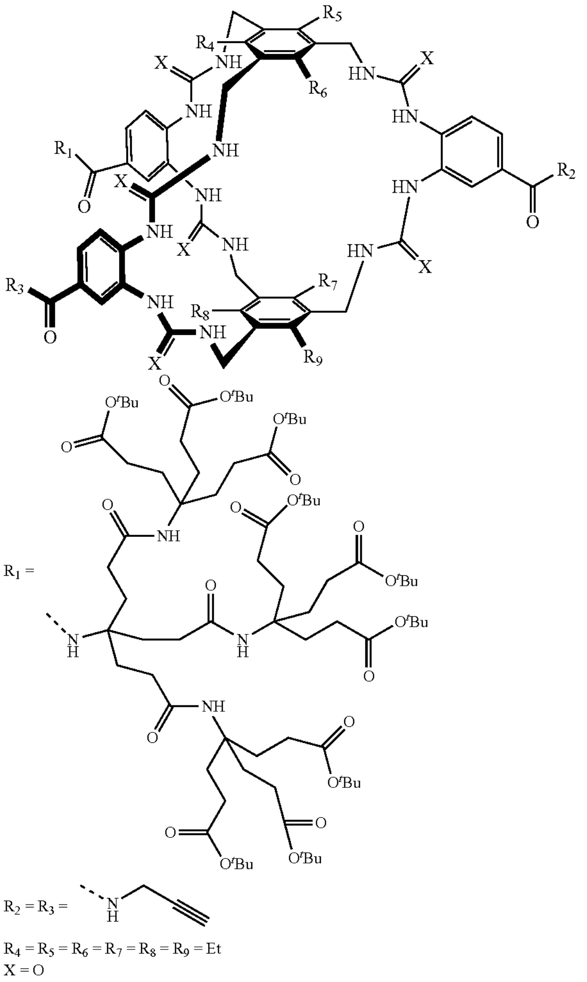

Dissolved Compound 212 (130.0 mg, 0.057 mmol, 1.0 eq) in anhydrous pyridine (23.8 mL) and heated the reaction to 40° C. in a dry syn, external temperature of heat probe set to 40° C. In a separate pear-shaped flask. Compound 5a (22.0 mg, 0.068 mmol, 1.2 eq) was dissolved in anhydrous $CH_2Cl_2$ (2.4 mL). The Compound 5a solution was added by syringe pump at 0.85 mL/h. Once the addition was complete the reaction was left overnight at 40° C. The reaction mixture was concentrated under vacuum on a liquid nitrogen cold finger rotary evaporator to dryness. The resulting foam was co-evaporated with toluene twice and the resulting foam purified by reverse phase chromatography (loading in MeCN and eluting on a SNAP Ultra C18 60 g cartridge starting at Acetone:Water 70:30 to 100:0 over 12 CV). Fraction 3-4 contained Compound 215 as a colourless foam (33 mg, 23%).

$^1$H NMR (500 MHz, $CD_3OD$) δ 8.03 (d, J=2.1 Hz, 2H, ArH), 7.99-7.92 (m, 4H, ArH), 7.66 (dd, J=8.6, 2.1 Hz, 1H, ArH), 7.61 (dd, J=8.6, 2.1 Hz, 2H, ArH), 7.45 (s, 1H, NH), 4.56-4.36 (m, 12H, benzylic $CH_2$), 4.15 (d, J=2.5 Hz, 4H, alkyne $CH_2$), 2.97-2.84 (m, 6H, ethyl $CH_2$), 2.84-2.72 (m, 6H, ethyl $CH_2$), 2.61 (t, J=2.5 Hz, 2H, alkyne CH), 2.32-2.09

(m, 30H, dendrimer $CH_2$), 2.01-1.88 (m, 18H, dendrimer $CH_2$), 1.43 (s, 81H, dendrimer $CH_3$), 1.28-1.13 (m, 18H, ethyl $CH_3$);

$^{13}C$ NMR (126 MHz, $CD_3OD$) δ 175.6, 175.5, 174.4, 169.4, 169.1, 158.4, 158.3, 157.3, 157.2, 144.5, 144.5, 144.5, 137.2, 136.9, 134.3, 134.2, 133.9, 133.8, 131.1, 130.1, 130.1, 129.3, 126.1, 126.0, 125.5, 125.3, 122.7, 122.2, 81.7, 80.8, 72.1, 59.5, 58.8, 58.7, 38.9, 38.8, 38.7, 38.7, 32.4, 32.2, 32.2, 30.7, 30.4, 30.0, 28.4, 23.6, 16.7, 16.6, 16.5;

HRMS (Nanospray $ESI^+$) calculated for $C_{139}H_{206}N_{18}O_{30}{}^{2+}$: requires 1304.2589, found $[M+2H]^{2+}$: 1304.2606.

Compound 216-Receptor 6

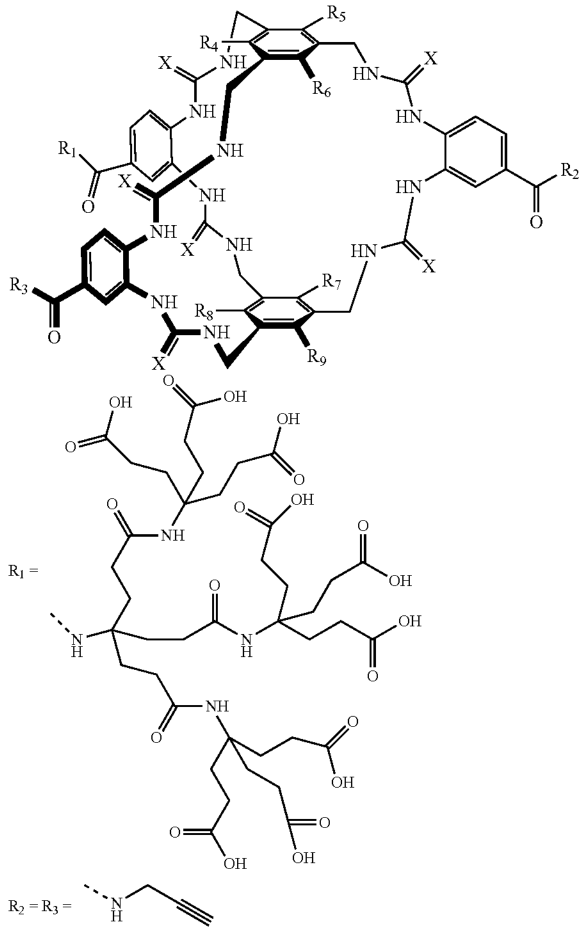

$R_4 = R_5 = R_6 = R_7 = R_8 = R_9 = Et$
X = O

Dissolved Compound 215 (30 mg, 0.012 mmol, 1.0 eq) in $CH_2Cl_2$ (3.0 m:) and TFA (0.81 mL) was added. The reaction was left overnight at RT and added dropwise to 300 mL of $H_2O$ to precipitate the acid. This suspension was centrifuged in 50 mL batches and then washed and sonicated with $H_2O$. The isolated solid was then dried under high vacuum to give Compound 216 as a colourless solid (17 mg, 67%).

$^1H$ NMR (500 MHz, DMSO-$d_6$) 12.03 (s, 27H, COOH), 8.75 (t, J=5.7 Hz, 1H, NH), 8.21-7.93 (m, 6H, ArH), 7.91-7.73 (m, 4H, NH), 7.60-7.42 (m, 3H, ArH), 7.38-7.21 (m, 6H, ArH and NH), 6.46 (s, 3H, NH), 6.37 (s, 3H, NH), 4.52-4.21 (m, 12H, benzylic $CH_2$), 4.03 (d, J=2.5 Hz, 2H, alkyne $CH_2$), 3.10 (t, J=2.5 Hz, 1H, alkyne CH), 2.83 (s, 6H, ethyl $CH_2$), 2.69 (m, 6H, ethyl $CH_2$), 2.18-1.72 (m, 144H, dendrimer $CH_2$), 1.19-1.09 (m, 18H, ethyl $CH_2$);

$^{13}C$ NMR (126 MHz, DMSO-$d_6$) 174.9, 172.9, 166.0, 165.9, 156.3, 156.1, 155.0, 149.3, 142.8, 142.8, 137.6, 135.5, 135.4, 133.9, 133.8, 133., 130.6, 129.2, 128.7, 128.3, 127.5, 124.7, 124.6, 123.9, 123.7, 123.1, 120.4, 119.9, 119.3, 82.1, 73.1, 57.8, 56.8, 37.5, 37.3, 31.2, 30.8, 29.5, 28.9, 28.58, 22.8, 22.5, 16.8, 16.7.

Compound 217

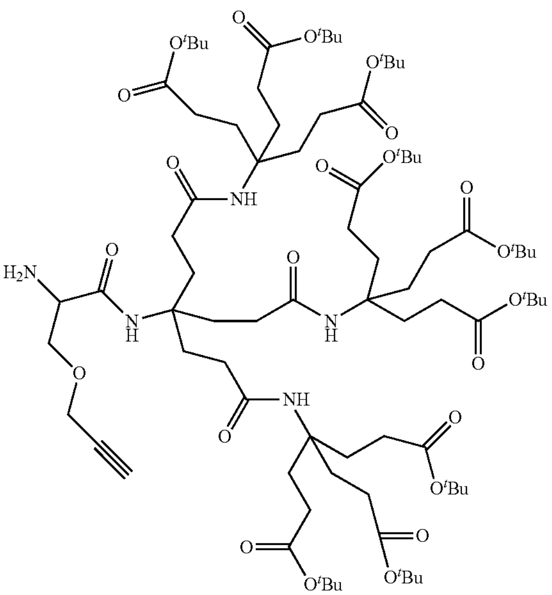

N-Boc-L-serine (5.00 g, 24.4 mmol, 1.0 eq) was dissolved in anhydrous DMF (50 mL), cooled to 0° C. and NaH (2.05 g, 51.1 mmol, 2.1 eq) (60% dispersion in mineral oil) was added. After stirring for 30 min at 0° C., 3-bromopropyne (2.52 mL, 26.7 mmol) (80% solution in toluene) was added dropwise. After stirring at 0° C. for 30 minutes the ice bath was removed and stirring continued overnight at ambient temperature. The solution was dark brown in colour after this time. Aqueous sulfate buffer (16 g $Na_2SO_4$, 2 mL $H_2SO_4$ made up to 150 mL with $H_2O$) was added to the flask gradually to avoid any exotherm generated upon quenching. A precipitate formed and then slowly dissolved to give an orange solution. Brine (150 mL) was added and the reaction mixture extracted with EtOAc (3×150 mL). The combined organics were washed with $H_{20}$ (3×150 mL), dried over MgSO4, filtered and the resulting filtrate concentrated under vacuum. Some DMF was transferred over during this step. Before the organic had completely concentrated silica gel was added and then concentrated to dryness. The silica was then washed with $CH_2Cl_2$ (500 mL) before eluting the desired compound with 10% MeCN/$CH_2Cl_2$ (500 mL) or until fractions did not contain the product (PMA stain, 10% MeCN/$CH_2Cl_2$, streaky black spot 0.3-0.4 $R_f$). The resulting filtrate was concentrated under vacuum to give the desired compound as a yellow gum after drying under high vacuum (4.9 g, 83%). (S)-2-[(tert-butoxycarbonyl)amino]-3-(prop-2-yn-1-yloxy)propanoic acid (2.1 g, 8.6 mmol, 1.0 eq) was dissolved in $CH_2Cl_2$ (33.6 mL) and TFA (33.1 mL) was added. The reaction was stirred at RT until complete by TLC. The reaction mixture was concentrated under vacuum and azeotrope with toluene to give the TFA salt of O-(prop-2-yn-1-yl)serine which was taken directly onto the next step. Dissolved O-(prop-2-yn-1-yl)serine (2.22 g, 8.63 mmol, 1.0 eq) in acetone (14.4 mL) and $H_2O$ (14.4 mL). Sodium carbonate (2.75 g, 25.9 mmol, 3.0 eq) and Fmoc-OSu (3.06 g, 9.07 mmol, 1.05 eq) was added and the reaction left to stir overnight. The reaction mixture was acidified to pH 3 with HCl (3 M) and extracted with EtOAc (3×100 mL). The combined organic phases were dried over $Na_2SO_4$ and the resulting filtrate concentrated under vacuum. The crude residue was purified by column chromatography (eluting with 2.5% MeOH in $CH_2Cl_2$) to give N-(((9H-fluoren-9-yl)methoxy)carbonyl)-O-(prop-2-yn-1-yl)serine as a white solid (2.83 g, 90%). Second generation dendritic amine (Compound 82, 600 mg, 0.417 mmol, 1.0 eq) was dissolved in THF (3.6 mL). N-(((9H-fluoren-9-yl)methoxy)carbonyl)-O-(prop-2-yn-1-yl)serine (183 mg, 0.500 mmol, 1.2 eq), COMU (0.21 g, 0.50 mmol, 1.2 eq), K-Oxyma (90 mg, 0.50 mmol, 1.2 eq) and DIPEA (0.22 mL, 1.25 mmol, 3.0 eq) were then added to the solution. The reaction was left to stir overnight at RT. The reaction was concentrated under vacuum to remove THF. The residue was redissolved in EtOAc (40 mL) and then washed sequentially with $KHSO_4$ (100 mL), sat. $NaHCO_3$ (100 mL) and brine (100 mL). The organic phase was dried over $MgSO_4$, filtered and concentrated under vacuum to give a crude yellow oil. Purification by reverse phase flash chromatography on a SNAP Ultra C18 120 g cartridge (eluting with Acetone:Water 78:22 for 3CV then 91:9 for 4CV) gave the Fmoc-protected intermediate (fr10-13) as an off white solid (602 mg, 81%). To a RBF dried under vacuum by heat-gun was added Fmoc-protected intermediate (1.2 g, 0.67 mmol, 1.0 eq). Anhydrous $CH_2Cl_2$ (33.6 mL) was added and the flask cooled to 0° C. DBU (0.20 mL, 1.3 mmol, 2.0 eq) was added dropwise and the reaction stirred until complete by TLC (5% MeOH/$CH_2Cl_2$, stain with ninhydrin to visualise). The reaction flask was warmed to RT after 2 h. The reaction was concentrated under vacuum and the crude residue purified by reverse phase chromatography on a SNAP Ultra C18 120 g cartridge (eluting with Acetone:Water 75:25 to 100:0 over 12 CV). Fr5-18 contained Compound 217 as a yellow foam (0.95 g, 91%).

$^1H$ NMR (400 MHz, $CD_3OD$) δ 4.58 (br. s, 1H, NH), 4.30-4.15 (m, 2H, alkyne $CH_2$), 3.72 (dd, J=9.2, 5.4 Hz, 1H, serine CHH), 3.63 (dd, J=9.2, 5.4 Hz, 1H, serine CHH), 3.48 (t, J=5.4 Hz, 1H, serine CH), 2.90 (t, J=2.4 Hz, 1H, alkyne CH), 2.29-1.90 (m, 48H, dendrimer $CH_2$), 1.45 (s, 81H, dendrimer $CH_3$);

HRMS ($ESI^+$) calculated for $C_{82}H_{142}N_5O_{23}Na^{2+}$: requires 793.9991, found $[M+H+Na]^{2+}$: 793.9974.

Compound 218

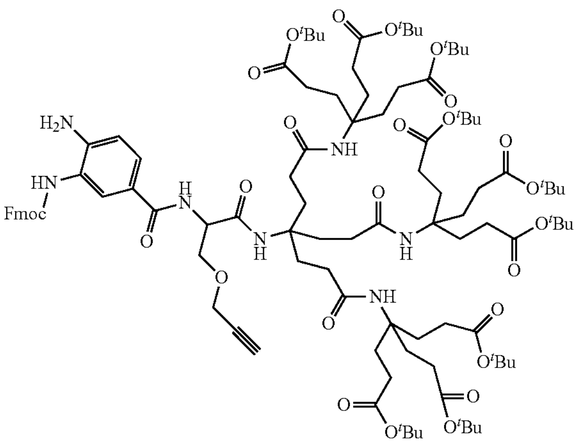

A RBF was dried under vacuum using a heat-gun. Once cool, Compound 217 (0.45 g, 0.29 mmol, 1.0 eq) and HBTU activated linker (0.21 g, 0.35 mmol, 1.2 eq) were added and suspended in anhydrous THF (1.44 mL). DIPEA (0.08 mL, 0.46 mmol, 1.6 eq) was then added and the reaction stirred overnight at RT. The reaction was heterogenous initially and became a homogeneous (dark brown) solution after 16 h at RT. The reaction was concentrated under vacuum and purified by reverse phase flash chromatography on a SNAP Ultra C18 120 g cartridge (eluting with Acetone:Water 66:34 for 3CV then 88:12 for 5CV). Fr7-11 contained the Compound 218 as a yellow solid (441 mg, 80%).

$^1H$ NMR (400 MHz, $CD_3OD$) δ 7.80-7.42 (m, 6H, ArH), 7.41-7.07 (m, 4H, ArH), 6.72 (d, J=8.5 Hz, 1H, ArH), 4.47 (d, J=5.3 Hz, 1H, serine CH), 4.39 (br. s, 2H, Fmoc $CH_2$), 4.19 (br. s, 1H, Fmoc CH), 4.17-4.07 (t, J=2.4 Hz, 2H, alkyne $CH_2$), 3.83 (dd, J=9.6, 5.3 Hz, 1H, serine CHH), 3.75 (dd, J=9.6, 5.3 Hz, 1H, serine CHH), 2.81 (t, J=2.4 Hz, 1H, alkyne CH), 2.17-1.73 (m, 48H, dendrimer $CH_2$), 1.32 (s, 81H, dendrimer $CH_3$);

HRMS ($ESI^+$) calculated for $C_{104}H_{157}N_7O_{26}Na_2^{2+}$: requires 983.5497, found $[M+2Na]^{2+}$: 983.5496.

Compound 219

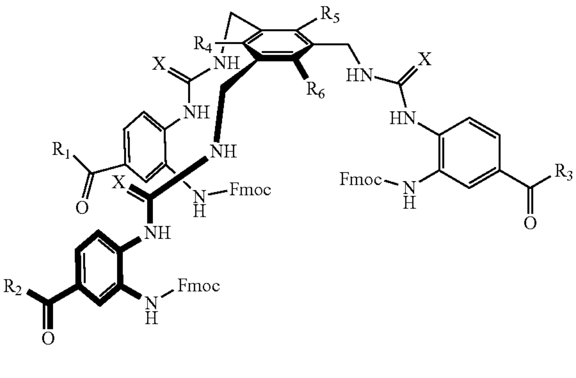

-continued

R1 = R2 = R3 =

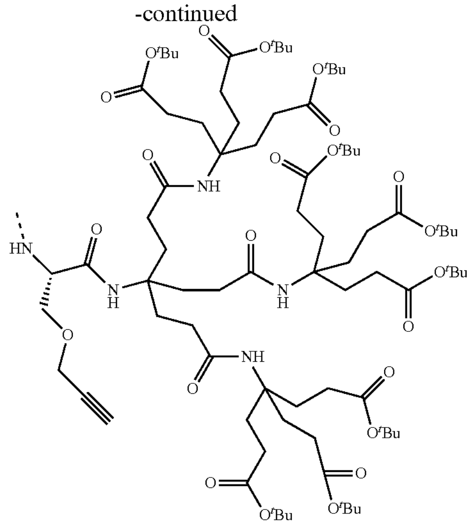

R4 = R5 = R6 = Et
X = O

-continued

R1 = R2 = R3 =

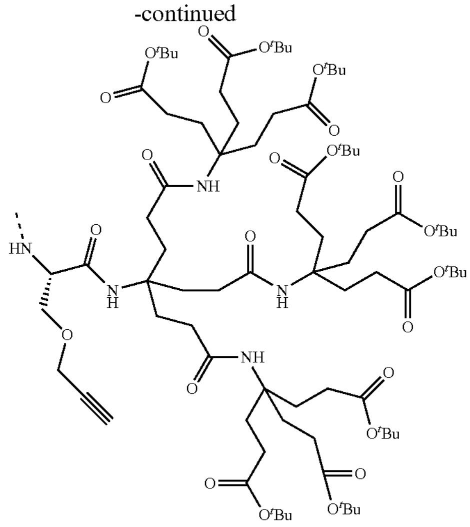

R4 = R5 = R6 = Et
X = O

Compound 218 (0.64 mg, 0.33 mmol, 3.5 eq) was concentrated into a pear-shaped flask and dried through azeotropic distillation with anhydrous toluene (5 mL) followed by drying under high vacuum for 30 min. The resulting residue was dissolved in anhydrous $CH_2Cl_2$ (4.7 mL), Compound 5a (31 mg, 0.095 mmol, 1.0 eq) and pyridine (0.046 mL, 0.57 mmol, 6.0 eq) were added and the reaction heated to 34° C. for 12 h. The reaction mixture was concentrated under vacuum and the resulting residue purified by flash column chromatography on a SNAP Ultra C18 120 g cartridge (eluting with Acetone:Water 70:30 to 95:5 over 12CV). Fr1-8 recovered Compound 218 and fr11-14 contained Compound 219 as an off-white solid (476 mg, 83%).

$^1$H NMR (400 MHz, $CD_3OD$) δ 7.93-7.36 (m, 19H, ArH), 7.34-7.05 (m, 14H, ArH), 4.49 (t, J=5.0 Hz, 3H, serine CH), 4.38 (br. s, 6H, benzylic $CH_2$), 4.27 (br. s, 6H, Fmoc $CH_2$), 4.15 (t, J=2.2 Hz, 6H, alkyne $CH_2$), 4.07 (s, 3H, Fmoc CH), 3.84 (dd, J=9.6, 5.0 Hz, 3H, serine CHH), 3.76 (dd, J=9.6, 5.0 Hz, 3H, serine CHH), 2.81 (t, J=2.2 Hz, 1H, alkyne CH), 2.74 (br. s, 6H, ethyl $CH_2$), 2.22-1.71 (m, 144H, dendrimer $CH_2$), 1.32 (s, 243H, dendrimer $CH_3$), 1.09 (t, J=7.4 Hz, 9H, ethyl $CH_3$).

HRMS (Nanospray ESI) calculated for $C_{330}H_{496}N_{24}O_{81}^{4+}$: requires 1523.6382, found $[M+4H]^{4+}$: 1523.6409.

A RBF charged with Compound 219 (0.451 g, 0.074 mmol, 1.0 eq) dissolved in anhydrous $CH_2Cl_2$ (3.7 mL) under nitrogen and cooled to 0° C. DBU (0.066 mL, 0.444 mmol, 6.0 eq) was added dropwise and the reaction mixture was left for 2 h at 0° C. The reaction mixture was then concentrated under vacuum and purified by reverse phase flash chromatography on a SNAP Ultra C18 60 g cartridge (eluting with Acetone:Water 70:30 to 100:0 over 12 CV). Fr3-7 contained Compound 220 as a colourless solid (0.279 g, 69%).

$^1$H NMR (400 MHz, $CD_3OD$) δ 7.37 (d, J=8.3 Hz, 3H, ArH), 7.24 (d, J=2.1 Hz, 3H, ArH), 7.15 (dd, J=8.2, 2.1 Hz, 3H, ArH), 4.48 (t, J=5.3 Hz, 3H, serine CH), 4.42 (br. s, 6H, benzylic $CH_2$), 4.25-4.10 (m, 6H, alkyne $CH_2$), 3.84 (dd, J=9.6, 5.3 Hz, 3H, serine CHH), 3.76 (dd, J=9.6, 5.3 Hz, 3H, serine CHH), 2.83 (t, J=2.4 Hz, 3H, alkyne CH), 2.80 (q, J=6.1 Hz, 6H, ethyl $CH_2$), 2.20-1.73 (m, 144H, dendrimer $CH_2$), 1.34 (s, 243H, dendrimer $CH_3$), 1.22-1.12 (m, 9H, ethyl $CH_2$).

$^{13}$C NMR (126 MHz, $CD_3OD$) δ 175.4, 174.4, 171.6, 170.4, 157.8, 145.1, 141.4, 133.9, 131.4, 130.5, 124.4, 119.0, 117.4, 81.7, 80.4, 77.0, 70.4, 59.4, 59.4, 58.7, 56.2, 39.3, 32.2, 32.1, 30.7, 30.5, 28.5, 23.9, 17.0;

HRMS (Nanospray $ESI^+$) calculated for $C_{285}H_{466}N_{24}O_{75}^{4+}$: requires 1357.0870, found $[M+4H]^{4+}$: 1357.0824.

Compound 220

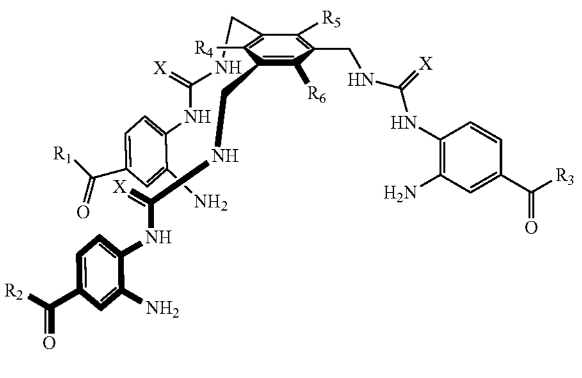

Compound 221

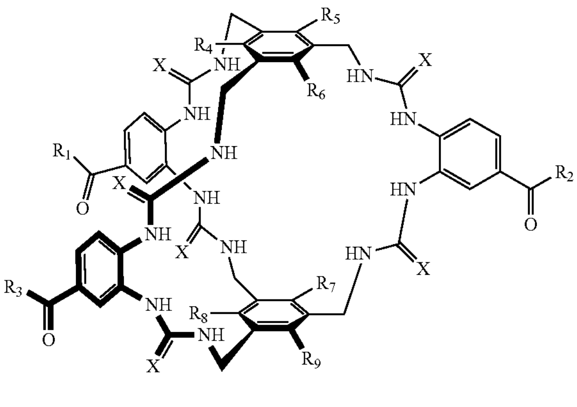

-continued

R1 = R2 = R3 =

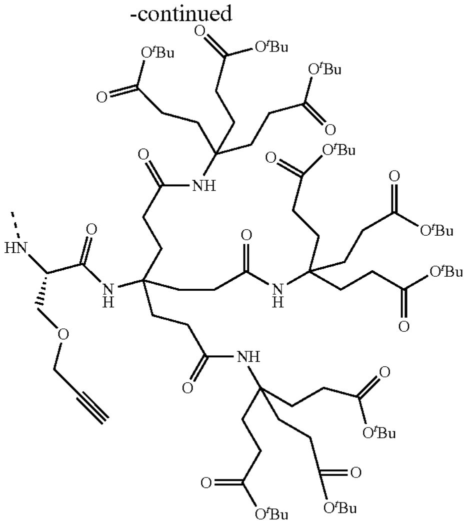

$R_4 = R_5 = R_6 = R_7 = R_8 = R_9 = Et$
X = O

Compound 220 (265.0 mg, 0.049 mmol, 1.0 eq), DMAP (18 mg, 0.147 mmol, 3.0 eq) and n-octyl glucoside (29 mg, 0.098 mmol, 2.0 eq) were weighed into a round bottom flask and anhydrous toluene was added. This was removed in situ under high vacuum. Procedure repeated, and the resulting foam allowed to dry for 30 min. The reagents were then dissolved in anhydrous $CH_2Cl_2$ (98 mL) and heated to 34° C. In a separate dried RBF, Compound 5a (19.2 mg, 0.059 mmol, 1.2 eq) was weighed into a flask and dissolved in anhydrous $CH_2Cl_2$ (9.8 mL).

This solution was then syringe pumped into the reaction mixture at 1 mL/hr. After completion, the reaction was left for a further 24 h at 34° C. The reaction mixture was cooled and concentrated under vacuum. Purification by reverse phase flash chromatography on a SNAP Ultra C18 120 g column (eluting with Acetone:Water 70:30 to 100:0 over 12 CV). Fr1-8 were taken and purified by prep HPLC (C18 20×150 mm, 5 μm, 20 mL/min, Acetone:Water 70:30 to 100:0 over 30 min). Analysis at this stage was difficult because of the presence of n-octyl glucose (110 mg, 39%). Mass spec confirmed material obtained after prep HPLC contained Compound 221.

HRMS (Nanospray $ESI^+$) calculated for $C_{303}H_{487}N_{27}O_{78}^{4+}$: requires 1438.6254, found $[M+4H]^{4+}$: 1438.6232.

Compound 222-Receptor 7

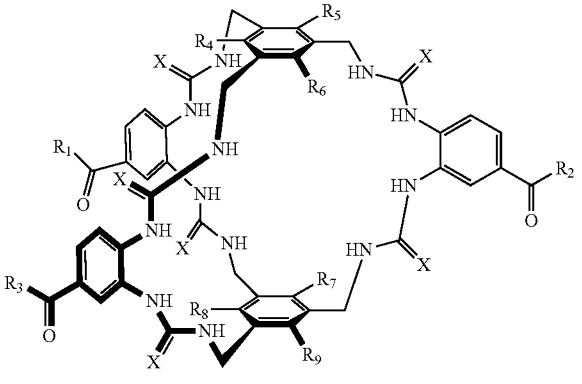

-continued

R1 =

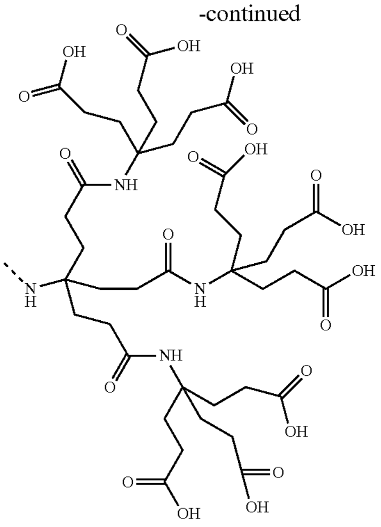

R2 = R3 =

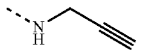

$R_4 = R_5 = R_6 = R_7 = R_8 = R_9 = Et$
X = O

Compound 221 (110 mg, 0.019 mmol, 1.0 eq) was dissolved in $CH_2Cl_2$ (4.8 mL) and TFA (1.3 mL) was added. The reaction was left overnight at RT and then concentrated under vacuum. Purification by reverse phase flash chromatography on a SNAP Ultra C18 30 g column (eluting with MeOH:Water+0.1% formic acid 10:90 to 100:0 over 12 CV). Fr30-32 were taken and purified by prep HPLC (C18 20×150 mm, 5 μm, 20 mL/min, MeOH:Water+0.1% formic acid 10:90 to 100:0 over 30 min) gave Compound 222 as a colourless solid (30 mg, 37%).

$^1H$ NMR (400 MHz, $CD_3OD$) δ 8.46 (s, 3H, NH), 8.17 (s, 3H, ArH), 8.02 (d, J=8.5 Hz, 3H, ArH), 7.62 (d, J=8.5 Hz, 3H, ArH), 4.65 (t, J=5.4 Hz, 3H, serine CH), 4.53-4.33 (m, 12H, benzylic $CH_2$), 4.37-4.23 (m, 6H, alkyne $CH_2$), 4.10-3.84 (m, 6H, serine $CH_2$), 2.98 (t, J=2.4 Hz, 3H, alkyne CH), 2.76 (s, 6H, ethyl $CH_2$), 2.69 (s, 6H, ethyl $CH_2$), 2.48-1.68 (s, 144H, dendrimer $CH_2$), 1.41-1.00 (m, 18H, ethyl $CH_3$);

$^{13}C$ NMR (126 MHz, $CD_3OD$) δ 182.8, 175.2, 175.0, 170.6, 170.0, 160.8, 157.4, 156.8, 144.2, 132.3, 131.9, 128.3, 127.8, 124.4, 68.7, 58.3, 58.2, 54.7, 37.6, 31.6, 30.8, 30.6, 22.6, 22.3, 15.4.

Compound 223

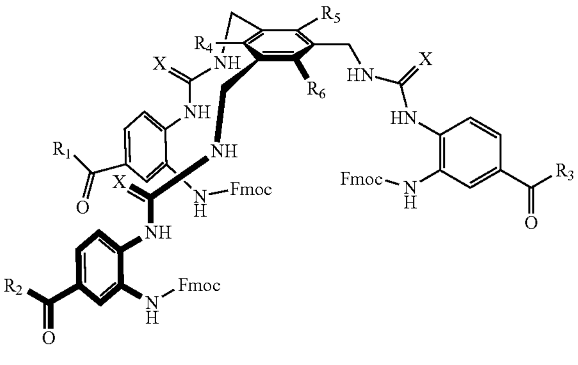

-continued

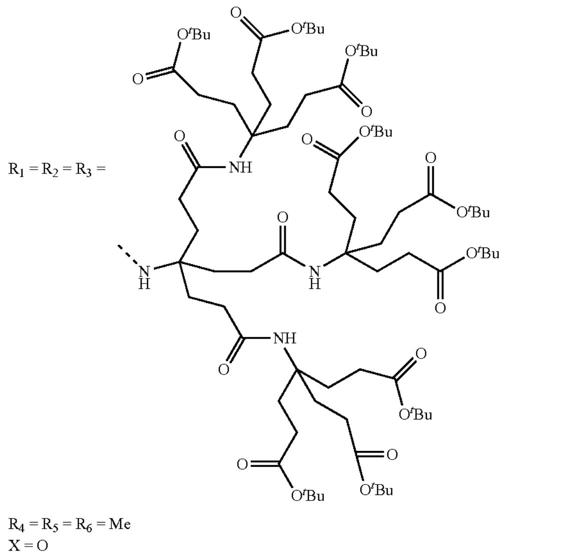

A pre-dried Schlenk tube was charged with Compound 84 (441 mg, 0.245 mmol) under a flow of nitrogen and a solution of Compound 5c (20 mg, 0.070 mmol) in THF (0.5 mL) added. Dry THF (3.5 mL) and anhydrous pyridine (0.006 mL, 0.070 mmol) was added. The reaction was stirred for 16 h at 50° C. The reaction mixture was concentrated to dryness and the crude residue purified by reverse phase MPLC on a 120 g SNAP Ultra C18 cartridge elution (70-95% acetone/$H_2O$) to give a Compound 223 white solid (197 mg, 0.035 mmol, 50%).

HRMS (Nanospray ESI) calculated for $C_{309}H_{469}N_{21}O_{75}^{4+}$: requires 1419.3407, found $[M+4H]^{4+}$: 1419.3391.

-continued

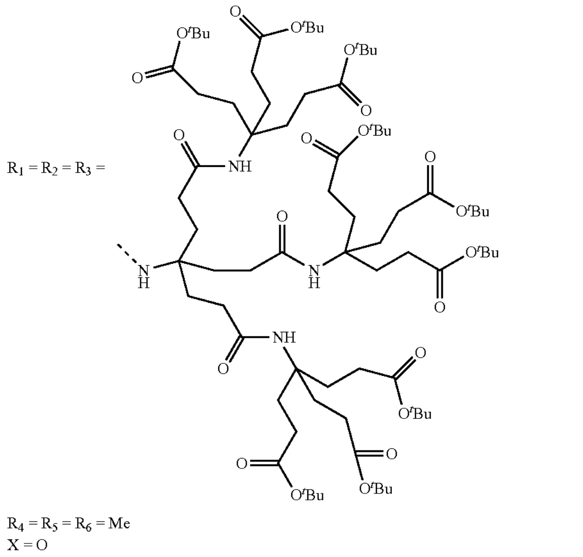

Prepared in a manner analogous to Compound 7b from Compound 223 (0.097 g, 0.017 mmol). Purified by reverse phase flash chromatography on a 120 g SNAP Ultra C18 cartridge elution (1CV 80% acetone/$H_2O$, 10 CV 80-95% acetone/$H_2O$, 2CV 95% acetone) to give a white solid (0.072 g, 0.014 mmol, 85%).

$^{1}H$ NMR (500 MHz, methanol-$d_4$) δ m. 7.42-7.30 (3H, C$\underline{H}$CNH (Ar)) m. 7.31-7.29 C$\underline{H}$CNH$_2$ (Ar)), m. 7.23-7.19 (3H, C$\underline{H}$CHCNH (Ar)), m. 4.54-4.48 (6H, ArC$\underline{H}_2$NH), s. 2.49 (6H, ArC$\underline{H}_3$), s. (3H, ArC$\underline{H}_3$), m. 2.28-1.90 (144H, NHC$\underline{H}_2$C$\underline{H}_2$C(O)), s. 1.44 (243H, $CO_2C(C\underline{H}_3)_3$).

$^{13}C$ NMR (125 MHz, methanol-$d_4$) δ 175.5 ($\underline{C}$ONH), 174.4, 174.3 ($\underline{C}O_2C(CH_3)_3$), 170.1 (Ar$\underline{C}$ONHR), 158.1 (NH $\underline{C}$(O)NH), 141.3 ($\underline{C}NH_2$), 135.4 ($\underline{C}CO_2$NHR), 134.7 ($\underline{C}$NHC(O)NH), 130.0 ($\underline{C}CH_3$), 124.4, 118.9 (CH$\underline{C}$HCNH), 117.4 ($\underline{C}HCNH_2$), 111.4 ($\underline{C}CH_2$NHC(O)NH), ($\underline{C}(CH_2CH_2CONH)_3$), 81.6 ($CO_2\underline{C}(CH_3)_3$), 58.7, ($\underline{C}(CH_2CH_2CO_2)_3$), 40.3 (Ar$\underline{C}H_2$NHC(O)NH), 32.5 ($CH_2\underline{C}H_2CO_2C(CH_3)_3$), 32.2 ($CH_2\underline{C}H_2$CONH), 30.7 ($\underline{C}H_2CH_2$CONH), 30.5, ($\underline{C}H_2CH_2CO_2C(CH_3)_3$), 28.4 ($CO_2C(\underline{C}H_3)_3$), 16.3 (Ar$\underline{C}H_3$).

Compound 224

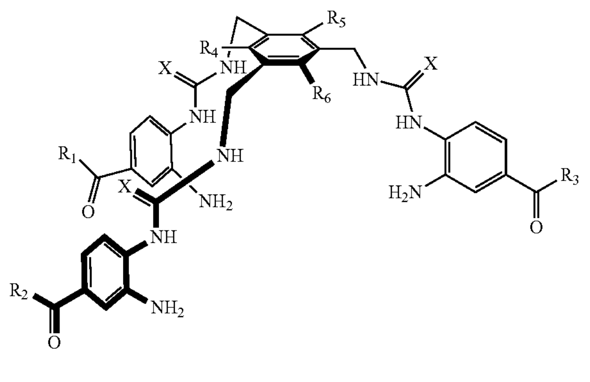

Compound 225

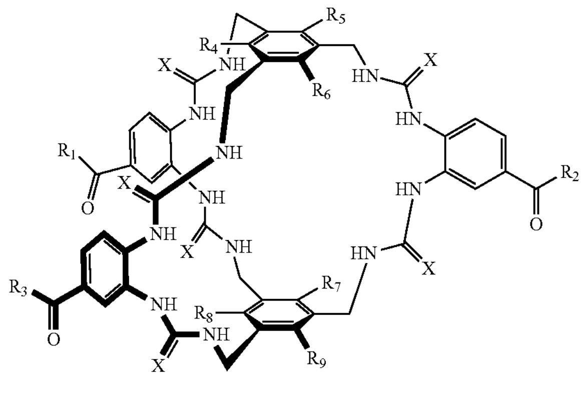

-continued $R_1 = R_2 = R_3 =$

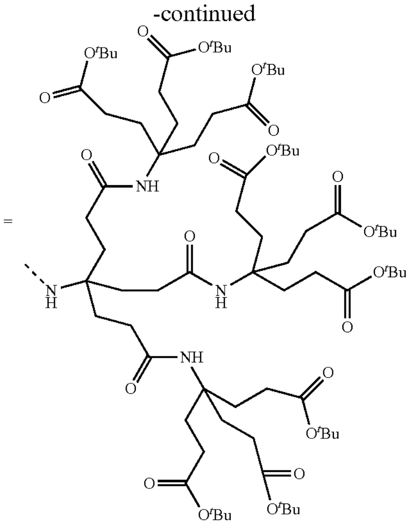

$R_4 = R_5 = R_6 = R_7 = R_8 = R_9 = Me$
X = O

Dissolved Compound 224 (200 mg, 0.040 mmol, 1.0 eq) in anhydrous pyridine (16.8 mL) and heated the reaction to 40° C. in a dry syn, external temperature of heat probe set to 40° C. In a separate pear-shaped flask Compound 5c (13.7 mg, 0.048 mmol, 1.2 eq) was dissolved in anhydrous $CH_2Cl_2$ (1.7 mL). The Compound 5c solution was added by syringe pump at 0.85 mL/h. Once the addition was complete the reaction was left overnight at 40° C. The reaction mixture was concentrated under vacuum on a liquid nitrogen cold finger rotary evaporator to dryness. The resulting foam was co-evaporated with toluene twice and the resulting foam purified by reverse phase chromatography (loading in MeCN and eluting on a SNAP Ultra C18 60 g cartridge starting at Acetone:Water 70:30 to 100:0 over 12 CV). Fraction 4-6 contained Compound 225 as a colourless foam (127 mg, 60%).

$^1H$ NMR (500 MHz, $CD_3OD$) δ 8.07 (s, 2H, NH), 7.95 (s, 3H, ArH), 7.89 (br. s, 3H, ArH), 7.66 (d, J=8.6 Hz, 3H, ArH), 7.44 (s, 6H, NH), 4.51 (s, 6H, benzylic $CH_2$), 4.45 (s, 1H, benzylic $CH_2$), 2.49 (s, 9H, methyl $CH_3$), 2.43 (s, 9H, methyl $CH_3$), 2.32-1.91 (m, 144H, dendrimer $CH_2$), 1.43 (s, 243H, dendrimer $CH_3$).

$^{13}C$ NMR (126 MHz, $CD_3OD$) δ 175.5, 174.4, 169.4, 158.6, 157.6, 137.5, 137.4, 135.1, 134.7, 131.4, 129.9, 126.0, 122.6, 81.6, 59.5, 58.8, 40.2, 40.0, 32.5, 32.2, 30.7, 30.5, 28.5, 16.7, 16.3.

HRMS (Nanospray $ESI^+$) calculated for $C_{279}H_{450}N_{24}O_{72}Na_4^{4+}$: requires 1345.7981, found $[M+4Na]^{4+}$: 1345.7994.

-continued $R_1 = R_2 = R_3 =$

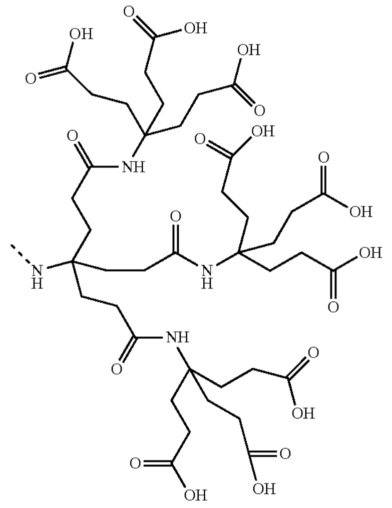

$R_4 = R_5 = R_6 = R_7 = R_8 = R_9 = Me$
X = O

Dissolved Compound 225 (120 mg, 0.023 mmol, 1.0 eq) in $CH_2Cl_2$ (5.8 mL) and TFA (1.5 mL) was added. The reaction was left overnight at RT and added dropwise to 300 mL of $H_2O$ to precipitate the acid. This suspension was centrifuged in 50 mL batches and then washed and sonicated with $H_2O$. The isolated solid was then dried under high vacuum to give Compound 226 as a colourless solid (80 mg, 91%).

$^1H$ NMR (500 MHz, DMSO-$d_6$) δ 12.04 (s, 27H, COOH), 8.00 (s, 3H, ArH), 7.93 (d, J=8.5 Hz, 3H, ArH), 7.78 (s, 3H, NH), 7.73 (s, 3H, NH), 7.54 (d, J=8.5 Hz, 3H, ArH), 7.41 (s, 3H, NH), 7.27 (s, 9H, NH), 6.54 (s, 3H, NH), 6.44 (s, 3H, NH), 4.36 (s, 12H, benzylic $CH_2$), 2.42 (s, 9H, methyl $CH_3$), 2.35 (s, 9H, methyl $CH_3$), 2.25-1.71 (m, 144H, dendrimer $CH_2$).

$^{13}C$ NMR (126 MHz, DMSO-$d_6$) δ 174.9, 172.8, 166.0, 156.6, 155.2, 135.9, 129.4, 128.8, 124.8, 123.7, 119.7, 67.5, 57.9, 56.8, 31.2, 30.8, 29.5, 28.5, 16.3.

Compound 226-Receptor 8

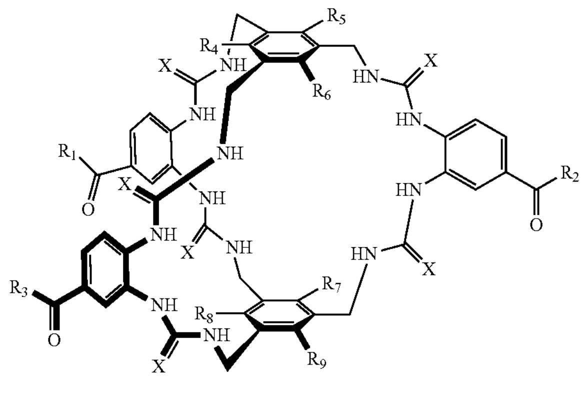

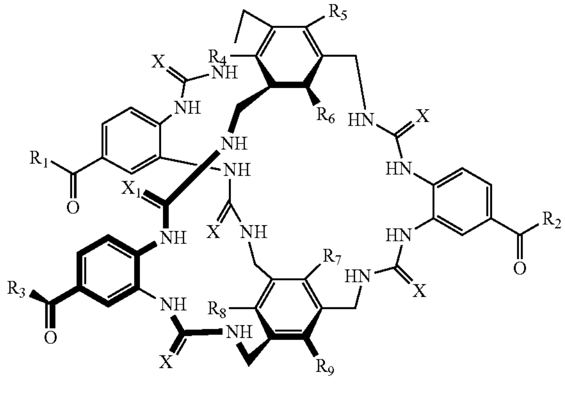

-continued $R_4 = R_5 = R_6 = Et$
$R_7 = R_8 = R^9 = H$
$X = O$ $R_1 = R_2 = R_3 =$

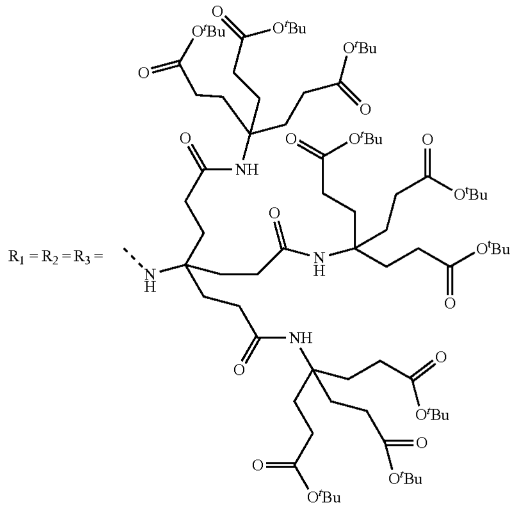

A Schlenk flask equipped with a magnetic stirrer was charged with Compound 108 (200 mg, 0.04 mmol, 1.0 eq), DMAP (14.5 mg, 0.12 mmol, 3.0 eq) and n-octyl glucoside (23.2 mg, 0.08 mmol, 2.0 eq) dissolved in anhydrous $CH_2Cl_2$ (40 mL) and then warmed to 34° C. A solution of 1,3,5-triisocyanatobenzene (12.5 mg, 0.051 mmol) in toluene (ca. 85% purity) was added to the flask and the reaction was left for 16 h. The solvent was removed under vacuum and the crude product was purified by reverse phase MPLC on a C18 SNAP Ultra 60 g cartridge (eluting with Acetone: Water 70:30 to 100:0 over 12CV) giving Compound 227 as a white solid (67 mg, 0.012 mmol, 32%).

$^1H$ NMR (500 MHz, $CD_3OD$) δ 8.11 (d, J=8.6 Hz, 3H, ArH), 7.76-7.69 (m, 6H, ArH), 7.14 (s, 3H, ArH), 4.43 (s, 6H, benzylic $CH_2$), 4.29 (s, 6H, benzylic $CH_2$), 2.80-2.70 (m, 6H, ethyl $CH_2$), 2.31-1.86 (m, 144H, dendrimer $CH_2$), 1.43 (s, 243H, dendrimer $CH_3$), 1.21 (t, J=7.4 Hz, 9H, ethyl $CH_3$).

HRMS ($ESI^+$) calculated for $C_{279}H_{450}N_{24}O_{72}Na_4^{4+}$: requires 1345.7981, found $[M+4Na]^{4+}$: 1345.7985.

-continued $R_4 = R_5 = R_6 = R_7 = R_8 = R^9 = Et$
$X = O$ $R_1 = R_2 = R_3 =$

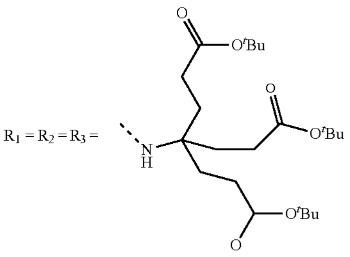

A 50 mL flask, equipped with a magnetic stirrer and a tapped gas adapter, was charged with Compound 13 (89 mg, 0.045 mmol). Compound 13 was placed under vacuum for 5 min, then placed under nitrogen. The Compound 13 was dissolved in dry pyridine (20 mL, 0.002 M), and the solution heated to 40° C. A solution of Compound 103 (16 mg, 0.050 mmol) in dry dichloromethane (1.0 mL, 0.050 M) was added at a rate of 0.1 mL/h. The reaction stirred for a further 12 h at 40° C. before being concentrated under vacuum. The residue was purified by reverse phase flash chromatography on a 60 g SNAP Ultra C18 cartridge elution (1 CV 60% acetone/water, 10 CV 60-100% acetone/water, 6 CV 100% acetone).

$^1H$ NMR (500 MHz, $CD_3OD$) δ 7.99 (d, J=8.5, 3H, ArH), 7.95 (d, J=2.1, 3H, ArH), 7.62 (s, 3H, RNHCO), 7.53 (dd, J=8.6, 2.1, 3H, ArH), 4.48 (s, 6H, BnH), 4.41 (s, 6H, BnH), 2.85 (q, J=7.5, 6H, $CH_2CH_3$), 2.75 (q, J=7.5, 6H, $CH_2CH_3$), 2.28 (t, J=8.0, 18H, $CCH_2CH_2$), 2.10 (t, J=8.0, 18H, $CCH_2CH_2$), 1.45 (s, 81H, $^tBuH$), 1.21 (t, J=7.4, 18H, $CH_2CH_3$).

$^{13}C$ NMR (126 MHz, $CD_3OD$) δ 208.96 (C), 173.18 (C), 168.38 (C), 156.81 (C), 155.83 (C), 143.16 (C), 143.10 (C), 134.95 (C), 132.69 (C), 132.24 (C), 129.85 (C), 127.95 (C), 123.89 (CH), 123.46 (CH), 120.73 (CH), 80.34 (C), 58.34 (C), 37.39 ($CH_2$), 29.42 ($CH_2$), 29.19 ($CH_2$), 26.98 ($CH_3$), 22.25 ($CH_2$), 15.25 ($CH_3$), 15.22 ($CH_3$).

HRMS (Nanospray) calculated for $C_{123}H_{185}N_{15}O_{27}$: requires 1152.6793, found $[M+2H]^{2+}$: 1152.6798.

Compound 228

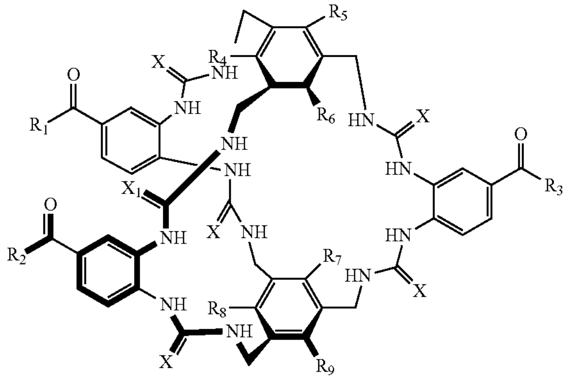

Compound 229-Receptor 9

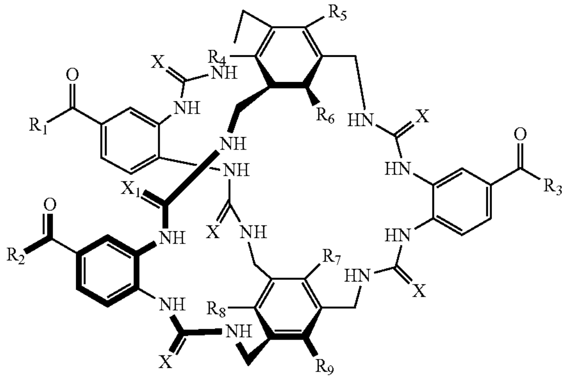

-continued $R_4 = R_5 = R_6 = R_7 = R_8 = R^9 = Et$
X = O $R_1 = R_2 = R_3 =$ 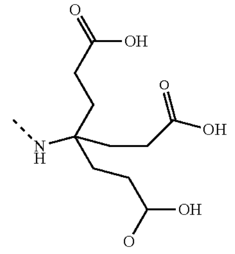

A 10 mL flask, equipped with a magnetic stirrer, was charged with Compound 228 (27 mg, 0.012 mmol). Compound 228 was dissolved in dichloromethane (2.9 mL, 0.004 M) before trifluoroacetic acid was added. The reaction stirred for 12 h at rt. The reaction mixture was dripped into rapidly stirring water (150 mL) which resulted in the formation of a white precipitate. The precipitate was centrifuged out and dissolved in acetone. After being transferred to a round bottomed flask, the acetone was removed under vacuum, and the white solid azeotroped with toluene.

$^1$H NMR (600 MHz, $D_2O$) δ 7.86 (s, 3H, ArH), 7.76 (d, J=8.5, 3H, ArH), 7.52 (d, J=8.5, 3H, ArH), 4.44 (s, 12H, BnH), 2.84-2.64 (m, 12H, $CH_2CH_3$), 2.29-2.16 (m, 18H, $CCH_2CH_2$), 2.15-2.01 (m, 18H, $CCH_2CH_2$), 1.24-1.10 (m, 18H, $CH_2CH_3$).

$^{13}$C NMR (126 MHz, DMSO-$d_8$) δ 174.50 (C), 166.09 (C), 155.49 (C), 154.56 (C), 142.30 (C), 134.21 (C), 132.81 (C), 128.34 (C), 128.20 (C), 123.05 (CH), 122.59 (CH), 119.33 (CH), 57.10 (C), 37.04 ($CH_2$), 29.06 ($CH_2$), 28.22 ($CH_2$), 21.04 ($CH_2$), 16.34 ($CH_3$).

Compound 230

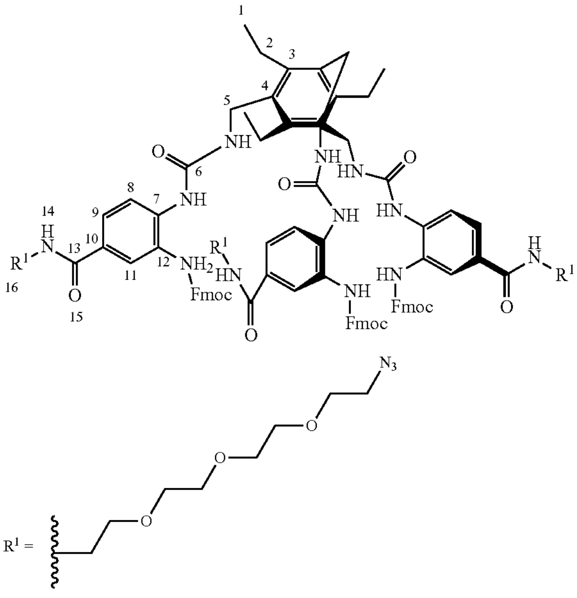

Compound 11 (1.384 g, 2.409 mmol) and Compound 5a (0.200 g, 0.611 mmol) were placed in a round bottomed flask under nitrogen and dissolved in anhydrous DMF (21 mL). To this solution was added dry pyridine (0.147 mL, 1.833 mmol) then heated to 30° C. for 100 hours. The solvent was evaporated under vacuum to give a gum which was purified by column chromatography by pre-adsorbing onto silica gel (20 g) by dissolving the crude in a mixture of dichloromethane and methanol and removing the solvent under vacuum to give a free-flowing powder. This pre-adsorbed material was loaded into an empty cartridge and put in line with a 100 g SNAP HP Sil cartridge and eluting with a gradient of dichloromethane with increasing concentration of methanol gave recovered Compound 11 (367 mg), and Compound 230 (1.171 g, 93%).

$^1$H NMR: (400 MHz, ($CD_3OD$): δ m.br. 7.95-7.20 (33H, ArH), s. 4.40 (6H, $ArCH_2NH$), m. 4.30-4.10 (9H, FmocH), m. 3.71-3.60 (42H, $C\underline{H}_2C\underline{H}_2O$, and $OC\underline{H}_2CH_2NH_2$), m. 3.33 (6H, $OCH_2C\underline{H}_2N_3$), m.br. 2.79 (6H, $ArC\underline{H}_2CH_3$), s.br. 1.19 (9H, $ArCH_2C\underline{H}_3$).

Compound 231

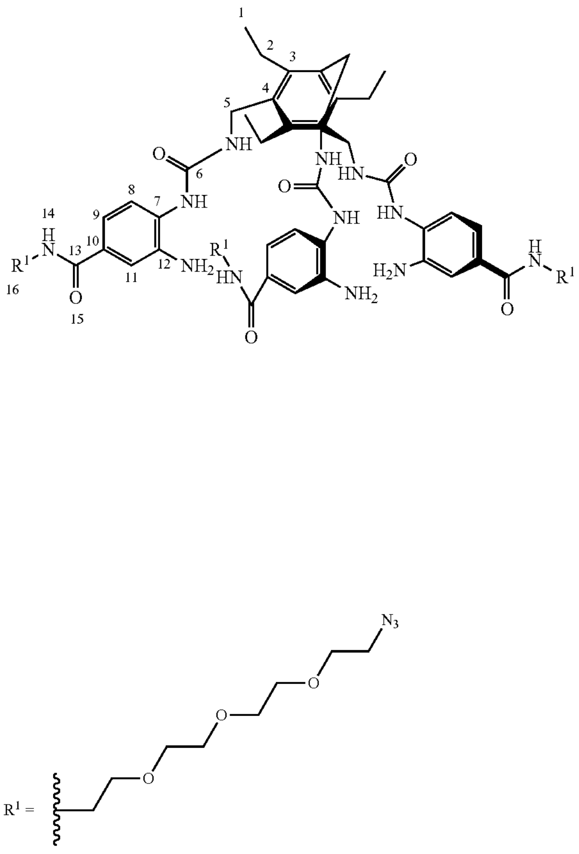

To a stirred suspension of Compound 230 (1.171 g, 0.571 mmol) in DCM (5 mL) at room temperature was added distilled DBU (0.426 mL, 2.854 mmol). After 10 minutes the reaction mixture became a clear solution and was stirred for a total of 2 hours before loading directly onto a flash chromatography column 50 g SNAP KP Sil cartridge that was equilibriated with dichloromethane and then eluting with a gradient of dichloromethane with increasing concentration of methanol to give the desired product contaminated with the fluorenyl by-product. Partial evaporation of the product-containing fractions gave a thick white slurry where the solid was separated by centrifuge. The wet solid was resuspended in methanol and centrifuged again and the solid dried to give Compound 231 as an off-white solid (0.344 g, 43%).

$^1$H NMR (400 MHz, $CDCl_3$/methanol-$d_4$) δ m. 7.12-6.85 (9H, ArH), s. 4.32 (6H, ArC$\underline{H_2}$NH), m. 3.50-3.40 (42H, C$\underline{H_2}$C$\underline{H_2}$O, and $OCH_2C\underline{H_2}N_3$), t. 3.20 (6H, $OCH_2CH_2N_3$), m.br. 2.66 (6H, $CH_2$), s.br. 1.09 (9H, $CH_3$).

Compound 232

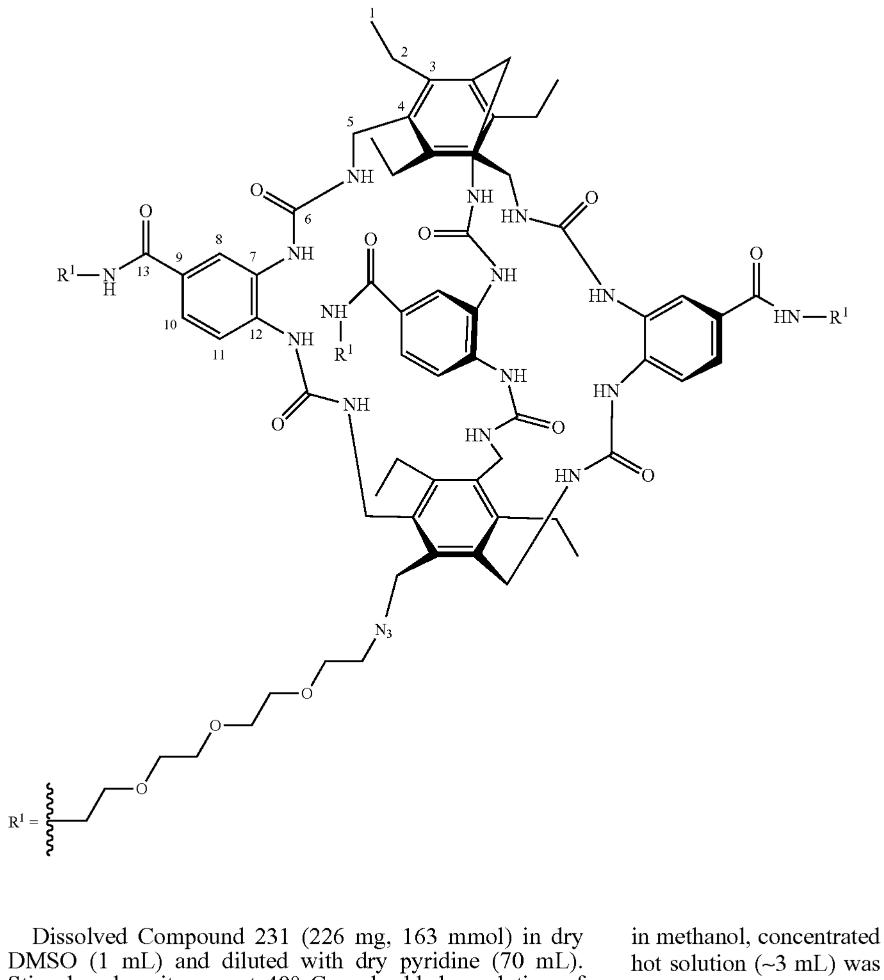

Dissolved Compound 231 (226 mg, 163 mmol) in dry DMSO (1 mL) and diluted with dry pyridine (70 mL). Stirred under nitrogen at 40° C. and added a solution of Compound 5a (60 mg, 183 mmol) in dry DCM (2 mL) by syringe pump over 6 hours, then left stirring at 40° C. for a further 60 hours. Evaporation of the solvent on a rotary evaporator gave an orange coloured gum which was dissolved in methanol containing a little water. This was loaded onto a Biotage 120 g reverse phase column and eluted with a water/methanol gradient. The compound which eluted at about 80% methanol was collected, evaporated, redissolved in methanol, concentrated by boiling off the solvent and the hot solution (~3 mL) was left to cool overnight to give the product (Compound 232) as clumps of white crystals (83 mg, 30%).

$^1$H NMR (400 MHz, $D_2O$) δ s. 8.09 (3H, ArH), d. 7.98 (3H, ArH), d. 7.58 (3H, ArH), m. 4.41-4.45 (12H, ArC$\underline{H_2}$NH), m. 3.5-3.7 (42H, $OC\underline{H_2}C\underline{H_2}$), m. 2.7-2.9 (12H, ArC$\underline{H_2}CH_3$), m. 1.20 (18H, $ArC\underline{H_2}CH_3$).

HRMS: ($ESI^+$) calculated for $C_{81}H_{116}N_{24}O_{18}{}^{2+}[M+2H]^{2+}$ 856.4449, found: 856.4470.

Compound 233-Receptor 10

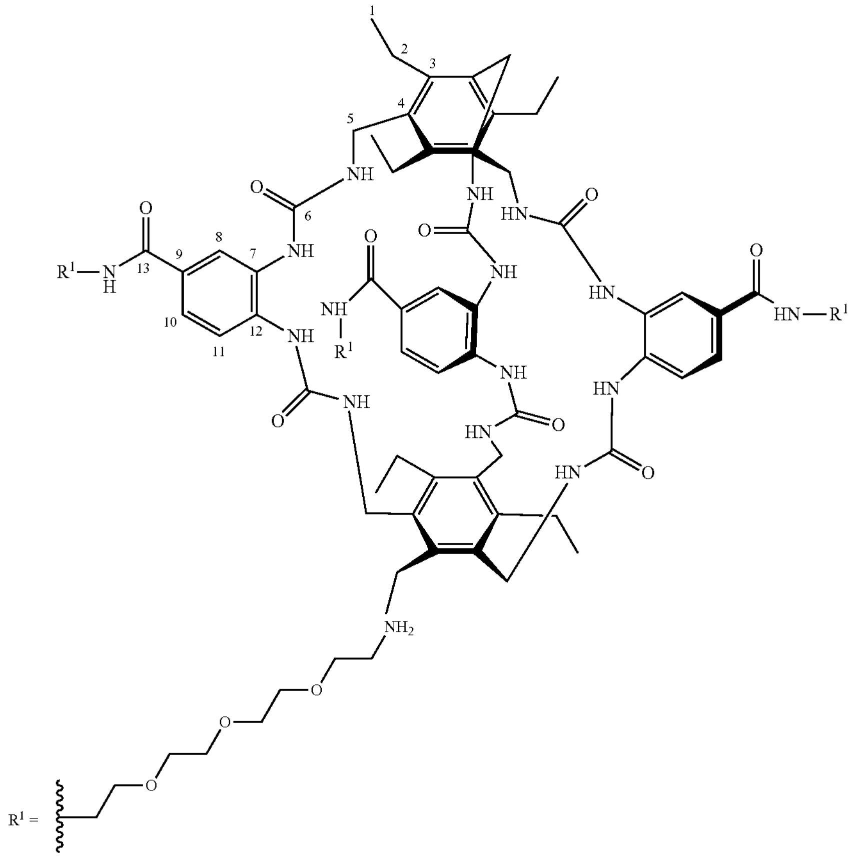

Compound 232 (22 mg, 0.013 mmol) was dissolved in a mixture of warm methanol (2 mL) and water (0.1 mL) and to this was added triphenylphosphine (26 mg, 0.099 mmol) under an atmosphere of nitrogen. The reaction mixture was then heated for 16 hours at 60° C. before allowing to cool to room temperature. The cloudy mixture was diluted with more methanol and water, followed by 40 μL of 1 M aqueous hydrochloric (until it was acidic). Added more water then extracted it a couple of times with DCM to remove the triphenylphosphine based compounds. The slightly cloudy aqueous layer was passed through a bond-elut (500 mg) several times until the eluant emerged clear and tic showed that no product was passing through. Then eluted with water 6 mL, then 2×4 mL of 25% MeOH in water, then 4×4 mL of 50%, 2×4 mL of 75% MeOH in water. Tlc showed that the product had eluted in the 25% to 75% methanol fractions which were combined and evaporated before being redissolved in water and freeze-dried to give Compound 233 (19 mg, 89%) as an off-white solid.

$^1H$ NMR (400 MHz, $D_2O$) δ s. 7.88 (3H, ArH), d. 7.71 (3H, ArH), d. 7.43 (3H, ArH), s.br. 4.20 (12H, $ArC\underline{H}_2NH$), m. 3.4-3.6 (42H, $OC\underline{H}_2C\underline{H}_2$, and $OC\underline{H}_2CH_2NH_2$), t. 3.00 (6H, $OCH_2C\underline{H}_2NH_2$), m. 2.48 (12H, $ArC\underline{H}_2CH_3$), m. 0.96 (18H, $ArCH_2C\underline{H}_3$).

HRMS: ($MALDI^+$) calculated for $C_{81}H_{120}N_{18}O_{18}Na^+$ $[M+Na]^+$ 1655.8920, found: 1655.8932.

Hexa-Carboxylate Macrocycle (Compound $H_8$—Receptor 11)

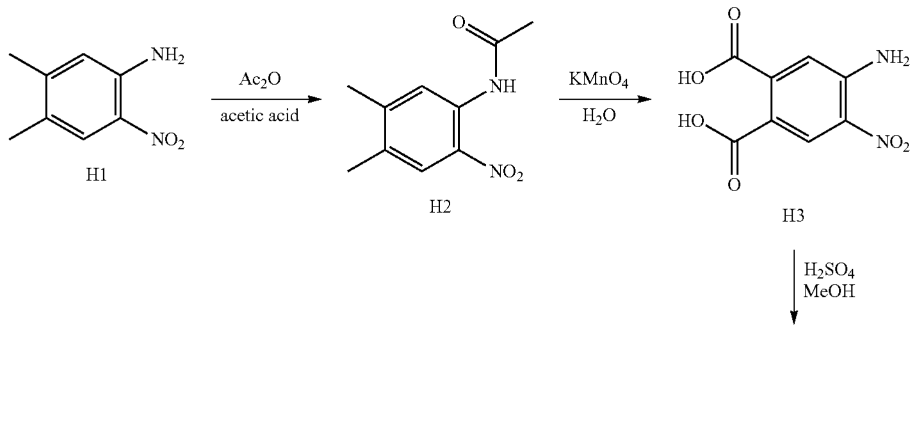

H1 H2 H3

-continued
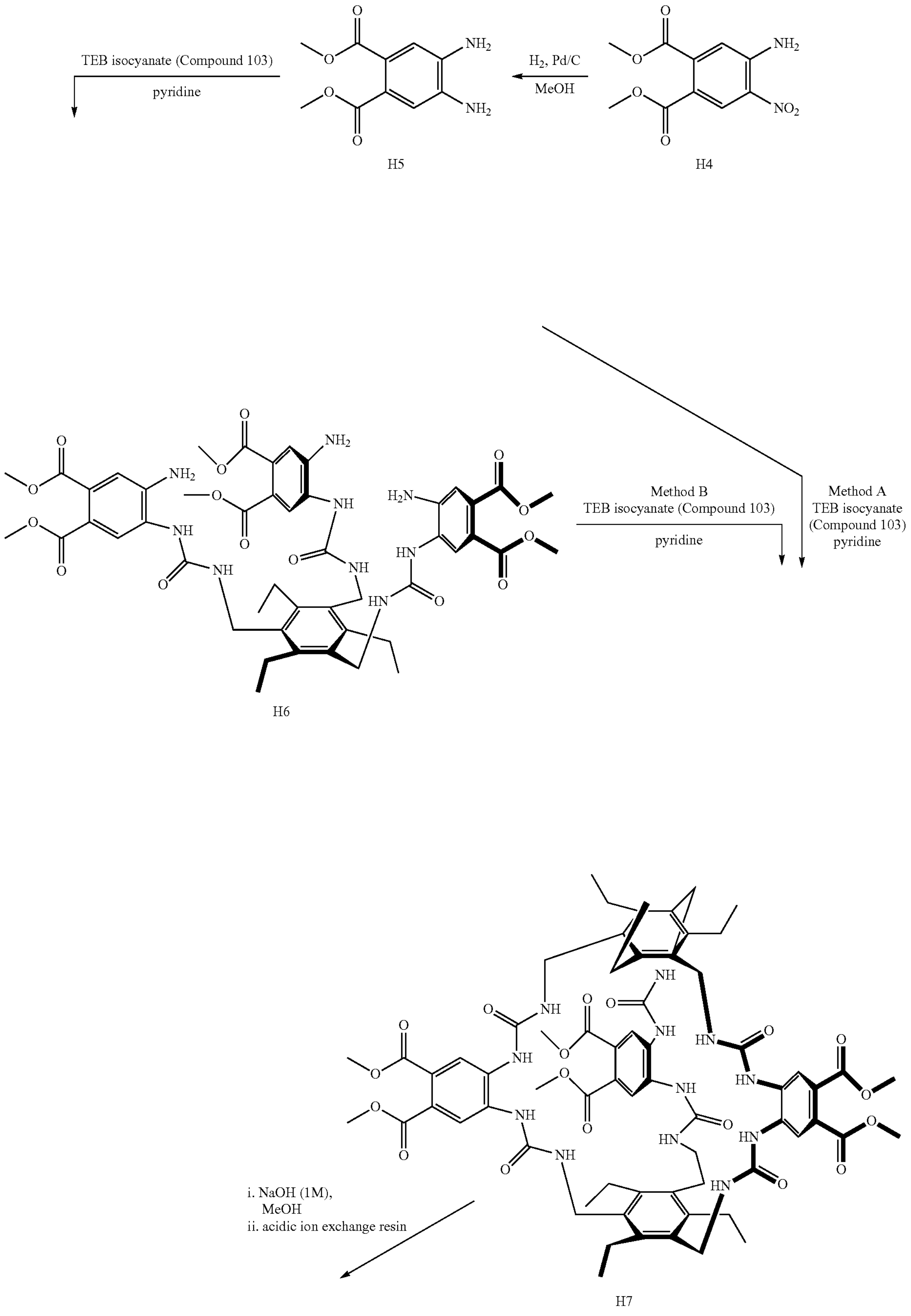

-continued

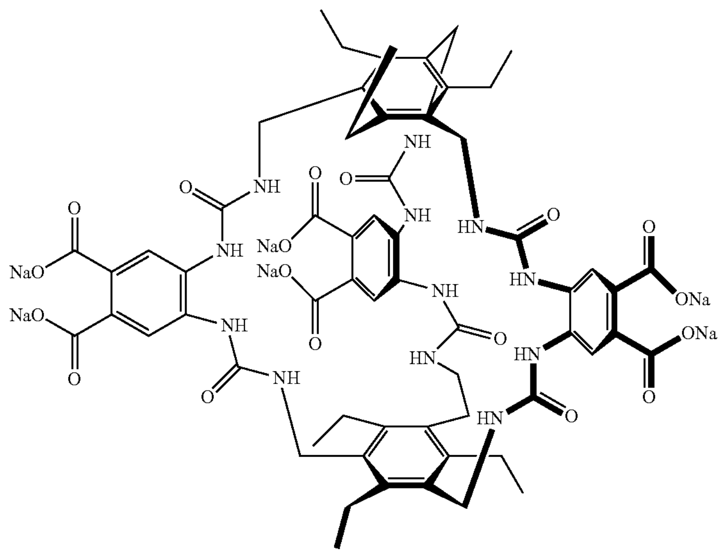

H8

N-(4, 5-dimethyl-2-nitrophenyl) acetamide (Compound $H_2$)

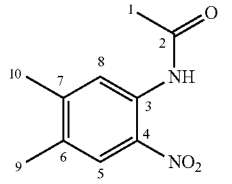

4,5-dimethyl-2-nitroaniline (Compound $H_{1,\ 2}$ g, 12 mmol) was suspended in glacial acetic acid (24 mL) and heated to 90° C. Acetic anhydride (1.2 mL, 13 mmol) was added and the mixture stirred at reflux for 2 hours. The reaction mixture was cooled to room temperature and poured into water (300 mL). The yellow precipitate was filtered, washed with water and recrystallized from ethanol to yield Compound $H_2$ (2.4 g, 11.6 mmol, 97%) as a yellow crystalline solid.

$^1$H NMR: (400 MHz, ($CDCl_3$): δ 2.25 (s, 6H, C(9, 10)$H_3$), 2.32 (s, 3H, C(1)$H_3$), 7.93 (s, 1H, C(8)H), 8.51 (s, 1H, C(5) H), 10.26 (br s, 1H, NH).

$^{13}$C NMR: (100 MHz, ($CDCl_3$): δ 19.1 (C10), 20.5 (C9), 25.6 (C1), 122.6 (C8), 125.9 (C5), 132.3 (C7), 132.7 (C6), 134.1 (C3), 146.8 (C4), 168.9 (C(2)O); $v_{max}$ 3341, 2987, 2901, 1708, 1695, 1576, 1323, 1151, 759 $cm^{-1}$.

HRMS: ($ESI^+$) Found $[M+Na]^+$: 231.0745.

4-amino-5-nitrophthalic acid (Compound $H_3$)

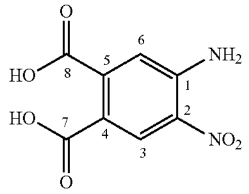 [SMILES: Nc1cc(C(=O)O)c(C(=O)O)cc1[N+](=O)[O-]]

Under an inert $N_2$ atmosphere, Compound $H_2$ (2 g, 9.6 mmol) and $KMnO_4$ (6 g, 37.9 mmol)) was suspended in water (50 mL) and stirred at reflux for 3 days. Additional $KMnO_4$ (3 g, 19 mmol) was added halfway through the reaction time. The resultant brown precipitate was filtered hot and washed with water. The yellow filtrate was acidified to pH 3 with 1M HCl, extracted with EtOAc (3×100 mL), washed with brine (100 mL) and dried ($MgSO_4$). The solvent was removed under vacuum to yield Compound $H_3$ (0.77 g, 2.88 mmol, 60%) as a yellow orange solid.

$^1$H NMR: (400 MHz, ($CDCl_3$): δ 7.25 (s, 1H, C(6)H), 7.63 (br s, 2H, $NH_2$), 8.70 (s, 1H, C(3)H), 11.50 (br s, 2H, C(7, 8)$O_2$H).

$^{13}$C NMR: (100 MHz, ($CDCl_3$): δ 117.7 (C4), 118.7 (C6), 129.3 (C3), 132.6 (C5), 141.5 (C2), 146.9 (C1), 167.8 (C7), 169.0 (C8); $v_{max}$ 3486, 3364, 2972, 2901, 1712, 1681, 1626, 1502, 1252, 1057, 882 $cm^{-1}$.

LRMS: (EI) Found $[M]^+$: 226.1.

dimethyl 4-amino-5-nitrophthalate (Compound $H_4$)

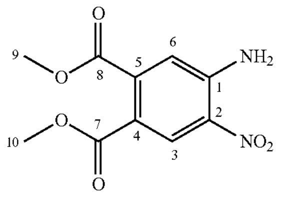 [SMILES: COC(=O)c1cc(N)c([N+](=O)[O-])cc1C(=O)OC]

Compound $H_3$ (0.8 g, 3.5 mmol) was dissolved in MeOH (30 mL) and concentrated $H_2SO_4$ (0.5 mL) added. The reaction mixture was stirred at reflux for 3 hours and then the solvent was removed under vacuum. The residue was dissolved in EtOAc (60 mL), washed with 5% $NaHCO_3$ (60 mL), brine (60 mL) and dried ($MgSO_4$). The solvent was removed under vacuum and the crude solid purified by flash column chromatography (100% $CH_2Cl_2$) to yield Compound $H_4$ (0.72 g, 2.8 mmol, 80%) as an orange solid.

$^1H$ NMR: (400 MHz, ($CDCl_3$): δ 3.88 (s, 3H, C(10)$H_3$), 3.92 (s, 3H, C(9)$H_3$), 6.91 (s, 1H, C(6)H), 7.26 (br s, 2H, N$H_2$), 8.74 (s, 1H, C(3)H).

$^{13}C$ NMR: (100 MHz, ($CDCl_3$): δ 52.5 (C9), 53.1 (C10), 116.9 (C4), 118.3 (C6), 129.7 (C3), 131.2 (C5), 140.7 (C2), 146.6 (C1), 164.7 (C7), 168.0 (C8); $v_{max}$ 3486, 3342, 2987, 2901, 1736, 1697, 1621, 1502, 1435, 1339, 1250, 1027, 762 $cm^{-1}$.

LRMS: (ESI) Found $[M+Na]^+$: 277.1.

dimethyl 4-amino-5-nitrophthalate (Compound $H_5$)

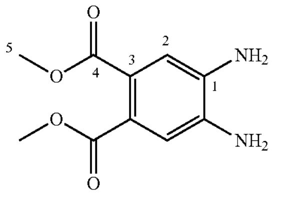

Under an inert $N_2$ atmosphere, a solution of Compound $H_4$ (0.1 g, 0.39 mmol) in MeOH (10 mL) was added to Pd/C (10 mg). The reaction vessel was then purged with hydrogen (1 atm) and the reaction mixture stirred at room temperature for 1 hour. After which, the reaction mixture was filtered through celite and washed with $CH_2Cl_2$, and the filtrate concentrated under vacuum. The crude product was then purified by flash column chromatography (5% MeOH: $CH_2Cl_2$) to afford Compound $H_5$ (81 mg, 0.36 mmol, 93%) as light brown solid.

$^1H$ NMR: (400 MHz, ($CDCl_3$): δ 3.84 (s, 6H, C(5)$H_3$), 7.02 (s, 2H, C(2)H).

$^{13}C$ NMR: (100 MHz, ($CDCl_3$): δ 52.4 (C5), 116.6 (C2), 124.1 (C3), 1136.6 (C1), 168.4 (C4).

HRMS: ($ESI^+$) Found $[M+Na]^+$: 247.0685.

Hexa-Ester Amino Half Receptor (Compound $H_6$)

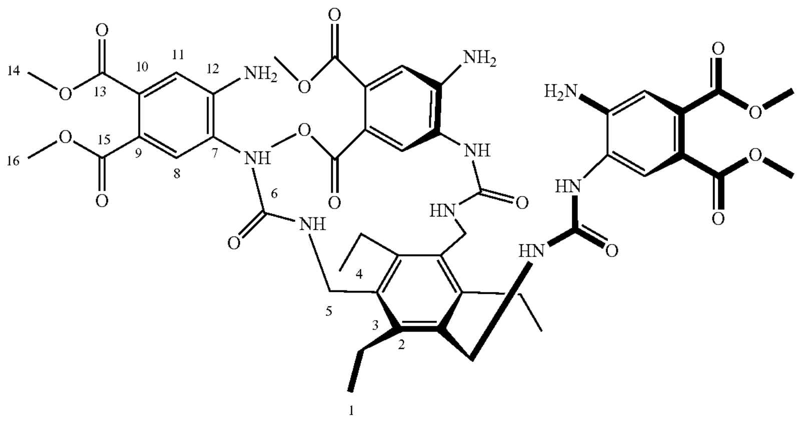

Under an inert $N_2$ atmosphere, Compound $H_5$ (80 mg, 0.36 mmol) was dissolved in dry pyridine (10 mL) and heated to 40° C. A solution of TEB isocyanate (Compound 103, 20 mg, 0.06 mmol) in dry $CH_2Cl_2$ (2 mL) was added over 1 hour and the reaction stirred at 40° C. for 16 hours. The reaction mixture was concentrated under vacuum and residual pyridine co-evaporated with toluene (3×30 mL). The crude product was then suspended in $CH_2Cl_2$, filtered and air dried to afford Compound $H_6$ (49 mg, 0.049 mmol, 82%) as a light brown solid.

$^1H$ NMR: (400 MHz, (($CD_3)_2SO$): δ 1.19 (t, J=7.2 Hz, 9H, C(1)$H_3$), 2.79 (br q, 6H, C(2)$H_2$), 3.72, 3.73 (s, 2×9H, C(14, 16)$H_3$), 4.36 (s, 6H, C(5)$H_2$), 5.87 (br s, 6H, $NH_2$), 6.51 (br t, 3H, NHC(5)), 6.84 (s, 3H, C(11)H), 8.13 (s, 3H, C(8)H), 8.60 (s, 3H, NH).

$^{13}C$ NMR: (100 MHz, (($CD_3)_2SO$): δ 16.9 (C1), 22.8 (C2), 37.7 (C5), 52.2, 52.5 (C14 and C16), 114.0 (C11), 117.3 (C9), 121.7 (C8), 126.9 (C7), 128.6 (C10), 133.2 (C4), 142.2 (C12), 143.4 (C4), 155.5 (C6), 167.3, 169.2 (C9).

HRMS: ($ESI^+$) Found $[M+H]^+$: 1000.4041.

Hexa-Ester Hexa-Urea Macrocycle (Compound $H_7$)

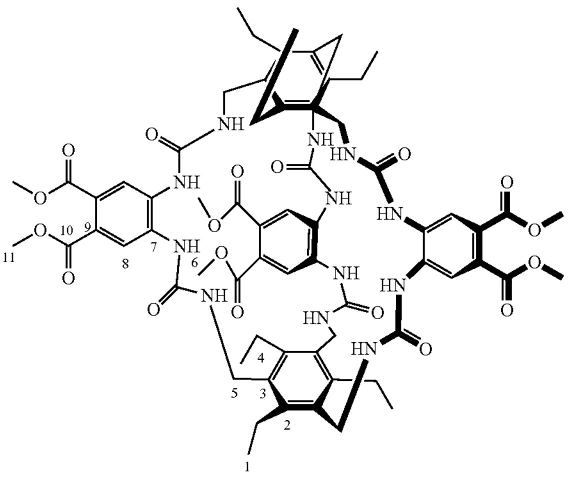

Method A:

Under an inert $N_2$ atmosphere, Compound $H_5$ (40 mg, 0.18 mmol) was dissolved in dry pyridine (100 mL) and heated to 40° C. A solution of TEB isocyanate (Compound 103, 38 mg, 0.12 mmol) in dry $CH_2Cl_2$ (2 mL) was added over 1 hour and the reaction stirred at 40° C. for 16 hours. The reaction mixture was concentrated under vacuum and residual pyridine co-evaporated with toluene (3×30 mL). The crude product was then purified by reverse phase HPLC (100% water→100% acetonitrile) to afford Compound $H_7$ (9.5 mg, 0.007 mmol, 12%) as a white solid.

Method B:

Under an inert $N_2$ atmosphere, Compound $H_6$ (20 mg, 0.02 mmol) was dissolved in dry pyridine (20 mL) and heated to 40° C. A solution of TEB isocyanate (Compound 103, 7.8 mg, 0.024 mmol) in dry $CH_2Cl_2$ (2 mL) was added and the reaction stirred at 40° C. for 16 hours. The reaction mixture was concentrated under vacuum and residual pyridine co-evaporated with toluene (3×30 mL). The crude product was then purified by reverse phase HPLC (100% water→100% acetonitrile) to afford Compound $H_7$ (8 mg, 0.006 mmol, 31%) as a white solid.

$^1$H NMR: (400 MHz, ($CD_3OD$): δ 1.22 (t, J=7.4 Hz, 18H, C(1)$\underline{H}_3$), 2.79 (q, J=7.4 Hz, 12H, C(2)$\underline{H}_2$), 3.86 (s, 18H, C(11)$\underline{H}_3$), 4.42 (s, 12H, C(5)$\underline{H}_2$), 8.34 (s, 6H, C(8)$\underline{H}$).

$^{13}$C NMR: (100 MHz, ($CD_3OD$): δ 15.3 ($\underline{C}$1), 22.4 ($\underline{C}$2), 37.5 ($\underline{C}$5), 51.5 ($\underline{C}$11), 121.6 ($\underline{C}$8), 126.3 ($\underline{C}$7), 131.6 ($\underline{C}$3), 131.9 ($\underline{C}$9), 143.2 ($\underline{C}$4), 155.6 ($\underline{C}$6), 168.1 ($\underline{C}$10).

HRMS: (ESI$^+$) Found $[M+H]^+$: 1327.5635.

Hexa-Carboxylate Hexa-Urea Macrocycle (Compound $H_8$—Receptor 11)

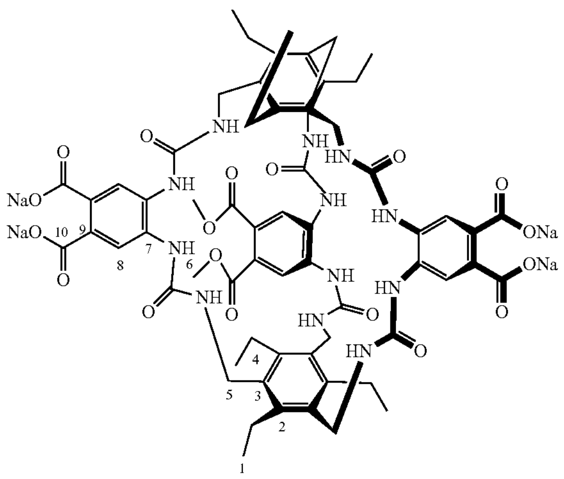

Compound $H_7$ (8 mg, 0.006 mmol) was dissolved in MeOH (4 mL) and then NaOH (5 M, 1 mL) added dropwise. The solution was stirred at 40° C. for 1 hour and the reaction diluted with water (5 mL). The MeOH was removed under vacuum and the aqueous solution neutralised to pH 7.4 with acidic ion exchange resin, filtered and freeze dried to afford Compound $H_8$ (7.8 mg, 0.0056 mmol, 93%) as a white solid.

$^1$H NMR: (600 MHz, $D_2O$): δ 1.19 (t, J=7.4 Hz, 18H, C(1)$\underline{H}_3$), 2.75 (br q, 12H, C(2)$\underline{H}_2$), 4.47 (s, 12H, C(5)$\underline{H}_2$), 7.73 (s, 6H, C(8)$\underline{H}$).

$^{13}$C NMR: (100 MHz, $D_2O$): δ 15.4 ($\underline{C}$1), 22.5 ($\underline{C}$2), 37.6 ($\underline{C}$5), 124.6 ($\underline{C}$8), 128.3 ($\underline{C}$7), 131.8 ($\underline{C}$3), 134.9 ($\underline{C}$9), 143.3 ($\underline{C}$4), 157.4 ($\underline{C}$6), 176.4 ($\underline{C}$10).

Compound 234

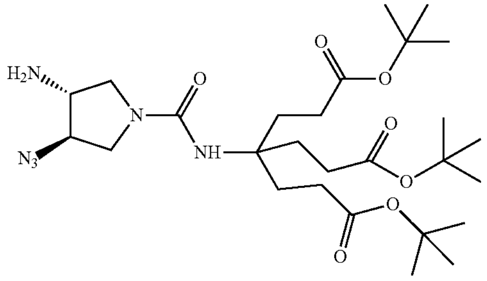

Compound 15 (2.000 g, 3.363 mmol) was dissolved in THF (145.0 mL) and mixed with triphenylphosphine (0.838 g, 3.195 mmol). The reaction was stirred at room temperature for 24 h. Water (75 mL) was added and the reaction heated at 50° C. for 3 h. After cooling the reaction mixture was diluted with water and extracted with EtOAc (3×100 mL). Combined organic layers were concentrated in vacuo and the crude residue purified by reverse phase MPLC on a C18 SNAP Ultra 120 g cartridge eluting (40% acetone:water to 60% acetone:water) to give Compound 234 as a white solid (1.510 g, 2.655 mmol, 79%).

$^1$H NMR (400 MHz, $CD_3OD$) δ 4.57 (s, 1H, NH), 3.86 (dt, J=5.8, 4.0 Hz, 1H, NC$\underline{H}_2$), 3.73 (dd, J=11.2, 5.8 Hz, 1H, NC$\underline{H}_2$), 3.59 (dd, J=10.6, 6.1 Hz, 1H, NC$\underline{H}_2$), 3.41-3.32 (m, 2H, C$\underline{H}N_3$, C$\underline{H}NH_2$), 3.13 (dd, J=10.6, 4.1 Hz, 1H NC$\underline{H}_2$), 2.22 (m, 6H, C$\underline{H}_2$C(O)), 1.95 (m, 6H, CC$\underline{H}_2$), 1.45 (s, 27H, C(C$\underline{H}_3$)$_3$).

$^{13}C$ NMR (100 MHz, $CD_3OD$) δ 174.9 (s, C$\underline{C}O_2$C), 157.8 (s, N$\underline{C}$(O)N), 81.7 (s, $CO_2\underline{C}(CH_3)_3$), 67.2 (s, $\underline{C}NH_2$), 58.3 ( $\underline{C}N_3$), 56.8 (s, $\underline{C}H_2N$), 52.5 ($\underline{C}H_2N$), 31.2 (s, $\underline{C}H_2C(O)$), 30.8 (s, $C\underline{C}H_2$), 28.4 (s, $CO_2C(\underline{C}H_3)_3$).

Compound 235

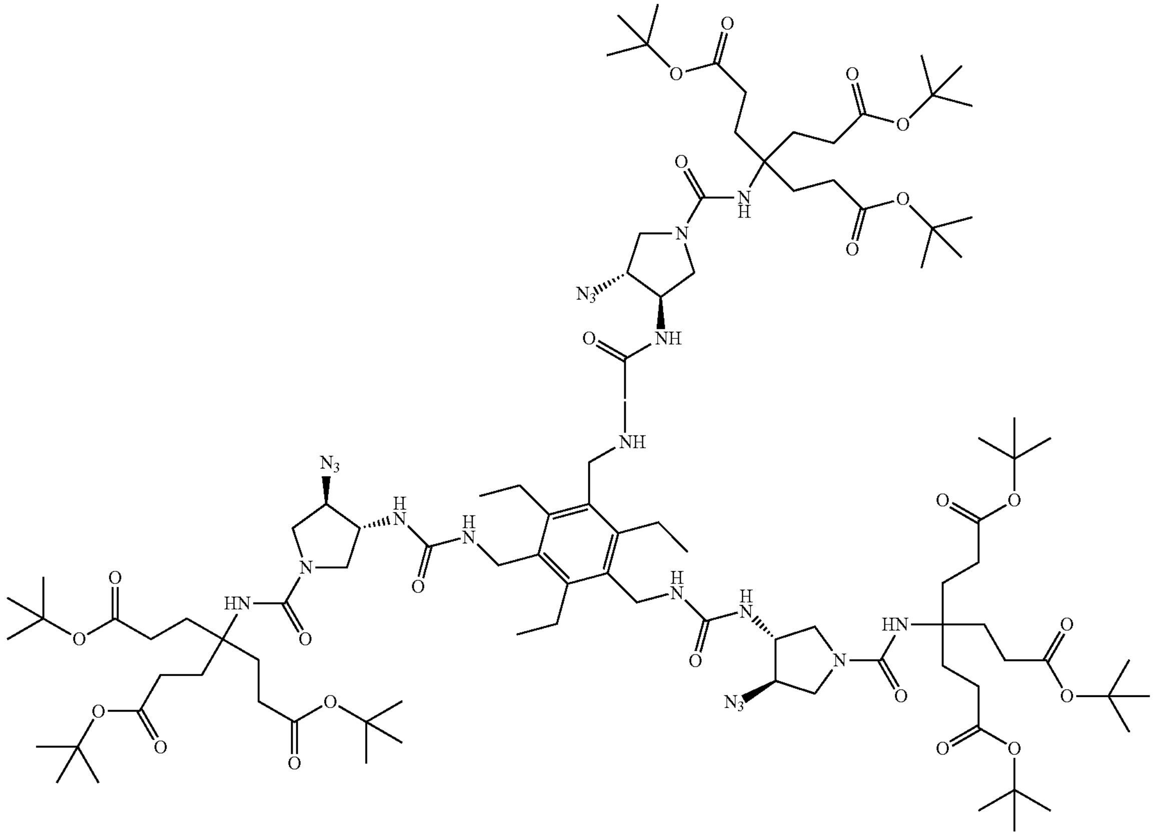

Chemical Formula: $C_{99}H_{165}N_{21}O_{24}$
Exact Mass: 2032.23
Molecular Weight: 2033.53

Compound 234 (67 mg, 0.118 mmol) and Compound 103 (11 mg, 0.034 mmol) were dissolved in DCM (1 mL) and stirred together for 18 h. The solvent was removed in vacuo and the residue purified by reverse phase MPLC on a C18 SNAP Ultra 120 g cartridge eluting 70% acetone:water to 100% acetone:water to give Compound 235 as a white solid (60 mg, 0.030 mmol, 89%).

$^1H$ NMR (400 MHz, $CD_3OD$) δ 4.39 (s, 6H, $ArC\underline{H}_2NH$), 4.24 (dt, J=6.7, 4.7 Hz, 3H, $C\underline{H}NH$), 4.05 (dt, J=6.0, 4.5 Hz, 3H, $NC\underline{H}_2$), 3.68 (dd, J=10.8, 6.7 Hz, 3H, $NC\underline{H}_2$), 3.61 (dd, J=11.3, 6.0 Hz, 3H, $NC\underline{H}_2$), 3.32 (m, 3H, $C\underline{H}N_3$), 3.17 (dd, J=10.8, 4.6 Hz, 3H $NC\underline{H}_2$), 2.78 (q, J=7.4 Hz, 6H, $ArC\underline{H}_2CH_3$), 2.21 (dd, J=9.3, 6.6 Hz, 18H, $C\underline{H}_2C(O)$), 1.94 (dd, J=9.3, 6.6 Hz, 18H, $CC\underline{H}_2$), 1.44 (s, 81H, $C(C\underline{H}_3)_3$), 1.18 (t, J=7.4 Hz, 9H, $ArCH_2C\underline{H}_3$).

$^{13}C$ NMR (100 MHz, $CD_3OD$) δ 174.9 (s, $\underline{C}CO_2C$), 157.8, 152.4 (s, N$\underline{C}$(O)N), 137.5, 133.7 (Ar), 81.8 (s, $CO_2\underline{C}(CH_3)_3$), 69.1 (s, $\underline{C}HNH$), 61.5 ($\underline{C}N_3$), 58.5 (s, $\underline{C}H_2N$), 51.0 ($\underline{C}H_2N$), 39.3 ($ArC\underline{H}_2NH$), 31.2 (s, $\underline{C}H_2C(O)$), 30.9 (s, $C\underline{C}H_2$), 28.4 (s, $CO_2C(\underline{C}H_3)_3$), 22.2 (s, $Ar\underline{C}H_2CH_3$), 15.6 (s, $ArCH_2\underline{C}H_3$).

Compound 236

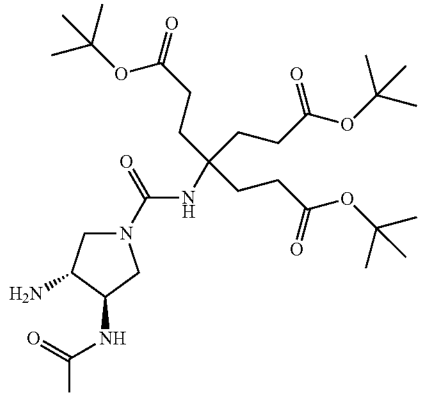

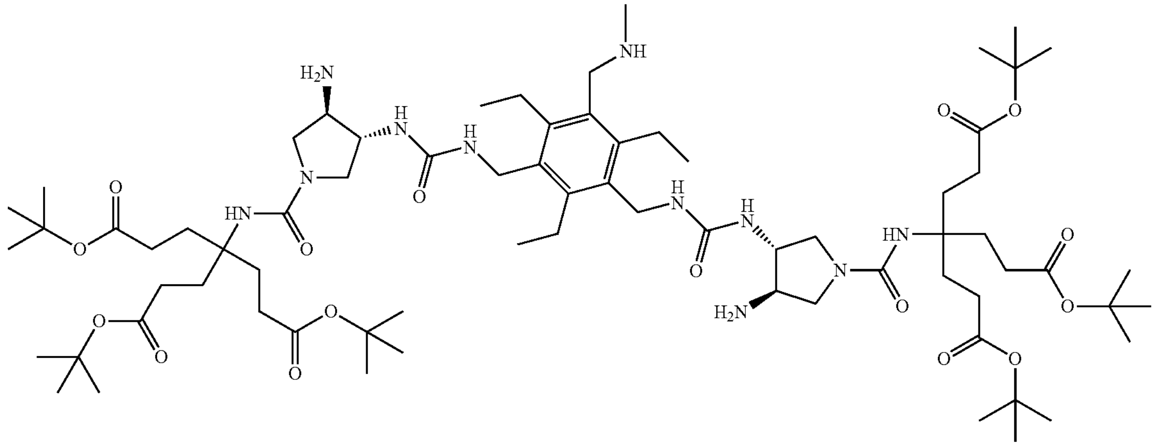

Chemical Formula: $C_{99}H_{171}N_{15}O_{24}$
Exact Mass: 1954.26
Molecular Weight: 1955.54

To a solution of Compound 235 (100 mg, 0.049 mmol) in MeOH (15 mL) was added a slurry of Pd/C (30 mg) in DCM. The reaction was placed under a hydrogen atmosphere and left to stir overnight. Filtration through Celite™ and concentration of the filtrate gave a white solid (91 mg, 0.047 mmol, 96%).

$^1H$ NMR (400 MHz, $CD_3OD$) δ 4.46-4.33 (m, 6H, $ArCH_2NH$), 4.25 (d, J=6.9 Hz, 3H, CHNH), 3.88-3.74 (m, 6H, $NCH_2$), 3.60 (d, J=6.4 Hz, 3H, $NCH_2$), 3.33-3.27 (m, 3H, $CHNH_2$), 3.20 (dd, J=10.4, 7.0z Hz, 3H, $NCH_2$), 2.78 (q, J=8.2 Hz, 6H, $ArCH_2CH_3$), 2.30-2.14 (m, 18H, $CH_2C(O)$), 2.04-1.85 (m, 18H, $CCH_2$), 1.44 (s, 81H, $C(CH_3)_3$), 1.19 (t, J=7.4 Hz, 9H, $ArCH_2CH_3$).

$^{13}C$ NMR (100 MHz, $CD_3OD$) δ 174.8 (s, $CCO_2C$), 157.9, 151.5 (s, NC(O)N), 137.2, 132.0 (Ar), 81.7 (s, $CO_2C(CH_3)_3$), 68.1 (s, CHNH), 67.5 ($CNH_2$), 58.2 (s, $CH_2N$), 54.8 ($CH_2N$), 43.6 ($ArCH_2NH$), 31.2 (s, $CH_2C(O)$), 30.8 (s, $CCH_2$), 28.4 (s, $CO_2C(CH_3)_3$), 22.3 (s, $ArCH_2CH_3$), 16.9 (s, $ArCH_2CH_3$).

Compound 237

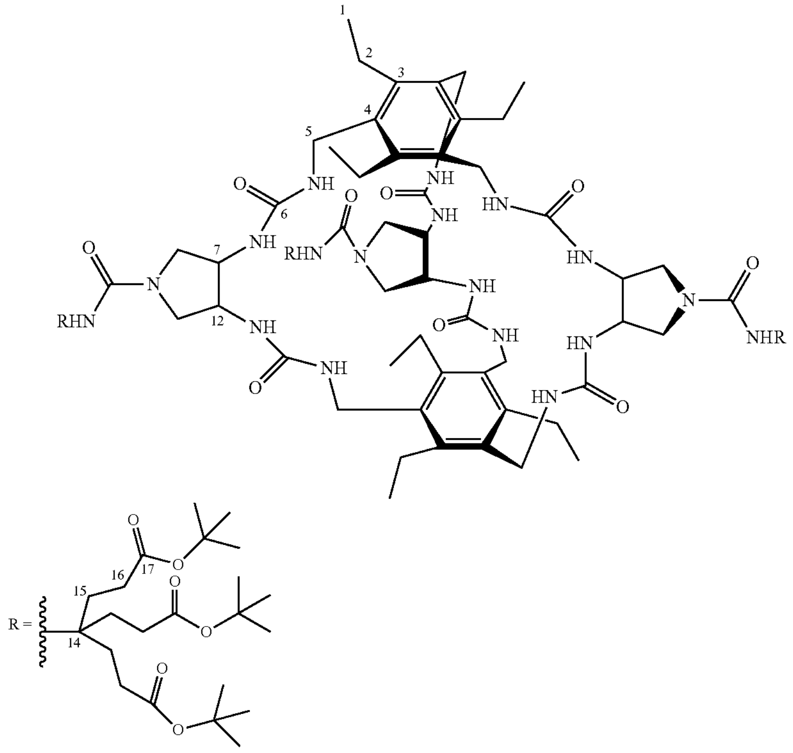

A mixture of Compound 236 (110 mg, 0.056 mmol), n-octyl glucoside (33 mg, 0.112 mmol) and DMAP (21 mg, 0.168 mmol) were azeotroped to dryness with toluene in a two-necked flask and then placed under $N_2$. The residue was then dissolved in DCM (110 mL) and cooled to 0° C. A solution of TEB NCO (Compound 103, 18 mg, 0.056 mmol) in DCM (20 mL) was added. The reaction mixture was heated to 35° C. for 16 h. Solvent was removed under reduced pressure, and the crude product purified by reverse phase MPLC on a C18 SNAP Ultra 60 g cartridge eluting 70% acetone:water to 100% acetone:water (46 mg, 0.020 mmol, 36%).

$^1$H NMR (500 MHz, $CD_3OD$) δ 4.79-4.33 (azeotroped, 6H, ArC$\underline{H}_2$NH), 4.31-4.10 (m, 6H, ArC$\underline{H}_2$NH), 3.97-3.80 (m, 6H, C$\underline{H}$NH), 3.73-3.37 (m, 9H, NC$\underline{H}_2$) 2.96-2.56 (m, 9H, NC$\underline{H}_2$, ArC$\underline{H}_2$CH$_3$), 2.35-2.20 (m, 24H, ArC$\underline{H}_2$CH$_3$, C$\underline{H}_2$C(O)), 2.10-1.87 (m, 18H, CC$\underline{H}_2$), 1.48-1.40 (m, 81H, C(C$\underline{H}_3$)$_3$), 1.24-1.10 (m, 18H, ArCH$_2$C$\underline{H}_3$).

$^{13}$C NMR (125 MHz, $(CD_3)_2SO$) δ 172.5 (s, C$\underline{C}$O$_2$C), 157.6, 155.4 (s, NC(O)N), 141.6, 133.9 (Ar), 79.7 (s, CO$_2$$\underline{C}$(CH$_3$)$_3$), 56.2 (NH$\underline{C}$(CH$_2$)$_3$), 52.7 (s, $\underline{C}$HNH), 50.2 (s, $\underline{C}$H$_2$N), 36.6 (ArC$\underline{H}_2$NH), 29.4 (s, $\underline{C}$H$_2$C(O)), 29.3 (s, C$\underline{C}$H$_2$), 27.8 (s, CO$_2$C($\underline{C}$H$_3$)$_3$), 22.0 (s, Ar$\underline{C}$H$_2$CH$_3$), 16.3 (s, ArCH$_2$$\underline{C}$H$_3$).

MS: (ESI$^+$) calculated for $C_{117}H_{195}N_{18}O_{27}^{2+}$: 1141.7180, found $[M+2H]^{2+}$: 1141.7196

Compound 238 - Receptor 12

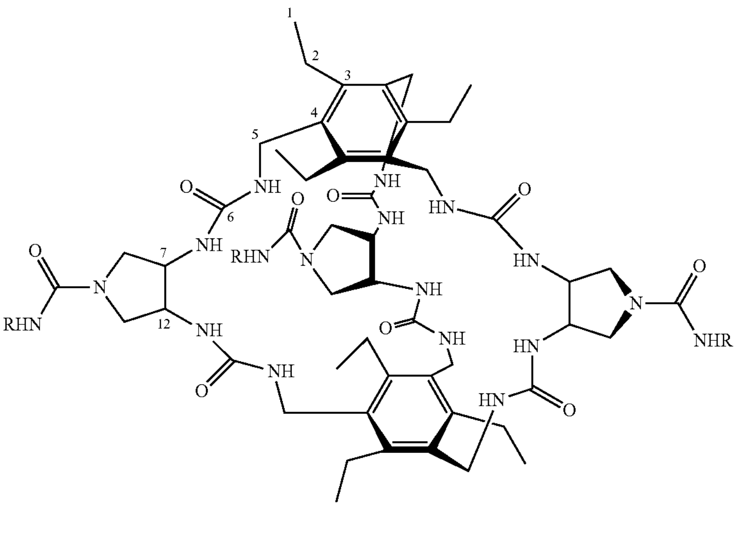

-continued

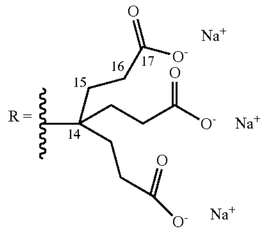

Compound 237 (8 mg, 3.504 μmol) dissolved in TFA (1.3 mL), and heated to 30° C. with stirring for 20 hours. The reaction mixture was allowed to cool, whereupon pentane (25 mL) was added. The resultant suspension was centrifuged, and the supernatant removed. The residual oil was dissolved in 0.2 M aq. $NaHCO_3$ solution (3.5 mL) and this solution was desalted by 20 mL column of G-25 sephadex. The resultant solution was freeze dried to give Compound 238 as a white solid (6.5 mg, 3.290 mmol, 94%).

$^1$H NMR (500 MHz, $D_2O$) δ 4.66-4.50 (m, 3H, $ArCH_2NH$), 4.27-4.03 (m, 9H, $ArCH_2NH$), 4.02-3.82 (m, 3H, CHNH), 3.79-3.34 (m, 12H, CHNH, $NCH_2$), 3.09-2.75 (m, 6H, $ArCH_2CH_3$), 2.75-2.27 (m, 9H, $NCH_2$, $ArCH_2CH_3$), 2.26-2.13 (m, 18H, $CH_2C(O)$), 2.03-1.89 (m, 18H, CCH2), 1.23-1.09 (m, 18H, $ArCH_2CH_3$).

$^{13}$C NMR (125 MHz, $D_2O$) δ 183.4 (s, $CCO_2$), 160.2, 159.7, 159.3 (NHC(O)NH), 157.6 (s, NHC(O)N), 144.9, 144.2, 144.1 (Ar), 58.1 ($NHC(CH_2)_3$), 58.0, 57.9 (s, CHNH), 49.1, 48.4, 47.7 (s, $CH_2N$), 39.8, 38.8, 37.6 ($ArCH_2NH$), 32.2, 32.1 (s, $CH_2C(O)$), 31.7 (s, $CCH_2$), 23.5, 22.7, 22.1 (s, $ArCH_2CH_3$), 16.1, 15.9, 15.5 (s, $ArCH_2CH_3$).

MS: ($ESI^+$) calculated for $C_{117}H_{195}N_{18}O_{27}^{2+}$: 1141.7180, found $[M+2H]^{2+}$: 1141.7196

Compound 239

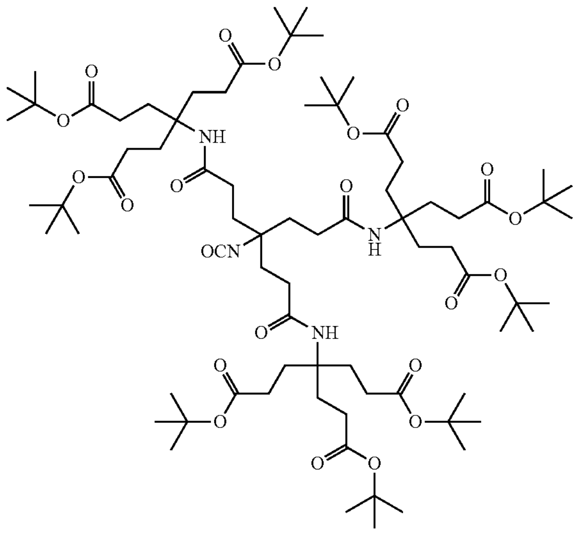

Chemical Formula: $C_{77}H_{132}N_4O_{22}$
Exact Mass: 1464.9333
Molecular Weight: 1465.9090

A 1 L flask, with a side-arm gas adaptor, equipped with a magnetic stirrer was dried under vacuum using a heat-gun. The flask was cooled to RT and charged with G2 amine (Compound 82, 2.50 g, 1.74 mmol) under flowing nitrogen. THF (100 mL) and $Et_3N$ (0.25 mL, 1.80 mmol) were added, and the flask cooled to 0° C. with an ice bath. A solution of triphosgene (0.26 g, 1.00 mmol) in THF (25 mL) was added dropwise over the course of 20 min. After 3 h, the solvent was removed under vacuum and the resultant residue taken up in chloroform (50 mL) and washed with water (50 mL). The organic layer was dried ($MgSO_4$) and concentrated under vacuum to give Compound 239 as a white foam (2.50 g, 1.71 mmol, 98%).

$^1$H NMR (400 MHz, toluene-$d_8$) δ 2.26 (m, 18H, $CH_2$), 2.07 (m, 30H, $CH_2$), 1.40 (s, 81H, $CH_3$).

$^{13}$C NMR (100 MHz, toluene-$d_8$) δ 173.3 ($CCO_2C$), 172.4 (CONH), 123.7 (N═C═O), 80.4 ($C(CH_3)_3$), 58.2 ($NHC(CH_2)_3$), 53.7 (C(NCO)), 30.7 ($CH_2$), 30.5 ($CH_2$), 28.7 ($CH_2$), 28.5 ($CH_3$).

Compound 240

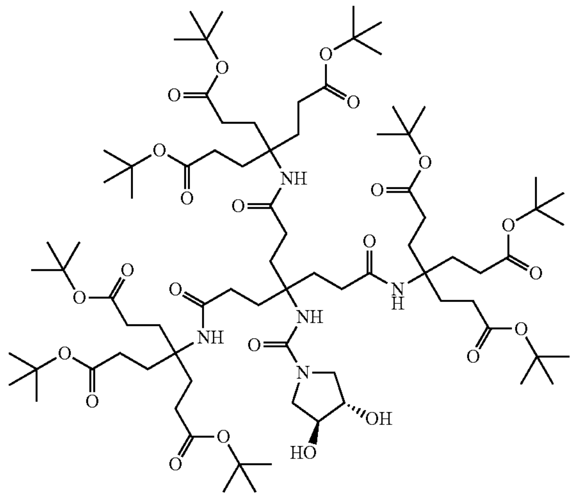

Chemical Formula: $C_{81}H_{141}N_5O_{24}$
Exact Mass: 1568.00
Molecular Weight: 1569.03

A Schlenk flash was charged with (3S,4S)-pyrrolidine-3,4-diol (185.0 mg, 1.790 mmol), G2 NCO (2.500 g, 2.000 mmol) and anhydrous DMF (100 mL) under $N_2$. The solution was left to stir for 16 hours, then poured into 5% aq. LiCl (700 mL) and extracted with EtOAc (300 mL). The organic layer was separated, dried and concentrated to a gummy solid (2.760 g, 1.759 mmol, 88%).

$^1$H NMR (400 MHz, $CDCl_3$) δ 6.24 (s, 3H, C(O)NH), 6.13 (2H, s, OH), 4.19 (s, 1H, NC(O)NH), 3.63 (dd, J=11.5, 3.7 Hz, 2H, CHOH), 3.54-3.37 (m, 4H, $NCH_2$), 2.17 (dd, J=10.3, 6.4 Hz, 24H, $CH_2C(O)$), 1.92 (dd, J=9.9, 6.4 Hz, 24H, $CCH_2$), 1.41 (s, 81H, $C(CH_3)_3$).

$^{13}C$ NMR (100 MHz, $CDCl_3$) δ 173.4 (C(O)NH), 172.9 ($CCO_2C$), 162.6 (s, NC(O)N), 80.8 (s, $CO_2C(CH_3)_3$), 80.7 (s, COH), 57.4 (s, $CH_2N$), 30.1 (s, $CH_2C(O)$), 30.0 (s, $CH_2C(O)NH$), 29.9 (s, $CCH_2$), 29.9 ($CCH_2$), 28.2 (s, $CO_2C(CH_3)_3$).

Compound 241

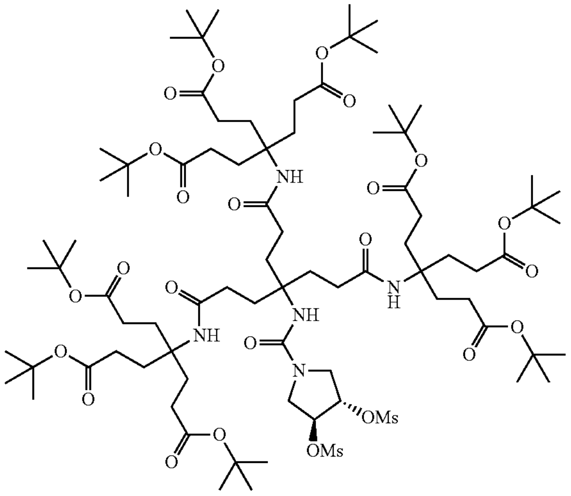

Chemical Formula: $C_{83}H_{145}N_5O_{28}S_2$
Exact Mass: 1723.95
Molecular Weight: 1725.19

Compound 240 (1.851 g 1.180 mmol) was dissolved in DCM (13.9 mL), and triethylamine (0.66 mL, 4.719 mmol) was added. The reaction was cooled to 0° C. and mesyl chloride (0.20 mL, 2.595 mmol) was added dropwise. The reaction was stirred at room temperature for 16 h, before being washed with 5% aq. $KHSO_4$, sat. aq. $NaHCO_3$ and brine. The organic layer was concentrated in vacuo to give Compound 241 as a white foam (1.350 g, 0.783 mmol, 66%).

$^1H$ NMR (400 MHz, $CDCl_3$) δ 6.95 (s, 1H, NC(O)NH), 6.17 (s, 3H, C(O)NH), 5.32-5.13 (m, 2H, $CHOSO_2$), 3.94-3.56 (m, 4H, $NCH_2$), 3.13 (s, J=1.6 Hz, 2H, $SO_2CH_3$), 2.31-2.11 (m, 24H, $CH_2C(O)$), 2.04-1.86 (m, 24H, $CCH_2$), 1.41 (s, 81H, $C(CH_3)_3$).

$^{13}C$ NMR (100 MHz, $CDCl_3$) δ 173.3 (C(O)NH), 172.7 ($CCO_2C$), 156.3 (s, NC(O)N), 80.6 (s, $CO_2C(CH_3)_3$), 80.1 (s, $COSO_2$), 57.4 (s, $CH_2N$), 38.6 ($SO_2CH_3$), 29.9 (s, $CH_2C(O)$), 29.9 (s, $CH_2C(O)NH$), 29.8 (s, $CCH_2$), 29.8 ($CCH_2$), 28.1 (s, $CO_2C(CH_3)_3$).

Compound 242

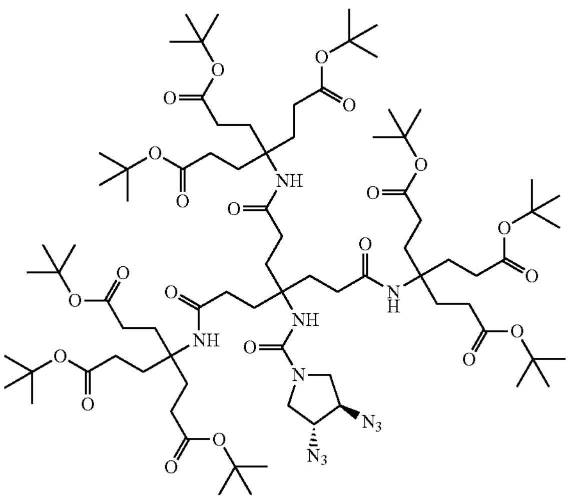

Chemical Formula: $C_{81}H_{139}N_{11}O_{22}$
Exact Mass: 1618.01
Molecular Weight: 1619.06

$NaN_3$ (0.131 g, 2.017 mmol) was added to a solution of Compound 241 (1.160 g, 0.672 mmol) in DMF (3.4 mL) at 0° C. The reaction was then heated at 100° C. for 16 h. The reaction was cooled and diluted with EtOAc (30 mL) and washed with water (30 mL), 5% aq. LiCl (2×30 mL) and brine (30 mL). The organic layer was concentrated in vacuo and the residue purified by reverse phase MPLC on a C18 SNAP Ultra 60 g cartridge eluting (70% acetone:water to 100% acetone:water) to give Compound 242 as a white solid (788 mg, 0.487 mmol, 72%).

$^1H$ NMR (400 MHz, $CD_3OD$) δ 4.29-4.18 (m, 2H, $CHN_3$), 3.84-3.70 (m, 2H, $NCH_2$), 3.55-3.44 (m, 2H, $NCH_2$), 2.32-2.19 (m, 24H, $CH_2C(O)$), 2.06-1.98 (m, 24H, $CCH_2$), 1.52 (s, 81H, $C(CH_3)_3$)

$^{13}C$ NMR (100 MHz, $CD_3OD$) δ 175.8 (C(O)NH), 174.4 ($CCO_2C$), 158.1 (s, NC(O)N), 81.7 (s, $CO_2C(CH_3)_3$), 65.1 (s, $CH_2N_3$), 62.2 ($NC(O)NHC(CH_2)_3$), 61.5 ($NHC(CH_2)_3$), 58z.8 ($CH_2N$), 30.7 (s, $CH_2C(O)$), 30.7 (s, $CH_2C(O)NH$), 30.5 (s, $CCH_2$), 30.5 ($CCH_2$), 28.4 (s, $CO_2C(CH_3)_3$).

Compound 243

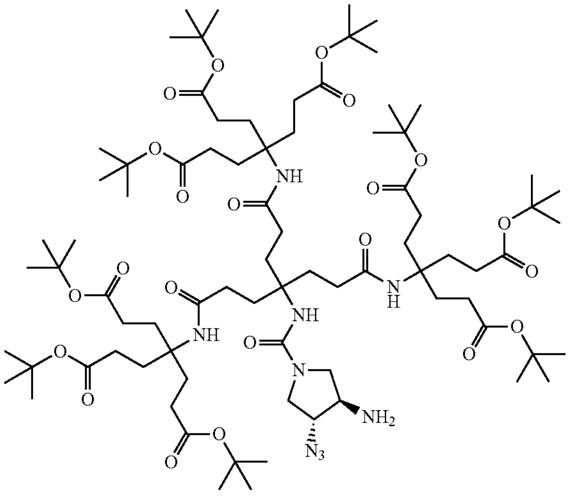

Chemical Formula: $C_{81}H_{141}N_9O_{22}$
Exact Mass: 1592.02
Molecular Weight: 1593.06

Compound 241 (300 mg, 0.185 mmol) was dissolved in THF (8.0 mL). Triphenylphosphine (46 mg, 0.176 mmol) was added and the reaction stirred for 18 h. Water (4.0 mL) was added and the reaction heated at 50° C. for 6 h. The reaction mixture was concentrated in vacuo and the residue purified by reverse phase MPLC on a C18 SNAP Ultra 60 g cartridge eluting (75% acetone:water to 100% acetone: water) to give a Compound 243 as a white solid (187 mg, 0.117 mmol, 66%).

$^1$H NMR (400 MHz, $CD_3OD$) δ 3.92-3.72 (m, J=5.8, 4.0 Hz, 3H, $NC\underline{H}_2$), 3.61 (dd, J=10.7, 6.0 Hz, 1H, $C\underline{H}N_3$), 3.41-3.32 (m, 1H, $C\underline{H}NH_2$), 3.24-3.12 (m, 1H $NC\underline{H}_2$), 2.23-2.16 (m, 24H, $C\underline{H}_2C(O)$), 1.99-1.91 (m, 24H, $CC\underline{H}_2$), 1.45 (s, 81H, $C(C\underline{H}_3)_3$).

$^{13}$C NMR (100 MHz, $CDCl_3$) δ 173.3 ($\underline{C}(O)NH$), 172.7 ($C\underline{C}O_2C$), 158.2 (s, $N\underline{C}(O)N$), 81.6 (s, $CO_2\underline{C}(CH_3)_3$), 58.7 ($\underline{C}NH_2$), 58.6 (s, $\underline{C}H_2N$), 58.4 ($\underline{C}N_3$), 33.1 (s, $\underline{C}H_2C(O)$), 32.3 (s, $\underline{C}H_2C(O)NH$), 30.7 (s, $C\underline{C}H_2$), 30.5 ($C\underline{C}H_2$), 28.4 (s, $CO_2C(\underline{C}H_3)_3$).

Compound 244

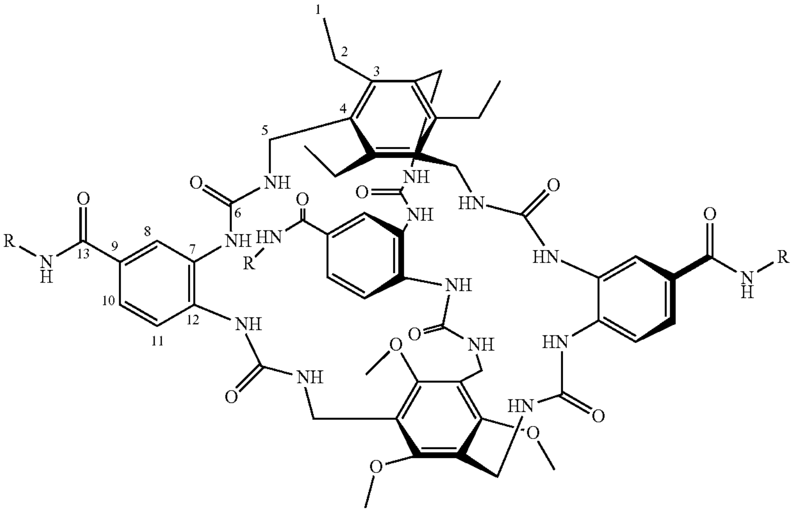

R =

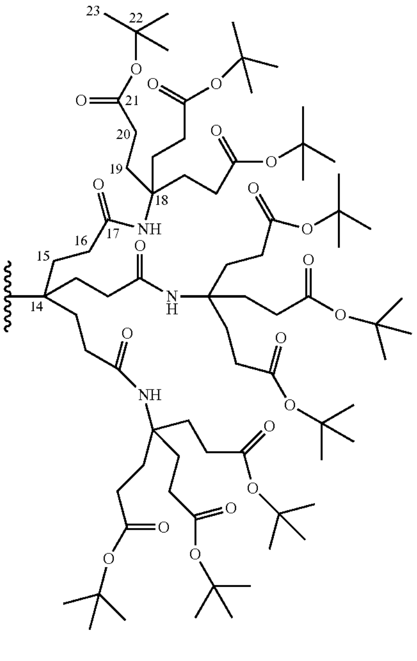

Compound 7b (80 mg, 0.016 mmol) was azeotroped with toluene to dryness in reaction flask and then redissolved in pyridine (8.0 mL). This was heated to 40° C. and a solution of Compound 5a (6.2 mg, 0.019 mmol) in DCM (0.7 mL) was added by syringe pump over 3 h. The reaction was then cooled to room temperature and stirred for a further 16 h. The reaction was concentrated under vacuum and the crude residue obtained was then purified by reverse phase flash chromatography on a 30 g SNAP Ultra C18 cartridge elution (1CV 80% acetone/$H_2O$, 10 CV 80-95% acetone/$H_2O$, 2CV 100% acetone) to give Compound 244 as a white solid (55 mg, 0.010 mmol, 64%).

$^1$H NMR (500 MHz, methanol-$d_4$) δ $^z$d. 8.12 (3H, J=2.1 Hz, Ar), dd. 7.56 (3H, J=8.4, 2.1 Hz, Ar), d. 7.41 (3H, J=8.4 Hz), s. 4.58 (6H, ArC<u>H</u>$_2$NH), s. 4.45 (6H, ArC<u>H</u>$_2$NH), s. 3.85 (9H, ArOC<u>H</u>$_3$), m. 2.82-2.72 (6H, ArC<u>H</u>$_2$CH$_3$), m. 2.35-1.89 (144H, NHC<u>H</u>$_2$C<u>H</u>$_2$C(O)), s. 1.43 (243H, CO$_2$C(C<u>H</u>$_3$)$_3$), t. 1.20 (9H, J=7.3 Hz, ArCH$_2$C<u>H</u>$_3$).

$^{13}$C NMR (125 MHz, methanol-$d_4$) δ 175.5 (CONH), 174.4 (<u>C</u>O$_2$C(CH$_3$)$_3$), 171.1 (Ar<u>C</u>ONHR), 81.6 (CO$_2$<u>C</u>(CH$_3$)$_3$), 59.3 (ArO<u>C</u>H$_3$), 58.7 (<u>C</u>(CH$_2$CH$_2$CO$_2$)$_3$), 54.6 (<u>C</u>(CH$_2$CH$_2$CONH)$_3$), 44.2, 43.7 (Ar<u>C</u>H$_2$NHC(O)NH), 32.2 (CH$_2$<u>C</u>H$_2$CONH, <u>C</u>H$_2$CH$_2$CONH), 30.7 (CH$_2$<u>C</u>H$_2$CO$_2$C(CH$_3$)$_3$), 30.5, (<u>C</u>H$_2$CH$_2$CO$_2$C(CH$_3$)$_3$), 28.5 (CO$_2$C(<u>C</u>H$_3$)$_3$), 16.9 (ArCH$_2$<u>C</u>H$_3$).

MS: (ESI) calculated for $C_{282}H_{456}N_{24}O_{75}^{3+}$: 1795.0979, found $[M+3H]^{3+}$: 1795.0938.

Compound 245 - Receptor 13

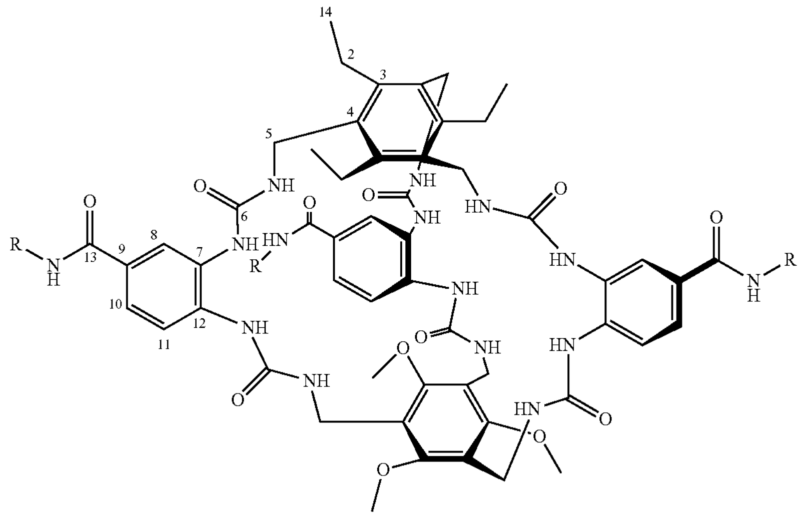

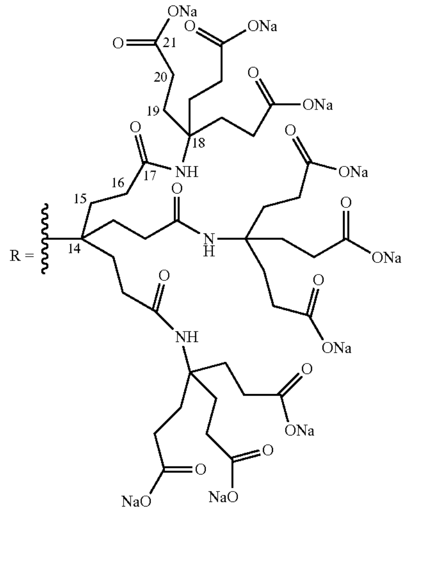

Compound 244 (8.5 mg, 0.002 mmol) was dissolved in DCM (0.5 mL) and formic acid (0.5 mL, 13.3 mmol) was added. After 24 h the reaction mixture was added dropwise into stirring water (20 mL) and the white precipitate collected by centrifuging. The supernatant was decanted off, and the white solid was neutralised using 10 mM NaOH solution to pH 7. The resulting solution was desalted by 10 mL column of G-25 sephadex. The resultant solution was freeze dried to give a white solid (1 mg, 0.32 μmol, 16%).

$^1$H NMR (500 MHz, $CD_2Cl_2$/formic acid-$d_2$, 1:1) δ $^1$H NMR (500 MHz, methanol-$d_4$) δ s. 8.18 (3H, Ar), s. 7.50 (6H, Ar), s. 4.48 (6H, ArC$\underline{H}_2$NH), s. 4.41 (6H, ArC$\underline{H}_2$NH), s. 3.83 (9H, ArOC$\underline{H}_3$), m. 2.69-2.60 (6H, ArC$\underline{H}_2$CH$_3$), m. 2.45-1.81 (144H, NHC$\underline{H}_2$C$\underline{H}_2$C(O)), m. 1.16-1.08 (9H, ArCH$_2$C$\underline{H}_3$).

Compound 246

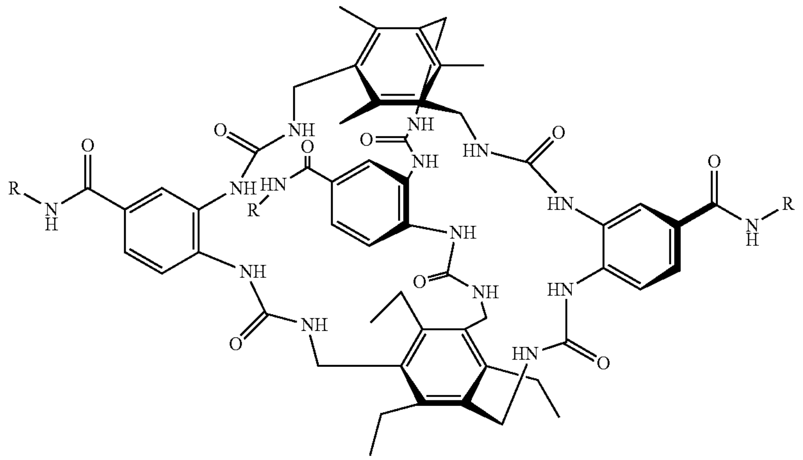

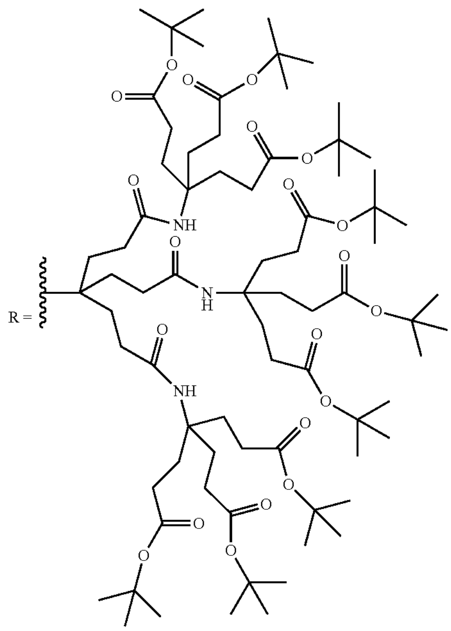

Prepared in a manner analogous to Compound 244 from Compounds 7a (202.0 mg, 0.040 mmol) and 5c (11.4 mg, 0.040 mmol). Purified by reverse phase flash chromatography on a 120 g SNAP Ultra C18 cartridge elution (1CV 80% acetone/$H_2O$, 10 CV 80-97% acetone/$H_2O$, 4CV 97% acetone) to give Compound 246 as a white solid (108.0 mg, 50.6%).

$^1H$ NMR (500 MHz, methanol-$d_4$) δ m. 8.08-7.58 (9H, Ar), m. 4.63-4.30 (12H, ArC$\underline{H}_2$NH), m. 2.95-2.60 (9H ArC$\underline{H}_3$), m. 2.32-1.84 (150H, NHC$\underline{H}_2$C$\underline{H}_2$C(O), ArC$\underline{H}_2$CH$_3$), s. 1.43 (243H, CO$_2$C(C$\underline{H}_3$)$_3$), s. 1.29 (9H, ArCH$_2$C$\underline{H}_3$).

Compound 247 - Receptor 14

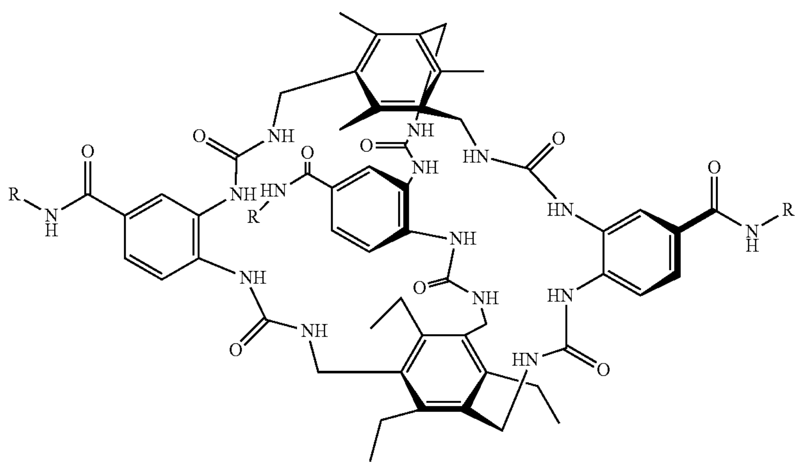

R =

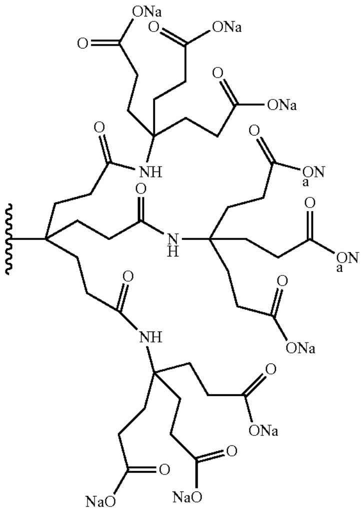

Compound 246 (108 mg, 0.02 mmol) was dissolved in anhydrous DCM (Vol: 20 mL) and TFA (4.8 mL, 60.0 mmol)_at RT. The resulting off yellow solution was stirred for 12 h at room temperature. Volatiles were removed under vacuum to give a yellow solid. The solid which was purified by reverse phase MPLC on a C18 SNAP Ultra 60 g cartridge by loading the sample in 1:1 MeOH/$H_2O$+0.1% formic acid). The resulting white solid was neutralised using 100 mM NaOH solution to pH 7 and the resulting solution concentrated to dryness under vacuum. White crystalline solid (30 mg, 0.008 mmol, 40%).

$^1$H NMR (500 MHz, methanol-$d_4$) δ m. 8.37-7.81 (9H, Ar), m. 4.57-4.22 (12H, ArC<u>H</u>$_2$NH), m. 2.85-1.66 (159H, ArC<u>H</u>$_3$, NHC<u>H</u>$_2$C<u>H</u>$_2$C(O), ArC<u>H</u>$_2$CH$_3$), t. 1.25 (9H, J=9.2 Hz, ArCH$_2$C<u>H</u>$_3$).

2,3:4,5-bis-O-(1-methylethylidene)-1-O-2-propynyl-L-arabinitol (Compound 248)

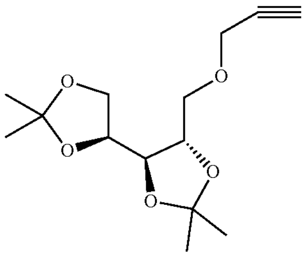 [SMILES: C#CCOC[C@@H]1OC(C)(C)O[C@H]1[C@@H]1COC(C)(C)O1]

To a suspension of the sodium hydride (500 mg of 60% by weight in oil, 12.9 mmol) in THF (20 mL) was added 2,3:4,5-bis-O-(1-methylethylidene)-L-arabinitol (2.00 g, 8.61 mmol). The suspension was heated at 50° C. for 30 minutes then cooled in an ice-bath before adding the propargyl bromide (2.56 g, 17.2 mmol). After stirring at 0° C. for 30 mins, the reaction mixture was warmed to room temp and stirred for another hour before working up by carefully adding water then evaporating the organic solvents away. The residue was dissolved in a mixture of DCM and aqueous citric acid, took organic layer and dried over sodium sulfate and evaporated to give an orange oil 2.38 g. Silica gel chromatography eluting with DCM to 10% diethyl ether in DCM gradient gave 1.47 g of a yellow oil. This material was subjected to another silica gel column eluting with 15% EtOAc in Petrol to give on evaporation 2,3:4,5-bis-O-(1-methylethylidene)-1-O-2-propynyl-L-arabinitol (1.26 g, 54%) as a colourless oil.

$^1$H NMR (400 MHz, $CDCl_3$) δ m. 4.23 (2H, OC<u>H</u>$_2$CCH), m. 4.15-4.02 (3H), dd. 3.95 (1H), dd. 3.82 (1H), t. 3.71 (1H), dd. 3.63 (1H), t. 2.42 (1H, OCH$_2$CC<u>H</u>), s. 1.405 (3H), s. 1.40 (3H), s. 1.37 (3H), s. 1.33 (3H).

$^{13}$C NMR (400 MHz, $CDCl_3$) δ 109.97, 109.78, 79.60, 79.60, 77.84, 77.24, 74.76, 70.43, 67.77, 58.81, 27.16, 27.12, 26.85, 25.36.

1-O-2-propynyl-L-arabinitol (Compound 249)

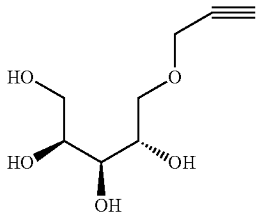

2,3:4,5-bis-O-(1-methylethylidene)-1-O-2-propynyl-L-arabinitol (1.26 g, 4.66 mmol) was dissolved in a mixture of TFA (4 mL) and water (2 mL). After 3 hours the solvent was evaporated and the residue dissolved in methanol with heating. After evaporating and redissolving several times in methanol, the residue was dissolved in the minimum amount of hot methanol and allowed to crystallise. The crystals were filtered and washed with a little cold methanol to give 1-O-2-propynyl-L-arabinitol (135 mg, 15%) as fine white crystals.

$^1$H NMR (400 MHz, $D_2O$) δ m. 4.22 (2H, OC<u>H</u>$_2$CCH), m. 4.03 (1H), dd. 3.79 (1H), m. 3.73-3.59 (4H), m. 3.52 (1H), t. 2.86 (1H, OCH$_2$CC<u>H</u>).

$^{13}$C NMR (400 MHz, $D_2O$) δ 79.55, 76.07, 71.58, 70.97, 70.87, 68.51, 63.03, 58.24.

Compound 250

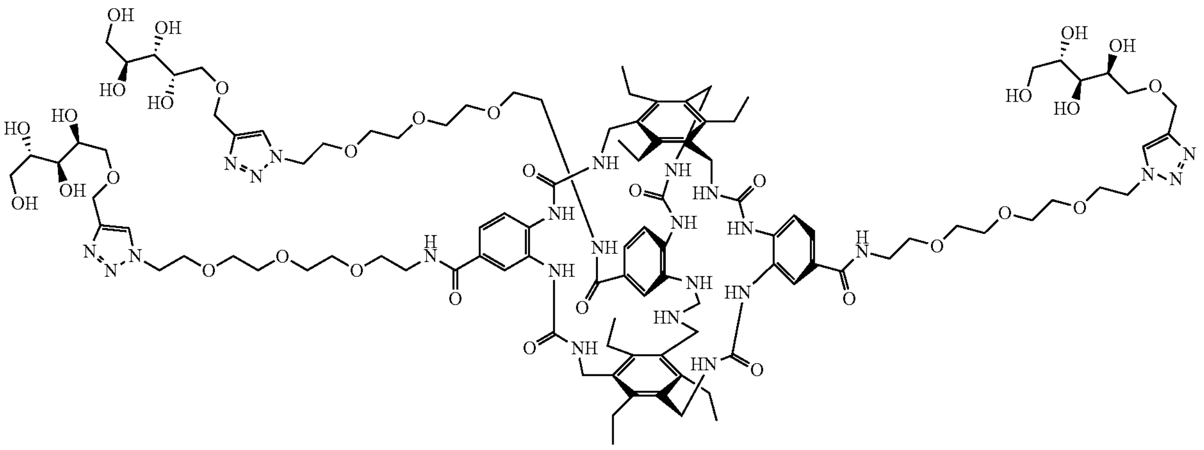

Compound 233 (25 mg, 0.015 mmol), sodium ascorbate (11.6 mg, 0.058 mmol) and Compound 249 (16.7 mg, 0.088 mmol) were dissolved in degassed THF (5 ml) and water (2 mL). To this was added a solution of copper sulfate (10.9 mg, 0.044 mmol) in water (0.5 mL), whereupon the blue copper colour rapidly turned to brown then faded over a few seconds to give a colourless solution. After 1 minute the solution started to turn cloudy then over an hour an orange solid had formed. The reaction mixture was evaporated to dryness and triturated in a mixture of DCM and methanol before loading the supernatant onto a normal phase column eluting with an increasing gradient (0 to 50%) methanol in DCM, however the solubility of the compound gave poor recovery of impure material. This impure material was purified by reverse phase chromatography eluting with a water-methanol gradient, and freeze-dried to give Compound 250 (7 mg, 20%) as a white solid.

HRMS: (nanospray$^+$) calculated for $C_{105}H_{158}N_{24}O_{33}{}^{2+}$ $[M+2H]^{2+}$ 1142.0726, found: 1142.0708.

Monocyclic Receptor Synthesis

Scheme 2 - Synthetic procedure used to prepare the anthracene diamine 37.

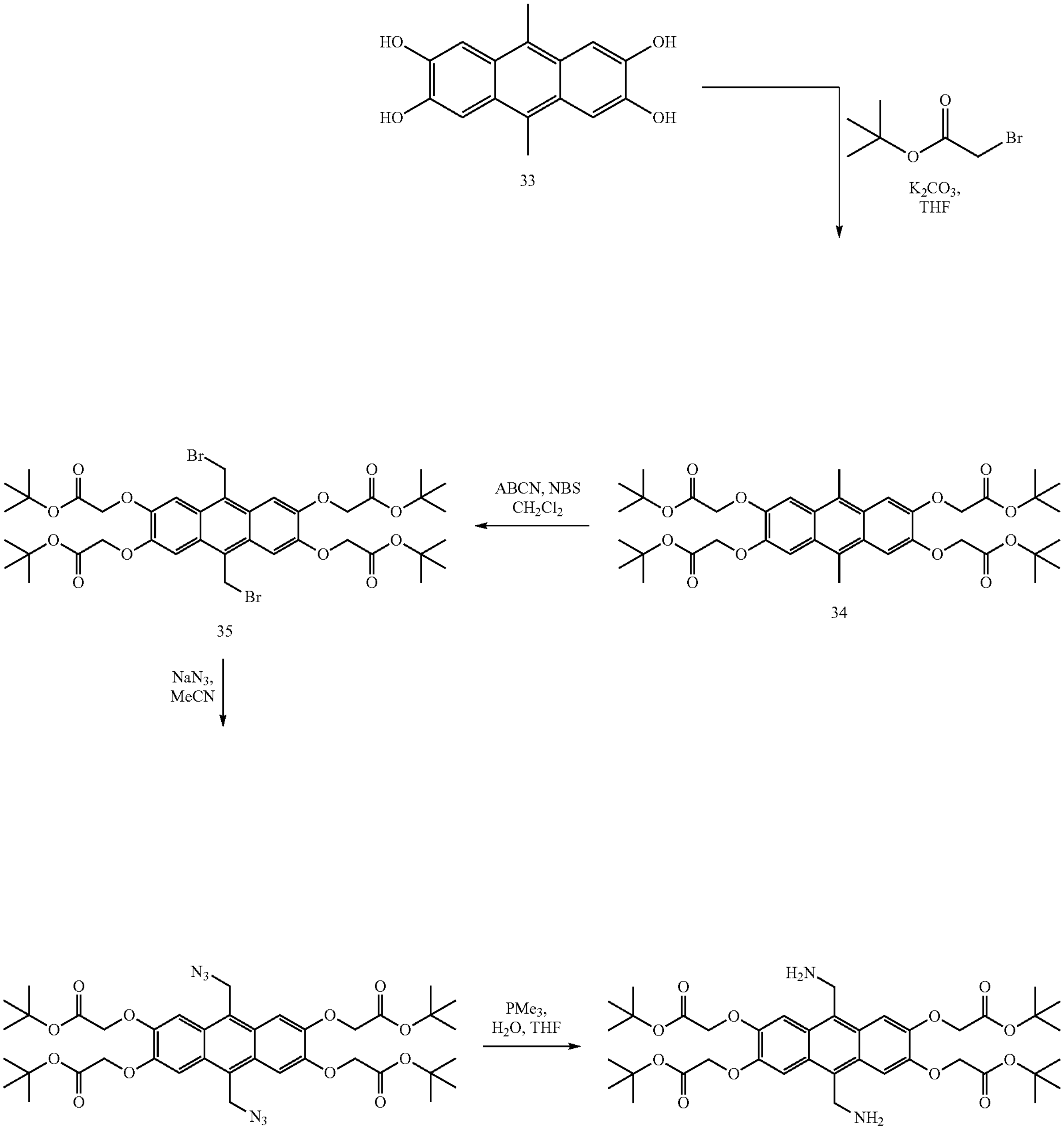

33

34

35

36

37

Tetra-hydroxy anthracene (33) was prepared according to literature procedure as described in *J. Org. Chem.*, 1989, 54, 1018.

Tetra-tert-butyl-2,2',2'',2'''-((9, 10-dimethylanthracene-2, 3, 6, 7-tetrayl)tetrakis(oxy))tetraacetate (34)

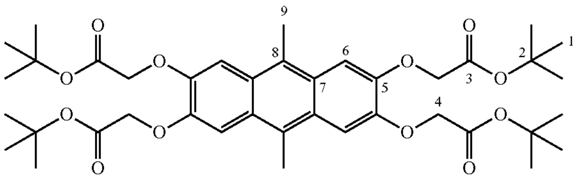 [SMILES: Cc1c2cc(OCC(=O)OC(C)(C)C)c(OCC(=O)OC(C)(C)C)cc2c(C)c2cc(OCC(=O)OC(C)(C)C)c(OCC(=O)OC(C)(C)C)cc12]

Under an inert $N_2$ atmosphere, tetra-hydroxy anthracene 33 (2.35 g, 8.7 mmol) was dissolved in anhydrous THF (500 mL). $K_2CO_3$ (4.9 g, 35.2 mmol) and tert-butyl bromoacetate (7 mL, 47.4 mmol) were added and the reaction mixture stirred under reflux for 16 hours. The mixture was cooled to room temperature and the solvent removed under vacuum. The crude residue was then dissolved in $CH_2Cl_2$ (500 mL) and washed with water (150 mL), brine (200 mL) and dried ($MgSO_4$). The solvent was removed under vacuum and the crude residue purified by flash column chromatography (1% MeOH:$CH_2Cl_2$) to yield 34 (3.8 g, 5.2 mmol, 60%) as a yellow solid. $^1$H NMR: (400 MHz, ($CDCl_3$): δ 1.49 (s, 36H, 3×C(1)$H_3$), 2.85 (s, 6H, 2×C(9)$H_3$), 4.76 (s, 8H, C(4)$H_2$), 7.38 (s, 4H, 4×C(6)H); $^{13}$C NMR: (100 MHz, ($CDCl_3$): δ 14.6 (C(9)$H_3$), 28.1 (C(1)$H_3$), 66.6 (C(4)$H_2$), 82.3 (C(2)($CH_3$)$_3$), 105.7 (C(6)H), 124.3 (C8), 126.2 (C7), 147.2 (C5), 167.8 (C(3)O); $V_{max}$ 2987, 2901, 1750, 1453, 1369, 1145, 1066 cm$^{-1}$; HRMS: (ESI$^+$) Found [M+Na]$^+$: 749.3520.

tetra-tert-butyl-2,2',2'',2'''-((9,10-bis(bromomethyl) anthracene-2,3,6,7-tetrayl)tetrakis(oxy)) tetraacetate (35)

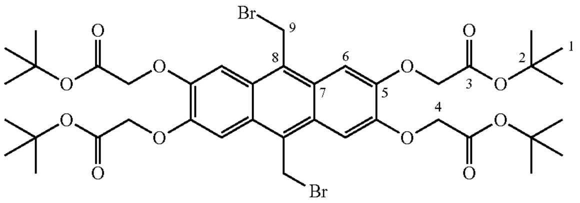 [SMILES: CC(C)(C)OC(=O)COc1cc2c(CBr)c3cc(OCC(=O)OC(C)(C)C)c(OCC(=O)OC(C)(C)C)cc3c(CBr)c2cc1OCC(=O)OC(C)(C)C]

Under an inert $N_2$ atmosphere, 34 (3 g, 4.1 mmol) was dissolved in anhydrous $CH_2Cl_2$ (500 mL). NBS (1.84 g, 10.3 mmol) and ABCN (50 mg, 5 mol %) were added, and the mixture stirred under reflux for 1.5 hours. The reaction mixture was then cooled to room temperature and diluted with $CH_2Cl_2$ (300 mL). The solution was washed with NaOH (300 mL, 1M), water (300 mL) and the solvent removed under vacuum to yield 35 (3.5 g, 4.0 mmol, 98%) as an orange solid. $^1$H NMR: (400 MHz, ($CDCl_3$): δ 1.52 (s, 36H, 3×C(1)$H_3$), 4.81 (s, 8H, C(4)$H_2$), 5.22 (s, 4H, 2×C(9) $H_2$), 7.38 (s, 4H, 4×C(6)H); $^{13}$C NMR: (100 MHz, ($CDCl_3$): δ 28.1 (C(1)$H_3$), 29.7 (C(9)$H_3$), 66.4 (C(4)$H_2$), 82.6 (C(2)($CH_3$)$_3$), 104.2 (C(6)H), 126.2 (C8), 126.4 (C7), 148.7 (C5), 167.4 (C(3)O); $V_{max}$ 2987, 2933, 1706, 1488, 1362, 1228, 1183, 1066 cm$^{-1}$; HRMS: (ESI$^+$) Found [M+Na]$^+$: 905.1709, 907.1692.

tetra-tert-butyl-2, 2',2'',2'''-((9,10-bis(azidomethyl) anthracene-2,3,6,7-tetrayl)tetrakis(oxy)) tetraacetate (36)

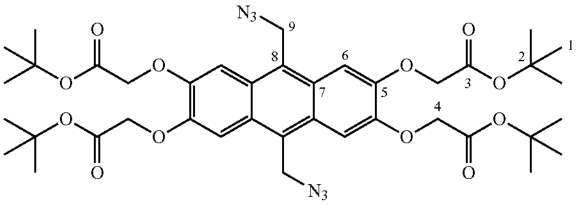 [SMILES: CC(C)(C)OC(=O)COc1cc2c(CN=[N+]=[N-])c3cc(OCC(=O)OC(C)(C)C)c(OCC(=O)OC(C)(C)C)cc3c(CN=[N+]=[N-])c2cc1OCC(=O)OC(C)(C)C]

Under an inert $N_2$ atmosphere, 35 (3.5 g, 4.0 mmol) was dissolved in anhydrous MeCN (300 mL). $NaN_3$ (1 g, 15.9 mmol) was added and the reaction stirred under reflux for 3 hours. The reaction mixture was cooled to room temperature and the solvent removed under vacuum. The crude product was dissolved in $CH_2Cl_2$ (400 mL), washed with water (3×100 mL) and the solvent removed under vacuum to yield 36 (3.2 g, 3.9 mmol, 98%) as an orange solid. $^1$H NMR: (400 MHz, ($CDCl_3$): δ 1.52 (s, 36H, 3×C(1)$H_3$), 4.78 (s, 8H, C(4) $H_2$), 5.08 (s, 4H, 2×C(9)$H_2$), 7.40 (s, 4H, 4×C(6)H); $^{13}$C NMR: (100 MHz, ($CDCl_3$): δ 28.1 (C(1)$H_3$), 46.9 (C(9)$H_3$), 66.4 (C(4)$H_2$), 82.6 (C(2)($CH_3$)$_3$), 104.6 (C(6)H), 124.2 (C8), 126.8 (C7), 148.7 (C5), 167.5 (C(3)O); $v_{max}$ 2988, 2931, 2091, 1736, 1498, 1364, 1227, 1186, 1062 cm$^{-1}$; HRMS: (ESI$^+$) Found [M+Na]$^+$: 831.3530.

tetra-tert-butyl-2,2',2'',2'''-((9, 1O-bis(aminomethyl) anthracene-2,3,6, 7-tetrayl)tetrakis(oxy)) tetraacetate (37)

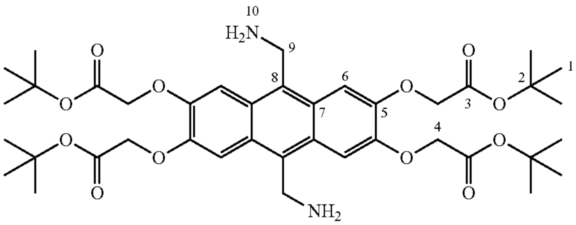 [SMILES: CC(C)(C)OC(=O)COc1cc2c(CN)c3cc(OCC(=O)OC(C)(C)C)c(OCC(=O)OC(C)(C)C)cc3c(CN)c2cc1OCC(=O)OC(C)(C)C]

Under an inert $N_2$ atmosphere, 36 (100 mg, 0.12 mmol) was dissolved in anhydrous degassed THF (8 mL). $PMe_3$ was added (2.5 mL, 2.5 mmol, 1M in THF) and the mixture stirred at room temperature for 3 hours. Degassed water (2 mL) was added and the reaction mixture stirred for 1 hour. The solvent was then evaporated under a flow of nitrogen and the crude residue dissolved in THF/$H_2O$ (5:1, 3 mL). The solvent was then removed by freeze-drying to yield 37 (90 mg, 0.12 mmol, 96%) as a pale brown solid. $^1$H NMR: (400 MHz, ($CDCl_3$): δ 1.50 (s, 36H, 3×C(1)$H_3$), 4.58 (s, 4H, 2×C(9)$H_2$), 4.77 (s, 8H, C(4)$H_2$), 7.49 (s, 4H, 4×C(6)H); $^{13}$C NMR: (100 MHz, ($CDCl_3$): δ 28.1 (C(1)$H_3$), 38.9 (C(9)$H_2$), 66.5 (C(4)$H_2$), 82.4 (C(2)($CH_3$)$_3$), 105.0 (C(6)H), 125.8 (C8), 126.2 (C7), 148.0 (C5), 167.6 (C(3)O); $v_{max}$ 2982, 2926, 1729, 1497, 1358, 1222, 1144, 1069 cm$^{-1}$; HRMS: (MALDI$^+$) Found [M+H]$^+$: 757.3909.

Scheme 3 - Synthetic procedure used to prepare the monocyclic receptor 40.

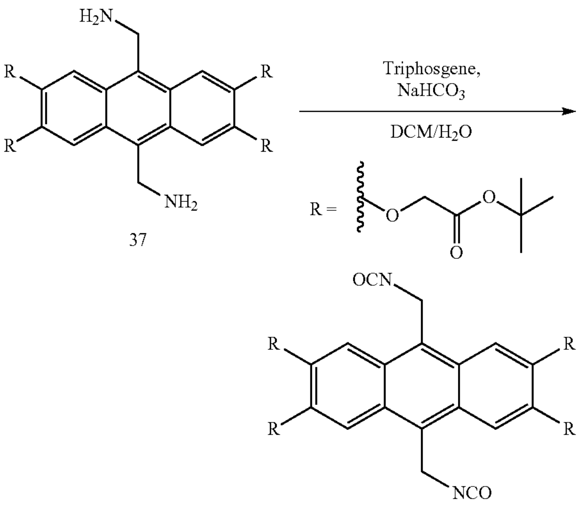

37

38

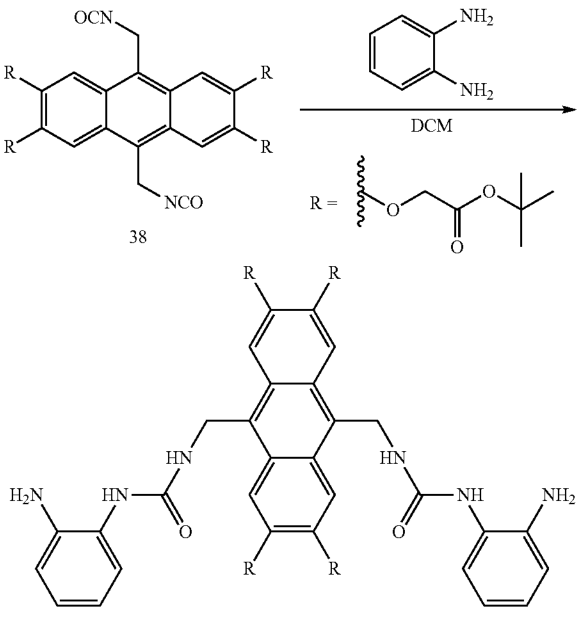

38

39

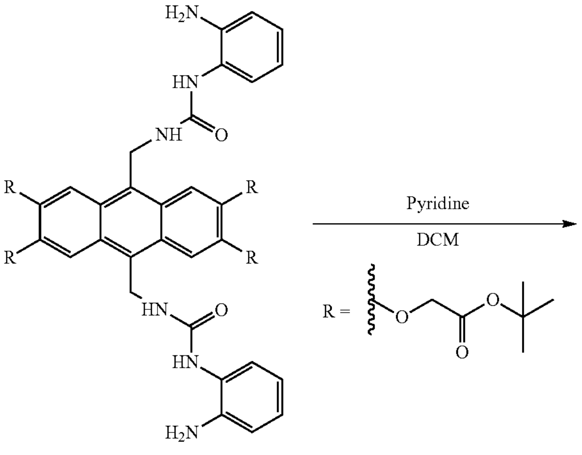

39

-continued

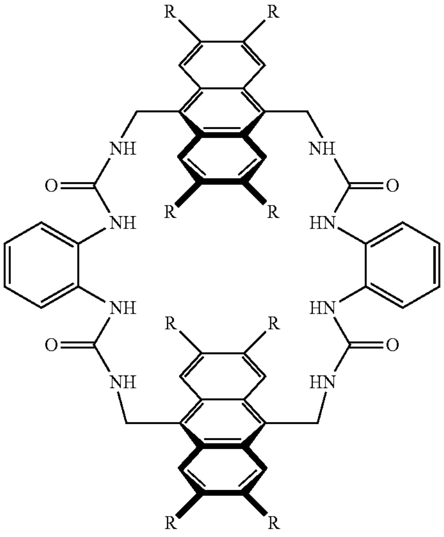

40 tetra-tert-butyl-2,2',2'',2'''-((9,10-bis(isocyanatomethyl)anthracene-2,3, 6, 7-tetrayl)tetrakis(oxy)) tetraacetate (38)

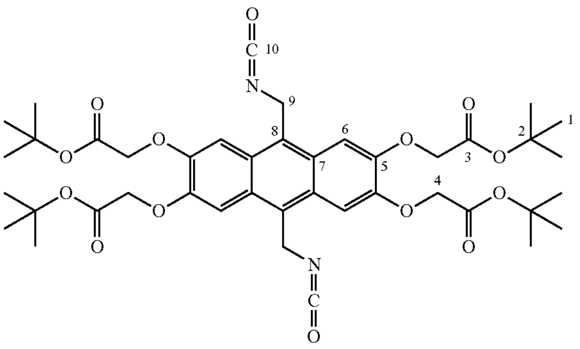 [SMILES: CC(C)(C)OC(=O)COc1cc2c(CN=C=O)c3cc(OCC(=O)OC(C)(C)C)c(OCC(=O)OC(C)(C)C)cc3c(CN=C=O)c2cc1OCC(=O)OC(C)(C)C]

Under an inert $N_2$ atmosphere, a flask was charged with 37 (30 mg, 0.04 mmol) and $NaHCO_3$ (12 mg, 0.14 mmol). $CH_2Cl_2$ (1 mL) and $H_2O$ (1 mL) were added, the mixture cooled to 0° C. and rapidly stirred. Triphosgene (9.4 mg, 0.016 mmol) was added and the reaction mixture stirred at room temperature for 30 minutes. The reaction mixture was diluted with $CH_2Cl_2$ (10 mL) and the organic layer separated, dried ($MgSO_4$) and the solvent removed under vacuum to afford 38 (29 mg, 0.036 mmol, 91%) as an orange solid. $^1H$ NMR: (400 MHz, ($CDCl_3$): δ 1.51 (s, 36H, 3×C(1)$H_3$), 4.78 (s, 8H, C(4)$H_2$), 5.07 (s, 4H, 2×C(9)$H_2$), 7.35 (s, 4H, 4×C(6)H); $^{13}C$ NMR: (100 MHz, ($CDCl_3$): δ 28.0 (C(1)$H_3$), 39.83 (C(9)$H_2$), 66.6 (C(4)$H_2$), 82.7 (C(2)($CH_3$)$_3$), 104.4 (C(6)H), 125.5 (C8), 126.0 (C7), 148.7 (C5), 167.3 (C(3)O); $V_{max}$ 2979, 2934, 2251, 1734, 1493, 1367, 1225, 1144, 1064 $cm^{-1}$; HRMS: (ESI) Found [M+Na]$^+$: 831.3319. tert-butyl protected half receptor (39)

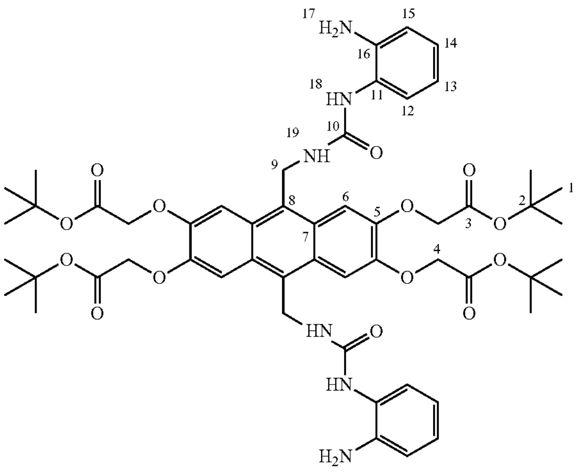 [SMILES: CC(C)(C)OC(=O)COc1cc2c(CNC(=O)Nc3ccccc3N)c3cc(OCC(=O)OC(C)(C)C)c(OCC(=O)OC(C)(C)C)cc3c(CNC(=O)Nc3ccccc3N)c2cc1OCC(=O)OC(C)(C)C]

Under an inert $N_2$ atmosphere, 1,2-phenylene diamine (0.3 g, 2.70 mmol) was dissolved in dry degassed $CH_2Cl_2$ (120 mL). A solution of 38 (55 mg, 0.068 mmol) in dry degassed $CH_2Cl_2$ (50 mL) was added dropwise over 10 minutes and then stirred at room temperature for 30 minutes. The solvent was removed under vacuum and the crude solid purified by flash column chromatography (80:20 EtOAc:hexane→5:95 MeOH:$CH_2Cl_2$→10:90 MeOH:$CH_2Cl_2$) to yield 39 (53 mg, 0.052 mmol, 77%) as an orange brown solid. $^1H$ NMR: (400 MHz, (($CD_3$)$_2$SO): δ 1.47 (s, 36H, 3×C(1)$H_3$), 4.59 (s, 4H, N(19)$H_2$), 4.87 (s, 8H, C(4)$H_2$), 5.12 (s, 4H, 2×C(9)$H_2$), 6.50-6.57 (m, 4H, C(13)H and N(18)H), 6.66-6.70 (m, 2H, C(15)H), 6.77 (t, J=7.6 Hz, 2H, C(14)H), 7.42-7.48 (m, 4H, C(12)H and N(18)H), 7.66 (s, 4H, 4×C(6)H); $^{13}C$ NMR: (100 MHz, (($CD_3$)$_2$SO): δ 28.2 (C(1)$H_3$), 36.7 (C(9)$H_2$), 66.8 (C(4)$H_2$), 82.9 (C(2)($CH_3$)$_3$), 105.2 (C(6)H), 114.5 (C15), 118.9 (C13), 122.8 (C11), 125.2, 125.5 (C12 and C14), 125.8 (C8), 126.2 (C7), 148.3 (C5), 149.5 (C16), 154.2 (C10), 167.5 (C(3)O); $V_{max}$ 3315, 2973, 2901, 1733, 1622, 1494, 1393, 1225, 1146, 1057, 742 $cm^{-1}$; HRMS: (ESI$^+$) Found [M+Na]$^+$: 1047.4689. tert-butyl protected tetra-urea macrocycle (40)

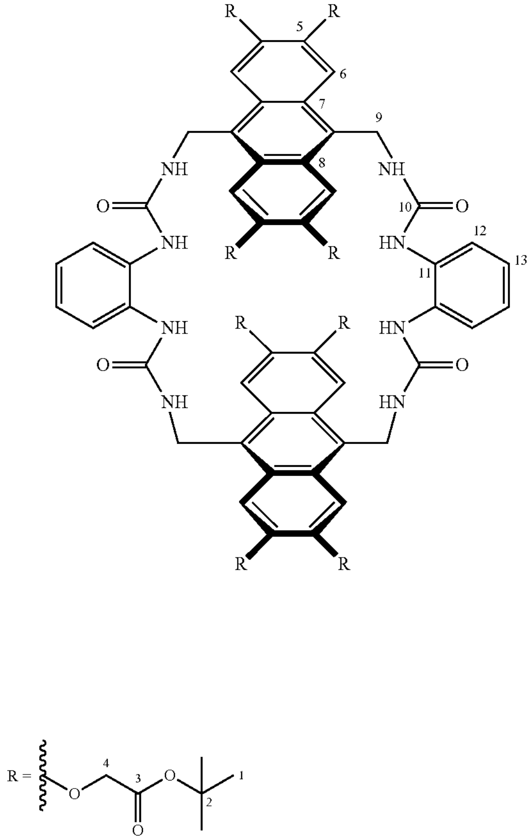

Under an inert $N_2$ atmosphere, 38 (40 mg, 0.049 mmol) was dissolved in dry degassed $CH_2Cl_2$ (600 mL). To this was added a solution of 39 (50 mg, 0.049 mmol) in dry degassed pyridine (60 mL) dropwise over 20 minutes. The reaction was stirred at room temperature for 16 hours and then the solvent removed under reduced pressure. The crude residue was suspended in HPLC grade water and freeze-dried to afford a fine crude solid. The product was then purified by reverse phase HPLC and freeze dried to afford 40 (50 mg, 0.027 mmol, 56%) as an off white solid. $^1H$ NMR: (400 MHz, (($CD_3$)$_2$CO): δ 1.49 (s, 36H, 3×C(1)$H_3$), 4.78 (m, 16H, C(4)$H_2$), 5.12 (m, 8H, C(9)$H_2$), 6.95 (s, 4H, C(13)H), 7.65 (s, 8H, C(6)H), 8.07 (s, 4H, C(12)H); $^{13}C$ NMR: (100 MHz, (($CD_3$)$_2$CO): δ 27.3 (C(1)$H_3$), 36.0 (C(9)$H_2$), 66.0 (C(4)$H_2$), 81.6 (C(2)($CH_3$)$_3$), 105.3 (C(6)H), 126.3 (C8), 126.9 (C7), 127.4 (C12), 132.2 (C13), 135.6 (C11), 147.8 (C5), 155.5 (C10), 167.9 (C(3)O); HRMS: (ESI$^+$) Found [M+Na]$^+$: 1856.8145, [M+2Na]$^{2+}$: 939.9019.

Scheme 4 - Synthetic procedure used to prepare the monocylic receptor 89.
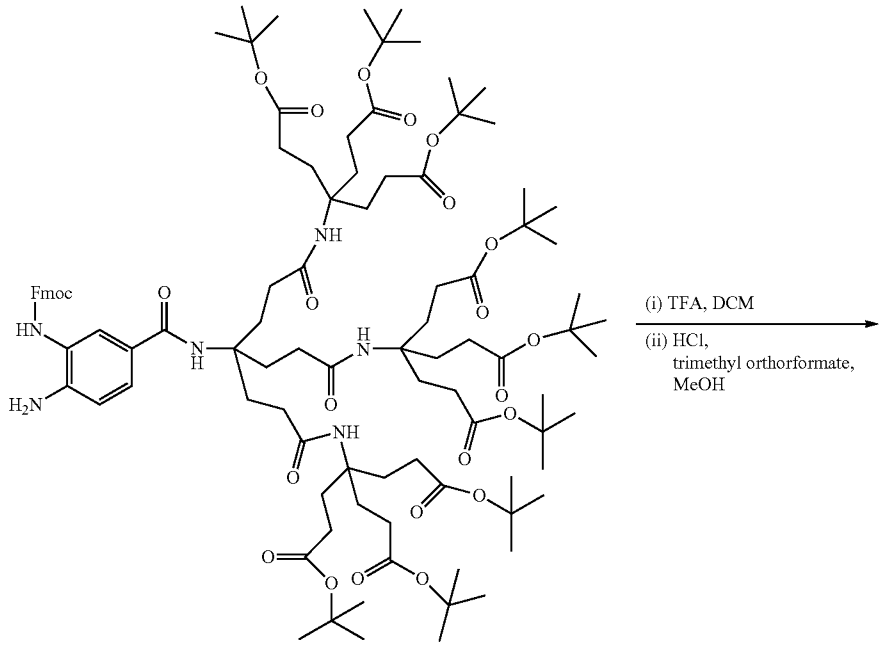
84
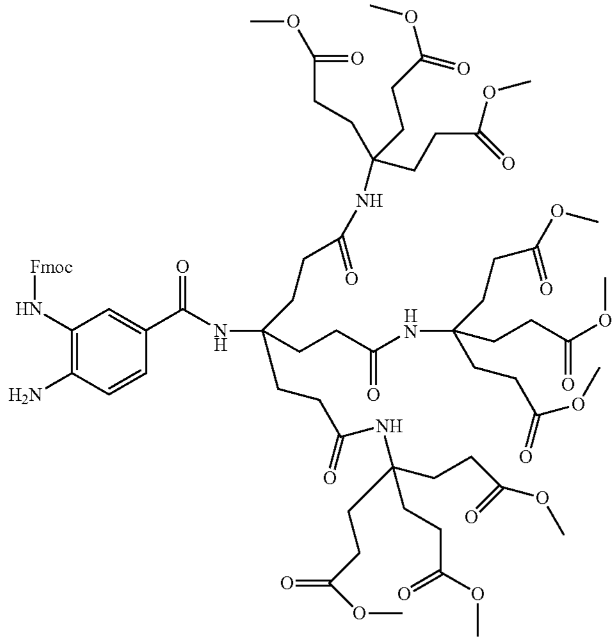
94

-continued
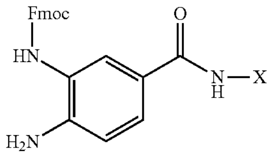
84 or 94
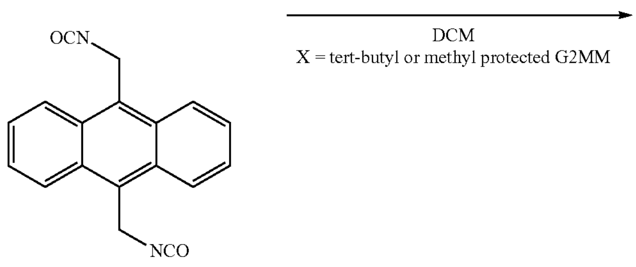
55
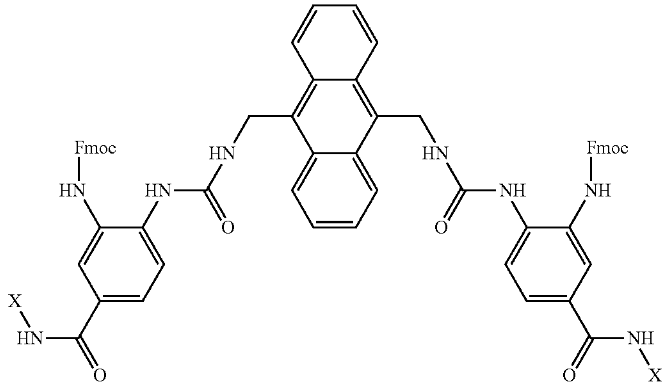
86 or 97a
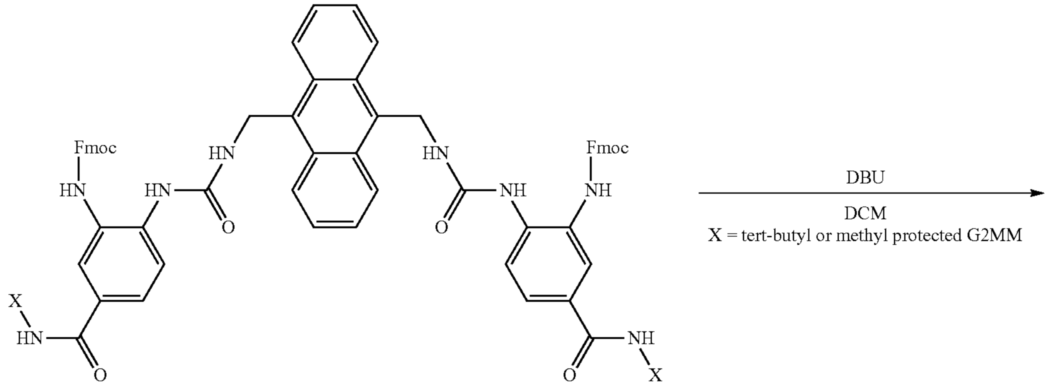
86 or 97a -continued
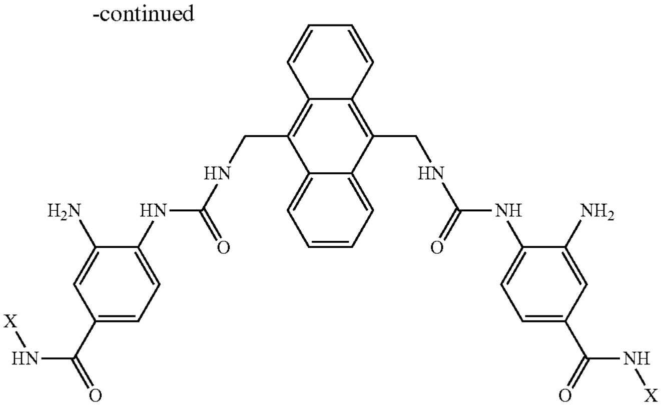
88 or 97
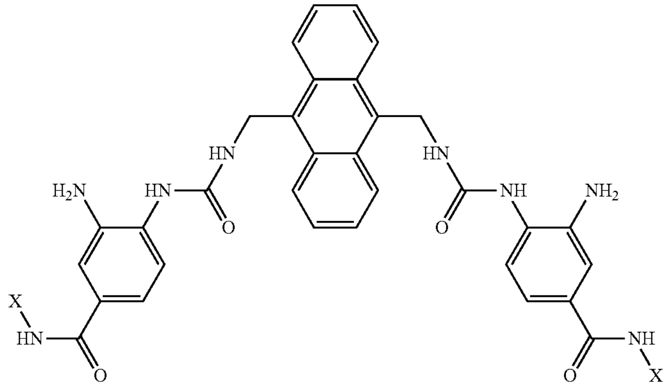
88 or 97
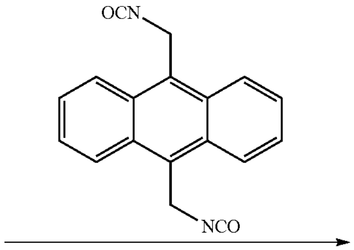
DCM
X = tert-butyl or methyl protected G2MM
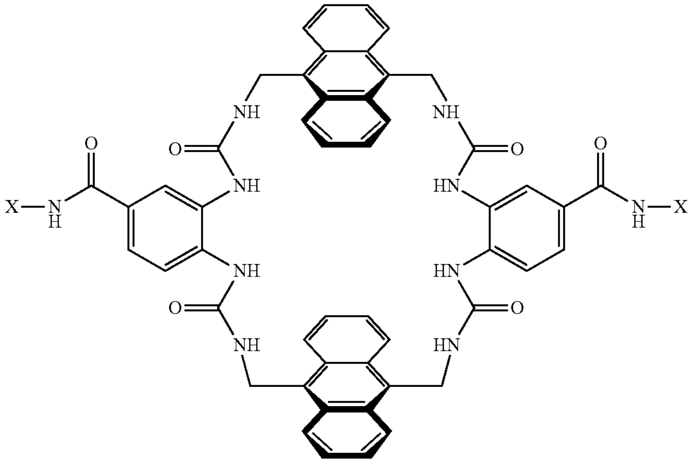
89 or 98

9,10-bis(isocyanatomethyl)anthracene (55)

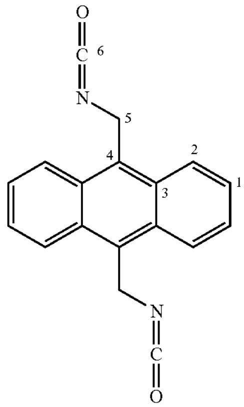 [SMILES: O=C=NCc1c2ccccc2c(CN=C=O)c2ccccc12]

Under an inert $N_2$ atmosphere, a flask was charged with anthracene-9,10-diyldimethanamine An-$NH_2$* (20 mg, 0.085 mmol) and $NaHCO_3$ (26 mg, excess). $CH_2Cl_2$ (1 mL) and $H_2O$ (1 mL) were added, the mixture cooled to 0° C. and rapidly stirred. Triphosgene (20 mg, 0.068 mmol) was added and the reaction mixture stirred at room temperature for 30 minutes. The reaction mixture was diluted with $CH_2Cl_2$ (10 mL) and the organic layer separated, dried ($MgSO_4$) and the solvent removed under vacuum to afford 55 (22 mg, 0.076 mmol, 91%) as a yellow solid. $^1H$ NMR: (400 MHz, ($CDCl_3$): δ 5.38 (s, 4H, C(5)$\underline{H}_2$), 7.66 (dd, J=6.9, 3.2 Hz, 4H, C(1)$\underline{H}$), 8.35 (dd, J=6.9, 3.2 Hz, 4H, C(2)$\underline{H}$); $^{13}C$ NMR: (100 MHz, ($CDCl_3$): δ 39.0 ($\underline{C}$(5)$H_2$), 124.1 ($\underline{C}$(1)H), 126.7 ($\underline{C}$(8)H), 127.3 ($\underline{C}$4), 129.3 ($\underline{C}$3), 167.3; $V_{max}$ 2921, 2234, 1620, 1491, 1448, 1324, 1185, 858, 751 $cm^{-1}$; HRMS: ($ESI^+$) Found $[M+Na]^+$: 311.0785.

* prepared according to the synthetic procedures described in literature procedure as described in *Org. Biomol. Chem.*, 2005, 3, 48.

Diamino Tert-Butyl Protected Anthracene Half Receptor (88)

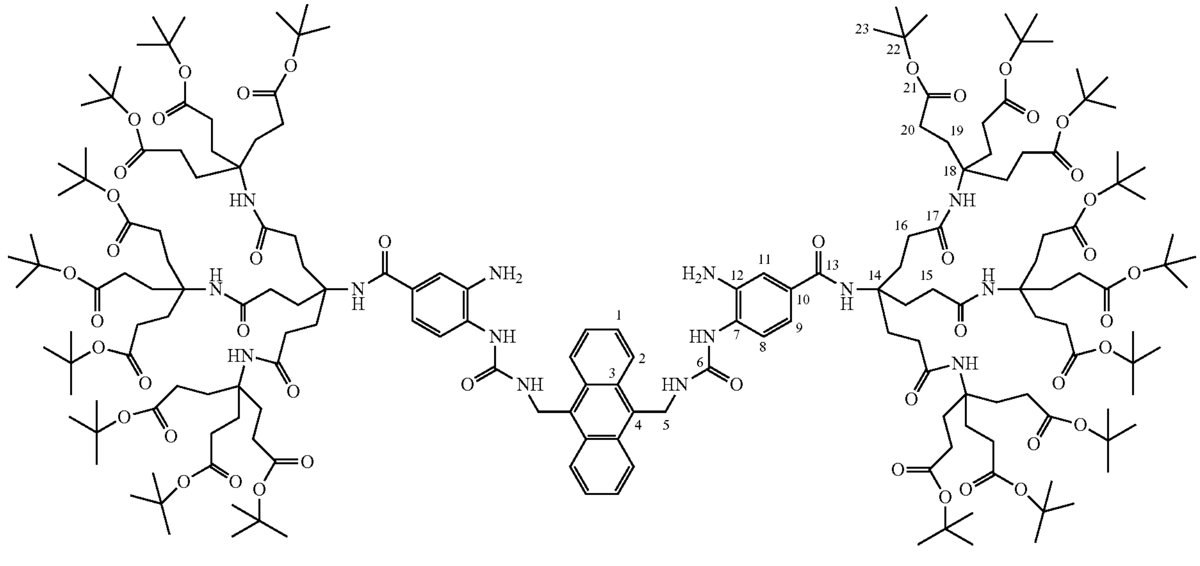 [SMILES: CC(C)(C)OC(=O)CCC(CCC(=O)OC(C)(C)C)(CCC(=O)OC(C)(C)C)NC(=O)CCC(CCC(=O)NC(CCC(=O)OC(C)(C)C)(CCC(=O)OC(C)(C)C)CCC(=O)OC(C)(C)C)(CCC(=O)NC(CCC(=O)OC(C)(C)C)(CCC(=O)OC(C)(C)C)CCC(=O)OC(C)(C)C)NC(=O)c1ccc(NC(=O)NCc2c3ccccc3c(CNC(=O)Nc3ccc(C(=O)NC(CCC(=O)NC(CCC(=O)OC(C)(C)C)(CCC(=O)OC(C)(C)C)CCC(=O)OC(C)(C)C)(CCC(=O)NC(CCC(=O)OC(C)(C)C)(CCC(=O)OC(C)(C)C)CCC(=O)OC(C)(C)C)CCC(=O)NC(CCC(=O)OC(C)(C)C)(CCC(=O)OC(C)(C)C)CCC(=O)OC(C)(C)C)cc3N)c3ccccc23)c(N)c1]

Under an inert $N_2$ atmosphere, 84 (350 mg, 0.195 mmol) was dissolved in anhydrous dichloromethane (10 mL). 55 (25 mg, 0.098 mmol) was added and the reaction heated to reflux for 2 days. The reaction was cooled to room temperature and the solvent removed under vacuum. The crude residue was purified by reverse phase HPLC to afford the Fmoc protected product 86 (254 mg, 0.66 mmol, 67%) as a white solid. Conversion to 86 was confirmed by limited NMR studies* and high resolution mass spectrometry ($ESI^+$): m/z calculated for $[M+2Na]^2$+1963.1077, found 1963.1067. Under an inert $N_2$ atmosphere, 86 was dissolved in anhydrous dichloromethane (10 mL) and cooled to 0° C. DBU (45 μL, 0.28 mmol) was added dropwise and the reaction mixture warmed to room temperature and stirred for 2 hours. The solvent was removed under vacuum and the crude product purified by flash column chromatography (5% $MeOH:CH_2Cl_2$) to afford 88 (215 mg, 0.063 mmol, 95%) as an off-white solid. $^1H$ NMR: (400 MHz, ($CD_3OD$): δ 1.43 (s, 162H, C(23)$\underline{H}_3$), 1.93 (m, 36H, C(20)$\underline{H}_2$), 2.08 (m, 12H, C(15)$\underline{H}_2$), 2.18 (m, 48H, C(19, 16)$\underline{H}_2$), 5.36 (s, 4H, C(5)$\underline{H}_2$), 7.18 (dd, J=2.1, 8.3 Hz, 2H, C(9)$\underline{H}$), 7.26 (d, J=2.1 Hz, 2H, C(11)$\underline{H}$), 7.41 (d, J=8.3 Hz, 2H, C(8)$\underline{H}$), 7.41 (s, 6H, NH), 7.60 (dd, J=3.3, 6.9 Hz, 4H, C(1)$\underline{H}$), 7.89 (s, 2H, NH), 8.47 (dd, J=3.3, 6.9 Hz, 4H, C(2)$\underline{H}$); $^{13}C$ NMR: (100 MHz, ($CDCl_3$): δ 27.1 ($\underline{C}$23), 29.1 ($\underline{C}$20), 29.3 ($\underline{C}$21), 31.0 ($\underline{C}$15), 31.1 ($\underline{C}$16), 57.4 ($\underline{C}$18), 58.0 ($\underline{C}$14), 80.2 ($\underline{C}$22), 115.9 ($\underline{C}$11), 117.4 ($\underline{C}$9) 123.1 ($\underline{C}$8), 124.6 ($\underline{C}$2), 125.9 ($\underline{C}$1), 128.5 ($\underline{C}$10), 130.1 ($\underline{C}$4), 130.5 ($\underline{C}$3), 131.4 ($\underline{C}$7), 140.0 ($\underline{C}$12), 156.7 ($\underline{C}$6), 168.6 ($\underline{C}$13), 173.0 ($\underline{C}$21), 174.1 ($\underline{C}$17); HRMS: ($ESI^+$). Found $[M+H+Na]^{2+}$: 1730.5507.

* Limited NMR studies were only possible due to believed slow conformational exchange of 86 resulting in very broad signals of low intensity.

Tert-butyl protected G2 anthracene tetra urea macrocycle (89)

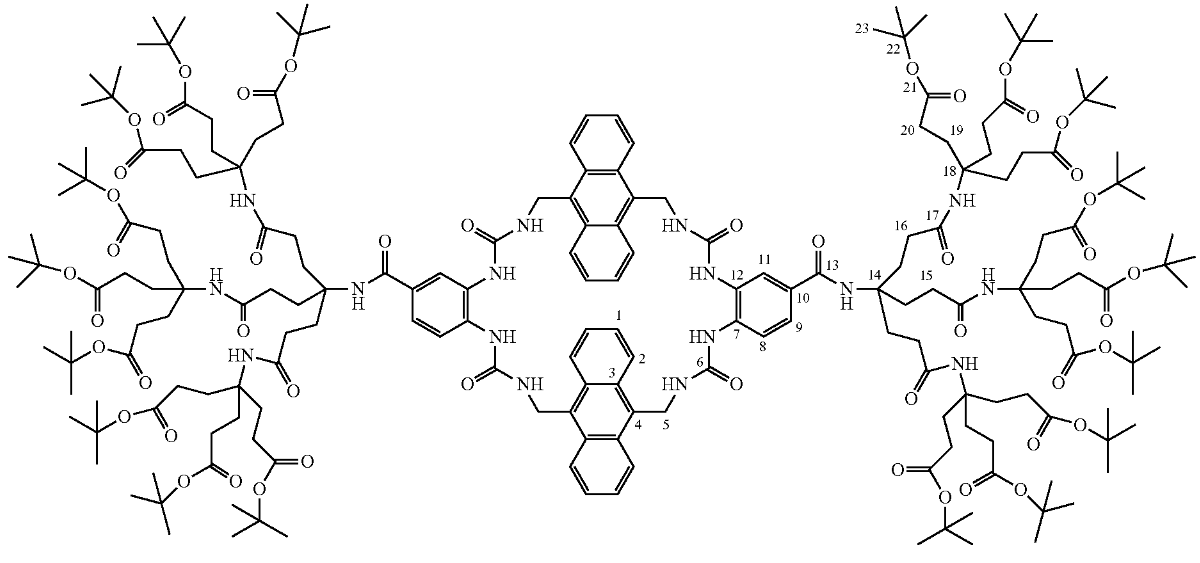 [SMILES: CC(C)(C)OC(=O)CCC(CCC(=O)OC(C)(C)C)(CCC(=O)OC(C)(C)C)NC(=O)CCC(CCC(=O)NC(CCC(=O)OC(C)(C)C)(CCC(=O)OC(C)(C)C)CCC(=O)OC(C)(C)C)(CCC(=O)NC(CCC(=O)OC(C)(C)C)(CCC(=O)OC(C)(C)C)CCC(=O)OC(C)(C)C)NC(=O)c1ccc2c(c1)NC(=O)NCc1c3ccccc3c(c3ccccc13)CNC(=O)Nc1cc(C(=O)NC(CCC(=O)NC(CCC(=O)OC(C)(C)C)(CCC(=O)OC(C)(C)C)CCC(=O)OC(C)(C)C)(CCC(=O)NC(CCC(=O)OC(C)(C)C)(CCC(=O)OC(C)(C)C)CCC(=O)OC(C)(C)C)CCC(=O)NC(CCC(=O)OC(C)(C)C)(CCC(=O)OC(C)(C)C)CCC(=O)OC(C)(C)C)ccc1NC(=O)NCc1c3ccccc3c(c3ccccc13)CNC(=O)N2]

Under an inert $N_2$ atmosphere, 55 (5.3 mg, 0.018 mmol) was dissolved in anhydrous degassed dichloromethane (600 mL) and heated to reflux. 88 (63 mg, 0.018 mmol) in anhydrous degassed dichloromethane (50 mL) was added over 30 mins and stirred at reflux for 4 days. The solvent was then removed under vacuum and the crude product purified by reverse phase HPLC and then freeze dried to afford 89 (25 mg, 6.7 μmol, 37%) as a white solid. $^1H$ NMR: (400 MHz, ($CD_3OD$): δ 1.45 (s, 162H, C(23)$\underline{H}_3$), 1.99 (m, 36H, C(20)$\underline{H}_2$), 2.17 (m, 12H, C(15)$\underline{H}_2$), 2.24 (m, 48H, C(19)$\underline{H}_2$), 2.31 (m, 12H, C(16)$\underline{H}_2$), 5.39 (s, 8H, C(5)$\underline{H}_2$), 7.31, 7.44 (br s, 4H, C(1)$\underline{H}$), 7.49 (s, 6H, NH), 7.70 (dd, J=2.1, 8.5 Hz, 2H, C(9)$\underline{H}$), 7.89 (d, J=8.5 Hz, 2H, C(8)$\underline{H}$), 7.98 (s, 2H, C(11) $\underline{H}$), 8.39 (br s, 8H, C(2)$\underline{H}$); $^{13}C$ NMR: (100 MHz, ($CDCl_3$): δ 27.0 ($\underline{C}$23), 29.1 ($\underline{C}$20), 29.3 ($\underline{C}$21), 30.8 ($\underline{C}$15), 31.1 ($\underline{C}$16), 57.3 ($\underline{C}$18), 58.1 ($\underline{C}$14), 80.3 ($\underline{C}$22), 121.6 ($\underline{C}$9), 121.77 (C12) 124.4 (C2), 124.7 (C11), 125.8, 125.9 (C1), 130.0 (C10), 130.4 (C3), 130.6 (C3), 131.4 (C7, 12), 156.0, 156.8 (C6), 168.1 (C13), 173.1 (C21), 174.1, 174.2 (C17); HRMS: (ESI+) Found $[M+3Na]^{3+}$: 1264.3835, $[M+4Na]^{4+}$: 954.0378.

Fmoc Protected Methyl Ester G2 Linker (94)

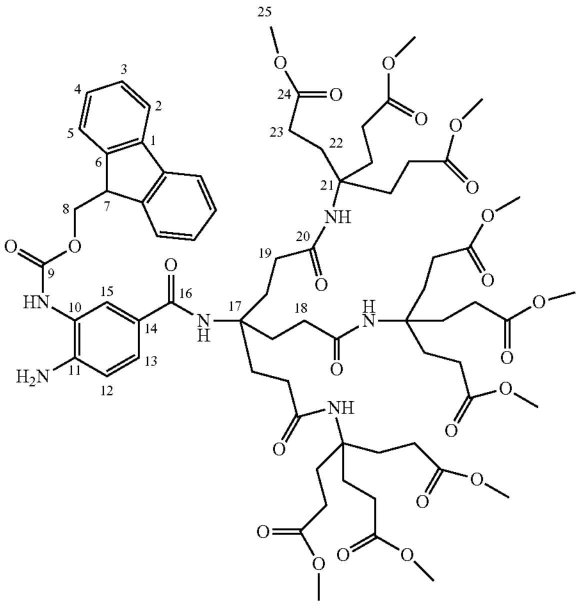 [SMILES: COC(=O)CCC(CCC(=O)OC)(CCC(=O)OC)NC(=O)CCC(CCC(=O)NC(CCC(=O)OC)(CCC(=O)OC)CCC(=O)OC)(CCC(=O)NC(CCC(=O)OC)(CCC(=O)OC)CCC(=O)OC)NC(=O)c1ccc(N)c(NC(=O)OCC2c3ccccc3-c3ccccc32)c1]

84 (215 mg, 0.12 mmol) was dissolved in dichloromethane (5 mL) and TFA (5 mL) added dropwise. The solution was stirred at room temperature for 16 hours and the TFA and solvent evaporated under a flow of $N_2$. The residue was redissolved in methanol (5 mL) and trimethyl orthoformate (5 mL). HCl (5% v/v, 0.5 mL) was added and the mixture stirred for 24 hours. The solvent was then removed under vacuum and the crude product purified by flash column chromatography (5% MeOH:$CH_2Cl_2$) to afford 94 (147 mg, 0.10 mmol, 87%). $^1$H NMR: (400 MHz, ($CDCl_3$)): δ 1.99 (m, 18H, C(23)$H_2$), 2.108 (m, 6H, C(18)$H_2$), 2.25 (m, 24H, C(22, 19)$H_2$), 3.60 (s, 27H, C(25)$H_3$), 4.23 (m, 1H, C(7)H), 4.48 (m, 2H, C(8)$H_2$), 6.31 (s, 3H, NH), 6.72 (d, J=8.4 Hz, 1H, C(13)H), 7.26 (m, 3H, C(4, 12)H), 7.38 (t, J=7.4 Hz, 2H, C(3)H), 7.63 (m, 2H, C(5)H), 7.75 (d, J=7.9 Hz, 3H, C(2, 15)H), 8.12 (s, 1H, NH); $^{13}$C NMR: (100 MHz, ($CDCl_3$)): 28.3 (C22), 29.6 (C23), 31.8 (C19), 32.2 (C18), 47.2 (C7), 51.8 (C25), 57.3 (C21), 58.2 (C17), 67.1 (C8), 116.4 (C12), 120.0 (C2), 122.6 (C10), 124.4 (C14), 125.1 (C4), 125.2 (C15), 126.6 (C13), 127.7 (C5), 127.8 (C3), 141.3 (C1), 143.6 (C11), 143.8 (C6), 155.0 (C9), 166.6 (C16), 173.3 (C20), 173.8 (C24); $V_{max}$ 3330, 2976, 2961, 1727, 1658, 1531, 1452, 1367, 1249, 1150, 846 $cm^{-1}$; HRMS: (ESI+) Found $[M+2Na]^{2+}$: 731.3279, $[M+Na]^{+}$: 1439.6353.

Diamino Methyl Ester Protected Anthracene Half Receptor (97)

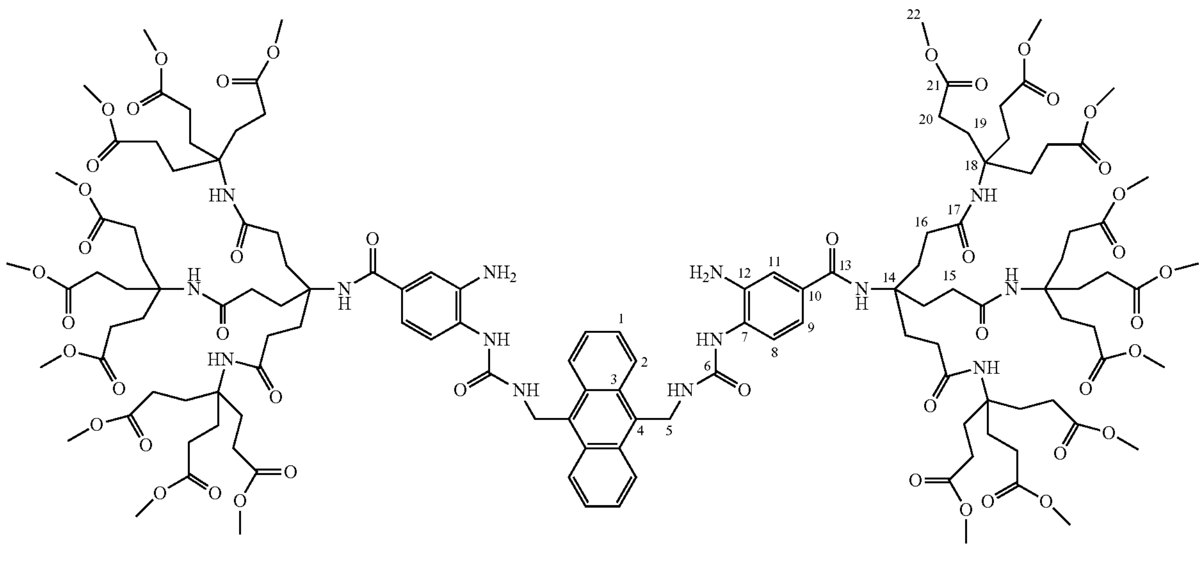

Under an inert $N_2$ atmosphere, 94 (160 mg, 0.11 mmol) was dissolved in anhydrous dichloromethane (5 mL). 55 (15 mg, 0.054 mmol) was added and the reaction heated to reflux for 4 days. The reaction was cooled to room temperature and the solvent removed under vacuum. The crude residue was purified by flash column chromatography (5% MeOH: $CH_2Cl_2$) to afford the Fmoc protected product 97a (190 mg, 0.061 mmol, 56%) as a white solid. Conversion to 97a was confirmed by limited NMR studies* and high resolution mass spectrometry ($ESI^+$): m/z calculated for $[M+2Na]^{2+}$ 1584.1834, found 1584.1849. Under an inert $N_2$ atmosphere, 97a was dissolved in anhydrous dichloromethane (10 mL) and cooled to 0° C. DBU (50 μL, 0.30 mmol) was added dropwise and the reaction mixture warmed to room temperature and stirred for 4 hours. The solvent was removed under vacuum and the crude product purified by flash column chromatography (4% MeOH:$CH_2Cl_2$) to afford 97

(151 mg, 0.057 mmol, 93%) as an off white solid. $^1$H NMR: (400 MHz, ($CD_3OD$): δ 1.94 (m, 36H, C(20)$\underline{H}_2$), 2.07 (m, 12H, C(15)$\underline{H}_2$), 2.24 (m, 48H, C(19, 16)$\underline{H}_2$), 3.60 (s, 54H, C(22)$\underline{H}_3$), 4.94 (s, 4H, C(5)$\underline{H}_2$), 7.05 (d, J=8.3 Hz, 2H, C(9)$\underline{H}$), 7.15 (m, 4H, C(11, 8)$\underline{H}$), 7.37 (s, 6H, NH), 7.48 (dd, J=3.3, 6.9 Hz, 4H, C(1)$\underline{H}$), 7.85 (s, 2H, NH), 8.21 (dd, J=3.3, 6.9 Hz, 4H, C(2)$\underline{H}$); $^{13}$C NMR: (100 MHz, ($CDCl_3$): δ 28.5 ($\underline{C}$20), 29.3 ($\underline{C}$21), 31.0 ($\underline{C}$15), 31.1 ($\underline{C}$16), 51.8 ($\underline{C}$22), 57.3 ($\underline{C}$18), 58.1 ($\underline{C}$14), 116.7 ($\underline{C}$11), 117.5 ($\underline{C}$9) 123.0 ($\underline{C}$8), 124.4 ($\underline{C}$2), 125.8 ($\underline{C}$1), 128.6 ($\underline{C}$10), 130.0 ($\underline{C}$4), 130.5 ($\underline{C}$3), 131.4 ($\underline{C}$7), 140.1 ($\underline{C}$12), 155.5 ($\underline{C}$6), 166.7 ($\underline{C}$13), 173.3 ($\underline{C}$17), 173.9 ($\underline{C}$21); HRMS: ($ESI^+$) Found $[M+2Na]^{2+}$: 1361.1096, Found $[M+3Na]^{3+}$: 915.7415.

* Limited NMR studies were only possible due to believed slow conformational exchange of 97a resulting in very broad signals of low intensity.

Methyl Ester Protected G2 Anthracene Tetra Urea Macrocycle (98)

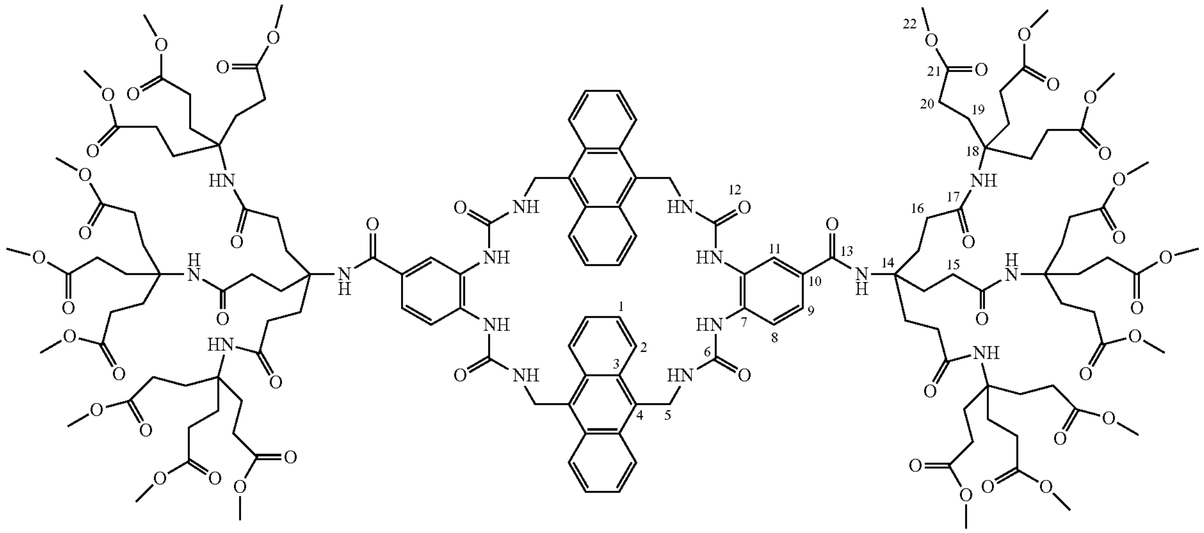

Under an inert $N_2$ atmosphere, 55 (7.9 mg, 0.027 mmol) was dissolved in anhydrous degassed dichloromethane (600 mL) and heated to reflux. 97 (73 mg, 0.027 mmol) in anhydrous degassed dichloromethane (50 mL) was added over 30 mins and stirred at reflux for δ days. The solvent was then removed under vacuum and the crude product purified by reverse phase HPLC and then freeze dried to afford 98 (21 mg, 7.0 μmol, 26%) as a pale yellow solid. $^1$H NMR: (400 MHz, $(CD_3)_2SO$): δ 1.89 (m, 36H, C(20)$H_2$), 1.95 (m, 12H, C(15)$H_2$), 2.12 (m, 12H, C(16)$H_2$), 2.22 (m, 36H, C(19)$H_2$), 5.25 (s, 8H, C(5)$H_2$), 7.32 (s, 6H, NH), 7.42 (br s, 4H, C(1)H), 7.52 (m, 6H, C(1, 9)H), 7.74 (s, 2H, NH), 7.87 (d, J=8.5 Hz, 2H, C(8)H), 8.07 (s, 2H, C(11)H), 8.37 (br s, 8H, C(2)H); 13C NMR: (100 MHz, $(CD_3)_2SO$): δ 28.3 (C20), 29.2 (C21), 29.5, 29.8 (C15), 30.7, 31.0 (C16), 35.7 (C5), 51.8 (C22), 56.8 (C18), 57.9 (C14), 120.0 (C8), 122.8 (C9), 123.3 (C11), 125.4 (C2), 125.7 (C12), 126.4, 126.5 (C1), 129.0, 129.5 (C3), 129.9 (C4), 135.6 (C7) 155.1, 155.7 (C6), 166.0 (C13), 172.9 (C17), 173.7 (C21); HRMS: (ESI$^+$) Found $[M+2Na]^{2+}$: 1506.1621, $[M+3Na]^{3+}$: 1011.7687.

Deprotected Anthracene Tetra Urea Macrocycle (90)

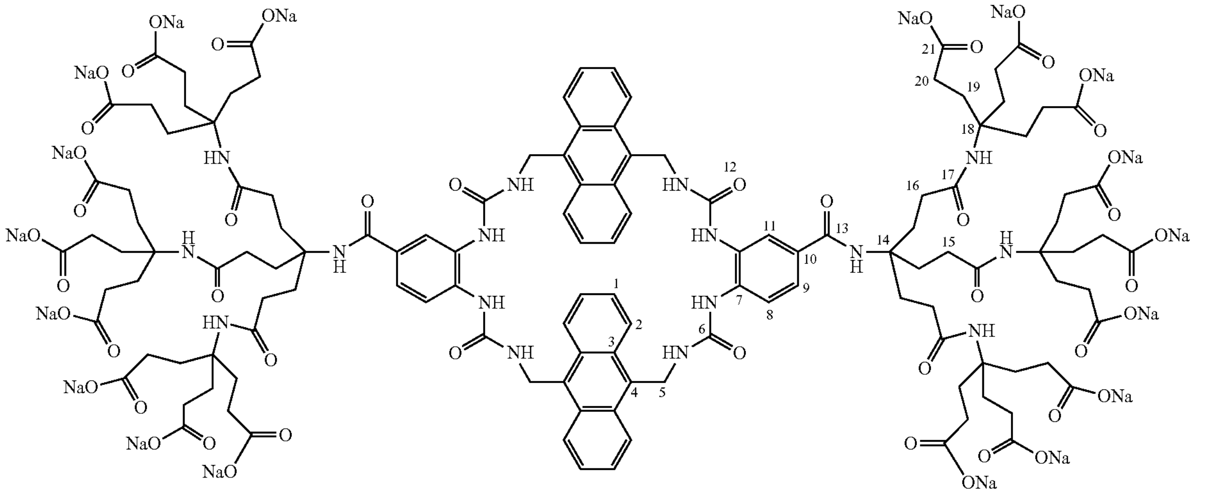

Protected receptor 89 (30 mg, 0.008 mmol) was dissolved in dichloromethane (HPLC grade, 2.7 ml) and cooled to 0° C. Trifluoroacetic acid (TFA) (0.3 mL) was added dropwise and the reaction warmed to room temperature and stirred for 4 hours. The solvent was then removed under a flow of nitrogen, then the residue was co-evaporated with toluene (3×10 mL) to remove residual TFA, suspended in water and freeze dried. The product was then purified by preparative HPLC (Waters CSH C18 5 μm 19×250 mm) eluting with 100% Water (buffered with 0.1% TFA)→100% methanol over 40 minutes. The solvent was removed under vacuum, the residue co-evaporated with toluene (3×10 mL), the product suspended in water and freeze dried. The solid was then suspended in water, neutralised to pH 7.4 with NaOH (aq), filtered and then freeze dried to afford 90 as a white solid (21 mg, 0.0068 mmol, 85%). $^1$H NMR: (400 MHz, 75° C., $D_2O$): b 2.40-2.50 (m, 36H, C(19)$H_2$), 2.58-2.71 (m, 48H, C(20)$H_2$, C(15)$H_2$), 2.80-2.90 (m, 12H, C(16)$H_2$), 5.63, 5.81 (br s, 4H, C(5)$H_2$), 7.43-7.50, 7.98-8.06 (br m, 4H, C(1)H), 8.25 (br s, 2H, C(11)H), 8.27 (d, 2H, C(9)H), 8.39 (d, 2H, C(8)H), 7.63 (d, J=8.3 Hz, 3H, C(10)H), 8.58-8.65, 8.82-8.89 (br m, 4H, C(2)H).

Scheme for Tetra-Methoxy Anthracene Isocyanate (95)

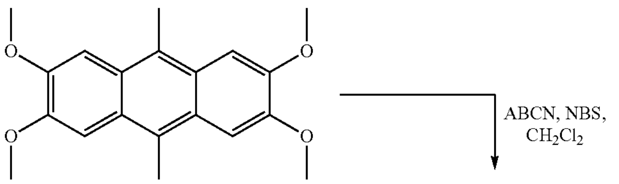

91

-continued

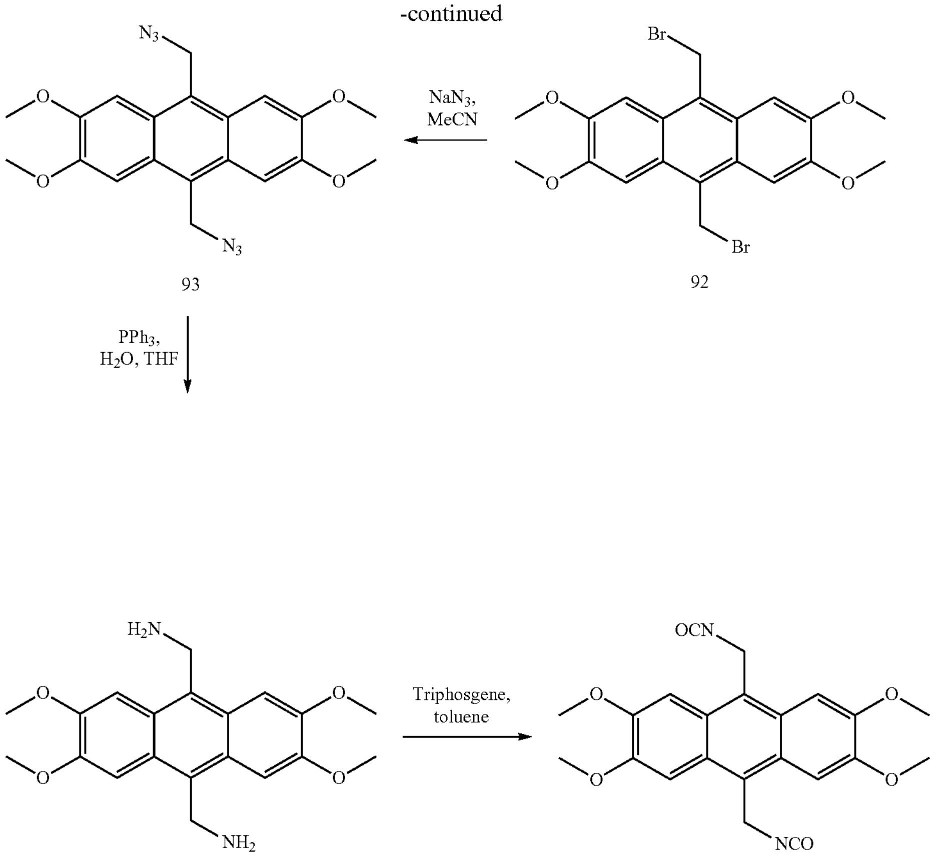

93

92

94

95

2,3,6,7-Tetramethoxy-9,
10-bis(bromomethyl)anthracene, (92)

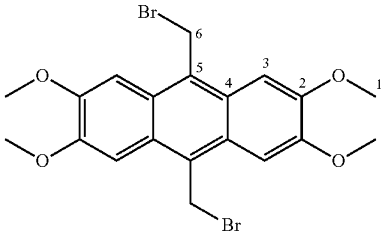

Under an inert $N_2$ atmosphere, 91 (2 g, 6.1 mmol), NBS (4 g, 22.6 mmol) and ABCN (73 mg, 0.3 mmol) were dissolved in anhydrous dichloromethane (150 mL), and the mixture stirred at reflux for 4 hours. The mixture was then cooled to 0° C. and filtered. The solid was then dried under high vacuum to afford 92 (2.1 g, 4.3 mmol, 71%) as a bright yellow solid. $^1$H NMR (400 MHz, $CDCl_3$) δ 4.11 (s, 12H, C(1)H), 5.35 (s, 4H, C(6)H), 7.40 (s, 4H, C(3)H), $^{13}$C NMR (100 MHz, $CDCl_3$) 28.7 (C6), 56.0 (C1), 101.8 (C3), 125.7 (C5), 125.9 (C4), 150.1 (C2).

2,3,6,7-Tetramethoxy-9,10-bis(azidoomethyl)anthracene, (93)

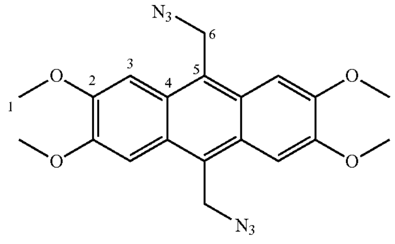

Under an inert $N_2$ atmosphere, 92 (2.7 g, 5.58 mmol) and $NaN_3$ were suspended in anhydrous MeCN (70 mL). The mixture was stirred at reflux for 16 hours and then cooled to room temperature and the solvent was evaporated in vacuo. The remaining residue was then suspended in water (200 mL) and filtered. The solid was washed with ethanol (3×100 mL) and dried under high vacuum to afford 93 (1.6 g, 3.9 mmol, 70%) as a brown solid. $^1$H NMR (400 MHz, $CDCl_3$) δ 4.10 (s, 12H, C(1)H), 5.19 (s, 4H, C(6)H), 7.42 (s, 4H, C(3)H), $^{13}$C NMR (100 MHz, $CDCl_3$) 47.7 (C6), 56.1 (C1), 101.8 (C3), 123.8 (C5), 126.9 (C4), 150.2 (C2); HRMS: (ESI$^+$). Found [M+Na]$^+$ 431.1448.

2,3,6,7-Tetramethoxy-9,10-bis(aminomethyl)anthracene, (94)

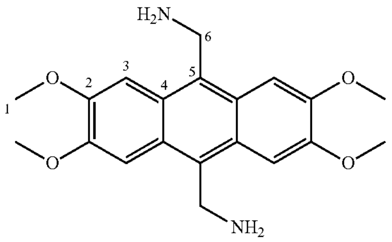

Under an inert $N_2$ atmosphere, azide 93 (1.6 g, 3.90 mmol) and $PPh_3$ (8 g, 31.4 mmol) were suspended in degassed THF (80 mL). Degassed water (4 mL) was added and the reaction heated to 60° C. for 16 hours. The reaction was cooled to room temperature and the solvent removed under vacuum. The crude residue was suspended in toluene (200 mL), filtered, washed with toluene (2×100 mL) and dried under high vacuum to afford 94 (1.05 g, 2.96 mmol, 76%) as a pale brown solid. $^1H$ NMR (400 MHz, $CDCl_3$) δ 4.08 (s, 12H, C(1)H), 4.69 (s, 4H, C(6)H), 7.49 (s, 4H, C(3)H), $^{13}C$ NMR (100 MHz, $CDCl_3$) δ 39.5 (C6), 56.0 (C1), 101.9 (C3), 125.3 (C5), 125.5 (C4), 149.7 (C2); HRMS: ($ESI^+$) Found $[M+Na]^+$ 379.1626.

9,10-bis(isocyanatomethyl)-2,3,6,7-tetramethoxyanthracene (95)

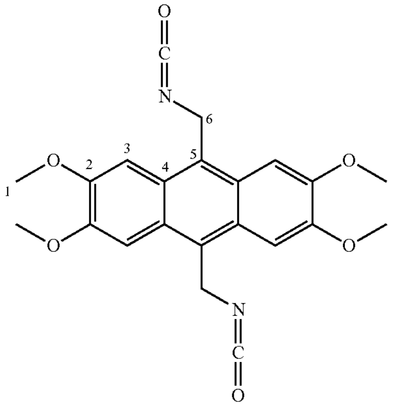

Under an inert $N_2$ atmosphere, a flask was charged with triphosgene (324 mg, 1.1 mmol) and anhydrous toluene (15 mL) was added A suspension of 94 (200 mg, 0.55 mmol) in anhydrous toluene (5 mL) was added dropwise and the reaction mixture stirred at reflux for 2 hours. The reaction mixture was cooled and the solvent removed under high vacuum. The crude solid was resuspended in dichloromethane (50 mL) and filtered. The filtrate was collected and the solvent removed under vacuum to afford 95 (121 mg, 0.30 mmol, 54%) as a brown solid. $^1H$ NMR (400 MHz, $CDCl_3$) δ 4.11 (s, 12H, C(1)H), 5.21 (s, 4H, C(6)H), 7.37 (s, 4H, C(3)H), $V_{max}$ 2934, 2832, 2255, 1498, 1435, 1245, 1204, 1169, 1028 $cm^{-1}$; HRMS: ($ESI^+$) Found $[M+Na]^+$ 431.1218.

Scheme for Octa-Methoxy Anthracene Bis Urea Receptor

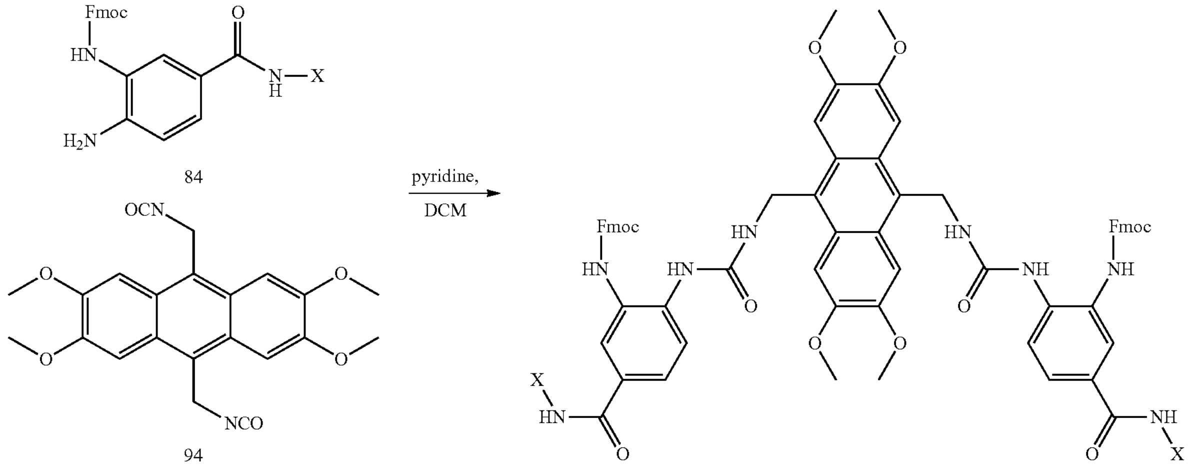

84

94

95

X = tert-butyl protected G2MM

-continued
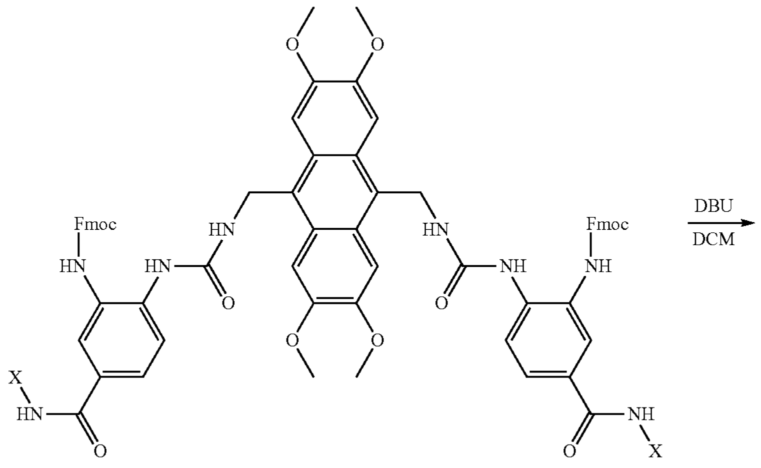
95
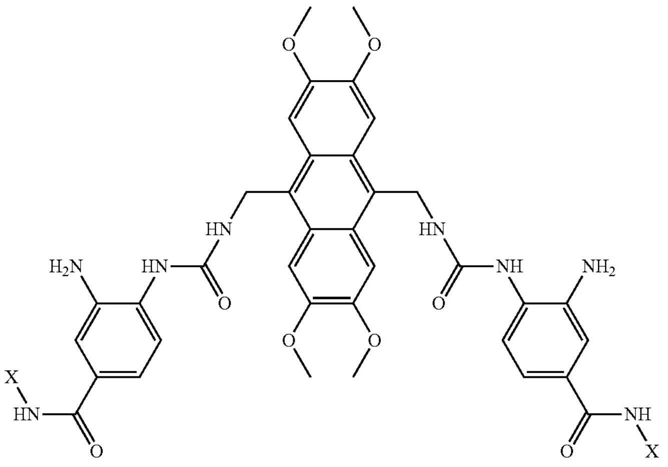
96
X = tert-butyl protected G2MM
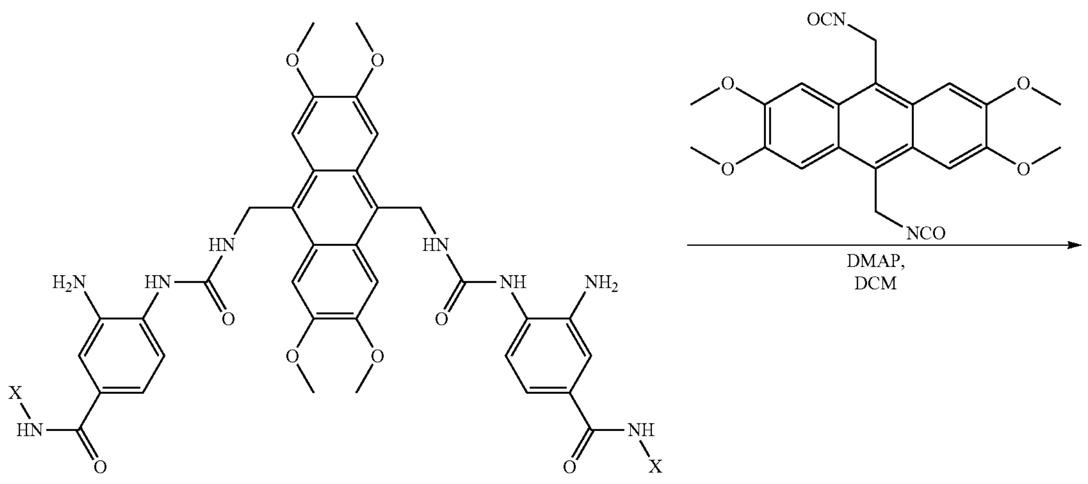
96

-continued

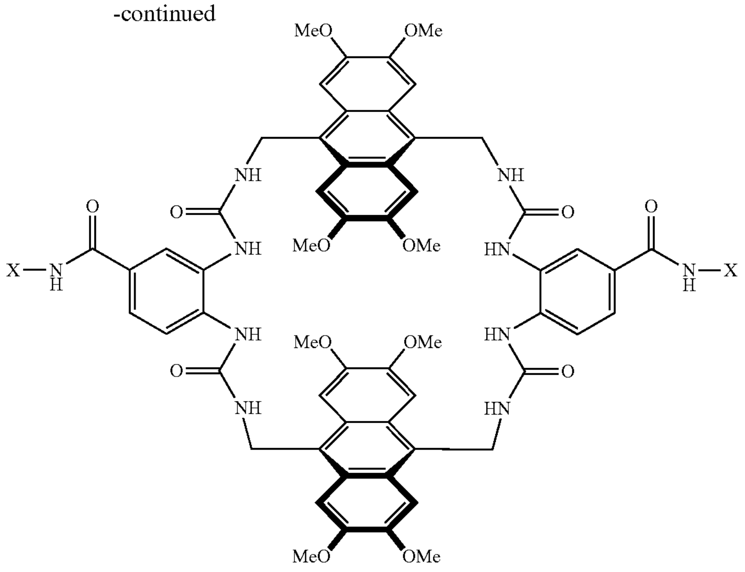

97

X = tert-butyl protected G2MM

Diamino Tert-Butyl Protected Methoxy-Anthracene Half Receptor (96)

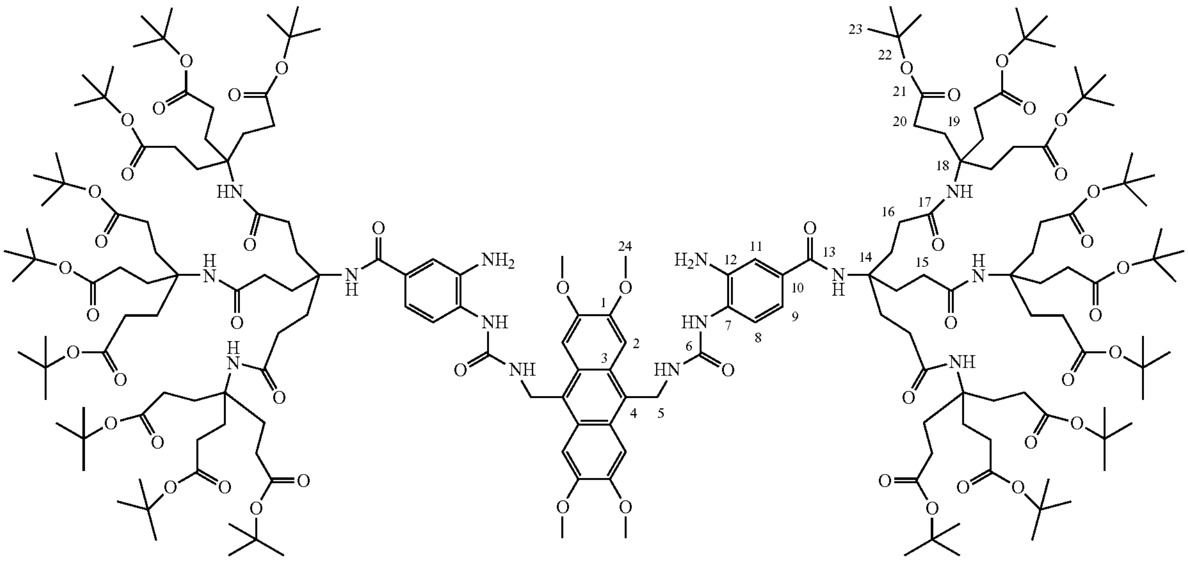 [SMILES: COc1cc2c(CNC(=O)Nc3ccc(C(=O)NC(CCC(=O)NC(CCC(=O)OC(C)(C)C)(CCC(=O)OC(C)(C)C)CCC(=O)OC(C)(C)C)(CCC(=O)NC(CCC(=O)OC(C)(C)C)(CCC(=O)OC(C)(C)C)CCC(=O)OC(C)(C)C)CCC(=O)NC(CCC(=O)OC(C)(C)C)(CCC(=O)OC(C)(C)C)CCC(=O)OC(C)(C)C)cc3N)c3cc(OC)c(OC)cc3c(CNC(=O)Nc3ccc(C(=O)NC(CCC(=O)NC(CCC(=O)OC(C)(C)C)(CCC(=O)OC(C)(C)C)CCC(=O)OC(C)(C)C)(CCC(=O)NC(CCC(=O)OC(C)(C)C)(CCC(=O)OC(C)(C)C)CCC(=O)OC(C)(C)C)CCC(=O)NC(CCC(=O)OC(C)(C)C)(CCC(=O)OC(C)(C)C)CCC(=O)OC(C)(C)C)cc3N)c2cc1OC]

Under an inert $N_2$ atmosphere, 84 (507 mg, 0.283 mmol) and 94 (50 mg, 0.13 mmol) were dissolved in anhydrous dichloromethane (8 mL). Pyridine (60 μL, 0.74 mmol) was added and the reaction heated to reflux for 16 hours. The reaction was cooled to room temperature and the solvent removed under vacuum. The crude residue was purified by reverse phase HPLC to afford the Fmoc protected product 95 (336 mg, 0.84 mmol, 65%) as a white solid. Conversion to 95 was confirmed by limited NMR studies* and high resolution mass spectrometry ($ESI^+$): m/z calculated for $[M+2Na]^{2+}$2015.6171, found 2015.6176. Under an inert $N_2$ atmosphere, 95 (100 mg, 0.028 mmol) was dissolved in anhydrous dichloromethane (10 mL) and cooled to 0° C. DBU (50 μL, 0.31 mmol) was added and the reaction mixture warmed to room temperature and stirred for 1 hour. The solvent was removed under vacuum and the crude product purified by flash column chromatography (6% $MeOH:CH_2Cl_2$) to afford 96 (91 mg, 0.026 mmol, 92%) as an off white solid. $^1H$ NMR: (400 MHz, ($CD_3OD$): δ 1.42 (s, 162H, C(23)$\underline{H}_3$), 1.84-2.0 (m, 36H, C(20)$\underline{H}_2$), 2.02-2.14 (m, 12H, C(15)$\underline{H}_2$), 2.13-2.31 (m, 48H, C(19, 16)$\underline{H}_2$), 3.95 (br s, 12H, C(24)$\underline{H}_3$), 4.58 (br s, 4H, C(5)$\underline{H}_2$), 7.13 (d, J=8.3 Hz, 2H, C(9)$\underline{H}$), 7.23 (s, 2H, C(11)$\underline{H}$), 7.31 (d, J=8.3 Hz, 2H, C(8)$\underline{H}$), 7.38 (br s, 4H, C(2)$\underline{H}$), 7.41 (s, 6H, NH), 7.89 (s, 2H, NH); $^{13}$C NMR: (100 MHz, ($CDCl_3$)): 527.1 (C23), 29.1 (C20), 29.3 (C21), 30.8 (C15), 31.1 (C16), 54.9 (C24), 57.4 (C18), 58.1 (C14), 80.3 (C22), 101.9 (C2), 115.8 (C11), 117.3 (C9) 123.3 (C8), 126.1 (C4), 126.1 (C3), 128.2 (C10), 131.6 (7), 140.3 (C12), 149.5 (C1), 157.0 (C6), 168.5 (C13), 173.0 (C21), 174.1 (C17); HRMS: ($ESI^+$) Found $[M+2Na]^{2+}$: 1208.3682.

* Limited NMR studies were only possible due to believed slow conformational exchange of 95 resulting in very broad signals of low intensity.

Tert-Butyl Protected Octa-Methoxy Anthracene Tetra Urea Macrocycle (97)

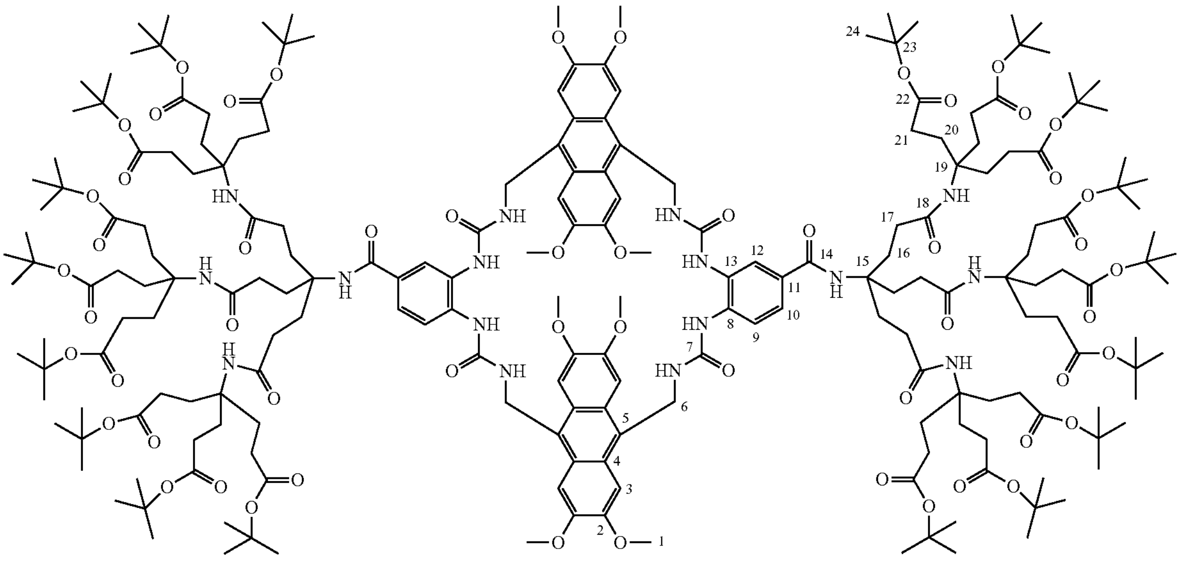

Under an inert $N_2$ atmosphere, 96 (25 mg, 0.007 mmol) and DMAP (1.7 mg, 0.014 mmol) were dissolved in anhydrous degassed dichloromethane (12 mL) and heated to reflux. 94 (2.7 mg, 0.007 mmol) in anhydrous degassed dichloromethane (2 mL) was added and the reaction stirred at reflux for 2 days. The solvent was then removed under vacuum and the crude product purified by reverse phase HPLC and then freeze dried to afford 89 as a white solid.

Binding Studies

Isothermal titration calorimetry (ITC) and $^1$H NMR were used to determine the binding affinities between the compounds of the present invention (e.g. receptor compound 1 and receptor compound 90) and a number of saccharides (e.g. glucose, mannose and cellobiose), together with other small molecules (e.g. uracil and uric acid). ITC and $^1$H NMR titrations were performed according to the general procedure described hereinabove and the ITC traces, $^1$H NMR spectra and binding affinities are summarised in FIGS. 2 to 75.

$^1$H NMR Titrations $^1$H-NMR titrations were performed on a Varian VNMR cryogenically cooled S600 spectrometer. Solutions of saccharides in $D_2O$ (99.9%), containing receptor at a known concentration to be used in the experiment, were prepared and allowed to equilibrate overnight before use if necessary. Aliquots were then added to an NMR tube containing a known concentration of receptor solution (typically 50 μM-250 μM). The receptor concentration was therefore held constant while the carbohydrate concentration was increased. The sample tube was shaken after each addition, centrifuged and $^1$H-NMR spectra were acquired at 298 K.

If the receptor bound saccharide slower than the NMR sample rate ("slow exchange"), the $K_a$ was determined by analysing the NMR integral of a peak assigned to the Host-Guest complex. The variable X was defined as the integral of an isolated resonance of the complex (typically in the aromatic region) divided by the integral of all the related resonances (typically the whole aromatic region). As X is proportional to fraction of host in the bound state, the change in X could be plotted as a function of the guest concentration to give a curve which could be fitted to a 1:1 binding model to yield the association constant $K_a$. Mathematically, the fitting process is essentially identical to that employed for binding with fast exchange, except that the integral of a peak due to the complex replaces the chemical shift of a peak due to bound+unbound receptor. The calculation was performed using a non-linear least squares curve-fitting programme implemented within Excel. The programme yields binding constants $K_a$ and limiting X ($X_{lim}$) as output. $K_a$ values are listed in Table 4 below. An estimated error for Ka was obtained from individual data points by assuming the determined $K_a$ and $X_{lim}$. These errors are reported in Table 4 and are typically well below 5%.

TABLE 1

| Relative integrations of α-H1 and β-H2 during NMR titration. | | |
|---|---|---|
| Glucose concentration (μM) | Relative integration (αH1:βH2) | β-D-glucose (%) |
| 57 | —[a] | — |
| 114 | —[a] | — |
| 170 | 1:2.08 | 67% |
| 225 | 1:2.01 | 66% |
| 280 | 1:1.85 | 64% |
| 334 | 1:2.04 | 67% |
| 387 | 1:1.88 | 65% |
| 440 | 1:1.84 | 64% |
| 492 | 1:1.82 | 64% |
| 544 | 1:1.82 | 64% |

[a]values for integration not obtained due to low intensity of and broadness of signals.

TABLE 2

Relative integrations of α-H1 and β-H2 over time from pure α-D-glucose, with and without Receptor 1 (0.2 mM) present.

| | Relative integration (αH1:βH2) | |
|---|---|---|
| Time (min) | D-glucose (5 mM) only | D-glucose (5 mM) and receptor X (0.2 mM) |
| 0 | 1:0.01 | 1:0.06 |
| 10 | 1:0.06 | 1:0.11 |
| 30 | 1:0.19 | 1:0.22 |
| 60 | — | 1:0.30 |
| 70 | 1:0.34 | — |
| 90 | — | 1:0.38 |
| 100 | 1:0.50 | — |
| 120 | 1:0.59 | 1:0.52 |
| 150 | 1:0.70 | 1:0.66 |
| 180 | 1:0.86 | — |
| 210 | 1:0.93 | — |

TABLE 3

Calculated values for $K_a$ when titrating cellobiose (250 mM) against receptor 1 (0.11 mM). The integrals of the peak at 8.02 ppm (denoted with *, see FIG. 31) were made relative to integral of the same peak (8.02 ppm) when all receptor is assumed to be saturated with guest (i.e. the final addition in the titration, row denoted with yellow). These relative integrals are then used to determine the amount of Host-Guest [HG]. This value for [HG] along with calculated values for free host $[H]_{free}$ and free guest $[G]_{free}$ can be used to calculate the $K_a$ at each point in the titration. An average of the values obtained (denoted in blue) was then used as the overall $K_a$ (31.1 $M^{-1}$) along with the associated standard deviation and error. Not all $K_a$ values calculated were included in the averaged $K_a$ value. The earlier integrations are unreliable due to the very small intensity of the peak at 8.02 ppm. The later integrations were also deemed unreliable due to large deviations in baseline of the spectra due to the large excess of guest present. The selected values for $K_a$ used for the average calculation and the averaged $K_a$ itself corroborate with the results obtained from ITC.

| Volume of Guest added (μL) | $[Host]_{free}$/ μM | $[Guest]_{free}$/ mM | $[Host]_{total}$/ μM | $[Guest]_{total}$/ mM | [Host-Guest]/ μM | Integral (peak 8.02 ppm*) | Integral of peak* vs integral of peak* when $[H]_{free}$ = 0. | $K_a$/ $M^{-1}$ |
|---|---|---|---|---|---|---|---|---|
| 0 | 110 | 0 | 110 | 0 | — | 0 | 0 | — |
| 4 | 110 | 20 | 110 | 20 | 0 | 0.00005 | 0.0011 | 0.55 |
| 4 | 99 | 39 | 110 | 39 | 11 | 0.00465 | 0.102 | 29.0 |
| 4 | 93 | 58 | 110 | 58 | 17 | 0.007 | 0.154 | 31.2 |
| 8 | 86 | 96 | 110 | 96 | 24 | 0.01 | 0.220 | 29.4 |
| 8 | 75 | 132 | 110 | 132 | 35 | 0.0143 | 0.315 | 34.9 |
| 8 | 47 | 167 | 110 | 167 | 63 | 0.0262 | 0.577 | 81.5 |
| 20 | 38 | 251 | 110 | 251 | 72 | 0.0296 | 0.650 | 74.0 |
| 20 | 8 | 329 | 110 | 329 | 102 | 0.0421 | 0.927 | 386 |
| 40 | 0 | 470 | 110 | 470 | 110 | 0.0455 | 1 | — |
| | | | | | | | Average $K_a/M^{-1}$ | 31.1 |
| | | | | | | | Std Dev (Error) | 2.66 (9%) |

Isothermal Titration MicroCalorimetry (ITC) Titrations

Isothermal Titration MicroCalorimetry (ITC) experiments were performed on a MicroCal iTC200 microcalorimeter and/or a MicroCali VP-ITC. ITC experiments were carried out at 298 K. Saccharide solutions were prepared in HPLC-grade water with 10 mM phosphate buffer solution (pH 7.4) and allowed to equilibrate overnight if necessary. The sample cell was charged with a known concentration of receptor solution in HPLC-grade water with 10 mM phosphate buffer solution at pH 7.4 (typically 50 µM-200 µM). Then, aliquots (typically 1.0 µL) of carbohydrate solution were added and the evolution of heat was followed as a function of time. Heats of dilution were measured by injecting the same carbohydrate solution into HPLC-grade water with 10 mM phosphate buffer solution at pH 7.4, using identical conditions. For every addition, the heat of dilution was subtracted from the heat of binding using a MicroCal software programme implemented in ORIGIN 7.0. This gave an XY matrix of heat vs. total guest concentration. This matrix was then imported into a specially written Excel programme to fit the data to a 1:1 binding model to give a $K_a$. $\Delta G$ can be derived from $K_a$ and thus $\Delta S$ can be derived from $\Delta H$ and $\Delta G$ using common thermodynamic equations. The fitting procedure also yields errors in $K_a$ as in the case of NMR described above. This method consistently produced more accurate fits than fitting the data to an S-curve, as in the MicroCal software (S-curves are typically not observed for binding constants below ~104-105 $M^{-1}$). Although fits produced using the supplied MicroCal software were generally similar to those calculated using the Excel programme, they also consistently overestimated the $K_a$ by approximately 10%. It was found that better corroboration of the ITC data with the equivalent NMR data was achieved using the Excel programme. ITC outputs for heat of dilution of substrates, binding events between substrates and receptor 1, and analysis curves are included in the Figures. An overview of the binding data, including thermodynamic quantities and errors is given in Table 4 below.

TABLE 4 binding affinities of various substrates for receptor 1.

| Substrate (medium) | Determined by NMR $K_a$ ($M^{-1}$) | Determined by ITC (kJ mol$^{-1}$) | | | |
|---|---|---|---|---|---|
| | | $K_a$ ($M^{-1}$) | $\Delta G$ | $\Delta H$ | $T\Delta S$ |
| D-Glucose | 18,026 ± 1.04% | 18,600 ± 14.3% | −24.4 | −7.8 | 16.6 |
| D-Glucose pH 6 (PBS) | — | 17,300 ± 3.8% | −24.2 | −2.6 | 21.6 |
| D-Glucose pH 7 (PBS) | — | 17,800 ± 5.5% | −24.3 | −2.2 | 22.0 |
| D-Glucose pH 8 (PBS) | — | 18,300 ± 1.8% | −24.3 | −2.6 | 21.8 |
| D-Glucose (human serum) | — | 2477 ± 5.7% | −19.4 | −4.1 | 15.3 |
| D-Glucose (DMEM cell culture) | — | 5637 ± 2.1% | −21.4 | −5.2 | 16.2 |
| D-Glucose (DMEM salt control) | — | 5164 ± 5.9% | −21.2 | −5.0 | 16.2 |
| D-Glucose (Leibovitz's L-15 cell culture) | — | 5214 ± 8.6% | −21.2 | −4.2 | 17.0 |
| Methyl β-D-Glucoside | 7522 ± 5.5% | 7886 ± 16.4% | −22.2 | −3.2 | 21.2 |
| Myo-inositol | 7328 ± 7.4% | 7563 ± 4.2% | −22.1 | −22.1 | −2.4 |
| D-Glucuronic Acid | n.d.$^a$ | 5348 ± 3.5% | −21.3 | −27.8 | −6.5 |
| D-Xylose | n.d.$^a$ | 5804 ± 3% | −21.5 | −8.0 | 13.5 |
| 2-Deoxy-D-Glucose | n.d.$^a$ | 725 ± 5.7% | −16.3 | −2.9 | 13.4 |
| D-Galactose | 132 ± 10% | 182 ± 2.3% | −12.9 | −8.8 | 4.2 |
| D-Mannose | 140 ± 1.3% | 143 ± 1.1% | −12.3 | −11.8 | 0.6 |
| D-Ribose | 267 ± 3.8% | 216 ± 1.9% | −13.3 | −23.0 | −9.7 |
| D-Fructose | 51 ± 5.5% | 60 ± 2.7% | −10.6 | −20.0 | −9.5 |
| D-Cellobiose | 31 ± 9% | 30 ± 15.9% | −8.5 | −9.2 | −0.7 |
| Mannitol | — | 0 | | | |
| Gluconate$^b$ | 0 | 0 | | | |
| Methyl α-D-Glucoside | 0 | 0 | | | |
| N-Acetyl-D-glucosamine | — | 0 | | | |
| D-Maltose | — | 0 | | | |
| L-Fucose | — | 0 | | | |
| Uracil (PBS) | — | 0 | | | |
| Uric Acid (PBS) | — | 0 | | | |
| Cytosine | — | 0 | | | |
| Adenosine | — | 0 | | | |
| Paracetamol | — | 0 | | | |
| Ascorbic Acid | — | 0 | | | |
| L-Phenylalanine | — | 0 | | | |
| L-Tryptophan | — | 0 | | | |

Affinities ($K_d$) were measured in $D_2O$ (NMR) or $H_2O$ (ITC) containing phosphate buffer (10 mM, pH = 7.4) at T = 298 K.
N.d. = not determined due to broadening of NMR signals on addition of substrate
All solutions at pH 7.4 in 10 mM Phosphate buffer solution unless otherwise stated. Human blood Serum and cell culture media were dialysed at 10k MWCO and then buffered with 10 mM phosphate buffer solution at pH 7.4. DMEM Salt control composition: ferric nitrate (0.2 µM), calcium chloride (1.8 mM), magnesium sulfate (0.81 mM), potassium chloride (5.3 mM), sodium bicarbonate (44 mM), sodium chloride (110 mM) and sodium phosphate monobasic (0.9 mM). PBS = phosphate buffered saline at pH 7.4, composition: sodium chloride (137 mM), potassium chloride (2.7 mM), disodium phosphate (10 mM), monopotassium phosphate (1.8 mM).
$^a$$K_a$ not determined due to intermediate exchange rate on NMR timescale resulting in complex broad spectra, evidence of binding was indicated regardless.
$^b$Prepared by dissolution of D-glucono-δ-lactone in 10 mM phosphate buffer, pH 7.4. After 4 h $^1$H NMR indicated that the lactone had hydrolysed to give the acyclic gluconate.

TABLE 5

| Summary of binding results for anthracene receptor 90. | | | | | |
|---|---|---|---|---|---|
| | Determined by NMR | Determined by ITC (kJ $mol^{-1}$) | | | |
| Substrate | $K_a$ ($M^{-1}$) | $K_a$ ($M^{-1}$) | ΔG | ΔH | TΔS |
| D-Glucose | 5 ± 3.6% | — | | | |
| D-Cellobiose | 46 ± 0.9% | 38 ± 6.5% | −9.0 | −5.7 | 3.3 |
| D-cellotriose | 950 ± 0.3% | 955 ± 1.2% | −17.0 | −16.5 | 0.6 |
| D-cellotetraose | n.d. | — | | | |
| D-cellopentaose | n.d. | — | | | |
| D-maltose | 15 ± 11.8% | — | | | |
| D-Maltotriose | 20 ± 3.3% | — | | | |
| Uric Acid | — | 0 | | | |

TABLE 6

| Measured binding affinities displayed by Receptors 2 to 14 towards D-glucose | | | |
|---|---|---|---|
| | Binding affinity for D-glucose ($K_a$ ($M^{-1}$)) | | |
| Receptor | Determined by ITC | Determined by $^1$H-NMR | Determined by CD |
| 2 | — | 13 ± 4 | — |
| 3 | 5760 ± 269 | — | — |
| 4 | 6490 ± 72.6 | — | — |
| 5 | 10400 ± 132 | — | — |
| 6 | — | — | — |
| 7 | — | 6886 ± 190 | — |
| 8 | 4210 ± 73 | — | — |
| 9 | — | 2554 ± 96 | — |
| 10 | — | 481 ± 57 | — |
| 11 | — | 2000 | 1819 ± 152 |
| 12 | 0* | — | — |
| 13 | 1310 ± 33 | — | — |
| 14 | — | 14926 ± 1566 | — |

*No measurable binding using a 7.1 mM L- or D-glucose solution and a 0.4 mM solution of Receptor 12.

While specific embodiments of the invention have been described for the purpose of reference and illustration, various modifications will be apparent to a person skilled in the art without departing from the scope of the invention as defined by the appended claims.

The invention claimed is:

1. A compound, salt, hydrate or solvate thereof, wherein the compound has the structural Formula Ie shown below:

Formula Ie

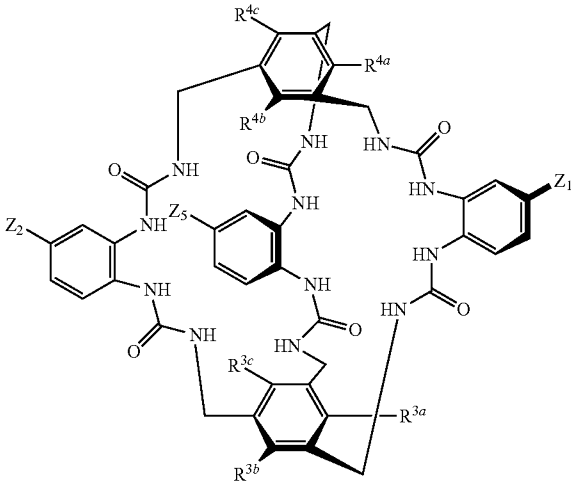

wherein:

$Z_1$, $Z_2$, and $Z_5$ are independently selected from a hydrophilic substituent group and $R^{3a}$, $R^{3b}$, $R^{3c}$, $R^{4a}$, $R^{4b}$ and $R^{4c}$ are independently selected from hydrogen, halo, (1-4C)alkyl, (1-4C)alkoxy, amino, nitro, (1-4C)alkylamino, (1-4C)dialkylamino, (1-4C)haloalkyl, (1-4C)haloalkoxy, cyano, (2-4C)alkenyl, (2-4C)alkynyl.

2. A compound according to claim 1, wherein $Z_1$, $Z_2$, and $Z_5$ are independently selected from a hydrophilic substituent group comprising one or more hydrophilic functional groups selected from carboxylic acids, carboxylate ions, carboxylate esters, hydroxyl, amines, amides, ethers, ketone and aldehyde groups, nitro groups, sulphates, sulphonates, phosphates, phosphonates, and combinations thereof.

3. A compound according to claim 1, wherein $Z_1$, $Z_2$, and $Z_5$ are independently selected from a hydrophilic substituent group, wherein said hydrophilic substituent group is a hydrophilic polymer or hydrophilic dendritic group.

4. A compound according to claim 1, wherein $Z_1$, $Z_2$, and $Z_5$ are independently selected from a hydrophilic polymer or a dendritic group comprising between 1 and 5 generations of building units and a terminal functional group $T_1$, and wherein each building unit is independently selected from a group of Formula A:

$$-L^2-L^{2a}-V— \quad \text{(Formula A)}$$

wherein:

$L^2$ is selected from O, C(O), C(O)O, OC(O), C(O)N($R_r$), N($R_r$)OC(O), N($R_s$)C(O)N($R_r$), N($R_r$)OC(O)O, OC(O)N($R_r$), $S(O)_2N(R_r)$, and $N(R_r)SO_2$, wherein $R_r$ and $R_s$ are each independently selected from hydrogen and (1-4C)alkyl;

$L^{2a}$ is a bond or a (1-4C)alkylene;

V is absent or a group of the formula:

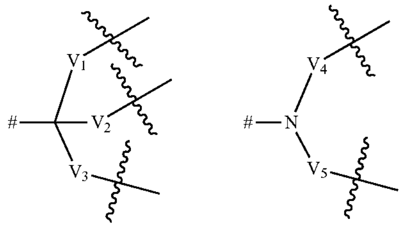

wherein:

$V_1$, $V_2$, $V_3$, $V_4$ and $V_5$ are independently selected from a (1-6C)alkylene optionally interrupted by one or more groups selected from O, S and $NR_t$, wherein $R_t$ is selected from hydrogen and (1-2C)alkyl;

# denotes the point of attachment to one of Rings A, B, C, D or E;

∿∿ denotes the point of attachment to either another group of Formula A or a terminal functional group $T_1$; and the terminal functional group $T_1$ is selected from OH, $C(O)OM_x$, $C(O)OR_u$ and $C(O)NHR_u$, wherein $R_u$ is selected from hydrogen, (1-4C)alkyl, (1-4C)alkoxy, hydroxy(1-4C)alkyl, (2-4C)alkenyl, (2-4C)alkynyl, ethylene gylycol and polyethylene glycol, and wherein $M_x$ is a cation.

5. A compound according to claim 4, wherein the dendritic group comprises between 1 and 4 generations of building units and a terminal functional group $T_1$, and wherein each building unit is independently selected from a group of Formula A:

$$-L^2-L^{2a}-V— \quad \text{(Formula A)}$$

wherein:

$L^2$ is selected from O, C(O), C(O)O and $C(O)N(R_r)$, wherein $R_r$ is selected from hydrogen and (1-4C)alkyl;

$L^{2a}$ is a bond or a (1-4C)alkylene;

V is absent or a group of the formula:

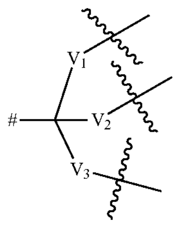

wherein:

$V_1$, $V_2$, and $V_3$ are independently selected from a (1-6C) alkylene optionally interrupted by one or more groups selected from oxygen atoms;

# denotes the point of attachment to one of Rings A, B, C, D or E;

∿∿ denotes the point of attachment to either another group of Formula A or a terminal functional group $T_1$; and the terminal functional group $T_1$ is selected from OH, $C(O)OM_x$, $C(O)OR_u$ and $C(O)NHR_u$, wherein $R_u$ is selected from hydrogen, (1-4C)alkoxy and hydroxy(l-4C)alkyl, wherein $M_x$ is a cation.

6. A compound according to claim 4, wherein the dendritic group comprises between 1 and 3 generations of building units and a terminal functional group $T_1$, and wherein each building unit is independently selected from a group of Formula A:

$$-L^2-L^{2a}-V— \quad \text{(Formula A)}$$

wherein:

$L^2$ is $C(O)N(R_r)$, wherein $R_r$ is selected from hydrogen and (1-4C)alkyl;

$L^{2a}$ is a bond or a (1-2C)alkylene;

V is a group of the formula:

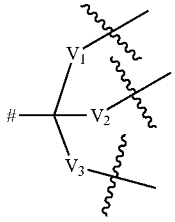

wherein:

$V_1$, $V_2$, and $V_3$ are independently selected from a (1-4C) alkylene optionally interrupted by one or more groups selected from oxygen atoms;

# denotes the point of attachment to one of Rings A, B, C, D or E;

∿∿ denotes the point of attachment to either another group of Formula A or a terminal functional group $T_1$; and the terminal functional group $T_1$ is selected is $C(O)OM_x$, wherein $M_x$ is a cation.

7. A compound selected from the group consisting of any one of:
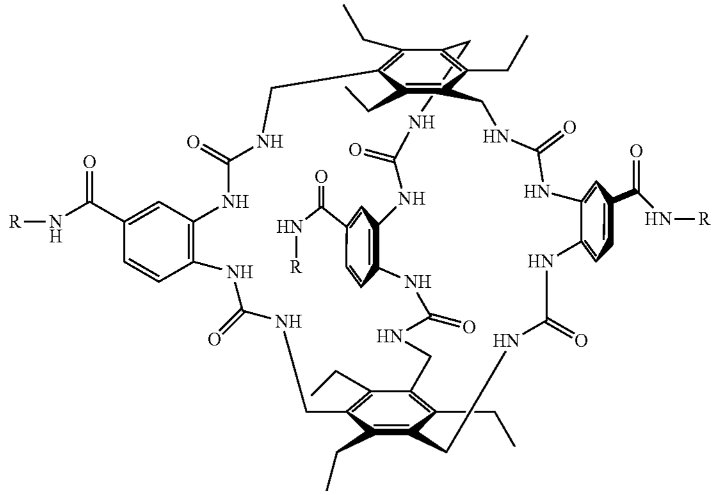
R =
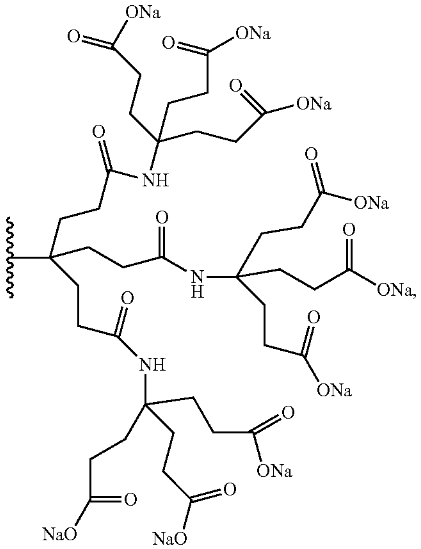
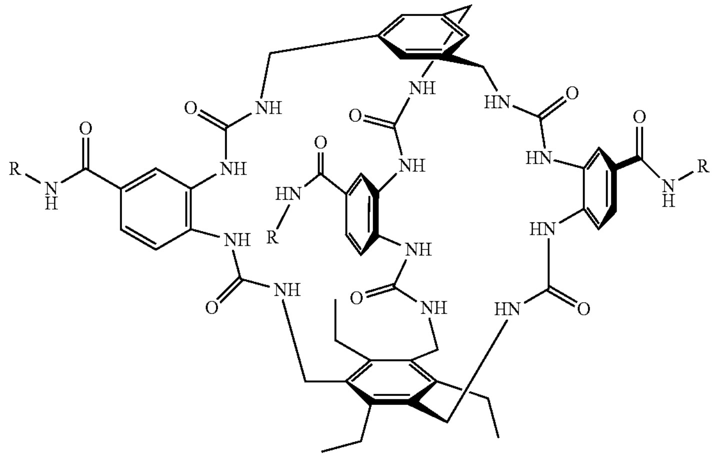
R =
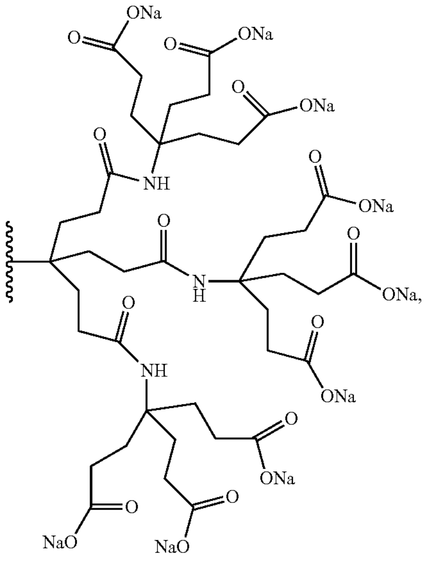
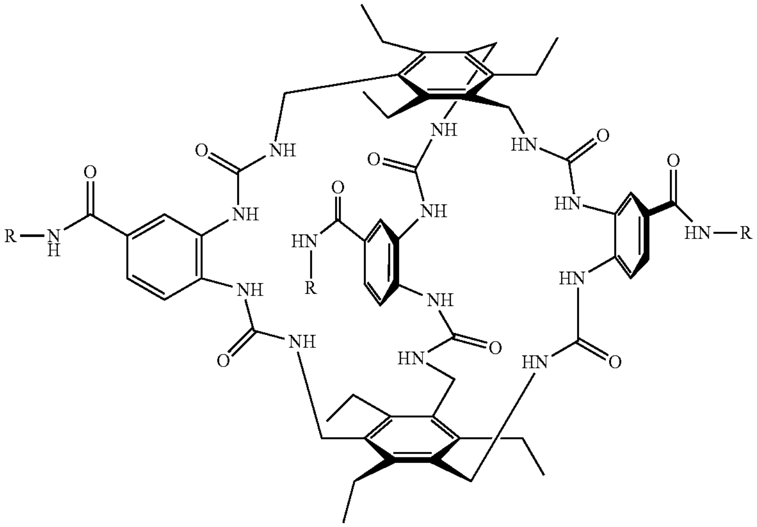

-continued
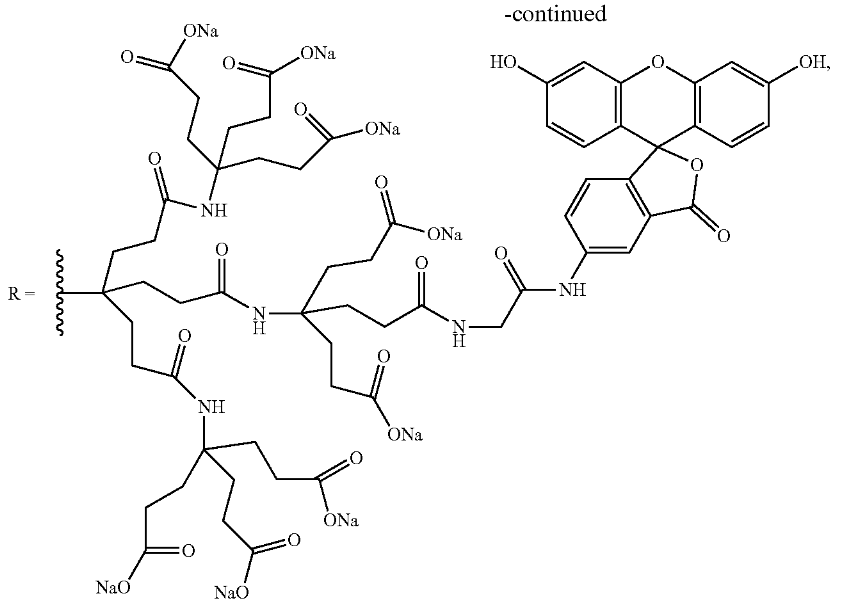
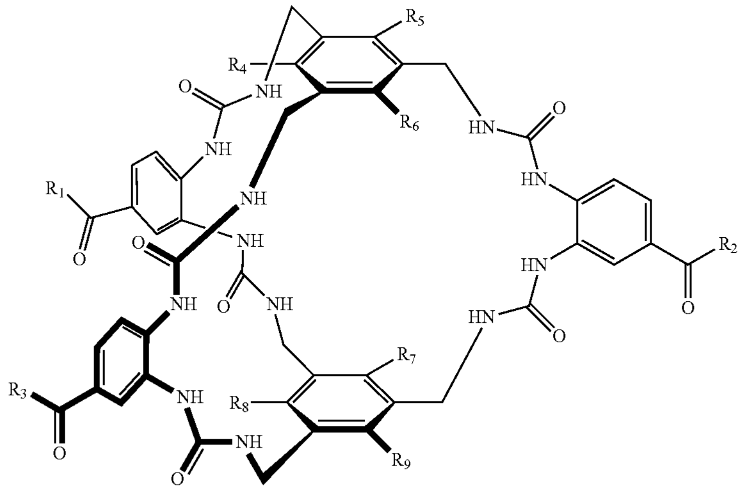
$R_4 = R_5 = Me$
$R_6 = Br$
$R_7, R_8 = R_9 = Et$
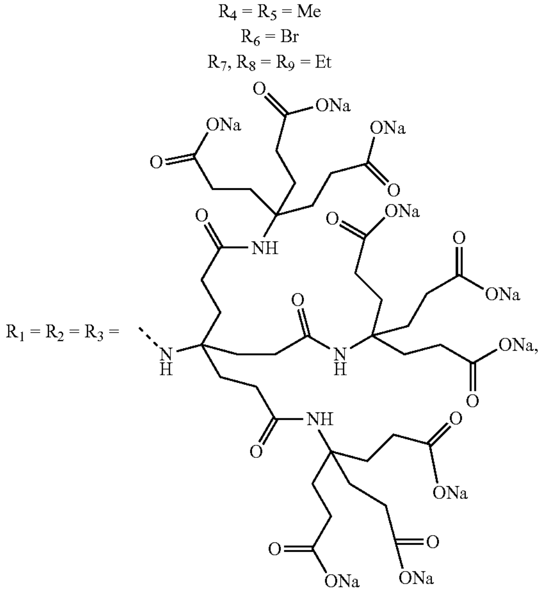

-continued
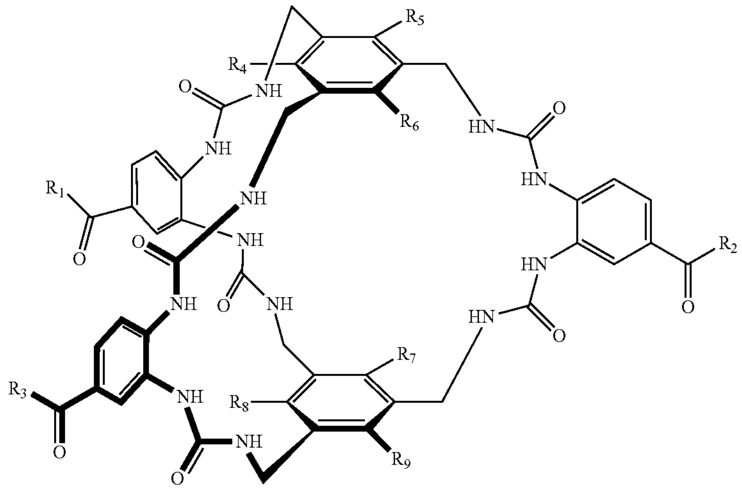
$R_4 = R_5 = R_6 = R_7 = R_8 = R_9 = Et$
$R_1 = R_2 =$ 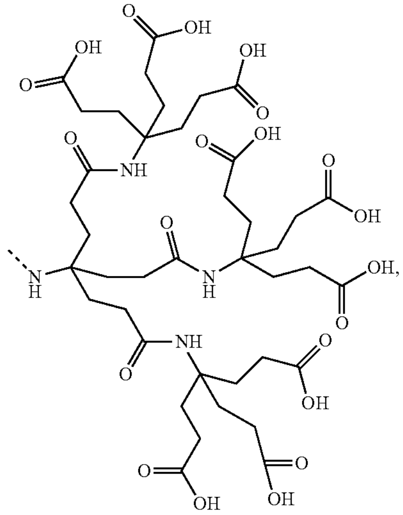
$R_3 =$ 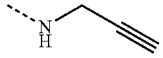
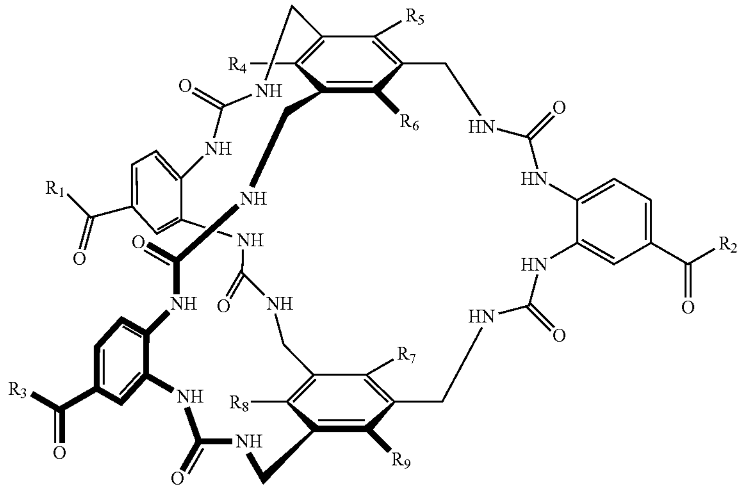
$R_4 = R_5 = R_6 = R_7 = R_8 = R_9 = Et$ -continued
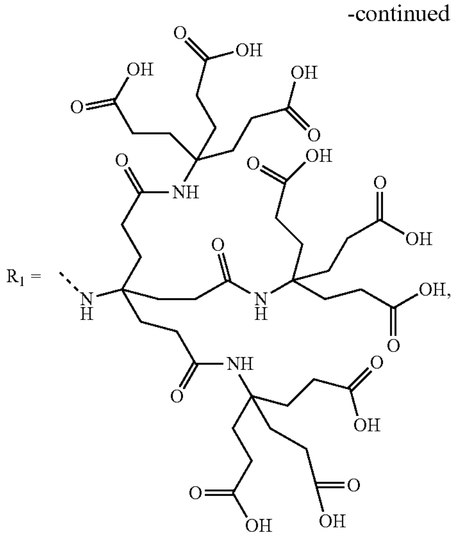
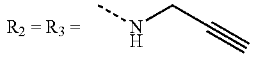
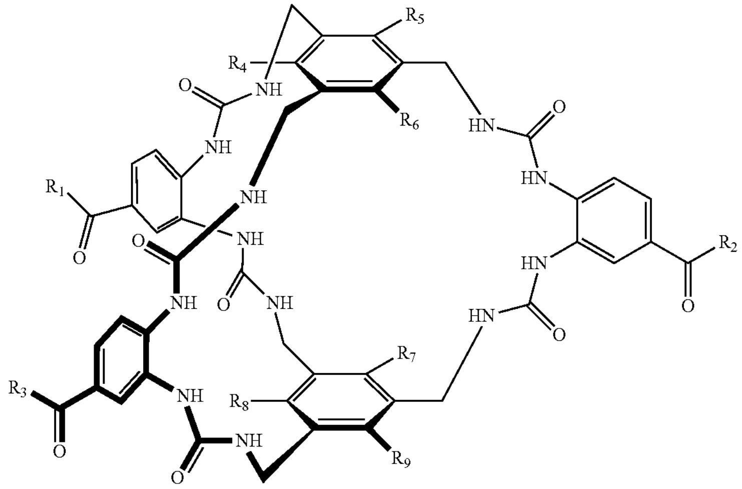
$R_4 = R_5 = R_6 = R_7 = R_8 = R_9 = Et$
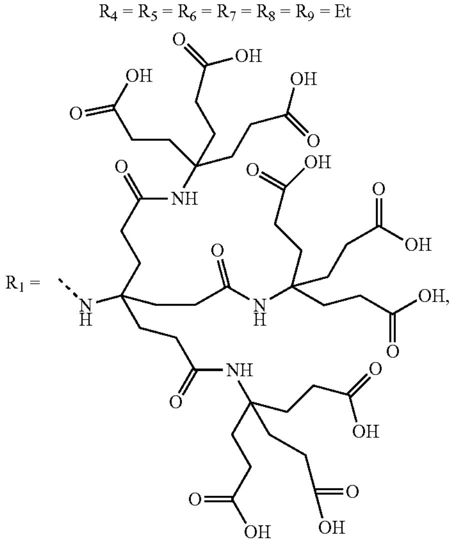
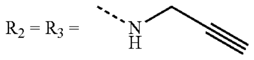

-continued
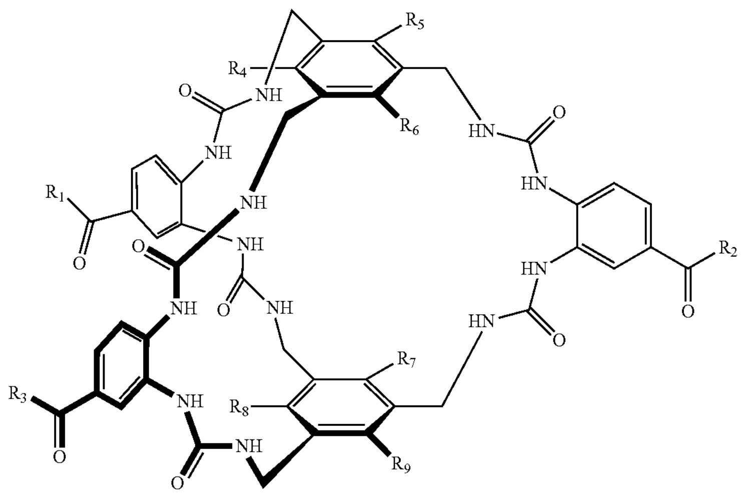
$R_4 = R_5 = R_6 = R_7 = R_8 = R_9 =$ Me
$R_1 = R_2 = R_3 =$
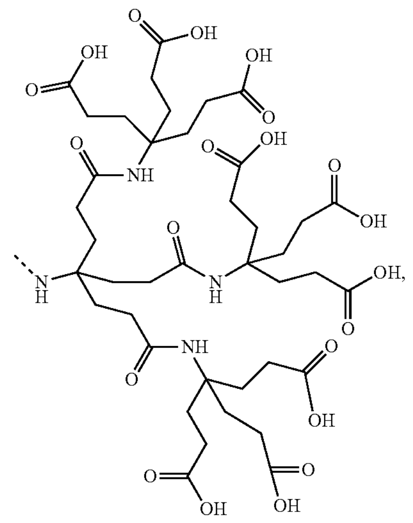
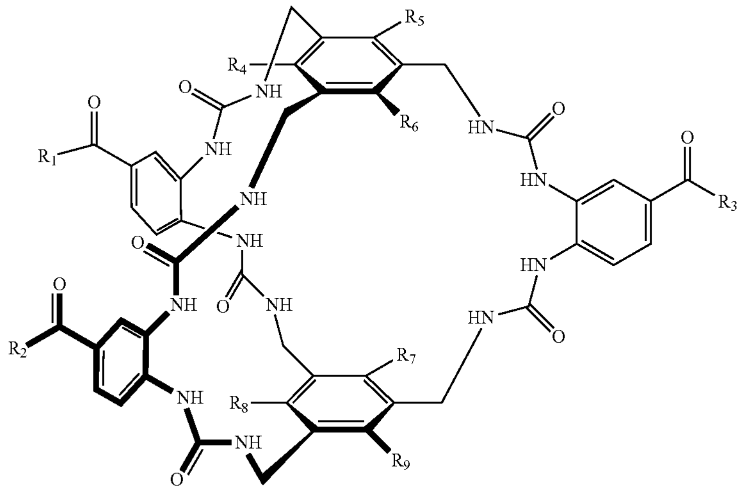
$R_4 = R_5 = R_6 = R_7 = R_8 = R_9 =$ Et
$R_1 = R_2 = R_3 =$
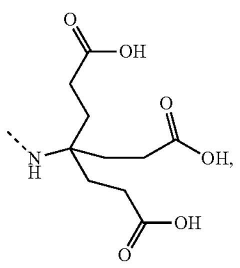

-continued
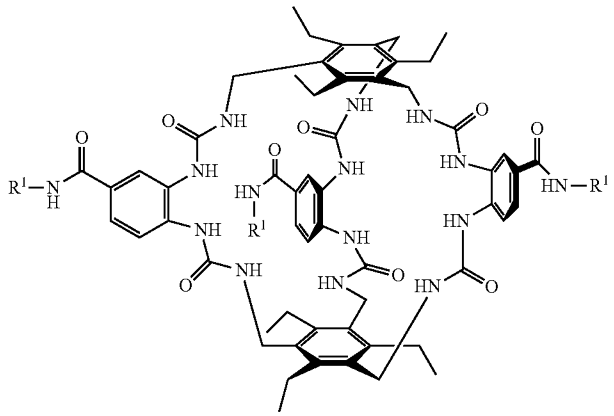
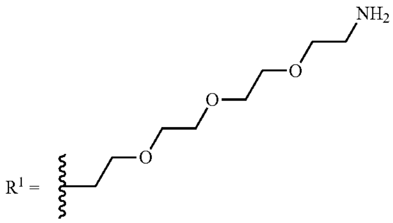
,
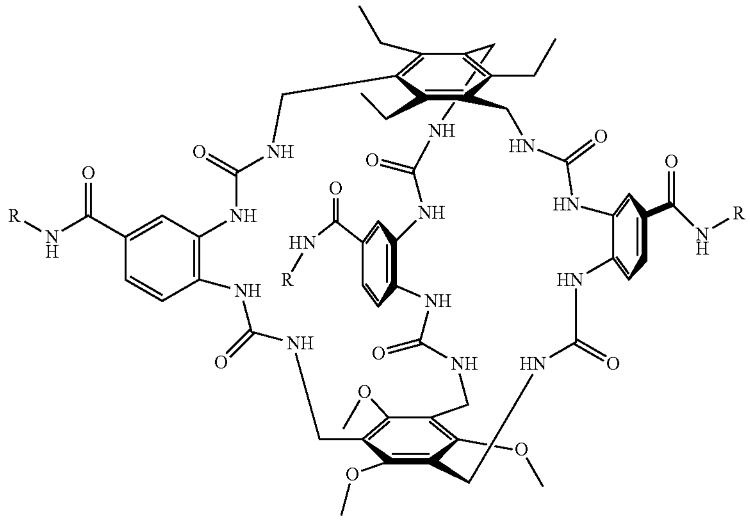

-continued
R = 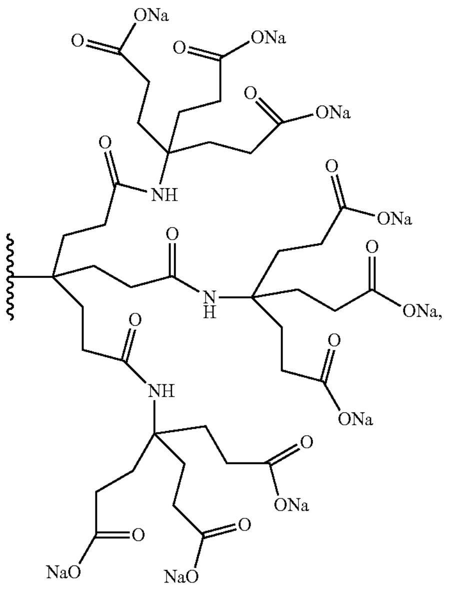 and
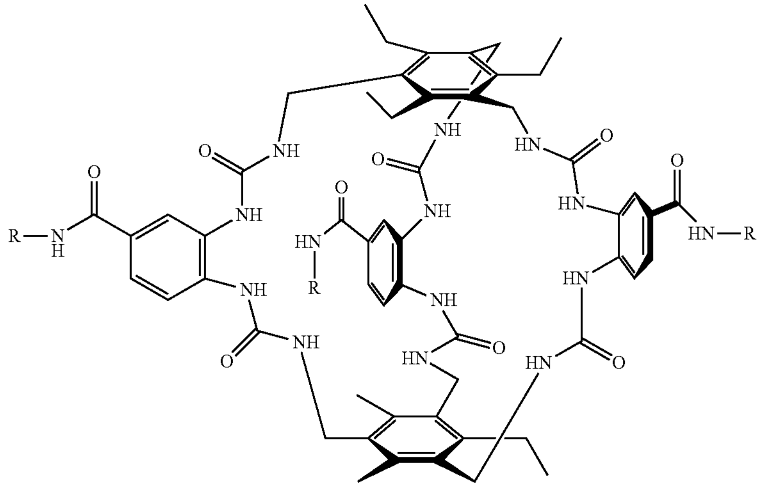
R = 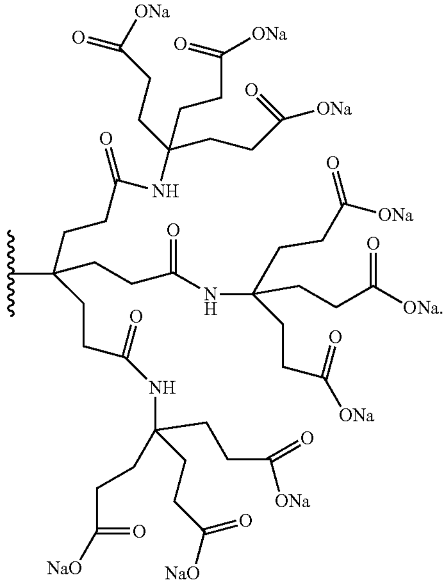.

8. A compound of the formula shown below:

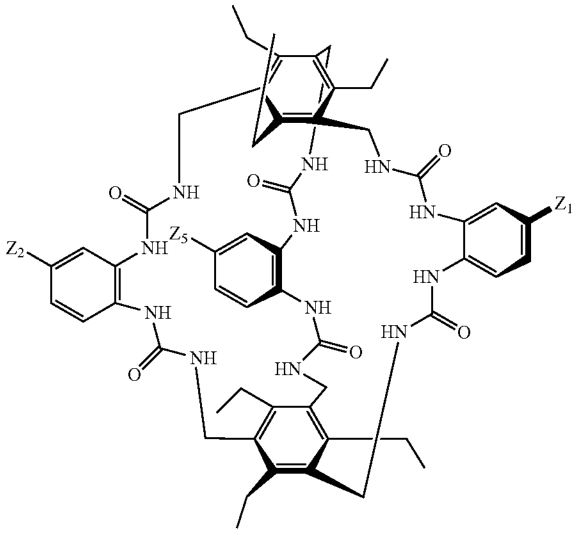

wherein each of $Z_1$, $Z_2$ and $Z_5$ is a group of the formula:

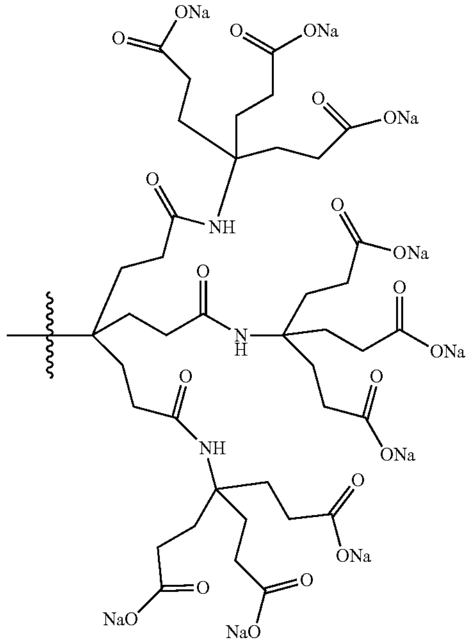

wherein denotes the point of attachment.

9. A complex comprising a compound according to claim 1, covalently attached to insulin.

10. A compound according to claim 1, wherein $Z_1$, $Z_2$, and $Z_5$ are independently selected from a hydrophilic polymer, a hydrophilic dendritic group or C(O)OM1, wherein M1 is hydrogen or a cation.

11. A compound according to claim 4, wherein $M_x$ is Na, Li, or $NH_4$.

* * * * *

UNITED STATES PATENT AND TRADEMARK OFFICE
CERTIFICATE OF CORRECTION

PATENT NO. : 10,800,747 B2
APPLICATION NO. : 16/491379
DATED : October 13, 2020
INVENTOR(S) : Anthony Davis et al.

Page 1 of 1

It is certified that error appears in the above-identified patent and that said Letters Patent is hereby corrected as shown below:

On the Title Page

The Applicant address reads:
"Unit DX, Saint Philips Central, Albert Road
Bristol, Great Britain, BS2 0XJ"

Should read:
--3 City Place, Beehive Ring Road
Gatwick, West Sussex
United Kingdom, RH6 0PA--

Signed and Sealed this
First Day of June, 2021

Drew Hirshfeld
*Performing the Functions and Duties of the*
*Under Secretary of Commerce for Intellectual Property and*
*Director of the United States Patent and Trademark Office*